(12) United States Patent
Arns et al.

(10) Patent No.: US 11,279,732 B2
(45) Date of Patent: Mar. 22, 2022

(54) SOMATOSTATIN RECEPTOR ANTAGONIST COMPOUNDS AND METHODS OF USING THE SAME

(71) Applicant: CDRD VENTURES INC., Vancouver (CA)

(72) Inventors: Stephen Paul Arns, North Vancouver (CA); James Brian Jaquith, Cobourg (CA); Davy Jérémy Baudelet, Vancouver (CA); Eric Roy Simonson, Vancouver (CA); Richard Tom Liggins, Coquitlam (CA); Nag Sharwan Kumar, Surrey (CA); Tom Han Hsiao Hsieh, Vancouver (CA)

(73) Assignee: CDRD VENTURES INC., Vancouver (CA)

( * ) Notice: Subject to any disclaimer, the term of this patent is extended or adjusted under 35 U.S.C. 154(b) by 50 days.

(21) Appl. No.: 16/076,826

(22) PCT Filed: Feb. 9, 2017

(86) PCT No.: PCT/CA2017/050156
§ 371 (c)(1),
(2) Date: Aug. 9, 2018

(87) PCT Pub. No.: WO2017/136943
PCT Pub. Date: Aug. 17, 2017

(65) Prior Publication Data
US 2019/0040102 A1 Feb. 7, 2019

Related U.S. Application Data

(60) Provisional application No. 62/293,216, filed on Feb. 9, 2016.

(51) Int. Cl.
C07K 7/50 (2006.01)
C07K 7/06 (2006.01)
C07K 7/02 (2006.01)
A61K 38/00 (2006.01)

(52) U.S. Cl.
CPC .............. *C07K 7/06* (2013.01); *C07K 7/02* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,508,711 A | 4/1985 | Coy et al. | |
| 5,846,934 A | 12/1998 | Bass et al. | |
| 5,874,227 A | 3/1999 | Rivier | |
| 7,019,109 B2 | 3/2006 | Rivier et al. | |
| 2004/0242842 A1 | 12/2004 | Maecke et al. | |
| 2005/0070470 A1 | 3/2005 | Coy et al. | |
| 2009/0004195 A1 | 1/2009 | Vranic et al. | |
| 2011/0178013 A1* | 7/2011 | Paternostre | A61P 3/10 514/11.1 |

FOREIGN PATENT DOCUMENTS

| | | |
|---|---|---|
| CA | 2741259 | 6/2010 |
| JP | 2010/506943 | 3/2010 |
| JP | 2011/520787 | 7/2011 |
| RU | 2242481 | 12/2004 |
| RU | 2328504 | 7/2008 |
| WO | WO 95/22341 | 8/1995 |
| WO | WO 2004/082722 | 9/2004 |

(Continued)

OTHER PUBLICATIONS

Search Report issued in Corresponding Russian Application No. 2018132050, dated Jun. 1, 2020 (English Translation Provided).

(Continued)

*Primary Examiner* — Ronald T Niebauer
(74) *Attorney, Agent, or Firm* — Norton Rose Fulbright US LLP

(57) ABSTRACT

The present invention is directed to somatostatin receptor antagonist compounds having the structure of Formula I, compositions comprising the same, and methods of using such compounds and compositions. The compounds may be useful in the prevention or treatment of hypoglycemia.

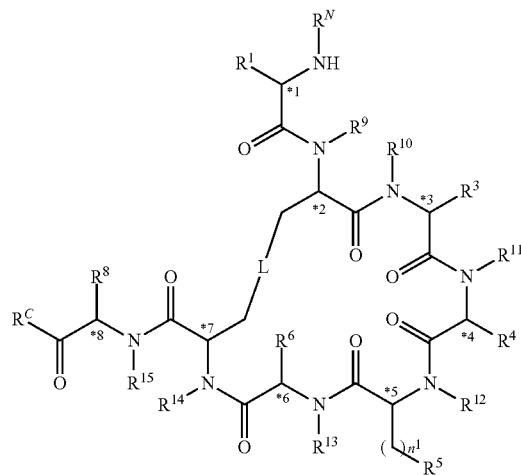

Formula I

48 Claims, 7 Drawing Sheets
Specification includes a Sequence Listing.

(56) References Cited

FOREIGN PATENT DOCUMENTS

| WO | 2008048942 A2 | 4/2008 |
|---|---|---|
| WO | WO 2009/129311 | 10/2009 |

OTHER PUBLICATIONS

Bass et al., "Identification and characterization of novel somatostatin antagonists" *Molecular Pharmacology*, 1996, 50(4):709-715.

Berge et al., "Pharmaceutical salts." *J. Pharm. Sci.*, 1977, 66(1):1-19.

Besret et al., "Thiocarbamate-linked peptides by chemoselective peptide ligation," *Journal of Peptide Science*, 2008, 14(12):1244-1250.

Boscaro et al., "Treatment of Pituitary-Dependent Cushing's disease with the Multireceptor Ligand Somatostatin Analog Pasireotide (SOM230): A Multicenter, Phase II Trial" *The Journal of Clinical Endocrinology and Metabolism*, 2009, 94(1):115-122.

Bregant et al., "Orthogonally Protected Lanthionines: Synthesis and Use for the Solid-Phase Synthesis of an Analogue of Nisin Ring C," *J. Org Chem.*, 2005, 70(7):2430-2438.

Brubaker et al., "Tissue-Specific Differences in the Levels of Proglucagon-Derived Peptides in Streptozotocin-Induced Diabetes" *Endocrinology*, 1989, 124:3003-3009.

Cejvan et al., "Intra-Islet Somatostatin Regulates Glucagon Release via Type 2 Somatostatin Receptors in Rats" *Diabetes*, 2003, 52:1176-1181.

Chatterjee et al., "Synthesis of N-methylated cyclic peptides" *Nature Protocols*, 2012, 7(3):432-444.

Chen et al., "Disulfide Bond Formation in Peptides," *Current Protocols in Protein Science*, 2001, 18.6.1-18.6.19.

Dugave et al., "Synthesis of natural and non-natural orthogonally protected lanthionines from N-tritylserine and allo-threonine derivatives," *Tetrahedron: Asymmetry*, 1997, 8(9):1453-1465.

Fehlmann et al., "Distribution and characterisation of somatostatin receptor mRNA and binding sites in the brain and periphery" *Journal of Physiology* (Paris), 2000, 94:265-281.

Freidinger et al., "Conformational modifications of cyclic hexapeptide somatostatin analogs," *Journal of Peptide and Protein Research*, 1984, 23(2):142-150.

Havel and Taborsky, "Stress-induced activation of the neuroendocrine system and its effects on carbohydrate metabolism," *Ellenberg and Rifkin's Diabetes Mellitus*, New York, McGraw-Hill, 2003, p. 127-149.

Hocart et al., "Highly Potent Cyclic Disulfide Antagonists of Somatostatin" *Journal of Medicinal Chemistry*, 1999, 42(11):1863-1871.

Holland-Nell et al., "Maintaining Biological Activity by Using Triazoles as Disulfide Bond Mimetics," *Angewandte Chemie Int. Ed.*, 2011, 50:5204-5206.

Inouye et al., "Effects of recurrent hyperinsulinemia with and without hypoglycemia on counterregulation in diabetic rats" *American Journal of Physiology Endocrinology and Metabolism*, 2002, 282:E1369-E1379.

International Search Report and Written Opinion issued in International Patent Application No. PCT/CA2017/050156, dated Apr. 26, 2017.

Karimian et al., "Somatostatin Receptor Type 2 Antagonism Improves Glucagon Counterregulation in Biobreeding Diabetic Rats" *Diabetes*, 2013, 62(8):2968-2977.

Kimura et al., "Immunohistochemical Localization of Somatostatin Receptor Type 2A in Rate and Human Tissues" *Endocrine Journal*, 2001, 48:95-102.

Kumar et al., "Subtype-selective expression of the five somatostatin receptors (hSSTR1-5) in human pancreatic islet cells: a quantitative double-label immunohistochemical analysis." *Diabetes*, 1999, 48:77-85.

Lanneau et al., "Somatostatin receptor subtypes sst1 and sst2 elicit opposite effects on the response to glutamate of mouse hypothalamic neurones: an electrophysiological and single cell RT-PCR study" *European Journal of Neuroscience*, 1998, 10:204-212.

Made et al., "Automated solid-phase peptide synthesis to obtain therapeutic peptides" *Beilstein J. Org. Chem.*, 2014, 10:1197-1212.

Maurer and Reubi, "Somatostatin receptors in the adrenal" *Molecular and Cellular Endocrinology*, 1986, 45:81-90.

Mizobe et al., "Pharmacological characterization of adrenal paraneurons: substance P and somatostatin as inhibitory modulators of the nicotinic response" *Brain Research*, 1979, 178:555-566.

Orci et al., "Hypertrophy and hyperplasia of somatostatin-containing D-cells in diabetes." *Proceedings of the National Academy of Sciences U.S.A.*, 1976, 73:1338-1342.

Patel, Y.C., "Somatostatin and its receptor family" *Frontiers in Neuroendocrinology*, 1999, 20(3):157-198.

Pattaroni et al., "Cyclic hexapeptides related to somatostatin. Synthesis and biological testing" *International Journal of Peptide and Protein Research*, 1990, 36(5):401-417.

Rajeswaran et al., "Highly Potent and Subtype Selective Ligands Derived by N-Methyl Scan of a Somatostatin Antagonist" *Journal of Medicinal Chemistry*, 2001, 44(8):1305-1311.

Rastogi et al., "Increase in somatostatin to glucagon ratio in islets of alloxan-diabetic dogs: effect of insulin-induced euglycemia." *Canadian Journal of Physiology and Pharmacology*, 1993, 71:512-517.

Rastogi et al., "Paradoxical Reduction in Pancreatic Glucagon with Normalization of Somatostatin and Decrease in Insulin in Normoglycemic Alloxan-Diabetic Dogs: A Putative Mechanism of Glucagon Irresponsiveness to Hypoglycemia" *Endocrinology*, 1990, 126:1096-1104.

Reubi et al., "Immunohistochemical Localization of Somatostatin Receptor sst2A in Human Pancreatic Islets" *J. Clin. Endocrinol. Metab.*, 1998, 83:3746-3749.

Rew et al., "Synthesis and Biological Activities of Cyclic Lanthionine Enkephalin Analogues: δ-Opioid Receptor Selective Ligands," *J. Med. Chem.*, 2002, 45(17):3746-3754.

Role et al., "Somatostatin and substance P inhibit catecholamine secretion from isolated cells of guinea-pig adrenal medulla" *Neuroscience*, 1981, 6:1813-1821.

Rossowski and Coy, "Specific Inhibition of Rat Pancreatic Insulin or Glucagon Release by Receptor-Selective Somatostatin Analogs" *Biochemical and Biophysical Research Communications*, 1994, 205:341-346.

Rossowski et al., "Examination of somatostatin involvement in the inhibitory action of GIP, GLP-1, amylin and adrenomedullin on gastric acid release using a new SRIF antagonist analogue" *British Journal of Pharmacology*, 1998, 125:1081-1087.

Shi et al., "Glucagon response to hypoglycemia is improved by insulin-independent restoration of normoglycemia in diabetic rats" *Endocrinology*, 1996, 137:3193-3199.

Strowski et al., "Somatostatin inhibits insulin and glucagon secretion via two receptors subtypes: an in vitro study of pancreatic islets from somatostatin receptor 2 knockout mice." *Endocrinology*, 2000, 141:111-117.

Stymiest et al., "Synthesis of Biologically Active Dicarba Analogues of the Peptide Hormone Oxytocin Using Ring-Closing Metathesis," *Org. Lett.*, 2003, 5(1):47-49.

Veber et al., "A super active cyclic hexapeptide analog of somatostatin" *Life Sciences*, 1984, 34(14):1371-1378.

Veber et al., "Highly active cyclic and bicyclic somatostatin analogues of reduced ring size" *Nature*, 1979, 280(5722):512-514.

Yue et al., "Amelioration of Hypoglycemia Via Somatostatin Receptor Type 2 Antagonism in Recurrently Hypoglycemic Diabetic Rats" *Diabetes*, 2013, 62(7):2215-2222.

Yue et al., "Somatostatin Receptor Type 2 Antagonism Improves Glucagon and Corticosterone Counterregulatory Responses to Hypoglycemia in Streptozotocin-Induced Diabetic Rats" *Diabetes*, 2012, 61(1):197-207.

Extended European Search Report issued in European Application No. 17749871.4, dated Sep. 18, 2019.

Office Action Issued in Japanese Application No. 2018-560701, dated Jan. 26, 2021.

Reubi, et al., "SST3-Selective Potent Peptidic Somatostatin Receptor Antagonists," *PNAS*, 97(25): 13973-13978, 2000.

(56) References Cited

OTHER PUBLICATIONS

Office Action Issued in Corresponding Indian Patent Application No. 201817031494, dated Mar. 8, 2021.

* cited by examiner

SOMATOSTATIN RECEPTOR ANTAGONIST COMPOUNDS AND METHODS OF USING THE SAME

CROSS REFERENCE TO RELATED APPLICATION

This application is a national phase application under 35 U.S.C. § 371 of International Application No. PCT/CA2017/050156 filed Feb. 9, 2017, which claims the benefit of U.S. Provisional Patent Application Ser. No. 62/293,216, filed 9 Feb. 2016, the entire contents of which are hereby incorporated by reference for all purposes as if fully set forth herein.

TECHNICAL FIELD

This invention relates to compounds that are somatostatin receptor antagonists. More particularly, this invention relates to cyclic peptides and more particularly to cyclic octapeptides that are somatostatin receptor antagonists.

BACKGROUND

Somatostatin receptors are ubiquitously expressed in most tissues of the body. Five different subtypes of somatostatin receptors have been discovered. The localization of particular receptor subtypes on different tissues allows for specific receptor antagonists to exert specific inhibitory effects.

In a series of structure activity relationship (SAR) studies of the 14 amino acid version of somatostatin (SST-14) and its analogs (Freidinger, R. M., et al., International journal of peptide and protein research 23(2):142-50, 1984; Pattaroni, C., et al., International journal of peptide and protein research 36(5):401-17, 1990; Veber, D. F., et al., Life sciences 34(14):1371-8, 1984), the four amino acid sequence Phe7-Trp8-Lys9-Thr10 (residues 7-10 of SST-14; SEQ ID NO: 85) was reported to be important for binding and activity of somatostatin. While Trp8-Lys9 appears essential, slight modifications in positions 7 and 10 were reportedly possible (Patel, Y. C., Frontiers in neuroendocrinology 20(3):157-98, 1999). Furthermore, cyclization (via the Cys-Cys pair at positions 3 and 14) apparently stabilizes the conformation of these residues, mimicking a β-turn, in a manner favorable for binding to SST receptors (Veber, D. F., et al., Life sciences 34(14):1371-8, 1984; Veber, D. F., et al., Nature 280(5722):512-4, 1979). Following these findings, several agonist analogs of somatostatin have been produced over the past several decades and several agonists have been used clinically to treat glandular tumors. Octreotide (Novartis) and lanreotide (Ipsen) are indicated for the treatment of acromegaly (somatotrophic adenoma) and thyrotrophic adenoma and in the management of certain neuroendocrine tumors in the pancreas (e.g., carcinoid tumors). A newer agonist, pasireotide (Novartis), is also used clinically for the treatment of Cushing's Disease (corticotropic adenoma) (Boscaro, M., et al., The Journal of clinical endocrinology and metabolism 94(1):115-22, 2009), (see www.signifor.com). Bass et al. (at American Cyanamid) (Bass, R. T., et al., Molecular pharmacology 50(4):709-15, 1996) reported that substitution of D-cysteine at the position equivalent to residue 3 of SST-14 gave analogs with antagonist activity. Since then, antagonists that bind to the various SST receptor subtypes with different affinities have been developed.

One approach to reducing hypoglycemia is to inhibit somatostatin receptors related to counterregulatory hormone release which are found in the pancreas, adrenal gland, and hypothalamus of the brain. Somatostatin receptor type 2 (SSTR2) are found in these tissues. Within the pancreas, SSTR2 are found nearly exclusively on glucagon-secreting α-cells in rodents (Rossowski, W. and Coy, D., *Biochemical and Biophysical Research Communications* 205:341-346, 1994; Strowski, M., et al., *Endocrinology* 141:111-117, 2000). In humans as well, somatostatin exerts its inhibitory effect on glucagon secretion via SSTR2 found on α-cells (Kumar, U., et al., *Diabetes* 48:77-85, 1999; Reubi, J., et al., *J. Clin. Endocrinol. Metab.* 83:3746-3749, 1998), while the receptor is also expressed in the β cells (Reubi, J., et al., *J. Clin. Endocrinol. Metab.* 83:3746-3749, 1998), where it is involved in regulating insulin secretion. In the adrenal gland, SSTR2 have been widely identified in the adrenal medulla of animals and humans (Kimura, N., et al., *Endocrine Journal* 48:95-102, 2001; Maurer, R. and Reubi, J., *Molecular and Cellular Endocrinology* 45:81-90, 1986). It has been shown that somatostatin inhibits acetylcholine-stimulated release of epinephrine from the adrenal medulla (Role, L., et al., *Neuroscience* 6:1813-1821, 1981; Mizobe, F., et al., *Brain Research* 178:555-566, 1979), and this is the mechanism whereby epinephrine is released during hypoglycemia (Havel P. and Taborsky, G. J., *Stress-induced activation of the neuroendocrine system and its effects on carbohydrate metabolism*. In Ellenberg and Rifkin's Diabetes Mellitus. Porte Jr D, Sherwin R, Baron A, Eds. New York, McGraw-Hill, 2003, p. 127-149). SSTR2 are also found in the hypothalamus of the brain (Fehlmann D., et al., *Journal of Physiology* (Paris) 94:265-281, 2000; Lanneau C., et al., *European Journal of Neuroscience* 10:204-212, 1998) where somatostatin also has an inhibitory effect on hormones involved in hypoglycemic counterregulation.

The approach of using SSTR2 antagonism to prevent hypoglycemia has been demonstrated in the STZ rat model, in which the glucagon response to hypoglycemia, which is absent in diabetic rats can be restored by administration of a SSTR2 antagonist (Yue J. T., et al., *Diabetes* 61(1):197-207, 2012). In this experiment, not only was the glucagon response restored, but the corticosterone response which was also deficient in diabetic rats was also improved in hypoglycemia after treatment with a SSTR2 antagonist. Furthermore, restoration of the counterregulatory responses corresponds to prevention or reduction in the severity of hypoglycemia in similar rats given an insulin dose to induce hypoglycemia (Yue J. T., et al., *Diabetes* 62(7):2215-2222, 2013).

Somatostatin levels in the pancreas in diabetic animals are elevated (Rastogi, K., et al., *Endocrinology* 126:1096-1104, 1990; Rastogi, K., et al., *Canadian Journal of Physiology and Pharmacology* 71:512-517, 1993) as well as in diabetic humans (Orci, L., et al., *Proceedings of the National Academy of Sciences U.S.A* 73:1338-1342, 1976). In streptozotocin (STZ)-diabetic rats, there is: (i) hyperplasia and hypertrophy of somatostatin-containing δ-cells in the pancreas (Orci, L., et al., *Proceedings of the National Academy of Sciences U.S.A* 73:1338-1342, 1976); (ii) increased expression of pancreatic prosomatostatin mRNA (Brubaker, P., et al., *Endocrinology* 124:3003-3009, 1989; Shi, Z., et al., *Endocrinology* 137:3193-3199, 1996); (iii) increased pancreatic somatostatin (Inouye, K., et al., *American Journal of Physiology Endocrinology and Metabolism* 282:E1369-E1379, 2002); and (iv) distribution of somatostatin-secreting δ-cells in the central portions of islets cells (Rossowski, W. and Coy, D., *Biochemical and Biophysical Research Communications* 205:341-346, 1994). It has been reported that excessive somatostatin may inhibit glucagon release during hypoglycemia (Rastogi, K., et al., *Endocrinology* 126:1096-

1104, 1990). Furthermore, it is well documented that somatostatin inhibits stimulated secretion of pancreatic glucagon. In STZ-diabetic rats, the expression of the gene for proglucagon and pro-somatostatin are both markedly increased (Inouye, K., et al., *American Journal of Physiology Endocrinology and Metabolism* 282:E1369-E1379, 2002). This increased concentration of somatostatin is observed in diabetic rats, both during euglycemia (i.e. normal blood glucose concentrations) and hypoglycemia (Shi, Z., et al., *Endocrinology* 137:3193-3199, 1996). Concentration of somatostatin in plasma is also increased during euglycemia and hypoglycemia in diabetic rats (Shi, Z., et al., *Endocrinology* 137:3193-3199, 1996). However, despite increased gene expression of proglucagon, plasma concentrations of glucagon are not increased during hypoglycemia in diabetic rats, presumably in part due to the marked elevation of somatostatin levels.

In isolated islets and in perifused isolated islets, the somatostatin receptor type 2 (SSTR2)-selective antagonist, DC-41-33, also known as PRL-2903, dose-dependently increases glucagon secretion to an arginine stimulus, and subsequently adding somatostatin dose-dependently reverses the actions of the SSTR2 antagonist (Cejvan, K., et al., *Diabetes* 51 Suppl 3:S381-S384, 2002; Cejvan, K., et al., *Diabetes* 52:1176-1181, 2003).

In isolated, perfused pancreas of non-diabetic rats, this antagonist enhances glucagon secretion without affecting insulin secretion (Cejvan, K., et al., *Diabetes* 52:1176-1181, 2003). Similar findings have been demonstrated in rat and human pancreatic tissue slices, prefused in hypoglycemic condition with and without SSTR2 antagonist (Karimian N., et al., *Diabetes* 62(8):2968-2977, 2013). It is also able to reverse the inhibitory effect of glucose-dependent insulinotropic polypeptides, GIP and GIP-(1-30)NH$_2$, and glucagon-like polypeptide, GLP-1(7-36)NH$_2$, on pentagastrin-stimulated gastric acid secretion in non-diabetic rats (Rossowski, W., et al., *British Journal of Pharmacology* 125:1081-1087, 1998). Somatostatin receptor antagonists are described in U.S. Pat. No. 4,508,711 (April 1985, Coy et al.) and in U.S. Pat. No. 5,846,934 (December 1998, Bass et al.) (Hocart, S. J., et al., *Journal of medicinal chemistry* 42(11):1863-71, 1999; Rajeswaran, W. G., et al., *Journal of medicinal chemistry* 44(8):1305-11, 2001).

The primary pharmacological treatments for hypoglycemia on the market today are based on various IV glucose or dextrose formulations and, as such, are considered reactionary treatments rather than true management strategies. There are a number of glucagon products on the market (e.g., GlucaGen®, Novo Nordisk), however this too is a rescue approach and is typically administered IV or SC in emergencies because the patient is unconscious. Importantly, glucagon must also be carefully dosed to avoid overstimulating glucose production (unlike a normalized endogenous glucagon response). These therapies are not directed to reducing the incidence of hypoglycemia, and as rescue therapies for severe hypoglycemia, they would not be expected to reduce the apprehension patients feel about the likelihood of experiencing a hypoglycemic event. Preventive therapies are required to reduce or eliminate this complication, and to enable insulin-dependent diabetic patients to more aggressively manage their blood glucose levels, resulting in overall improved long-term health outcomes. There is thus a real and strong demand for the development of a long-term therapeutic approach for the prevention of hypoglycemia.

SUMMARY

This invention is based, in part, on novel cyclic peptides that exhibit somatostatin receptor (SSTR) antagonist activity. Cyclic peptides of the present invention are often selective for a particular SSTR, such as SSTR 2. This invention is also based, in part, on novel amino acids that can be used in cyclic peptides of the present invention.

In illustrative embodiments of the present invention, there is provided a compound having the structure of Formula I:

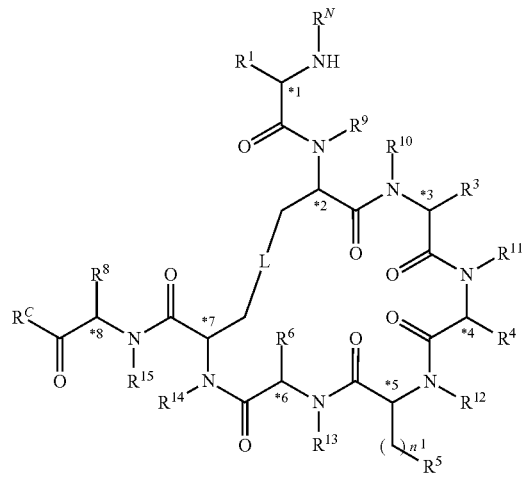

Formula I or a salt thereof, wherein:

$R^C$ is OH or NHR$^{16}$, wherein R$^{16}$ is H or C$_{1-6}$ alkyl optionally substituted with one or more substituents;

$R^N$ is selected from the group consisting of:
  (i) H;
  (ii) C$_{1-6}$ alkyl;
  (iii) —C(O)R$^{17}$, wherein R$^{17}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
  (iv) —C(O)C$_{1-6}$ alkylene-C(O)OR$^{18}$, wherein R$^{18}$ is H or C$_{1-6}$ alkyl optionally substituted with one or more substituents;
  (v) —C(O)C$_{1-6}$ alkylene-N(R$^{20}$)C(O)R$^{19}$, wherein R$^{19}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents, and wherein R$^{20}$ is H or C$_{1-6}$ alkyl;
  (vi) —C(O)C$_{1-6}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
  (vii) —C(O)C$_{1-6}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(viii) —C(O)C$_{1-6}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and (ix) —S(O)$_2$R$^{26}$, wherein R$^{26}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

R$^1$ is selected from the group consisting of C$_{1-6}$ alkyl, C$_{6-10}$ aryl, 5- to 10-membered heteroaryl, —C$_{1-6}$ alkylene(C$_{6-10}$ aryl) and —C$_{1-6}$ alkylene(5- to 10-membered heteroaryl), wherein the C$_{1-6}$ alkyl, the C$_{6-10}$ aryl, the C$_{6-10}$ aryl of —C$_{1-6}$ alkylene(C$_{6-10}$ aryl), the 5- to 10-membered heteroaryl and the 5- to 10-membered heteroaryl of —C$_{1-6}$ alkylene(5- to 10-membered heteroaryl) are optionally substituted with one or more substituents, and wherein the C$_{1-6}$ alkylene of —C$_{1-6}$ alkylene(C$_{6-10}$ aryl) and —C$_{1-6}$ alkylene(5- to 10-membered heteroaryl) is optionally substituted with one or more substituents;

R$^3$ is selected from the group consisting of:
(i) C$_{6-10}$ aryl which is optionally substituted with one or more substituents;
(ii) 5- to 10-membered heteroaryl which is optionally substituted with one or more substituents;
(iii) —C$_{1-6}$ alkylene(C$_{6-10}$ aryl), wherein the C$_{6-10}$ aryl is optionally substituted with one or more substituents, and wherein the C$_{1-6}$ alkylene is optionally substituted with one or more substituents;
(iv) —C$_{1-6}$ alkylene(5- to 10-membered heteroaryl), wherein the 5- to 10-membered heteroaryl is optionally substituted with one or more substituents, and wherein the C$_{1-6}$ alkylene is optionally substituted with one or more substituents;
(v) —C$_{1-6}$ alkylene-NR$^{27}$C(O)R$^{28}$, wherein:
R$^{27}$ is H or C$_{1-6}$ alkyl;
R$^{28}$ is selected from the group consisting of C$_{1-6}$ alkyl, C$_{6-10}$ aryl, 5- to 10-membered heteroaryl, and —NR$^{29}$R$^{30}$, wherein the C$_{1-6}$ alkyl is optionally substituted with one or more substituents, and wherein the C$_{6-10}$ aryl and 5- to 10-membered heteroaryl are optionally substituted with one or more substituents; and
wherein each of R$^{29}$ and R$^{30}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
(vi) —(C$_{6-10}$ arylene)-C(O)NR$^{31}$R$^{32}$ or —C$_{1-6}$ alkylene-(C$_{6-10}$ arylene)-C(O)NR$^{31}$R$^{32}$, wherein each of R$^{31}$ and R$^{32}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
(vii) —(C$_{6-10}$ arylene)-NR$^{33}$R$^{34}$ or —C$_{1-6}$ alkylene-(C$_{6-10}$ arylene)-NR$^{33}$R$^{34}$, wherein:
each of R$^{33}$ and R$^{34}$ is independently selected from the group consisting of H, C$_{1-6}$ alkyl, C$_{6-10}$ aryl, 5- to 10-membered heteroaryl, —C(O)R$^{35}$, —C(O)NR$^{36}$R$^{37}$, and —SO$_2$R$^{38}$, wherein the C$_{1-6}$ alkyl is optionally substituted with one or more substituents, and wherein the C$_{6-10}$ aryl and 5- to 10-membered heteroaryl are optionally substituted with one or more substituents;
R$^{35}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents, and wherein the C$_{6-10}$ aryl, 5- to 10-membered heteroaryl, and 5- to 10-membered heterocycloalkyl are optionally substituted with one or more substituents;
each of R$^{36}$ and R$^{37}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and
R$^{38}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
(viii) —(C$_{6-10}$ arylene)-SO$_2$NR$^{39}$R$^{40}$ or —C$_{1-6}$ alkylene-(C$_{6-10}$ arylene)-SO$_2$NR$^{39}$R$^{40}$, wherein each of R$^{39}$ and R$^{40}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
(ix) —(C$_{6-10}$ arylene)-(C$_{1-6}$ alkylene)-NR$^{41}$R$^{42}$ or —C$_{1-6}$ alkylene-(C$_{6-10}$ arylene)-(C$_{1-6}$ alkylene)-NR$^{41}$R$^{42}$, wherein:
each of R$^{41}$ and R$^{42}$ is independently selected from the group consisting of H, C$_{1-6}$ alkyl, C$_{6-10}$ aryl, 5- to 10-membered heteroaryl, —C(O)R$^{43}$, and —C(O)NR$^{44}$R$^{45}$, wherein the C$_{1-6}$ alkyl is optionally substituted with one or more substituents, and wherein the C$_{6-10}$ aryl and 5- to 10-membered heteroaryl are optionally substituted with one or more substituents;
R$^{43}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and
each of R$^{44}$ and R$^{45}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
(x) —(C$_{6-10}$ arylene)-OR$^{46}$ or —C$_{1-6}$ alkylene-(C$_{6-10}$ arylene)-OR$^{46}$, wherein R$^{46}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and
(xi) —C$_{1-6}$ alkylene-(C$_{6-10}$ arylene)-N(R$^{47}$)—C(O)—CHR$^{48}$—NR$^{49}$R$^{50}$, wherein R$^{47}$ is H or CH$_3$, R$^{48}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{49}$ and $R^{50}$ is independently H, CH$_3$ or acetyl;

$R^4$ is selected from the group consisting of:

(i) —$C_{1-6}$ alkylene-N($R^{53}$)C(O)N$R^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl;

(ii) —$C_{1-6}$ alkylene-N($R^{55}$)C(O)$R^{54}$, wherein $R^{54}$ is selected from the group consisting of $C_{1-6}$alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl;

(iii) —($C_{6-10}$ arylene)-C(O)N$R^{56}R^{57}$ or —$C_{1-6}$ alkylene-($C_{6-10}$ arylene)-C(O)N$R^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —($C_{6-10}$ arylene)-N($R^{59}$)C(O)$R^{58}$ or —$C_{1-6}$ alkylene-($C_{6-10}$ arylene)-N($R^{59}$)C(O)$R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl;

(v) —($C_{6-10}$ arylene)-N($R^{62}$)C(O)N$R^{60}R^{61}$ or —$C_{1-6}$ alkylene-($C_{6-10}$ arylene)-N($R^{62}$)C(O)N$R^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl;

(vi) —($C_{6-10}$ arylene)-N($R^{64}$)SO$_2R^{63}$ or —$C_{1-6}$ alkylene-($C_{6-10}$ arylene)-N($R^{64}$)SO$_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl;

(vii) —($C_{6-10}$ arylene)-SO$_2$N$R^{65}R^{66}$ or —$C_{1-6}$ alkylene-($C_{6-10}$ arylene)-SO$_2$N$R^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-($C_{1-6}$ alkylene)-N$R^{67}R^{68}$ or —$C_{1-6}$ alkylene-($C_{6-10}$ arylene)-($C_{1-6}$ alkylene)-N$R^{67}R^{68}$, wherein:

each of $R^{67}$ and $R^{68}$ is independently selected from the group consisting of H, $C_{1-6}$ alkyl, $C_{6-10}$ aryl, 5- to 10-membered heteroaryl, —C(O)$R^{69}$, and —C(O)N$R^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents;

$R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-N$R^{72}R^{73}$ or —$C_{1-6}$ alkylene-($C_{6-10}$ arylene)-N$R^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-O$R^{74}$ or —$C_{1-6}$ alkylene-($C_{6-10}$ arylene)-O$R^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(xi) —$C_{1-6}$ alkylene-($C_{6-10}$ arylene)-N($R^{75}$)—C(O)—CH$R^{76}$—N$R^{77}R^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{77}$ and $R^{78}$ is independently H, CH$_3$ or acetyl; and (xii) —$C_{1-6}$ alkylene-($C_{6-10}$ arylene)-CN;

$R^5$ is selected from the group consisting of:

(i) —N$R^{79}R^{80}$, wherein each of $R^{79}$ and $R^{80}$ is independently selected from the group consisting of H, $C_{1-6}$ alkyl, —C(O)$R^{81}$, and —C(=N$R^{82}$)N$R^{83}R^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, $R^{81}$ is selected from the group consisting of H, —NH$_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl; and (ii) —N$^+R^{85}R^{86}R^{87}$, wherein each of $R^{85}$, $R^{86}$, and $R^{87}$ is independently $C_{1-6}$ alkyl; $n^1$ is 1, 2, 3, 4, 5, or 6; $R^6$ is $C_{1-6}$ alkyl optionally substituted with one or more substituents; $R^8$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents; $R^9$ is H or $C_{1-6}$ alkyl; $R^{10}$ is H or $C_{1-6}$ alkyl; $R^{11}$ is H or $C_{1-6}$ alkyl; $R^{12}$ is H or $C_{1-6}$ alkyl; $R^{13}$ is H or $C_{1-6}$ alkyl; $R^{14}$ is H or $C_{1-6}$ alkyl; $R^{15}$ is H or $C_{1-6}$ alkyl; and L is selected from the group consisting of:

i)

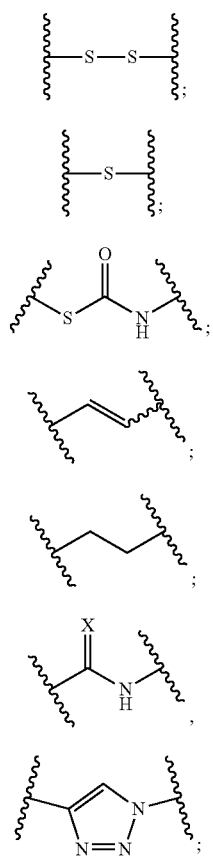

wherein X is S or O; and vii)

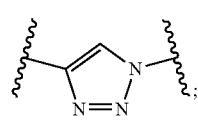

chiral centre *1 is in the S configuration or the R configuration; chiral centre *2 is in the S configuration or the R configuration; chiral centre *3 is in the S configuration or the R configuration; chiral centre *4 is in the S configuration or the R configuration; chiral centre *5 is in the S configuration or the R configuration; chiral centre *6 is in the S configuration or the R configuration; chiral centre *7 is in the S configuration or the R configuration; and chiral centre *8 is in the S configuration or the R configuration, provided that:

i) when $R^C$ is $NH_2$, $R^N$ is H or —$C(O)CH_2N_3$, $R^1$ is

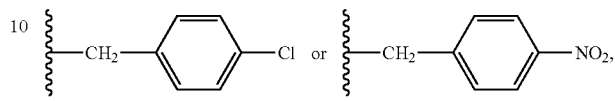

$R^3$ is

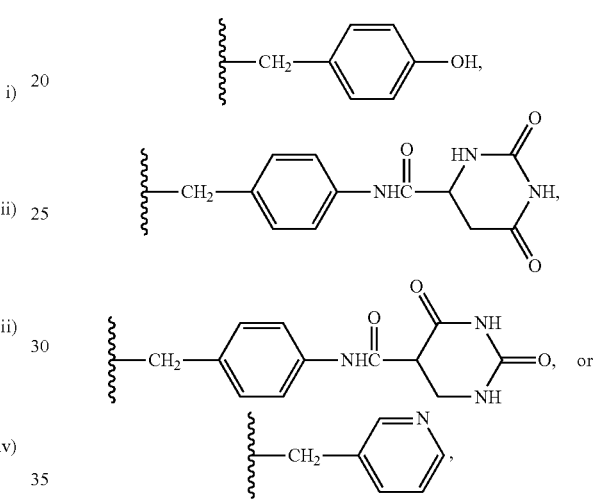

$R^5$ is $NH_2$, $n^1$ is 4, $R^6$ is —$CH(OH)(CH_3)$, $R^8$ is

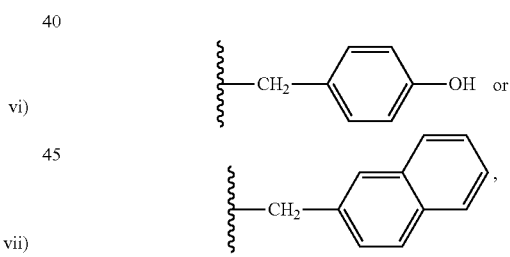

each of $R^9$, $R^{10}$, $R^{11}$, $R^{12}$, $R^{13}$, $R^{14}$ and $R^{15}$ is H, and L is

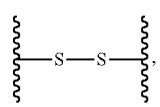

then $R^4$ is not

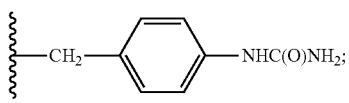

and ii) when $R^C$ is $NH_2$, $R^N$ is H, $R^1$ is

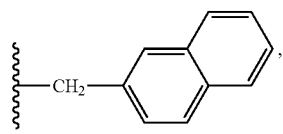 [SMILES: *Cc1ccc2ccccc2c1]

$R^3$ is

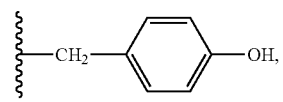

$R^5$ is $NH_2$, $n^1$ is 4, $R^6$ is $-CH(CH_3)_2$, $R^8$ is $-CH(OH)(CH_3)$, each of $R^9$, $R^{10}$, $R^{11}$, $R^{12}$, $R^{13}$, $R^{14}$ and $R^{15}$ is H, and L is

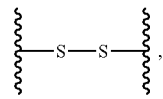

then $R^4$ is not

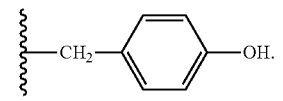

In illustrative embodiments of the present invention, a compound as defined anywhere herein or a pharmaceutically acceptable salt thereof may be for use in the prevention or treatment of hypoglycemia. In illustrative embodiments of the present invention, the hypoglycemia may be insulin-induced hypoglycemia. In illustrative embodiments of the present invention, a compound as defined anywhere herein or a pharmaceutically acceptable salt thereof may be for use in the treatment of diabetes.

In illustrative embodiments of the present invention, there is provided a pharmaceutical composition comprising a compound as defined anywhere herein or a pharmaceutically acceptable salt thereof and a pharmaceutically acceptable carrier. In illustrative embodiments of the present invention, the pharmaceutical composition may be for use in the prevention or treatment of hypoglycemia. In illustrative embodiments of the present invention, the hypoglycemia may be insulin-induced hypoglycemia. In illustrative embodiments of the present invention, the pharmaceutical composition may be for use in the treatment of diabetes.

In illustrative embodiments of the present invention, there is provided a method of inhibiting an activity of an SSTR2 receptor in a subject, the method comprising administering a compound as defined anywhere herein or a pharmaceutically acceptable salt thereof, to a subject in need thereof. In illustrative embodiments of the present invention, there is provided a method of preventing or treating hypoglycemia in a subject, the method comprising administering a compound as defined anywhere herein or a pharmaceutically acceptable salt thereof, to a subject in need thereof. In illustrative embodiments of the present invention, the hypo- glycemia is insulin-induced hypoglycemia. In illustrative embodiments of the present invention, there is provided a method of treating diabetes in a subject, the method comprising administering a compound as defined anywhere herein or a pharmaceutically acceptable salt thereof, to a subject in need thereof.

In illustrative embodiments of the present invention, there is provided a use of a compound as defined anywhere herein or a pharmaceutically acceptable salt thereof for the prevention or treatment of hypoglycemia. In illustrative embodiments of the present invention, the hypoglycemia is insulin-induced hypoglycemia.

In illustrative embodiments of the present invention, there is provided a use of a compound as defined anywhere herein or a pharmaceutically acceptable salt thereof in the treatment of diabetes. In illustrative embodiments of the present invention, there is provided a use of a compound as defined anywhere herein or a pharmaceutically acceptable salt thereof in the preparation of a medicament for the prevention or treatment of hypoglycemia. In illustrative embodiments of the present invention, the hypoglycemia is insulin-induced hypoglycemia. In illustrative embodiments of the present invention, there is provided a use of a compound as defined anywhere herein or a pharmaceutically acceptable salt thereof in the preparation of a medicament for the treatment of diabetes.

In illustrative embodiments of the present invention, there is provided an amino acid selected from the group consisting of:

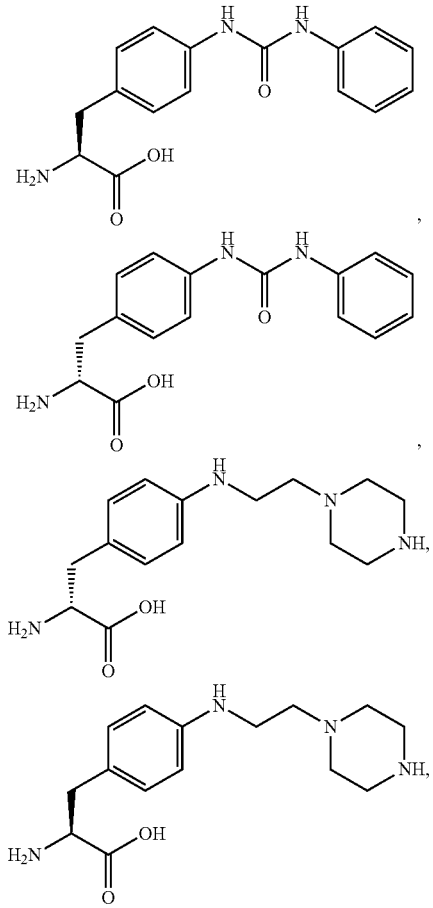

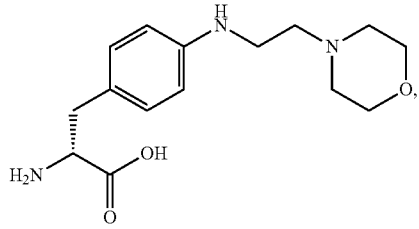
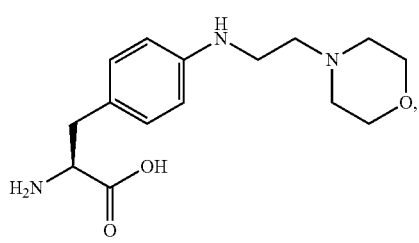
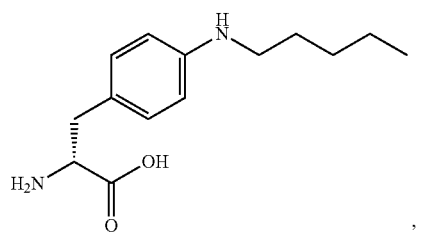
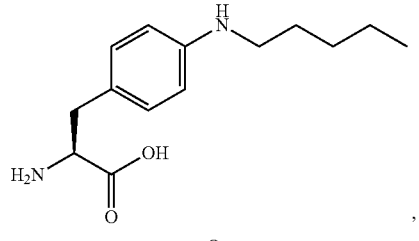
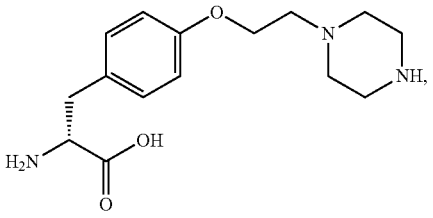
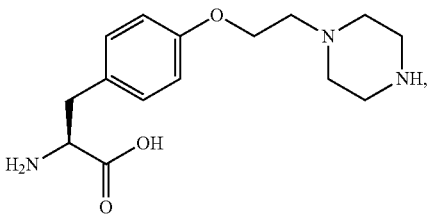
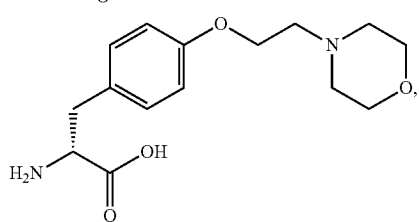
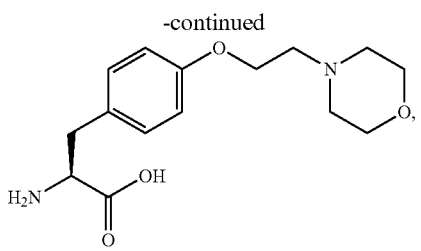
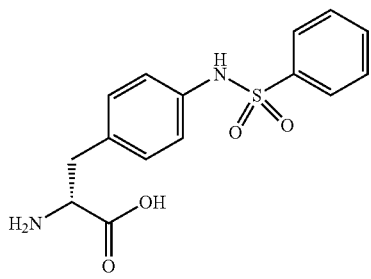
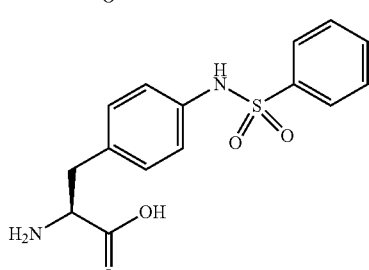
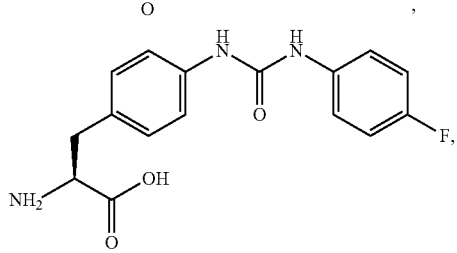
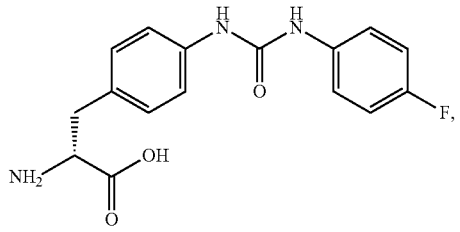
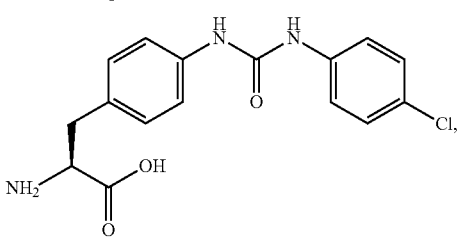
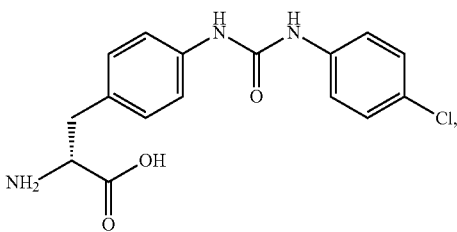

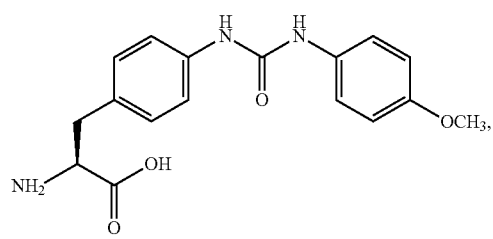
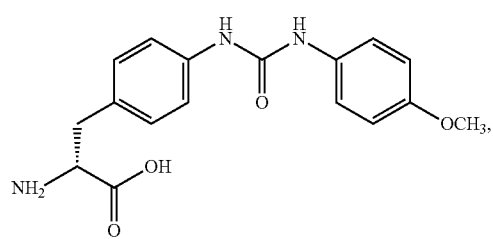
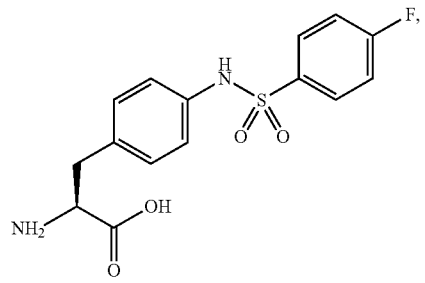
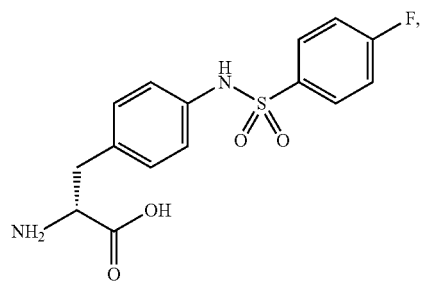
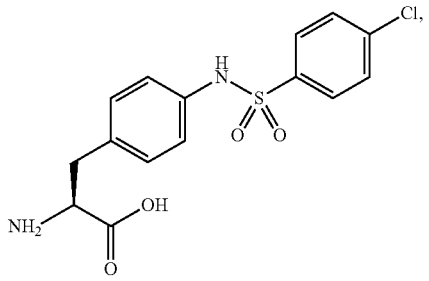
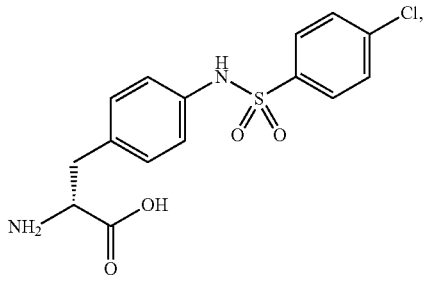
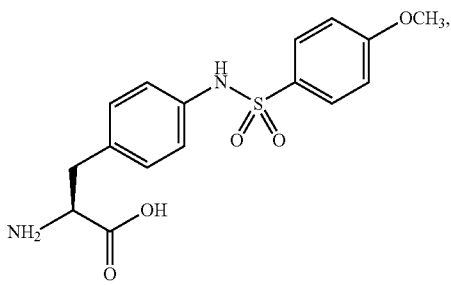
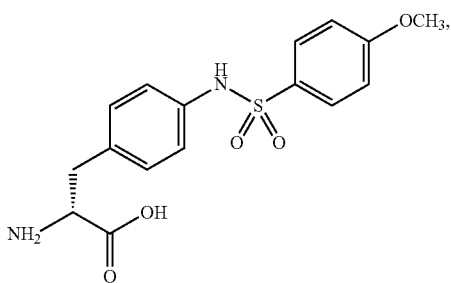
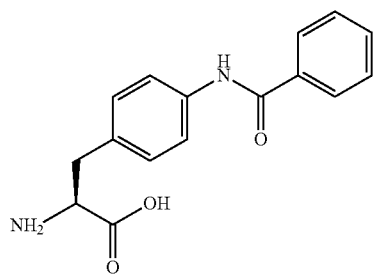
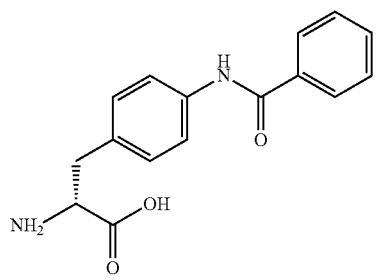
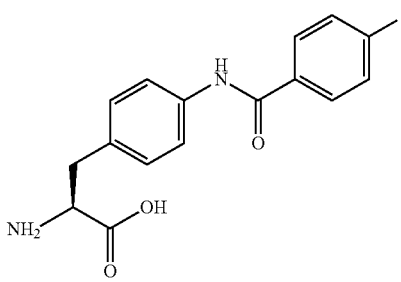
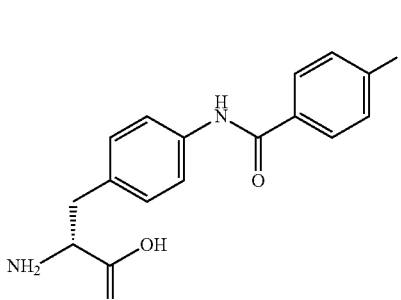

-continued

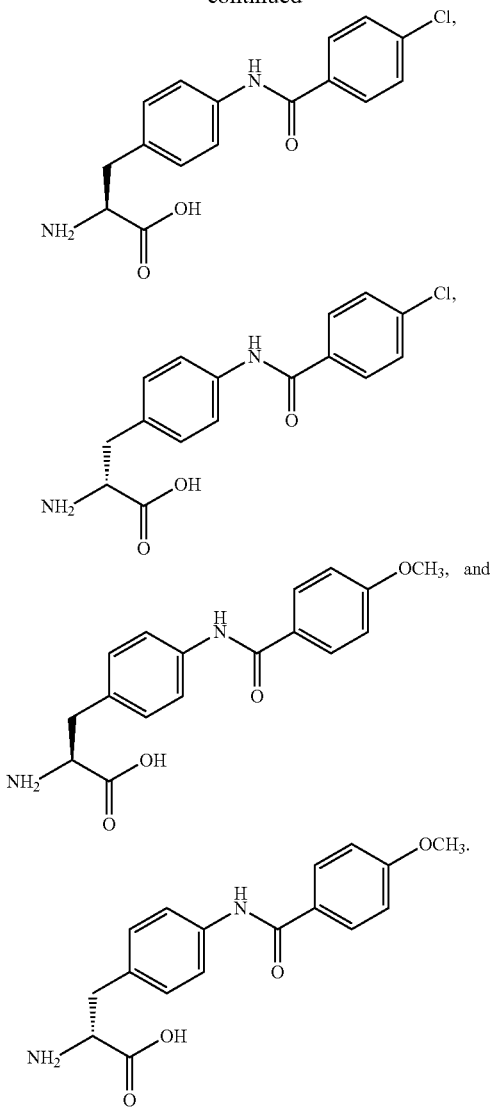

Other aspects and features of the present invention will become apparent to those ordinarily skilled in the art upon review of the following description of specific embodiments of the invention.

BRIEF DESCRIPTION OF THE DRAWINGS

FIG. 2B—Hypoglycemia Challenge #2) and the timing of measurements and sample collections.

DETAILED DESCRIPTION

Figure 1:
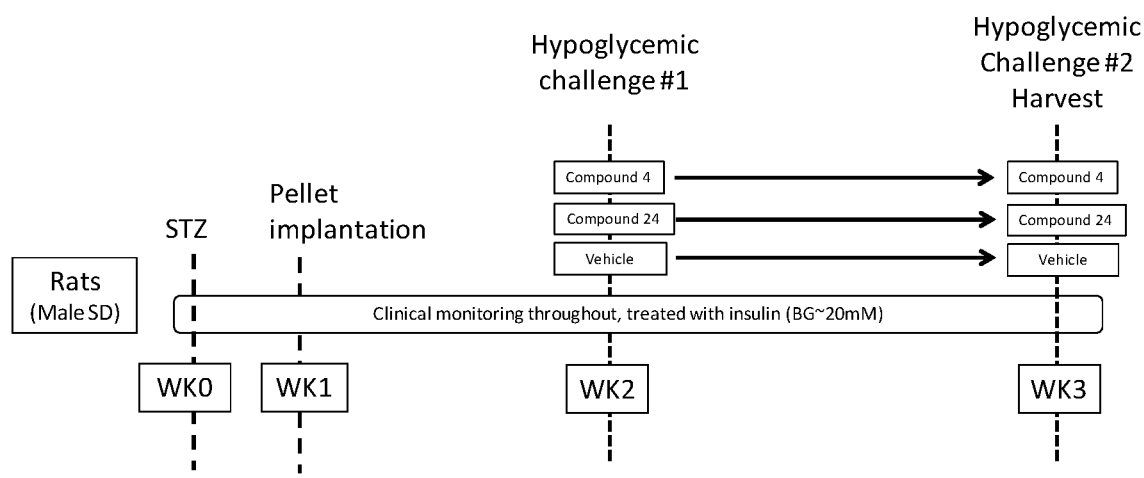
FIG. 1 is a schematic of the study design indicating when animals were made diabetic with STZ injection (week 0) followed by insulin pellet implantation (week 1) to control diabetes, then the subsequent hypoglycemic challenges (weeks 2 and 3).

As used herein, "optional" or "optionally" means that the subsequently described event or circumstance may but need not occur, and the description includes instances where the event or circumstance occurs and instances in which it does not.

If an item is described as being "independently selected" from a group, each item is selected independent of the other(s). Each item therefore may be the same as or different from the other item(s).

As used herein, the term "substituted," refers to a group wherein a non-hydrogen substituent is in the place of a hydrogen substituent on a carbon or nitrogen of the group. For example, a substituted alkyl is an alkyl group wherein at least one non-hydrogen substituent is in the place of a hydrogen substituent on the alkyl group. Non-limiting examples of substituents include halogen, —OH, —NO$_2$, $C_{1-6}$ alkoxy, $C_{1-6}$ haloalkoxy, —NH$_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl.

A group may be substituted with one or more than one substituent provided that the normal valency of the group is not exceeded, and that the substitution results in a stable compound. For example, if a methyl group (i.e., CH$_3$) is substituted, then 1, 2 or 3 hydrogen atoms on the carbon atom may be replaced with substituents. Where a substituent is attached via a double bond, such as an oxo (=O) substituent, the substituent occupies two available valences, so the total number of other substituents that may be included is reduced by two. If a group is described as being substituted with up to a particular number of substituents, that group may be substituted by up to that particular number of substituents provided that the normal valency of the group is not exceeded, and that the substitution results in a stable compound. Thus, for example, if a group is described as a heteroaryl substituted with up to 3 substituents, then any heteroaryl with less than 3 substitutable positions would be substituted by up to only as many substituents as the heteroaryl has substitutable positions.

For example, tetrazolyl (which has only one substitutable position) would be substituted with up to one substituent. As a further example, if an amino nitrogen is described as being substituted with up to 2 substituents, then the nitrogen will be substituted with up to 2 substituents if the amino nitrogen is a primary nitrogen, whereas the amino nitrogen will be substituted with up to only 1 substituent if the amino nitrogen is a secondary nitrogen. If there is more than one substitution on a group, each substituent may be the same or different, unless otherwise stated.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable, unless otherwise specified or otherwise implicit from the context.

As used herein, the terms "optionally substituted" and "substituted or unsubstituted" may be used interchangeably to indicate that the particular group being described may have no non-hydrogen substituents (i.e., unsubstituted), or the group may have one or more non-hydrogen substituents (i.e., substituted).

If substituents are described as being "independently selected" from a group, each substituent is selected independent of the other(s). Each substituent therefore may be the same as or different from the other substituent(s).

As used herein, the term "halo" or "halogen," by itself or as part of another group or substituent, refers to fluorine, chlorine, bromine, or iodine. Fluorine may also be depicted as F, —F or fluoro. Chlorine may also be depicted as Cl, —Cl or chloro. Bromine may also be depicted as Br, —Br or bromo. Iodine may also be depicted as I, —I or iodo.

As used herein, the term "alkyl," by itself or as part of another group or substituent, refers to a saturated, monovalent aliphatic hydrocarbon radical (i.e., a radical obtained from a hydrocarbon by removal of a hydrogen) having a specified number of carbon atoms. Alkyl includes hydrocarbon radicals having straight or branched chains. The term "$C_{x-y}$ alkyl" refers to an alkyl group comprising a number from x to y (with all individual integers within the range included, including integers x and y) of carbon atoms in its carbon skeleton. For example, a "$C_{1-6}$ alkyl" refers to an alkyl group comprising 1, 2, 3, 4, 5, or 6 carbon atom(s) in its carbon skeleton. Non-limiting examples of alkyl groups include methyl, ethyl, n-propyl, isopropyl, n-butyl, isobutyl, sec-butyl, tert-butyl, n-pentyl, isopentyl, neopentyl, 2-pentyl, 3-pentyl, 2-methylbutyl, 3-methylbutyl, 2,3-dimethylpropyl, n-hexyl, and 2,3-dimethylbutyl.

Alkyl groups may be optionally substituted. Alkyl groups described herein as optionally substituted may be substituted by one or more substituents, which are selected independently unless otherwise indicated. Non-limiting examples of substituents for alkyl groups include halogen, —OH, —NO$_2$, $C_{1-6}$ alkoxy, $C_{1-6}$ haloalkoxy, —NH$_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl. Alkyl groups may be substituted by 1, 2, 3, 4, 5, 6, 7, 8, 9, or 10 substituent(s).

As used herein, the term "alkylene," by itself or as part of another group or substituent, refers to a saturated, divalent aliphatic hydrocarbon group which can link two other groups together. Alkylene includes hydrocarbon groups having straight or branched chains. The open valences of an alkylene need not be at opposite ends of the chain. The term "$C_{x-y}$ alkylene" refers to an alkylene group comprising a number from x to y (with all individual integers within the range included, including integers x and y) of carbon atoms in its carbon skeleton. For example, a "$C_{1-6}$ alkylene" refers to an alkylene group comprising 1, 2, 3, 4, 5, or 6 carbon atom(s) in its carbon skeleton. Non-limiting examples of alkylene include methylene (—CH$_2$—), 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), —CH(Me)-, and —C(Me)$_2$-. Alkylene may also be depicted as —(CH$_2$)$_n$— wherein n is 1, 2, 3, 4, 5, or 6, or —(CR'R")$_n$— wherein R' and R" are H or $C_{1-6}$ alkyl and n$^1$ is 1, 2, 3, 4, 5, or 6.

Alkylene groups may be optionally substituted. Alkylene groups described herein as optionally substituted may be substituted by one or more substituents, which are selected independently unless otherwise indicated. Non-limiting examples of substituents for alkylene groups include halogen, —OH, —NO$_2$, $C_{1-6}$ alkoxy, $C_{1-6}$ haloalkoxy, —NH$_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl. Alkylene groups may be substituted by 1, 2, 3, 4, 5, 6, 7, 8, 9 or 10 substituent(s).

As used herein, the term "alkoxy," by itself or as part of another group or substituent, refers to an alkyl group that is single bonded to an oxygen atom. The point of attachment of an alkoxy group to the base molecule is through the oxygen atom. An alkoxy group may be depicted as —O-alkyl. The alkoxy group may contain a straight or branched chain. The term "$C_{x-y}$ alkoxy" refers to an alkoxy group comprising from x to y (with all individual integers within the range included, including integers x and y) of carbon atoms. For example, the term "$C_{1-6}$ alkoxy" refers to an alkoxy group comprising 1, 2, 3, 4, 5, or 6 carbon atom(s). Non-limiting examples of alkoxy groups include methoxy, ethoxy, propoxy, butoxy, and hexyloxy.

As used herein, the term "aryl," by itself or as part of another group or substituent, refers to a monocyclic ring or a fused bicyclic or polycyclic ring system, wherein the monocyclic ring contains a conjugated pi-electron system or at least one ring of the fused ring system contains: (i) a conjugated pi-electron system; and (ii) a ring-forming carbon atom that is the point of attachment to the base molecule. A ring-forming carbon atom of a monocyclic ring may not be replaced by a ring-forming heteroatom. A ring-forming carbon atom of a fused ring system may be replaced by a ring-forming heteroatom selected from N, O and S; however, if a fused ring system contains any ring-forming heteroatoms, the ring-forming heteroatoms are not contained in the ring that contains the ring-forming carbon atom that is the point of attachment to the base molecule. The monocyclic ring or fused ring system may contain from 6 to 14 ring-forming atoms, where ring-forming atom includes both ring-forming carbon atoms and heteroatoms. The term "$C_{x-y}$ aryl" refers to a monocyclic ring or fused ring system comprising a number from x to y (with all individual integers within the range included, including integers x and y) of ring-forming atoms. For example, a "$C_{6-10}$ aryl" refers to a monocyclic ring or fused ring system comprising 6, 7, 8, 9 or 10 ring-forming atoms. As a further example, where an aryl group contains any ring-forming heteroatoms, "$C_{6-10}$ aryl" refers to a fused ring system comprising 6, 7, 8, 9 or 10 ring-forming atoms, where ring-forming atom includes both ring-forming carbon atoms and heteroatoms. Fused bicyclic or polycyclic ring systems include a fused ring system comprising an aromatic ring fused to: (i) one or more aromatic rings; ii) one or more non-aromatic cycloalkyl rings; (iii) one or more non-aromatic heterocycloalkyl rings; (iv) one or more heteroaromatic rings; or (v) any combination or subcombination of (i), (ii), (iii), and (iv). The point of attachment to the base molecule on an aryl group is a ring-forming carbon atom. For greater clarity, where an aryl group is a fused ring system, the point of attachment to the base molecule on the fused ring system is a ring-forming carbon atom of an aromatic ring of the fused ring system, wherein the aromatic ring does not contain any ring-forming heteroatoms. Non-limiting examples of aryl groups include phenyl, naphthyl, anthracyl, phenanthrenyl, indanyl, indenyl, and tetrahydronaphthyl.

Aryl groups may be optionally substituted. Aryl groups described herein as optionally substituted may be substituted by one or more substituents, which are selected independently unless otherwise indicated. Non-limiting examples of substituents for aryl groups include halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl. Aryl groups may be substituted by 1, 2, 3, 4, 5, 6, 7, 8, 9, or 10 substituent(s).

As used herein, the term "arylene," by itself or as part of another group or substituent, refers to a divalent form of an aryl group as defined herein. Arylene groups may be optionally substituted by one or more substituents, which are selected independently unless otherwise indicated. Non-limiting examples of substituents for arylene groups include halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl. Arylene groups may be substituted by 1, 2, 3, 4, 5, 6, 7, 8, 9, or 10 substituent(s).

As used herein, the term "heteroaryl," by itself or as part of another group or substituent, refers to a monocyclic ring or a fused bicyclic or polycyclic ring system, wherein the monocyclic ring contains a conjugated pi-electron system and at least one ring-forming heteroatom selected from N, O and S, or at least one ring of the fused ring system contains: (i) a conjugated pi-electron system; (ii) at least one ring-forming heteroatom selected from N, O and S; and (iii) a ring-forming atom that is the point of attachment to the base molecule. The monocyclic ring or fused ring system may contain from 1, 2, 3, 4, 5, or 6 ring-forming heteroatom(s) selected from N, O and S. The monocyclic ring or fused ring system may contain from 5 to 14 ring-forming atoms, where ring-forming atom includes both ring-forming carbon atoms and heteroatoms. The term "x- to y-membered heteroaryl" refers to a monocyclic ring or a fused ring system comprising a number from x to y (with all individual integers within the range included, including integers x and y) of ring-forming atoms. For example, a "5- to 10-membered heteroaryl" refers to a monocyclic ring or a fused ring system comprising 5, 6, 7, 8, 9 or 10 ring-forming atoms. Fused bicyclic or polycyclic ring systems include a fused ring system comprising a heteroaromatic ring fused to: (i) one or more heteroaromatic rings; (ii) one or more aromatic rings; (iii) one or more non-aromatic cycloalkyl rings; (iv) one or more non-aromatic heterocycloalkyl rings; or (v) any combination or subcombination of (i), (ii), (iii), (iv) and (v). The point of attachment to the base molecule on a heteroaryl group is a ring-forming atom. For greater clarity, where a heteroaryl group is a fused ring system, the point of attachment to the base molecule on the fused ring system is a ring-forming atom of a heteroaromatic ring of the fused ring system. Non-limiting examples of heteroaryl groups include pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl, benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyidinyl, pyrazolo[4,3-c]pyidinyl, pyrazolo[3,4-c]pyidinyl, pyrazolo[3,4-b]pyidinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1-2,b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

Heteroaryl groups may be optionally substituted. Heteroaryl groups described herein as optionally substituted may be substituted by one or more substituents, which are selected independently unless otherwise indicated. Non-limiting examples of substituents for heteroaryl groups include halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl. Heteroaryl groups may be substituted by 1, 2, 3, 4, 5, 6, 7, 8, 9, or 10 substituent(s).

As used herein, the term "cycloalkyl," by itself or as part of another group or substituent, refers to a non-aromatic, saturated, monocyclic hydrocarbon ring or a spiro, bridged or fused bicyclic or polycyclic hydrocarbon ring system, wherein at least one ring of the ring system: (i) is a non-aromatic hydrocarbon ring wherein all unfused ring-forming carbon atoms are saturated; and (ii) contains a ring-forming carbon atom that is the point of attachment to the base molecule. A ring-forming carbon atom of a ring system may be replaced by a ring-forming heteroatom selected from N, O and S; however, if a ring system contains any ring-forming heteroatoms, the ring-forming heteroatoms are not contained in the ring that contains the ring-forming carbon atom that is the point of attachment to the base molecule. The monocyclic ring or spiro, bridged or fused polycyclic ring system contains from 5 to 14 ring-forming atoms, where ring-forming atom includes both ring-forming carbon atoms and heteroatoms. The term "C$_{x-y}$ cycloalkyl" refers to a monocyclic ring or spiro, bridged or fused polycyclic ring system comprising a number from x to y (with all individual integers within the range included, including integers x and y) of ring-forming atoms. For example, a "C$_{5-10}$ cycloalkyl" refers to a monocyclic ring or spiro, bridged or fused polycyclic ring system comprising 5, 6, 7, 8, 9, or 10 ring-forming atoms. As a further example, where a cycloalkyl group contains any ring-forming heteroatoms, "C$_{5-10}$ cycloalkyl" refers to a monocyclic ring or spiro, bridged or fused polycyclic ring system comprising 5, 6, 7, 8, 9, or 10 ring-forming atoms, where ring-forming atom includes both ring-forming carbon atoms and heteroatoms. Fused bicyclic or polycyclic ring systems include a fused ring system comprising a non-aromatic cycloalkyl ring fused to: (i) one or more non-aromatic cycloalkyl rings; (ii) one or more aromatic rings; (iii) one or more non-aromatic heterocycloalkyl rings; (iv) one or more heteroaromatic rings; or (v) any combination or subcombination of (i), (ii), (iii), and (iv). The point of attachment to the base molecule on a cycloalkyl group is a ring-forming carbon atom. For greater clarity, where a cycloalkyl group is a ring system, the point of attachment to the base molecule on the ring system is a ring-forming carbon atom of a non-aromatic cycloalkyl ring of the fused ring system, wherein the non-aromatic cycloalkyl ring does not contain any ring-forming heteroatoms. Non-limiting examples of cycloalkyl groups include cyclopropyl, cyclobutyl, cyclopentyl, cyclohexyl, cycloheptyl, cyclooctyl, cyclononyl, cyclodecanyl, octahydropentalenyl, octahydro-1H-indenyl, bicyclo[1.1.1]pentanyl, bicyclo[2.2.1]heptanyl, bicyclo[3.2.1]octanyl, bicyclo[5.2.0]nonanyl, adamantanyl, and decahydronaphthalenyl.

Cycloalkyl groups may be optionally substituted. Cycloalkyl groups described herein as optionally substituted may be substituted by one or more substituents, which are selected independently unless otherwise indicated. Non-limiting examples of substituents for cycloalkyl groups include halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, oxo (═O), —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl. Cycloalkyl groups may be substituted by 1, 2, 3, 4, 5, 6, 7, 8, 9, or 10 substituent(s).

As used herein, the term "heterocycloalkyl," by itself or as part of another group or substituent, refers to a non-aromatic saturated monocyclic hydrocarbon ring or a spiro, bridged or fused bicyclic or polycyclic hydrocarbon ring system, wherein the monocyclic ring contains at least one ring-forming heteroatom selected from N, O and S, or at least one ring of the spiro, bridged or fused ring system: (i) is a non-aromatic hydrocarbon ring wherein all unfused ring-forming atoms are saturated; (ii) contains at least one ring-forming heteroatom selected from N, O and S; and (iii) contains a ring-forming atom that is the point of attachment to the base molecule. The monocyclic ring or spiro, bridged or fused polycyclic ring system may contain from 1, 2, 3, 4, 5, or 6 ring-forming heteroatom(s) selected from N, O and S. The monocyclic ring or spiro, bridged or fused polycyclic ring system may contain from 5 to 14 ring-forming atoms, where ring-forming atom includes both ring-forming carbon atoms and heteroatoms. The term "x- to y-membered heterocycloalkyl" refers to a monocyclic ring or spiro, bridged or fused polycyclic ring system comprising a number from x to y (with all individual integers within the range included, including integers x and y) of ring-forming atoms. For example, a "5- to 10-membered heterocycloalkyl" refers to a monocyclic ring or spiro, bridged or fused polycyclic ring system comprising 5 to 10 ring-forming atoms. Fused bicyclic or polycyclic ring systems include a fused ring system comprising a non-aromatic heterocycloalkyl ring fused to: (i) one or more non-aromatic cycloalkyl rings; (ii) one or more aromatic rings; (iii) one or more non-aromatic heterocycloalkyl rings; (iv) one or more heteroaromatic rings; or (v) any combination or subcombination of (i), (ii), (iii), and (iv). The point of attachment to the base molecule on a heterocycloalkyl group is a ring-forming atom. For greater clarity, where a heterocycloalkyl group is a ring system, the point of attachment to the base molecule on the ring system is a ring-forming atom of a non-aromatic heterocycloalkyl ring of the fused ring system. Non-limiting examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, and 1,4-diazepanyl.

Heterocycloalkyl groups may be optionally substituted. Heterocycloalkyl groups described herein as optionally substituted may be substituted by one or more substituents, which are selected independently unless otherwise indicated. Non-limiting examples of substituents for heterocycloalkyl groups include halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, oxo (═O), —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and $R^{209}$ is $C_{1-6}$ alkyl. Heterocycloalkyl groups may be substituted by 1, 2, 3, 4, 5, 6, 7, 8, 9, or 10 substituent(s).

As used herein, the term "-alkylene(aryl)" refers to an aryl group, as defined herein, which is attached to the base compound through an alkylene linker. The term "—$C_{1-6}$ alkylene($C_{6-10}$ aryl)" refers to a $C_{6-10}$ aryl group, as defined herein, which is attached to the base compound through a $C_{1-6}$ alkylene linker. The aryl of the -alkylene(aryl) group may be optionally substituted. The aryl groups described herein as optionally substituted may be substituted by one or more substituents, which are selected independently unless otherwise indicated. Non-limiting examples of substituents for the aryl groups or alkylene groups include halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl. The aryl groups and alkylene groups may each be substituted by 1, 2, 3, 4, 5, 6, 7, 8, 9, or 10 substituent(s).

As used herein, the term "-alkylene(heteroaryl)" refers to a heteroaryl group, as defined herein, which is attached to the base compound through an alkylene linker. The term "—$C_{1-6}$ alkylene(5- to 10-membered heteroaryl)" refers to a 5- to 10-membered heteroaryl group, as defined herein, which is attached to the base compound through a $C_{1-6}$ alkylene linker. The heteroaryl of the -alkylene(heteroaryl) may be optionally substituted. The heteroaryl groups described herein as optionally substituted may be substituted by one or more substituents, which are selected independently unless otherwise indicated. Non-limiting examples of substituents for the heteroaryl groups or alkylene groups include halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, oxo (=O), —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl. The heteroaryl groups and alkylene groups may each be substituted by 1, 2, 3, 4, 5, 6, 7, 8, 9, or 10 substituent(s).

As used herein, the symbol

indicates the point at which the displayed moiety is attached to the remainder of the molecule. This is sometimes referred to as a point of attachment. A point of attachment may also be denoted by a dash symbol "-", for example, —Br.

This invention is based, at least in part, on cyclic peptides that are somatostatin receptor (SSTR) antagonists. Cyclic peptides of the present invention are often selective for a particular SSTR, such as SSTR 2.

Illustrative embodiments of the present invention include a compound having a structure of Formula II:

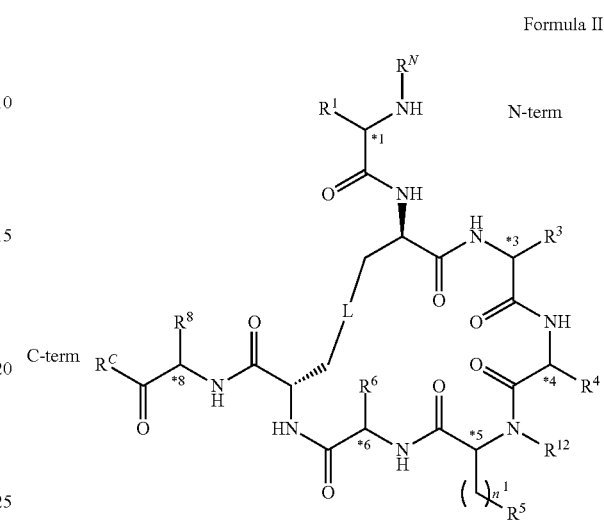

Formula II or a salt thereof, wherein:

$R^C$ is OH or $NH_2$;

$R^N$ is H, $CH_3$ or acetyl;

$R^1$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents;

$R^3$ is selected from the group consisting of:
(i) $C_{6-10}$ aryl which is optionally substituted with one or more substituents;
(ii) 5- to 10-membered heteroaryl which is optionally substituted with one or more substituents;
(iii) —$C_{1-6}$ alkylene($C_{6-10}$ aryl), wherein the $C_{6-10}$ aryl is optionally substituted with one or more substituents, and wherein the $C_{1-6}$ alkylene is optionally substituted with one or more substituents;
(iv) —$C_{1-6}$ alkylene(5- to 10-membered heteroaryl), wherein the 5- to 10-membered heteroaryl is optionally substituted with one or more substituents, and wherein the $C_{1-6}$ alkylene is optionally substituted with one or more substituents;
(v) —$NR^{27}C(O)R^{28}$ or —$C_{1-6}$ alkylene-$NR^{27}C(O)R^{28}$, wherein:
$R^{27}$ is H or $C_{1-6}$ alkyl;
$R^{28}$ is selected from the group consisting of $C_{1-6}$ alkyl, $C_{6-10}$ aryl, 5- to 10-membered heteroaryl, and —$NR^{29}R^{30}$, wherein the $C_{1-6}$ alkyl is optionally substituted with one or more substituents, and wherein the $C_{6-10}$ aryl and 5- to 10-membered heteroaryl are optionally substituted with one or more substituents; and wherein each of $R^{29}$ and $R^{30}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vi) —($C_{6-10}$ arylene)-C(O)$NR^{31}R^{32}$ or —$C_{1-6}$ alkylene-($C_{6-10}$ arylene)-C(O)$NR^{31}R^{32}$, wherein each of $R^{31}$ and $R^{32}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vii) —($C_{6-10}$ arylene)-$NR^{33}R^{34}$ or —$C_{1-6}$ alkylene-($C_{6-10}$ arylene)-$NR^{33}R^{34}$, wherein:
  each of $R^{33}$ and $R^{34}$ is independently selected from the group consisting of H, $C_{1-6}$ alkyl, $C_{6-10}$ aryl, 5- to 10-membered heteroaryl, —C(O)$R^{35}$, —C(O)$NR^{36}R^{37}$, and —$SO_2R^{38}$, wherein the $C_{1-6}$ alkyl is optionally substituted with one or more substituents, and wherein the $C_{6-10}$ aryl and 5- to 10-membered heteroaryl are optionally substituted with one or more substituents;
  $R^{35}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents;
  each of $R^{36}$ and $R^{37}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
  $R^{38}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-$SO_2NR^{39}R^{40}$ or —$C_{1-6}$ alkylene-($C_{6-10}$ arylene)-$SO_2NR^{39}R^{40}$, wherein each of $R^{39}$ and $R^{40}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-($C_{1-6}$ alkylene)-$NR^{41}R^{42}$ or —$C_{1-6}$ alkylene-($C_{6-10}$ arylene)-($C_{1-6}$ alkylene)-$NR^{41}R^{42}$, wherein:
  each of $R^{41}$ and $R^{42}$ is independently selected from the group consisting of H, $C_{1-6}$ alkyl, $C_{6-10}$ aryl, 5- to 10-membered heteroaryl, —C(O)$R^{43}$, and —C(O)$NR^{44}R^{45}$, wherein the $C_{1-6}$ alkyl is optionally substituted with one or more substituents, and wherein the $C_{6-10}$ aryl and 5- to 10-membered heteroaryl are optionally substituted with one or more substituents;
  $R^{43}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{47}$)—C(O)—$CHR^{48}$—$NR^{49}R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and each of $R^{49}$ and $R^{50}$ is independently H, $CH_3$ or acetyl;

$R^4$ is selected from the group consisting of:
(i) —N($R^{53}$)C(O)$NR^{51}R^{52}$ or —$C_{1-6}$ alkylene-N($R^{53}$)C(O)$NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl;

(ii) —N($R^{55}$)C(O)$R^{54}$ or —$C_{1-6}$ alkylene-N($R^{55}$)C(O)$R^{54}$, wherein $R^{54}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl;

(iii) —($C_{6-10}$ arylene)-C(O)$NR^{56}R^{57}$ or —$C_{1-6}$ alkylene-($C_{6-10}$ arylene)-C(O)$NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —($C_{6-10}$ arylene)-N($R^{59}$)C(O)$R^{58}$ or —$C_{1-6}$ alkylene-($C_{6-10}$ arylene)-N($R^{59}$)C(O)$R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl;

(v) —($C_{6-10}$ arylene)-N($R^{62}$)C(O)$NR^{60}R^{61}$ or —$C_{1-6}$ alkylene-($C_{6-10}$ arylene)-N($R^{62}$)C(O)$NR^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl;

(vi) —($C_{6-10}$ arylene)-N($R^{64}$)$SO_2R^{63}$ or —$C_{1-6}$ alkylene-($C_{6-10}$ arylene)-N($R^{64}$)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl;

(vii) —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-($C_{1-6}$ alkylene)-$NR^{67}R^{68}$ or —$C_{1-6}$ alkylene-($C_{6-10}$ arylene)-($C_{1-6}$ alkylene)-$NR^{67}R^{68}$, wherein:
each of $R^{67}$ and $R^{68}$ is independently selected from the group consisting of H, $C_{1-6}$ alkyl, $C_{6-10}$ aryl, 5- to 10-membered heteroaryl, —C(O)$R^{69}$, and —C(O)$NR^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents;
$R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-$NR^{72}R^{73}$ or —$C_{1-6}$ alkylene-($C_{6-10}$ arylene)-$NR^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{74}$ or —$C_{1-6}$ alkylene-($C_{6-10}$ arylene)-$OR^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{75}$)—C(O)—$CHR^{76}$—$NR^{77}R^{78}$, wherein $R^{75}$ is H or $CH_3$, $R^{76}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and each of $R^{77}$ and $R^{78}$ is independently H, $CH_3$ or acetyl;

$R^5$ is selected from the group consisting of:
(i) —$NR^{79}R^{80}$, wherein each of $R^{79}$ and $R^{80}$ is independently selected from the group consisting of H, $C_{1-6}$ alkyl, —C(O)$R^{81}$, and —C(=$NR^{82}$)$NR^{83}R^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents,
$R^{81}$ is selected from the group consisting of H, —$NH_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl; and (ii) —$N^+R^{85}R^{86}R^{87}$, wherein each of $R^{85}$, $R^{86}$, and $R^{87}$ is independently $C_{1-6}$ alkyl; $n^1$ is 1, 2, 3, 4, 5, or 6; $R^{12}$ is H or $CH_3$; $R^6$ is $C_{1-6}$ alkyl optionally substituted with one or more substituents; $R^8$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents; and L is selected from the group consisting of:

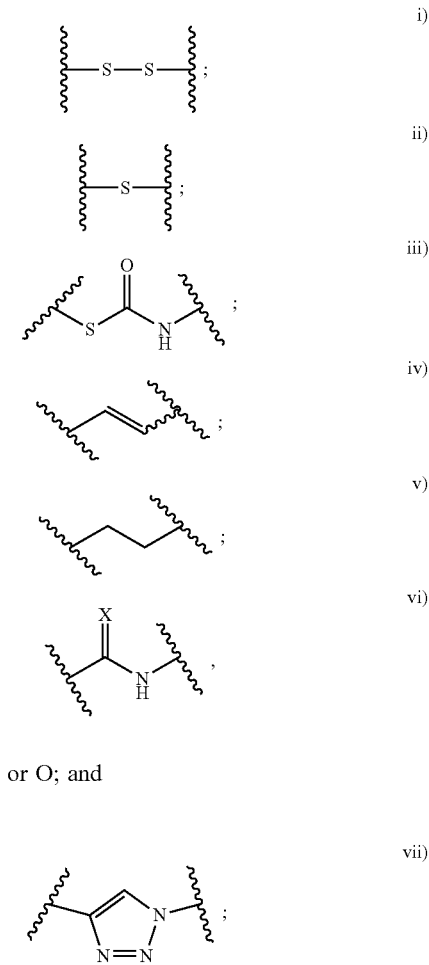

wherein X is S or O; and chiral centre *1 is in the S configuration or the R configuration; chiral centre *3 is in the S configuration or the R configuration; chiral centre *4 is in the S configuration or the R configuration; chiral centre *5 is in the S configuration; chiral centre *6 is in the S configuration or the R configuration; and chiral centre *8 is in the S configuration or the R configuration, provided that:
when L is

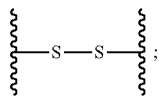

$R^4$ is —$CH_2$-(phenylene)-N(H)C(O)$NH_2$; $R^3$ is —$CH_2$-(phenyl) or —$CH_2$-(phenylene)-N(H)C(O)$R^{35}$, wherein the phenyl of —$CH_2$-(phenyl) is substituted with hydroxy and wherein $R^{35}$ is 2,6-dioxohexahydropyrimidine; $R^5$ is $NH_2$; $n^1$ is 4; $R^{12}$ is H; $R^6$ is —CH(OH)($CH_3$); and $R^8$ is —$CH_2$-(phenyl) or —$CH_2$-(napthyl), wherein the phenyl is substituted with hydroxy,
then $R^1$ is not —$CH_2$-(phenyl), wherein the phenyl is substituted with —Cl or —$NO_2$.

In accordance with another embodiment, there is provided a compound having a structure of Formula II or a salt thereof, wherein each of $R^N$, $R^C$, $R^1$, $R^3$, $R^4$, $R^5$, $R^6$, $R^8$, $R^{12}$, $n^1$, L, chiral centre *1, chiral centre *3, chiral centre *4, chiral centre *5, chiral centre *6, and chiral centre *8 is as defined anywhere herein provided that the compound is not: (i) H-Cpa-cyclo[DCys-Tyr-D-4Aph(Cbm)-Lys-Thr-Cys]-2Nal-$NH_2$; (ii) H-Cpa-cyclo[DCys-Tyr-D-4Aph(Cbm)-Lys-Thr-Cys]-D-Tyr-$NH_2$; (iii) H-p$NO_2$-Phe-cyclo[DCys-Tyr-D-4Aph(Cbm)-Lys-Thr-Cys]-2Nal-$NH_2$; (iv) H-Cpa-cyclo[DCys-4Aph(Hor)-D-4Aph(Cbm)-Lys-Thr-Cys]-D-Tyr-$NH_2$; (v) H-p$NO_2$-Phe-cyclo[DCys-Tyr-D-4Aph(Cbm)-Lys-Thr-Cys]-D-Tyr-$NH_2$; (vi) H-p$NO_2$-Phe-cyclo[DCys-4Aph(Hor)-D-4Aph(Cbm)-Lys-Thr-Cys]-D-Tyr-$NH_2$; (vii) H-Cpa-cyclo[DCys-4Aph(Hor)-D-4Aph(Cbm)-Lys-Thr-Cys]-2Nal-$NH_2$; and (viii) H-p$NO_2$-Phe-cyclo[DCys-4Aph(Hor)-D-4Aph(Cbm)-Lys-Thr-Cys]-2Nal-$NH_2$, wherein DCys and Cys of each of (i), (ii), (iii), (iv), (v), (vi), (vii) and (viii) are linked by

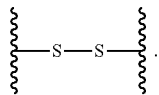 [SMILES: *SS*]

Embodiments of $R^C$ and $R^N$
In some embodiments, $R^C$ is OH or $NHR^{16}$, wherein $R^{16}$ is H or $C_{1-6}$ alkyl optionally substituted with one or more substituents. In other embodiments, $R^C$ is OH or $NHR^{16}$, wherein $R^{16}$ is H or $C_{1-6}$ alkyl optionally substituted with one or more substituents each independently selected from the group consisting of halogen, —OH, —$NO_2$, $C_{1-6}$ alkoxy, and $C_{6-10}$ aryl. In some embodiments, $R^C$ is OH or $NHR^{16}$, wherein $R^{16}$ is H or $C_{1-6}$ alkyl optionally substituted with one or more substituents each independently selected from the group consisting of halogen, —OH, —$NO_2$, and $C_{1-6}$ alkoxy. In some embodiments, $R^C$ is OH or $NHR^{16}$, wherein $R^{16}$ is H or $C_{1-6}$ alkyl. In some embodiments, $R^C$ is OH or $NHR^{16}$, wherein $R^{16}$ is H or $C_{1-5}$ alkyl. In some embodiments, $R^C$ is OH or $NHR^{16}$, wherein $R^{16}$ is H or $C_{1-4}$ alkyl. In some embodiments, $R^C$ is OH or $NHR^{16}$, wherein $R^{16}$ is H or $C_{1-3}$ alkyl. In some embodiments, $R^C$ is OH or $NHR^{16}$, wherein $R^{16}$ is H or $C_{1-2}$ alkyl. In some embodiments, $R^C$ is OH or $NHR^{16}$, wherein $R^{16}$ is H or $CH_3$. In some embodiments, $R^C$ is OH or $NH_2$. In other embodiments, $R^C$ is OH. In other embodiments, $R^C$ is $NH_2$.

In some embodiments, $R^N$ is selected from the group consisting of:
(i) H;
(ii) $C_{1-6}$ alkyl;
(iii) —C(O)$R^{17}$, wherein $R^{17}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
(iv) —C(O)$C_{1-6}$ alkylene-C(O)O$R^{18}$, wherein $R^{18}$ is H or $C_{1-6}$ alkyl optionally substituted with one or more substituents;
(v) —C(O)$C_{1-6}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{20}$ is H or $C_{1-6}$ alkyl;
(vi) —C(O)$C_{1-6}$ alkylene-N$R^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
(vii) —C(O)$C_{1-6}$ alkylene-C(O)N$R^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
(viii) —C(O)$C_{1-6}$ alkylene-S(O)$_2R^{25}$, wherein $R^{25}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
(ix) —S(O)$_2R^{26}$, wherein $R^{26}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents.

In other embodiments, $R^N$ is selected from the group consisting of:
(i) H;
(ii) $C_{1-6}$ alkyl;
(iii) —C(O)$R^{17}$, wherein $R^{17}$ is selected from the group consisting of $C_{1-6}$ alkyl, $C_{6-10}$ aryl, and 5- to 10-membered heteroaryl;
(iv) —C(O)$C_{1-6}$ alkylene-C(O)O$R^{18}$, wherein $R^{18}$ is H or $C_{1-6}$ alkyl;
(v) —C(O)$C_{1-6}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl;

(vi) —C(O)C$_{1-6}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl;

(vii) —C(O)C$_{1-6}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl;

(viii) —C(O)C$_{1-6}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl; and (ix) —S(O)$_2$R$^{26}$, wherein R$^{26}$ is selected from the group consisting of C$_{1-6}$ alkyl, C$_{6-10}$ aryl, and 5- to 10-membered heteroaryl.

In some embodiments, R$^N$ is selected from the group consisting of:

(i) H;

(ii) C$_{1-6}$ alkyl;

(iii) —C(O)R$^{17}$, wherein R$^{17}$ is selected from the group consisting of C$_{1-6}$ alkyl, C$_{6-10}$ aryl, and 5- to 10-membered heteroaryl;

(iv) —C(O)C$_{1-3}$ alkylene-C(O)OR$^{18}$, wherein R$^{18}$ is H or C$_{1-6}$ alkyl;

(v) —C(O)C$_{1-3}$ alkylene-N(R$^{20}$)C(O)R$^{19}$, wherein R$^{19}$ is selected from the group consisting of C$_{1-6}$ alkyl, C$_{6-10}$ aryl, and 5- to 10-membered heteroaryl, and wherein R$^{20}$ is H or C$_{1-6}$ alkyl;

(vi) —C(O)C$_{1-3}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl;

(vii) —C(O)C$_{1-3}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl; and (viii) —C(O)C$_{1-3}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl.

In other embodiments, R$^N$ is selected from the group consisting of H, C$_{1-6}$ alkyl, —C(O)R$^{17}$, —C(O)C$_{1-6}$ alkylene-C(O)OR$^{18}$, —C(O)C$_{1-6}$ alkylene-N(R$^{20}$)C(O)R$^{19}$, —C(O)C$_{1-6}$ alkylene-NR$^{21}$R$^{22}$, —C(O)C$_{1-6}$ alkylene-C(O)NR$^{23}$R$^{24}$, and —C(O)C$_{1-6}$ alkylene-S(O)$_2$R$^{25}$, wherein R$^{17}$ is C$_{1-6}$ alkyl or 5- to 6-membered heteroaryl, R$^{18}$ is C$_{1-6}$ alkyl, R$^{19}$ is C$_{1-6}$ alkyl or C$_6$ aryl, each of R$^{20}$, R$^{21}$, R$^{22}$, R$^{23}$ and R$^{24}$ is H, and R$^{25}$ is C$_6$ aryl. In some embodiments, R$^N$ is selected from the group consisting of H, C$_{1-3}$ alkyl, —C(O)R$^{17}$, —C(O)C$_{1-3}$ alkylene-C(O)OR$^{18}$, —C(O)C$_{1-3}$ alkylene-N(R$^{20}$)C(O)R$^{19}$, —C(O)C$_{1-3}$ alkylene-NR$^{21}$R$^{22}$, —C(O)C$_{1-3}$ alkylene-C(O)NR$^{23}$R$^{24}$, and —C(O)C$_{1-3}$ alkylene-S(O)$_2$R$^{25}$, wherein R$^{17}$ is C$_{1-6}$ alkyl or 5- to 6-membered heteroaryl, R$^{18}$ is C$_{1-3}$ alkyl, R$^{19}$ is C$_{1-3}$ alkyl or C$_6$ aryl, each of R$^{20}$, R$^{21}$, R$^{22}$, R$^{23}$ and R$^{24}$ is H, and R$^{25}$ is C$_6$ aryl. In some embodiments, R$^N$ is H, CH$_3$ or acetyl. In some embodiments, R$^N$ is H or CH$_3$. In other embodiments, R$^N$ is H or acetyl. In other embodiments, R$^N$ is CH$_3$ or acetyl. In some embodiments, R$^N$ is H. In other embodiments, R$^N$ is CH$_3$. In still other embodiments, R$^N$ is acetyl.

Those of ordinary skill in the art will appreciate that the cyclic octa-peptides of the instant invention may be functionalized either at the C- or N-terminus by methods known in the art. For example, two methods of functionalization include PEGylation and lipidation (Beilstien J. Org. Chem. 2014, 10, 1197-1212). Functionalized peptides of this nature are also contemplated within the scope of the instant invention. For example, in some embodiments, R$^C$ is —N(H)[CH$_2$CH$_2$O]$_n^{16}$—R$^{210}$, wherein R$^{210}$ may be H or C$_{1-6}$ alkyl.

A person of skill in the art is readily able to ascertain a suitable range of values for n$^{16}$ in the above-referenced formulae for PEG. For example, and without limitation, n$^{16}$ may be an integer from 1 to 40. In some embodiments, R$^N$ is —C(O)—[CH$_2$]$^{17}$—O—[CH$_2$CH$_2$O]$_n^{18}$—R$^{211}$, wherein R$^{211}$ may be H or C$_{1-6}$ alkyl and n$^{17}$ may be an integer from 1 to 6. In another embodiment, n$^{17}$ may be 1 or 2. In some embodiments, R$^N$ is —C(O)—[CH$_2$CH$_2$O]$_n^{19}$—R$^{211}$, wherein R$^{211}$ may be H or C$_{1-6}$ alkyl. In another embodiment, R$^N$ is —[CH$_2$]$_n^{20}$—O—[CH$_2$CH$_2$O]$_n^{21}$—R$^{212}$, wherein R$^{212}$ may be H or C$_{1-6}$ alkyl and n$^{20}$ may be an integer from 1 to 6. In other embodiments, n$^{20}$ may be 3. In some embodiments, R$^N$ is —[CH$_2$CH$_2$O]$_n^{22}$—R$^{212}$, wherein R$^{212}$ may be H or C$_{1-6}$ alkyl. A person of skill in the art is readily able to ascertain a suitable range of values for n$^{18}$, n$^{19}$, n$^{21}$, and n$^{22}$ in the above-referenced formulae for PEG. For example, and without limitation, each of n$^{18}$, n$^{19}$, n$^{21}$, and n$^{22}$ may independently be an integer from 1 to 40.

Embodiments of R$^1$

In some embodiments, R$^1$ is selected from the group consisting of C$_{1-6}$ alkyl, C$_{6-10}$ aryl, 5- to 10-membered heteroaryl, —C$_{1-6}$ alkylene(C$_{6-10}$ aryl) and —C$_{1-6}$ alkylene (5- to 10-membered heteroaryl), wherein the C$_{1-6}$ alkyl, the C$_{6-10}$ aryl, the C$_{6-10}$ aryl of —C$_{1-6}$ alkylene(C$_{6-10}$ aryl), the 5- to 10-membered heteroaryl and the 5- to 10-membered heteroaryl of —C$_{1-6}$ alkylene(5- to 10-membered heteroaryl) are optionally substituted with one or more substituents, and wherein the C$_{1-6}$ alkylene of —C$_{1-6}$ alkylene (C$_{6-10}$ aryl) and —C$_{1-6}$ alkylene(5- to 10-membered heteroaryl) is optionally substituted with one or more substituents.

In some embodiments, R$^1$ is selected from the group consisting of C$_{1-6}$ alkyl, C$_{6-10}$ aryl, 5- to 10-membered heteroaryl, —C$_{1-6}$ alkylene(C$_{6-10}$ aryl) and —C$_{1-6}$ alkylene (5- to 10-membered heteroaryl), wherein the C$_{1-6}$ alkyl, the C$_{6-10}$ aryl, the C$_{6-10}$ aryl of —C$_{1-6}$ alkylene(C$_{6-10}$ aryl), the 5- to 10-membered heteroaryl and the 5- to 10-membered heteroaryl of —C$_{1-6}$ alkylene(5- to 10-membered heteroaryl) are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{1-6}$ alkylene of —C$_{1-6}$ alkylene(C$_{6-10}$ aryl) and —C$_{1-6}$ alkylene(5- to 10-membered heteroaryl) is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, $R^1$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene (5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, and $C_{1-6}$ alkoxy, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, $C_{1-6}$ alkoxy, and $C_{6-10}$ aryl.

In some embodiments, $R^1$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents.

In some embodiments, $R^1$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl.

In some embodiments, $R^1$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, and $C_{1-6}$ alkoxy, and wherein the $C_{1-6}$ alkylene of —$C_{1-6}$ alkylene($C_{6-10}$ aryl) and —$C_{1-6}$ alkylene (5- to 10-membered heteroaryl) is optionally substituted with one or more substituents each independently selected from the group consisting of halogen, —OH, —$NO_2$, $C_{1-6}$ alkoxy, and $C_{6-10}$ aryl.

In some embodiments, $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy, and wherein the $C_{1-3}$ alkylene is optionally substituted with one or more substituents each independently selected from the group consisting of $C_{6-10}$ aryl. In some embodiments, $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy. In other embodiments, $R^1$ is —$C_{1-3}$ alkylene(5- to 10-membered heteroaryl), wherein the 5- to 10-membered heteroaryl is optionally substituted with one or more substituents each independently selected from the group consisting of halogen, hydroxy, —$NO_2$, and $C_{1-6}$ alkoxy. In some embodiments, $R^1$ is —$C_{1-2}$ alkylene(6-membered heteroaryl), wherein the 6-membered heteroaryl is optionally substituted with one or more substituents each independently selected from the group consisting of halogen, hydroxy, —$NO_2$, and $C_{1-6}$ alkoxy.

In some embodiments, $R^1$ is —$C_{1-2}$ alkylene($C_{6-10}$ aryl), wherein the $C_{6-10}$ aryl is optionally substituted with one or more substituents each independently selected from the group consisting of halogen, hydroxyl, —$NO_2$, and $C_{1-6}$ alkoxy. In some embodiments, $R^1$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$. In some embodiments, $R^1$ is —$C_{1-2}$ alkylene($C_{6-10}$ aryl), wherein the $C_{6-10}$ aryl is optionally substituted with one or more substituents each independently selected from the group consisting of halogen and hydroxy. In some embodiments, $R^1$ is —$C_{1-2}$ alkylene($C_{6-10}$ aryl), wherein the $C_{6-10}$ aryl is optionally substituted with halogen. In some embodiments, $R^1$ is —$C_{1-2}$ alkylene($C_{6-10}$ aryl), wherein the $C_{6-10}$ aryl is optionally substituted with Cl. In some embodiments, $R^1$ is —$C_{1-2}$ alkylene($C_6$ aryl), wherein the $C_6$ aryl is optionally substituted with one or more substituents each independently selected from the group consisting of halogen, hydroxy, —$NO_2$, and $C_{1-6}$ alkoxy.

In some embodiments, $R^1$ is —$CH_2$-phenyl or —$CH_2$-naphthyl, wherein phenyl or naphthyl may be optionally substituted with 1 or 2 substituents each independently selected from the group consisting of halogen, hydroxy, —$NO_2$, and $C_{1-6}$ alkoxy. In other embodiments, $R^1$ is —$CH_2$-phenyl or —$CH_2$-naphthyl, wherein the phenyl is optionally substituted with one or more substituents each independently selected from the group consisting of halogen, hydroxyl, and —$NO_2$. In some embodiments, $R^1$ is —$CH_2$-phenyl or —$CH_2$-naphthyl, wherein the phenyl is optionally substituted with one or more substituents each independently selected from the group consisting of halogen and hydroxyl. In some embodiments, $R^1$ is —$CH_2$-phenyl or —$CH_2$-naphthyl, wherein the phenyl is optionally substituted with halogen. In some embodiments, $R^1$ is —$CH_2$-phenyl or —$CH_2$-naphthyl, wherein the phenyl is optionally substituted with Cl.

In some embodiments, $R^1$ is —CH$_2$-phenyl, wherein phenyl may be optionally substituted with 1 or 2 substituents each independently selected from the group consisting of halogen, hydroxy, —NO$_2$, and C$_{1-6}$ alkoxy. In some embodiments, $R^1$ is —CH$_2$-phenyl, wherein phenyl may be optionally substituted with 1 or 2 substituents each independently selected from the group consisting of halogen, hydroxy, and —NO$_2$. In some embodiments, $R^1$ is —CH$_2$-phenyl, wherein phenyl is unsubstituted. In some embodiments, $R^1$ is —CH$_2$-phenyl, wherein phenyl is substituted with 1 or 2 substituents each independently selected from the group consisting of halogen, hydroxy, —NO$_2$, and C$_{1-6}$ alkoxy. In some embodiments, $R^1$ is —CH$_2$-phenyl, wherein phenyl is substituted with 1 or 2 substituents each independently selected from the group consisting of halogen, hydroxy, and —NO$_2$. In some embodiments, $R^1$ is —CH$_2$-phenyl, wherein phenyl is substituted with 1 or 2 substituents each independently selected from the group consisting of halogen and hydroxy.

In some embodiments, $R^1$ is —CH$_2$-phenyl, wherein phenyl is substituted with 1 or 2 substituents each independently selected from the group consisting of —F, —Cl, —Br, and —I. In some embodiments, $R^1$ is —CH$_2$-phenyl, wherein phenyl is substituted with 1 or 2 substituents each of which is —F. In some embodiments, $R^1$ is —CH$_2$-phenyl, wherein phenyl is substituted with 1 or 2 substituents each of which is —Cl. In some embodiments, $R^1$ is —CH$_2$-phenyl, wherein phenyl is substituted with 1 or 2 substituents each of which is —Br. In some embodiments, $R^1$ is —CH$_2$-phenyl, wherein phenyl is substituted with 1 or 2 substituents each of which is —I. In some embodiments, $R^1$ is —CH$_2$-phenyl, wherein phenyl is substituted with 1 substituent which is —F. In some embodiments, $R^1$ is —CH$_2$-phenyl, wherein phenyl is substituted with 1 substituent which is —Cl. In some embodiments, $R^1$ is —CH$_2$-phenyl, wherein phenyl is substituted with 1 substituent which is —Br. In some embodiments, $R^1$ is —CH$_2$-phenyl, wherein phenyl is substituted with 1 substituent which is —I.

In some embodiments, $R^1$ is —CH$_2$-phenyl, wherein phenyl is substituted with 1 or 2 substituents each of which is hydroxy. In some embodiments, $R^1$ is —CH$_2$-phenyl, wherein phenyl is substituted with 1 substituent which is hydroxy. In some embodiments, $R^1$ is —CH$_2$-phenyl, wherein phenyl is substituted with 1 or 2 substituents each of which is —NO$_2$. In some embodiments, $R^1$ is —CH$_2$-phenyl, wherein phenyl is substituted with 1 substituent which is —NO$_2$. In some embodiments, $R^1$ is —CH$_2$-phenyl, wherein phenyl is substituted with 1 or 2 substituents each of which is independently C$_{1-6}$ alkoxy. In some embodiments, $R^1$ is —CH$_2$-phenyl, wherein phenyl is substituted with 1 or 2 substituents each of which is independently C$_{1-3}$ alkoxy. In some embodiments, $R^1$ is —CH$_2$-phenyl, wherein phenyl is substituted with 1 substituent which is methoxy.

In some embodiments, $R^1$ is

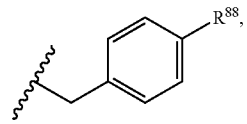

wherein $R^{88}$ is H, halogen, hydroxyl or C$_{1-3}$ alkoxy. In some embodiments, $R^{88}$ is H, halogen or hydroxyl. In some embodiments, $R^{88}$ is H, Cl or hydroxyl. In some embodiments, $R^{88}$ is Cl or hydroxyl. In some embodiments, $R^{88}$ is Cl.

In some embodiments, $R^1$ is —C$_{1-2}$ alkylene(C$_{10}$ aryl), wherein the C$_{10}$ aryl is optionally substituted with one or more substituents each independently selected from the group consisting of halogen, hydroxyl and —NO$_2$, and C$_{1-6}$ alkoxy. In some embodiments, $R^1$ is —CH$_2$-naphthyl.

In some embodiments, $R^1$ is selected from the group consisting of —CH$_2$-pyridinyl, —CH$_2$-indolyl, —CH$_2$-thiophenyl, —CH$_2$-thiazolyl, —CH$_2$-furanyl, —CH$_2$-benzothiophenyl, and —CH$_2$-imidazolyl. In some embodiments, $R^1$ is —CH$_2$-pyridinyl. In some embodiments, $R^1$ is —CH$_2$-indolyl. In some embodiments, $R^1$ is —CH$_2$-thiophenyl. In some embodiments, $R^1$ is —CH$_2$-thiazolyl. In some embodiments, $R^1$ is —CH$_2$-furanyl. In some embodiments, $R^1$ is —CH$_2$-benzothiophenyl. In some embodiments, $R^1$ is —CH$_2$-imidazolyl.

Embodiments of $R^3$

In some embodiments, $R^3$ is selected from the group consisting of:
  (i) C$_{6-10}$ aryl which is optionally substituted with one or more substituents;
  (ii) 5- to 10-membered heteroaryl which is optionally substituted with one or more substituents;
  (iii) —C$_{1-6}$ alkylene(C$_{6-10}$ aryl), wherein the C$_{6-10}$ aryl is optionally substituted with one or more substituents, and wherein the C$_{1-6}$ alkylene is optionally substituted with one or more substituents;
  (iv) —C$_{1-6}$ alkylene(5- to 10-membered heteroaryl), wherein the 5- to 10-membered heteroaryl is optionally substituted with one or more substituents, and wherein the C$_{1-6}$ alkylene is optionally substituted with one or more substituents;
  (v) —C$_{1-6}$ alkylene-N(R$^{27}$)C(O)R$^{28}$, wherein:
    $R^{27}$ is H or C$_{1-6}$ alkyl;
    $R^{28}$ is selected from the group consisting of C$_{1-6}$ alkyl, C$_{6-10}$ aryl, 5- to 10-membered heteroaryl, and —NR$^{29}$R$^{30}$, wherein the C$_{1-6}$ alkyl is optionally substituted with one or more substituents, and wherein the C$_{6-10}$ aryl and 5- to 10-membered heteroaryl are optionally substituted with one or more substituents; and
    each of $R^{29}$ and $R^{30}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
  (vi) —(C$_{6-10}$ arylene)-C(O)NR$^{31}$R$^{32}$ or —C$_{1-6}$ alkylene-(C$_{6-10}$ arylene)-C(O)NR$^{31}$R$^{32}$, wherein each of $R^{31}$ and $R^{32}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;
  (vii) —(C$_{6-10}$ arylene)-NR$^{33}$R$^{34}$ or —C$_{1-6}$ alkylene-(C$_{6-10}$ arylene)-NR$^{33}$R$^{34}$, wherein:
    each of $R^{33}$ and $R^{34}$ is independently selected from the group consisting of H, C$_{1-6}$ alkyl, C$_{6-10}$ aryl, 5- to 10-membered heteroaryl, —C(O)R$^{35}$, —C(O)NR$^{36}$R$^{37}$, and —SO$_2$R$^{38}$, wherein the C$_{1-6}$ alkyl is optionally substituted with one or more substituents, and wherein the $C_{6-10}$ aryl and 5- to 10-membered heteroaryl are optionally substituted with one or more substituents;

$R^{35}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents;

each of $R^{36}$ and $R^{37}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and $R^{38}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-$SO_2NR^{39}R^{40}$ or —$C_{1-6}$ alkylene-($C_{6-10}$ arylene)-$SO_2NR^{39}R^{40}$, wherein each of $R^{39}$ and $R^{40}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-($C_{1-6}$ alkylene)-$NR^{41}R^{42}$ or —$C_{1-6}$ alkylene-($C_{6-10}$ arylene)-($C_{1-6}$ alkylene)-$NR^{41}R^{42}$, wherein:

each of $R^{41}$ and $R^{42}$ is independently selected from the group consisting of H, $C_{1-6}$ alkyl, $C_{6-10}$ aryl, 5- to 10-membered heteroaryl, —C(O)$R^{43}$, and —C(O)$NR^{44}R^{45}$, wherein the $C_{1-6}$ alkyl is optionally substituted with one or more substituents, and wherein the $C_{6-10}$ aryl and 5- to 10-membered heteroaryl are optionally substituted with one or more substituents;

$R^{43}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{47}$)—C(O)—CHR$^{48}$—NR$^{49}R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and each of $R^{49}$ and $R^{50}$ is independently H, $CH_3$ or acetyl.

In other embodiments, $R^3$ is selected from the group consisting of:

(i) $C_{6-10}$ aryl which is optionally substituted with one or more substituents;

(ii) 5- to 10-membered heteroaryl which is optionally substituted with one or more substituents;

(iii) —$C_{1-6}$ alkylene($C_{6-10}$ aryl), wherein the $C_{6-10}$ aryl is optionally substituted with one or more substituents, and wherein the $C_{1-6}$ alkylene is optionally substituted with one or more substituents;

(iv) —$C_{1-6}$ alkylene(5- to 10-membered heteroaryl), wherein the 5- to 10-membered heteroaryl is optionally substituted with one or more substituents, and wherein the $C_{1-6}$ alkylene is optionally substituted with one or more substituents;

(v) —$C_{1-6}$ alkylene-N(H)C(O)$R^{28}$, wherein:

$R^{28}$ is selected from the group consisting of $C_{1-6}$ alkyl, $C_{6-10}$ aryl, 5- to 10-membered heteroaryl, and —$NR^{29}R^{30}$, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{29}$ and $R^{30}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vi) —($C_{6-10}$ arylene)-C(O)$NR^{31}R^{32}$ or —$C_{1-6}$ alkylene-($C_{6-10}$ arylene)-C(O)$NR^{31}R^{32}$, wherein each of $R^{31}$ and $R^{32}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vii) —($C_{6-10}$ arylene)-$NR^{33}R^{34}$ or —$C_{1-6}$ alkylene-($C_{6-10}$ arylene)-$NR^{33}R^{34}$, wherein:

each of $R^{33}$ and $R^{34}$ is independently selected from the group consisting of H, $C_{1-6}$ alkyl, $C_{6-10}$ aryl, 5- to 10-membered heteroaryl, —C(O)$R^{35}$, —C(O)$NR^{36}R^{37}$, and —$SO_2R^{38}$, wherein the $C_{1-6}$ alkyl is optionally substituted with one or more substituents, and wherein the $C_{6-10}$ aryl and 5- to 10-membered heteroaryl are optionally substituted with one or more substituents;

$R^{35}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents;

each of $R^{36}$ and $R^{37}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and $R^{38}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-$SO_2NR^{39}R^{40}$ or —$C_{1-6}$ alkylene-($C_{6-10}$ arylene)-$SO_2NR^{39}R^{40}$, wherein each of $R^{39}$ and $R^{40}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-($C_{1-6}$ alkylene)-$NR^{41}R^{42}$ or —$C_{1-6}$ alkylene-($C_{1-10}$ arylene)-($C_{1-6}$ alkylene)-$NR^{41}R^{42}$, wherein:
  each of $R^{41}$ and $R^{42}$ is independently selected from the group consisting of H, $C_{1-6}$ alkyl, $C_{6-10}$ aryl, 5- to 10-membered heteroaryl, —C(O)$R^{43}$, and —C(O)NR^{44}R^{45}$, wherein the $C_{1-6}$ alkyl is optionally substituted with one or more substituents, and wherein the $C_{6-10}$ aryl and 5- to 10-membered heteroaryl are optionally substituted with one or more substituents;
  $R^{43}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
  each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{47}$)—C(O)—$CHR^{48}$—N(H)$R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{50}$ is H, $CH_3$ or acetyl.

In some embodiments, $R^3$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents.

In some embodiments, $R^3$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl.

In some embodiments, $R^3$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, and $C_{1-6}$ alkoxy, and wherein the $C_{1-6}$ alkylene of —$C_{1-6}$ alkylene($C_{6-10}$ aryl) and —$C_{1-6}$ alkylene (5- to 10-membered heteroaryl) is optionally substituted with one or more substituents each independently selected from the group consisting of halogen, —OH, —$NO_2$, $C_{1-6}$ alkoxy, and $C_{6-10}$ aryl.

In some embodiments, $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy, and wherein the $C_{1-3}$ alkylene is optionally substituted with one or more substituents each independently selected from the group consisting of $C_{6-10}$ aryl. In some embodiments, $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy.

In some embodiments, $R^3$ is selected from the group consisting of —$C_{1-2}$ alkylene($C_{6-10}$ aryl) and —$C_{1-2}$ alkylene(5- to 10-membered heteroaryl), wherein the $C_{6-10}$ aryl and the 5- to 10-membered heteroaryl are optionally substituted with one or more substituents each independently selected from the group consisting of halogen, hydroxy, —$NO_2$, and $C_{1-6}$ alkoxy, and wherein the $C_{1-2}$ alkylene of —$C_{1-2}$ alkylene($C_{6-10}$ aryl) and —$C_{1-2}$ alkylene (5- to 10-membered heteroaryl) is optionally substituted with one or more substituents each independently selected from the group consisting of halogen, hydroxy, —$NO_2$, $C_{1-6}$ alkoxy, and $C_{6-10}$ aryl.

In other embodiments, $R^3$ is —$C_{1-2}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy, and wherein the $C_{1-2}$ alkylene is optionally substituted with one or more substituents each independently selected from the group consisting of halogen, hydroxy, —$NO_2$, $C_{1-6}$ alkoxy, and $C_{6-10}$ aryl.

In some embodiments, $R^3$ is —$C_{1-2}$ alkylene($C_{6-10}$ aryl), wherein the $C_{6-10}$ aryl is optionally substituted with one or more substituents each independently selected from the group consisting of halogen, hydroxyl, —$NO_2$, and $C_{1-6}$ alkoxy. In some embodiments, $R^3$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$. In some embodiments, $R^3$ is —$C_{1-2}$ alkylene($C_{6-10}$ aryl), wherein the $C_{6-10}$ aryl is optionally substituted with one or more substituents each independently selected from the group consisting of halogen and hydroxy. In some embodiments, $R^3$ is —$C_{1-2}$ alkylene($C_{6-10}$ aryl), wherein the $C_{6-10}$ aryl is optionally substituted with hydroxy.

In some embodiments, $R^3$ is —$CH_2$-phenyl or —$CH_2$-naphthyl, wherein phenyl or naphthyl may be optionally substituted with 1 or 2 substituents each independently selected from the group consisting of halogen, hydroxy, —$NO_2$, and $C_{1-6}$ alkoxy. In other embodiments, $R^3$ is —$CH_2$-phenyl or —$CH_2$-naphthyl, wherein the phenyl is optionally substituted with one or more substituents each independently selected from the group consisting of halogen, hydroxyl, and —$NO_2$. In some embodiments, $R^3$ is —$CH_2$-phenyl or —$CH_2$-naphthyl, wherein the phenyl is optionally substituted with one or more substituents each independently selected from the group consisting of halogen and hydroxyl. In some embodiments, $R^3$ is —$CH_2$-phenyl or —$CH_2$-naphthyl, wherein the phenyl is optionally substituted with hydroxyl.

In some embodiments, $R^3$ is —$CH_2$-phenyl, wherein phenyl may be optionally substituted with 1 or 2 substituents each independently selected from the group consisting of halogen, hydroxy, —$NO_2$, and $C_{1-6}$ alkoxy. In some embodiments, $R^3$ is —$CH_2$-phenyl, wherein phenyl may be optionally substituted with 1 or 2 substituents each independently selected from the group consisting of halogen, hydroxy, and —$NO_2$. In some embodiments, $R^3$ is —$CH_2$-phenyl, wherein phenyl is unsubstituted. In some embodiments, $R^3$ is —$CH_2$-phenyl, wherein phenyl is substituted with 1 or 2 substituents each independently selected from the group consisting of halogen, hydroxy, —$NO_2$, and $C_{1-6}$ alkoxy. In some embodiments, $R^3$ is —$CH_2$-phenyl, wherein phenyl is substituted with 1 or 2 substituents each independently selected from the group consisting of halogen, hydroxy, and —$NO_2$. In some embodiments, $R^3$ is —$CH_2$-phenyl, wherein phenyl is substituted with 1 or 2 substituents each independently selected from the group consisting of halogen and hydroxy.

In some embodiments, $R^3$ is —$CH_2$-phenyl, wherein phenyl is substituted with 1 or 2 substituents each independently selected from the group consisting of —F, —Cl, —Br, and —I. In some embodiments, $R^3$ is —$CH_2$-phenyl, wherein phenyl is substituted with 1 or 2 substituents each of which is —F. In some embodiments, $R^3$ is —$CH_2$-phenyl, wherein phenyl is substituted with 1 or 2 substituents each of which is —Cl. In some embodiments, $R^3$ is —$CH_2$-phenyl, wherein phenyl is substituted with 1 or 2 substituents each of which is —Br. In some embodiments, $R^3$ is —$CH_2$-phenyl, wherein phenyl is substituted with 1 or 2 substituents each of which is —I. In some embodiments, $R^3$ is —$CH_2$-phenyl, wherein phenyl is substituted with 1 substituent which is —F. In some embodiments, $R^3$ is —$CH_2$-phenyl, wherein phenyl is substituted with 1 substituent which is —Cl. In some embodiments, $R^3$ is —$CH_2$-phenyl, wherein phenyl is substituted with 1 substituent which is —Br. In some embodiments, $R^3$ is —$CH_2$-phenyl, wherein phenyl is substituted with 1 substituent which is —I.

In some embodiments, $R^3$ is —$CH_2$-phenyl, wherein phenyl is substituted with 1 or 2 substituents each of which is hydroxy. In some embodiments, $R^3$ is —$CH_2$-phenyl, wherein phenyl is substituted with 1 substituent which is hydroxy. In some embodiments, $R^3$ is —$CH_2$-phenyl, wherein phenyl is substituted with 1 or 2 substituents each of which is —$NO_2$. In some embodiments, $R^3$ is —$CH_2$-phenyl, wherein phenyl is substituted with 1 substituent which is —$NO_2$. In some embodiments, $R^3$ is —$CH_2$-phenyl, wherein phenyl is substituted with 1 or 2 substituents each of which is independently $C_{1-6}$ alkoxy. In some embodiments, $R^3$ is —$CH_2$-phenyl, wherein phenyl is substituted with 1 or 2 substituents each of which is independently $C_{1-3}$ alkoxy. In some embodiments, $R^3$ is —$CH_2$-phenyl, wherein phenyl is substituted with 1 substituent which is methoxy.

In some embodiments, $R^3$ is

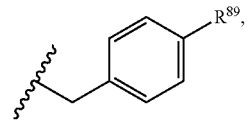

wherein $R^{89}$ is H, halogen, hydroxyl or $C_{1-3}$ alkoxy. In some embodiments, $R^{89}$ is H, halogen or hydroxyl. In some embodiments, $R^{89}$ is H, Cl or hydroxyl. In some embodiments, $R^{89}$ is Cl or hydroxyl. In some embodiments, $R^{89}$ is hydroxyl.

In some embodiments, $R^3$ is —$C_{1-2}$ alkylene($C_{10}$ aryl), wherein the $C_{10}$ aryl is optionally substituted with one or more substituents each independently selected from the group consisting of halogen, hydroxyl and —$NO_2$, and $C_{1-6}$ alkoxy. In some embodiments, $R^3$ is —$CH_2$-naphthyl.

In some embodiments, $R^3$ is —$C_{1-2}$ alkylene(6-membered heteroaryl), wherein the 6-membered heteroaryl is optionally substituted with one or more substituents each independently selected from the group consisting of halogen, hydroxy, —$NO_2$, and $C_{1-6}$ alkoxy.

In some embodiments, $R^3$ is selected from the group consisting of —$CH_2$-pyridinyl, —$CH_2$-indolyl, —$CH_2$-thiophenyl, —$CH_2$-thiazolyl, —$CH_2$-furanyl, —$CH_2$-benzothiophenyl, and —$CH_2$-imidazolyl. In some embodiments, $R^3$ is —$CH_2$-pyridinyl. In some embodiments, $R^3$ is —$CH_2$-indolyl. In some embodiments, $R^3$ is —$CH_2$-thiophenyl. In some embodiments, $R^3$ is —$CH_2$-thiazolyl. In some embodiments, $R^3$ is —$CH_2$-furanyl. In some embodiments, $R^3$ is —$CH_2$-benzothiophenyl. In some embodiments, $R^3$ is —$CH_2$-imidazolyl.

In some embodiments, $R^3$ is selected from the group consisting of —$C_{1-2}$ alkylene($C_6$ aryl) and —$C_{1-2}$alkylene (6-membered heteroaryl), wherein the $C_6$ aryl and the 6-membered heteroaryl are optionally substituted with hydroxyl. In other embodiments, $R^3$ is —$CH_2$-phenyl or —$CH_2$-pyridinyl, wherein the phenyl is optionally substituted with hydroxyl.

Embodiments of $R^4$

In some embodiments, $R^4$ is selected from the group consisting of:
- (i) —$C_{1-6}$ alkylene-$N(R^{53})C(O)NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl;
- (ii) —$C_{1-6}$ alkylene-$N(R^{55})C(O)R^{54}$, wherein $R^{54}$ is selected from the group consisting of $C_{1-6}$alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl;
- (iii) —($C_{6-10}$ arylene)-$C(O)NR^{56}R^{57}$ or —$C_{1-6}$ alkylene-($C_{6-10}$ arylene)-$C(O)NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
- (iv) —($C_{6-10}$ arylene)-$N(R^{59})C(O)R^{58}$ or —$C_{1-6}$ alkylene-($C_{6-10}$ arylene)-$N(R^{59})C(O)R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl;
- (v) —($C_{6-10}$ arylene)-$N(R^{62})C(O)NR^{60}R^{61}$ or —$C_{1-6}$ alkylene-($C_{6-10}$ arylene)-$N(R^{62})C(O)NR^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl;
- (vi) —($C_{6-10}$ arylene)-$N(R^{64})SO_2R^{63}$ or —$C_{1-6}$ alkylene-($C_{6-10}$ arylene)-$N(R^{64})SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl;
- (vii) —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
- (viii) —($C_{6-10}$ arylene)-($C_{1-6}$ alkylene)-$NR^{67}R^{68}$ or —$C_{1-6}$ alkylene-($C_{6-10}$ arylene)-($C_{1-6}$ alkylene)-$NR^{67}R^{68}$, wherein:
  each of $R^{67}$ and $R^{68}$ is independently selected from the group consisting of H, $C_{1-6}$ alkyl, $C_{6-10}$ aryl, 5- to 10-membered heteroaryl, —$C(O)R^{69}$, and —$C(O)NR^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents;
  $R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
  each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
- (ix) —($C_{6-10}$ arylene)-$NR^{72}R^{73}$ or —$C_{1-6}$ alkylene-($C_{6-10}$ arylene)-$NR^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
- (x) —($C_{6-10}$ arylene)-$OR^{74}$ or —$C_{1-6}$ alkylene-($C_{6-10}$ arylene)-$OR^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;
- (xi) —$C_{1-6}$ alkylene-($C_{6-10}$ arylene)-$N(R^{75})$—$C(O)$—$CHR^{76}$—$NR^{77}R^{78}$, wherein $R^{75}$ is H or $CH_3$, $R^{76}$ is H or $C_{1-6}$ alkyl optionally substituted with one or more substituents each independently selected from the group consisting of hydroxyl, —COOH, —$NH_2$, —$C(O)NH_2$, and —$N(H)C(O)NH_2$, and each of $R^{77}$ and $R^{78}$ is independently H, $CH_3$ or acetyl; and
- (xii) —$C_{1-6}$ alkylene-($C_{6-10}$ arylene)-CN.

In some embodiments, $R^4$ is selected from the group consisting of:
- (i) —$C_{1-6}$ alkylene-$N(R^{53})C(O)NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl;
- (ii) —$C_{1-6}$ alkylene-$N(R^{55})C(O)R^{54}$, wherein $R^{54}$ is selected from the group consisting of $C_{1-6}$alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl;
- (iii) —($C_{6-10}$ arylene)-$C(O)NR^{56}R^{57}$ or —$C_{1-6}$ alkylene-($C_{6-10}$ arylene)-$C(O)NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —($C_{6-10}$ arylene)-N($R^{59}$)C(O)$R^{58}$ or —$C_{1-6}$ alkylene-($C_{6-10}$ arylene)-N($R^{59}$)C(O)$R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl;

(v) —($C_{6-10}$ arylene)-N($R^{62}$)C(O)NR$^{60}R^{61}$ or —$C_{1-6}$ alkylene-($C_{6-10}$ arylene)-N($R^{62}$)C(O)NR$^{60}R^{61}$, wherein $R^{60}$ is selected from the group consisting of H, $C_{1-6}$ alkyl, $C_{6-10}$ aryl, and 5- to 10-membered heteroaryl, and $R^{61}$ is selected from the group consisting of $C_{1-6}$ alkyl, $C_{6-10}$ aryl, and 5- to 10-membered heteroaryl, wherein the $C_{1-6}$ alkyl of $R^{60}$ or $R^{61}$ is optionally substituted with one or more substituents, and wherein the $C_{6-10}$ aryl and 5- to 10-membered heteroaryl of $R^{60}$ or $R^{61}$ are optionally substituted with one or more substituents, and wherein $R^{62}$ is H or $C_{1-6}$ alkyl;

(vi) —($C_{6-10}$ arylene)-N($R^{64}$)SO$_2$R$^{63}$ or —$C_{1-6}$ alkylene-($C_{6-10}$ arylene)-N($R^{64}$)SO$_2$R$^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl;

(vii) —($C_{6-10}$ arylene)-SO$_2$NR$^{65}R^{66}$ or —$C_{1-6}$ alkylene-($C_{6-10}$ arylene)-SO$_2$NR$^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-($C_{1-6}$ alkylene)-NR$^{67}R^{68}$ or —$C_{1-6}$ alkylene-($C_{6-10}$ arylene)-($C_{1-6}$ alkylene)-NR$^{67}R^{68}$, wherein:
each of $R^{67}$ and $R^{68}$ is independently selected from the group consisting of H, $C_{1-6}$ alkyl, $C_{6-10}$ aryl, 5- to 10-membered heteroaryl, —C(O)$R^{69}$, and —C(O)NR$^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents;
$R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-NR$^{72}R^{73}$ or —$C_{1-6}$ alkylene-($C_{6-10}$ arylene)-NR$^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-OR$^{74}$ or —$C_{1-6}$ alkylene-($C_{6-10}$ arylene)-OR$^{74}$, wherein $R^{74}$ is selected from the group consisting of $C_{2-6}$ alkyl, $C_{6-10}$ aryl, and 5- to 10-membered heteroaryl, wherein the $C_{2-6}$ alkyl is optionally substituted with one or more substituents, and wherein the $C_{6-10}$ aryl and 5- to 10-membered heteroaryl are optionally substituted with one or more substituents;

(xi) —$C_{1-6}$ alkylene-($C_{6-10}$ arylene)-N($R^{75}$)—C(O)—CHR$^{76}$—NR$^{77}R^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{77}$ and $R^{78}$ is independently H, CH$_3$ or acetyl; and (xii) —$C_{1-6}$ alkylene-($C_{6-10}$ arylene)-CN.

In other embodiments, $R^4$ is selected from the group consisting of:

(i) —$C_{1-6}$ alkylene-N(H)C(O)NR$^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ii) —$C_{1-6}$ alkylene-N(H)C(O)$R^{54}$, wherein $R^{54}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iii) —($C_{6-10}$ arylene)-C(O)NR$^{56}R^{57}$ or —$C_{1-6}$ alkylene-($C_{6-10}$ arylene)-C(O)NR$^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —($C_{6-10}$ arylene)-N(H)C(O)$R^{58}$ or —$C_{1-6}$ alkylene-($C_{6-10}$ arylene)-N(H)C(O)$R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents;

(v) —($C_{6-10}$ arylene)-N(H)C(O)NR$^{60}R^{61}$ or —$C_{1-6}$ alkylene-($C_{6-10}$ arylene)-N(H)C(O)NR$^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vi) —($C_{6-10}$ arylene)-N(H)$SO_2R^{63}$ or —$C_{1-6}$ alkylene-($C_{6-10}$ arylene)-N(H)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vii) —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-($C_{1-6}$ alkylene)-$NR^{67}R^{68}$ or —$C_{1-6}$ alkylene-($C_{6-10}$ arylene)-($C_{1-6}$ alkylene)-$NR^{67}R^{68}$, wherein:
  each of $R^{67}$ and $R^{68}$ is independently selected from the group consisting of H, $C_{1-6}$ alkyl, $C_{6-10}$ aryl, 5- to 10-membered heteroaryl, —C(O)$R^{69}$, and —C(O)$NR^{70}R^{71}$, wherein the $C_{1-6}$ alkyl is optionally substituted with one or more substituents, and the $C_{6-10}$ aryl and 5- to 10-membered heteroaryl are optionally substituted with one or more substituents;
  $R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and
  each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-$NR^{72}R^{73}$ or —$C_{1-6}$ alkylene-($C_{6-10}$ arylene)-$NR^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{74}$ or —$C_{1-6}$ alkylene-($C_{6-10}$ arylene)-$OR^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(xi) —$C_{1-6}$ alkylene-($C_{6-10}$ arylene)-N($R^{75}$)—C(O)—$CHR^{76}$—N(H)$R^{78}$, wherein $R^{75}$ is H or $CH_3$, $R^{76}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{78}$ is H, $CH_3$ or acetyl; and (xii) —$C_{1-6}$ alkylene-($C_{6-10}$ arylene)-CN.

In some embodiments, $R^4$ is —$C_{1-6}$ alkylene-N($R^{53}$)C(O)$NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or alkyl.

In other embodiments, $R^4$ is —$C_{1-6}$ alkylene-N($R^{53}$)C(O)$NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein $R^{53}$ is H or $C_{1-6}$ alkyl.

In some embodiments, $R^4$ is —$C_{1-6}$ alkylene-N(H)C(O)$NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents.

In other embodiments, $R^4$ is —$C_{1-6}$ alkylene-N(H)C(O)$NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl. In some embodiments, R$^4$ is —C$_{3-4}$ alkylene-N(H)C(O)NR$^{51}$R$^{52}$ and each of R$^{51}$ and R$^{52}$ is H.

In some embodiments, R$^4$ is:

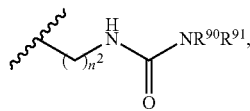

wherein each of R$^{90}$ and R$^{91}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^2$ is 1, 2, 3 or 4. In some embodiments, each of R$^{90}$ and R$^{91}$ is H. In some embodiments, n$^2$ is 3 or 4. In some embodiments, n$^2$ is 3. In other embodiments, n$^2$ is 4.

In some embodiments, R$^4$ is

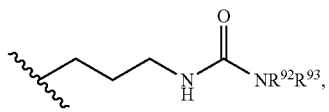

wherein each of R$^{92}$ and R$^{93}$ is independently selected from the group consisting of H, C$_{1-6}$ alkyl, C$_{6-10}$ aryl, and 6- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 6- to 10-membered heteroaryl are optionally substituted with one or more substituents each independently selected from the group consisting of halogen, —OH, —NO$_2$, and C$_{1-6}$ alkoxy. In some embodiments, each of R$^{92}$ and R$^{93}$ is H.

In some embodiments, R$^4$ is

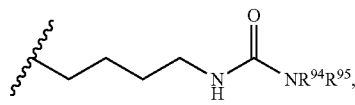

wherein each of R$^{94}$ and R$^{95}$ is independently selected from the group consisting of H, C$_{1-6}$ alkyl, C$_{6-10}$ aryl, and 6- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 6- to 10-membered heteroaryl are optionally substituted with one or more substituents each independently selected from the group consisting of halogen, —OH, —NO$_2$, and C$_{1-6}$ alkoxy. In other embodiments, each of R$^{94}$ and R$^{95}$ is H.

In some embodiments, R$^4$ is —C$_{1-6}$ alkylene-N(R$^{55}$)C(O)R$^{54}$, wherein R$^{54}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents, and wherein R$^{55}$ is H or C$_{1-6}$ alkyl.

In other embodiments, R$^4$ is —C$_{1-6}$ alkylene-N(R$^{55}$)C(O) R$^{54}$, wherein R$^{54}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein R$^{55}$ is H or C$_{1-6}$ alkyl.

In some embodiments, R$^4$ is —C$_{1-6}$ alkylene-NHC(O) R$^{54}$, wherein R$^{54}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents.

In other embodiments, R$^4$ is —C$_{1-6}$ alkylene-NHC(O)R$^{54}$, wherein R$^{54}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl.

In some embodiments, R$^4$ is —$C_{3-4}$ alkylene-NHC(O)R$^{54}$ and R$^{54}$ is 5- to 10-membered heteroaryl optionally substituted with one or more substituents each independently selected from the group consisting of halogen, hydroxy, —NO$_2$, and $C_{1-6}$ alkoxy.

In other embodiments, R$^4$ is —$C_{3-4}$ alkylene-NHC(O)R$^{54}$ and R$^{54}$ is pyridinyl optionally substituted with one or more substituents each independently selected from the group consisting of halogen, hydroxy, —NO$_2$, and $C_{1-6}$ alkoxy.

In some embodiments, R$^4$ is:

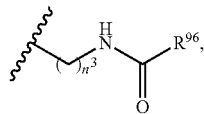

wherein R$^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein n$^3$ is 1, 2, 3, or 4. In some embodiments, R$^{96}$ is pyridinyl. In some embodiments, n$^3$ is 3 or 4. In some embodiments, n$^3$ is 3. In other embodiments, n$^3$ is 4.

In some embodiments, R$^4$ is

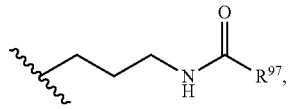

wherein R$^{97}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy. In some embodiments, R$^{97}$ is $C_6$ aryl or 5- to 6-membered heteroaryl.

In some embodiments, R$^4$ is

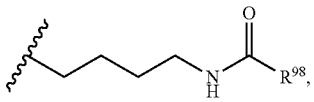

wherein R$^{98}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy. In some embodiments, R$^{98}$ is $C_6$ aryl or 5- to 6-membered heteroaryl.

In some embodiments, R$^4$ is —($C_{6-10}$ arylene)-C(O)NR$^{56}$R$^{57}$ or —$C_{1-6}$ alkylene-($C_{6-10}$ arylene)-C(O)NR$^{56}$R$^{57}$, wherein each of R$^{56}$ and R$^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents.

In other embodiments, R$^4$ is —($C_{6-10}$ arylene)-C(O)NR$^{56}$R$^{57}$ or —$C_{1-6}$ alkylene-($C_{6-10}$ arylene)-C(O)NR$^{56}$R$^{57}$, wherein each of R$^{56}$ and R$^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, $C_{1-6}$ haloalkoxy, —NH$_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, $C_{1-6}$ haloalkoxy, —NH$_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR$^{200}$ wherein R$^{200}$ is $C_{1-6}$ alkyl or $C_{6-10}$ aryl, —CO$_2$R$^{201}$ wherein R$^{201}$ is H or $C_{1-6}$ alkyl, —CONR$^{202}$R$^{203}$ wherein R$^{202}$ and R$^{203}$ is H or $C_{1-6}$ alkyl, —NR$^{204}$COR$^{205}$ wherein R$^{204}$ is H or $C_{1-6}$ alkyl and R$^{205}$ is $C_{1-6}$ alkyl, —SO$_2$NR$^{206}$R$^{207}$ wherein R$^{206}$ and R$^{207}$ is H or $C_{1-6}$ alkyl, and —NR$^{208}$SO$_2$R$^{209}$ wherein R$^{208}$ is H or $C_{1-6}$ alkyl and R$^{209}$ is $C_{1-6}$ alkyl. In some embodiments, R$^4$ is —$C_{1-2}$ alkylene-($C_6$ arylene)-C(O)NR$^{56}$R$^{57}$ and each of R$^{56}$ and R$^{57}$ is H.

In some embodiments, R$^4$ is:

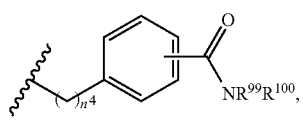

wherein each of R$^{99}$ and R$^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^4$ is 0, 1, 2, 3, or 4. In other embodiments, each of R$^{99}$ and R$^{100}$ is independently selected from the group consisting of H, C$_{1-6}$ alkyl, C$_{6-10}$ aryl, and 5- to 10-membered heteroaryl. In some embodiments, each of R$^{99}$ and R$^{100}$ is independently selected from the group consisting of H and C$_{1-6}$ alkyl. In some embodiments, each of R$^{99}$ and R$^{100}$ is H. In some embodiments, n$^4$ is 1 or 2. In some embodiments, n$^4$ is 1. In other embodiments, n$^4$ is 2.

In some embodiments, R$^4$ is:

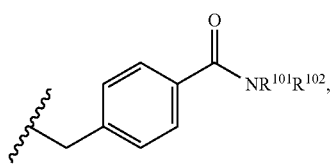

wherein each of R$^{101}$ and R$^{102}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy. In other embodiments, each of R$^{101}$ and R$^{102}$ is independently selected from the group consisting of H, C$_{1-6}$ alkyl, C$_{6-10}$ aryl, and 5- to 10-membered heteroaryl. In some embodiments, each of R$^{101}$ and R$^{102}$ is independently selected from the group consisting of H and C$_{1-6}$alkyl. In some embodiments, each of R$^{101}$ and R$^{102}$ is H.

In some embodiments, R$^4$ is —(C$_{6-10}$ arylene)-N(R$^{59}$)C(O)R$^{58}$ or —C$_{1-6}$ alkylene-(C$_{6-10}$ arylene)-N(R$^{59}$)C(O)R$^{58}$, wherein R$^{58}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents, and wherein the C$_{6-10}$ aryl, 5- to 10-membered heteroaryl, and 5- to 10-membered heterocycloalkyl are optionally substituted with one or more substituents, and wherein R$^{59}$ is H or C$_{1-6}$ alkyl.

In some embodiments, R$^4$ is —(C$_{6-10}$ arylene)-N(R$^{59}$)C(O)R$^{58}$ or —C$_{1-6}$ alkylene-(C$_{6-10}$ arylene)-N(R$^{59}$)C(O)R$^{58}$, wherein R$^{58}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl, 5- to 10-membered heteroaryl, and 5- to 10-membered heterocycloalkyl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein R$^{59}$ is H or C$_{1-6}$alkyl.

In some embodiments, R$^4$ is —(C$_{6-10}$ arylene)-N(H)C(O)R$^{58}$ or —C$_{1-6}$ alkylene-(C$_{6-10}$ arylene)-N(H)C(O)R$^{58}$, wherein R$^{58}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents, and wherein the C$_{6-10}$ aryl, 5- to 10-membered heteroaryl, and 5- to 10-membered heterocycloalkyl are optionally substituted with one or more substituents.

In some embodiments, R$^4$ is —(C$_{6-10}$ arylene)-N(H)C(O)R$^{58}$ or —C$_{1-6}$ alkylene-(C$_{6-10}$ arylene)-N(H)C(O)R$^{58}$, wherein R$^{58}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl, 5- to 10-membered heteroaryl, and 5- to 10-membered heterocycloalkyl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, R$^4$ is —C$_1$ alkylene-(C$_6$ arylene)-N(H)C(O)R$^{58}$ and R$^{58}$ is selected from the group consisting of C$_{1-6}$ alkyl, C$_{6-10}$ aryl, 5- to 10-membered heteroaryl, and 5- to 10-membered heterocycloalkyl. In some embodiments, R$^4$ is —C$_1$ alkylene-(C$_6$ arylene)-N(H)C(O)R$^{58}$ and R$^{58}$ is selected from the group consisting of C$_{6-10}$ aryl and 5- to 10-membered heterocycloalkyl. In some embodiments, R$^4$ is —C$_1$ alkylene-(C$_6$ arylene)-N(H)C(O)R$^{58}$ and R$^{58}$ is selected from the group consisting of C$_6$ aryl, 5- to 6-membered heteroaryl, and 5- to 6-membered heterocycloalkyl. In some embodiments, R$^4$ is —C$_1$ alkylene-(C$_6$ arylene)-N(H)C(O)R$^{58}$ and R$^{58}$ is pyrrolidinyl. In other embodiments, R$^4$ is —C$_1$ alkylene-(C$_6$ arylene)-N(H)C(O)R$^{58}$ and R$^{58}$ is phenyl.

In some embodiments, $R^4$ is

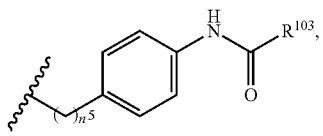

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, $-NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, $-NO_2$, and $C_{1-6}$ alkoxy, and wherein $n^5$ is 0, 1, 2, 3, or 4.

In some embodiments, $R^4$ is

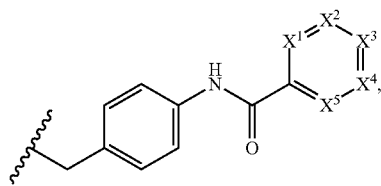

wherein $X^1$ is CH, $CR^{104}$, or N, $X^2$ is CH, $CR^{105}$, or N, $X^3$ is CH, $CR^{106}$, or N, $X^4$ is CH, $CR^{107}$, or N, and $X^5$ is CH, $CR^{108}$, or N, and each of $R^{104}$, $R^{105}$, $R^{106}$, $R^{107}$, and $R^{108}$ is independently selected from the group consisting of halogen, hydroxy, $-NO_2$, and $C_{1-6}$ alkoxy.

In some embodiments, $R^4$ is

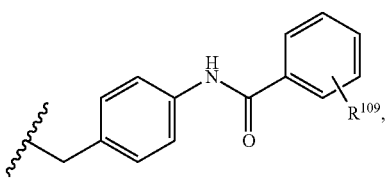

wherein $R^{109}$ is selected from the group consisting of H, halogen, hydroxy, $-NO_2$, and $C_{1-6}$ alkoxy. In other embodiments, $R^{109}$ is H.

In some embodiments, $R^4$ is $-(C_{6-10}$ arylene$)-N(R^{62})C(O)NR^{60}R^{61}$ or $-C_{1-6}$ alkylene-$(C_{6-10}$ arylene$)-N(R^{62})C(O)NR^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl.

In some embodiments, $R^4$ is $-(C_{6-10}$ arylene$)-N(R^{62})C(O)NR^{60}R^{61}$ or $-C_{1-6}$ alkylene-$(C_{6-10}$ arylene$)-N(R^{62})C(O)NR^{60}R^{61}$, wherein $R^{60}$ is selected from the group consisting of H, $C_{1-6}$ alkyl, $C_{6-10}$ aryl, and 5- to 10-membered heteroaryl, and $R^{61}$ is selected from the group consisting of $C_{1-6}$ alkyl, $C_{6-10}$ aryl, and 5- to 10-membered heteroaryl, wherein the C-6 alkyl of $R^{60}$ or $R^{61}$ is optionally substituted with one or more substituents, and wherein the $C_{6-10}$ aryl and 5- to 10-membered heteroaryl of $R^{60}$ or $R^{61}$ are optionally substituted with one or more substituents, and wherein $R^{62}$ is H or $C_{1-6}$ alkyl.

In some embodiments, $R^4$ is $-(C_{6-10}$ arylene$)-N(R^{62})C(O)NR^{60}R^{61}$ or $-C_{1-6}$ alkylene-$(C_{6-10}$ arylene$)-N(R^{62})C(O)NR^{60}R^{61}$, wherein each of $R^{60}$ and $R^{61}$ is independently selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl.

In some embodiments, $R^4$ is $-(C_{6-10}$ arylene$)-N(R^{62})C(O)NR^{60}R^{61}$ or $-C_{1-6}$ alkylene-$(C_{6-10}$ arylene$)-N(R^{62})C(O)NR^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, $-OH$, $-NO_2$, $C_{1-6}$ alkoxy, $C_{1-6}$ haloalkoxy, $-NH_2$, $-NH(C_{1-6}$ alkyl), $-N(C_{1-6}$ alkyl$)_2$, $-C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, $-CN$, $-COR^{200}$ wherein $R^{200}$ is $C_{1-6}$ alkyl or $C_{6-10}$ aryl, $-CO_2R^{201}$ wherein $R^{201}$ is H or $C_{1-6}$ alkyl, $-CONR^{202}R^{203}$ wherein $R^{202}$ and $R^{203}$ is H or $C_{1-6}$ alkyl, $-NR^{204}COR^{205}$ wherein $R^{204}$ is H or $C_{1-6}$ alkyl and $R^{205}$ is $C_{1-6}$ alkyl, $-SO_2NR^{206}R^{207}$ wherein $R^{206}$ and $R^{207}$ is H or $C_{1-6}$ alkyl, and $-NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, $-OH$, $-NO_2$, $C_{1-6}$ alkoxy, $C_{1-6}$ haloalkoxy, $-NH_2$, $-NH(C_{1-6}$ alkyl), $-N(C_{1-6}$ alkyl$)_2$, $-C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, $-CN$, $-COR^{200}$ wherein $R^{200}$ is $C_{1-6}$ alkyl or $C_{6-10}$ aryl, $-CO_2R^{201}$ wherein $R^{201}$ is H or $C_{1-6}$ alkyl, $-CONR^{202}R^{203}$ wherein $R^{202}$ and $R^{203}$ is H or $C_{1-6}$ alkyl, $-NR^{204}COR^{205}$ wherein $R^{204}$ is H or $C_{1-6}$ alkyl and $R^{205}$ is $C_{1-6}$ alkyl, $-SO_2NR^{206}R^{207}$ wherein $R^{206}$ and $R^{207}$ is H or $C_{1-6}$ alkyl, and $-NR^{208}SO_2R^{209}$ wherein $R^{208}$ is H or $C_{1-6}$ alkyl and $R^{209}$ is $C_{1-6}$ alkyl, and wherein $R^{62}$ is H or $C_{1-6}$ alkyl.

In some embodiments, $R^4$ is $-(C_{6-10}$ arylene$)-N(R^{62})C(O)NR^{60}R^{61}$ or $-C_{1-6}$ alkylene-$(C_{6-10}$ arylene$)-N(R^{62})C(O)NR^{60}R^{61}$, wherein $R^{60}$ is selected from the group consisting of H, $C_{1-6}$ alkyl, $C_{6-10}$ aryl, and 5- to 10-membered heteroaryl, and $R^{61}$ is selected from the group consisting of $C_{1-6}$ alkyl, $C_{6-10}$ aryl, and 5- to 10-membered heteroaryl, wherein the $C_{1-6}$ alkyl of $R^{60}$ or $R^{61}$ is optionally substituted with one or more substituents each independently selected from the group consisting of halogen, $-OH$, $-NO_2$, $C_{1-6}$ alkoxy, $C_{1-6}$ haloalkoxy, $-NH_2$, $-NH(C_{1-6}$ alkyl), $-N(C_{1-6}$ alkyl$)_2$, $-C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, $-CN$, $-COR^{200}$ wherein $R^{200}$ is $C_{1-6}$ alkyl or $C_{6-10}$ aryl, $-CO_2R^{201}$ wherein $R^{201}$ is H or $C_{1-6}$ alkyl, $-CONR^{202}R^{203}$ wherein $R^{202}$ and $R^{203}$ is H or $C_{1-6}$ alkyl, $-NR^{204}COR^{205}$ wherein $R^{204}$ is H or $C_{1-6}$ alkyl and $R^{205}$ is $C_{1-6}$ alkyl, $-SO_2NR^{206}R^{207}$ wherein $R^{206}$ and $R^{207}$ is H or $C_{1-6}$ alkyl, and $-NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl of $R^{60}$ or $R^{61}$ are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein R$^{62}$ is H or C$_{1-6}$ alkyl.

In some embodiments, R$^4$ is —(C$_{6-10}$ arylene)-N(R$^{62}$)C(O)NR$^{60}$R$^{61}$ or —C$_{1-6}$ alkylene-(C$_{6-10}$ arylene)-N(R$^{62}$)C(O)NR$^{60}$R$^{61}$, wherein each of R$^{60}$ and R$^{61}$ is independently selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein R$^{62}$ is H or C$_{1-6}$ alkyl.

In some embodiments, R$^4$ is —(C$_{6-10}$ arylene)-N(H)C(O)NR$^{60}$R$^{61}$ or —C$_{1-6}$ alkylene-(C$_{6-10}$ arylene)-N(H)C(O)NR$^{60}$R$^{61}$, wherein each of R$^{60}$ and R$^{61}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents.

In some embodiments, R$^4$ is —(C$_{6-10}$ arylene)-N(H)C(O)NR$^{60}$R$^{61}$ or —C$_{1-6}$ alkylene-(C$_{6-10}$ arylene)-N(H)C(O)NR$^{60}$R$^{61}$, wherein R$^{60}$ is selected from the group consisting of H, C$_{1-6}$ alkyl, C$_{6-10}$ aryl, and 5- to 10-membered heteroaryl, and R$^{61}$ is selected from the group consisting of C$_{1-6}$ alkyl, C$_{6-10}$ aryl, and 5- to 10-membered heteroaryl, wherein the C$_{1-6}$ alkyl of R$^{60}$ or R$^{61}$ is optionally substituted with one or more substituents, and wherein the C$_{6-10}$ aryl and 5- to 10-membered heteroaryl of R$^{60}$ or R$^{61}$ are optionally substituted with one or more substituents.

In some embodiments, R$^4$ is —(C$_{6-10}$ arylene)-N(H)C(O)NR$^{60}$R$^{61}$ or —C$_{1-6}$ alkylene-(C$_{6-10}$ arylene)-N(H)C(O)NR$^{60}$R$^{61}$, wherein each of R$^{60}$ and R$^{61}$ is independently selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents.

In some embodiments, R$^4$ is —(C$_{6-10}$ arylene)-N(H)C(O)NR$^{60}$R$^{61}$ or —C$_{1-6}$ alkylene-(C$_{6-10}$ arylene)-N(H)C(O)NR$^{60}$R$^{61}$, wherein each of R$^{60}$ and R$^{61}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, R$^4$ is —(C$_{6-10}$ arylene)-N(H)C(O)NR$^{60}$R$^{61}$ or —C$_{1-6}$ alkylene-(C$_{6-10}$ arylene)-N(H)C(O)NR$^{60}$R$^{61}$, wherein R$^{60}$ is selected from the group consisting of H, C$_{1-6}$ alkyl, C$_{6-10}$ aryl, and 5- to 10-membered heteroaryl, and R$^{61}$ is selected from the group consisting of C$_{1-6}$ alkyl, C$_{6-10}$ aryl, and 5- to 10-membered heteroaryl, wherein the C$_{1-6}$ alkyl of R$^{60}$ or R$^{61}$ is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl of R$^{60}$ or R$^{61}$ are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein $R^{206}$ and $R^{207}$ is H or $C_{1-6}$ alkyl, and $-NR^{208}SO_2R^{209}$ wherein $R^{208}$ is H or $C_{1-6}$ alkyl and $R^{209}$ is $C_{1-6}$ alkyl.

In some embodiments, $R^4$ is $-(C_{6-10}$ arylene)-N(H)C(O)NR$^{60}$R$^{61}$ or $-C_{1-6}$ alkylene-(C$_{6-10}$ arylene)-N(H)C(O)NR$^{60}$R$^{61}$, wherein each of $R^{60}$ and $R^{61}$ is independently selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, $C_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, $R^4$ is —C$_{1-2}$ alkylene-(C$_6$ arylene)-N(H)C(O)NR$^{60}$R$^{61}$, wherein R$^{60}$ is selected from the group consisting of H, C$_{1-6}$ alkyl, C$_{6-10}$ aryl, and 5- to 10-membered heteroaryl, and R$^{61}$ is selected from the group consisting of C$_{1-6}$ alkyl, C$_{6-10}$ aryl, and 5- to 10-membered heteroaryl. In some embodiments, R$^4$ is —C$_{1-2}$ alkylene-(C$_6$ arylene)-N(H)C(O)NR$^{60}$R$^{61}$ and R$^{60}$ is H and R$^{61}$ is phenyl.

In some embodiments, $R^4$ is

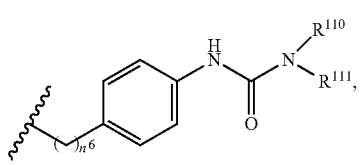

wherein each of $R^{110}$ and $R^{111}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^6$ is 0, 1, 2, 3, or 4.

In some embodiments, $R^4$ is

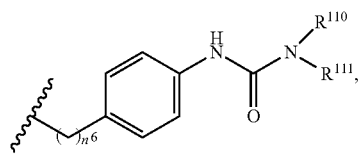

wherein $R^{110}$ is selected from the group consisting of H, C$_{1-6}$ alkyl, C$_{6-10}$ aryl, and 5- to 10-membered heteroaryl, and $R^{111}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^6$ is 0, 1, 2, 3, or 4.

In some embodiments, $R^{110}$ is selected from the group consisting of H, C$_{1-6}$ alkyl, C$_{6-10}$ aryl, and 5- to 10-membered heteroaryl, and $R^{111}$ is selected from the group consisting of C$_{1-6}$ alkyl, C$_{6-10}$ aryl, and 5- to 10-membered heteroaryl.

In some embodiments, $R^4$ is

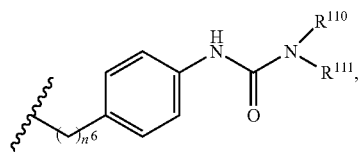

wherein each of $R^{110}$ and $R^{111}$ is independently selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^6$ is 0, 1, 2, 3, or 4.

In some embodiments, $R^4$ is

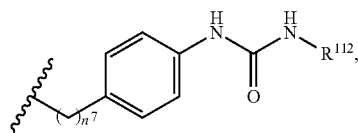

wherein $R^{112}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^7$ is 0, 1, 2, 3, or 4.

In some embodiments, $R^4$ is

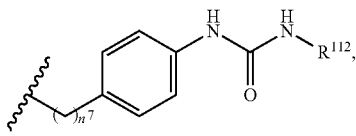

wherein $R^{112}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^7$ is 0, 1, 2, 3, or 4. In some embodiments, $R^{112}$ is selected from the group consisting of $C_{1-6}$ alkyl, $C_{6-10}$ aryl, and 5- to 10-membered heteroaryl.

In some embodiments, $R^4$ is

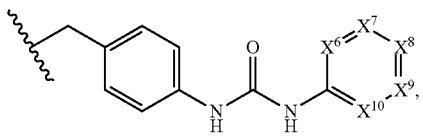

wherein $X^6$ is CH, $CR^{113}$ or N, $X^7$ is CH, $CR^{114}$ or N, $X^8$ is CH, $CR^{115}$ or N, $X^9$ is CH, $CR^{116}$ or N, and $X^{10}$ is CH, $CR^{117}$ or N, and each $R^{113}$, $R^{114}$, $R^{115}$, $R^{116}$, and $R^{117}$ is independently selected from the group consisting of halogen, hydroxy, —$NO_2$, and $C_{1-6}$ alkoxy.

In some embodiments, $R^4$ is

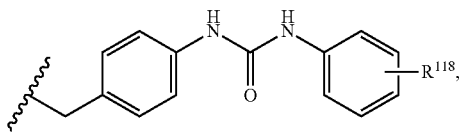

wherein $R^{118}$ is selected from the group consisting of H, halogen, hydroxy, —$NO_2$, and $C_{1-6}$ alkoxy. In other embodiments, $R^{118}$ is H.

In some embodiments, $R^4$ is —($C_{6-10}$ arylene)-N($R^{64}$)$SO_2R^{63}$ or —$C_{1-6}$ alkylene-($C_{6-10}$ arylene)-N($R^{64}$)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl.

In some embodiments, $R^4$ is —($C_{6-10}$ arylene)-N($R^{64}$)$SO_2R^{63}$ or —$C_{1-6}$ alkylene-($C_{6-10}$ arylene)-N($R^{64}$)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein $R^{64}$ is H or $C_{1-6}$ alkyl.

In some embodiments, $R^4$ is —($C_{6-10}$ arylene)-N(H)$SO_2R^{63}$ or —$C_{1-6}$ alkylene-($C_{6-10}$ arylene)-N(H)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents.

In some embodiments, $R^4$ is —($C_{6-10}$ arylene)-N(H)$SO_2R^{63}$ or —$C_{1-6}$ alkylene-($C_{6-10}$ arylene)-N(H)$SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl.

In some embodiments, $R^4$ is —$C_{1-2}$ alkylene-($C_6$ arylene)-N(H)$SO_2R^{63}$ and $R^{63}$ is $C_6$ aryl optionally substituted with one or more substituents each independently selected from the group consisting of halogen, hydroxy, —$NO_2$, and $C_{1-6}$ alkoxy. In other embodiments, $R^4$ is —$C_{1-2}$ alkylene-($C_6$ arylene)-N(H)$SO_2R^{63}$ and $R^{63}$ is phenyl. In some embodiments, $R^4$ is —$C_1$ alkylene-($C_6$ arylene)-N(H)$SO_2R^{63}$ and $R^{63}$ is phenyl.

In some embodiments, $R^4$ is:

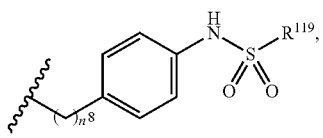

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 0, 1, 2, 3, or 4. In other embodiments, $R^{119}$ is selected from the group consisting of $C_{1-6}$ alkyl, $C_{6-10}$ aryl, and 5- to 10-membered heteroaryl.

In some embodiments, $R^4$ is:

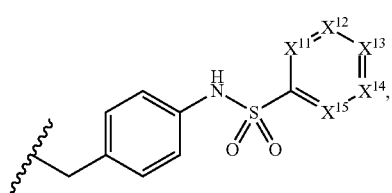

wherein $X^{11}$ is CH, $CR^{120}$ or N, $X^{12}$ is CH, $CR^{121}$ or N, $X^{13}$ is CH, $CR^{122}$ or N, $X^{14}$ is CH, $CR^{123}$ or N, and $X^{15}$ is CH, $CR^{124}$ or N, and each of $R^{120}$, $R^{121}$, $R^{122}$, $R^{123}$ and $R^{124}$ is independently selected from the group consisting of halogen, hydroxy, —$NO_2$, and $C_{1-6}$ alkoxy.

In some embodiments, $R^4$ is:

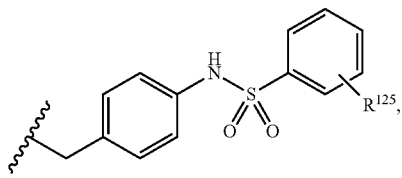

wherein $R^{125}$ is selected from the group consisting of H, halogen, hydroxy, —$NO_2$, and $C_{1-6}$ alkoxy. In some embodiments, $R^{125}$ is H.

In some embodiments, $R^4$ is —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents.

In some embodiments, $R^4$ is —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl.

In some embodiments, $R^4$ is

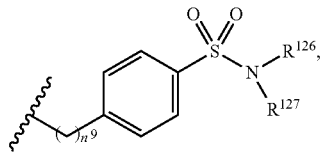

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^9$ is 0, 1, 2, 3, or 4. In some embodiments, each of $R^{126}$ and $R^{127}$ is independently selected from the group consisting of H, $C_{1-6}$ alkyl, $C_{6-10}$ aryl, and 5- to 10-membered heteroaryl.

In some embodiments, $R^4$ is

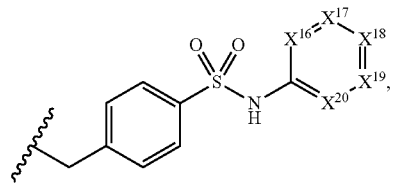

wherein $X^{16}$ is CH, $CR^{128}$ or N, $X^{17}$ is CH, $CR^{129}$ or N, $X^{18}$ is CH, $CR^{130}$ or N, $X^{19}$ is CH, $CR^{131}$ or N, and $X^{20}$ is CH, $CR^{132}$ or N, and each of $R^{128}$, $R^{129}$, $R^{130}$, $R^{131}$ and $R^{132}$ is independently selected from the group consisting of halogen, —OH, —$NO_2$, and $C_{1-6}$ alkoxy.

In some embodiments, $R^4$ is

[structure: a sulfonamide linker — CH2 connected to a phenyl ring bearing -S(=O)(=O)-NH- connected to another phenyl ring substituted with $R^{133}$], wherein $R^{33}$ is selected from the group consisting of H, halogen, —OH, —NO$_2$, and C$_{1-6}$ alkoxy. In other embodiments, $R^{33}$ is H.

In some embodiments, $R^4$ is —(C$_{6-10}$ arylene)-(C$_{1-6}$ alkylene)-NR$^{67}$R$^{68}$ or —C$_{1-6}$ alkylene-(C$_{6-10}$ arylene)-(C$_{1-6}$ alkylene)-NR$^{67}$R$^{68}$, wherein:

each of R$^{67}$ and R$^{68}$ is independently selected from the group consisting of H, C$_{1-6}$ alkyl, C$_{6-10}$ aryl, 5- to 10-membered heteroaryl, —C(O)R$^{69}$, and —C(O)NR$^{70}$R$^{71}$, wherein the C$_{1-6}$ alkyl is optionally substituted with one or more substituents, and wherein the C$_{6-10}$ aryl and 5- to 10-membered heteroaryl are optionally substituted with one or more substituents;

R$^{69}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and each of R$^{70}$ and R$^{71}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents.

In some embodiments, $R^4$ is —(C$_{6-10}$ arylene)-(C$_{1-6}$ alkylene)-NR$^{67}$R$^{68}$ or —C$_{1-6}$ alkylene-(C$_{6-10}$ arylene)-(C$_{1-6}$ alkylene)-NR$^{67}$R$^{68}$, wherein:

each of R$^{67}$ and R$^{68}$ is independently selected from the group consisting of H, C$_{1-6}$ alkyl, C$_{6-10}$ aryl, 5- to 10-membered heteroaryl, —C(O)R$^{69}$, and —C(O)NR$^{70}$R$^{71}$, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl;

R$^{69}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, $R^4$ is —(C$_{6-10}$ arylene)-(C$_{1-6}$ alkylene)-NR$^{67}$R$^{68}$ or —C$_{1-6}$ alkylene-(C$_{6-10}$ arylene)-(C$_{1-6}$ alkylene)-NR$^{67}$R$^{68}$, wherein:

each of R$^{67}$ and R$^{68}$ is independently selected from the group consisting of H, C$_{1-6}$ alkyl, C$_{6-10}$ aryl, 5- to 10-membered heteroaryl, —C(O)R$^{69}$, and —C(O)NR$^{70}$R$^{71}$, wherein the C$_{1-6}$ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy; R⁶⁹ is selected from the group consisting of C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy; and each of R⁷⁰ and R⁷¹ is independently selected from the group consisting of H, C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy.

In some embodiments, R⁴ is —C alkylene-(C₆ arylene)-(C₁ alkylene)-NR⁶⁷R⁶⁸ and each of R⁶⁷ and R⁶⁸ is H. In other embodiments, R⁴ is —C₁ alkylene-(C₆ arylene)-(C₁ alkylene)-NR⁶⁷R⁶⁸, R⁶⁷ is H, R⁶⁸ is —C(O)R⁶⁹, and R⁶⁹ is C₁ alkyl. In some embodiments, R⁴ is —C₁ alkylene-(C₆ arylene)-(C₁ alkylene)-NR⁶⁷R⁶⁸, R⁶⁷ is H, R⁶⁸ is —C(O)NR⁷⁰R⁷¹, and each of R⁷⁰ and R⁷¹ is H.

In some embodiments, R⁴ is:

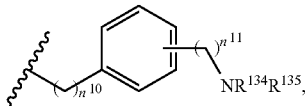

wherein:
each of R¹³⁴ and R¹³⁵ is independently selected from the group consisting of H, C₁₋₆ alkyl, C₆₋₁₀ aryl, 5- to 10-membered heteroaryl, —C(O)R¹³⁶, and —C(O)NR¹³⁷R¹³⁸, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy, and wherein n¹⁰ is 0, 1, 2, 3, or 4, and wherein n¹¹ is 0, 1, 2, 3, or 4;
R¹³⁶ is selected from the group consisting of C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy; and each of R¹³⁷ and R¹³⁸ is independently selected from the group consisting of H, C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy.

In some embodiments, R⁴ is

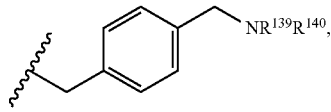

wherein:
each of R¹³⁹ and R¹⁴⁰ is independently selected from the group consisting of H, C₁₋₆ alkyl, C₆₋₁₀ aryl, 5- to 10-membered heteroaryl, —C(O)R¹⁴¹, and —C(O)NR¹⁴²R¹⁴³, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy;
R¹⁴¹ is selected from the group consisting of C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy; and each of R¹⁴² and R¹⁴³ is independently selected from the group consisting of H, C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, and C₁₋₆ alkoxy, and wherein the C₆₋₁₀ aryl and 5- to 10-membered heteroaryl are optionally substituted with one or more substituents each independently selected from the group consisting of halogen, —OH, —NO₂, and C₁₋₆ alkoxy. In some embodiments, each of R¹³⁹ and R¹⁴⁰ is independently selected from the group consisting of H, —C(O)R¹⁴¹, and —C(O)NR¹⁴²R¹⁴³, wherein R¹⁴¹ is C₁₋₆ alkyl and each of R¹⁴² and R¹⁴³ is H.

In some embodiments, R⁴ is —(C₆₋₁₀ arylene)-NR⁷²R⁷³ or —C₁₋₆ alkylene-(C₆₋₁₀ arylene)-NR⁷²R⁷³, wherein each of R⁷² and R⁷³ is independently selected from the group consisting of H, C₁₋₆ alkyl, C₆₋₁₀ aryl, and 5- to 10-membered heteroaryl, wherein the C₁₋₆ alkyl is optionally substituted with one or more substituents, and wherein the C₆₋₁₀ aryl and 5- to 10-membered heteroaryl are optionally substituted with one or more substituents.

In some embodiments, R⁴ is —(C₆₋₁₀ arylene)-NR⁷²R⁷³ or —C₁₋₆ alkylene-(C₆₋₁₀ arylene)-NR⁷²R⁷³, wherein each of R⁷² and R⁷³ is independently selected from the group consisting of H, C₁₋₆ alkyl, C₆₋₁₀ aryl, and 5- to 10-membered heteroaryl, wherein the C₁₋₆ alkyl is optionally substituted with one or more substituents each independently selected from the group consisting of halogen, —OH, —NO₂, C₁₋₆ alkoxy, C₁₋₆ haloalkoxy, —NH₂, —NH(C₁₋₆ alkyl), —N(C₁₋₆ alkyl)₂, —C₁₋₆ alkyl, haloC₁₋₆ alkyl, aminoC₁₋₆ alkyl, C₆₋₁₀ aryl, 5- to 10-membered heteroaryl, 5- to 10-membered heterocycloalkyl, C₅₋₁₀ cycloalkyl, azido, —CN, —COR²⁰⁰ wherein R²⁰⁰ is C₁₋₆ alkyl or C₆₋₁₀ aryl, —CO₂R²⁰¹ wherein R²⁰¹ is H or C₁—6 alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, R$^4$ is —C$_{1-2}$ alkylene-(C$_6$ arylene)-NR$^{72}$R$^{73}$ and each of R$^{72}$ and R$^{73}$ is independently selected from the group consisting of H and C$_{1-6}$ alkyl, wherein the C$_{1-6}$ alkyl is optionally substituted with one or more substituents each independently selected from the group consisting of 5- to 10-membered heterocycloalkyl, halogen, hydroxy, —NO$_2$, and C$_{1-6}$ alkoxy. In other embodiments, R$^4$ is —C$_{1-2}$ alkylene-(C$_6$ arylene)-NR$^{72}$R$^{73}$ and R$^{72}$ is H and R$^{73}$ is C$_{1-6}$ alkyl optionally substituted with one or more substituents each independently selected from the group consisting of 5- to 10-membered heterocycloalkyl, halogen, hydroxy, —NO$_2$, and C$_{1-6}$ alkoxy. In some embodiments, R$^4$ is —C$_{1-2}$ alkylene-(C$_6$ arylene)-NR$^{72}$R$^{73}$ and R$^{72}$ is H and R$^{73}$ is C$_2$ alkyl substituted with morpholinyl. In some embodiments, R$^4$ is —C$_{1-2}$ alkylene-(C$_6$ arylene)-NR$^{72}$R$^{73}$ and R$^{72}$ is H and R$^{73}$ is C$_{1-6}$ alkyl. In other embodiments, R$^4$ is —C$_{1-2}$ alkylene-(C$_6$ arylene)-NR$^{72}$R$^{73}$ and R$^{72}$ is H and R$^{73}$ is C$_5$ alkyl.

In some embodiments, R$^4$ is:

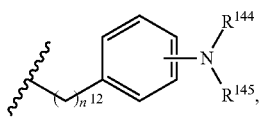

wherein each of R$^{144}$ and R$^{145}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{12}$ is 0, 1, 2, 3, or 4. In some embodiments, n$^{12}$ is 1 or 2. In other embodiments, n$^{12}$ is 1. In other embodiments, R$^{144}$ is H and R$^{145}$ is C$_{1-6}$ alkyl optionally substituted with one or more substituents each independently selected from the group consisting of halogen, —OH, —NO$_2$, C$_{1-6}$ alkoxy, and 5- to 10-membered heteroaryl. In some embodiments, R$^{144}$ is H and R$^{145}$ is C$_2$ alkyl substituted with morpholinyl. In other embodiments, R$^{144}$ is H and R$^{145}$ is C$_{1-6}$ alkyl. In other embodiments, R$^{144}$ is H and R$^{145}$ is C$_5$ alkyl.

In some embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents. In other embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of C$_{2-6}$ alkyl, C$_{6-10}$ aryl, and 5- to 10-membered heteroaryl, wherein the C$_{2-6}$alkyl is optionally substituted with one or more substituents, and wherein the C$_{6-10}$ aryl and 5- to 10-membered heteroaryl are optionally substituted with one or more substituents. In some embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of C$_{3-6}$ alkyl, C$_{6-10}$ aryl, and 5- to 10-membered heteroaryl, wherein the C$_{3-6}$alkyl is optionally substituted with one or more substituents, and wherein the C$_{6-10}$ aryl and 5- to 10-membered heteroaryl are optionally substituted with one or more substituents.

In some embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, C$_{1-6}$ haloalkoxy, —NH$_2$, —NH(C$_{1-6}$ alkyl), —N(C$_{1-6}$ alkyl)$_2$, —C$_{1-6}$ alkyl, haloC$_{1-6}$ alkyl, aminoC$_{1-6}$ alkyl, C$_{6-10}$ aryl, 5- to 10-membered heteroaryl, 5- to 10-membered heterocycloalkyl, C$_{5-10}$ cycloalkyl, azido, —CN, —COR$^{200}$ wherein R$^{200}$ is C$_{1-6}$ alkyl or C$_{6-10}$ aryl, —CO$_2$R$^{201}$ wherein R$^{201}$ is H or C$_{1-6}$ alkyl, —CONR$^{202}$R$^{203}$ wherein R$^{202}$ and R$^{203}$ is H or C$_{1-6}$ alkyl, —NR$^{204}$COR$^{205}$ wherein R$^{204}$ is H or C$_{1-6}$ alkyl and R$^{205}$ is C$_{1-6}$ alkyl, —SO$_2$NR$^{206}$R$^{207}$ wherein R$^{206}$ and R$^{207}$ is H or C$_{1-6}$ alkyl, and —NR$^{208}$SO$_2$R$^{209}$ wherein R$^{208}$ is H or C$_{1-6}$ alkyl and R$^{209}$ is C$_{1-6}$ alkyl.

In some embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl. In other embodiments, R$^4$ is —(C$_{6-10}$ arylene)-OR$^{74}$ or —C$_{1-6}$ alkylene-(C$_{6-10}$ arylene)-OR$^{74}$, wherein R$^{74}$ is selected from the group consisting of C$_{2-6}$ alkyl, C$_{6-10}$ aryl, and 5- to 10-membered heteroaryl, wherein the $C_{2-6}$alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl.

In some embodiments, $R^4$ is —$C_{1-2}$ alkylene-($C_6$ arylene)-OR$^{74}$ and $R^{74}$ is $C_{1-6}$ alkyl optionally substituted with one or more substituents each independently selected from the group consisting of 5- to 10-membered heterocycloalkyl, halogen, hydroxy, —NO$_2$, and $C_{1-6}$ alkoxy. In some embodiments, $R^4$ is —$C_{1-2}$ alkylene-($C_6$ arylene)-OR$^{74}$ and $R^{74}$ is $C_{2-6}$alkyl optionally substituted with one or more substituents each independently selected from the group consisting of 5- to 10-membered heterocycloalkyl, halogen, hydroxy, —NO$_2$, and $C_{1-6}$ alkoxy. In some embodiments, $R^4$ is —$C_{1-2}$ alkylene-($C_6$ arylene)-OR$^{74}$ and $R^{74}$ is $C_{2-6}$ alkyl. In other embodiments, $R^4$ is —$C_{1-2}$ alkyene-($C_6$ arylene)-OR$^{74}$ and $R^{74}$ is $C_2$ alkyl substituted with morpholinyl.

In some embodiments, $R^4$ is:

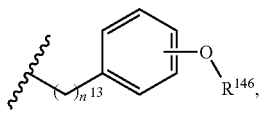

wherein $R^{146}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein n$^{13}$ is 0, 1, 2, 3, or 4. In some embodiments, n$^{13}$ is 1 or 2. In other embodiments, n$^{13}$ is 1. In some embodiments, $R^{146}$ is selected from the group consisting of $C_{2-6}$ alkyl, $C_{6-10}$ aryl, and 5- to 10-membered heteroaryl, wherein the $C_{1-6}$alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl. In other embodiments, $R^{146}$ is selected from the group consisting of $C_{2-6}$ alkyl, $C_{6-10}$ aryl, and 5- to 10-membered heteroaryl.

In some embodiments, $R^4$ is

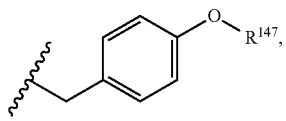

wherein $R^{147}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl. In other embodiments, $R^{147}$ is selected from the group consisting of $C_{2-6}$ alkyl, $C_{6-10}$ aryl, and 5- to 10-membered heteroaryl, wherein the $C_{2-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl. In some embodiments, $R^{147}$ is selected from the group consisting of $C_{2-6}$ alkyl, $C_{6-10}$ aryl, and 5- to 10-membered heteroaryl. In other embodiments, $R^{147}$ is $C_{2-6}$alkyl optionally substituted with one or more substituents each independently selected from the group consisting of halogen, —OH, —NO$_2$, $C_{1-6}$ alkoxy, and 5- to 10-membered heterocycloalkyl. In some embodiments, $R^{147}$ is $C_2$ alkyl substituted with morpholinyl. In other embodiments, $R^{147}$ is $C_2$ alkyl.

In some embodiments, $R^4$ is —$C_{1-6}$ alkylene-($C_{6-10}$ arylene)-N($R^{75}$)—C(O)—CHR$^{76}$—NR$^{77}$R$^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{77}$ and $R^{78}$ is independently H, CH$_3$ or acetyl.

In some embodiments, $R^4$ is —$C_{1-6}$ alkylene-($C_{6-10}$ arylene)-N($R^{75}$)—C(O)—CHR$^{76}$—N(H)R$^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and $R^{78}$ is H, CH$_3$ or acetyl.

In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is H, and $R^{78}$ is H or acetyl. In other embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is H, and $R^{78}$ is H. In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is H, and $R^{78}$ is acetyl.

In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is $C_{1-6}$ alkyl optionally substituted with one or more substituents each independently selected from the group consisting of hydroxyl, —COOH, —NH$_2$, —C(O)NH$_2$, and —N(H)C(O)NH$_2$, and $R^{78}$ is H.

In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is $C_{1-6}$ alkyl substituted with hydroxyl, and $R^{78}$ is H. In some embodiments, $R^4$ is —$C_{1-2}$ alkylene-($C_{6-10}$ arylene)-N ($R^{75}$)—C(O)—CHR$^{76}$—N(H)R$^{78}$, $R^{75}$ is H, $R^{76}$ is $C_{1-6}$ alkyl substituted with —COOH, and $R^{78}$ is H. In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is $C_{1-6}$ alkyl substituted with —NH$_2$, and $R^{78}$ is H. In some embodiments, $R^4$ is —$C_{1-2}$ alkylene-($C_{6-10}$ arylene)-N($R^{75}$)—C(O)—CHR$^{76}$—N(H)R$^{78}$, $R^{75}$ is H, $R^{76}$ is $C_{1-6}$ alkyl substituted with —C(O)NH$_2$, and $R^{78}$ is H. In some embodiments, $R^4$ is —C$_{1-2}$ alkylene-(C$_{6-10}$ arylene)-N(R$^{75}$)—C(O)—CHR$^{76}$—N(H)R$^{78}$, R$^{75}$ is H, R$^{76}$ is C$_{1-6}$ alkyl substituted with —N(H)C(O)NH$_2$, and R$^{78}$ is H.

In some embodiments, R$^4$ is:

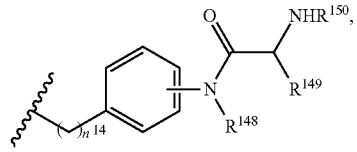

wherein R$^{148}$ is H or CH$_3$, R$^{149}$ is H or C$_{1-6}$ alkyl optionally substituted with one or more substituents each independently selected from the group consisting of hydroxyl, —COOH, —NH$_2$, —C(O)NH$_2$, and —N(H)C(O)NH$_2$, and R$^{150}$ is H, CH$_3$ or acetyl, and wherein n$^{14}$ is 0, 1, 2, 3, or 4. In other embodiments, n$^{14}$ is 1 or 2. In some embodiments, n$^{14}$ is 1. In some embodiments, R$^{148}$ is H, R$^{149}$ is H, and R$^{150}$ is H or acetyl. In other embodiments, R$^{148}$ is H, R$^{149}$ is H, and R$^{150}$ is H. In some embodiments, R$^{148}$ is H, R$^{149}$ is H, and R$^{150}$ is acetyl. In some embodiments, R$^{148}$ is H, R$^{149}$ is C$_{1-6}$ alkyl optionally substituted with one or more substituents each independently selected from the group consisting of hydroxyl, —COOH, —NH$_2$, —C(O)NH$_2$, and —N(H)C(O)NH$_2$, and R$^{150}$ is H. In some embodiments, R$^{148}$ is H, R$^{149}$ is C$_{1-6}$ alkyl substituted with hydroxyl, and R$^{150}$ is H. In some embodiments, R$^{148}$ is H, R$^{149}$ is C$_{1-6}$ alkyl substituted with —COOH, and R$^{150}$ is H. In some embodiments, R$^{148}$ is H, R$^{149}$ is C$_{1-6}$ alkyl substituted with —NH$_2$, and R$^{150}$ is H. In some embodiments, R$^{148}$ is H, R$^{149}$ is C$_{1-6}$ alkyl substituted with —C(O)NH$_2$, and R$^{150}$ is H. In some embodiments, R$^{148}$ is H, R$^{149}$ is C$_{1-6}$ alkyl substituted with —N(H)C(O)NH$_2$, and R$^{150}$ is H.

In some embodiments, R$^4$ is —C$_{1-6}$ alkylene-(C$_{6-10}$ arylene)-CN. In other embodiments, R$^4$ is —C$_{1-2}$ alkylene-(C$_6$ arylene)-CN. In other embodiments, R$^4$ is —C$_1$ alkylene-(C$_6$ arylene)-CN. In some embodiments, R$^4$ is

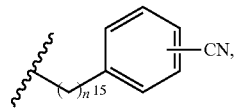

wherein n$^{15}$ is 0, 1, 2, 3, or 4. In other embodiments, n$^{15}$ is 1 or 2. In some embodiments, R$^4$ is

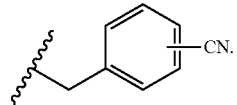

In some embodiments, R$^4$ is selected from the group consisting of:

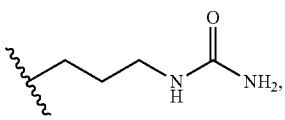 [SMILES: *CCCNC(N)=O]

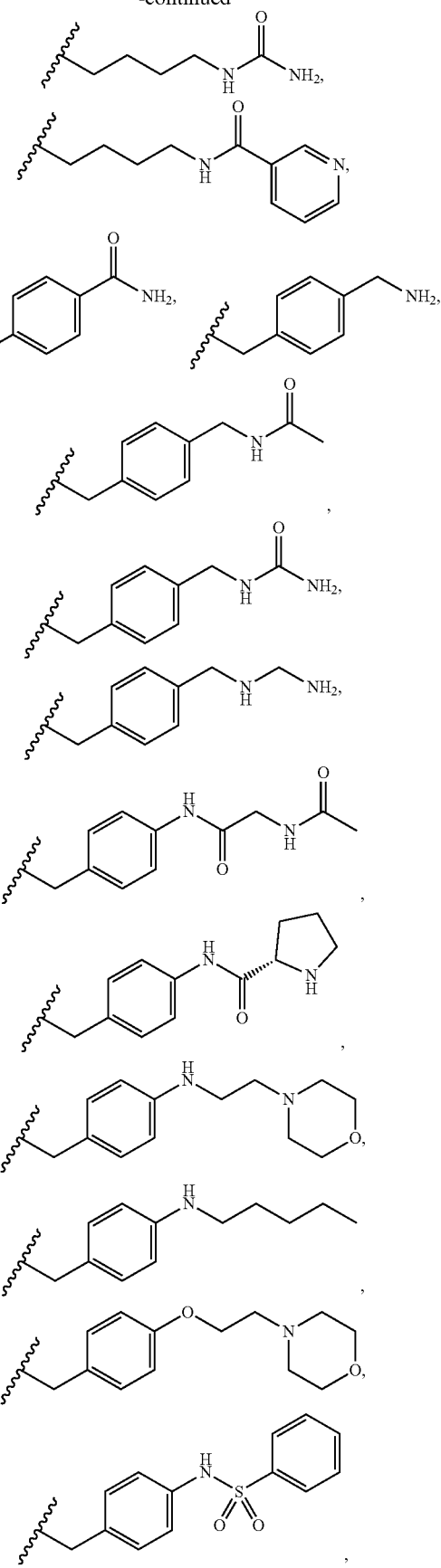

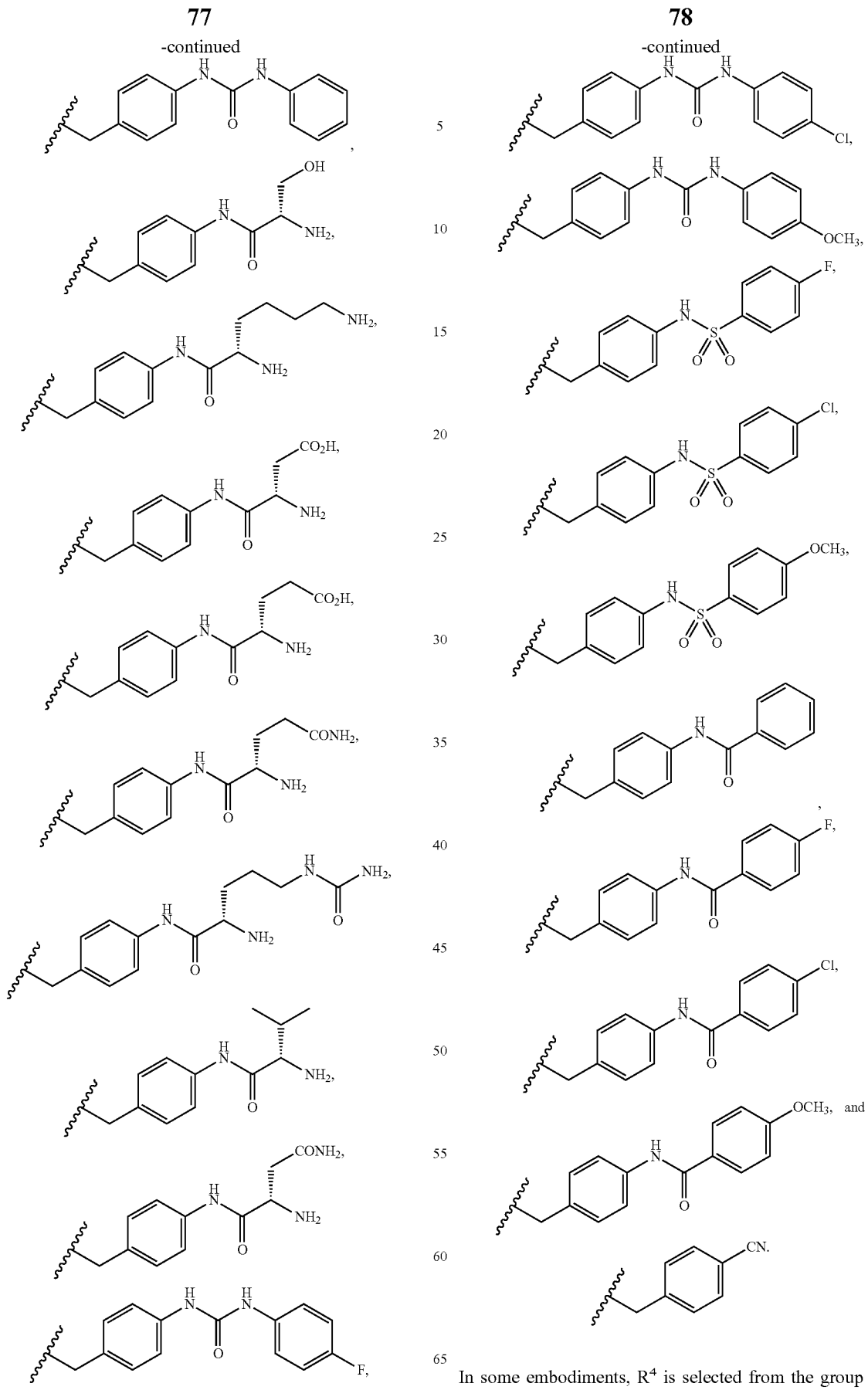
In some embodiments, $R^4$ is selected from the group consisting of:

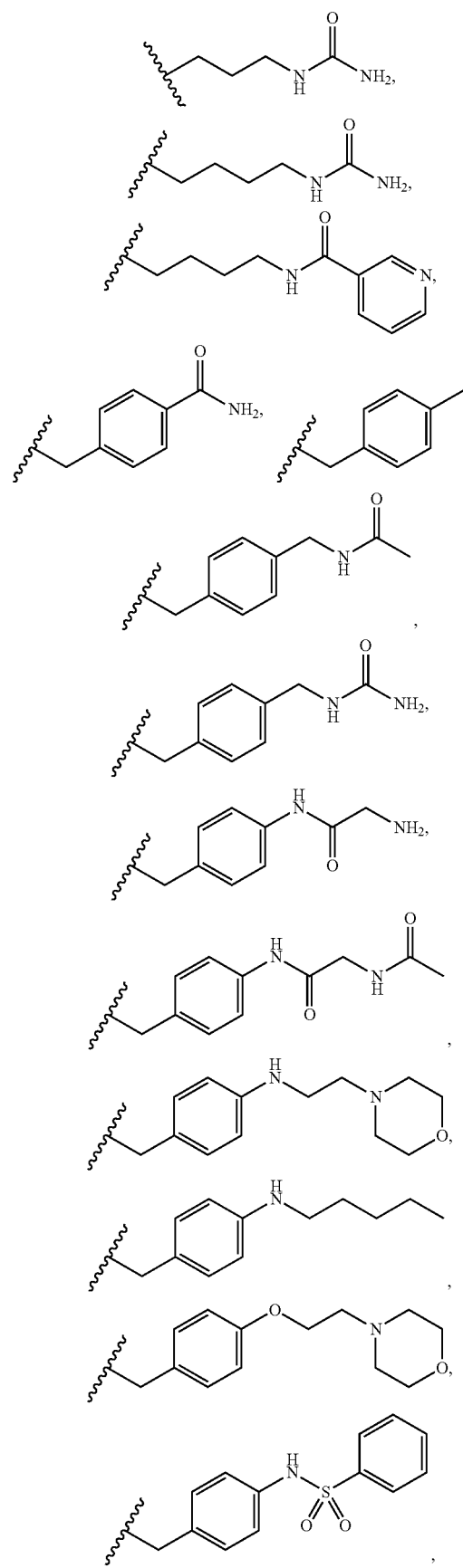
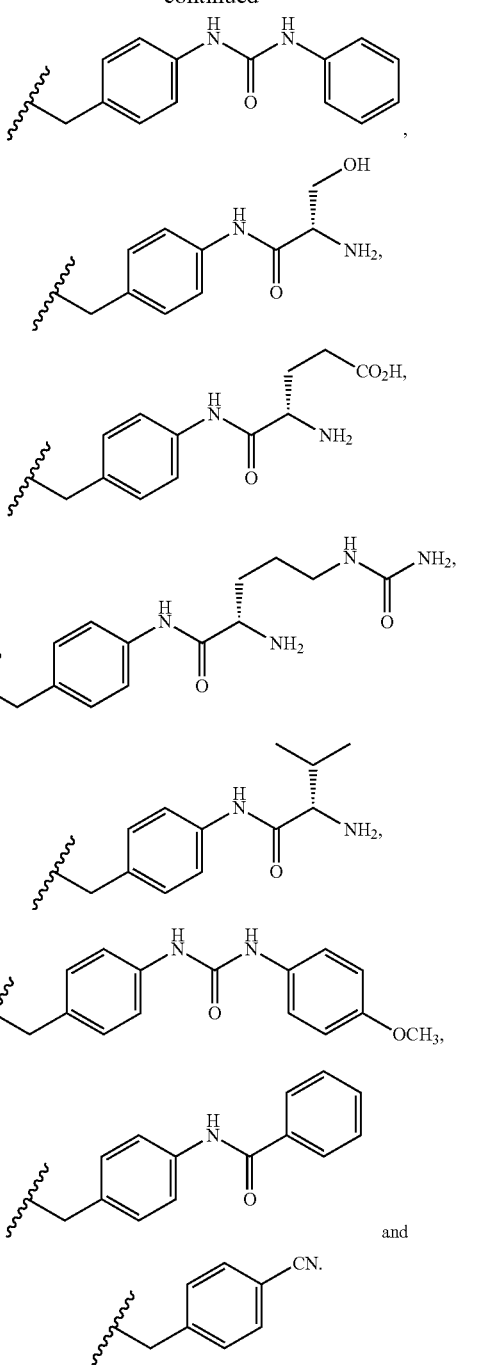
In some embodiments, R[4] is selected from the group consisting of:
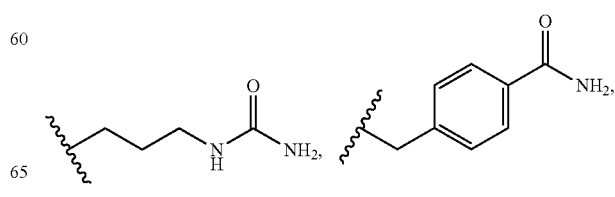

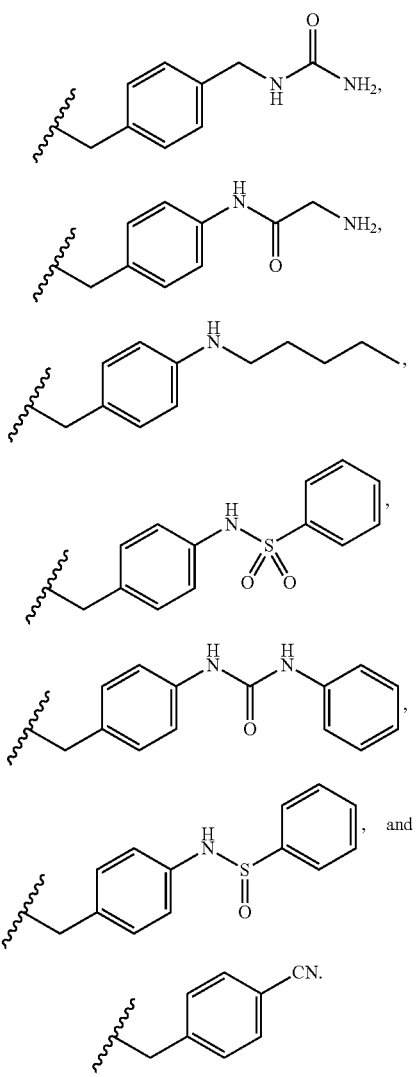
In some embodiments, R⁴ is selected from the group consisting of:
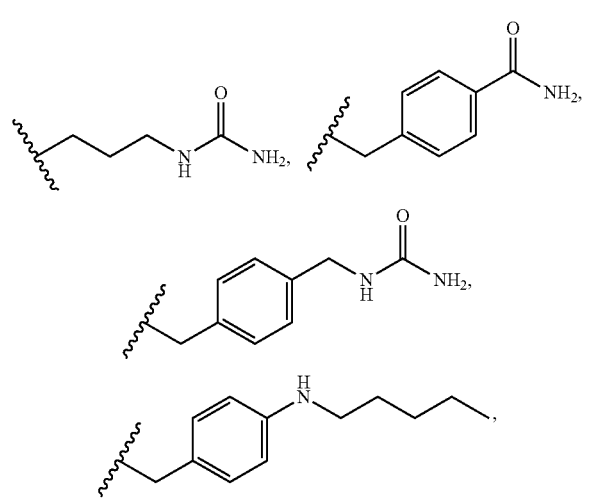
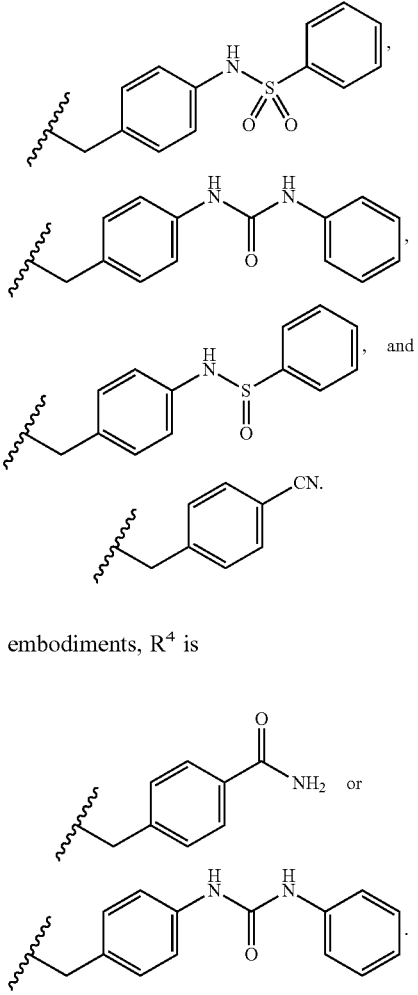
In some embodiments, R⁴ is
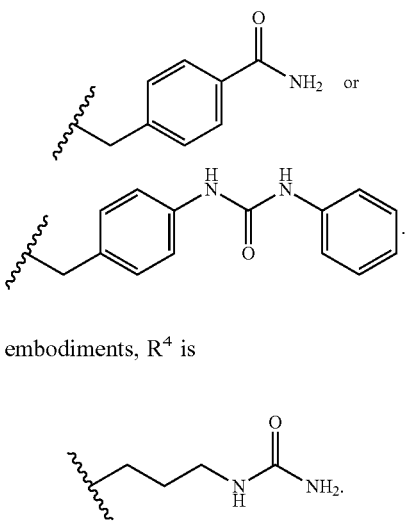
In some embodiments, R⁴ is
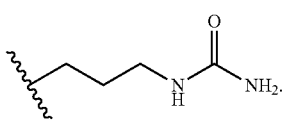
In some embodiments, R⁴ is
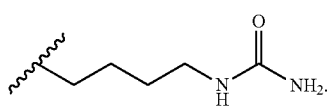 [SMILES: *CCCCNC(N)=O]
In some embodiments, R⁴ is
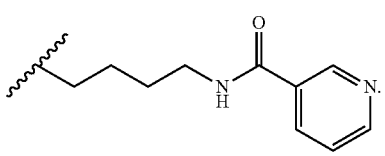 [SMILES: *CCCCNC(=O)c1cccnc1]

In some embodiments, R⁴ is
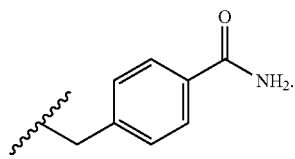 [SMILES: *Cc1ccc(C(N)=O)cc1]
In some embodiments, R⁴ is
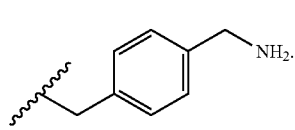 [SMILES: *Cc1ccc(CN)cc1]
In some embodiments, R⁴ is
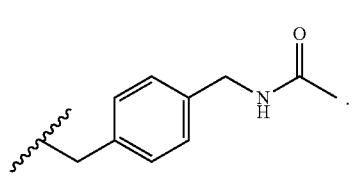 [SMILES: *Cc1ccc(CNC(C)=O)cc1]
In some embodiments, R⁴ is
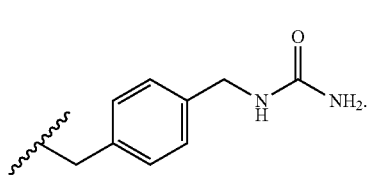 [SMILES: *Cc1ccc(CNC(N)=O)cc1]
In some embodiments, R⁴ is
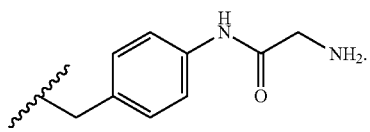 [SMILES: *Cc1ccc(NC(=O)CN)cc1]
In some embodiments, R⁴ is
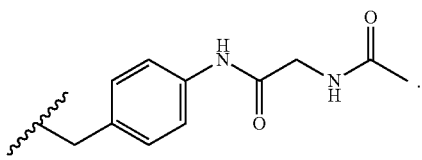 [SMILES: *Cc1ccc(NC(=O)CNC(C)=O)cc1]
In some embodiments, R⁴ is
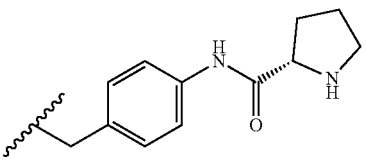
In some embodiments, R⁴ is
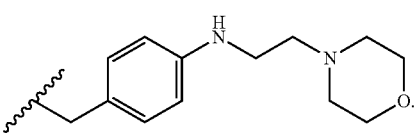 [SMILES: *Cc1ccc(NCCN2CCOCC2)cc1]
In some embodiments, R⁴ is
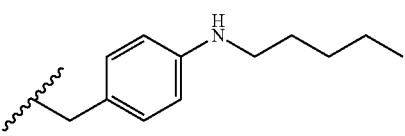
In some embodiments, R⁴ is
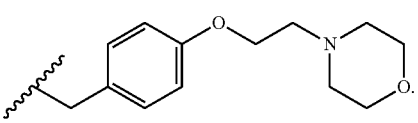 [SMILES: *Cc1ccc(OCCN2CCOCC2)cc1]
In some embodiments, R⁴ is
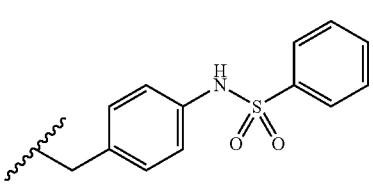
In some embodiments, R⁴ is
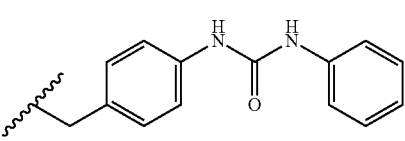
In some embodiments, R⁴ is
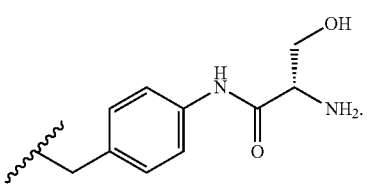 [SMILES: *Cc1ccc(NC(=O)[C@@H](N)CO)cc1]

In some embodiments, $R^4$ is
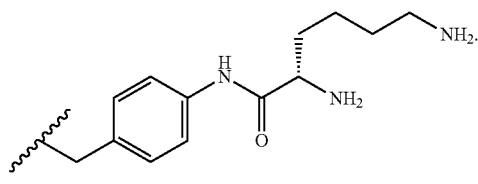 [SMILES: *Cc1ccc(NC(=O)[C@@H](N)CCCCN)cc1]
In some embodiments, $R^4$ is
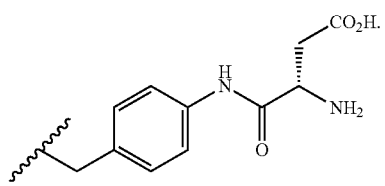 [SMILES: *Cc1ccc(NC(=O)[C@@H](N)CC(=O)O)cc1]
In some embodiments, $R^4$ is
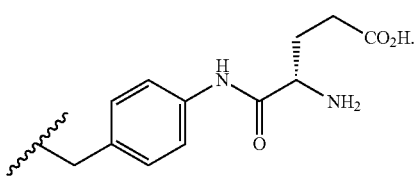 [SMILES: *Cc1ccc(NC(=O)[C@@H](N)CCC(=O)O)cc1]
In some embodiments, $R^4$ is
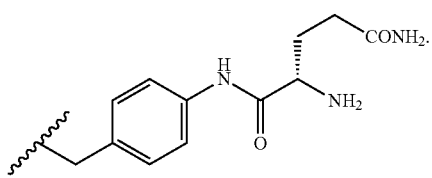 [SMILES: *Cc1ccc(NC(=O)[C@@H](N)CCC(N)=O)cc1]
In some embodiments, $R^4$ is
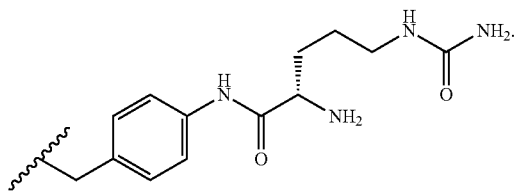 [SMILES: *Cc1ccc(NC(=O)[C@@H](N)CCCNC(N)=O)cc1]
In some embodiments, $R^4$ is
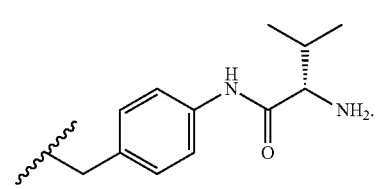 [SMILES: *Cc1ccc(NC(=O)[C@@H](N)C(C)C)cc1]
In some embodiments, $R^4$ is
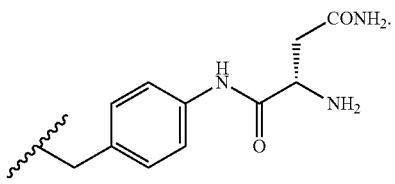 [SMILES: *Cc1ccc(NC(=O)[C@@H](N)CC(N)=O)cc1]
In some embodiments, $R^4$ is
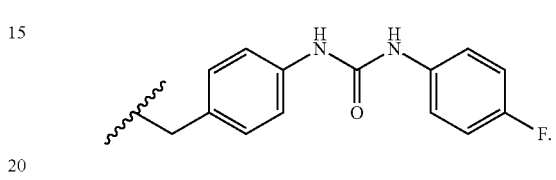
In some embodiments, $R^4$ is
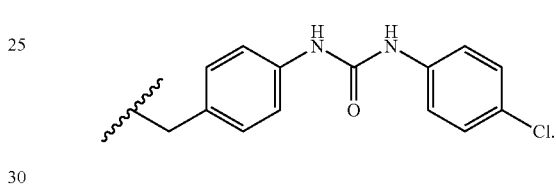
In some embodiments, $R^4$ is
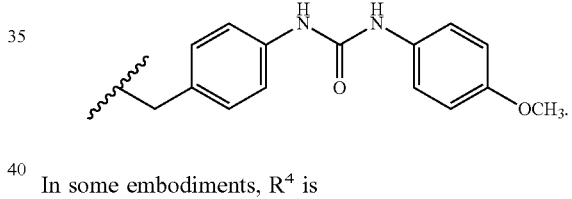
In some embodiments, $R^4$ is
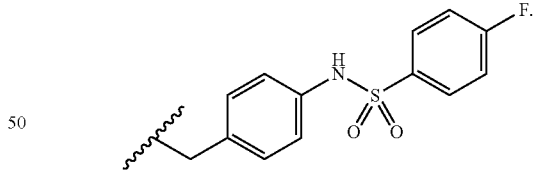
In some embodiments, $R^4$ is
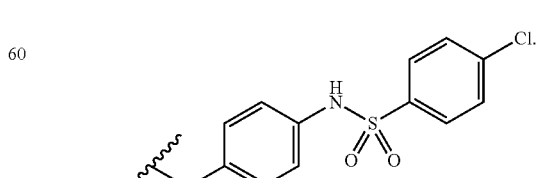

In some embodiments, R⁴ is

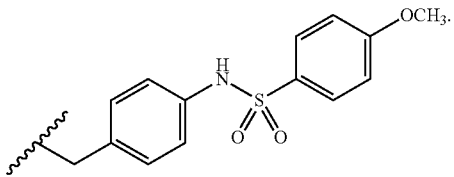 [SMILES: *Cc1ccc(NS(=O)(=O)c2ccc(OC)cc2)cc1]

In some embodiments, R⁴ is

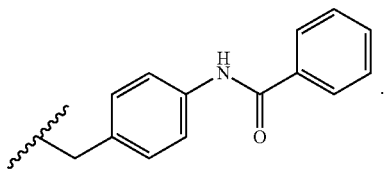 [SMILES: *Cc1ccc(NC(=O)c2ccccc2)cc1]

In some embodiments, R⁴ is

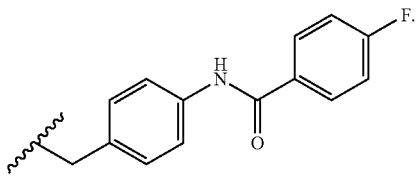 [SMILES: *Cc1ccc(NC(=O)c2ccc(F)cc2)cc1]

In some embodiments, R⁴ is

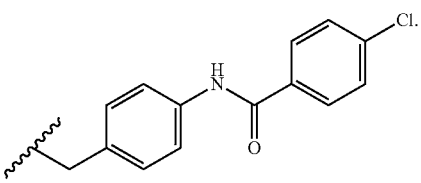 [SMILES: *Cc1ccc(NC(=O)c2ccc(Cl)cc2)cc1]

In some embodiments, R⁴ is

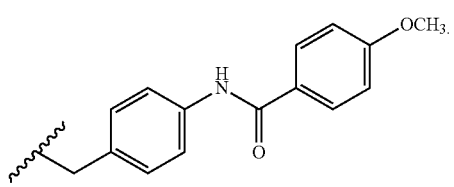 [SMILES: *Cc1ccc(NC(=O)c2ccc(OC)cc2)cc1]

In some embodiments, R⁴ is

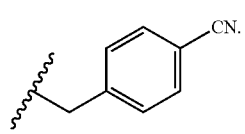 [SMILES: *Cc1ccc(C#N)cc1]

Embodiments of R⁵ and n¹

In some embodiments, R⁵ is selected from the group consisting of:

(i) —NR⁷⁹R⁸⁰, wherein each of R⁷⁹ and R⁸⁰ is independently selected from the group consisting of H, $C_{1-6}$ alkyl, —C(O)R⁸¹, and —C(=NR⁸²)NR⁸³R⁸⁴, or R⁷⁹ and R⁸⁰, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, R⁸¹ is selected from the group consisting of H, —NH₂, $C_{1-16}$ alkyl, $C_{1-6}$ haloalkyl, $C_{6-10}$ aryl, and 5- to 10-membered heteroaryl; and each of R⁸², R⁸³, and R⁸⁴ is independently selected from the group consisting of H, $C_{1-16}$ alkyl, $C_{1-6}$ haloalkyl, $C_{6-10}$ aryl, and 5- to 10-membered heteroaryl; and (ii) —N⁺R⁸⁵R⁸⁶R⁸⁷, wherein each of R⁸⁵, R⁸⁶, and R⁸⁷ is independently $C_{1-6}$ alkyl.

In some embodiments, R⁵ is selected from the group consisting of:

(i) —NR⁷⁹R⁸⁰, wherein each of R⁷⁹ and R⁸⁰ is independently selected from the group consisting of H, $C_{1-6}$ alkyl, —C(O)R⁸¹, and —C(=NR⁸²)NR⁸³R⁸⁴, or R⁷⁹ and R⁸⁰, together with the N atom to which they are attached, form 5- to 10-membered heteroaryl or 5- to 10-membered heterocycloalkyl, wherein the $C_{1-6}$ alkyl is optionally substituted with one or more substituents each independently selected from the group consisting of halogen, —OH, —NO₂, $C_{1-6}$ alkoxy, $C_{1-6}$ haloalkoxy, —NH₂, —NH($C_{1-6}$ alkyl), —N($C_{1-6}$ alkyl)₂, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR²⁰⁰ wherein R²⁰⁰ is $C_{1-6}$ alkyl or $C_{6-10}$ aryl, —CO₂R²⁰¹ wherein R²⁰¹ is H or $C_{1-6}$ alkyl, —CONR²⁰²R²⁰³ wherein R²⁰² and R²⁰³ is H or $C_{1-6}$ alkyl, —NR²⁰⁴COR²⁰⁵ wherein R²⁰⁴ is H or $C_{1-6}$ alkyl and R²⁰⁵ is $C_{1-6}$ alkyl, —SO₂NR²⁰⁶R²⁰⁷ wherein R²⁰⁶ and R²⁰⁷ is H or $C_{1-6}$ alkyl, and —NR²⁰⁸SO₂R²⁰⁹ wherein R²⁰⁸ is H or $C_{1-6}$ alkyl and R²⁰⁹ is $C_{1-6}$ alkyl, and wherein the 5- to 10-membered heteroaryl and 5- to 10-membered heterocycloalkyl are optionally substituted with one or more substituents each independently selected from the group consisting of halogen, —OH, —NO₂, $C_{1-6}$ alkoxy, $C_{1-6}$ haloalkoxy, —NH₂, —NH($C_{1-6}$ alkyl), —N($C_{1-6}$ alkyl)₂, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —COR²⁰⁰ wherein R²⁰⁰ is $C_{1-6}$ alkyl or $C_{6-10}$ aryl, —CO₂R²⁰¹ wherein R²⁰¹ is H or $C_{1-6}$ alkyl, —CONR²⁰²R²⁰³ wherein R²⁰² and R²⁰³ is H or $C_{1-6}$ alkyl, —NR²⁰⁴COR²⁰⁵ wherein R²⁰⁴ is H or $C_{1-6}$ alkyl and R²⁰⁵ is $C_{1-6}$ alkyl, —SO₂NR²⁰⁶R²⁰⁷ wherein R²⁰⁶ and R²⁰⁷ is H or $C_{1-6}$ alkyl, and —NR²⁰⁸SO₂R²⁰⁹ wherein R²⁰⁸ is H or $C_{1-6}$ alkyl and R²⁰⁹ is $C_{1-6}$ alkyl, R⁸¹ is selected from the group consisting of H, —NH₂, $C_{1-16}$ alkyl, $C_{1-6}$ haloalkyl, $C_{6-10}$ aryl, and 5- to 10-membered heteroaryl; and each of R⁸², R⁸³, and R⁸⁴ is independently selected from the group consisting of H, $C_{1-16}$ alkyl, $C_{1-6}$ haloalkyl, $C_{6-10}$ aryl, and 5- to 10-membered heteroaryl; and (ii) —N⁺R⁸⁵R⁸⁶R⁸⁷, wherein each of R⁸⁵, R⁸⁶, and R⁸⁷ is independently $C_{1-6}$ alkyl.

In other embodiments, R⁵ is —NR⁷⁹R⁸⁰, wherein:

each of R⁷⁹ and R⁸⁰ is independently selected from the group consisting of H, $C_{1-6}$ alkyl, —C(O)R⁸¹, and —C(=NR⁸²)NR⁸³R⁸⁴, or R⁷⁹ and R⁸⁰, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, $R^{81}$ is selected from the group consisting of H, —$NH_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl.

In other embodiments, $R^5$ is —$NR^{79}R^{80}$, wherein:
each of $R^{79}$ and $R^{80}$ is independently selected from the group consisting of H, $C_{1-6}$ alkyl, —$C(O)R^{81}$, and —$C(=NR^{82})NR^{83}R^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —$NH(C_{1-6}$ alkyl), —$N(C_{1-6}$ alkyl$)_2$, —$C_{1-6}$ alkyl, halo$C_{1-6}$ alkyl, amino$C_{1-6}$ alkyl, $C_{6-10}$ aryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the 5- to 10-membered heteroaryl and 5- to 10-membered heterocycloalkyl are optionally substituted with one or more substituents each independently selected from the group consisting of halogen, —OH, —$NO_2$, $C_{1-6}$ alkoxy, $C_{1-6}$ haloalkoxy, —$NH_2$, —$NH(C_{1-6}$ alkyl), —$N(C_{1-6}$ alkyl$)_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, $R^{81}$ is selected from the group consisting of H, —$NH_2$, $C_{1-16}$ alkyl, $C_{1-6}$ haloalkyl, $C_{6-10}$ aryl, and 5- to 10-membered heteroaryl; and
each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl.

In other embodiments, $R^5$ is —$NR^{79}R^{80}$, wherein each of $R^{79}$ and $R^{80}$ is independently selected from the group consisting of H and $C_{1-6}$ alkyl, wherein the $C_{1-6}$ alkyl is optionally substituted with one or more substituents each independently selected from the group consisting of halogen, —OH, —$NO_2$, $C_{1-6}$ alkoxy, $C_{1-6}$ haloalkoxy, —$NH_2$, —$NH(C_{1-6}$ alkyl), —$N(C_{1-6}$ alkyl$)_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl. In other embodiments, $R^5$ is —$NR^{79}R^{80}$, wherein each of $R^{79}$ and $R^{80}$ is H. In other embodiments, $R^5$ is —$NR^{79}R^{80}$, wherein each of $R^{79}$ and $R^{80}$ is independently $C_{1-6}$ alkyl. In other embodiments, $R^5$ is —$NR^{79}R^{80}$, wherein each of $R^{79}$ and $R^{80}$ is independently $C_{1-3}$ alkyl. In other embodiments, $R^5$ is —$NR^{79}R^{80}$, wherein each of $R^{79}$ and $R^{80}$ is $CH_3$. In other embodiments, $R^5$ is —$NR^{79}R^{80}$, wherein $R^{79}$ is H and $R^{80}$ is $C_{1-6}$ alkyl. In other embodiments, $R^5$ is —$NR^{79}R^{80}$, wherein $R^{79}$ is H and $R^{80}$ is $C_{1-3}$ alkyl. In other embodiments, $R^5$ is —$NR^{79}R^{80}$, wherein $R^{79}$ is H and $R^{80}$ is $CH_3$.

In other embodiments, $R^5$ is —$NR^{79}R^{80}$, wherein each of $R^{79}$ and $R^{80}$ is independently selected from the group consisting of H and —$C(O)R^{81}$, wherein $R^{81}$ is selected from the group consisting of H, —$NH_2$, $C_{1-16}$ alkyl, $C_{1-6}$ haloalkyl, $C_{6-10}$ aryl, and 5- to 10-membered heteroaryl. In other embodiments, $R^5$ is —$NR^{79}R^{80}$, wherein each of $R^{79}$ and $R^{80}$ is independently selected from the group consisting of H and —$C(=NR^{82})NR^{83}R^{84}$, wherein each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl. In some embodiments, $R^5$ is —$NR^{79}R^{80}$ and each of $R^{79}$ and $R^{80}$ is independently selected from the group consisting of H, $C_{1-6}$ alkyl, —$C(O)R^{81}$, and —$C(=NR^{82})NR^{83}R^{84}$, wherein $R^{81}$ is $C_{1-6}$ alkyl and each of $R^{82}$, $R^{83}$, and $R^{84}$ is H. In other embodiments, $R^5$ is —$NR^{79}R^{80}$ and each of $R^{79}$ and $R^{80}$ is independently selected from the group consisting of H and $C_{1-6}$ alkyl. In some embodiments, $R^5$ is —$NH_2$, —$NHCH_3$ or —$N(CH_3)_2$. In other embodiments, $R^5$ is —$NH_2$. In some embodiments, $R^5$ is —$NHCH_3$. In some embodiments, $R^5$ is —$N(CH_3)_2$. In other embodiments, $R^5$ is —$NR^{79}R^{80}$, wherein $R^{79}$ and $R^{80}$, together with the N atom to which they are attached, form 5- to 10-membered heteroaryl or 5- to 10-membered heterocycloalkyl, wherein the 5- to 10-membered heteroaryl and 5- to 10-membered heterocycloalkyl are optionally substituted with one or more substituents each independently selected from the group consisting of halogen, —OH, —$NO_2$, $C_{1-6}$ alkoxy, $C_{1-6}$ haloalkoxy, —$NH_2$, —$NH(C_{1-6}$ alkyl), —$N(C_{1-6}$ alkyl$)_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl. In some embodiments, $R^5$ is —$N^+R^{85}R^{86}R^{87}$, wherein each of $R^{85}$, $R^{86}$, and $R^{87}$ is independently $C_{1-6}$ alkyl. In other embodiments, each of $R^{85}$, $R^{86}$, and $R^{87}$ is independently $C_{1-3}$ alkyl. In other embodiments, each of $R^{85}$, $R^{86}$, and $R^{87}$ is $CH_3$. In some embodiments, $n^1$ is 1, 2, 3, 4, 5, or 6. In some embodiments, $n^1$ is 2, 3, 4, 5, or 6. In some embodiments, $n^1$ is 2, 3, 4, or 5. In some embodiments, $n^1$ is 3, 4, or 5. In some embodiments, $n^1$ is 3 or 4. In some embodiments, $n^1$ is 1. In some embodiments, $n^1$ is 2. In some embodiments, $n^1$ is 3. In some embodiments, $n^1$ is 4. In some embodiments, $n^1$ is 5. In some embodiments, $n^1$ is 6.

Embodiments of $R^6$

In some embodiments, $R^6$ is alkyl optionally substituted with one or more substituents. In other embodiments, $R^6$ is $C_{1-6}$ alkyl optionally substituted with one or more substituents. In some embodiments, $R^6$ is $C_{1-6}$ alkyl optionally substituted with one or more substituents each independently selected from the group consisting of halogen, hydroxy, —$NO_2$, and $C_{1-6}$ alkoxy. In some embodiments, $R^6$ is $C_{1-6}$ alkyl optionally substituted with hydroxy. In other embodiments, $R^6$ is $C_{1-5}$ alkyl optionally substituted with hydroxy. In some embodiments, $R^6$ is $C_{1-4}$ alkyl optionally substituted with hydroxy. In some embodiments, $R^6$ is $C_{1-3}$ alkyl optionally substituted with hydroxy. In some embodiments, $R^6$ is $C_{1-2}$ alkyl optionally substituted with hydroxy. In some embodiments, $R^6$ is selected from the group consisting of —$CH_2CH_2CH_2CH_3$, —$CH(CH_3)CH_2CH_3$, —$CH_2CH(CH_3)_2$, —$CH_2CH_2CH_3$, —$CH(CH_3)CH_2OH$, —$CH(CH_3)_2$, —$C(CH_3)_3$, —$CH(CH_3)OH$, and —$CH_2CH_3$. In other embodiments, $R^6$ is selected from the group consisting of —$CH(CH_3)OH$, —$CH(CH_3)_2$, —$C(CH_3)_3$, —$CH_2OOH$ and —$CH_2CH_3$. In some embodiments, $R^6$ is selected from the group consisting of —$CH(CH_3)OH$, —$CH(CH_3)_2$, —$C(CH_3)_3$, and —$CH_2CH_3$. In some embodiments, $R^6$ is —$CH(CH_3)OH$. In some embodiments, $R^6$ is —$CH(CH_3)_2$. In some embodiments, $R^6$ is —$C(CH_3)_3$. In some embodiments, $R^6$ is —$CH_2CH_3$. In some embodiments, $R^6$ is —$CH_2OH$.

Embodiments of $R^8$

In some embodiments, $R^8$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents.

In some embodiments, $R^8$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, and $C_{1-6}$ alkoxy.

In some embodiments, $R^8$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene (5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, and $C_{1-6}$ alkoxy, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, $C_{1-6}$ alkoxy, and $C_{6-10}$ aryl.

In some embodiments, $R^8$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents.

In some embodiments, $R^8$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents each independently selected from the group consisting of halogen, —OH, —$NO_2$, $C_{1-6}$ alkoxy, $C_{1-6}$ haloalkoxy, —$NH_2$, —NH($C_{1-6}$ alkyl), —N($C_{1-6}$ alkyl)$_2$, —$C_{1-6}$ alkyl, halo$C_{1-6}$ alkyl, amino$C_{1-6}$ alkyl, $C_{6-10}$ aryl, 5- to 10-membered heteroaryl, 5- to 10-membered heterocycloalkyl, $C_{5-10}$ cycloalkyl, azido, —CN, —$COR^{200}$ wherein $R^{200}$ is $C_{1-6}$ alkyl or $C_{6-10}$ aryl, —$CO_2R^{201}$ wherein $R^{201}$ is H or $C_{1-6}$ alkyl, —$CONR^{202}R^{203}$ wherein $R^{202}$ and $R^{203}$ is H or $C_{1-6}$ alkyl, —$NR^{204}COR^{205}$ wherein $R^{204}$ is H or $C_{1-6}$ alkyl and $R^{205}$ is $C_{1-6}$ alkyl, —$SO_2NR^{206}R^{207}$ wherein $R^{206}$ and $R^{207}$ is H or $C_{1-6}$ alkyl, and —$NR^{208}SO_2R^{209}$ wherein $R^{208}$ is H or $C_{1-6}$ alkyl and $R^{209}$ is $C_{1-6}$ alkyl.

In some embodiments, $R^8$ is selected from the group consisting of $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents each independently selected from the group consisting of halogen, —OH, —$NO_2$, and $C_{1-6}$ alkoxy, and wherein the $C_{1-6}$ alkylene of —$C_{1-6}$ alkylene($C_{6-10}$ aryl) and —$C_{1-6}$ alkylene (5- to 10-membered heteroaryl) is optionally substituted with one or more substituents each independently selected from the group consisting of halogen, —OH, —$NO_2$, $C_{1-6}$ alkoxy, and $C_{6-10}$ aryl.

In some embodiments, $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy, and wherein the $C_{1-3}$ alkylene is optionally substituted with one or more substituents each independently selected from the group consisting of $C_{6-10}$ aryl. In some embodiments, $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy.

In some embodiments, $R^8$ is —$C_{1-2}$ alkylene($C_{6-10}$ aryl), wherein the $C_{6-10}$ aryl is optionally substituted with one or more substituents each independently selected from the group consisting of halogen, hydroxyl, —$NO_2$, and $C_{1-6}$ alkoxy. In some embodiments, $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$. In some embodiments, $R^8$ is —$C_{1-2}$ alkylene($C_{6-10}$ aryl), wherein the $C_{6-10}$ aryl is optionally substituted with one or more substituents each independently selected from the group consisting of halogen and hydroxy. In some embodiments, $R^8$ is —$C_{1-2}$ alkylene($C_{6-10}$ aryl), wherein the $C_{6-10}$ aryl is optionally substituted with hydroxy. In other embodiments, $R^8$ is —$C_{1-2}$ alkylene($C_6$ aryl), wherein the $C_6$ aryl is optionally substituted with one or more substituents each independently selected from the group consisting of halogen, hydroxyl, —$NO_2$, and $C_{1-6}$ alkoxy.

In some embodiments, $R^8$ is —$CH_2$-phenyl or —$CH_2$-naphthyl, wherein phenyl or naphthyl may be optionally substituted with 1 or 2 substituents each independently selected from the group consisting of halogen, hydroxy, —$NO_2$, and $C_{1-6}$ alkoxy. In other embodiments, $R^8$ is —$CH_2$-phenyl or —$CH_2$-naphthyl, wherein the phenyl is optionally substituted with one or more substituents each independently selected from the group consisting of halogen, hydroxyl, and —$NO_2$. In some embodiments, $R^8$ is —$CH_2$-phenyl or —$CH_2$-naphthyl, wherein the phenyl is optionally substituted with one or more substituents each independently selected from the group consisting of halogen and hydroxyl. In some embodiments, $R^8$ is —$CH_2$-phenyl or —$CH_2$-naphthyl, wherein the phenyl is optionally substituted with hydroxyl.

In some embodiments, $R^8$ is —$CH_2$-phenyl, wherein phenyl may be optionally substituted with 1 or 2 substituents each independently selected from the group consisting of halogen, hydroxy, —$NO_2$, and $C_{1-6}$ alkoxy. In some embodiments, $R^8$ is —$CH_2$-phenyl, wherein phenyl may be optionally substituted with 1 or 2 substituents each independently selected from the group consisting of halogen, hydroxy, and —$NO_2$. In some embodiments, $R^8$ is —$CH_2$-phenyl, wherein phenyl is unsubstituted. In some embodiments, $R^8$ is —$CH_2$-phenyl, wherein phenyl is substituted with 1 or 2 substituents each independently selected from the group consisting of halogen, hydroxy, —$NO_2$, and $C_{1-6}$ alkoxy. In some embodiments, $R^8$ is —$CH_2$-phenyl, wherein phenyl is substituted with 1 or 2 substituents each independently selected from the group consisting of halogen, hydroxy, and —$NO_2$. In some embodiments, $R^8$ is —$CH_2$-phenyl, wherein phenyl is substituted with 1 or 2 substituents each independently selected from the group consisting of halogen and hydroxy.

In some embodiments, $R^8$ is —$CH_2$-phenyl, wherein phenyl is substituted with 1 or 2 substituents each independently selected from the group consisting of —F, —Cl, —Br, and —I. In some embodiments, $R^8$ is —$CH_2$-phenyl, wherein phenyl is substituted with 1 or 2 substituents each of which is —F. In some embodiments, $R^8$ is —$CH_2$-phenyl, wherein phenyl is substituted with 1 or 2 substituents each of which is —Cl. In some embodiments, $R^8$ is —$CH_2$-phenyl, wherein phenyl is substituted with 1 or 2 substituents each of which is —Br. In some embodiments, $R^8$ is —$CH_2$-phenyl, wherein phenyl is substituted with 1 or 2 substituents each of which is —I. In some embodiments, $R^8$ is —$CH_2$-phenyl, wherein phenyl is substituted with 1 substituent which is —F. In some embodiments, $R^8$ is —$CH_2$-phenyl, wherein phenyl is substituted with 1 substituent which is —Cl. In some embodiments, $R^8$ is —$CH_2$-phenyl, wherein phenyl is substituted with 1 substituent which is —Br. In some embodiments, $R^8$ is —$CH_2$-phenyl, wherein phenyl is substituted with 1 substituent which is —I.

In some embodiments, $R^8$ is —$CH_2$-phenyl, wherein phenyl is substituted with 1 or 2 substituents each of which is hydroxy. In some embodiments, $R^8$ is —$CH_2$-phenyl, wherein phenyl is substituted with 1 substituent which is hydroxy. In some embodiments, $R^8$ is —$CH_2$-phenyl, wherein phenyl is substituted with 1 or 2 substituents each of which is —$NO_2$. In some embodiments, $R^8$ is —$CH_2$-phenyl, wherein phenyl is substituted with 1 substituent which is —$NO_2$. In some embodiments, $R^8$ is —$CH_2$-phenyl, wherein phenyl is substituted with 1 or 2 substituents each of which is independently $C_{1-6}$ alkoxy. In some embodiments, $R^8$ is —$CH_2$-phenyl, wherein phenyl is substituted with 1 or 2 substituents each of which is independently $C_{1-3}$ alkoxy. In some embodiments, $R^8$ is —$CH_2$-phenyl, wherein phenyl is substituted with 1 substituent which is methoxy.

In some embodiments, $R^8$ is

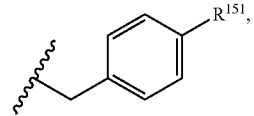

wherein $R^{151}$ is H, halogen, hydroxyl or $C_{1-3}$ alkoxy. In some embodiments, $R^{151}$ is H, halogen or hydroxyl. In some embodiments, $R^{151}$ is H, Cl or hydroxyl. In some embodiments, $R^{151}$ is Cl or hydroxyl. In some embodiments, $R^{151}$ is hydroxyl.

In some embodiments, $R^8$ is —$C_{1-2}$ alkylene($C_{10}$ aryl), wherein the $C_{10}$ aryl is optionally substituted with one or more substituents each independently selected from the group consisting of halogen, hydroxyl and —$NO_2$, and $C_{1-6}$ alkoxy. In some embodiments, $R^8$ is —$CH_2$-naphthyl.

In some embodiments, $R^8$ is selected from the group consisting of —$CH_2$-pyridinyl, —$CH_2$-indolyl, —$CH_2$-thiophenyl, —$CH_2$-thiazolyl, —$CH_2$-furanyl, —$CH_2$-benzothiophenyl, and —$CH_2$-imidazolyl. In some embodiments, $R^8$ is —CH$_2$-pyridinyl. In some embodiments, R$^8$ is —CH$_2$-indolyl. In some embodiments, R$^8$ is —CH$_2$-thiophenyl. In some embodiments, R$^8$ is —CH$_2$-thiazolyl. In some embodiments, R$^8$ is —CH$_2$-furanyl. In some embodiments, R$^8$ is —CH$_2$-benzothiophenyl. In some embodiments, R$^8$ is —CH$_2$-imidazolyl.

Embodiments of R$^9$, R$^{10}$, R$^{11}$, R$^{12}$, R$^{13}$, R$^{14}$ and R$^{15}$ In some embodiments, R$^9$ is H or C$_{1-6}$ alkyl. In other embodiments, R$^9$ is H or C$_{1-5}$ alkyl. In some embodiments, R$^9$ is H or C$_{1-4}$ alkyl. In some embodiments, R$^9$ is H or C$_{1-3}$ alkyl. In other embodiments, R$^9$ is H or C$_{1-2}$ alkyl. In some embodiments, R$^9$ is H or CH$_3$. In some embodiments, R$^9$ is H. In other embodiments, R$^9$ is CH$_3$. In some embodiments, R$^{10}$ is H or C$_{1-6}$ alkyl. In other embodiments, R$^{10}$ is H or C$_{1-5}$ alkyl. In some embodiments, R$^{10}$ is H or C$_{1-4}$ alkyl. In some embodiments, R$^{10}$ is H or C$_{1-3}$ alkyl. In other embodiments, R$^{10}$ is H or C$_{1-2}$ alkyl. In some embodiments, R$^{10}$ is H or CH$_3$. In some embodiments, R$^{10}$ is H. In other embodiments, R$^{10}$ is CH$_3$. In some embodiments, R$^{11}$ is H or C$_{1-6}$ alkyl. In other embodiments, R$^{11}$ is H or C$_{1-5}$ alkyl. In some embodiments, R$^{11}$ is H or C$_{1-4}$ alkyl. In some embodiments, R$^{11}$ is H or C$_{1-3}$ alkyl. In other embodiments, R$^{11}$ is H or C$_{1-2}$ alkyl. In some embodiments, R$^{11}$ is H or CH$_3$. In some embodiments, R$^{11}$ is H. In other embodiments, R$^{11}$ is CH$_3$. In some embodiments, R$^{12}$ is H or C$_{1-6}$ alkyl. In other embodiments, R$^{12}$ is H or C$_{1-5}$ alkyl. In some embodiments, R$^{12}$ is H or C$_{1-4}$ alkyl. In some embodiments, R$^{12}$ is H or C$_{1-3}$ alkyl. In other embodiments, R$^{12}$ is H or C$_{1-2}$ alkyl. In some embodiments, R$^{12}$ is H or CH$_3$. In some embodiments, R$^{12}$ is H. In other embodiments, R$^{12}$ is CH$_3$. In some embodiments, R$^{13}$ is H or C$_{1-6}$ alkyl. In other embodiments, R$^{13}$ is H or C$_{1-5}$ alkyl. In some embodiments, R$^{13}$ is H or C$_{1-4}$ alkyl. In some embodiments, R$^{13}$ is H or C$_{1-3}$ alkyl. In other embodiments, R$^{13}$ is H or C$_{1-2}$ alkyl. In some embodiments, R$^{13}$ is H or CH$_3$. In some embodiments, R$^{13}$ is H. In other embodiments, R$^{13}$ is CH$_3$. In some embodiments, R$^{14}$ is H or C$_{1-6}$ alkyl. In other embodiments, R$^{14}$ is H or C$_{1-5}$ alkyl. In some embodiments, R$^{14}$ is H or C$_{1-4}$ alkyl. In some embodiments, R$^{14}$ is H or C$_{1-3}$ alkyl. In other embodiments, R$^{14}$ is H or C$_{1-2}$ alkyl. In some embodiments, R$^{14}$ is H or CH$_3$. In some embodiments, R$^{14}$ is H. In other embodiments, R$^{14}$ is CH$_3$. In some embodiments, R$^{15}$ is H or C$_{1-6}$ alkyl. In other embodiments, R$^{15}$ is H or C$_{1-5}$ alkyl. In some embodiments, R$^{15}$ is H or C$_{1-4}$ alkyl. In some embodiments, R$^{15}$ is H or C$_{1-3}$ alkyl. In other embodiments, R$^{15}$ is H or C$_{1-2}$ alkyl. In some embodiments, R$^{15}$ is H or CH$_3$. In some embodiments, R$^{15}$ is H. In other embodiments, R$^{15}$ is CH$_3$. In other embodiments, each of R$^9$, R$^{10}$, R$^{11}$, R$^{12}$, R$^{13}$, R$^{14}$ and R$^{15}$ is independently H or CH$_3$. In some embodiments, each of R$^9$, R$^{10}$, R$^{11}$, R$^{12}$, R$^{13}$, R$^{14}$ and R$^{15}$ is H.

Embodiments of L

In some embodiments, L is selected from the group consisting of:

i)
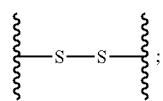 [SMILES: *SS*]

ii)
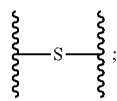

iii)
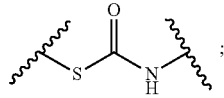 [SMILES: *NC(=O)S*]

iv)
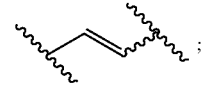

v)
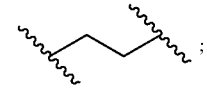

vi)
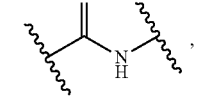

wherein X is S or O; and vii)
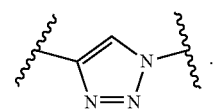

For each L moiety, either point of attachment may bond to either of the two carbon atoms on the remainder of the compound of Formula I or II to which L is bonded (as set out in Formula I or II above) provided that they are not bonded to the same carbon atom. In other words, the L moieties set out herein are able to bond to the remainder of the compound of Formula I or II in either direction. In some embodiments, L is

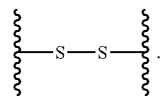

L may be made using techniques known to a person of skill in the art. For example, when L is

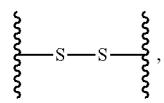

suitable methods are described in Lin Chen, L., et al., "Disulfide Bond Formation in Peptides", *Current Protocols in Protein Science* (2001) 18.6.1-18.6.19, John Wiley & Sons, Inc. In some embodiments, L is

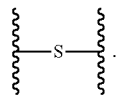

When L is

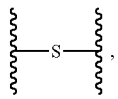

suitable methods are described in, Rew, Y., et al. "Synthesis and Biological Activities of Cyclic Lanthionine Enkephalin Analogues: δ-Opioid Receptor Selective Ligands", *J. Med. Chem.*, 2002, 45 (17), pp 3746-3754; Bregant S., et al., "Orthogonally Protected Lanthionines: Synthesis and Use for the Solid-Phase Synthesis of an Analogue of Nisin Ring C'", *J. Org. Chem.*, 2005, 70 (7), pp 2430-2438; and Dugave, C., et al., "Synthesis of natural and non natural orthogonally protected lanthionines from N-tritylserine and allo-threonine derivatives", Tetrahedron: Asymmetry, Volume 8, Number 9, 8 May 1997, pp. 1453-1465(13). In some embodiments, L is

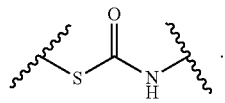

When L is

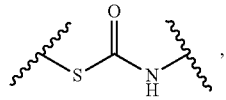

suitable methods are described in Besret, S., et al., "Thiocarbamate-linked peptides by chemoselective peptide ligation", Journal of Peptide Science Volume 14, Issue 12, pages 1244-1250, December 2008. In some embodiments, L is

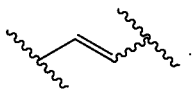

In some embodiments, L is

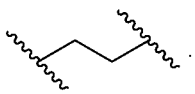 [SMILES: *CC*]

When L is

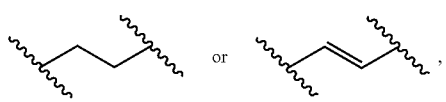

suitable methods are described in Stymiest, J. L., et al., "Synthesis of Biologically Active Dicarba Analogues of the Peptide Hormone Oxytocin Using Ring-Closing Metathesis", *Org. Lett.*, 2003, 5 (1), pp 47-49. In some embodiments, L is

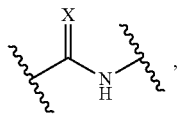

wherein X is S or O. In some embodiments, L is

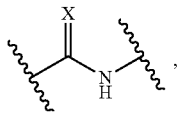

wherein X is S. In some embodiments, L is

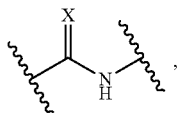

wherein X is O. In some embodiments, L is

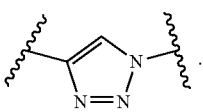 [SMILES: *c1cn(*)nn1]

When L is

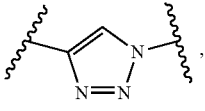

suitable methods are described in Holland-Nell, K., et al., "Maintaining Biological Activity by Triazoles as Disufide Bond Mimetics", *Angewandte Chemie Int Ed* 2011, 50, 5204-5206.

Embodiments of Chiral Centres *1, *2, *3, *4, *5, *6, *7, and *8

In some embodiments, chiral centre *1 is in the S configuration or the R configuration. In some embodiments, chiral centre *1 is in the S configuration. In some embodiments, chiral centre *1 is in the R configuration. In some embodiments, chiral centre *2 is in the S configuration or the R configuration. In some embodiments, chiral centre *2 is in the S configuration. In some embodiments, chiral centre *2 is in the R configuration. In some embodiments, chiral centre *3 is in the S configuration or the R configuration. In some embodiments, chiral centre *3 is in the S configuration. In some embodiments, chiral centre *3 is in the R configuration. In some embodiments, chiral centre *4 is in the S configuration or the R configuration. In some embodiments, chiral centre *4 is in the S configuration. In some embodiments, chiral centre *4 is in the R configuration. In some embodiments, chiral centre *5 is in the S configuration or the R configuration. In some embodiments, chiral centre *5 is in the S configuration. In some embodiments, chiral centre *5 is in the R configuration. In some embodiments, chiral centre *6 is in the S configuration or the R configuration. In some embodiments, chiral centre *6 is in the S configuration. In some embodiments, chiral centre *6 is in the R configuration. In some embodiments, chiral centre *7 is in the S configuration or the R configuration. In some embodiments, chiral centre *7 is in the S configuration. In some embodiments, chiral centre *7 is in the R configuration. In some embodiments, chiral centre *8 is in the S configuration or the R configuration. In some embodiments, chiral centre *8 is in the S configuration. In some embodiments, chiral centre *8 is in the R configuration. In some embodiments, chiral centre *1 is in the S configuration or the R configuration, chiral centre *2 is in the S configuration or the R configuration, chiral centre *3 is in the S configuration or the R configuration, chiral centre *4 is in the S configuration or the R configuration, chiral centre *5 is in the S configuration or the R configuration, chiral centre *6 is in the S configuration or the R configuration, chiral centre *7 is in the S configuration or the R configuration, and chiral centre *8 is in the S configuration or the R configuration. In some embodiments, chiral centre *1 is in the S configuration or the R configuration, chiral centre *2 is in the S configuration, chiral centre *3 is in the S configuration or the R configuration, chiral centre *4 is in the S configuration or the R configuration, chiral centre *5 is in the S configuration, chiral centre *6 is in the S configuration or the R configuration, chiral centre *7 is in the R configuration, and chiral centre *8 is in the S configuration or the R configuration. In some embodiments, chiral centre *1 is in the S configuration or the R configuration, chiral centre *2 is in the S configuration or the R configuration, chiral centre *3 is in the S configuration or the R configuration, chiral centre *4 is in the S configuration or the R configuration, chiral centre *5 is in the S configuration, chiral centre *6 is in the S configuration or the R configuration, chiral centre *7 is in the R configuration, and chiral centre *8 is in the S configuration or the R configuration. In some embodiments, chiral centre *1 is in the S configuration, chiral centre *2 is in the S configuration or the R configuration, chiral centre *3 is in the S configuration, chiral centre *4 is in the R configuration, chiral centre *5 is in the S configuration, chiral centre *6 is in the S configuration or the R configuration, chiral centre *7 is in the R configuration, and chiral centre *8 is in the R configuration. In some embodiments, chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration. In some embodiments, chiral centre *1 is in the S configuration, chiral centre *2 is in the R configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration. In some embodiments, chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the R configuration, chiral centre *7 is in the R configuration, and chiral centre *8 is in the R configuration. In some embodiments, chiral centre *1 is in the S configuration, chiral centre *2 is in the R configuration, chiral centre *3 is in the S configuration, chiral centre *4 is in the R configuration, chiral centre *5 is in the S configuration,
chiral centre *6 is in the R configuration, chiral centre *7 is in the R configuration, and chiral centre *8 is in the R configuration.

Illustrative embodiments of the present invention include a compound having the structure of Formula I or a salt thereof, wherein: $R^C$ is OH or $NHR^{16}$, wherein $R^{16}$ is H or $C_{1-6}$ alkyl; $R^N$ is selected from the group consisting of: (i) H; (ii) $C_{1-6}$ alkyl; (iii) —$C(O)R^{17}$, wherein $R^{17}$ is selected from the group consisting of $C_{1-6}$ alkyl, $C_{6-10}$ aryl, and 5- to 10-membered heteroaryl; (iv) —$C(O)C_{1-3}$ alkylene-$C(O)OR^{18}$, wherein $R^{18}$ is H or $C_{1-6}$ alkyl; (v) —$C(O)C_{1-3}$ alkylene-$N(R^{20})C(O)R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —$C(O)C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —$C(O)C_{1-3}$ alkylene-$C(O)NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —$C(O)C_{1-3}$ alkylene-$S(O)_2R^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy;

$R^4$ is selected from the group consisting of:

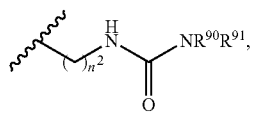

(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

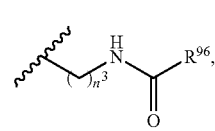

(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^3$ is 3 or 4;

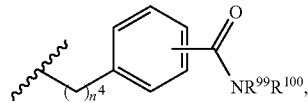

(iii)

wherein each of R$^{99}$ and R$^{100}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^4$ is 1 or 2;

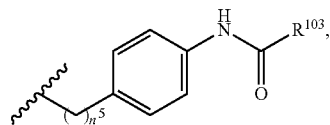

(iv)

wherein R$^{103}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents each independently selected from the group consisting of halogen, hydroxy, —NO$_2$, and C$_{1-6}$ alkoxy, and wherein the C$_{6-10}$ aryl, 5- to 10-membered heteroaryl, and 5- to 10-membered heterocycloalkyl are optionally substituted with one or more substituents each independently selected from the group consisting of halogen, hydroxy, —NO$_2$, and C$_{1-6}$ alkoxy, and wherein n$^5$ is 1 or 2;

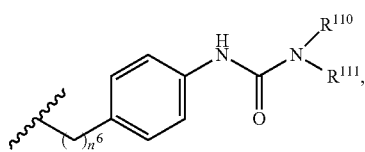

(v)

wherein R$^{110}$ is selected from the group consisting of H, C$_{1-6}$ alkyl, C$_{6-10}$ aryl, and 5- to 10-membered heteroaryl, R$^{111}$ is selected from the group consisting of C$_{1-6}$ alkyl, C$_{6-10}$ aryl, and 5- to 10-membered heteroaryl, wherein the C$_{1-6}$ alkyl of R$^{110}$ or R$^{111}$ is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl of R$^{110}$ or R$^{111}$ are optionally substituted with one or more substituents each independently selected from the group consisting of halogen, —OH, —NO$_2$, and C$_{1-6}$ alkoxy, and wherein n$^6$ is 1 or 2;

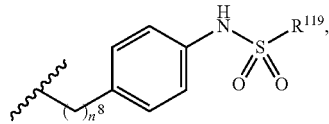

(vi)

wherein R$^{119}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, hydroxy, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, hydroxy, —NO$_2$, and C$_{1-6}$ alkoxy, and wherein n$^8$ is 1 or 2;

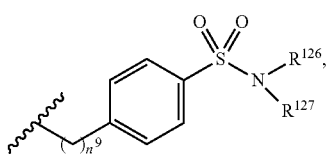

(vii)

wherein each of R$^{126}$ and R$^{127}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^9$ is 1 or 2;

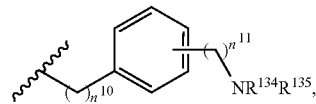

(viii)

wherein: each of R$^{134}$ and R$^{135}$ is independently selected from the group consisting of H, C$_{1-6}$ alkyl, C$_{6-10}$ aryl, 5- to 10-membered heteroaryl, —C(O)R$^{16}$, and —C(O)NR$^{137}$R$^{138}$, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^{10}$ is 1 or 2, and wherein n$^{11}$ is 1 or 2;

R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

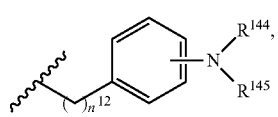

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2;

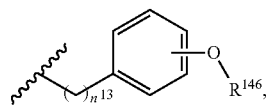

(x)

wherein $R^{146}$ is selected from the group consisting of $C_{2-6}$ alkyl, $C_{6-10}$ aryl, and 5- to 10-membered heteroaryl, wherein the $C_{2-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{13}$ is 1 or 2;

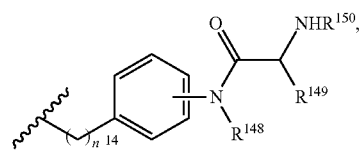

(xi)

wherein $R^{148}$ is H or CH$_3$, $R^{149}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and $R^{150}$ is H, CH$_3$ or acetyl, and wherein $n^{14}$ is 1 or 2; and

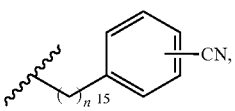

(xii)

wherein $n^{15}$ is 1 or 2; $R^5$ is —NR$^{79}$R$^{80}$ and each of $R^{79}$ and $R^{80}$ is independently selected from the group consisting of H, $C_{1-6}$ alkyl, —C(O)R$^{81}$, and —C(=NR$^{82}$)NR$^{83}$R$^{84}$, wherein $R^{81}$ is $C_{1-6}$ alkyl and each of $R^{82}$, $R^{83}$, and $R^{84}$ is H; n is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy; each of $R^9$, $R^{10}$, $R^{11}$, $R^{12}$, $R^{13}$, $R^{14}$, and $R^{15}$ is independently H or CH$_3$; L is

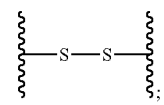

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or NHR$^{16}$, wherein $R^{16}$ is H or $C_{1-6}$ alkyl; $R^N$ is selected from the group consisting of: (i) H; (ii) $C_{1-6}$ alkyl; (iii) —C(O)R$^{17}$, wherein $R^{17}$ is selected from the group consisting of $C_{1-6}$ alkyl, $C_{6-10}$ aryl, and 5- to 10-membered heteroaryl; (iv) —C(O)C$_{1-3}$ alkylene-C(O)OR$^{18}$, wherein $R^{18}$ is H or $C_{1-6}$ alkyl; (v) —C(O)C$_{1-3}$ alkylene-N(R$^{20}$)C(O)R$^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —C(O)C$_{1-3}$ alkylene-NR$^{21}$R$^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —C(O)C$_{1-3}$ alkylene-C(O)NR$^{23}$R$^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —C(O)C$_{1-3}$ alkylene-S(O)$_2$R$^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy; $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy;

$R^4$ is selected from the group consisting of:

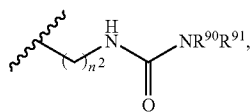
(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

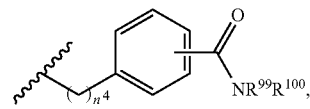
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

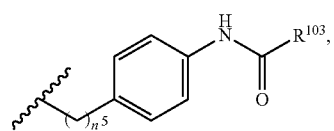
(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

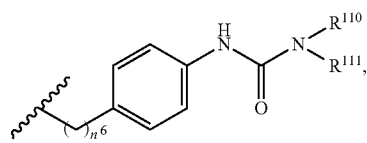
(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —$NO_2$, and $C_{1-6}$ alkoxy, and wherein $n^6$ is 1 or 2;

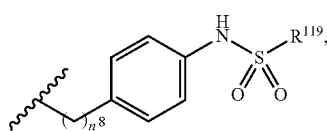
(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2;

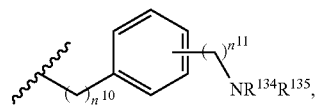
(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)N$R^{137}R^{138}$, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

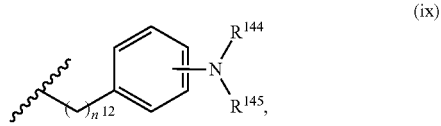

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2; and

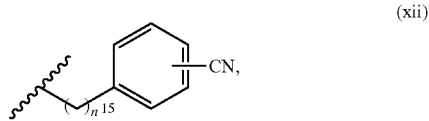

(xii)

wherein $n^{15}$ is 1 or 2;
$R^5$ is —NR$^{79}$R$^{80}$ and each of $R^{79}$ and $R^{80}$ is independently selected from the group consisting of H, $C_{1-6}$ alkyl, —C(O)R$^{81}$, and —C(=NR$^{82}$)NR$^{83}$R$^{84}$, wherein $R^{81}$ is $C_{1-6}$ alkyl and each of $R^{82}$, $R^{83}$, and $R^{84}$ is H; n is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy; each of $R^9$, $R^{10}$, $R^{11}$, $R^{12}$, $R^{13}$, $R^{14}$, and $R^{15}$ is independently H or CH$_3$; L is

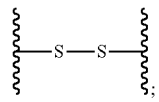 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or NHR$^{16}$, wherein $R^{16}$ is H or $C_{1-6}$ alkyl; $R^N$ is selected from the group consisting of: (i) H; (ii) $C_{1-6}$ alkyl; (iii) —C(O)R$^{17}$, wherein $R^{17}$ is selected from the group consisting of $C_{1-6}$ alkyl, $C_{6-10}$ aryl, and 5- to 10-membered heteroaryl; (iv) —C(O)$C_{1-3}$ alkylene-C(O)OR$^{18}$, wherein $R^{18}$ is H or $C_{1-6}$ alkyl; (v) —C(O)$C_{1-3}$ alkylene-N(R$^{20}$)C(O)R$^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —C(O)$C_{1-3}$ alkylene-NR$^{21}$R$^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —C(O)$C_{1-3}$ alkylene-C(O)NR$^{23}$R$^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —C(O)$C_{1-3}$ alkylene-S(O)$_2$R$^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy; $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy;
$R^4$ is selected from the group consisting of:

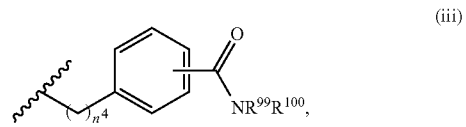

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2; and

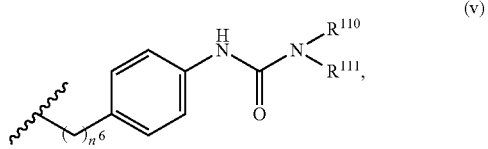

(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;
$R^5$ is —NR$^{79}$R$^{80}$ and each of $R^{79}$ and $R^{80}$ is independently selected from the group consisting of H, $C_{1-6}$ alkyl, —C(O)R$^{81}$, and —C(=NR$^{82}$)NR$^{83}$R$^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and C$_{1-6}$ alkoxy; each of R$^9$, R$^{10}$, R$^{11}$, R$^{12}$, R$^{13}$, R$^{14}$, and R$^{15}$ is independently H or CH$_3$; L is

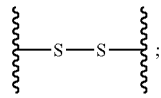

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R$^C$ is OH or NHR$^{16}$, wherein R$^{16}$ is H or C$_{1-6}$ alkyl; R$^N$ is selected from the group consisting of: (i) H; (ii) C$_{1-6}$ alkyl; (iii) —C(O)R$^{17}$, wherein R$^{17}$ is selected from the group consisting of C$_{1-6}$ alkyl, C$_{6-10}$ aryl, and 5- to 10-membered heteroaryl; (iv) —C(O)C$_{1-3}$ alkylene-C(O)OR$^{18}$, wherein R$^{18}$ is H or C$_{1-6}$ alkyl; (v) —C(O)C$_{1-3}$ alkylene-N(R$^{20}$)C(O)R$^{19}$, wherein R$^{19}$ is selected from the group consisting of C$_{1-6}$ alkyl, C$_{6-10}$ aryl, and 5- to 10-membered heteroaryl, and wherein R$^{20}$ is H or C$_{1-6}$ alkyl; (vi) —C(O)C$_{1-3}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl; (vii) —C(O)C$_{1-3}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl; and (viii) —C(O)C$_{1-3}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl; R$^1$ is —C$_{1-3}$ alkylene(C$_{6-10}$ aryl), wherein the C$_{6-10}$ aryl is optionally substituted with one or more substituents each independently selected from the group consisting of halogen, hydroxy, —NO$_2$, and C$_{1-6}$ alkoxy; R$^3$ is —C$_{1-3}$ alkylene(C$_{6-10}$ aryl), wherein the C$_{6-10}$ aryl is optionally substituted with one or more substituents each independently selected from the group consisting of halogen, hydroxy, —NO$_2$, and C$_{1-6}$ alkoxy; R$^4$ is selected from the group consisting of:

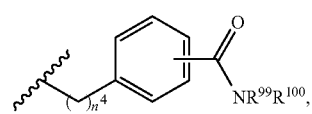

(iii)

wherein each of R$^{99}$ and R$^{100}$ is independently selected from the group consisting of H, C$_{1-6}$ alkyl, C$_{6-10}$ aryl, and 5- to 10-membered heteroaryl, and wherein n$^4$ is 1 or 2; and

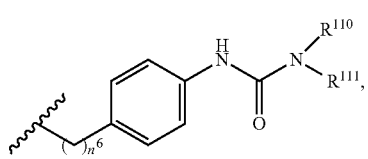

(v)

wherein R$^{110}$ is selected from the group consisting of H, C$_{1-6}$ alkyl, C$_{6-10}$ aryl, and 5- to 10-membered heteroaryl, and R$^{111}$ is selected from the group consisting of C$_{1-6}$ alkyl, C$_{6-10}$ aryl, and 5- to 10-membered heteroaryl, and wherein n$^6$ is 1 or 2; R$^5$ is —NR$^{79}$R$^{80}$ and each of R$^{79}$ and R$^{80}$ is independently selected from the group consisting of H, C$_{1-6}$ alkyl, —C(O)R$^{81}$, and —C(=NR$^{82}$)NR$^{83}$R$^{84}$, wherein R$^{81}$ is C$_{1-6}$ alkyl and each of R$^{82}$, R$^{83}$, and R$^{84}$ is H; n$^1$ is 3 or 4; R$^6$ is C$_{1-6}$ alkyl optionally substituted with hydroxyl; R$^8$ is —C$_{1-3}$ alkylene(C$_{6-10}$ aryl), wherein the C$_{6-10}$ aryl is optionally substituted with one or more substituents each independently selected from the group consisting of halogen, hydroxy, —NO$_2$, and C$_{1-6}$ alkoxy; each of R$^9$, R$^{10}$, R$^{11}$, R$^{12}$, R$^{13}$, R$^{14}$, and R$^{15}$ is independently H or CH; L is

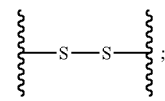

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R$^C$ is OH or NHR$^{16}$, wherein R$^{16}$ is H or C$_{1-6}$ alkyl; R$^N$ is selected from the group consisting of: (i) H; (ii) C$_{1-6}$ alkyl; (iii) —C(O)R$^{17}$, wherein R$^{17}$ is selected from the group consisting of C$_{1-6}$ alkyl, C$_{6-10}$ aryl, and 5- to 10-membered heteroaryl; (iv) —C(O)C$_{1-3}$ alkylene-C(O)OR$^{18}$, wherein R$^{18}$ is H or C$_{1-6}$ alkyl; (v) —C(O)C$_{1-3}$ alkylene-N(R$^{20}$)C(O)R$^{19}$, wherein R$^{19}$ is selected from the group consisting of C$_{1-6}$ alkyl, C$_{6-10}$ aryl, and 5- to 10-membered heteroaryl, and wherein R$^{20}$ is H or C$_{1-6}$ alkyl; (vi) —C(O)C$_{1-3}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl; (vii) —C(O)C$_{1-3}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl; and (viii) —C(O)C$_{1-3}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl; R$^1$ is —C$_{1-3}$ alkylene(C$_{6-10}$ aryl), wherein the C$_{6-10}$ aryl is optionally substituted with one or more substituents each independently selected from the group consisting of halogen, hydroxy, —NO$_2$, and C$_{1-6}$ alkoxy; R$^3$ is —C$_{1-3}$ alkylene(C$_{6-10}$ aryl), wherein the C$_{6-10}$ aryl is optionally substituted with one or more substituents each independently selected from the group consisting of halogen, hydroxy, —NO$_2$, and C$_{1-6}$ alkoxy; R$^4$ is selected from the group consisting of:

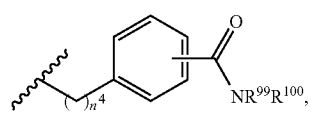

(iii)

wherein each of R$^{99}$ and R$^{100}$ is independently selected from the group consisting of H and C$_{1-6}$ alkyl, and wherein n$^4$ is 1 or 2; and

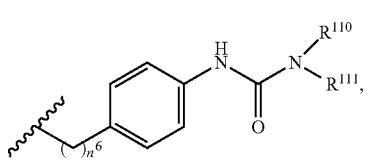

(v)

wherein $R^{110}$ is H, and $R^{111}$ is $C_6$ aryl, and wherein $n^6$ is 1 or 2; $R^5$ is —$NR^{79}R^{80}$ and each of $R^{79}$ and $R^{80}$ is independently selected from the group consisting of H, $C_{1-6}$ alkyl, —$C(O)R^{81}$, and —$C(=NR^{82})NR^{83}R^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; each of $R^9$, $R^{10}$, $R^{11}$, $R^{12}$, $R^{13}$, $R^{14}$, and $R^{15}$ is independently H or $CH_3$; L is

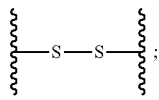

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NHR^{16}$, wherein $R^{16}$ is H or $C_{1-6}$ alkyl; $R^N$ is selected from the group consisting of: (i) H; (ii) $C_{1-6}$ alkyl; (iii) —$C(O)R^{17}$, wherein $R^{17}$ is selected from the group consisting of $C_{1-6}$ alkyl, $C_{6-10}$ aryl, and 5- to 10-membered heteroaryl; (iv) —$C(O)C_{1-3}$ alkylene-$C(O)OR^{18}$, wherein $R^{18}$ is H or $C_{1-6}$ alkyl; (v) —$C(O)C_{1-3}$ alkylene-$N(R^{20})C(O)R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —$C(O)C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —$C(O)C_{1-3}$ alkylene-$C(O)NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —$C(O)C_{1-3}$ alkylene-$S(O)_2R^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^3$ is —$C_{1-3}$ alkylene ($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^4$ is:

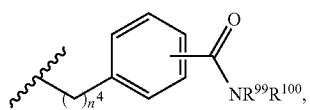

(iii)

wherein each of $R^{99}$ and $R^{100}$ is independently selected from the group consisting of H and $C_{1-6}$ alkyl, and wherein $n^4$ is 1 or 2; $R^5$ is —$NR^{79}R^{80}$ and each of $R^{79}$ and $R^{80}$ is independently selected from the group consisting of H, $C_{1-6}$ alkyl, —$C(O)R^{81}$, and —$C(=NR^{82})NR^{83}R^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; each of $R^9$, $R^{10}$, $R^{11}$, $R^{12}$, $R^{13}$, $R^{14}$, and $R^{15}$ is independently H or $CH_3$; L is

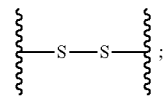

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NHR^{16}$, wherein $R^{16}$ is H or $C_{1-6}$ alkyl; $R^N$ is selected from the group consisting of: (i) H; (ii) $C_{1-6}$ alkyl; (iii) —$C(O)R^{17}$, wherein $R^{17}$ is selected from the group consisting of $C_{1-6}$ alkyl, $C_{6-10}$ aryl, and 5- to 10-membered heteroaryl; (iv) —$C(O)C_{1-3}$ alkylene-$C(O)OR^{18}$, wherein $R^{18}$ is H or $C_{1-6}$ alkyl; (v) —$C(O)C_{1-3}$ alkylene-$N(R^{20})C(O)R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —$C(O)C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —$C(O)C_{1-3}$ alkylene-$C(O)NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —$C(O)C_{1-3}$ alkylene-$S(O)_2R^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^3$ is —$C_{1-3}$ alkylene ($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^4$ is:

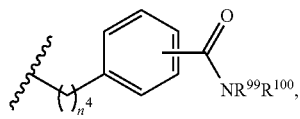

(iii)

wherein each of $R^{99}$ and $R^{100}$ is H, and wherein $n^4$ is 1 or 2; $R^5$ is —$NR^{79}R^{80}$ and each of $R^{79}$ and $R^{80}$ is independently selected from the group consisting of H, $C_{1-6}$ alkyl, —C(O)$R^{81}$, and —C(=$NR^{82}$)$NR^{83}R^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; each of $R^9$, $R^{10}$, $R^{11}$, $R^{12}$, $R^{13}$, $R^{14}$, and $R^{15}$ is independently H or $CH_3$; L is

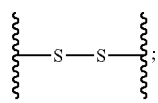

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NHR^{16}$, wherein $R^{16}$ is H or $C_{1-6}$ alkyl; $R^N$ is selected from the group consisting of: (i) H; (ii) $C_{1-6}$ alkyl; (iii) —C(O)$R^{17}$, wherein $R^{17}$ is selected from the group consisting of $C_{1-6}$ alkyl, $C_{6-10}$ aryl, and 5- to 10-membered heteroaryl; (iv) —C(O)$C_{1-3}$ alkylene-C(O)$OR^{18}$, wherein $R^{18}$ is H or $C_{1-6}$ alkyl; (v) —C(O)$C_{1-3}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —C(O)$C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —C(O)$C_{1-3}$ alkylene-C(O)$NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —C(O)$C_{1-3}$ alkylene-S(O)$_2R^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^4$ is

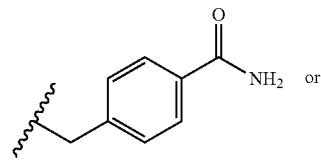 or

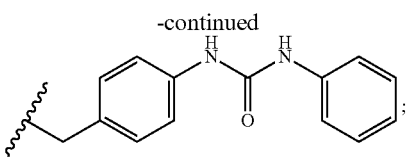

$R^5$ is —$NR^{79}R^{80}$ and each of $R^{79}$ and $R^{80}$ is independently selected from the group consisting of H, $C_{1-6}$ alkyl, —C(O)$R^{81}$, and —C(=$NR^{82}$)$NR^{83}R^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; each of $R^9$, $R^{10}$, $R^{11}$, $R^{12}$, $R^{13}$, $R^{14}$, and $R^{15}$ is independently H or $CH_3$; L is

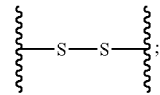

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NHR^{16}$, wherein $R^{16}$ is H or $C_{1-6}$ alkyl;

$R^N$ is selected from the group consisting of: (i) H; (ii) $C_{1-6}$ alkyl; (iii) —C(O)$R^{17}$, wherein $R^{17}$ is selected from the group consisting of $C_{1-6}$ alkyl, $C_{6-10}$ aryl, and 5- to 10-membered heteroaryl; (iv) —C(O)$C_{1-3}$ alkylene-C(O)$OR^{18}$, wherein $R^{18}$ is H or $C_{1-6}$ alkyl; (v) —C(O)$C_{1-3}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl; (vi) —C(O)$C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl; (vii) —C(O)$C_{1-3}$ alkylene-C(O)$NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and (viii) —C(O)$C_{1-3}$ alkylene-S(O)$_2R^{25}$, wherein $R^{25}$ is selected from the group consisting of $C_{1-6}$ alkyl, $C_{6-10}$ aryl, and 5- to 10-membered heteroaryl; $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^3$ is —$C_{1-3}$ alkylene ($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; $R^4$ is

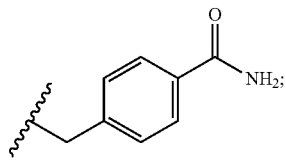

$R^5$ is —$NR^{79}R^{80}$ and each of $R^{79}$ and $R^{80}$ is independently selected from the group consisting of H, $C_{1-6}$ alkyl, —C(O)$R^{81}$, and —C(=$NR^{82}$)$NR^{83}R^{84}$, wherein $R^{81}$ is $C_{1-6}$ alkyl and each of $R^{82}$, $R^{83}$, and $R^{84}$ is H; $n^1$ is 3 or 4; $R^6$ is $C_{1-6}$ alkyl optionally substituted with hydroxyl; $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy; each of $R^9$, $R^{10}$, $R^{11}$, $R^{12}$, $R^{13}$, $R^{14}$, and $R^{15}$ is independently H or $CH_3$; L is

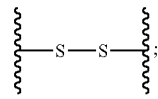

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —C(O)$R^{17}$, —C(O)$C_{1-3}$ alkylene-C(O)$OR^{18}$, —C(O)$C_{1-3}$ alkylene-N($R^{20}$)C(O)$R^{19}$, —C(O)$C_{1-3}$ alkylene-$NR^{21}R^{22}$, —C(O)$C_{1-3}$ alkylene-C(O)$NR^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

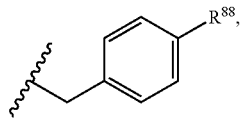

wherein $R^{88}$ is H, halogen, hydroxyl or $C_{1-3}$ alkoxy; $R^3$ is

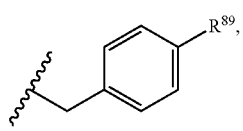

wherein $R^{89}$ is H, halogen, hydroxyl or $C_{1-3}$ alkoxy; $R^4$ is selected from the group consisting of:

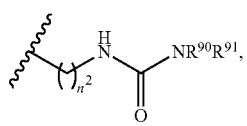

(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

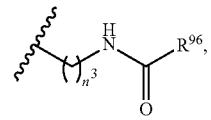

(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4;

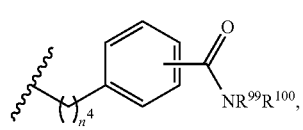

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

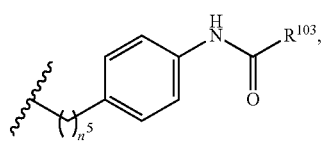

(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

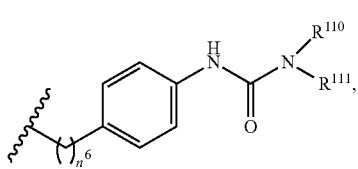

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;

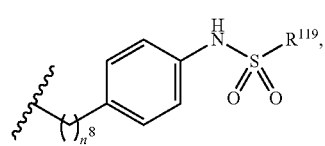

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

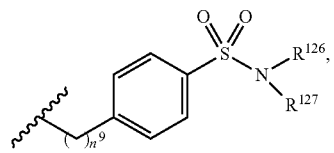

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^9$ is 1 or 2;

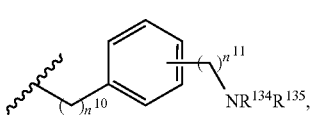

wherein: each of $R^{134}$ and $R^{135}$ is independently selected from the group consisting of H, $C_{1-6}$ alkyl, $C_{6-10}$ aryl, 5- to 10-membered heteroaryl, —C(O)R$^{136}$, and —C(O)NR$^{137}$R$^{138}$, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

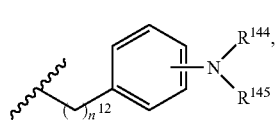

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2;

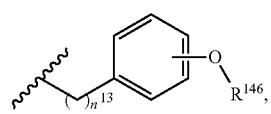

wherein $R^{146}$ is selected from the group consisting of $C_{2-6}$alkyl, $C_{6-10}$ aryl, and 5- to 10-membered heteroaryl, wherein the $C_{2-6}$alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{13}$ is 1 or 2;

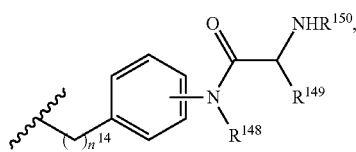

(xi)

wherein $R^{148}$ is H or CH$_3$, $R^{149}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and $R^{150}$ is H, CH$_3$ or acetyl, and wherein $n^{14}$ is 1 or 2; and

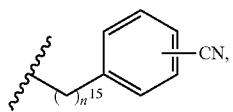

(xii)

wherein $n^{15}$ is 1 or 2;
$R^5$ is —NH$_2$, —NHCH$_3$ or —N(CH$_3$)$_2$; $n^1$ is 4; $R^6$ is selected from the group consisting of —CH(CH$_3$)OH, —CH(CH$_3$)$_2$, —C(CH$_3$)$_3$, —CH$_2$OH and —CH$_2$CH$_3$; $R^8$ is

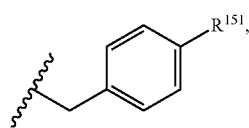

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

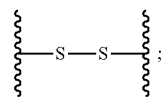

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or NH$_2$; $R^N$ is selected from the group consisting of H, $C_{1-3}$ alkyl, —C(O)R$^{17}$, —C(O)C$_{1-3}$ alkylene-C(O)OR$^{18}$, —C(O)C$_{1-3}$ alkylene-N(R$^{20}$)C(O)R$^{19}$, —C(O)C$_{1-3}$ alkylene-NR$^{21}$R$^{22}$, —C(O)C$_{1-3}$ alkylene-C(O)NR$^{23}$R$^{24}$, and —C(O)C$_{1-3}$ alkylene-S(O)$_2$R$^{25}$, wherein R$^{17}$ is $C_{1-6}$ alkyl or 5- to 6-membered heteroaryl, R$^{18}$ is $C_{1-3}$ alkyl, R$^{19}$ is $C_{1-3}$ alkyl or $C_6$ aryl, each of R$^{20}$, R$^{21}$, R$^{22}$, R$^{23}$ and R$^{24}$ is H, and R$^{25}$ is $C_6$ aryl; $R^1$ is

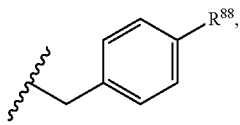

wherein $R^{88}$ is H, halogen, hydroxyl or $C_{1-3}$ alkoxy; $R^3$ is

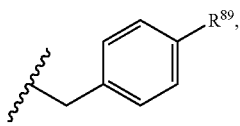

wherein $R^{89}$ is H, halogen, hydroxyl or $C_{1-3}$ alkoxy; $R^4$ is selected from the group consisting of:

(i)

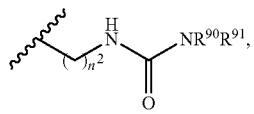

wherein each of R$^{90}$ and R$^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^2$ is 3 or 4;

(iii)

wherein each of R$^{99}$ and R$^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2;

(iv)

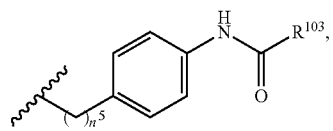

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

(v)

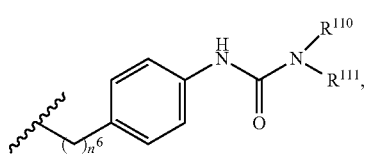

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^1 11$ are optionally substituted with one or more substituents each independently selected from the group consisting of halogen, —OH, —$NO_2$, and $C_{1-6}$ alkoxy, and wherein $n^6$ is 1 or 2;

(vi)

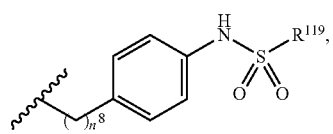

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2;

(viii)

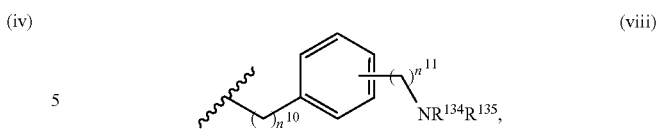

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)$NR^{137}R^{138}$, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy;

(ix)

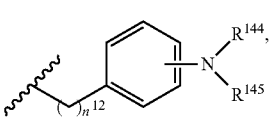

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, and 5- to 10-membered heterocycloalkyl, and wherein $n^{12}$ is 1 or 2; and (xii)

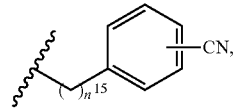

wherein $n^{15}$ is 1 or 2;
$R^5$ is —$NH_2$, —$NHCH_3$ or —$N(CH_3)_2$; $n^1$ is 4; $R^6$ is selected from the group consisting of —$CH(CH_3)OH$, —$CH(CH_3)_2$, —$C(CH_3)_3$, —$CH_2OH$ and —$CH_2CH_3$; $R^8$ is

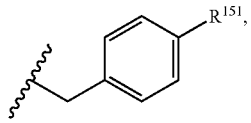

wherein $R^{151}$ is halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

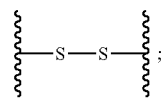

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

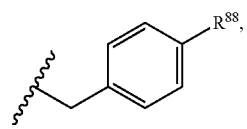

wherein $R^{88}$ is H, halogen, hydroxyl or $C_{1-3}$ alkoxy; $R^3$ is

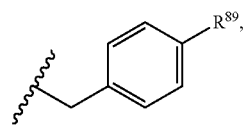

wherein $R^{89}$ is H, halogen, hydroxyl or $C_{1-3}$ alkoxy; $R^4$ is selected from the group consisting of:

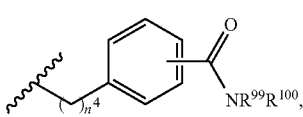

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2; and

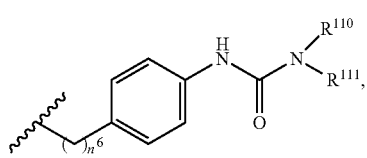

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —$NO_2$, and $C_{1-6}$ alkoxy, and wherein $n^6$ is 1 or 2;
$R^5$ is —$NH_2$, —$NHCH_3$ or —$N(CH_3)_2$; $n^1$ is 4; $R^6$ is selected from the group consisting of —$CH(CH_3)OH$, —$CH(CH_3)_2$, —$C(CH_3)_3$, —$CH_2OH$ and —$CH_2CH_3$; $R^8$ is

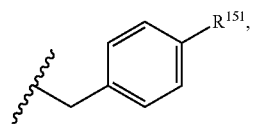

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

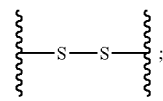 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

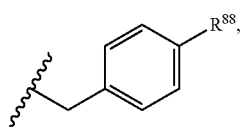

wherein R$^{88}$ is H, halogen, hydroxyl or C$_{1-3}$ alkoxy; R$^3$ is

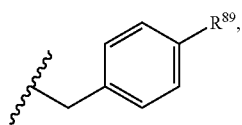

wherein R$^{89}$ is H, halogen, hydroxyl or C$_{1-3}$ alkoxy; R$^4$ is selected from the group consisting of:

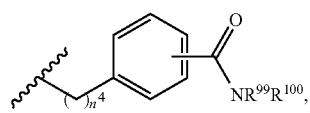

(iii)

wherein each of R$^{99}$ and R$^{100}$ is independently selected from the group consisting of H, C$_{1-6}$ alkyl, C$_{6-10}$ aryl, and 5- to 10-membered heteroaryl, and wherein n$^4$ is 1 or 2; and

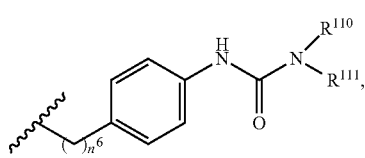

(v)

wherein R$^{110}$ is selected from the group consisting of H, C$_{1-6}$ alkyl, C$_{6-10}$ aryl, and 5- to 10-membered heteroaryl, and R$^{111}$ is selected from the group consisting of C$_{1-6}$ alkyl, C$_{6-10}$ aryl, and 5- to 10-membered heteroaryl, and wherein n$^6$ is 1 or 2;
R$^5$ is —NH$_2$, —NHCH$_3$ or —N(CH$_3$)$_2$; n$^1$ is 4; R$^6$ is selected from the group consisting of —CH(CH$_3$)OH, —CH(CH$_3$)$_2$, —C(CH$_3$)$_3$, —CH$_2$OH and —CH$_2$CH$_3$; R$^5$ is

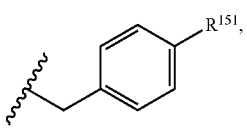

wherein R$^{151}$ is H halogen, hydroxyl or C$_{1-3}$ alkoxy; each of R$^9$, R$^{10}$, R$^{11}$, R$^{12}$, R$^{13}$, R$^{14}$, and R$^{15}$ is H; L is

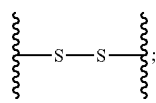 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R$^C$ is OH or NH$_2$; R$^N$ is selected from the group consisting of H, C$_{1-3}$ alkyl, —C(O)R$^{17}$, —C(O)C$_{1-3}$ alkylene-C(O)OR$^{18}$, —C(O)C$_{1-3}$ alkylene-N(R$^{20}$)C(O)R$^{19}$, —C(O)C$_{1-3}$ alkylene-NR$^{21}$R$^{22}$, —C(O)C$_{1-3}$ alkylene-C(O)NR$^{23}$R$^{24}$, and —C(O)C$_{1-3}$ alkylene-S(O)$_2$R$^{25}$, wherein R$^{17}$ is C$_{1-6}$ alkyl or 5- to 6-membered heteroaryl, R$^{18}$ is C$_{1-3}$ alkyl, R$^{19}$ is C$_{1-3}$ alkyl or C$_6$ aryl, each of R$^{20}$, R$^{21}$, R$^{22}$, R$^{23}$ and R$^{24}$ is H, and R$^{25}$ is C$_6$ aryl; R$^1$ is

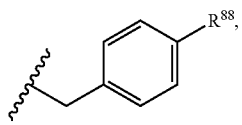

wherein R$^{88}$ is H, halogen, hydroxyl or C$_{1-3}$ alkoxy; R$^3$ is

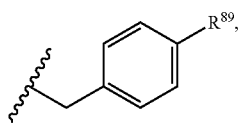

wherein R is H, halogen, hydroxyl or C$_{1-3}$ alkoxy; R$^4$ is selected from the group consisting of:

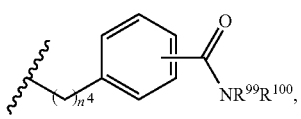

(iii)

wherein each of R$^{99}$ and R$^{100}$ is independently selected from the group consisting of H and C$_{1-6}$ alkyl, and wherein n$^4$ is 1 or 2; and

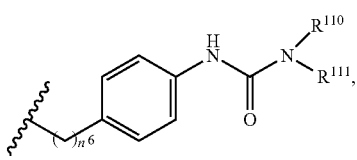

(v)

wherein R$^{110}$ is H, and R$^{111}$ is C$_6$ aryl, and wherein n$^6$ is 1 or 2; R$^5$ is —NH$_2$, —NHCH$_3$ or —N(CH$_3$)$_2$; n$^1$ is 4; R$^6$ is selected from the group consisting of —CH(CH$_3$)OH, —CH(CH$_3$)$_2$, —C(CH$_3$)$_3$, —CH$_2$OH and —CH$_2$CH$_3$; R$^8$ is

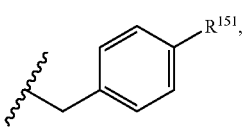

wherein $R^{151}$ is H, halogen, hydroxyl or $C_{1-3}$ alkoxy; each of $R^9$, $R^{11}$, $R^{12}$, $R^{13}$, $R^{14}$, and $R^{15}$ is H; L is

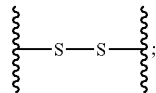 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

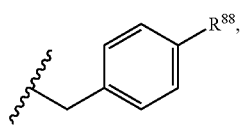

wherein $R^{88}$ is H, halogen, hydroxyl or $C_{1-3}$ alkoxy; $R^3$ is

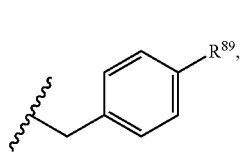

wherein $R^{89}$ is H, halogen, hydroxyl or $C_{1-3}$ alkoxy; $R^4$ is:

(iii)

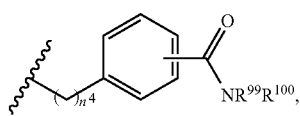

wherein each of $R^{99}$ and $R^{100}$ is independently selected from the group consisting of H and $C_{1-6}$ alkyl, and wherein $n^4$ is 1 or 2; $R^5$ is —$NH_2$, —$NHCH_3$ or —$N(CH_3)_2$; $n^1$ is 4; $R^6$ is selected from the group consisting of —CH($CH_3$)OH, —CH($CH_3$)$_2$, —C($CH_3$)$_3$, —$CH_2$OH and —$CH_2CH_3$; $R^8$ is

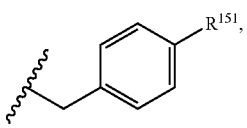

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

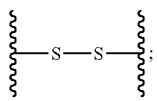

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

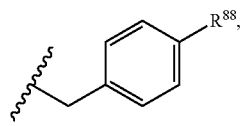

wherein $R^{88}$ is H, halogen, hydroxyl or $C_{1-3}$ alkoxy; $R^3$ is

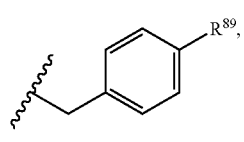

wherein $R^{89}$ is H, halogen, hydroxyl or $C_{1-3}$ alkoxy; $R^4$ is: (iii)

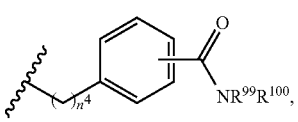

wherein each of $R^{99}$ and $R^{100}$ is H, and wherein $n^4$ is 1 or 2; $R^5$ is —$NH_2$, —$NHCH_3$ or —$N(CH_3)_2$; $n^1$ is 4; $R^6$ is selected from the group consisting of —CH($CH_3$)OH, —CH($CH_3$)$_2$, —C($CH_3$)$_3$, —$CH_2$OH and —$CH_2CH_3$; $R^8$ is

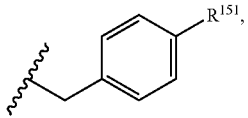

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

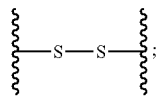

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

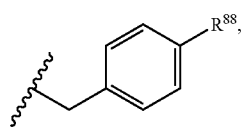

wherein $R^{88}$ is H, halogen, hydroxyl or $C_{1-3}$ alkoxy; $R^3$ is

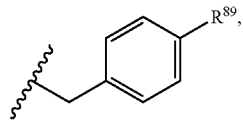

wherein $R^{89}$ is H, halogen, hydroxyl or $C_{1-3}$ alkoxy; $R^4$ is

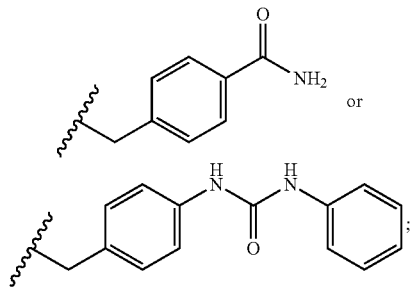

$R^5$ is —$NH_2$, —$NHCH_3$ or —$N(CH_3)_2$; $n^1$ is 4; $R^6$ is selected from the group consisting of —CH($CH_3$)OH, —CH($CH_3$)$_2$, —C($CH_3$)$_3$, —$CH_2$OH and —$CH_2CH_3$; $R^8$ is

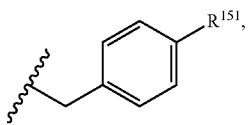

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

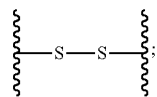

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is OH or $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

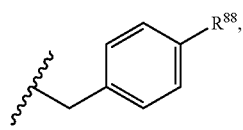

wherein $R^{88}$ is H, halogen, hydroxyl or $C_{1-3}$ alkoxy; $R^3$ is

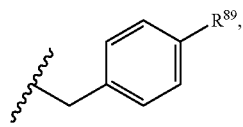

wherein $R^{89}$ is H, halogen, hydroxyl or $C_{1-3}$ alkoxy; $R^4$ is

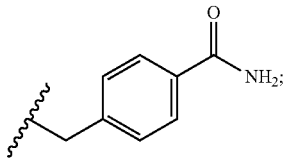 [SMILES: *Cc1ccc(C(N)=O)cc1]

$R^5$ is —$NH_2$, —$NHCH_3$ or —$N(CH_3)_2$; $n^1$ is 4; $R^6$ is selected from the group consisting of —CH($CH_3$)OH, —CH($CH_3$)$_2$, —C($CH_3$)$_3$, —$CH_2$OH and —$CH_2CH_3$; $R^8$ is

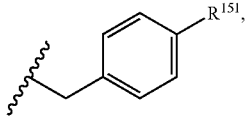

wherein $R^{151}$ is H, halogen, hydroxyl or $C_{1-3}$ alkoxy; each of $R^9$, $R^{10}$, $R^{11}$, $R^{12}$, $R^{13}$, $R^{14}$, and $R^{15}$ is H; L is

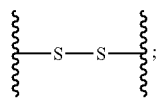

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

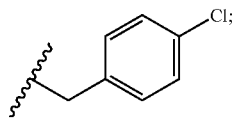 [SMILES: *Cc1ccc(Cl)cc1]

$R^3$ is

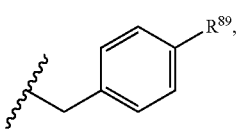

wherein $R^{89}$ is Cl or hydroxyl;
$R^4$ is selected from the group consisting of:

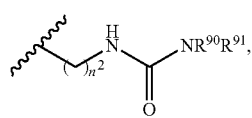

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^2$ is 3 or 4;

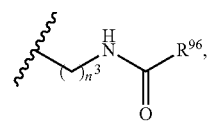

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^3$ is 3 or 4;

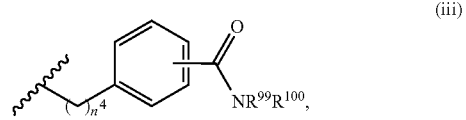

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2;

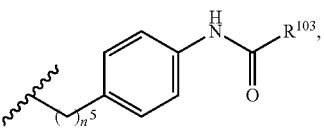

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —NO$_2$, and $C_{1-6}$ alkoxy, and wherein $n^5$ is 1 or 2;

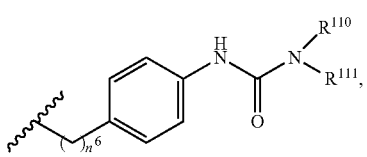

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and C$_{1-6}$ alkoxy, and wherein $n^6$ is 1 or 2;

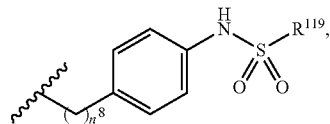

(vi)

wherein $R^{119}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, hydroxy, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, hydroxy, —NO$_2$, and C$_{1-6}$ alkoxy, and wherein $n^8$ is 1 or 2;

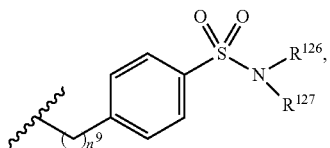

(vii)

wherein each of $R^{126}$ and $R^{127}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein $n^9$ is 1 or 2;

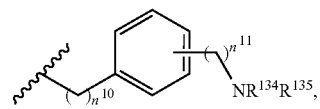

(viii)

wherein: each of $R^{134}$ and $R^{135}$ is independently selected from the group consisting of H, C$_{1-6}$ alkyl, C$_{6-10}$ aryl, 5- to 10-membered heteroaryl, —C(O)R$^{136}$, and —C(O)NR$^{137}$R$^{138}$, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein $n^{10}$ is 1 or 2, and wherein $n^{11}$ is 1 or 2;

$R^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and each of $R^{137}$ and $R^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;

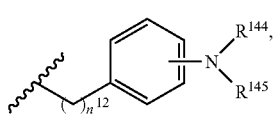

(ix)

wherein each of $R^{144}$ and $R^{145}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein $n^{12}$ is 1 or 2;

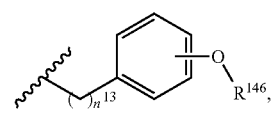

(x)

wherein $R^{146}$ is selected from the group consisting of C$_{2-6}$ alkyl, C$_{6-10}$ aryl, and 5- to 10-membered heteroaryl, wherein the C$_{2-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein $n^{13}$ is 1 or 2;

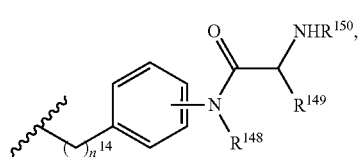

(xi)

wherein $R^{148}$ is H or $CH_3$, $R^{149}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{150}$ is H, $CH_3$ or acetyl, and wherein $n^{14}$ is 1 or 2; and (xii)

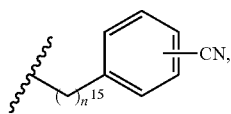

wherein $n^{15}$ is 1 or 2;
$R^5$ is —$NH_2$, —$NHCH_3$ or —N($CH_3$)$_2$; $n^1$ is 4; $R^6$ is —CH($CH_3$)OH; $R^8$ is

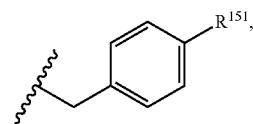

wherein $R^{151}$ is Cl or hydroxyl; each of $R^9$, $R^{10}$, $R^{11}$, $R^{12}$, $R^{13}$, $R^{14}$, and $R^{15}$ is H; L is

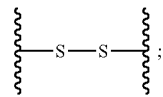

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-N$R^{21}R^{22}$, —C(O)$C_{1-3}$ alkylene-C(O)N$R^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

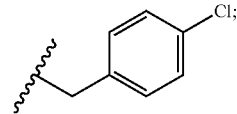 [SMILES: *Cc1ccc(Cl)cc1]

$R^3$ is

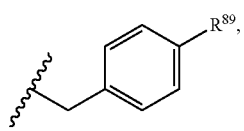

wherein $R^{89}$ is Cl or hydroxyl;

$R^4$ is selected from the group consisting of:

(i)

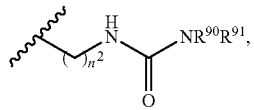

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

(iii)

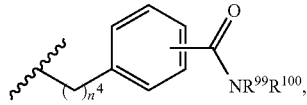

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

(iv)

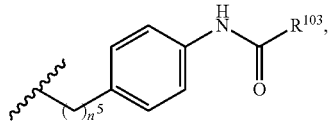

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

(v)

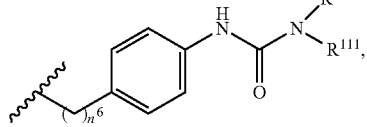

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;

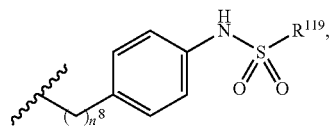

(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

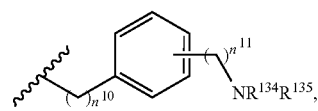

(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)NR$^{137}$R$^{138}$, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

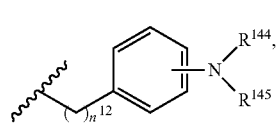

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2; and

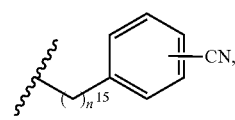

(xii)

wherein $n^{15}$ is 1 or 2;
$R^5$ is —NH$_2$, —NHCH$_3$ or —N(CH$_3$)$_2$; $n^1$ is 4; $R^6$ is —CH(CH$_3$)OH; $R^8$ is

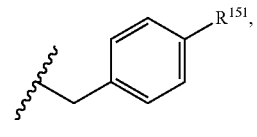

wherein $R^{151}$ is Cl or hydroxyl; each of $R^9$, $R^{10}$, $R^{11}$, $R^{12}$, $R^{13}$, $R^{14}$, and $R^{15}$ is H; L is

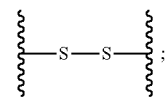 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is selected from the group consisting of H, $C_{1-3}$ alkyl, —C(O)$R^{17}$, —C(O)$C_{1-3}$ alkylene-C(O)OR$^{18}$, —C(O)$C_{1-3}$ alkylene-N(R$^{20}$)C(O)R$^{19}$, —C(O)$C_{1-3}$ alkylene-NR$^{21}$R$^{22}$, —C(O)$C_{1-3}$ alkylene-C(O)NR$^{23}$R$^{24}$, and —C(O)$C_{1-3}$ alkylene-S(O)$_2$R$^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

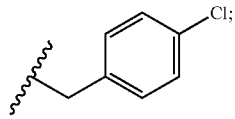 [SMILES: *Cc1ccc(Cl)cc1]

$R^3$ is

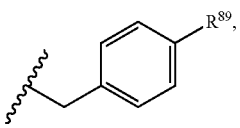

wherein $R^{89}$ is Cl or hydroxyl;

$R^4$ is selected from the group consisting of:

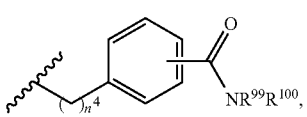
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO₂, and $C_{1-6}$ alkoxy, and wherein the $C_{6-10}$ aryl and 5- to 10-membered heteroaryl are optionally substituted with one or more substituents each independently selected from the group consisting of halogen, —OH, —NO₂, and $C_{1-6}$ alkoxy, and wherein $n^4$ is 1 or 2; and

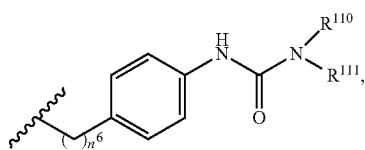
(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO₂, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO₂, and $C_{1-6}$ alkoxy, and wherein $n^6$ is 1 or 2;

$R^5$ is —NH₂, —NHCH₃ or —N(CH₃)₂; $n^1$ is 4; $R^6$ is —CH(CH₃)OH; $R^8$ is

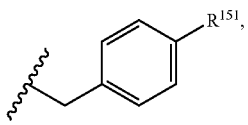

wherein $R^{151}$ is Cl or hydroxyl; each of $R^9$, $R^{10}$, $R^{11}$, $R^{12}$, $R^{13}$, $R^{14}$, and $R^{15}$ is H; L is

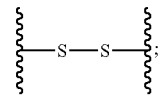

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH₂; $R^N$ is selected from the group consisting of H, $C_{1-3}$ alkyl, —C(O)R¹⁷, —C(O)$C_{1-3}$ alkylene-C(O)OR¹⁸, —C(O)$C_{1-3}$ alkylene-N(R²⁰)C(O)R¹⁹, —C(O)$C_{1-3}$ alkylene-NR²¹R²², —C(O)$C_{1-3}$ alkylene-C(O)NR²³R²⁴, and —C(O)$C_{1-3}$ alkylene-S(O)₂R²⁵, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

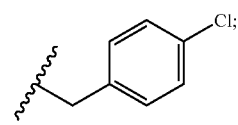 [SMILES: *Cc1ccc(Cl)cc1]

$R^3$ is

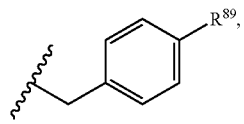

wherein $R^{89}$ is Cl or hydroxyl;

$R^4$ is selected from the group consisting of:

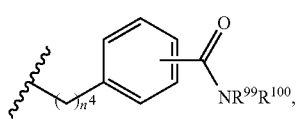
(iii)

wherein each of $R^{99}$ and $R^{100}$ is independently selected from the group consisting of H, $C_{1-6}$ alkyl, $C_{6-10}$ aryl, and 5- to 10-membered heteroaryl, and wherein $n^4$ is 1 or 2; and

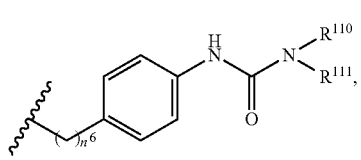
(v)

wherein $R^{110}$ is selected from the group consisting of H, $C_{1-6}$ alkyl, $C_{6-10}$ aryl, and 5- to 10-membered heteroaryl, and $R^{111}$ is selected from the group consisting of $C_{1-6}$ alkyl, $C_{6-10}$ aryl, and 5- to 10-membered heteroaryl, and wherein $n^6$ is 1 or 2;
$R^5$ is —$NH_2$, —$NHCH_3$ or —$N(CH_3)_2$; $n^1$ is 4; $R^6$ is —$CH(CH_3)OH$; $R^8$ is

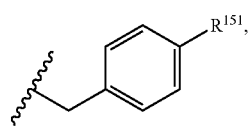

wherein $R^{151}$ is Cl or hydroxyl; each of $R^9$, $R^{10}$, $R^{11}$, $R^{12}$, $R^{13}$, $R^{14}$, and $R^{15}$ is H; L is

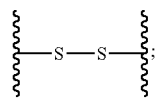

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

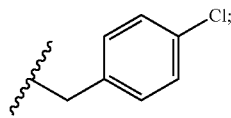

$R^3$ is

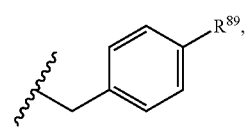

wherein $R^{89}$ is Cl or hydroxyl; $R^4$ is selected from the group consisting of:

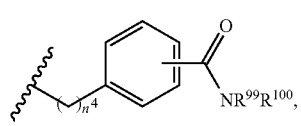
(iii)

wherein each of $R^{99}$ and $R^{100}$ is independently selected from the group consisting of H and $C_{1-6}$ alkyl, and wherein $n^4$ is 1 or 2; and

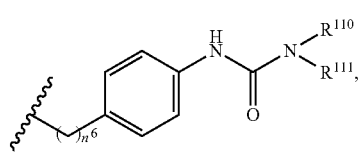
(v)

wherein $R^{110}$ is H, and $R^{111}$ is $C_6$ aryl, and wherein $n^6$ is 1 or 2; $R^5$ is —$NH_2$, —$NHCH_3$ or —$N(CH_3)_2$; $n^1$ is 4; $R^6$ is —$CH(CH_3)OH$; $R^8$ is

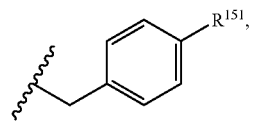

wherein $R^{151}$ is Cl or hydroxyl; each of $R^9$, $R^{10}$, $R^{11}$, $R^{12}$, $R^{13}$, $R^{14}$, and $R^{15}$ is H; L is

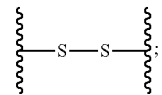 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

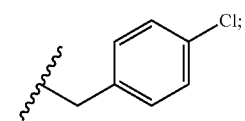 [SMILES: *Cc1ccc(Cl)cc1]

$R^3$ is

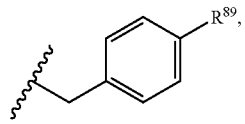

wherein $R^{89}$ is Cl or hydroxyl; $R^4$ is:

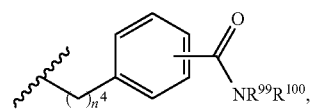
(iii)

wherein each of $R^{99}$ and $R^{100}$ is independently selected from the group consisting of H and $C_{1-6}$ alkyl, and wherein $n^4$ is 1 or 2; $R^5$ is —$NH_2$, —$NHCH_3$ or —$N(CH_3)_2$; $n^1$ is 4; $R^6$ is —$CH(CH_3)OH$; $R^8$ is

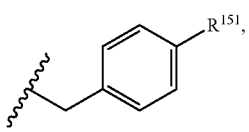

wherein $R^{151}$ is Cl or hydroxyl; each of $R^9$, $R^{10}$, $R^{11}$, $R^{12}$, $R^{13}$, $R^{14}$, and $R^{15}$ is H; L is

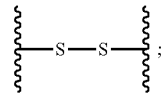

and chiral centre is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

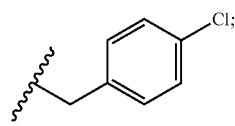 [SMILES: *Cc1ccc(Cl)cc1]

$R^3$ is

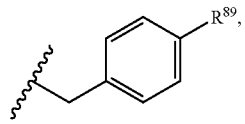

wherein $R^{89}$ is Cl or hydroxyl; $R^4$ is:

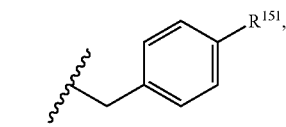
(iii)

wherein each of $R^{99}$ and $R^{100}$ is H, and wherein $n^4$ is 1 or 2; $R^5$ is —$NH_2$, —$NHCH_3$ or —$N(CH_3)_2$; $n^1$ is 4; $R^6$ is —$CH(CH_3)OH$; $R^8$ is

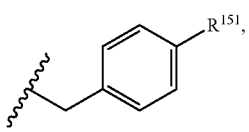

wherein $R^{151}$ is Cl or hydroxyl; each of $R^9$, $R^{10}$, $R^{11}$, $R^{12}$, $R^{13}$, $R^{14}$, and $R^{15}$ is H; L is

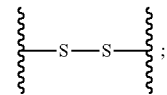 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

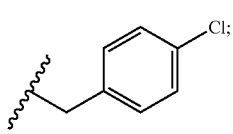

$R^3$ is

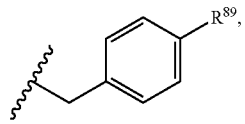

wherein $R^{89}$ is Cl or hydroxyl; $R^4$ is

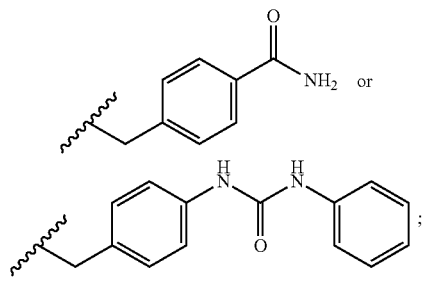

$R^5$ is —$NH_2$, —$NHCH_3$ or —$N(CH_3)_2$; $n^1$ is 4; $R^6$ is —$CH(CH_3)OH$; $R^8$ is

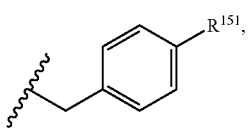

wherein $R^{151}$ is Cl or hydroxyl; each of $R^9$, $R^{10}$, $R^{11}$, $R^{12}$, $R^{13}$, $R^{14}$, and $R^{15}$ is H; L is

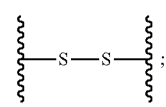

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is selected from the group consisting of H, $C_{1-3}$ alkyl, —$C(O)R^{17}$, —$C(O)C_{1-3}$ alkylene-$C(O)OR^{18}$, —$C(O)C_{1-3}$ alkylene-$N(R^{20})C(O)R^{19}$, —$C(O)C_{1-3}$ alkylene-$NR^{21}R^{22}$, —$C(O)C_{1-3}$ alkylene-$C(O)NR^{23}R^{24}$, and —$C(O)C_{1-3}$ alkylene-$S(O)_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl; $R^1$ is

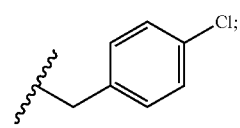 [SMILES: *Cc1ccc(Cl)cc1]

$R^3$ is

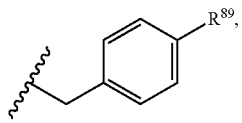

wherein $R^{89}$ is Cl or hydroxyl; $R^4$ is

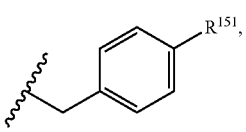

$R^5$ is —$NH_2$, —$NHCH_3$ or —$N(CH_3)_2$; $n^1$ is 4; $R^6$ is —$CH(CH_3)OH$; $R^8$ is

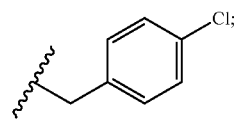

wherein $R^{151}$ is Cl or hydroxyl; each of $R^9$, $R^{10}$, $R^{11}$, $R^{12}$, $R^{13}$, $R^{14}$, and $R^{15}$ is H; L is

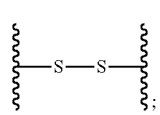

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

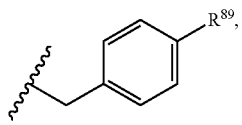

$R^3$ is, wherein $R^{89}$ is Cl or hydroxyl;

R⁴ is selected from the group consisting of:

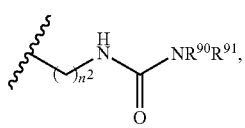
(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^2$ is 3 or 4;

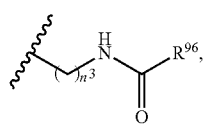
(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^3$ is 3 or 4;

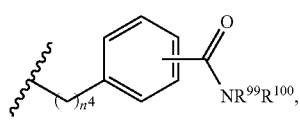
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2;

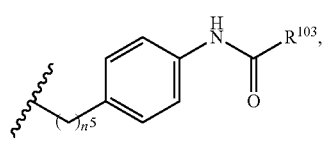
(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —NO$_2$, and $C_{1-6}$ alkoxy, and wherein $n^5$ is 1 or 2;

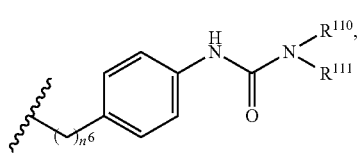
(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;

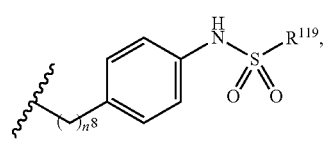
(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

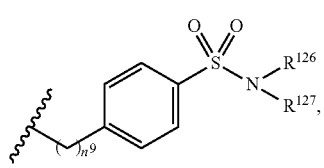
(vii)

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^9$ is 1 or 2;

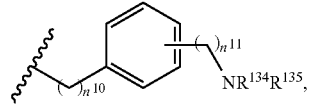
(viii)

wherein: each of R$^{134}$ and R$^{135}$ is independently selected from the group consisting of H, C$_{1-6}$ alkyl, C$_{6-10}$ aryl, 5- to 10-membered heteroaryl, —C(O)R$^{136}$, and —C(O)NR$^{137}$R$^{138}$, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^{10}$ is 1 or 2, and wherein n$^{11}$ is 1 or 2;

- R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and
- each of R$^{137}$ and R$^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;

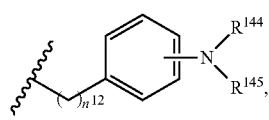
(ix)

wherein each of R$^{144}$ and R$^{145}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{12}$ is 1 or 2;

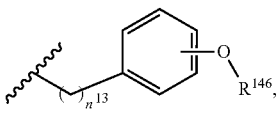
(x)

wherein R$^{146}$ is selected from the group consisting of C$_{2-6}$alkyl, C$_{6-10}$ aryl, and 5- to 10-membered heteroaryl, wherein the C$_{2-6}$alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{13}$ is 1 or 2;

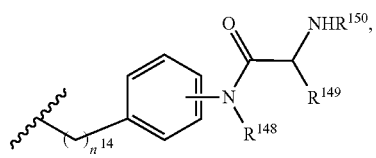
(xi)

wherein R$^{148}$ is H or CH$_3$, R$^{149}$ is H or C$_{1-6}$ alkyl optionally substituted with one or more substituents each independently selected from the group consisting of hydroxyl, —COOH, —NH$_2$, —C(O)NH$_2$, and —N(H)C(O)NH$_2$, and R$^{150}$ is H, CH$_3$ or acetyl, and wherein n$^{14}$ is 1 or 2; and

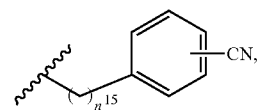
(xii)

wherein n$^{15}$ is 1 or 2;
R$^5$ is —NH$_2$, —NHCH$_3$ or —N(CH$_3$)$_2$; n$^1$ is 4; R$^6$ is —CH(CH$_3$)OH; R$^8$ is

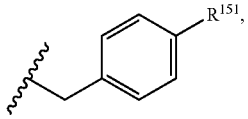

wherein R$^{151}$ is Cl or hydroxyl; each of R$^9$, R$^{10}$, R$^{11}$, R$^{12}$, R$^{13}$, R$^{14}$, and R$^{15}$ is H; L is

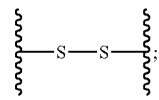 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

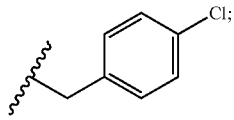 [SMILES: *Cc1ccc(Cl)cc1]

$R^3$ is

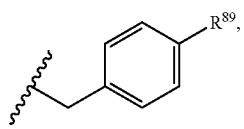

wherein $R^{89}$ is Cl or hydroxyl;
$R^4$ is selected from the group consisting of:

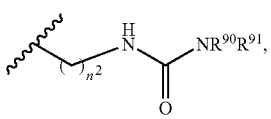

(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

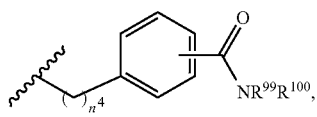

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

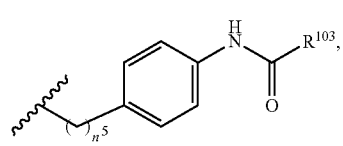

(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

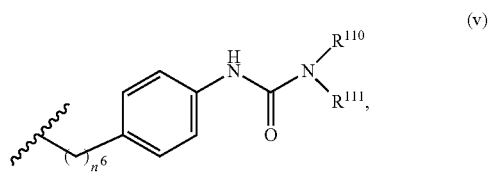

(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —$NO_2$, and $C_{1-6}$ alkoxy, and wherein $n^6$ is 1 or 2;

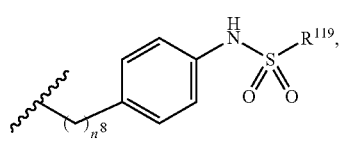

(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2;

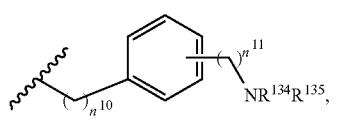

(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)N$R^{137}R^{138}$, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

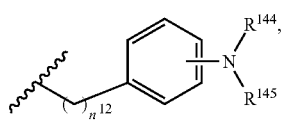

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2; and

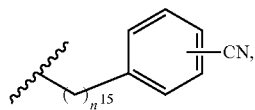

(xii)

wherein $n^{15}$ is 1 or 2;
$R^5$ is —NH$_2$, —NHCH$_3$ or —N(CH$_3$)$_2$; $n^1$ is 4; $R^6$ is —CH(CH$_3$)OH; $R^8$ is

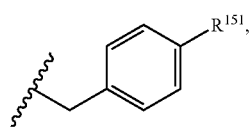

wherein $R^{151}$ is Cl or hydroxyl; each of $R^9$, $R^{10}$, $R^{11}$, $R^{12}$, $R^{13}$, $R^{14}$, and $R^{15}$ is H; L is

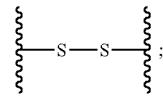 [SMILES: *SS*]

and centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

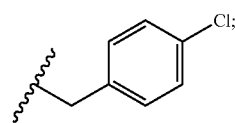

$R^3$ is

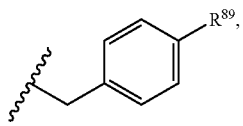

wherein $R^{89}$ is Cl or hydroxyl;
$R^4$ is selected from the group consisting of:

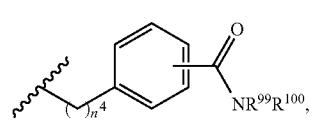

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2; and

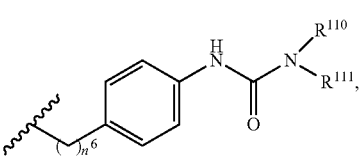

(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;
$R^5$ is —NH$_2$, —NHCH$_3$ or —N(CH$_3$)$_2$; $n^1$ is 4; $R^6$ is —CH(CH$_3$)OH; $R^8$ is

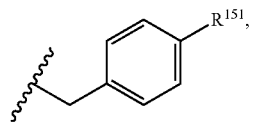

wherein $R^{151}$ is Cl or hydroxyl; each of $R^9$, $R^{10}$, $R^{11}$, $R^{12}$, $R^{13}$, $R^{14}$, and $R^{15}$ is H; L is

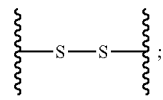

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

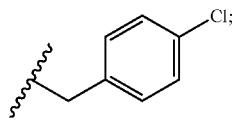 [SMILES: *Cc1ccc(Cl)cc1]

$R^3$ is

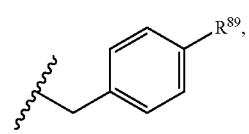

wherein $R^{89}$ is Cl or hydroxyl; $R^4$ is selected from the group consisting of:

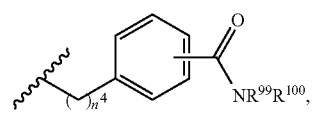

(iii)

wherein each of $R^{99}$ and $R^{100}$ is independently selected from the group consisting of H, $C_{1-6}$ alkyl, $C_{6-10}$ aryl, and 5- to 10-membered heteroaryl, and wherein $n^4$ is 1 or 2; and

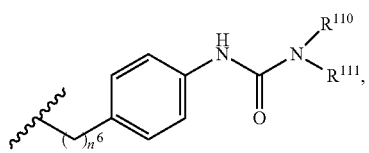

(v)

wherein $R^{110}$ is selected from the group consisting of H, $C_{1-6}$ alkyl, $C_{6-10}$ aryl, and 5- to 10-membered heteroaryl, and $R^{111}$ is selected from the group consisting of $C_{1-6}$ alkyl, $C_{6-10}$ aryl, and 5- to 10-membered heteroaryl, and wherein $n^6$ is 1 or 2; $R^5$ is —NH$_2$, —NHCH$_3$ or —N(CH$_3$)$_2$; $n^1$ is 4; $R^6$ is —CH(CH$_3$)OH; $R^8$ is

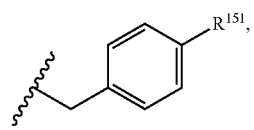

wherein $R^{151}$ is Cl or hydroxyl; each of $R^9$, $R^{10}$, $R^{11}$, $R^{12}$, $R^{13}$, $R^{14}$, and $R^{15}$ is H; L is

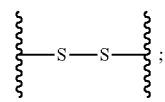 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

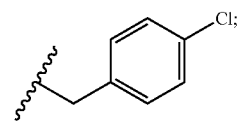 [SMILES: *Cc1ccc(Cl)cc1]

$R^3$ is

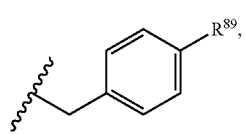

wherein $R^{89}$ is Cl or hydroxyl;

R$^4$ is selected from the group consisting of:

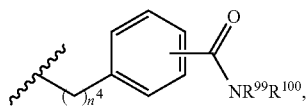
(iii)

wherein each of R$^{99}$ and R$^{100}$ is independently selected from the group consisting of H and C$_{1-6}$ alkyl, and wherein n$^4$ is 1 or 2; and

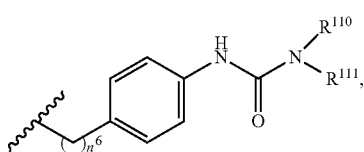
(v)

wherein R$^{110}$ is H, and R$^{111}$ is C$_6$ aryl, and wherein n$^6$ is 1 or 2; R$^5$ is —NH$_2$, —NHCH$_3$ or —N(CH$_3$)$_2$; n$^1$ is 4; R$^6$ is —CH(CH$_3$)OH; R$^8$ is

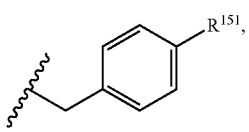

wherein R$^{151}$ is Cl or hydroxyl; each of R$^9$, R$^{10}$, R$^{11}$, R$^{12}$, R$^{13}$, R$^{14}$, and R$^{15}$ is H; L is

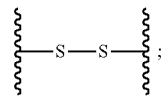

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R$^C$ is NH$_2$; R$^N$ is H; R$^1$ is

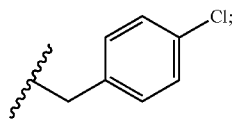

R$^3$ is

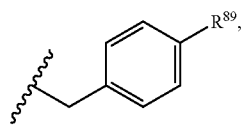

wherein R$^{89}$ is Cl or hydroxyl; R$^4$ is:

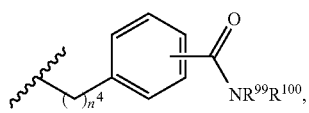
(iii)

wherein each of R$^{99}$ and R$^{100}$ is independently selected from the group consisting of H and C$_{1-6}$ alkyl, and wherein n$^4$ is 1 or 2; R$^5$ is —NH$_2$, —NHCH$_3$ or —N(CH$_3$)$_2$; n$^1$ is 4; R$^6$ is —CH(CH$_3$)OH; R$^8$ is

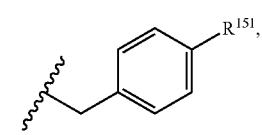

wherein R$^{51}$ is Cl or hydroxyl; each of R$^9$, R$^{10}$, R$^{11}$, R$^{12}$, R$^{13}$, R$^{14}$, and R$^{15}$ is H; L is

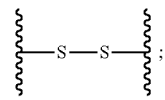 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R$^C$ is NH$_2$; R$^N$ is H; R$^1$ is

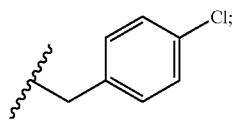 [SMILES: *Cc1ccc(Cl)cc1]

R$^3$ is

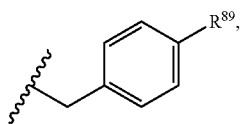

wherein R$^{89}$ is Cl or hydroxyl; R$^4$ is:

(iii)

wherein each of R$^{99}$ and R$^{100}$ is H, and wherein n$^4$ is 1 or 2; R$^5$ is —NH$_2$, —NHCH$_3$ or —N(CH$_3$)$_2$; n$^1$ is 4; R$^6$ is —CH(CH$_3$)OH; R$^8$ is

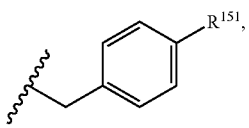

wherein $R^{151}$ is Cl or hydroxyl; each of $R^9$, $R^{10}$, $R^{11}$, $R^{12}$, $R^{13}$, $R^{14}$, and $R^{15}$ is H; L is

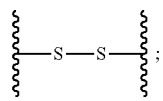 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

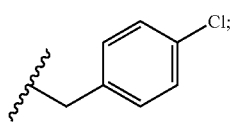

$R^3$ is

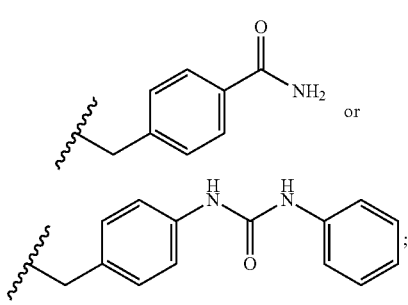

wherein $R^{89}$ is Cl or hydroxyl; $R^4$ is

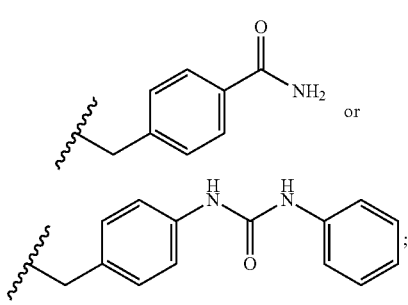

or $R^5$ is $—NH_2$, $—NHCH_3$ or $—N(CH_3)_2$; $n^1$ is 4; $R^6$ is $—CH(CH_3)OH$; $R^8$ is

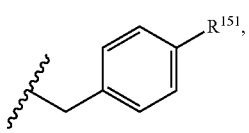

wherein $R^{151}$ is Cl or hydroxyl; each of $R^9$, $R^{10}$, $R^{11}$, $R^{12}$, $R^{13}$, $R^{14}$, and $R^{15}$ is H; L is

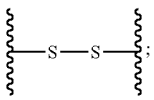

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

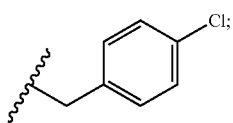 [SMILES: *Cc1ccc(Cl)cc1]

$R^3$ is

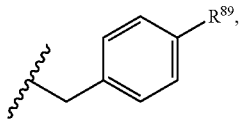

wherein $R^{89}$ is Cl or hydroxyl; $R^4$ is

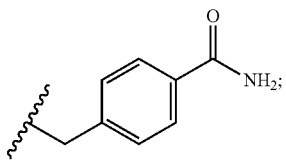 [SMILES: *Cc1ccc(C(N)=O)cc1]

$R^5$ is $—NH_2$, $—NHCH_3$ or $—N(CH_3)_2$; $n^1$ is 4; $R^6$ is $—CH(CH_3)OH$; $R^8$ is

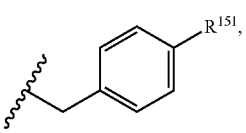

wherein $R^{151}$ is Cl or hydroxyl; each of $R^9$, $R^{10}$, $R^{11}$, $R^{12}$, $R^{13}$, $R^{14}$, and $R^{15}$ is H; L is

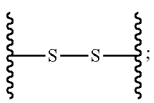

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

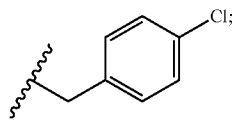 [SMILES: *Cc1ccc(Cl)cc1]

$R^3$ is

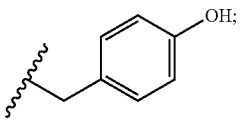 [SMILES: *Cc1ccc(O)cc1]

$R^4$ is selected from the group consisting of:

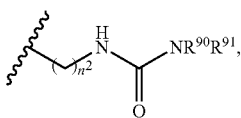

(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

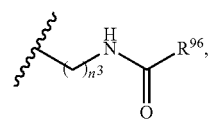

(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4;

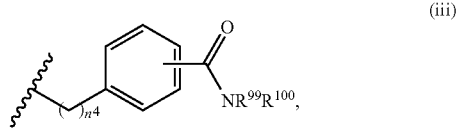

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

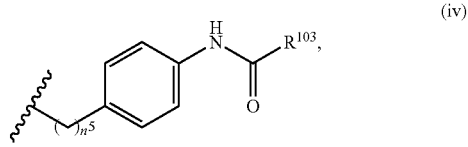

(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

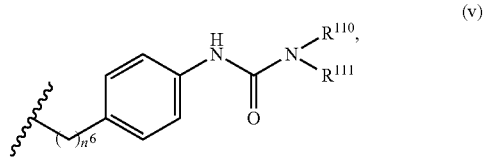

(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —$NO_2$, and $C_{1-6}$ alkoxy, and wherein $n^6$ is 1 or 2;

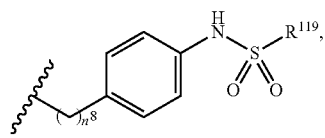

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, $-NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, $-NO_2$, and $C_{1-6}$ alkoxy, and wherein $n^8$ is 1 or 2;

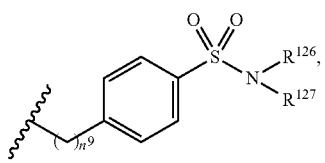

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, $-OH$, $-NO_2$, and $C_{1-6}$ alkoxy, and wherein the $C_{6-10}$ aryl and 5- to 10-membered heteroaryl are optionally substituted with one or more substituents each independently selected from the group consisting of halogen, $-OH$, $-NO_2$, and $C_{1-6}$ alkoxy, and wherein $n^9$ is 1 or 2;

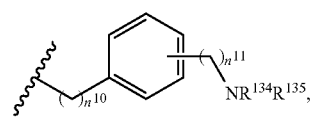

wherein: each of $R^{134}$ and $R^{135}$ is independently selected from the group consisting of H, $C_{1-6}$ alkyl, $C_{6-10}$ aryl, 5- to 10-membered heteroaryl, $-C(O)R^{136}$, and $-C(O)NR^{137}R^{138}$, wherein the $C_{1-6}$ alkyl is optionally substituted with one or more substituents each independently selected from the group consisting of halogen, $-OH$, $-NO_2$, and $C_{1-6}$ alkoxy, and wherein the $C_{6-10}$ aryl and 5- to 10-membered heteroaryl are optionally substituted with one or more substituents each independently selected from the group consisting of halogen, $-OH$, $-NO_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, $-OH$, $-NO_2$, and $C_{1-6}$ alkoxy, and wherein the $C_{6-10}$ aryl and 5- to 10-membered heteroaryl are optionally substituted with one or more substituents each independently selected from the group consisting of halogen, $-OH$, $-NO_2$, and $C_{1-6}$ alkoxy; and each of $R^{37}$ and $R^{38}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, $-OH$, $-NO_2$, and $C_{1-6}$ alkoxy, and wherein the $C_{6-10}$ aryl and 5- to 10-membered heteroaryl are optionally substituted with one or more substituents each independently selected from the group consisting of halogen, $-OH$, $-NO_2$, and $C_{1-6}$ alkoxy;

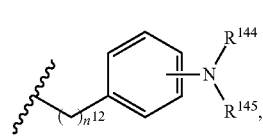

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, $-OH$, $-NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, $-OH$, $-NO_2$, $C_{1-6}$ alkoxy, and 5- to 10-membered heterocycloalkyl, and wherein $n^{12}$ is 1 or 2;

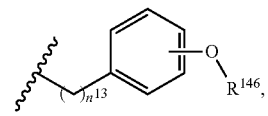

wherein $R^{146}$ is selected from the group consisting of $C_{2-6}$ alkyl, $C_{6-10}$ aryl, and 5- to 10-membered heteroaryl, wherein the $C_{2-6}$ alkyl is optionally substituted with one or more substituents each independently selected from the group consisting of halogen, $-OH$, $-NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, $-OH$, $-NO_2$, $C_{1-6}$ alkoxy, and 5- to 10-membered heterocycloalkyl, and wherein $n^{13}$ is 1 or 2;

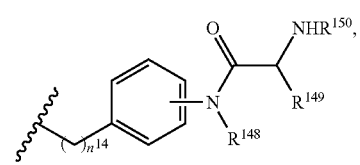

wherein $R^{148}$ is H or $CH_3$, $R^{149}$ is H or $C_{1-6}$ alkyl optionally substituted with one or more substituents each independently selected from the group consisting of hydroxyl, $-COOH$, $-NH_2$, $-C(O)NH_2$, and $-N(H)C(O)NH_2$, and $R^{150}$ is H, $CH_3$ or acetyl, and wherein $n^{14}$ is 1 or 2; and

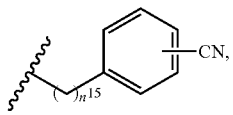
(xii)

wherein $n^{15}$ is 1 or 2;
$R^5$ is —NH$_2$, —NHCH$_3$ or —N(CH$_3$)$_2$; $n^1$ is 4; $R^6$ is —CH(CH$_3$)OH; $R^8$ is

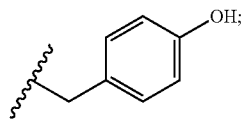 [SMILES: *Cc1ccc(O)cc1]

each of $R^9$, $R^{10}$, $R^{11}$, $R^{12}$, $R^{13}$, $R^{14}$, and $R^{15}$ is H; L is

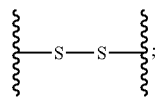

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

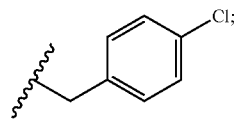 [SMILES: *Cc1ccc(Cl)cc1]

$R^3$ is

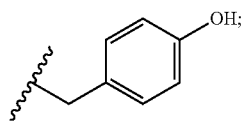 [SMILES: *Cc1ccc(O)cc1]

$R^4$ is selected from the group consisting of:

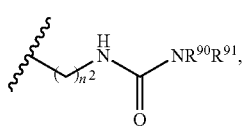
(i)

wherein each of $R^{90}$ and $R^{91}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein $n^2$ is 3 or 4;

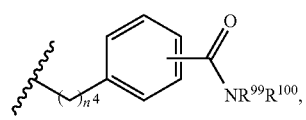
(iii)

wherein each of $R^{99}$ and $R^{100}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein $n^4$ is 1 or 2;

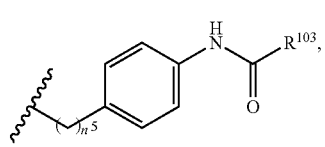
(iv)

wherein $R^{103}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents each independently selected from the group consisting of halogen, hydroxy, —NO$_2$, and C$_{1-6}$ alkoxy, and wherein the C$_{6-10}$ aryl, 5- to 10-membered heteroaryl, and 5- to 10-membered heterocycloalkyl are optionally substituted with one or more substituents each independently selected from the group consisting of halogen, hydroxy, —NO$_2$, and C$_{1-6}$ alkoxy, and wherein $n^5$ is 1 or 2;

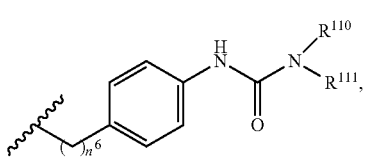
(v)

wherein $R^{110}$ is selected from the group consisting of H, C$_{1-6}$ alkyl, C$_{6-10}$ aryl, and 5- to 10-membered heteroaryl, $R^{111}$ is selected from the group consisting of C$_{1-6}$ alkyl, C$_{6-10}$ aryl, and 5- to 10-membered heteroaryl, wherein the C$_{1-6}$ alkyl of $R^{110}$ or $R^{111}$ is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl of $R^{110}$ or $R^{111}$ are optionally substituted with one or more substituents each independently selected from the group consisting of halogen, —OH, —NO$_2$, and C$_{1-6}$ alkoxy, and wherein $n^6$ is 1 or 2;

(vi)

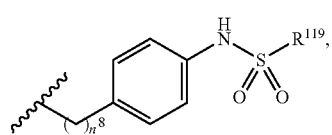

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2;

(viii)

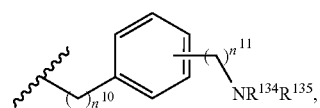

wherein: each of $R^{134}$ and $R^{135}$ is independently selected from the group consisting of H, $C_{1-6}$ alkyl, $C_{6-10}$ aryl, 5- to 10-membered heteroaryl, —$C(O)R^{136}$, and —$C(O)NR^{137}R^{138}$, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy;

(ix)

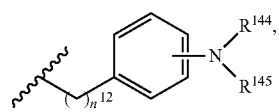

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, and 5- to 10-membered heterocycloalkyl, and wherein $n^{12}$ is 1 or 2; and (xii)

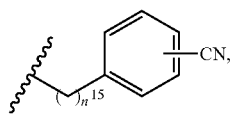

wherein $n^{15}$ is 1 or 2;

$R^5$ is —$NH_2$, —$NHCH_3$ or —$N(CH_3)_2$; $n^1$ is 4; $R^6$ is —$CH(CH_3)OH$; $R^8$ is

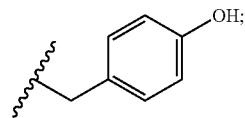 [SMILES: *Cc1ccc(O)cc1]

each of $R^9$, $R^{10}$, $R^{11}$, $R^{12}$, $R^{13}$, $R^{14}$, and $R^{15}$ is H; L is

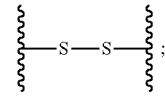 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

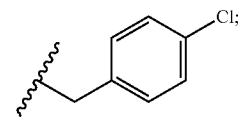 [SMILES: *Cc1ccc(Cl)cc1]

$R^3$ is

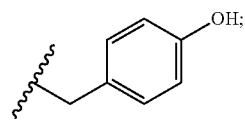 [SMILES: *Cc1ccc(O)cc1]

$R^4$ is selected from the group consisting of:

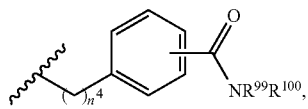
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2; and

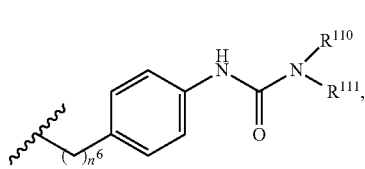
(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —$NO_2$, and $C_{1-6}$ alkoxy, and wherein $n^6$ is 1 or 2;
$R^5$ is —$NH_2$, —$NHCH_3$ or —$N(CH_3)_2$; $n^1$ is 4; $R^6$ is —$CH(CH_3)OH$; $R^8$ is

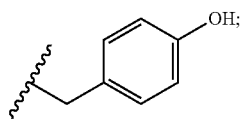 [SMILES: *Cc1ccc(O)cc1]

each of $R^9$, $R^{10}$, $R^{11}$, $R^9$, $R^{13}$, $R^{14}$, and $R^{15}$ is H; L is

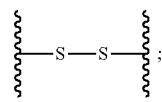

and chiral centre 1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

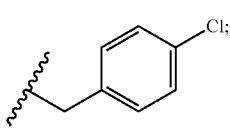 [SMILES: *Cc1ccc(Cl)cc1]

$R^3$ is

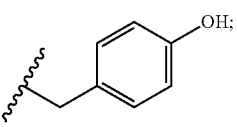 [SMILES: *Cc1ccc(O)cc1]

$R^4$ is selected from the group consisting of:

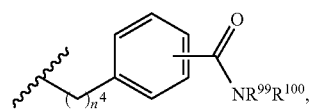
(iii)

wherein each of $R^{99}$ and $R^{00}$ is independently selected from the group consisting of H, $C_{1-6}$ alkyl, $C_{6-10}$ aryl, and 5- to 10-membered heteroaryl, and wherein $n^4$ is 1 or 2; and

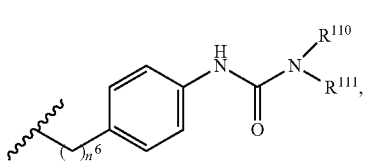
(v)

wherein $R^{110}$ is selected from the group consisting of H, $C_{1-6}$ alkyl, $C_{6-10}$ aryl, and 5- to 10-membered heteroaryl, and $R^{111}$ is selected from the group consisting of $C_{1-6}$ alkyl, $C_{6-10}$ aryl, and 5- to 10-membered heteroaryl, and wherein $n^6$ is 1 or 2; $R^5$ is —$NH_2$, —$NHCH_3$ or —$N(CH_3)_2$; $n^1$ is 4; $R^6$ is —$CH(CH_3)OH$; $R^8$ is

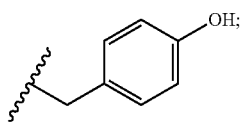 [SMILES: *Cc1ccc(O)cc1]

each of $R^9$, $R^{10}$, $R^{11}$, $R^{12}$, $R^{13}$, $R^{14}$, and $R^{15}$ is H; L is

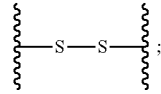

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

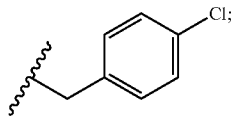 [SMILES: *Cc1ccc(Cl)cc1]

$R^3$ is

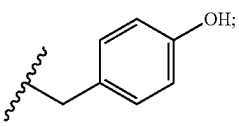 [SMILES: *Cc1ccc(O)cc1]

$R^4$ is selected from the group consisting of:

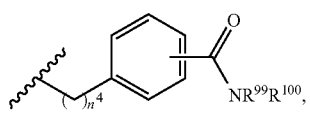 (iii)

wherein each of $R^{99}$ and $R^{100}$ is independently selected from the group consisting of H and $C_{1-6}$ alkyl, and wherein $n^4$ is 1 or 2; and

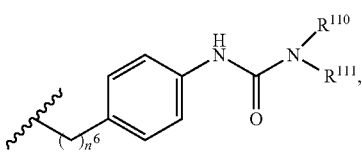 (v)

wherein $R^{110}$ is H, and $R^{111}$ is $C_6$ aryl, and wherein $n^6$ is 1 or 2; $R^5$ is $-NH_2$, $-NHCH_3$ or $-N(CH_3)_2$; $n^1$ is 4; $R^6$ is $-CH(CH_3)OH$; $R^8$ is

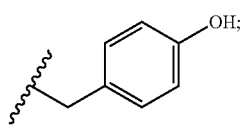 [SMILES: *Cc1ccc(O)cc1]

each of $R^9$, $R^{10}$, $R^{11}$, $R^{12}$, $R^{13}$, $R^{14}$, and $R^{15}$ is H; L is

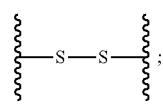

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

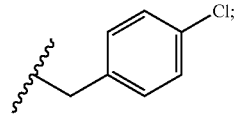 [SMILES: *Cc1ccc(Cl)cc1]

$R^3$ is

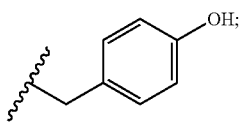 [SMILES: *Cc1ccc(O)cc1]

$R^4$ is:

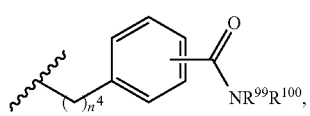 (iii)

wherein each of $R^{99}$ and $R^{00}$ is independently selected from the group consisting of H and $C_{1-6}$ alkyl, and wherein $n^4$ is 1 or 2; $R^5$ is $-NH_2$, $-NHCH_3$ or $-N(CH_3)_2$; $n^1$ is 4; $R^6$ is $-CH(CH_3)OH$; $R^8$ is

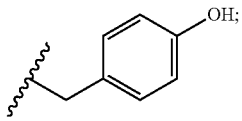 [SMILES: *Cc1ccc(O)cc1]

each of $R^9$, $R^{10}$, $R^{11}$, $R^{12}$, $R^{13}$, $R^{14}$, and $R^{15}$ is H; L is

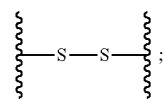

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

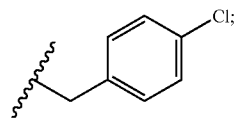

R³ is

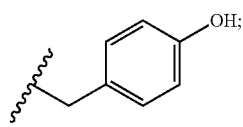 [SMILES: *Cc1ccc(O)cc1]

R⁴ is:

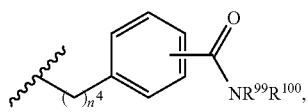
(iii)

wherein each of R⁹⁹ and R¹⁰⁰ is H, and wherein n⁴ is 1 or 2; R⁵ is —NH₂, —NHCH₃ or —N(CH₃)₂; n¹ is 4; R⁶ is —CH(CH₃)OH; R⁸ is

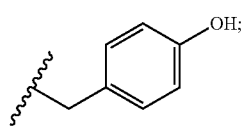 [SMILES: *Cc1ccc(O)cc1]

each of R⁹, R¹⁰, R¹¹, R¹², R¹³, R¹⁴, and R¹⁵ is H; L is

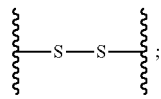 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R^C is NH₂; R^N is H; R¹ is

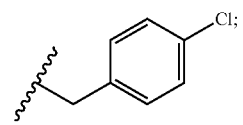 [SMILES: *Cc1ccc(Cl)cc1]

R³ is

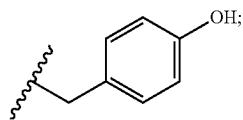

R⁴ is

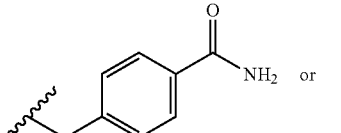

R⁵ is —NH₂, —NHCH₃ or —N(CH₃)₂; n¹ is 4; R⁶ is —CH(CH₃)OH; R⁸ is

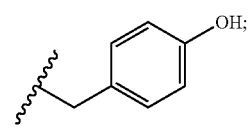 [SMILES: *Cc1ccc(O)cc1]

each of R⁹, R¹⁰, R¹¹, R¹², R¹³, R¹⁴, and R¹⁵ is H; L is

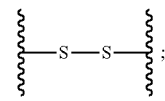

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: R^C is NH₂; R^N is H; R¹ is

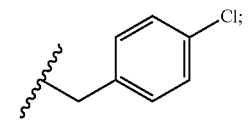 [SMILES: *Cc1ccc(Cl)cc1]

R³ is

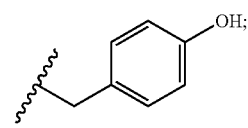 [SMILES: *Cc1ccc(O)cc1]

R⁴ is

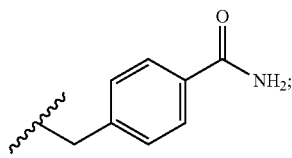 [SMILES: *Cc1ccc(C(N)=O)cc1]

$R^5$ is —$NH_2$, —$NHCH_3$ or —$N(CH_3)_2$; $n^1$ is 4; $R^6$ is —$CH(CH_3)OH$; $R^8$ is

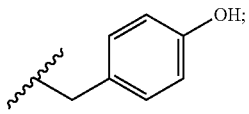 [SMILES: *Cc1ccc(O)cc1]

each of $R^9$, R, R, $R^{12}$, $R^{13}$, $R^{14}$, and $R^{15}$ is H; L is

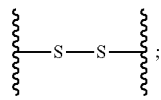

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

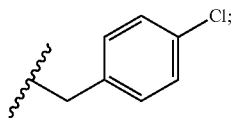 [SMILES: *Cc1ccc(Cl)cc1]

$R^3$ is

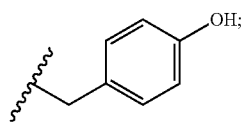 [SMILES: *Cc1ccc(O)cc1]

$R^4$ is selected from the group consisting of:

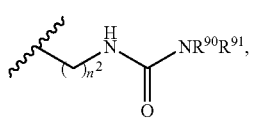
(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

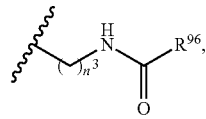
(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4;

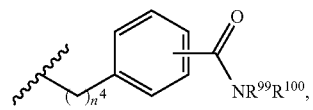
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

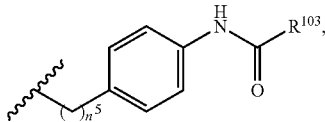
(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

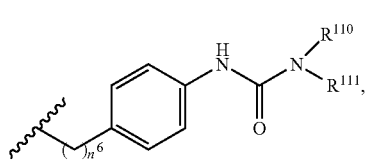
(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;

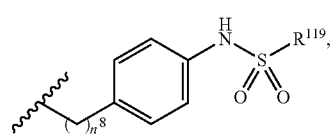

(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

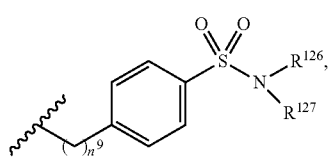

(vii)

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^9$ is 1 or 2;

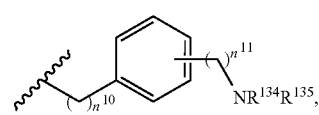

(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)NR$^{137}R^{138}$, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

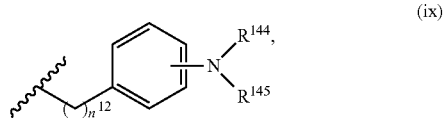

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2;

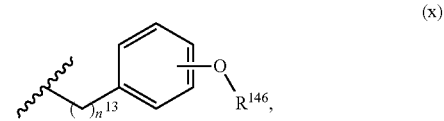

(x)

wherein $R^{146}$ is selected from the group consisting of $C_{2-6}$ alkyl, $C_{6-10}$ aryl, and 5- to 10-membered heteroaryl, wherein the $C_{2-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{13}$ is 1 or 2;

(xi)

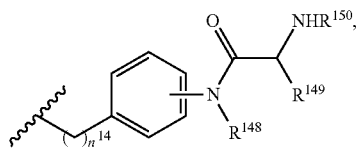

wherein $R^{148}$ is H or $CH_3$, $R^{149}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{150}$ is H, $CH_3$ or acetyl, and wherein $n^{14}$ is 1 or 2; and (xii)

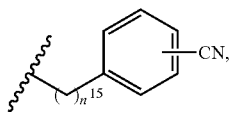

wherein $n^{15}$ is 1 or 2;
$R^5$ is —$NH_2$ or —$NHCH_3$; $n^1$ is 4; $R^6$ is —CH($CH_3$)OH; $R^8$ is

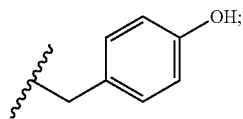 [SMILES: *Cc1ccc(O)cc1]

each of $R^9$, $R^{10}$, $R^{11}$, $R^{12}$, $R^{13}$, $R^{14}$, and $R^{15}$ is H; L is

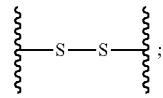

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

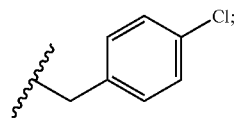

$R^3$ is

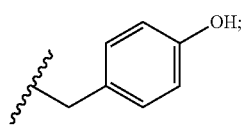

$R^4$ is selected from the group consisting of:

(i)

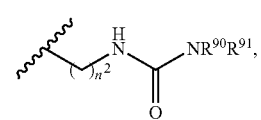

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

(iii)

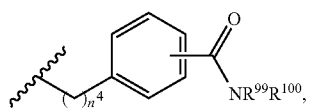

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

(iv)

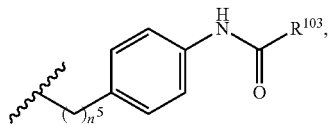

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

(v)

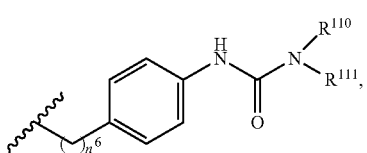

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;

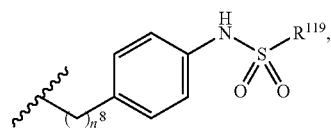

(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

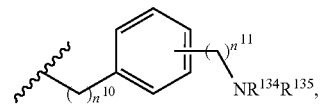

(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)NR$^{137}$R$^{138}$, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2; and (xii)

wherein $n^{15}$ is 1 or 2;
$R^5$ is —NH$_2$ or —NHCH$_3$; $n^1$ is 4; $R^6$ is —CH(CH$_3$)OH; $R^8$ is each of $R^9$, $R^{10}$, $R^{11}$, $R^{12}$, $R^{13}$, $R^{14}$, and $R^{15}$ is H; L is and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

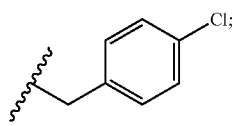

$R^3$ is

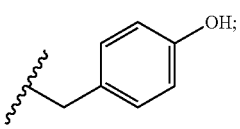

$R^4$ is selected from the group consisting of:

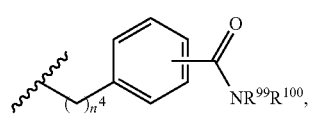
(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2; and

(v)

wherein $R^{110}$ is selected from the group consisting of H, $C_{1-6}$ alkyl, $C_{6-10}$ aryl, and 5- to 10-membered heteroaryl, $R^{111}$ is selected from the group consisting of $C_{1-6}$ alkyl, $C_{6-10}$ aryl, and 5- to 10-membered heteroaryl, wherein the $C_{1-6}$ alkyl of $R^{110}$ or $R^{111}$ is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl of $R^{110}$ or $R^{111}$ are optionally substituted with one or more substituents each independently selected from the group consisting of halogen, —OH, —NO$_2$, and $C_{1-6}$ alkoxy, and wherein $n^6$ is 1 or 2;
$R^5$ is —NH$_2$ or —NHCH$_3$; $n^1$ is 4; $R^6$ is —CH(CH$_3$)OH; $R^8$ is

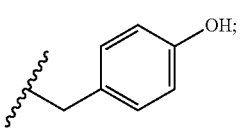

each of $R^9$, $R^{10}$, $R^{11}$, $R^{12}$, $R^{13}$, $R^{14}$, and $R^{15}$ is H; L is

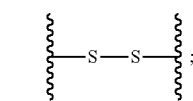 [SMILES: *SS*]

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is NH$_2$; $R^N$ is H; $R^1$ is

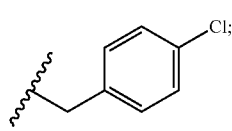 [SMILES: *Cc1ccc(Cl)cc1]

$R^3$ is

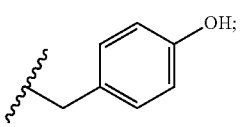

$R^4$ is selected from the group consisting of:

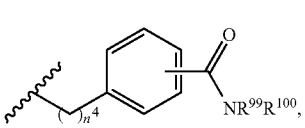
(iii)

wherein each of $R^{99}$ and $R^{100}$ is independently selected from the group consisting of H, $C_{1-6}$ alkyl, $C_{6-10}$ aryl, and 5- to 10-membered heteroaryl, and wherein $n^4$ is 1 or 2; and

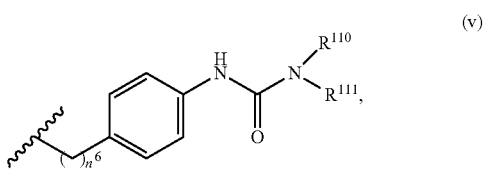
(v)

wherein $R^{110}$ is selected from the group consisting of H, $C_{1-6}$ alkyl, $C_{6-10}$ aryl, and 5- to 10-membered heteroaryl, and $R^{111}$ is selected from the group consisting of $C_{1-6}$ alkyl, $C_{6-10}$ aryl, and 5- to 10-membered heteroaryl, and wherein $n^6$ is 1 or 2; $R^5$ is —NH$_2$ or —NHCH$_3$; $n^1$ is 4; $R^6$ is —CH(CH$_3$)OH; $R^8$ is

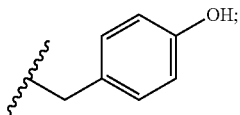 [SMILES: *Cc1ccc(O)cc1]

each of $R^9$, $R^{10}$, $R^{11}$, $R^{12}$, $R^{13}$, $R^{14}$, and $R^{15}$ is H; L is

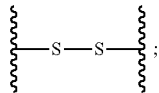

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

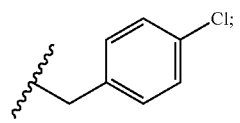 [SMILES: *Cc1ccc(Cl)cc1]

$R^3$ is

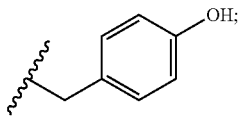 [SMILES: *Cc1ccc(O)cc1]

$R^4$ is selected from the group consisting of:

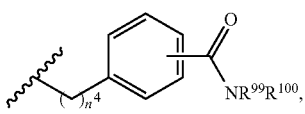
(iii)

wherein each of $R^{99}$ and $R^{100}$ is independently selected from the group consisting of H and $C_{1-6}$ alkyl, and wherein $n^4$ is 1 or 2; and

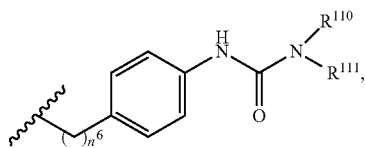
(v)

wherein $R^{110}$ is H, and $R^{111}$ is $C_6$ aryl, and wherein $n^6$ is 1 or 2; $R^5$ is $-NH_2$ or $-NHCH_3$; $n^1$ is 4; $R^6$ is $-CH(CH_3)OH$; $R^8$ is

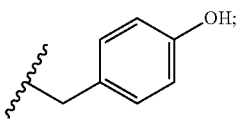

each of $R^9$, $R^{10}$, $R^{11}$, $R^{12}$, $R^{13}$, $R^{14}$, and $R^{15}$ is H; L is

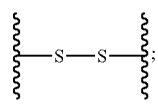

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

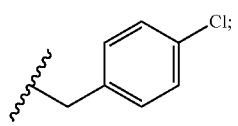 [SMILES: *Cc1ccc(Cl)cc1]

$R^3$ is

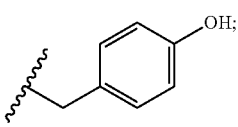 [SMILES: *Cc1ccc(O)cc1]

$R^4$ is:

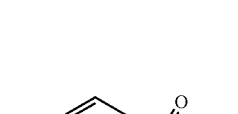
(iii)

wherein each of $R^{99}$ and $R^{100}$ is independently selected from the group consisting of H and $C_{1-6}$ alkyl, and wherein $n^4$ is 1 or 2; $R^5$ is $-NH_2$ or $-NHCH_3$; $n^1$ is 4; $R^6$ is $-CH(CH_3)OH$; $R^8$ is

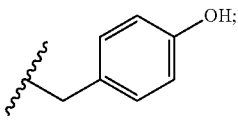 [SMILES: *Cc1ccc(O)cc1]

each of $R^9$, $R^{10}$, $R^{11}$, $R^{12}$, $R^{13}$, $R^{14}$, and $R^{15}$ is H; L is

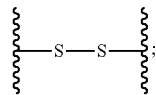

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

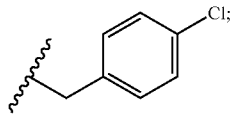 [SMILES: *Cc1ccc(Cl)cc1]

$R^3$ is

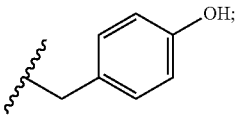 [SMILES: *Cc1ccc(O)cc1]

$R^4$ is:

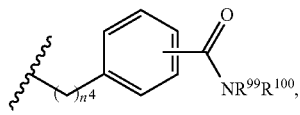

(iii)

wherein each of $R^{99}$ and $R^{100}$ is H, and wherein $n^4$ is 1 or 2; $R^5$ is $-NH_2$ or $-NHCH_3$; $n^1$ is 4; $R^6$ is $-CH(CH_3)OH$; $R^8$ is

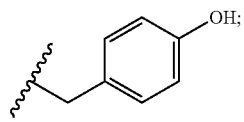 [SMILES: *Cc1ccc(O)cc1]

each of $R^9$, $R^{10}$, $R^{11}$, $R^{12}$, $R^{13}$, $R^{14}$, and $R^{15}$ is H; L is

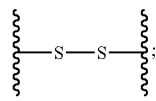

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is

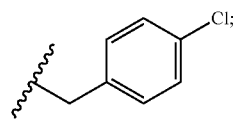 [SMILES: *Cc1ccc(Cl)cc1]

$R^3$ is

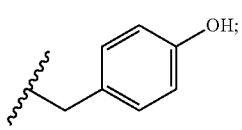

$R^4$ is

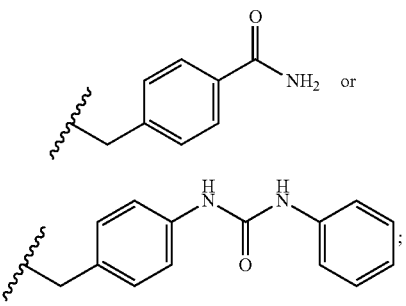

$R^5$ is $-NH_2$ or $-NHCH_3$; $n^1$ is 4; $R^6$ is $-CH(CH_3)OH$; $R^8$ is

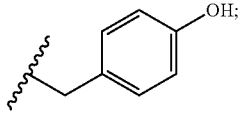

each of $R^9$, $R^{10}$, $R^{11}$, $R^{12}$, $R^{13}$, $R^{14}$, and $R^{15}$ is H; L is

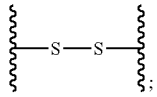

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula I or a salt thereof, wherein: $R^C$ is $NH_2$; $R^N$ is H; $R^1$ is $R^3$ is

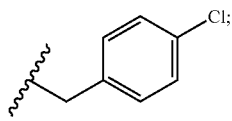 [SMILES: *Cc1ccc(Cl)cc1]

$R^4$ is

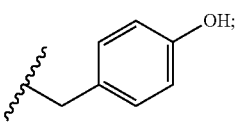 [SMILES: *Cc1ccc(O)cc1]

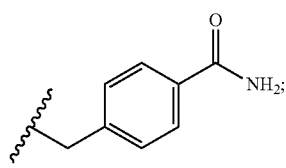 [SMILES: *Cc1ccc(C(N)=O)cc1]

$R^5$ is —$NH_2$ or —$NHCH_3$; $n^1$ is 4; $R^6$ is —$CH(CH_3)OH$; $R^8$ is

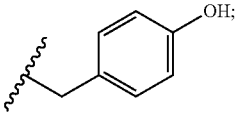 [SMILES: *Cc1ccc(O)cc1]

each of $R^9$, $R^{10}$, $R^{11}$, $R^{12}$, $R^{13}$, $R^{14}$, and $R^{15}$ is H; L is

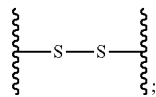

and chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy;

$R^4$ is selected from the group consisting of:

(i) —$N(H)C(O)NR^{51}R^{52}$ or —$C_{1-6}$ alkylene-$N(H)C(O)NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ii) —$NHC(O)R^{54}$ or —$C_{1-6}$ alkylene-$NHC(O)R^{54}$, wherein $R^{54}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iii) —($C_{6-10}$ arylene)-$C(O)NR^{56}R^{57}$ or —$C_{1-6}$ alkylene-($C_{6-10}$ arylene)-$C(O)NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —($C_{6-10}$ arylene)-$N(H)C(O)R^{58}$ or —$C_{1-6}$ alkylene-($C_{6-10}$ arylene)-$N(H)C(O)R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents;

(v) —($C_{6-10}$ arylene)-$N(H)C(O)NR^{60}R^{61}$ or —$C_{1-6}$ alkylene-($C_{6-10}$ arylene)-$N(H)C(O)NR^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vi) —($C_{6-10}$ arylene)-$N(H)SO_2R^{63}$ or —$C_{1-6}$ alkylene-($C_{6-10}$ arylene)-$N(H)SO_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(vii) —($C_{6-10}$ arylene)-$SO_2NR^{65}R^{66}$ or —$C_{1-6}$ alkylene-($C_{6-10}$ arylene)-$SO_2NR^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(viii) —($C_{6-10}$ arylene)-($C_{1-6}$ alkylene)-$NR^{67}R^{68}$ or —$C_{1-6}$ alkylene-($C_{6-10}$ arylene)-($C_{1-6}$ alkylene)-$NR^{67}R^{68}$, wherein:
each of $R^{67}$ and $R^{68}$ is independently selected from the group consisting of H, $C_{1-6}$ alkyl, $C_{6-10}$ aryl, 5- to 10-membered heteroaryl, —$C(O)R^{69}$, and —$C(O)NR^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents;
$R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(ix) —($C_{6-10}$ arylene)-$NR^{72}R^{73}$ or —$C_{1-6}$ alkylene-($C_{6-10}$ arylene)-$NR^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{74}$ or —$C_{1-6}$ alkylene-($C_{6-10}$ arylene)-$OR^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{75}$)—C(O)—$CHR^{76}$—N(H)$R^{78}$, wherein $R^{75}$ is H or $CH_3$, $R^{76}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{78}$ is H, $CH_3$ or acetyl;

$R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

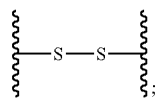

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy;

$R^4$ is selected from the group consisting of:

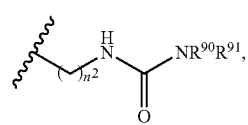

(i)

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

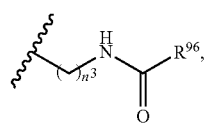

(ii)

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4;

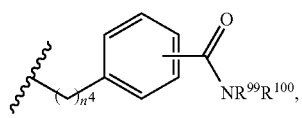

(iii)

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

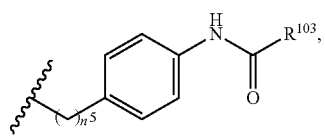

(iv)

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —NO$_2$, and C$_{1-6}$ alkyl, and wherein the C$_{6-10}$ aryl, 5- to 10-membered heteroaryl, and 5- to 10-membered heterocycloalkyl are optionally substituted with one or more substituents each independently selected from the group consisting of halogen, hydroxy, —NO$_2$, and C$_{1-6}$ alkoxy, and wherein n$^5$ is 1 or 2;

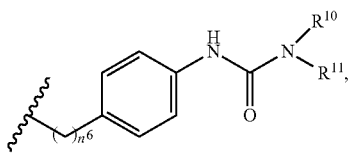
(v)

wherein each of R$^{110}$ and R$^{111}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^6$ is 1 or 2;

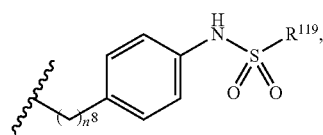
(vi)

wherein R$^{119}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, hydroxy, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, hydroxy, —NO$_2$, and C$_{1-6}$ alkoxy, and wherein n$^8$ is 1 or 2;

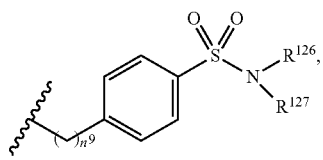
(vii)

wherein each of R$^{126}$ and R$^{127}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^9$ is 1 or 2;

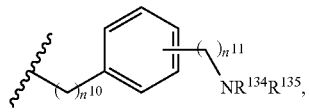
(viii)

wherein: each of R$^{134}$ and R$^{135}$ is independently selected from the group consisting of H, C$_{1-6}$ alkyl, C$_{6-10}$ aryl, 5- to 10-membered heteroaryl, —C(O)R$^{36}$, and —C(O)NR$^{37}$R$^{38}$, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^{10}$ is 1 or 2, and wherein n$^{11}$ is 1 or 2;

R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and each of R$^{137}$ and R$^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;

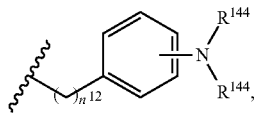
(ix)

wherein each of R$^{144}$ and R$^{145}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{12}$ is 1 or 2;

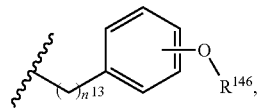
(x)

wherein $R^{146}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, and 5- to 10-membered heterocycloalkyl, and wherein $n^{13}$ is 1 or 2; and

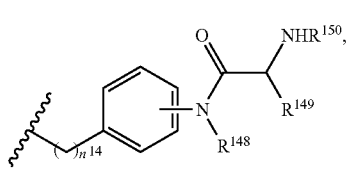

(xi)

wherein $R^{148}$ is H or $CH_3$, $R^{149}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{150}$ is H, $CH_3$ or acetyl, and wherein $n^{14}$ is 1 or 2; $R^5$ is —$NR^{79}R^{80}$, thereof, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

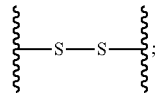

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

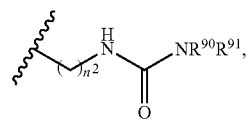

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

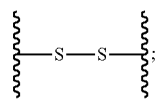

chiral centre *i is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

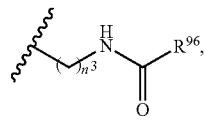

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

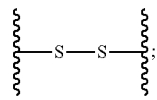

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

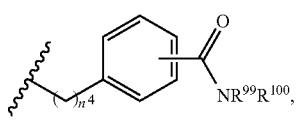

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

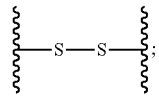

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

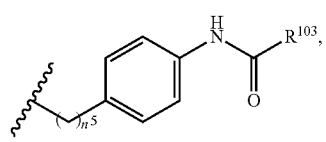

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

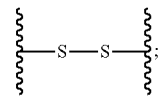

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

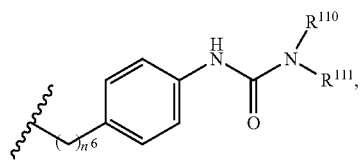

wherein each of $R^{110}$ and $R^{111}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^6$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

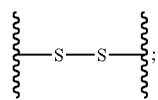

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

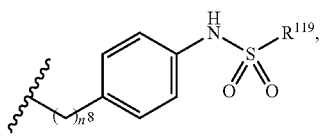

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

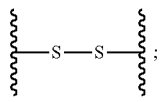

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

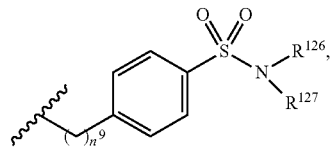

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^9$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene($C_{6-10}$ aryl), wherein the $C_{6-10}$ aryl is optionally substituted with one or more substituents each independently selected from the group consisting of halogen, hydroxy and —$NO_2$; and L is

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

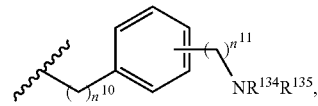

wherein:
each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)$NR^{137}R^{138}$, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^{10}$ is 1 or 2, and wherein n$^{11}$ is 1 or 2;
R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and each of R$^{137}$ and R$^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;
R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —C$_{1-2}$ alkylene(C$_{6-10}$ aryl), wherein the C$_{6-10}$ aryl is optionally substituted with one or more substituents each independently selected from the group consisting of halogen, hydroxy and —NO$_2$; and L is

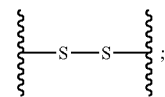

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —C$_{1-2}$ alkylene(C$_{6-10}$ aryl), wherein the C$_{6-10}$ aryl is optionally substituted with one or more substituents each independently selected from the group consisting of halogen and —NO$_2$; R$^3$ is selected from the group consisting of —C$_{1-2}$ alkylene(C$_6$ aryl) and —C$_{1-2}$ alkylene(6-membered heteroaryl), wherein the C$_6$ aryl and the 6-membered heteroaryl are optionally substituted with hydroxy; R$^4$ is

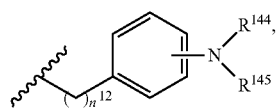

wherein each of R$^{144}$ and R$^{145}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{12}$ is 1 or 2; R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —C$_{1-2}$ alkylene (C$_{6-10}$ aryl), wherein the C$_{6-10}$ aryl is optionally substituted with one or more substituents each independently selected from the group consisting of halogen, hydroxy and —NO$_2$; and L is

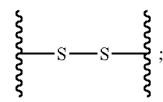

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —C$_{1-2}$ alkylene(C$_{6-10}$ aryl), wherein the C$_{6-10}$ aryl is optionally substituted with one or more substituents each independently selected from the group consisting of halogen and —NO$_2$; R$^3$ is selected from the group consisting of —C$_{1-2}$ alkylene(C$_6$ aryl) and —C$_{1-2}$ alkylene(6-membered heteroaryl), wherein the C$_6$ aryl and the 6-membered heteroaryl are optionally substituted with hydroxy; R$^4$ is

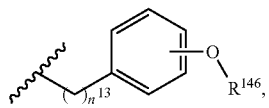

wherein R$^{146}$ is selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, C$_{1-6}$ alkoxy, and 5- to 10-membered heterocycloalkyl, and wherein the C$_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{13}$ is 1 or 2; R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —C$_{1-2}$ alkylene(C$_{6-10}$ aryl), wherein the C$_{6-10}$ aryl is optionally substituted with one or more substituents each independently selected from the group consisting of halogen, hydroxy and —NO$_2$; and L is

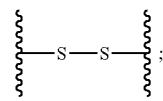 [SMILES: *SS*]

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$C_{1-2}$ alkylene($C_{6-10}$ aryl), wherein the $C_{6-10}$ aryl is optionally substituted with one or more substituents each independently selected from the group consisting of halogen and —$NO_2$; $R^3$ is selected from the group consisting of —$C_{1-2}$ alkylene($C_6$ aryl) and —$C_{1-2}$ alkylene(6-membered heteroaryl), wherein the $C_6$ aryl and the 6-membered heteroaryl are optionally substituted with hydroxy; $R^4$ is

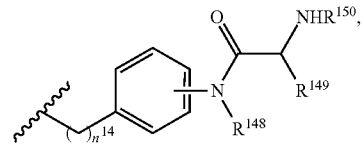

wherein $R^{148}$ is H or $CH_3$, $R^{149}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and $R^{150}$ is H, $CH_3$ or acetyl, and wherein $n^{14}$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$C_{1-2}$ alkylene ($C_{6-10}$ aryl), wherein the $C_{6-10}$ aryl is optionally substituted with one or more substituents each independently selected from the group consisting of halogen, hydroxy and —$NO_2$; and L is

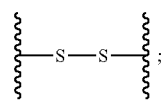

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is selected from the group consisting of:

(i)

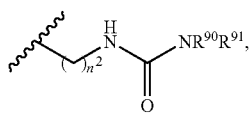

wherein each of $R^{90}$ and $R^{91}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^2$ is 3 or 4;

(ii)

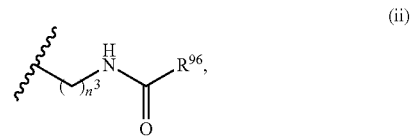

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^3$ is 3 or 4;

(iii)

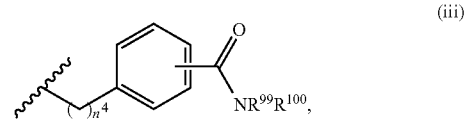

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^4$ is 1 or 2;

(iv)

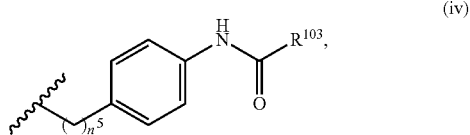

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2;

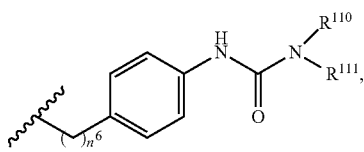

(v)

wherein each of $R^{110}$ and $R^{111}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^6$ is 1 or 2;

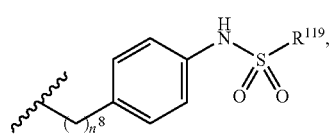

(vi)

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —NO$_2$, and $C_{1-6}$ alkoxy, and wherein $n^8$ is 1 or 2;

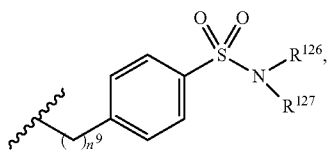

(vii)

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^9$ is 1 or 2;

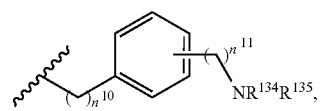

(viii)

wherein: each of $R^{134}$ and $R^{135}$ is independently selected from the group consisting of H, $C_{1-6}$ alkyl, $C_{6-10}$ aryl, 5- to 10-membered heteroaryl, —C(O)$R^{136}$, and —C(O)NR$^{137}$R$^{138}$, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^{10}$ is 1 or 2, and wherein $n^{11}$ is 1 or 2;

$R^{136}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy; and each of $R^{137}$ and $R^{138}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy;

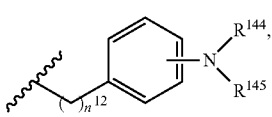

(ix)

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, $C_{1-6}$ alkoxy, and 5- to 10-membered heterocycloalkyl, and wherein $n^{12}$ is 1 or 2;

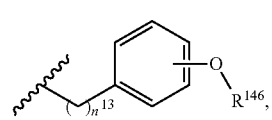

(x)

wherein $R^{146}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —NO$_2$, C$_{1-6}$ alkoxy, and 5- to 10-membered heterocycloalkyl, and wherein n$^{13}$ is 1 or 2; and

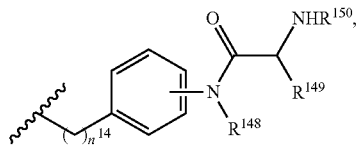
(xi)

wherein R$^{148}$ is H or CH$_3$, R$^{149}$ is H or C$_{1-6}$ alkyl optionally substituted with one or more substituents each independently selected from the group consisting of hydroxyl, —COOH, —NH$_2$, —C(O)NH$_2$, and —N(H)C(O)NH$_2$, and R$^{150}$ is H, CH$_3$ or acetyl, and wherein n$^{14}$ is 1 or 2; R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

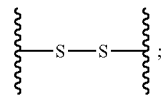

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —CH$_2$-phenyl or —CH$_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

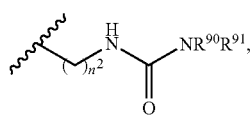

wherein each of R$^{90}$ and R$^{91}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^2$ is 3 or 4; R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

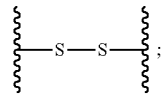 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —CH$_2$-phenyl or —CH$_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

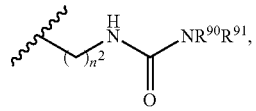

wherein each of R$^{90}$ and R$^{91}$ is H, and wherein n$^2$ is 3 or 4; R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

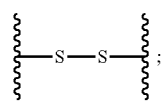 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —CH$_2$-phenyl or —CH$_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

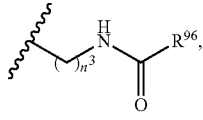

wherein $R^{96}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^3$ is 3 or 4; $R^5$ is —NR$^{79}$R$^{80}$, wherein each of $R^{79}$ and $R^{80}$ is independently H or CH$_3$; $n^1$ is 3, 4 or 5; $R^{12}$ is H or CH$_3$; $R^6$ is $C_{1-4}$ alkyl optionally substituted with hydroxy; $R^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

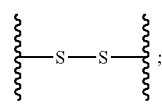

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or NH$_2$; $R^N$ is H, CH$_3$ or acetyl; $R^1$ is —CH$_2$-phenyl or —CH$_2$-naphthyl, wherein the phenyl is optionally substituted with one or more substituents each independently selected from the group consisting of halogen and —NO$_2$; $R^3$ is —CH$_2$-phenyl or —CH$_2$-pyridinyl, wherein the phenyl is optionally substituted with hydroxyl; $R^4$ is

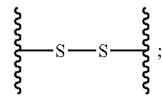

wherein $R^{96}$ is 5- to 10-membered heteroaryl optionally substituted with one or more substituents each independently selected from the group consisting of halogen, hydroxy, —NO$_2$, and $C_{1-6}$ alkoxy, and $n^3$ is 1; $R^5$ is —NR$^{79}$R$^{80}$, wherein each of $R^{79}$ and $R^{80}$ is independently H or CH$_3$; $n^1$ is 3, 4 or 5; $R^{12}$ is H or CH$_3$; $R^6$ is $C_{1-4}$ alkyl optionally substituted with hydroxy; $R^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

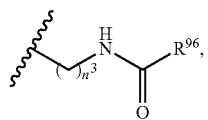

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or NH$_2$; $R^N$ is H, CH$_3$ or acetyl; $R^1$ is —CH$_2$-phenyl or —CH$_2$-naphthyl, wherein the phenyl is optionally substituted with one or more substituents each independently selected from the group consisting of halogen and —NO$_2$; $R^3$ is —CH$_2$-phenyl or —CH$_2$-pyridinyl, wherein the phenyl is optionally substituted with hydroxyl; $R^4$ is

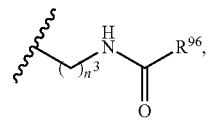

wherein $R^{96}$ is pyridinyl optionally substituted with one or more substituents each independently selected from the group consisting of halogen, hydroxy, —NO$_2$, and $C_{1-6}$ alkoxy, and $n^3$ is 1; $R^5$ is —NR$^{79}$R$^{80}$, wherein each of $R^{79}$ and $R^{80}$ is independently H or CH$_3$; $n^1$ is 3, 4 or 5; $R^{12}$ is H or CH$_3$; $R^6$ is $C_{1-4}$ alkyl optionally substituted with hydroxy; $R^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

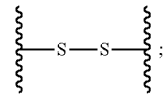 [SMILES: *SS*]

chiral centre *f is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or NH$_2$; $R^N$ is H, CH$_3$ or acetyl; $R^1$ is —CH$_2$-phenyl or —CH$_2$-naphthyl, wherein the phenyl is optionally substituted with one or more substituents each independently selected from the group consisting of halogen and —NO$_2$; $R^3$ is —CH$_2$-phenyl or —CH$_2$-pyridinyl, wherein the phenyl is optionally substituted with hydroxyl; $R^4$ is

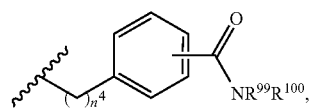

wherein each of $R^{99}$ and $R^{100}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —NO$_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —NO$_2$, and $C_{1-6}$ alkoxy, and wherein $n^4$ is 1 or 2; $R^5$ is —NR$^{79}$R$^{80}$, wherein each of $R^{79}$ and $R^{80}$ is independently H or CH$_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

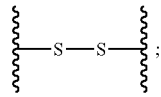

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

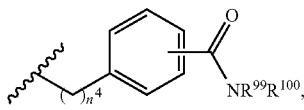

wherein each of $R^{99}$ and $R^{100}$ is H, and $n^4$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

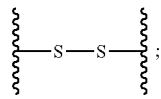

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is n

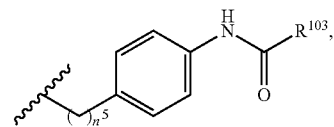

wherein $R^{103}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl, 5- to 10-membered heteroaryl, and 5- to 10-membered heterocycloalkyl are optionally substituted with one or more substituents each independently selected from the group consisting of halogen, hydroxy, —$NO_2$, and $C_{1-6}$ alkoxy, and wherein $n^5$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

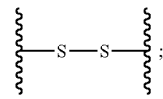 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

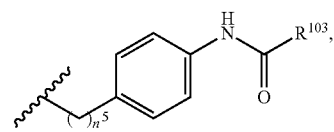

wherein $R^{103}$ is pyrrolidinyl and $n^5$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$— phenyl or —$CH_2$-naphthyl, wherein the phenyl is optionally substituted with one or more substituents each independently selected from the group consisting of halogen, hydroxyl, and —$NO_2$; and L

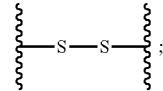 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

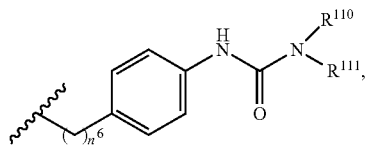

wherein each of $R^{110}$ and $R^{111}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^6$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

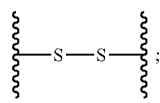

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

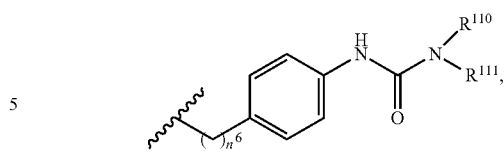

wherein $R^{110}$ is H and $R^{111}$ is phenyl, and $n^6$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

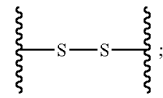 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

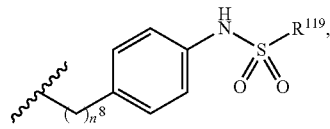

wherein $R^{119}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, hydroxy, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, hydroxy, —$NO_2$, and $C_{1-6}$ alkoxy, and wherein $n^8$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

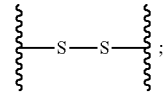 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$—

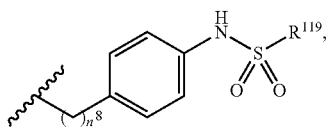

pyridinyl, wherein the phenyl is optionally substituted with hydroxyl; $R^4$ is n wherein $R^{119}$ is $C_6$ aryl optionally substituted with one or more substituents each independently selected from the group consisting of halogen, hydroxy, —$NO_2$, and $C_{1-6}$ alkoxy, and $n^8$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

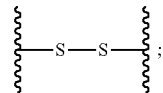

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

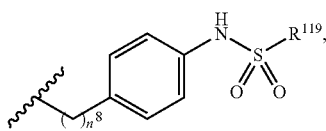

wherein $R^{119}$ is phenyl, and $n^8$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

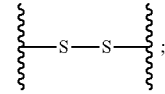 [SMILES: *SS*]

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

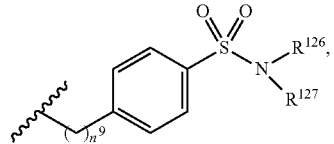

wherein each of $R^{126}$ and $R^{127}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, and $C_{1-6}$ alkoxy, and wherein the $C_{6-10}$ aryl and 5- to 10-membered heteroaryl are optionally substituted with one or more substituents each independently selected from the group consisting of halogen, —OH, —$NO_2$, and $C_{1-6}$ alkoxy, and wherein $n^9$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

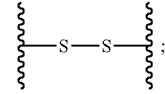

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

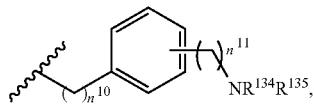

wherein:
  each of R$^{134}$ and R$^{135}$ is independently selected from the group consisting of H, C$_{1-6}$ alkyl, C$_{6-10}$ aryl, 5- to 10-membered heteroaryl, —C(O)R$^{136}$, and —C(O)NR$^{137}$R$^{138}$, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy, and wherein n$^{10}$ is 1 or 2, and wherein n$^{11}$ is 1 or 2;
  R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and
  each of R$^{137}$ and R$^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;
R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

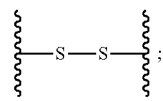

chiral centre 1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —CH$_2$-phenyl or —CH$_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

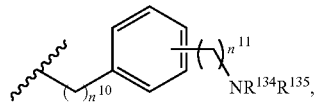

wherein:
  each of R$^{134}$ and R$^{135}$ is independently selected from the group consisting of H, —C(O)R$^{136}$, and —C(O)NR$^{137}$R$^{38}$, and wherein n$^{10}$ is 1, and wherein n$^{11}$ is 1;
  R$^{136}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy; and
  each of R$^{137}$ and R$^{138}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents each independently selected from the group consisting of halogen, —OH, —NO$_2$, and C$_{1-6}$ alkoxy, and wherein the C$_{6-10}$ aryl and 5- to 10-membered heteroaryl are optionally substituted with one or more substituents each independently selected from the group consisting of halogen, —OH, —NO$_2$, and C$_{1-6}$ alkoxy;
R$^5$ is —NR$^{79}$R$^{80}$, wherein each of R$^{79}$ and R$^{80}$ is independently H or CH$_3$; n$^1$ is 3, 4 or 5; R$^{12}$ is H or CH$_3$; R$^6$ is C$_{1-4}$ alkyl optionally substituted with hydroxy; R$^8$ is —CH$_2$-phenyl or —CH$_2$-naphthyl, wherein the phenyl is optionally substituted with one or more substituents each independently selected from the group consisting of halogen, hydroxyl, and —NO$_2$; and L is

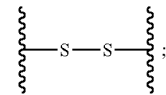 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: R$^C$ is OH or NH$_2$; R$^N$ is H, CH$_3$ or acetyl; R$^1$ is —CH$_2$-phenyl or —CH$_2$-naphthyl, wherein the phenyl is optionally substituted with one or more substituents each independently selected from the group consisting of halogen and —NO$_2$; R$^3$ is —CH$_2$-phenyl or —CH$_2$-pyridinyl, wherein the phenyl is optionally substituted with hydroxyl; R$^4$ is

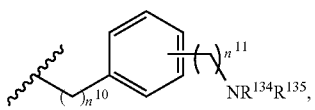

wherein each of $R^{134}$ and $R^{135}$ is H, $n^{10}$ is 1 and $n^{11}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

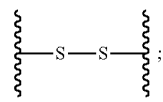

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

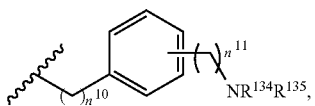

wherein $R^{134}$ is H, $R^{135}$ is —$C(O)R^{136}$, $R^{136}$ is $C_1$ alkyl, $n^{10}$ is 1, and $n^{11}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

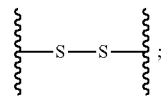

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

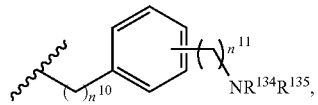

$R^{134}$ is H, $R^{135}$ is —$C(O)NR^{137}R^{138}$, each of $R^{137}$ and $R^{138}$ is H, $n^{10}$ is 1, and $n^{11}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

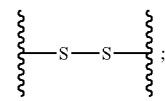

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

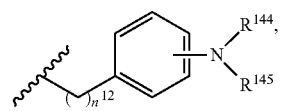

wherein each of $R^{144}$ and $R^{145}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, and 5- to 10-membered heterocycloalkyl, and wherein $n^{12}$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

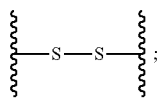

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

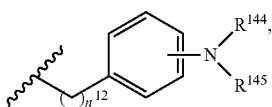

wherein each of $R^{144}$ and $R^{145}$ is independently selected from the group consisting of H and $C_{1-6}$ alkyl, wherein the $C_{1-6}$ alkyl is optionally substituted with one or more substituents each independently selected from the group consisting of 5- to 10-membered heterocycloalkyl, halogen, hydroxy, —$NO_2$, and $C_{1-6}$ alkoxy, and $n^{12}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

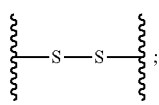

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

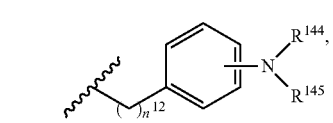

wherein $R^{144}$ is H and $R^{145}$ is $C_{1-6}$ alkyl optionally substituted with one or more substituents each independently selected from the group consisting of 5- to 10-membered heterocycloalkyl, halogen, hydroxy, —$NO_2$, and $C_{1-6}$ alkoxy, and wherein $n^{12}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

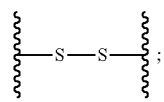 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

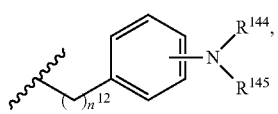

wherein $R^{144}$ is H and $R^{145}$ is $C_2$ alkyl substituted with morpholinyl, and wherein $n^{12}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

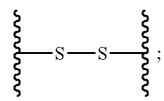

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

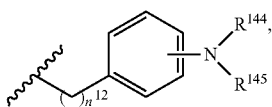

wherein $R^{144}$ is H and $R^{145}$ is $C_5$ alkyl, and wherein $n^{12}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

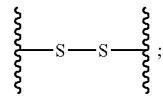

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

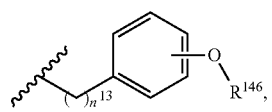

wherein $R^{146}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents each independently selected from the group consisting of halogen, —OH, —$NO_2$, $C_{1-6}$ alkoxy, and 5- to 10-membered heterocycloalkyl, and wherein the $C_{6-10}$ aryl and 5- to 10-membered heteroaryl are optionally substituted with one or more substituents each independently selected from the group consisting of halogen, —OH, —$NO_2$, $C_{1-6}$ alkoxy, and 5- to 10-membered heterocycloalkyl, and wherein $n^{13}$ is 1 or 2; and $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

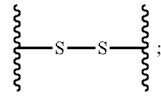 [SMILES: *SS*]

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

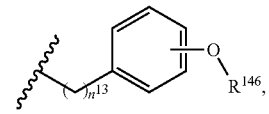

wherein $R^{146}$ is $C_{1-6}$ alkyl optionally substituted with one or more substituents each independently selected from the group consisting of 5- to 10-membered heterocycloalkyl, halogen, hydroxy, —$NO_2$, and $C_{1-6}$ alkoxy, and wherein $n^{13}$ is 1; and $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

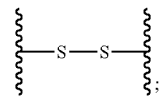

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

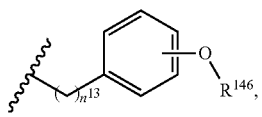

wherein $R^{146}$ is $C_2$ alkyl substituted with morpholinyl, and wherein $n^{13}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

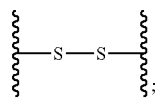

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

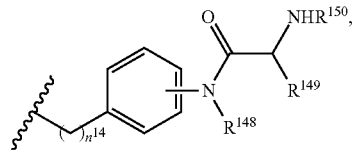

wherein $R^{148}$ is H or $CH_3$, $R^{149}$ is H or $C_{1-6}$ alkyl optionally substituted with one or more substituents each independently selected from the group consisting of hydroxyl, —COOH, —$NH_2$, —$C(O)NH_2$, and —$N(H)C(O)NH_2$, and $R^{150}$ is H, $CH_3$ or acetyl, and wherein $n^{14}$ is 1 or 2; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

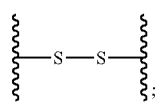

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$-pyridinyl, wherein the phenyl is optionally substituted with hydroxyl; $R^4$ is

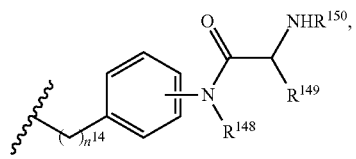

wherein $R^{148}$ is H, $R^{149}$ is H, and $R^{150}$ is H or acetyl, and wherein $n^{14}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —$NO_2$; and L is

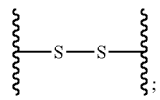

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

Illustrative embodiments of the present invention include a compound having the structure of Formula II or a salt thereof, wherein: $R^C$ is OH or $NH_2$; $R^N$ is H, $CH_3$ or acetyl; $R^1$ is —$CH_2$-phenyl or —$CH_2$-naphthyl, wherein the phenyl is optionally substituted with one or more substituents each independently selected from the group consisting of halogen and —$NO_2$; $R^3$ is —$CH_2$-phenyl or —$CH_2$—pyridinyl, wherein the phenyl is optionally substituted with hydroxyl; $R^4$ is

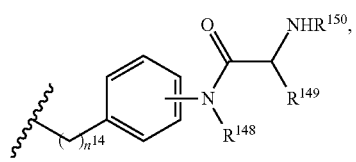

wherein $R^{148}$ is H, $R^{149}$ is $C_{1-6}$ alkyl optionally substituted with one or more substituents each independently selected from the group consisting of hydroxyl, —COOH, —$NH_2$, —$C(O)NH_2$, and —$N(H)C(O)NH_2$, and $R^{150}$ is H, and wherein $n^{14}$ is 1; $R^5$ is —$NR^{79}R^{80}$, wherein each of $R^{79}$ and $R^{80}$ is independently H or $CH_3$; $n^1$ is 3, 4 or 5; $R^{12}$ is H or $CH_3$; $R^6$ is $C_{1-4}$ alkyl optionally substituted with hydroxy; $R^8$ is —$CH_2$-phenyl or —$CH_2$-naphthyl, wherein the phenyl is optionally substituted with one or more substituents each independently selected from the group consisting of halogen, hydroxyl, and —NO$_2$; and L is

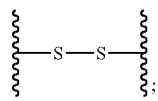

chiral centre *1 is in the S configuration; chiral centre *3 is in the S configuration; chiral centre *4 is in the R configuration; chiral centre *5 is in the S configuration; chiral centre *6 is in the S configuration; and chiral centre *8 is in the R configuration.

In certain embodiments, the compound may be selected from Table 5 and salts thereof. In certain embodiments, the compound may be selected from: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 67, 69, 70, 71, 72, 73, 74, 75, 76, 77, 78, 79, 80, 81, and 82, and salts thereof. In certain embodiments, the compound may be selected from: 1, 2, 3, 4, 5, 6, 7, 8, 9, 11, 12, 13, 14, 15, 16, 20, 22, 23, 24, 25, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 65, 71, 72, 73, 74, 76, 77, 78, and 79, and salts thereof. In certain embodiments, the compound may be selected from: 1, 2, 3, 4, 5, 6, 7, 8, 9, 11, 12, 13, 14, 15, 16, 22, 23, 24, 25, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 71, 72, 74, 76, 77, 78, and 79, and salts thereof. In certain embodiments, the compound may be selected from: 1, 4, 7, 8, 12, 14, 15, 24, 25, 27, 31, 32, 33, 34, 35, 36, 37, 38, 40, 41, 42, 43, 44, 45, 46, 47, 48, 49, 50, 51, 52, 53, 54, 55, 56, 57, 58, 59, 71, 72, 77, 78, and 79, and salts thereof. In certain embodiments, the compound may be selected from: 1, 4, 7, 12, 14, 15, 24, 25, 27, 32, 34, 35, 36, 37, 38, 40, 41, 42, 43, 44, 45, 46, 47, 48, 49, 50, 51, 52, 53, 54, 55, 56, 57, 58, 59, 71, 72, 77, 78, and 79, and salts thereof. In certain embodiments, the compound may be selected from: 15, 24, 25, 32, 42, 46, 47, 48, 49, 50, 51, 52, 53, 54, 55, 56, 57, 58, 72, 77, and 78, and salts thereof. In certain embodiments, the compound may be selected from: 1, 4, 7, 8, 12, 14, 15, 24, 31, 32, 33, 34, 35, 36, 37, 38, 43, 46, 47, 48, 49, 50, 51, 52, 53, 54, 55, 56, 57, 58, 59, 71, 72, 77, 78, and 79, and salts thereof. In certain embodiments, the compound may be selected from: 1, 4, 7, 12, 14, 15, 24, 32, 34, 35, 36, 37, 38, 43, 46, 47, 48, 49, 50, 51, 52, 53, 54, 55, 56, 57, 58, 59, 71, 72, 77, 78, and 79, and salts thereof. In certain embodiments, the compound may be selected from: 15, 24, 32, 46, 47, 48, 49, 50, 51, 52, 53, 54, 55, 56, 57, 58, 72, 77, and 78, and salts thereof. In certain embodiments, the compound may be selected from: 15, 24, 32, 46, 47, 48, 49, 50, 51, 52, 53, 54, 55, 56, 57, 58, and 77, and salts thereof. In certain embodiments, the compound may be selected from: 15, 24, 25, 32, 46, 47, 48, 49, 50, 51, 52, 53, 54, 55, 56, 57, 58, and 77, and salts thereof. In certain embodiments, the compound may be selected from: 15, 24, 46, 47, 48, 50, 51, 52, and 56, and salts thereof. In certain embodiments, the compound may be selected from: 24 and 46, and salts thereof. In certain embodiments, the compound may be selected from: 4 and 24, and salts thereof.

In embodiments of the cyclic peptides where cysteine residues are joined by a cyclizing disulfide bond, those of ordinary skill in the art will appreciate that the compounds may also be depicted using the notation: R$^N$N(H)-Xaa$^1$-cyclo[DCys-Xaa$^3$-Xaa$^4$-Xaa$^5$-Xaa$^6$-Cys]-Xaa$^8$-R$^C$ or R$^N$N(H)-Xaa$^1$-(Cys-Cys bridge)[DCys-Xaa$^3$-Xaa$^4$-Xaa$^5$-Xaa$^6$-Cys]-Xaa$^8$-R$^C$ using terminology or abbreviations commonly used in the art and the annotation "(Cys-Cys bridge)" or "cyclo[ ]" for the disulfide bond linkage. For example, the compound having the structure:

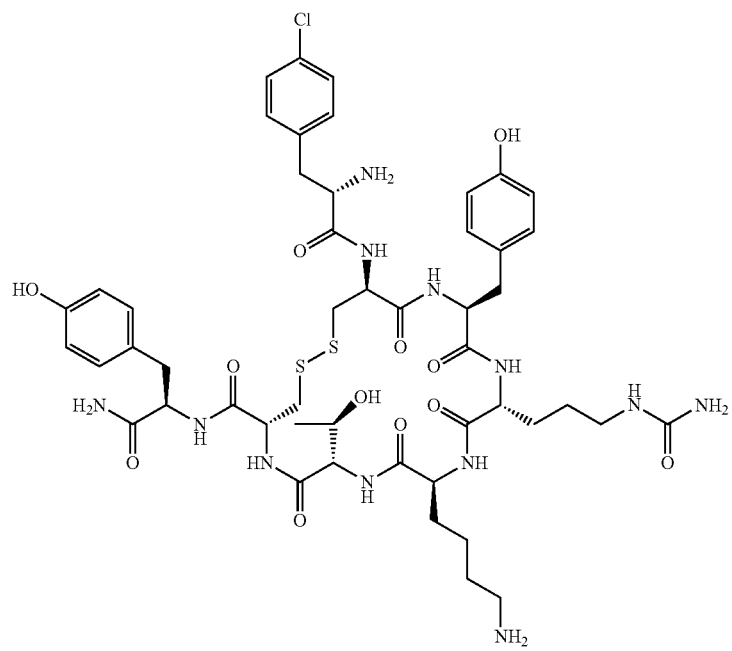 [SMILES: C[C@@H](O)[C@@H]1NC(=O)[C@H](CCCCN)NC(=O)[C@@H](CCCNC(N)=O)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

may also be depicted as H-Cpa-cyclo[DCys-Tyr-DCit-Lys-Thr-Cys]-DTyr-NH$_2$ or H-Cpa-(Cys-Cys bridge)[DCys-Tyr-DCit-Lys-Thr-Cys]-DTyr-NH$_2$.

Other embodiments where the peptides are cyclized with linkages other than a disulfide bond linking cysteine residues may be depicted as $R^N N(H)$-Xaa$^1$-(L' bridge)[Xaa$^2$-Xaa$^3$-Xaa$^4$-Xaa$^5$-Xaa$^6$-Xaa$^7$]-Xaa$^8$-R$^C$ using terminology or abbreviations commonly used in the art and the annotation "(L' bridge)" for the cyclizing linkage where L' indicates the type of linkage. Terminology or abbreviations commonly used in the art include, but are not limited to, those listed in the table below.

| Abbreviations |
|---|
| 4Aph(Cbm): 4-ureido-phenylalanine |
| 4Aph(Hor): 4-[(2,6-dioxo-hexahydro-pyrimidine-4-carbonyl)-amino]-phenylalanine |
| 2,4-dichloro-Phe: β-[2,4-dichlorophenyl]-alanine |
| 1-Nal: 3-(1-naphthyl)alanine |
| 2Fpa: 2-fluorophenylalanine |
| 2-Nal: 3-(2-naphthyl)alanine |
| 2-Pal: [2-pyridyl]-alanine or 3-(2-pyridyl)alanine |
| 2-Pal: β-[2-pyridyl]-alanine, |
| 3Fpa: 3-fluorophenylalanine |
| 3-Pal: 3-(3-pyridyl)alanine |
| 4-Pal: 3-(4-pyridyl)alanine |
| Abu: 2-aminobutyric acid or α-aminobutyric acid |
| Ahp: 7-aminoheptanoic acid |
| Aib: 2-aminoisobutyric acid or α-aminoisobutyric acid |
| Amp: 4-amino-phenylalanine |
| Ava: 5-aminovaleric acid |
| β-Ala: β-alanine or 3-aminopropionic acid |
| β-1-Nal: β-[1-naphthyl]-alanine |
| β-Nal: β-[2-napthyl]-alanine |
| Bip: biphenylalanine or 4,4'-biphenylalanine |
| Bpa: 4-bromophenylalanine |
| Bta: benzothienylalanine or 3-benzothienylalanine |
| Cha: cyclohexylalanine or β-(cyclohexyl)-alanine |
| Cit: citrulline |
| Cpa: 3-(4-chlorophenyl)alanine or β-[4-chlorophenyl]-alanine |
| Dab: 2,4-diaminobutyric acid |
| Dap: 2,3-diaminopropionic acid |
| Dip: 3,3'-diphenylalanine |
| F$_5$-Phe: 2,3,4,5,6-pentafluorophenyl]-alanine or β-[2,3,4,5,6-pentafluorophenyl]-alanine |
| Fpa: 4-fluorophenylalanine |
| Gaba: ɣ-aminobutyric acid or 4-aminobutyric acid |
| HSer or HoSer: homoserine |
| HoCit or HCit: homocitrulline |
| HoLys or HLys: homolysine |
| HoCys or HCys: homocysteine |
| Igl: 2-indanylglycine |
| Iph: 4-iodophenylalanine |
| Nal: 3-(2-naphthyl)alanine |
| Nle: norleucine |
| Npa or pNO$_2$-Phe: 4-nitrophenylalanine or p-NO$_2$-phenylalanine |
| Nva: norvaline |
| Pal: 3-pyridylalanine or β-[3-pyridyl]-alanine |
| Pen: peniciliamine |
| Tba: tert-butylalanine |
| TfmA: 4-trifluoromethylphenyl-alanine |
| Thr(Bzl): O-benzyl-threonine |
| Tic: 1,2,3,4-tetrahydroisoquinoline-3-carboxylic acid |
| Tle: tert-leucine or α-[t-butyl]-glycine |
| Tyr(Bzl): O-benzyl-tyrosine |
| Tyr(I) or ITyr: an iodinated tyrosine residue (e.g., 3-I-Tyr, 5-I-Tyr, 3,5-I-Tyr) |
| Ypa: 4-cyanophenylalanine |

Unless specified, the trivial name or symbol refers to the L-amino acid.

In one aspect, the invention provides compounds of Formula I exhibiting SSTR2 binding activity. In one aspect the invention provides compounds of Formula II exhibiting SSTR2 binding activity. Determination of SSTR2 binding activity is routine and well within the capability of the artisan of reasonable skill in the art. For example, competitive binding assays using SSTR2 and a known SSTR2 ligand, for example SST or a compound exemplified below (for example, compound 24) may be performed to determine SSTR2 binding activity of a subject compound.

In one aspect, the invention provides compounds of Formula I exhibiting SSTR2 antagonistic activity. In one aspect the invention provides compounds of Formula II exhibiting SSTR2 antagonistic activity. Determination of SSTR2 antagonistic activity is routine and well within the capability of the artisan of reasonable skill in the art. For example, SSTR2 activity assays using SSTR2-expressing cells and a known SSTR2 agonist, for example SST, may be performed to determine SSTR2 antagonist activity of a subject compound. In one embodiment, a control SSTR2 antagonist compound may be used (for example, compound 24).

Compounds as described herein may be in the free form or in the form of a salt thereof. In some embodiments, compounds as described herein may be in the form of a pharmaceutically acceptable salt, which are known in the art (Berge et al., J. Pharm. Sci. 1977, 66, 1). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, the compounds of the present invention or their pharmaceutically acceptable salts may be for use in the prevention or treatment of hypoglycemia. In some embodiments, the hypoglycemia is insulin-induced hypoglycemia. In other embodiments, the compounds of the present invention or their pharmaceutically acceptable salts may be for use in the treatment of diabetes. In other embodiments, the compounds of the present invention or their pharmaceutically acceptable salts may be for use in increasing release of insulin in a subject.

In accordance with another embodiment of the present invention, there is provided a pharmaceutical composition comprising a compound of the present invention or a pharmaceutically acceptable salt thereof and a pharmaceutically acceptable carrier.

In one aspect, the invention provides a pharmaceutical composition comprising a compound of the present invention or a pharmaceutically acceptable salt thereof, a second agent, and a pharmaceutically acceptable carrier. In one embodiment, the second agent is an agent useful in the treatment of diabetes. In one embodiment, the second agent is insulin or an insulin analog.

Pharmaceutical compositions will typically comprise one or more carriers, excipients or diluents acceptable for the mode of administration of the preparation, be it by injection, inhalation, topical administration, lavage, oral, sublingual, transmucosal, transdermal, rectal, vaginal, subcutaneous, intramuscular, intravenous, intra-arterial, intrathecal, via catheter, via implant, or other modes suitable for the selected treatment. Suitable carriers, excipients or diluents are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. The formulations may be specifically prepared for intranasal delivery. For example, nasal inhalation. Formulations for subcutaneous administration may comprise, for example, glycerol, α-tocopherol polyethylene glycol succinate (TPGS) and a buffer.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

The compounds of the present invention or pharmaceutically acceptable salts thereof, or compositions may be contained in pharmaceutical kits or packs. In those embodiments in which the compounds of the present invention are intended for use as part of a combination therapy, the kit may optionally contain the other therapeutic agents that make up the combination. For example, pharmaceutical kits and packs comprising compounds of the present invention may further comprise a therapeutic agent useful in the treatment of diabetes. In one embodiment, the therapeutic agent is insulin or an insulin analog. Individual components of the kit may be packaged in separate containers and, associated with such containers, can be a notice in the form prescribed by a governmental agency regulating the manufacture, use or sale of pharmaceuticals or biological products, which notice reflects approval by the agency of manufacture, for use or sale for human or animal administration. In those embodiments in which the compound of the present invention, is included in the kit in the form of a pharmaceutical composition suitable for administration to a subject, the container may optionally be itself in a form allowing for administration to a subject, for example, an inhaler, syringe, pipette, eye dropper, pre-soaked gauze or pad, or other such like apparatus, from which the composition may be administered to the subject.

There are also provided drug conjugates comprising a compound of the present invention as defined anywhere herein or a pharmaceutically acceptable salt thereof.

Method or Uses

The compositions of the invention, including the cyclic peptides of the invention and pharmaceutical compositions of the invention, have a wide range of uses.

In some embodiments, the cyclic peptides or pharmaceutical compositions may be for use in the prevention or treatment of hypoglycemia. In some embodiments, the hypoglycemia is insulin-induced hypoglycemia. In some embodiments, the cyclic peptide or pharmaceutical composition may be for use in the treatment of diabetes. In some embodiments, the cyclic peptide or pharmaceutical composition may be for use in increasing release of insulin in a subject.

In accordance with another embodiment, there is provided a method of inhibiting an activity of an SSTR2 receptor in a subject, the method comprising administering a compound of the present invention or pharmaceutically acceptable salt thereof, to a subject in need thereof. In another embodiment, there is provided a method of preventing or treating hypoglycemia in a subject, the method comprising administering a compound of the present invention or a pharmaceutically acceptable salt thereof, to a subject in need thereof. In some embodiments, the hypoglycemia is insulin-induced hypoglycemia. In accordance with another embodiment, there is provided a method of treating diabetes in a subject, the method comprising administering a compound of the present invention, or a pharmaceutically acceptable salt thereof, to a subject in need thereof. In a further embodiment, there is provided a method of increasing insulin release in a subject, the method comprising administering a compound of the present invention, or a pharmaceutically acceptable salt thereof, to a subject in need thereof.

In accordance with a further embodiment, there is provided a use of a compound of the present invention or a pharmaceutically acceptable salt thereof for the prevention or treatment of hypoglycemia. In some embodiments, the hypoglycemia is insulin-induced hypoglycemia. In other embodiments, there is provided a use of a compound of the present invention or a pharmaceutically acceptable salt thereof in the treatment of diabetes. In other embodiments, there is provided a use of a compound of the present invention or a pharmaceutically acceptable salt thereof for increasing release of insulin in a subject. In still another embodiment, there is provided a use of a compound of the present invention or a pharmaceutically acceptable salt thereof in the preparation of a medicament for the prevention or treatment of hypoglycemia. In some embodiments, the hypoglycemia is insulin-induced hypoglycemia. In further embodiments, there is provided a use a compound of the present invention or a pharmaceutically acceptable salt thereof in the preparation of a medicament for the treatment of diabetes. In accordance with another embodiment, there is provided a use of a compound of the present invention or a pharmaceutically acceptable salt thereof in the preparation of a medicament for increasing the release of insulin in a subject.

In one aspect, the invention provides a method for decreasing the severity of hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for preventing hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for preventing severe hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for decreasing the duration of hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for decreasing the duration of severe hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for decreasing the probability of hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for decreasing the probability of severe hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for delaying the onset of hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for delaying the onset of severe hypoglycemia in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for restoring a glucagon response to low blood glucose level in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for facilitating an increase in glucagon secretion in response to low blood glucose level in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for de-repressing glucagon secretion under conditions of low blood glucose level in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

In one aspect, the invention provides a method for facilitating an increase in glucagon levels in the portal vein in response to low blood glucose level in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

Low blood glucose level means a blood glucose level below that of euglycemia. In one embodiment, the low blood glucose level is between that of euglycemia and hypoglycemia. In one embodiment, the low blood glucose level is indicative of hypoglycemia. In one embodiment, the low blood glucose level is indicative of severe hypoglycemia. In one embodiment, the low blood glucose level is below 4 mM. In one embodiment, the low blood glucose level is 3.9 mM or below. In one embodiment, the low blood glucose level is 2.9 mM or below. In one embodiment, the low blood glucose level is 1.9 mM or below.

In one aspect, the invention provides a method for delaying a hypoglycemic event in a subject, the method comprising administering a compound of the present invention or pharmaceutically acceptable salt thereof, to the subject. In one embodiment, the subject has diabetes. In one embodiment, the method involves coadministration of a compound of the present invention or pharmaceutically acceptable salt thereof with a second agent useful in the treatment of diabetes. In one embodiment, the second agent is linsulin or an insulin analog.

Administration of a compound as disclosed herein "in combination with" one or more further agents, or "coadministration" with one or more further agents, for example insulin, is intended to include simultaneous (concurrent) administration and consecutive administration. Simultaneous administration may involve coformulation of a compound disclosed herein with one or more further agents, for example, insulin, or may involve separate formulations. Consecutive administration is intended to encompass various orders of administration of the agents to a subject, with administration of the agent being separated by a time period that may be short (for example, on the order of minutes) or extended (for example in the order of hours, days or weeks).

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as increasing blood glucose to a desired level, decreasing the duration of hypoglycemia, decreasing the duration of severe hypoglycemia, decreasing the severity of hypoglycemia, increasing life span or increasing life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as maintaining blood glucose levels in a desired range, preventing hypoglycemia, preventing severe hypoglycemia, decreasing the duration of hypoglycemia, decreasing the duration of severe hypoglycemia, decreasing the severity of hypoglycemia, decreasing the probability of hypoglycemia, decreasing the probability of severe hypoglycemia, increasing life span, increasing life expectancy or prevention of the progression of the condition. Typically, a prophylactic dose is used in subjects prior to or at an earlier stage of disease or condition. In some instances a prophylactically effective amount may be less than a therapeutically effective amount. In the present context, a compound of the invention may be administered prophylactically in order to prevent or reduce the hypoglycemia or severe hypoglycemia that would otherwise occur in the absence of administration of the subject compound. For example, compound of the invention may be administered prophylactically to a diabetic subject receiving insulin in order to prevent or reduce the hypoglycemia or severe hypoglycemia that would otherwise occur in the subject in the absence of such compound.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods.

Compounds as described herein may be administered to a subject. In some embodiments, the subject may be a mammal. In other embodiments, the subject may be a human, non-human primate, rat, mouse, cow, horse, pig, sheep, goat, dog, cat, etc. In some embodiments, the subject has diabetes. In other embodiments, the subject has type 1 or type 2 diabetes. In other embodiments, the subject has type 1 diabetes. In other embodiments, the subject has type 2 diabetes.

It will be understood by the artisan of reasonable skill in the art that the cyclic peptides of the invention exhibiting affinity for SSTR2 or SSTR2 antagonistic activity may be used in place of known SSTR2 ligands and antagonists in certain applications and methods. For example, see WO 2009/129311, which is expressly incorporated herein in its entirety by reference.

A variety of additions may be made, for example, to the N-terminal amino acid of a cyclic peptide disclosed herein, in the form of a complexing or conjugating agent (Z) that can then be used to join a desired moiety to the peptide or to provide labeling. Such a moiety Z generally can be selected from the group consisting of DOTA- and DTPA-based chelators, NOTA-based chelators, carbonyl compounds, 2-hydrazino nicotinamide (HYNIC), $N_4$-chelators, desferrioxamin, and $N_xS_y$-chelators, all optionally complexed with a radioisotope, Tyrosine (Tyr) for halogenation, a fluorescent dye or biotin. Cpa can also serve as a precursor for tritiation. A chelator, such as, for example, DTPA, DOTA, HYNIC and $P_2S_2$—COOH can be attached. Chelators include, for example, p-$NH_2$-Bz-DOTA(2-p-aminobenzyl-I,4,7,10-tetraazacyclodo-I,4,7,10-tetraacetic acid), and DOTA-p-$NH_2$-anilide [I,4,7,10-tetraazacyclododecane-I,4,7,10-tetraacetic acid mono(p-aminoanilide)]. Alternatively, a chelating agent can be covalently linked to the N-terminus via a suitable linker if desired. Suitable linkers include, for example, tyrosine, lysine, diaminobutyric acid, diaminopropionic acid, polyethylene glycol, fatty acids and their derivatives, β-alanine, 5-amino valeric acid, sarcosine, and glucronic acid. Where Tyr appears at the N-terminus, it can be radioiodinated or otherwise labeled. Acyl groups having not more than about 20 amino acids can also be present at the N-terminus, as the N-terminal residue can also be acylated, if desired, with a bulky moiety without loss of selectivity.

The invention is also directed to, for example, a method of intraoperatively detecting malignant tumors in the body of a human being in tissues that in healthy condition do not contain substantial quantities of SSTR2. The method includes, for example (i) administering to such being a composition comprising, in a quantity sufficient for detection by a gamma detecting probe, cyclic peptide disclosed herein, wherein the peptide is labeled, e.g., radioactively with $^{99m}$Tc, $^{161}$Tb,$^{90}$Y, $^{177}$Lu, $^{123}$I or $^{125}$I, and (ii) after allowing the active substance to be bound and taken up in the tumors and after blood clearance of radioactivity, and subjecting such being to a radiodetection technique in the relevant area of the body by using a gamma-detecting probe.

The use of external imaging by radioactive scanning or by magnetic resonance allows semiquantitative detection within the body.

The compositions of the present invention are also useful in scintigraphy to determine the distribution of cells and tissues expressing SSTR2 throughout the body.

The compositions of the present invention are also useful as therapeutic agents comprising radioisotopes that are targeted to tumor cells expressing SSTR2. In one embodiment, radiolabeled compositions of the invention are useful for the therapeutic treatment of malignant tumors in the body of a human being in tissues that, in healthy condition, do not contain substantial quantities of SSTR2. Radiolabeled compositions can be administered in a composition that includes a quantity effective for scintigraphy or for combating or controlling tumors. The radiolabeled peptides can be labeled, for example, with $^{186}$Re, $^{188}$Re, $^{111}$In, $^{113m}$In, $^{71}$As, $^{90}$Y, $^{67}$Cu, $^{99m}$Tc, $^{169}$Er, $^{121}$Sn, $^{127}$Te, $^{142}$Pr, $^{143}$Pr, $^{66}$Ga, $^{67}$Ga, $^{68}$Ga, $^{72}$Ga, $^{127}$Te, $^{195}$Pt, $^{211}$At, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, $^{114}$Ag, $^{124}$I or $^{131}$I.

The present disclosure provides methods for assessing the affinity of compositions toward SSTR. The present disclosure provides methods for assessing the antagonistic activity of compositions toward SSTR. In one embodiment, there are provided methods for assessing the affinity and/or antagonistic activity of compositions toward SSTR2. In one embodiment, there are provided methods for assessing the affinity and/or antagonistic activity of compositions toward SSTR5. In one embodiment, there are provided methods for determining the selectivity of a composition for SSTR2 and/or SSTR5 as compared to other SSTRs.

In one embodiment, labeled compositions of the invention are useful in drug-screening assays to screen for new effective peptide and non-peptide agents that bind with high affinity to SSTR2 and are highly effective antagonists. Using a ligand as described herein that is selective for the receptor SSTR2, one can obtain a baseline activity for a recombinantly-produced receptor. A competitive binding assay for SSTR2 with the labeled ligand and the candidate can then be carried out to determine the relative binding affinity. Alternatively, prospective candidates for inhibitors or modifiers, e.g., antagonists of the receptor function, can be directly incorporated into an assay mixture to determine the effect of such candidate on the receptor. By comparing the extent of receptor activity in the presence or absence of the candidate substance, one can then obtain information regarding the effect of the candidate substance on the normal function of the receptor and thus determine its function as either an agonist or an antagonist compared to a known SSTR2-selective analog.

The compositions of the present invention are also useful for selectively blocking certain of the pharmacological effects that are mediated by particular SSTRs. In one embodiment, compositions of the invention are useful for selectively blocking certain of the pharmacological effects that are mediated by SSTR2. In one embodiment, compositions of the invention are useful for selectively blocking certain of the pharmacological effects that are mediated by SSTR2 and/or SSTR5. The many effects of SSTRs are known in the art. In one embodiment, non-radiolabeled compositions of the invention may be used to treat diseases of an organ or tissue known to express SSTR2, including but not limited to, lung, gastrointestinal tract and kidneys.

In one embodiment, compositions of the invention can be complexed with a radioactive nuclide for the purpose of carrying that agent to a tumor or other tissue for which apoptosis is desired. For example, suitable chelating agents, such as DOTA or DTPA or others, can be used to complex the composition with a highly radioactive metal as indicated hereinbefore. Some examples of suitable chelating groups for chelating a radioactive metal atom are tetradentate chelating agents or groups derived from ethylene diamine tetra-acetic acid (EDTA), diethylene triamine penta-acetic acid (DTPA), cyclohexyl 1,2-diamine tetra-acetic acid (CDTA), ethyleneglycol-0,0'-bis(2-aminoethyl)-N,N,N',N'-tetra-acetic acid (EGTA), N,N-bis(hydroxybenzyl)-ethylenediamine-N,N'-diacetic acid (HBED), Methylene tetramine hexa-acetic acid (TTHA), I,4,7,10-tetraazacyclododecane-N,N',N'',N'''-tetra-acetic acid (DOTA), hydroxyethyldiamine triacetic acid (HEDTA), 1,4,8,11-tetraazacyclo-tetradecane-N,N',N'',N'''-tetra-acetic acid (TETA), substituted DTPA, substituted EDTA. Other chelators, as well as radioactive agents, are disclosed in WO 95/22341 and WO 04/082722 and in U.S. Patent Publications 2004/0242842 and 2005/0070470, the entire contents of which are incorporated herein by reference. Chelators can be derived from, for example, EDTA and DOTA. Some suitable salts are $^m$In-oxinte, $^{99m}$Tc-tartrate, which can generally be formed in a simple manner under conditions that are not detrimental to the peptide antagonist.

The cyclic peptides of the present invention can be synthesized by methods known to those of ordinary skill in the art, including classical solution synthesis and solid-phase techniques. For example, the cyclic peptides may be synthesized using solid-phase techniques such as on a methylbenzhydrylamine (MBHA) resin or a BHA resin, as is known in this art. Peptides having a free carboxyl C-terminus can be synthesized as taught in U.S. Pat. No. 7,019,109, the contents of which are herein incorporated by reference in their entirety. Peptides having an amidated C-terminus can be synthesized as taught in U.S. Pat. No. 5,874,227, the contents of which are herein incorporated by reference in their entirety. Solid-phase synthesis is conducted in a manner that adds amino acids in the chain beginning at the C-terminus in a stepwise manner. Side-chain protecting groups, which are known in the art, are included as a part of any amino acid that has a particularly reactive side chain, and optionally can be used in the case of others such as Trp, where such amino acids are coupled onto the chain being built upon the resin. Such synthesis provides a fully protected intermediate peptidoresin. Protecting groups are generally split off and the peptide is cleaved from the resin support before cyclizing the peptide. For example, in the case of a disulfide linkage, protecting groups are generally split off and the peptide is cleaved from the resin support before oxidizing to create a disulfide bond between the Cys side chains.

Various alternative embodiments and examples are described herein. These embodiments and examples are illustrative and should not be construed as limiting the scope of the invention. All references and citations are expressly incorporated herein in their entirety by reference.

EXAMPLES

General Methodologies
Chemical Synthesis

Compounds of the present invention were prepared in an iterative fashion. The linear 8-mer peptide intermediates were prepared by solid phase peptide synthesis (SPPS) using Fmoc protected amino acids and Rink Amide MBHA resin according to routine solid phase peptide synthesis (see, for example, Beilstien J. Org. Chem. 2014, 10, 1197-1212). Combinations of natural and non-natural Fmoc protected amino acids were prepared or obtained from commercial sources. After final Fmoc deprotection and acid induced cleavage of the peptide intermediates from the resin (with concurrent in situ deprotection of acid labile protecting groups), the resulting linear 8-mer peptide intermediates were further cyclized using cysteine-cysteine dithiol coupling conditions, including iodine ($I_2$) oxidation. Final purification by preparative HPLC provided the desired cyclic compounds.

Alternatively, it was possible to cyclize the peptides via the cysteine-cysteine dithiol bond by selectively deprotecting the cysteine residues while the peptide remained bound to the resin. Peptides that were cyclized via a cysteine-cysteine disulfide isostere in place of the disulfide employed conditions specific to that particular linker.

Abbreviations referred to in the chemical synthesis methodologies and examples represent the following: Ac=acetyl; ACN=acetonitrile; All=allyl; Aph=4-aminophenylalanine; Arg=arginine; Asn=asparagine; Asp=aspartic acid; Boc=tert-butyloxycarbonyl; Cit=citrulline; Cpa=4-chlorophenylalanine; Cys=cysteine; Dap=2,3-diaminoproprionic acid; DCE=1,2-dichloroethane; DCM=dichloromethane; DIC=N,N'-diisopropylcarbodiimide; DIPEA=diisopropylethylamine; DMF=N,N-dimethylformamide; EDT=1,2-ethanedithiol; Fmoc=9-fluorenylmethoxycarbonyl; Gln=glutamine; Glu=glutamic acid; Gly=glycine; HATU=1-[Bis(dimethylamino)methylene]-1H-1,2,3-triazolo[4,5-b]pyridinium 3-oxid hexafluorophosphate; HBTU=2-(1H-benzotriazol-1-yl)-1,1,3,3-tetramethyluronium hexafluorophosphate; HOAt=1-hydroxy-7-azabenzotriazole; HoCit=homocitrulline; HPLC=high performance liquid chromatography; Lys=Lysine; MBHA=4-methylbenzhydrylamine; Mtt=4-methyltrityl; NMM=N-methylmorpholine; OxymaPure=ethyl (hydroxyimino)cyanoacetate; Pbf=2,2,4,6,7-pentamethyldihydrobenzofuran-5-sulfonyl; Phe=phenylalanine; Pro=proline; Ser=serine; SPPS=solid phase peptide synthesis; Su=succinate; tBu=tert-butyl; TEA=triethylamine; TFA=trifluoroacetic acid; THF=tetrahydrofuran; Thr=threonine; TIPS=triisopropylsilane; Tle=tert-leucine=tert-butylglycine; Trt=trityl=triphenylmethyl; Tyr=tyrosine; Val=valine;

Example 1: H-Cpa-cyclo[D-Cys-Tyr-D-Phe(4-n-pentylamino)-Lys-Thr-Cys]-D-Tyr-NH$_2$ (Compound 12)

Preparation of the peptidyl-MBHA Resin

Rink Amide MBHA resin (0.1 mmol) was swelled in DMF (10 mL) for 2.0 hours. The suspension was filtered. 20% piperidine in DMF (10 mL) was added into the resin. The suspension was kept at room temperature for 0.5 h while a stream of nitrogen was bubbled through it. Then the suspension was filtered. The resin was washed with DMF (6×10 mL). Fmoc-D-Tyr(tBu)-OH (0.138 g, 0.3 mmol), HBTU (0.108 g, 0.285 mmol), N-methylmorpholine (0.067 mL, 0.6 mmol) and DMF (5 mL) were added into the resin. The suspension was kept at room temperature for 2.0 h while a stream of nitrogen was bubbled through it. Once a ninhydrin test indicated the completion of the coupling, the peptidyl resin was washed with DMF (3×10 mL) and dried.

Peptide Synthesis

Fmoc-deprotection was performed using 20% piperidine/DMF, followed by resin washing. Repeat coupling and deprotection cycles with the appropriately protected Fmoc-amino acids followed to provide the full peptide sequence. The peptidyl-MBHA resin was washed with DMF (3×10 mL), MeOH (2×10 mL), DCM (2×10 mL) and MeOH (2×10 mL), then it was dried under vacuum overnight to provide the peptidyl-MBHA resin.

Cleavage of the Peptide Intermediate from the RINK Resin 3 mL of TFA:thioanisole:phenol:EDT:H$_2$O (87.5:5:2.5:2.5:2.5) was added to the peptidyl-MBHA resin in a glass vessel. The mixture was stirred for 3 hours. The suspension was filtered and the filtrate was collected and further treated with cold diethyl ether (30 mL). The resulting precipitate was centrifuged. The diethyl ether layer was removed and the cake was washed with cold diethyl ether (2×30 mL), and dried under vacuum to provide 50 mg of crude peptide intermediate 12-vi.

Cyclization of the Linear 8-Mer Peptide Intermediates 50 mg of crude peptide intermediate 12-vi was oxidized by I$_2$ in an appropriate solvent, concentrated under reduced pressure and the residue was purified by preparative HPLC to provide 9.4 mg of Compound 12, as a white solid (95.1% purity by HPLC, TFA salt).

Example 2: H-Cpa-cyclo[D-Cys-Tyr-D-Lys(N$^E$-nicotinoyl)-Lys(N$^\varepsilon$-Me)-Thr-Cys]-D-Tyr-NH$_2$ (Compound 30)

Preparation of the Peptidyl-MBHA Resin

Rink Amide MBHA resin (0.1 mmol) was swelled in DMF (10 mL) for 2.0 hours. The suspension was filtered. 20% piperidine in DMF (10 mL) was added into the resin. The suspension was shaken gently at room temperature for 0.5 h. Then the suspension was filtered. The resin was washed with DMF (6×10 mL). Fmoc-D-Tyr(tBu)-OH (0.138 g, 0.3 mmol), HBTU (0.108 g, 0.285 mmol), N-methylmorpholine (0.067 mL, 0.6 mmol) and DMF (5 mL) were added into the resin. The suspension was kept at room temperature for 2.0 h while being shaken gently. Once a ninhydrin test indicated the completion of the coupling, the peptidyl resin was washed with DMF (6×10 mL).

Peptide Synthesis

Fmoc-deprotection was performed using 20% piperidine/DMF, followed by resin washing. Repeat coupling and deprotection cycles with the appropriately protected Fmoc-amino acids followed to provide the full peptide sequence. Cysteines were added to the peptide sequence using DIC (3.0 eq) and OxymaPure (3.0 eq) in place of HBTU/NMM. The final amino acid used in the peptide synthesis could be either an Fmoc- or Boc-amino acid; Fmoc amino acids require a final piperidine deprotection whereas Boc amino acids are deprotected during cleavage of the peptide from the resin. The peptidyl-MBHA resin was washed with DMF (3×10 mL), MeOH (2×10 mL), DCM (2×10 mL) and MeOH (2×10 mL), then it was dried under vacuum overnight to provide the peptidyl-MBHA resin.

Cleavage of the Peptide Intermediate from the Rink Resin 3 mL of TFA:thioanisole:phenol:EDT:H$_2$O (87.5:5:2.5:2.5:2.5) was added to the peptidyl-MBHA resin in a glass vessel. The mixture was stirred for 3 hours. The suspension was filtered and the filtrate was collected and further treated with cold diethyl ether (30 mL). The resulting precipitate was centrifuged. The diethyl ether layer was removed and the cake was washed with cold diethyl ether (2×30 mL), and dried under vacuum to provide 50 mg of crude peptide intermediate 12-vi.

Cyclization of the Linear 8-Mer Peptide Intermediate 50 mg of crude peptide intermediate 12-vi was oxidized by I$_2$ in an appropriate solvent, concentrated under reduced pressure and the residue was purified by preparative HPLC (reverse phase, ACN/water+0.1% TFA modifier) to provide 9.4 mg of compound 12, as a white solid (95.1% purity by HPLC).

General Cleavage and Cyclization Methods

General Method A: Alternative Method for the Cleavage of a Cyclic Peptide from the Rink Resin 3 mL of TFA:TIPS:H$_2$O (96.5:2.5:1) was added to the peptidyl-MBHA resin. The mixture was agitated for 3 h, drained and rinsed with DCM (3×5 mL) and MeOH (3×5 mL). The combined filtrate was concentrated in vacuo to a minimal amount, treated with cold diethyl ether (30 mL) and the resulting precipitate was centrifuged. The diethyl ether layer was decanted and the cake was washed with cold diethyl ether (2×30 mL) to provide an off-white solid. The crude material was purified by preparative HPLC (reverse phase, ACN/water+0.1% TFA modifier) to provide the cyclic peptide as a white solid.

General Method B: On-Resin Cyclization of Peptides Containing a Cysteine-Cysteine Disulfide Bridge Some peptides described in this invention were prepared by forming the cysteine-cysteine disulfide bridge while the peptide was still bound to the resin. The linear, resin-bound peptides were formed according to Example 2.

The peptidyl-MBHA resin was treated with TFA:TIPS:DCM (5:2:93, 0.025 M, 3×10 min) and then rinsed with DCM (3×5 mL). The resin was suspended in DMF:MeOH (9:1, 0.025M) and treated with I$_2$ (3 eq). After agitation for 2 h, the mixture was drained and then rinsed with DMF (3×5 mL), MeOH (2×5 mL), DCM (2×5 mL), and MeOH (2×5 mL) and then it was dried in vacuo overnight. The cyclization was deemed complete via an Ellman's test. The cyclic peptide was cleaved from the resin using General Method A to give the desired peptide.

General Method C: Preparation of N-Terminal Acylated Peptides

Some peptides described in this invention are acylated on the N-terminal nitrogen (peptides 49-58). The linear, resin-bound peptides were prepared according to Example 2, using an Fmoc-protected amino acid at the N-terminus. Following removal of the N-terminal Fmoc, the acyl group is added by HBTU mediated coupling of the corresponding carboxylic acid to the resin-bound peptide. Alternatively, activated acids such as acid chlorides and acid anhydrides could be used to attach the acyl group to the N-terminus of the peptide. The final peptides were cyclized, cleaved from the resin and purified according to General Method B.

General Method D: Synthesis of Peptides Containing a Thiocarbamate —NH—(C=O)—S— Bridge (60-63)

The Dap-containing intermediate peptidyl-MBHA resin (60-ii to 63-i) was treated with either 20% piperidine/DMF for 30 min and then rinsed with DMF (3×5 mL) and THF (3×5 mL) (Fmoc protected Dap) or TFA:TIPS:DCM (3:3:94, 0.05 M, 3×10 min) and then rinsed with THF (3×5 mL) (Mtt protected Dap). The resin was suspended in THF (0.025 M) and successively treated with DIPEA (4 eq) and PhS(C=O)Cl (4 eq). After agitation for 2 h, the mixture was drained and then rinsed with THF (3×5 mL), DCM (3×5 mL) and DMF (3×5 mL). The thiocarbamate formation was deemed complete via a Kaiser test. The resin was then suspended in PhSH:DIPEA:DMF (6:9:85, 0.02 M), agitated for 16-72 h, drained and rinsed with DMF (3×5 mL) and DCM (3×5 mL). The cyclic peptide was cleaved from the resin using General Method A to give peptides 60-63.

Note: Resin-bound peptide intermediate 60-ii was prepared using Boc-Cpa-D-Dap(Fmoc)-OH (60-i) to form the N-terminal end of the peptide. The synthesis of this dipeptide is described below.

General Method E: Synthesis of Peptides Containing a Triazole Bridge (64-66)

The intermediate peptidyl-MBHA resin (64-i to 66-i) was treated with DMF (0.02M), DIPEA (10 eq., 2,4-lutidine (10 eq.), sodium L-ascorbate (3 eq.) and CuBr (1 eq., 0.014M in ACN). The mixture was purged with Ar for 5 min and then agitated for 5 h. The resin was filtered and successively washed with DMF (3×10 mL), $H_2O$ (2×10 mL), and MeOH (2×10 mL) and then it was dried in vacuo overnight. The cyclic peptide was cleaved from the resin using General Method A to give the desired peptides 64-66.

Note: For compound 64-i, the N-terminal Fmoc protecting group was removed using standard Fmoc deprotection conditions before the cyclic peptide was cleaved from the resin.

General Method F: Synthesis of Stapled Peptides (67-68, Alkene Bridge)

The intermediate peptidyl-MBHA (67-i to 68-i) resin was treated with DCM (0.03M) and Grubbs Catalyst™ 2nd Generation (0.25 eq., 0.04M in DCM). The mixture was purged with Ar for 10 min and then heated at 40° C. in a sealed vessel for 3 d. The resin was filtered and successively washed with DCM (3×10 mL), and MeOH (2×10 mL) and then it was dried in vacuo overnight. The cyclic peptide was cleaved from the resin using General Method A to give the desired peptides 67-68.

General Method G: Synthesis of Peptides Containing an Amide Bridge (69-71)

The intermediate peptidyl-MBHA (69-i-71-i) resin was treated with morpholine (2 eq.) and DCM (0.03M). The resulting mixture was purged with Ar for 10 min. $Pd(PPh_3)_4$ (0.25 eq.) was added and the mixture was agitated for 20 h. The resin was filtered and successively washed with DMF (3×10 mL) and DCM (2×10 mL). The Mtt protecting group was selectively cleaved via treatment with TFA:TIPS:DCM (3:3:94, v/v/v, 3×10 min). The resin was filtered and successively washed with DCM (3×10 mL) and DMF (2×10 mL). HBTU (3 eq.), NMM (3 eq.) and DMF (0.03M) were added to the resin and the mixture was agitated for 24 h. The resin was filtered and successively washed with DMF (3×10 mL) and DCM (2×10 mL), and then it was dried in vacuo overnight. The cyclic peptide was cleaved from the resin using General Method A to give the desired peptides 69-71.

General Method H: Counterion Exchange from Trifluoroacetate to Acetate.

The peptides in this invention were generally purified by preparative HPLC, producing the peptides as TFA salts. Selected compounds were converted to acetic acid salts using the following anion exchange method. A column of strong anion exchange resin was prepared (Amberlite IRA-400 (Cl)) with an 80 fold excess of anion sites relative to the peptide. The column was eluted with a 1M aqueous solution of sodium acetate. The column was washed with deionized water to remove the excess sodium acetate. The peptide was dissolved in distilled water and applied to the column. The column was eluted with distilled water and the fraction(s) containing the peptide were collected. The combined fractions were lyophilized, obtaining the desired peptides as the acetate salts.

General Method I: Synthesis of $N^\alpha$-Methylated Peptides

The synthesis of $N^\alpha$-methylated peptides generally followed the procedure described in Example 2, with some modifications. The $N^\alpha$-methyl groups were either introduced on-resin during the solid phase peptide synthesis according to Chatterjee et. al., Nature Protocols, Vol. 7, No. 3, 2012, p 432-444., or by purchasing commercially available N-methyl amino acid(s). Extending the resin-bound peptide by coupling an Fmoc amino acid to an N-terminal methylated intermediate required the use of HATU (3 eq), HOAt (3 eq) and DIPEA (6 eq) in place of HBTU/NMM. Completion of this coupling was monitored by the chloranil test, and repeated when necessary. In examples where cysteine is coupled to an N-terminal methylated intermediate, Oxyma-Pure was used as the coupling reagent as described in Example 2. Completion was again monitored by the chloranil test, and repeated where necessary.

General Method J: Preparation of N-Terminal Sulfonylated Peptides

The synthesis of N-terminal sulfonamide peptides generally followed the procedure described in Example 2, with some modifications. Following removal of the N-terminal Fmoc from the linear, resin-bound peptides, the sulfonamide derivatives were made by treating the linear resin bound peptide with the corresponding sulfonyl chloride (3 eq.) and DIPEA (6 eq.) in DMF (0.02M). After agitation for 2 h, the mixture was drained and rinsed with DMF (3×), MeOH (2×), DCM (2×), and MeOH (2×) and then it was dried in vacuo overnight. The linear peptide was cleaved from the resin and cyclized as described in Example 2 to give the desired peptides 81-82.

Example 3: H-Cpa-cyclo[D-Cys-Tyr-D-Phe(4-phenylureido)-Lys($N^\epsilon$-Me)-Thr-Cys]-D-Tyr-$NH_2$ (Compound 25)

Compound 25 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys($N^\epsilon$-Boc-$N^E$-Me)-OH, 15-ii, Fmoc-Tyr (tBu)-OH, Fmoc-D-Cys(Trt)-OH and Fmoc-Cpa-OH. Compound 25 was a white solid, recovered as the 2.TFA salt in 10% yield.

Example 4: H-Cpa-cyclo[D-Cys-Tyr-D-Phe(4-carbamoyl)-Lys(N-diMe)-Thr-Cys]-D-Tyr-NH$_2$ (Compound 32)

Compound 32 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(N$^\varepsilon$-diMe)-OH, Fmoc-D-Phe(4-carbamoyl)-OH, Fmoc-Tyr(tBu)-OH, Fmoc-D-Cys(Trt)-OH and Fmoc-Cpa-OH. Compound 32 was a white solid, recovered as the 2.TFA salt in 9% yield.

Example 5: H-Cpa-cyclo[D-Cys-Tyr-D-Phe(4-carbamoyl)-Lys(N$^\varepsilon$-Me)-Thr-Cys]-D-Cpa-NH$_2$ (Compound 46)

Compound 46 was prepared according to the procedure described in Example 2, using the following amino acids: Fmoc-D-Cpa-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH and Boc-Cpa-OH. Compound 46 was a white solid, recovered as the 2.TFA salt in 29% yield.

Example 6: H-Cpa-cyclo[D-Cys-Cpa-D-Phe(4-carbamoyl)-Lys(N$^\varepsilon$-Me)-Thr-Cys]-D-Cpa-NH$_2$ (Compound 47)

Compound 47 was prepared according to the procedure described in Example 2, using the following amino acids: Fmoc-D-Cpa-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Cpa-OH, Fmoc-D-Cys(Trt)-OH and Boc-Cpa-OH. Compound 47 was a white solid, recovered as the 2.TFA salt in 23% yield.

Example 7: H-Cpa-cyclo[D-Cys-Cpa-D-Phe(4-carbamoyl)-Lys(N$^\varepsilon$-Me)-Thr-Cys]-D-Tyr-NH$_2$ (Compound 48)

Compound 48 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Cpa-OH, Fmoc-D-Cys(Trt)-OH and Boc-Cpa-OH. Compound 48 was a white solid, recovered as the 2.TFA salt in 33% yield.

Example 8: H-β-Ala-Cpa-cyclo[D-Cys-Tyr-D-Phe(4-carbamoyl)-Lys(Nε-Me)-Thr-Cys]-D-Tyr-NH2 (Compound 49)

Compound 49 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and Boc-β-Ala-OH. Compound 49 was a white solid, recovered as the 2.TFA salt in 6% yield.

Example 9: Ph(CO)NHCH$_2$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 50)

Compound 50 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and benzoylglycine. Compound 50 was a white solid, recovered as the TFA salt in 3% yield.

Example 10: PhSO$_2$CH$_2$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 51)

Compound 51 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and 2-(phenylsulfonyl)acetic acid. Compound 51 was a white solid, recovered as the TFA salt in 4% yield.

Example 11: t-BuCH$_2$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 52)

Compound 52 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and 3,3-dimethylbutanoic acid. Compound 52 was a white solid, recovered as the TFA salt in 10% yield.

Example 12: 2-Pyridyl(CO)-Cpa-cyclo[D-Cys-Tyr-D-Phe(4-carbamoyl)-Lys(N$^\varepsilon$-Me)-Thr-Cys]-D-Tyr-NH$_2$ (Compound 53)

Compound 53 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and picolinic acid. Compound 53 was a white solid, recovered as the TFA salt in 8% yield.

Example 13: H$_2$N(CO)(CH$_2$)$_2$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 54)

Compound 54 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and succinamic acid. Compound 54 was a white solid, recovered as the TFA salt in 5% yield.

Example 14: Ac-Gly-Cpa-cyclo[D-Cys-Tyr-D-Phe(4-carbamoyl)-Lys(N$^\varepsilon$-Me)-Thr-Cys]-D-Tyr-NH$_2$ (Compound 55)

Compound 55 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and Ac-Gly-OH. Compound 55 was a white solid, recovered as the TFA salt in 4% yield.

Example 15: CH$_3$(CH$_2$)$_4$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 56)

Compound 56 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and hexanoic acid. Compound 56 was a white solid, recovered as the TFA salt in 8% yield.

Example 16: (Furan-2-carboxy)-Cpa-cyclo[D-Cys-Tyr-D-Phe(4-carbamoyl)-Lys(N$^\varepsilon$-Me)-Thr-Cys]-D-Tyr-NH$_2$ (Compound 57)

Compound 57 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and 2-furoic acid. Compound 57 was a white solid, recovered as the TFA salt in 8% yield.

Example 17: CH$_3$O$_2$C(CH$_2$)$_2$(CO)-Cpa-cyclo[D-Cys-Tyr-D-Phe(4-carbamoyl)-Lys(N$^\varepsilon$-Me)-Thr-Cys]-D-Tyr-NH$_2$ (Compound 58)

Compound 58 was prepared according to the procedures described in Example 2 and General Method C, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH, Fmoc-Cpa-OH and succinic anhydride. Compound 58 was a white solid, recovered as the TFA salt in 9% yield.

Example 18: H—(N-Me)Cpa-cyclo[D-Cys-Tyr-D-Phe(4-carbamoyl)-Lys-Thr-Cys]-D-Tyr-NH$_2$ (Compound 77)

Compound 77 was prepared according to the procedures described in Example 2 and General Method I, using the following amino acids: Fmoc-D-Tyr(tBu)-OH, Fmoc-Cys(Trt)-OH, Fmoc-Thr(tBu)-OH, Fmoc-Lys(Boc)-OH, Fmoc-D-Phe(4-carbamoyl)-OH, Fmoc-Tyr(tBu)-OH, Fmoc-D-Cys(Trt)-OH and Boc-(N-Me)Cpa-OH. Compound 77 was a white solid, recovered as the 2.TFA salt in 10% yield.

Example 19: H-Cpa-cyclo[D-Cys-Tyr-D-Cit-Lys-Thr-Cys]-D-Tyr-NH$_2$ (Compound 1)

Compound 1 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(Boc)-OH, Fmoc-D-Cit-OH, Fmoc-Tyr(tBu)-OH, Fmoc-D-Cys(Trt)-OH and Boc-Cpa-OH. Compound 1 was a white solid, recovered as the 2.TFA salt. Compound 1 was then subjected to General Method H where the final peptide was a white solid, recovered as the bis acetate salt in 32% overall yield.

Example 20: H-Cpa-cyclo[D-Cys-Tyr-D-s-Tyr-D-Phe(4-carbamoyl)-Lys-Thr-Cys]-D-Tyr-NH$_2$ (Compound 4)

Compound 4 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(Boc)-OH, Fmoc-D-Phe(4-carbamoyl)-OH, Fmoc-Tyr(tBu)-OH, Fmoc-D-Cys(Trt)-OH and Boc-Cpa-OH. Compound 4 was a white solid, recovered as the 2.TFA salt. Compound 4 was then subjected to General Method H where the final peptide was a white solid, recovered as the bis acetate salt in 33% overall yield.

Example 21: H-Cpa-cyclo[D-Cys-Tyr-D-Phe(4-phenylureido)-Lys-Thr-Cys]-D-Tyr-NH$_2$ (Compound 15)

Compound 15 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(Boc)-OH, 15-ii, Fmoc-Tyr(tBu)-OH, Fmoc-D-Cys(Trt)-OH and Boc-Cpa-OH. Compound 15 was a white solid, recovered as the 2.TFA salt. Compound 15 was then subjected to General Method H where the final peptide was a white solid, recovered as the bis acetate salt in 30% overall yield.

Example 22: H-Cpa-cyclo[D-Cys-Tyr-D-Phe(4-carbamoyl)-Lys(N$^\varepsilon$-Me)-Thr-Cys]-D-Tyr-NH$_2$ (Compound 24)

Compound 24 was prepared according to the procedure described in Example 2, using the following amino acids: Fmoc-D-Tyr(tBu)-OH, Fmoc-Cys(Trt)-OH, Fmoc-Thr(tBu)-OH, Fmoc-Lys(N$^\varepsilon$-Boc-N$^\varepsilon$-Me)-OH, Fmoc-D-Phe(4-carbamoyl)-OH, Fmoc-Tyr(tBu)-OH, Fmoc-D-Cys(Trt)-OH and Boc-Cpa-OH. Compound 24 was a white solid, recovered as the 2.TFA salt. Compound 24 was then subjected to General Method H where the final peptide was a white solid, recovered as the bis acetate salt in 40% overall yield.

Synthesis of Non-Natural Amino Acid Intermediates

The following methods describe general methods for the preparation of non-natural amino acid intermediates used in the preparation of compounds of the instant invention.

Synthesis of Intermediate 11-iii

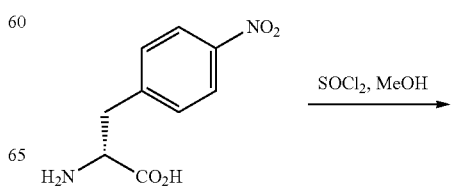

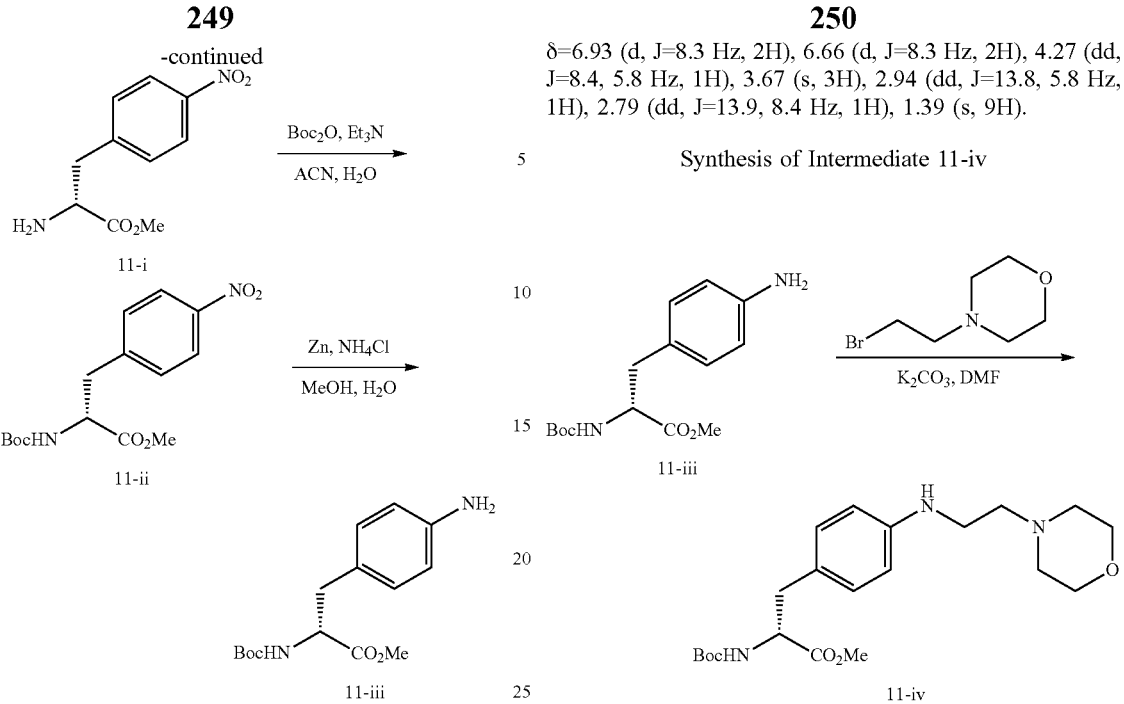

4-nitro-D-phenylalanine monohydrate (20.01 g, 87.7 mmol, 1.0 eq) was suspended in MeOH (440 mL, 0.2 M) and cooled to 0° C. Thionyl chloride (12.7 mL, 175 mmol, 2.0 eq) was added dropwise to the stirring solution, and the reaction was warmed to room temperature over 30 minutes and then heated to reflux for 24 h. After that time the reaction was cooled and the solvent was evaporated. The residue was taken up in EtOAc (750 mL) and saturated aqueous NaHCO$_3$ (1 L). The layers were separated and the organic layer was extracted with EtOAc (2×250 mL). The organic layers were combined, washed with brine, dried over Na$_2$SO$_4$, filtered and concentrated to give 4-nitro-D-phenylalanine methyl ester (11-i) as an orange oil (17.30 g, 77.2 mmol, 88%) that was used without further purification.

4-nitro-D-phenylalanine methyl ester (11-i, 17.30 g, 77.2 mmol, 1.0 eq) was dissolved in acetonitrile/water (2:1, 510 mL, 0.15 M) and treated with Et$_3$N (22.6 mL, 162 mmol, 2.1 eq) and Boc$_2$O (21.9 g, 100 mmol, 1.3 eq). After stirring at room temperature for 18 h, the solvent was evaporated and the residue was taken up in EtOAc (750 mL). This organic solution was washed with saturated aqueous NH$_4$Cl (250 mL), saturated aqueous NaHCO$_3$ (250 mL) and brine (250 mL), dried over Na$_2$SO$_4$, filtered and concentrated to afford Boc-4-nitro-D-phenylalanine methyl ester (11-ii, 22.57 g, 69.6 mmol, 90%) as a pale yellow solid that was used without further purification.

Boc-4-nitro-D-phenylalanine methyl ester (11-ii, 22.57 g, 69.6 mmol) was dissolved in MeOH/H$_2$O (10:1, 660 mL, 0.1 M). While vigorously stirring, Zn dust (45.5 g, 696 mmol, 10 eq) and NH$_4$Cl (55.8 g, 1043 mmol, 15 eq) were added and the mixture was heated to reflux for 90 min. The reaction was cooled to room temperature and the solids were removed by filtration through a pad of Celite. The filter cake was washed with MeOH. The filtrate was concentrated and the residue was dissolved in EtOAc (750 mL). This organic solution was washed with water (250 mL), saturated aqueous NH$_4$Cl (250 mL) and brine (250 mL), dried over Na$_2$SO$_4$, filtered and concentrated to afford Boc-4-amino-D-phenylalanine methyl ester (11-iii, 17.93 g, 60.9 mmol, 88%) as an orange oil. $^1$H NMR (400 MHz, d$_4$-MeOH) δ=6.93 (d, J=8.3 Hz, 2H), 6.66 (d, J=8.3 Hz, 2H), 4.27 (dd, J=8.4, 5.8 Hz, 1H), 3.67 (s, 3H), 2.94 (dd, J=13.8, 5.8 Hz, 1H), 2.79 (dd, J=13.9, 8.4 Hz, 1H), 1.39 (s, 9H).

Synthesis of Intermediate 11-iv

Boc-4-amino-D-phenylalanine methyl ester (11-iii, 1.39 g, 4.72 mmol, 1.0 eq) was dissolved in DMF (45 mL, 0.1 M) and treated with K$_2$CO$_3$ (2.62 g, 18.9 mmol, 4.0 eq) and the mixture was stirred for 15 min at room temperature. 4-(2-bromoethyl)morpholine hydrobromide (1.30 g, 4.73 mmol, 1.0 eq) was added and the mixture was stirred at room temperature for 48 h. Solids were removed by filtration. The filtrate was diluted with water (450 mL) and it was extracted with EtOAc (3×). The organic layers were combined, dried over Na$_2$SO$_4$, filtered and concentrated to afford 11-iv as an orange oil (1.52 g, 79%) which was used in the next step without further purification. LCMS (M+1)=408.6.

Synthesis of Intermediate 12-i

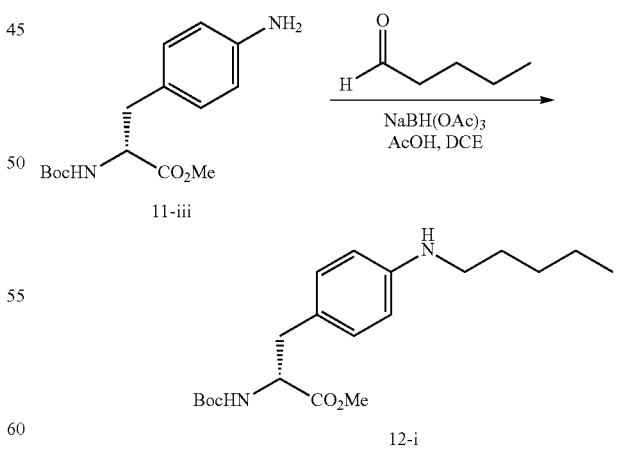

Boc-4-amino-D-phenylalanine methyl ester (11-iii, 929 mg, 3.16 mmol, 1.0 eq) was dissolved in DCE (16 mL, 0.2 M) and treated with valeraldehyde (336 μL, 3.16 mmol, 1.0 eq), NaBH(OAc)$_3$ (1003 mg, 4.73 mmol, 1.5 eq) and AcOH (180 μL, 2.15 mmol, 1.0 eq). The reaction was stirred at room temperature for 18 h, after which it was quenched by the addition of saturated aqueous NaHCO₃ followed by 1 h of stirring. The layers were separated and the aqueous phase was washed with DCM (2×10 mL). The organic layers were combined, dried over Na₂SO₄, filtered and concentrated. The residue was purified by flash chromatography (EtOAc/hexanes) to afford intermediate 12-i (738 mg, 2.02 mmol, 64%) as a pale yellow solid. ¹H NMR (400 MHz, d₄-MeOH) δ=6.94 (d, J=8.4 Hz, 2H), 6.58 (d, J=8.5 Hz, 2H), 4.31-4.23 (m, 1H), 3.67 (s, 3H), 3.04 (t, J=7.2 Hz, 2H), 2.93 (dd, J=13.9, 5.8 Hz, 1H), 2.78 (dd, J=13.9, 8.4 Hz, 1H), 1.66-1.52 (m, 2H), 1.42-1.34 (m, 4H), 1.39 (s, 9H), 0.93 (t, J=7.0 Hz, 3H).

Synthesis of Intermediate 14-i

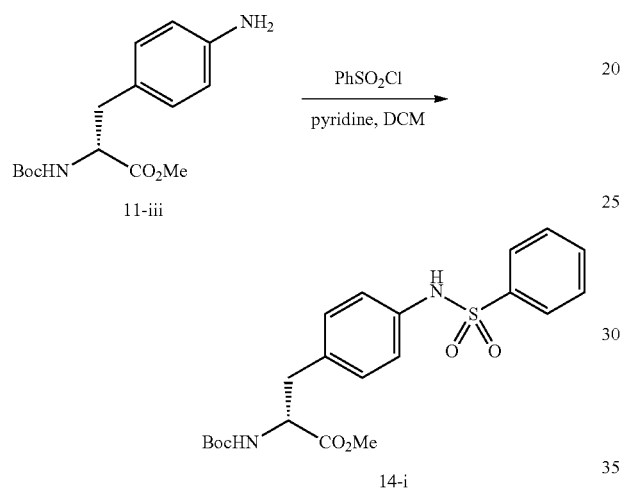

Boc-4-amino-D-phenylalanine methyl ester (11-iii, 1.00 g, 3.39 mmol, 1.0 eq) was dissolved in DCM (20 mL) and treated with pyridine (0.30 mL, 3.73 mmol, 1.1 eq) and phenylsulfonyl chloride (0.43 mL, 3.39 mmol, 1.0 eq). The reaction was stirred at room temperature for 24 h, after which is was quenched by the addition of saturated aqueous NH₄Cl. The layers were separated and the organic layer was washed with saturated aqueous NaHCO₃ and brine, dried over Na₂SO₄, filtered and concentrated. The residue was purified by flash chromatography (EtOAc/hexanes) to afford intermediate 14-i (1.39 g, 3.20 mmol, 94%) as a yellow oil. ¹H NMR (400 MHz, d₄-MeOH) δ=7.74 (d, J=7.5 Hz, 2H), 7.57 (t, J=7.5 Hz, 1H), 7.48 (t, J=7.5 Hz, 2H), 7.08 (d, J=8.4 Hz, 2H), 7.02 (d, J=8.4 Hz, 2H), 4.29 (dd, J=8.7, 5.4 Hz, 1H), 3.65 (s, 3H), 3.02 (dd, J=8.7, 5.4 Hz, 1H), 2.83 (dd, J=13.8, 5.4 Hz, 1H), 1.39 (s, 9H).

Synthesis of Intermediate 15-i

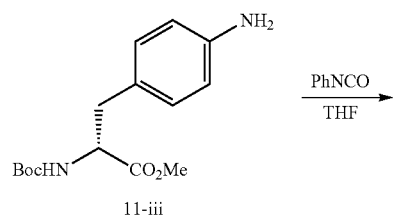

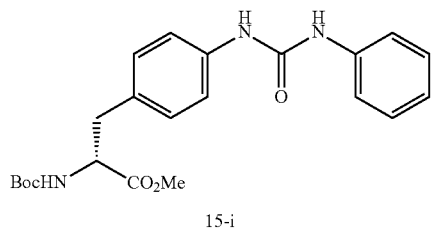

Boc-4-amino-D-phenylalanine methyl ester (11-iii, 1.00 g, 3.39 mmol, 1.0 eq) was dissolved in THF (20 mL) and treated with PhNCO (0.37 mL, 3.39 mmol, 1.0 eq). The reaction was heated to reflux for 4 h after which it was cooled. The mixture was concentrated to give a yellow solid. This solid was triturated with Et₂O. The solid was isolated by suction filtration yielding intermediate 15-i (1.20 g, 2.90 mmol, 87%) as a white solid. 1H NMR (400 MHz, d₄-MeOH) δ=7.43 (d, J=8.1 Hz, 2H), 7.38 (d, J=8.1 Hz, 2H), 7.30 (t, J=8.3 Hz, 2H), 7.16 (d, J=8.3 Hz, 2H), 7.03 (t, J=8.3 Hz, 1H), 4.35 (dd, J=8.7, 5.6 Hz, 1H), 3.72 (s, 3H), 3.08 (dd, J=13.8, 5.6 Hz, 1H), 2.90 (dd, J=13.8, 8.8 Hz, 1H), 1.42 (s, 9H).

Synthesis of Intermediate 38-i

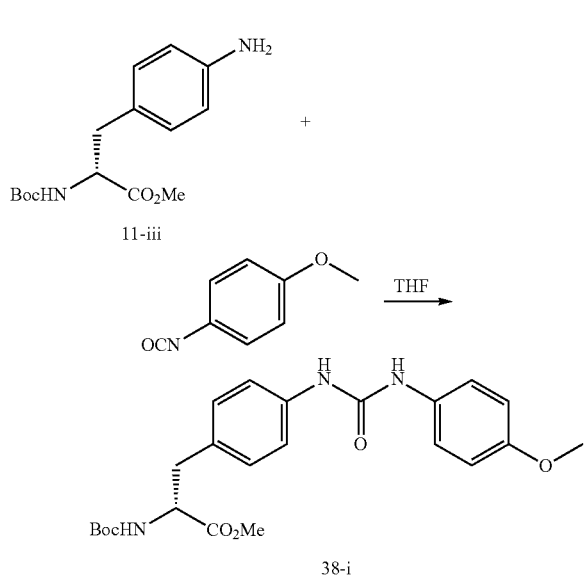

Boc-4-amino-D-phenylalanine methyl ester (11-iii, 1.00 g, 3.39 mmol, 1.0 eq) was dissolved in THF (20 mL) and treated with 4-Methoxyphenyl isocyanate (0.44 mL, 3.39 mmol, 1.0 eq). The reaction was heated to reflux for 16 h after which it was cooled. The mixture was concentrated to give a yellow solid. This solid was triturated with Et₂O. The solid was isolated by suction filtration yielding intermediate BD-00481-161 (1.23 g, 2.77 mmol, 83%) as a white powder. ¹H NMR (400 MHz, d₄-MeOH) δ=7.36 (d, J=8.2 Hz, 2H), 7.32 (d, J=9.0 Hz, 2H), 7.15 (d, J=8.2 Hz, 2H), 6.89 (d, J=9.0 Hz, 2H), 4.34 (dd, J=8.8, 5.6 Hz, 1H), 3.79 (s, 3H), 3.71 (s, 3H), 3.07 (dd, J=13.8, 5.6 Hz, 1H), 2.88 (dd, J=13.8, 8.9 Hz, 1H), 1.42 (s, 9H).

Synthesis of Intermediate 27-i

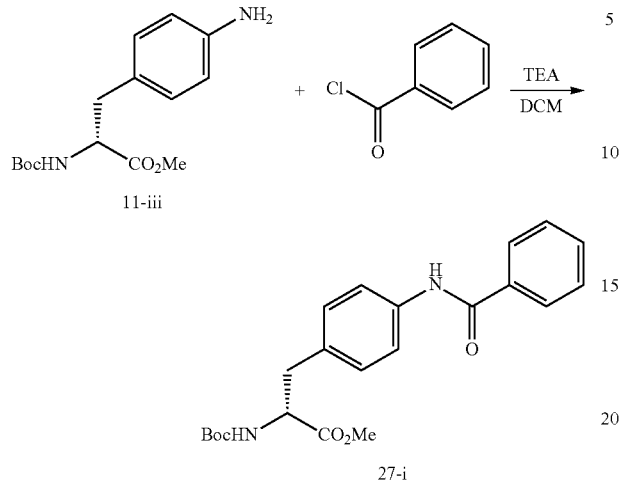

Boc-4-amino-D-phenylalanine methyl ester (11-iii, 1.00 g, 3.39 mmol, 1.0 eq) was dissolved in DCM (20 mL) and treated with triethylamine (TEA, 0.71 ml, 5.1 mmol, 1.5 eq). The mixture was cooled to 0° C. and the benzoyl chloride was added (0.40 mL, 3.39 mmol, 1.0 eq). The mixture was stirred at 0° C. for 15 minutes, and allowed to warm up to room temperature. The reaction was stirred at the same temperature for 3 hours, after which it was quenched by the addition of saturated aqueous $NH_4Cl$. The layers were separated and the organic layer was washed with saturated aqueous $NaHCO_3$, deionized water and brine, dried over $Na_2SO_4$, filtered and concentrated. This solid was triturated with $Et_2O$. The solid was isolated by suction filtration yielding intermediate 27-i (0.64 g, 1.62 mmol, 47%) as a white powder. $^1$H NMR (400 MHz, $d_6$-DMSO) δ=10.21 (s, 1H), 7.95 (d, J=7.1 Hz, 2H), 7.69 (d, J=8.2 Hz, 2H), 7.60 (t, J=7.2 Hz, 1H), 7.54 (m, 2H), 7.30 (d, J=8.0 Hz, 1H), 7.21 (d, J=8.2 Hz, 2H), 4.16 (m, 1H) 3.63 (s, 3H), 2.97 (dd, J=13.6, 5.3 Hz, 1H), 2.84 (m, 1H), 1.35 (s, 9H).

General Method Q: Conversion of Boc-D-Phenylalanine Methyl Ester Intermediates to Fmoc-D-Phenylalanine Intermediates

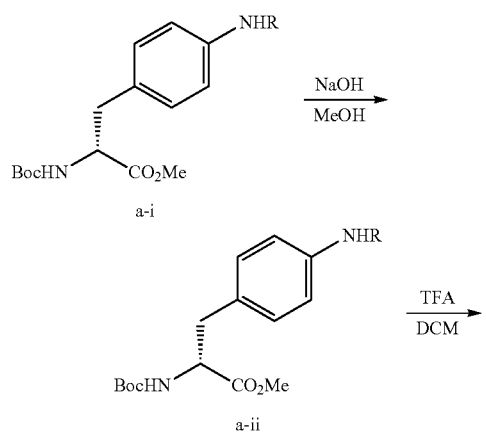

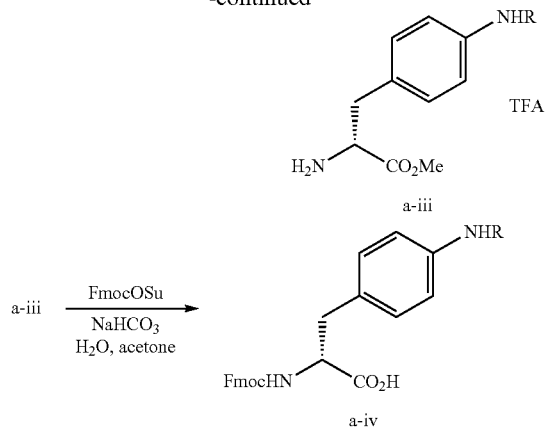

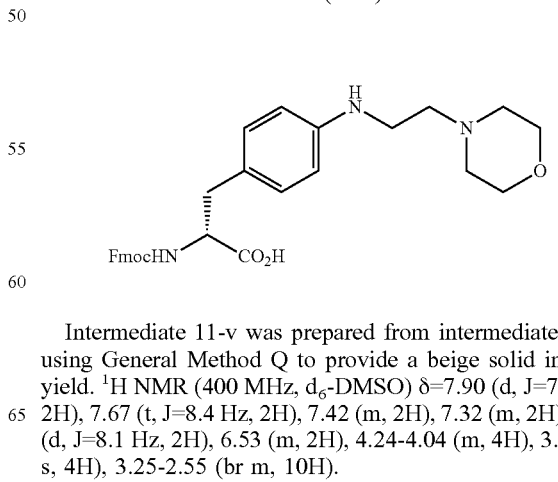

The substituted Boc-D-phenylalanine methyl ester intermediate a-i (1.0 eq) was dissolved in MeOH (0.1 M) and treated with NaOH (2.0 M in $H_2O$, 2.0 eq). The reaction was stirred at room temperature for 18 h after which the solvents were evaporated. The solid residue was taken up into water and the pH was adjusted with 1 M HCl until a precipitate formed. The precipitate was isolated by suction filtration to afford a substituted Boc-D-phenylalanine intermediate a-ii as a solid that was used without further purification.

The substituted Boc-D-phenylalanine a-ii (1.0 eq) was dissolved in DCM/TFA (1:1, 0.1 M) and stirred at room temperature. After 2 hours, the solvents were evaporated to give a crude substituted D-phenylalanine intermediate a-iii. This residue was dissolved in acetone/$H_2O$ (1:1, 0.1 M). The mixture was treated with $NaHCO_3$ (2.0 eq) and FmocOSu (1.1 eq), and it was stirred at room temperature for 24 hours. The solvents were removed by evaporation and the residue was dissolved in EtOAc/$H_2O$. The layers were separated and the aqueous layer was washed with EtOAc (×2). The resulting organic layers were discarded. The aqueous layer was acidified to pH 3 and it was extracted with EtOAc (×3). The remaining organic layers were combined, dried over $Na_2SO_4$, filtered and concentrated. The product was purified by preparative HPLC, affording a substituted Fmoc-D-phenylalanine a-iv as a solid.

Fmoc-4-((2-morpholinoethyl)amino)-D-phenylalanine (11-v)

Intermediate 11-v was prepared from intermediate 11-iv using General Method Q to provide a beige solid in 58% yield. $^1$H NMR (400 MHz, $d_6$-DMSO) δ=7.90 (d, J=7.5 Hz, 2H), 7.67 (t, J=8.4 Hz, 2H), 7.42 (m, 2H), 7.32 (m, 2H), 7.02 (d, J=8.1 Hz, 2H), 6.53 (m, 2H), 4.24-4.04 (m, 4H), 3.68 (br s, 4H), 3.25-2.55 (br m, 10H).

Fmoc-4-(n-pentylamino)-D-phenylalanine (12-ii)

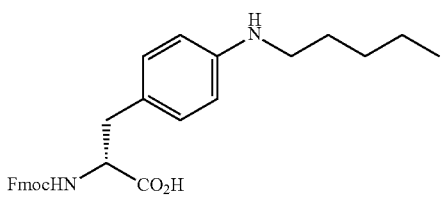

Fmoc-4-(pentylamino)-D-phenylalanine (12-ii) was prepared from intermediate 12-i using General Method Q to provide a white solid in 25% yield. $^1$H NMR (400 MHz, d$_4$-MeOH) δ=7.78 (d, J=7.6 Hz, 2H), 7.60 (d, J=7.4 Hz, 2H), 7.40-7.35 (m, 2H), 7.34-7.24 (m, 2H), 7.02 (d, J=8.4 Hz, 2H), 6.57 (d, J=8.5 Hz, 2H), 4.38-4.29 (m, 2H), 4.18-4.10 (m, 2H), 3.09 (dd, J=13.9, 4.7 Hz, 1H), 2.97 (t, J=7.3 Hz, 2H), 2.81 (dd, J=13.9, 9.3 Hz, 1H), 1.61-1.49 (m, 2H), 1.38-1.28 (m, 4H), 0.90 (t, J=7.0 Hz, 3H).

Fmoc-4-(phenylsulfonamido)-D-phenylalanine (14-ii)

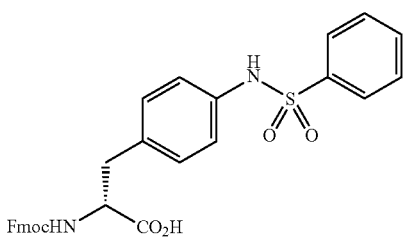

Intermediate 14-ii was prepared from intermediate 14-i using General Method Q to provide a white solid in 23% yield. $^1$H NMR (400 MHz, d$_6$-DMSO) δ=10.21 (br s, 1H), 7.89 (d, J=7.6 Hz, 2H), 7.72 (d, J=7.2 Hz, 2H), 7.67-7.37 (m, 9H), 7.11 (d, J=8.3 Hz, 2H), 6.99 (d, J=8.2 Hz, 2H), 4.24-4.01 (m, 4H), 2.96 (dd, J=13.9, 4.4 Hz, 1H), 2.76 (dd, J=13.8, 4.4 Hz, 1H).

Fmoc-4-(3-phenylureido)-D-phenylalanine (15-ii)

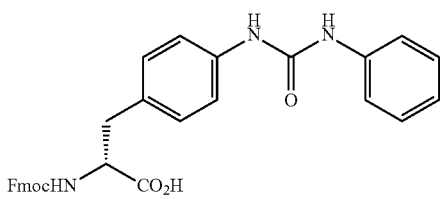

Intermediate 15-ii was prepared from intermediate 15-i using General Method Q to provide a white solid in 58% yield. $^1$H NMR (400 MHz, d$_6$-DMSO) δ=8.65 (s, 1H), 8.61 (s, 1H), 7.89 (d, J=7.5 Hz, 2H), 7.74-7.62 (m, 3H), 7.49-7.24 (m, 9H, ArH), 7.18 (d, J=8.2 Hz, 2H), 6.97 (t, J=7.4 Hz, 1H), 4.25-4.10 (m, 4H), 3.03 (dd, J=13.9, 4.5 Hz, 1H), 2.82 (dd, J=13.8, 10.4 Hz, 1H).

Fmoc-4-(3-(4-methoxyphenyl)uriedo)-D-phenylalanine (38-ii)

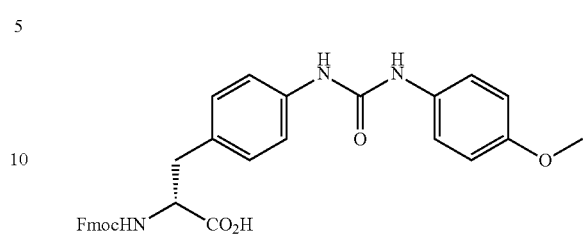

Intermediate 38-ii was prepared from intermediate 38-i using General Method Q to provide a white solid in 54% yield. $^1$H NMR (400 MHz, d$_6$-DMSO) δ=8.53 (s, 1H), 8.46 (s, 1H), 7.89 (d, J=7.6 Hz, 2H), 7.74 (d, J=8.4 Hz, 1H), 7.66 (t, J=8.5 Hz, 2H), 7.47-7.27 (m, 8H), 7.17 (d, J=8.1 Hz, 2H), 6.87 (d, J=8.7 Hz, 2H), 4.20 (m, 4H), 3.72 (s, 3H), 3.02 (dd, J=13.7, 4.3 Hz, 1H), 2.80 (m, 1H).

Fmoc-4-(benzamidophenyl)-D-phenylalanine (27-ii)

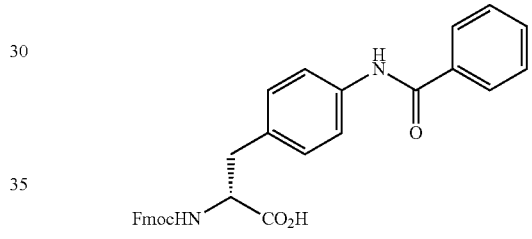

Intermediate 27-ii was prepared from intermediate 27-i using General Method Q to provide a beige powder in 43% yield. $^1$H NMR (400 MHz, d$_6$-DMSO) δ=12.76 (s, 1H), 10.21 (s, 1H), 7.94 (d, J=7.0 Hz, 2H), 7.89 (d, J=7.6 Hz, 2H), 7.77-7.51 (m, 8H), 7.41 (q, J=7.0 Hz, 2H), 7.33 (m, 2H), 7.26 (d, J=8.2 Hz, 2H), 4.28-4.10 (m, 4H), 3.07 (dd, J=13.9, 4.4 Hz, 1H), 2.91-2.82 (m, 1H).

Fmoc-O-(2-morpholinoethyl)-D-tyrosine (13-ii)

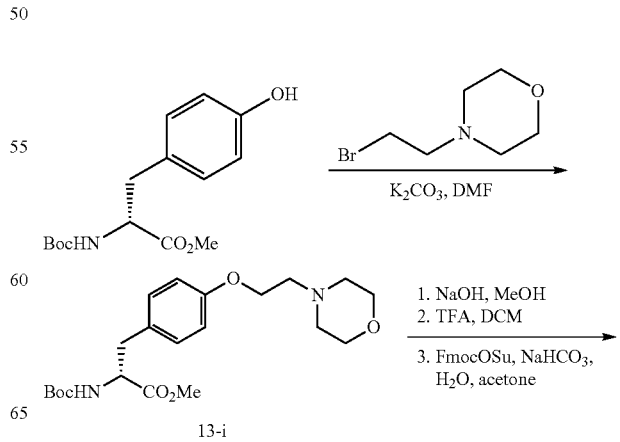

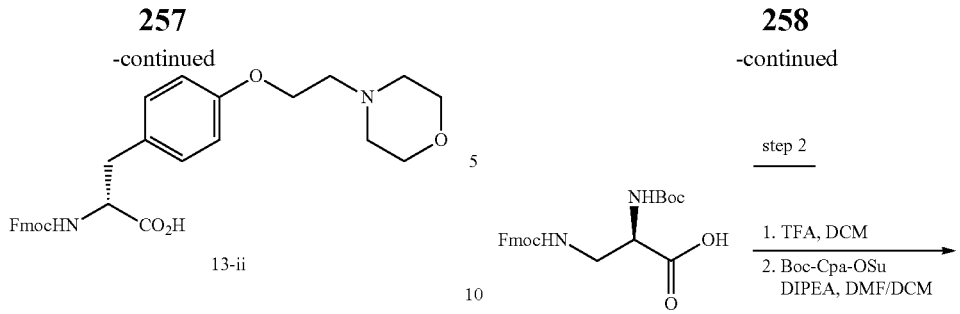

Boc-D-tyrosine methyl ester (1.00 g, 3.39 mmol) was dissolved in DMF (35 mL, 0.1 M) and treated with K₂CO₃ (2.34 g, 17.0 mmol, 5.0 eq) and the mixture was stirred for 15 min at room temperature. 4-(2-bromoethyl)morpholine hydrobromide (1.39 g, 5.08 mmol, 1.5 eq) was added and the mixture was stirred at room temperature for 48 h. Solids were removed by filtration. The filtrate was diluted with water (500 mL) and it was extracted with EtOAc (3×). The organic layers were washed with combined, washed with brine, dried over Na₂SO₄, filtered and concentrated to afford intermediate 13-i as an orange oil (1.30 g, 3.18 mmol, 94%) which was used in the next step without further purification.

Intermediate 13-i was converted to Fmoc-O-(2-morpholinoethyl)-D-tyrosine (13-ii) using General Procedure I to provide a white solid in 37% yield. $^1$H NMR (400 MHz, d$_6$-DMSO) δ=7.89 (d, J=7.5 Hz, 2H), 7.71 (d, J=8.5 Hz, 1H), 7.65 (t, J=6.7 Hz, 2H), 7.42 (td, J=7.5, 2.8 Hz, 2H), 7.31 (m, 2H), 7.20 (d, J=8.3 Hz, 2H), 6.86 (d, J=8.3 Hz, 2H), 4.17 (m, 6H), 3.63 (br s, 4H), 3.02 (dd, J=13.9, 4.4 Hz, 1H), 2.97-2.55 (br m, 7H).

Synthesis of Boc-Cpa-D-Dap(Fmoc)-OH (60-i)

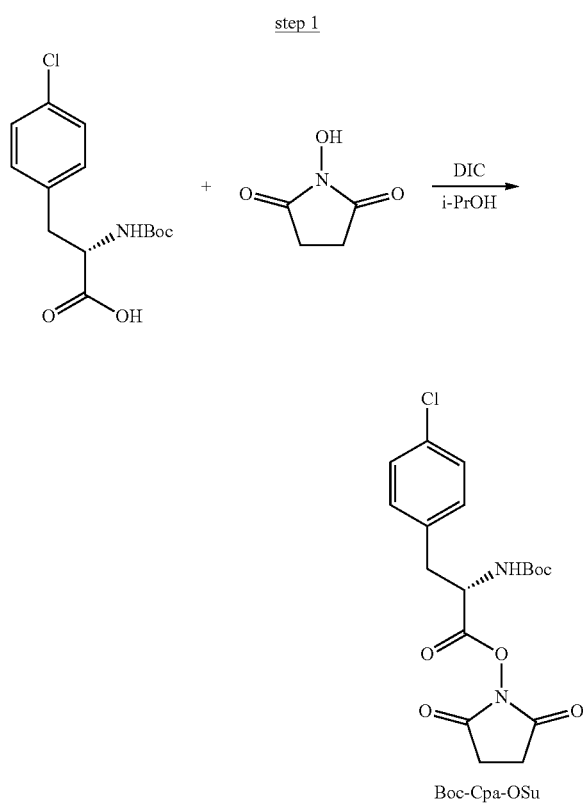

To a cold (0° C.) stirring solution of Boc-Cpa-OH (1.0 g, 3.39 mmol) in i-PrOH (15 mL) was added HOSu (0.62 g, 5.42 mmol). After stirring for 10 min, DIC (0.68 mL, 4.39 mmol) was added and continued stirring cold. Within 10 min, a white suspension resulted and stirred cold for an additional 1.5 h. The reaction mixture was filtered, rinsed with i-PrOH and dried in vacuo to afford the desired activated acid Boc-Cpa-OSu as a white solid (1.0 g, 2.52 mmol) in 77% yield. It was used in the next step without further purification. Mass calculated for (C$_{18}$H$_{21}$ClN$_2$O$_6$+H)$^+$ 397.1, found 397.3.

To a cold (0° C.) stirring suspension of Boc-D-(Fmoc)Dap-OH (1.2 g, 2.72 mmol) in DCM (22 mL) was added TFA (22 mL, 286 mmol). The resulting yellow solution was stirred cold for 5 min then at ambient temperature for an additional 30 min. The reaction solution was concentrated in vacuo, successively co-evaporated with DCM (2×), PhMe (1×) and DCM (1×). The resulting pale orange solid residue was suspended in a 1:1 (v/v) mixture of DCM/DMF (26 mL) and then successively treated with DIPEA (1.85 mL, 10.6 mmol) and Boc-Cpa-OSu (1.0 g, 2.52 mmol). The pale yellow milky mixture was stirred at ambient temperature for 16 h. The resulting pale yellow solution was concentrated in vacuo, diluted with EtOAc and then successively washed with H₂O (2×60 mL), 0.5M HCl (1×20 mL) and brine (2×30 mL). The organic layer was dried (MgSO₄), filtered, concentrated in vacuo and purified by column chromatography (eluted with 5% MeOH/DCM) to afford the desired dipeptide Boc-Cpa-D-Dap(Fmoc)-OH as an off-white solid in 61% yield. Mass calculated for (C$_{32}$H$_{34}$ClN$_3$O$_7$+H)$^+$ 608.2, found 608.4.

TABLE 1

Intermediate Linear Peptides Prepared Using Example 1

| Intermediate Peptide | Intermediate Linear Peptide Sequence |
|---|---|
| 1-i | H-Cpa-D-Cys-Tyr-D-Cit-Lys-Thr-Cys-D-Tyr-NH$_2$ |
| 2-i | H-Cpa-D-Cys-Tyr-D-HoCit-Lys-Thr-Cys-D-Tyr-NH$_2$ |
| 3-i | H-Cpa-D-Cys-Tyr-D-Lys(N$^\varepsilon$-nicotinoyl)-Lys-Thr-Cys-D-Tyr-NH$_2$ |
| 4-i | H-Cpa-D-Cys-Tyr-D-Phe(4-carbamoyl)-Lys-Thr-Cys-D-Tyr-NH$_2$ |
| 5-i | H-Cpa-D-Cys-Tyr-D-Phe(4-aminomethyl)-Lys-Thr-Cys-D-Tyr-NH$_2$ |
| 6-i | H-Cpa-D-Cys-Tyr-D-Phe(4-acetamidomethyl)-Lys-Thr-Cys-D-Tyr-NH$_2$ |
| 7-i | H-Cpa-D-Cys-Tyr-D-Phe(4-ureidomethyl)-Lys-Thr-Cys-D-Tyr-NH$_2$ |
| 8-i | H-Cpa-D-Cys-Tyr-D-Aph(Gly)-Lys-Thr-Cys-D-Tyr-NH$_2$ |
| 9-i | H-Cpa-D-Cys-Tyr-D-Aph(Gly-Ac)-Lys-Thr-Cys-D-Tyr-NH$_2$ |
| 10-i | H-Cpa-D-Cys-Tyr-D-Aph(Pro)-Lys-Thr-Cys-D-Tyr-NH$_2$ |
| 11-vi | H-Cpa-D-Cys-Tyr-D-Aph(2-(4-morpholinyl)ethyl)-Lys-Thr-Cys-D-Tyr-NH$_2$ |
| 12-vi | H-Cpa-D-Cys-Tyr-D-Phe(4-n-pentylamino)-Lys-Thr-Cys-D-Tyr-NH$_2$ |
| 13-iii | H-Cpa-D-Cys-Tyr-D-Tyr(2-(4-morpholinyl)ethyl)-Lys-Thr-Cys-D-Tyr-NH$_2$ |
| 14-vi | H-Cpa-D-Cys-Tyr-D-Aph(benzenesulfonyl)-Lys-Thr-Cys-D-Tyr-NH$_2$ |
| 15-vi | H-Cpa-D-Cys-Tyr-D-Phe(4-phenylureido)-Lys-Thr-Cys-D-Tyr-NH$_2$ |
| 16-i | H-Cpa-D-Cys-Tyr-D-Aph(Ser)-Lys-Thr-Cys-D-Tyr-NH$_2$ |
| 17-i | H-Cpa-D-Cys-Tyr-D-Aph(Lys)-Lys-Thr-Cys-D-Tyr-NH$_2$ |
| 18-i | H-Cpa-D-Cys-Tyr-D-Aph(Asp)-Lys-Thr-Cys-D-Tyr-NH$_2$ |
| 19-i | H-Cpa-D-Cys-Tyr-D-Aph(Asn)-Lys-Thr-Cys-D-Tyr-NH$_2$ |
| 20-i | H-Cpa-D-Cys-Tyr-D-Aph(Glu)-Lys-Thr-Cys-D-Tyr-NH$_2$ |
| 21-i | H-Cpa-D-Cys-Tyr-D-Aph(Gln)-Lys-Thr-Cys-D-Tyr-NH$_2$ |
| 22-i | H-Cpa-D-Cys-Tyr-D-Aph(Cit)-Lys-Thr-Cys-D-Tyr-NH$_2$ |
| 23-i | H-Cpa-D-Cys-Tyr-D-Aph(Val)-Lys-Thr-Cys-D-Tyr-NH$_2$ |
| 24-i | H-Cpa-D-Cys-Tyr-D-Phe(4-carbamoyl)-Lys-(N$^\varepsilon$-Me)-Thr-Cys-D-Tyr-NH$_2$ |

TABLE 2

Resin-Bound Intermediate Linear Peptides Prepared Using Example 2

| Intermediate Peptide | Resin-Bound Intermediate Linear Peptide Sequence |
|---|---|
| 25-i | Fmoc-Cpa-D-Cys(Trt)-Tyr(tBu)-D-Phe(4-phenylureido)-Lys(N$^\varepsilon$-Boc-N$^\varepsilon$-Me)-Thr(tBu)-Cys(Trt)-D-Tyr(t-Bu)-NH-MBHA resin |
| 26-i | Fmoc-Cpa-D-Cys(Trt)-Tyr(tBu)-D-Phe(4-carbamoyl)-Lys(N$^\varepsilon$-Ac)-Thr(tBu)-Cys(Trt)-D-Tyr(t-Bu)-NH-MBHA resin |
| 27-iii | Fmoc-Cpa-D-Cys(Trt)-Tyr(tBu)-D-Phe(4-benzamidophenyl)-Lys(Boc)-Thr(tBu)-Cys(Trt)-D-Tyr(t-Bu)-NH-MBHA resin |
| 28-i | Fmoc-Cpa-D-Cys(Trt)-Tyr(tBu)-D-Phe(4-(4-methoxyphenyl)ureido)-Lys(Boc)-Thr(tBu)-Cys(Trt)-D-Tyr(t-Bu)-NH-MBHA resin |
| 29-i | Fmoc-Cpa-D-Cys(Trt)-Tyr(tBu)-D-Phe(4-carbamoyl)-Arg(Pbf)-Thr(tBu)-Cys(Trt)-D-Tyr(t-Bu)-NH-MBHA resin |
| 30-i | Fmoc-Cpa-D-Cys(Trt)-Tyr(tBu)-D-Lys(N$^\varepsilon$-nicotinoyl)-Lys(N$^\varepsilon$-Boc-N$^\varepsilon$-Me)-Thr(tBu)-Cys(Trt)-D-Tyr(t-Bu)-NH-MBHA resin |
| 31-i | Fmoc-Cpa-D-Cys(Trt)-Tyr(tBu)-D-Cit-Lys(N$^\varepsilon$-Boc-N$^\varepsilon$-Me)-Thr(tBu)-Cys(Trt)-D-Tyr(t-Bu)-NH-MBHA resin |
| 32-i | Fmoc-Cpa-D-Cys(Trt)-Tyr(tBu)-D-Phe(4-carbamoyl)-Lys(N$^\varepsilon$-diMe)-Thr(tBu)-Cys(Trt)-D-Tyr(t-Bu)-NH-MBHA resin |
| 33-i | Boc-Cpa-D-Cys(Trt)-Tyr(tBu)-D-Phe(4-carbamoyl)-Lys(Boc)-Val-Cys(Trt)-D-Tyr(t-Bu)-NH-MBHA resin |
| 34-i | Boc-Cpa-D-Cys(Trt)-Tyr(tBu)-D-Phe(4-carbamoyl)-Lys(Boc)-Tle-Cys(Trt)-D-Tyr(t-Bu)-NH-MBHA resin |
| 35-i | Boc-Cpa-D-Cys(Trt)-Phe-D-Phe(4-carbamoyl)-Lys(Boc)-Thr(tBu)-Cys(Trt)-D-Tyr(t-Bu)-NH-MBHA resin |
| 36-i | Boc-Cpa-D-Cys(Trt)-Cpa-D-Phe(4-carbamoyl)-Lys(Boc)-Thr(tBu)-Cys(Trt)-D-Tyr(t-Bu)-NH-MBHA resin |
| 37-i | Boc-Cpa-D-Cys(Trt)-Tyr(tBu)-D-Phe(4-carbamoyl)-Lys(Boc)-Ser(tBu)-Cys(Trt)-D-Tyr(t-Bu)-NH-MBHA resin |
| 38-iii | Boc-Cpa-D-Cys(Trt)-Tyr(Me)-D-Phe(4-carbamoyl)-Lys(Boc)-Thr(tBu)-Cys(Trt)-D-Tyr(t-Bu)-NH-MBHA resin |
| 39-i | Boc-Cpa-Cys(Trt)-Tyr(tBu)-D-Phe(4-carbamoyl)-Lys(Boc)-Thr(tBu)-Cys(Trt)-D-Tyr(t-Bu)-NH-MBHA resin |
| 40-i | Boc-Cpa-D-Cys(Trt)-Tyr(tBu)-D-Phe(4-carbamoyl)-Lys(Boc)-Thr(tBu)-Cys(Trt)-D-Phe-NH-MBHA resin |
| 41-i | Boc-Cpa-D-Cys(Trt)-Phe-D-Phe(4-carbamoyl)-Lys(Boc)-Thr(tBu)-Cys(Trt)-D-Phe-NH-MBHA resin |
| 42-i | Boc-Cpa-D-Cys(Trt)-Tyr(tBu)-D-Phe(4-carbamoyl)-Lys(Boc)-Thr(tBu)-Cys(Trt)-D-Cpa-NH-MBHA resin |
| 43-i | Boc-Cpa-D-Cys(Trt)-Cpa-D-Phe(4-carbamoyl)-Lys(Boc)-Thr(tBu)-Cys(Trt)-D-Cpa-NH-MBHA resin |
| 44-i | Boc-Cpa-D-Cys(Trt)-Tyr(tBu)-D-Phe(4-carbamoyl)-Lys(Boc)-Thr(tBu)-Cys(Trt)-D-Tyr(Me)-NH-MBHA resin |

TABLE 2-continued

Resin-Bound Intermediate Linear Peptides Prepared Using Example 2

| Intermediate Peptide | Resin-Bound Intermediate Linear Peptide Sequence |
| --- | --- |
| 45-i | Boc-Cpa-D-Cys(Trt)-Tyr(Me)-D-Phe(4-carbamoyl)-Lys(Boc)-Thr(tBu)-Cys(Trt)-D-Tyr(Me)-NH-MBHA resin |
| 46-i | Boc-Cpa-D-Cys(Trt)-Try(tBu)-D-Phe(4-carbamoyl)-Lys($N^\epsilon$-Boc-$N^\epsilon$-Me)-Thr(tBu)-Cys(Trt)-D-Cpa-NH-MBHA resin |
| 47-i | Boc-Cpa-D-Cys(Trt)-Cpa-D-Phe(4-carbamoyl)-Lys($N^\epsilon$-Boc-$N^\epsilon$-Me)-Thr(tBu)-Cys(Trt)-D-Cpa-NH-MBHA resin |
| 48-i | Boc-Cpa-D-Cys(Trt)-Cpa-D-Phe(4-carbamoyl)-Lys($N^\epsilon$-Boc-$N^\epsilon$-Me)-Thr(tBu)-Cys(Trt)-D-Tyr(tBu)-NH-MBHA resin |
| 49-i | Boc-☒-Ala-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 50-i | Ph(CO)NHCH$_2$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 51-i | PhSO$_2$CH$_2$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 52-i | t-BuCH$_2$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 53-i | 2-Pyridyl(CO)-Cpa-D-Cys (Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 54-i | H$_2$N(CO)(CH$_2$)$_2$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 55-i | Ac-Gly-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 56-i | CH$_3$(CH$_2$)$_4$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 57-i | (Furan-2-carboxy)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 58-i | CH$_3$O$_2$C(CH$_2$)$_2$(CO)-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(trt)-D-Tyr(t-Bu)-NH-MBHA resin |
| 59-i | Boc-Cpa-D-Cys(Trt)-Tyr(tBu)-D-Phe(4-CN)-Lys(Boc)-Thr(tBu)-Cys(Trt)-D-Tyr(tBu)-NH-MBHA resin |
| 81-i | CH$_3$SO$_2$-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |
| 82-i | PhSO$_2$-Cpa-D-Cys(Trt)-Tyr(t-Bu)-D-Phe(4-carbamoyl)-Lys($N^\epsilon$-Boc-$N^\epsilon$-Me)-Thr(t-Bu)-Cys(Trt)-D-Tyr(t-Bu)-NH-MBHA resin |

TABLE 3

Resin-Bound Intermediate Linear Peptides with a Disulfide Isostere Prepared Using Example 2

| Intermediate Peptide | Resin-Bound Intermediate Linear Peptide Sequence |
| --- | --- |
| 60-ii | Boc-Cpa-D-Dap(Fmoc)-Tyr(t-Bu)-D-Phe(4-carbamoyl)-Lys(Boc)-Thr(t-Bu)-Cys(t-Bu)-D-Tyr(t-Bu)-NH-MBHA resin |
| 61-i | Boc-Cpa-Dap(Mtt)-Tyr(t-Bu)-D-Phe(4-carbamoyl)-Lys(Boc)-Thr(t-Bu)-Cys(t-Bu)-D-Tyr(t-Bu)-NH-MBHA resin |
| 62-i | Boc-Cpa-D-Cys(t-Bu)-Tyr(t-Bu)-D-Phe(4-carbamoyl)-Lys(Boc)-Thr(t-Bu)-Dap(Mtt)-D-Tyr(t-Bu)-NH-MBHA resin |
| 63-i | Boc-Cpa-D-Cys(t-Bu)-Tyr(t-Bu)-D-Phe(4-carbamoyl)-Lys($N^\epsilon$-Boc-$N^\epsilon$-Me)-Thr(t-Bu)-Dap(Mtt)-D-Tyr(t-Bu)-NH-MBHA resin |
| 64-i | Fmoc-Cpa-D-Dap(N$_3$)-Tyr(t-Bu)-D-Phe(4-carbamoyl)-Lys(Boc)-Thr(t-Bu)-Gly(Propargyl)-D-Tyr(t-Bu)-NH-MBHA Resin |
| 65-i | Boc-Cpa-Gly(Propargyl)-Tyr(t-Bu)-D-Phe(4-carbamoyl)-Lys(Boc)-Thr(t-Bu)-Dap(N$_3$)-D-Tyr(t-Bu)-NH-MBHA Resin |
| 66-i | Boc-Cpa-D-Gly(Propargyl)-Tyr(t-Bu)-D-Phe(4-carbamoyl)-Lys(Boc)-Thr(t-Bu)-Dap(N$_3$)-D-Tyr(t-Bu)-NH-MBHA Resin |
| 67-i | Boc-Cpa-D-Gly(Allyl)-Tyr(t-Bu)-D-Phe(4-carbamoyl)-Lys(Boc)-Thr(t-Bu)-Gly(Allyl)-D-Tyr(t-Bu)-NH-MBHA Resin |
| 68-i | Boc-Cpa-Gly(Allyl)-Tyr(t-Bu)-D-Phe(4-carbamoyl)-Lys(Boc)-Thr(t-Bu)-Gly(Allyl)-D-Tyr(t-Bu)-NH-MBHA Resin |
| 69-i | Boc-Cpa-D-Asp(OAll)-Tyr(t-Bu)-D-Phe(4-carbamoyl)-Lys(Boc)-Thr(t-Bu)-Dap(Mtt)-D-Tyr(t-Bu)-NH-MBHA Resin |
| 70-i | Boc-Cpa-D-Asp(OAll)-Tyr(t-Bu)-D-(4-phenylureido)Phe-Lys(Boc)-Thr(t-Bu)-Dap(Mtt)-D-Tyr(t-Bu)-NH-MBHA Resin |
| 71-i | Boc-Cpa-D-Asp(OAll)-Tyr(t-Bu)-D-Phe(4-carbamoyl)-Lys($N^\epsilon$-Boc-$N^\epsilon$-Me)-Thr(t-Bu)-Dap(Mtt)-D-Tyr(t-Bu)-NH-MBHA Resin |

TABLE 4

Resin-Bound Intermediate Linear Peptides with N-Methylated Backbones Prepared Using Example 2

| Intermediate Peptide | Resin-Bound Intermediate Linear Peptide Sequence |
| --- | --- |
| 72-i | Boc-Cpa-D-Cys(Trt)-Tyr(tBu)-D-Phe(4-carbamoyl)-($N^{\alpha}$-Me)Lys(Boc)-Thr(tBu)-Cys(Trt)-D-Tyr(tBu)-NH-MBHA resin |
| 73-i | Boc-Cpa-D-Cys(Trt)-Tyr(tBu)-D-Phe(4-carbamoyl)-Lys(Boc)-(N-Me)Thr(tBu)-Cys(Trt)-D-Tyr(tBu)-NH-MBHA resin |
| 74-i | Boc-Cpa-D-Cys(Trt)-(N-Me)Tyr(tBu)-D-Phe(4-carbamoyl)-Lys(Boc)-Thr(tBu)-Cys(Trt)-D-Tyr(tBu)-NH-MBHA resin |
| 75-i | Boc-Cpa-D-Cys(Trt)-(N-Me)Tyr(tBu)-D-Phe(4-carbamoyl)-Lys(Boc)-(N-Me)Thr(tBu)-Cys(Trt)-D-Tyr(tBu)-NH-MBHA resin |
| 76-i | Boc-Cpa-D-Cys(Trt)-Tyr(tBu)-D-Phe(4-carbamoyl)-Lys(Boc)-Thr(tBu)-(N-Me)Cys(Trt)-D-Tyr(tBu)-NH-MBHA resin |
| 77-i | Boc-(N-Me)Cpa-D-Cys(Trt)-Tyr(tBu)-D-Phe(4-carbamoyl)-Lys(Boc)-Thr(tBu)-Cys(Trt)-D-Tyr(tBu)-NH-MBHA resin |
| 78-i | Boc-Cpa-D-(N-Me)Cys(Trt)-Tyr(tBu)-D-Phe(4-carbamoyl)-Lys(Boc)-Thr(tBu)-Cys(Trt)-D-Tyr(tBu)-NH-MBHA resin |
| 79-i | Boc-Cpa-D-Cys(Trt)-Tyr(tBu)-D-Phe(4-carbamoyl)-Lys(Boc)-Thr(tBu)-Cys(Trt)-D-(N-Me)Tyr(tBu)-NH-MBHA resin |
| 80-i | Boc-(N-Me)Cpa-D-Cys(Trt)-(N-Me)Tyr(tBu)-D-Phe(4-carbamoyl)-Lys(Boc)-(N-Me)Thr(tBu)-Cys(Trt)-D-(N-Me)Tyr(tBu)-NH-MBHA resin |

TABLE 5

Cyclic 8-mer Compounds and Characterization Data

| Compound No. | SEQ ID NO. | Structure | Methods |
| --- | --- | --- | --- |
| 1 | 1 | 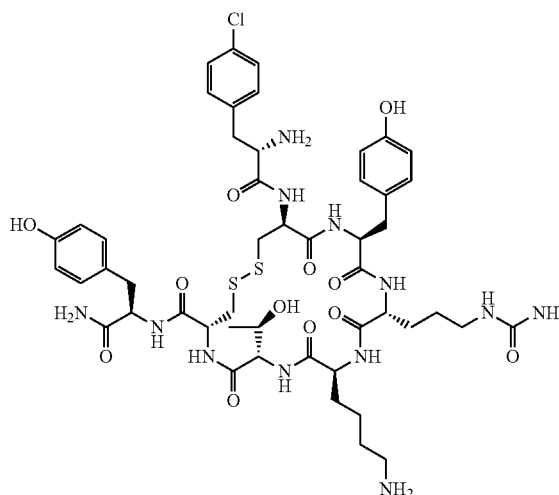<br>H-Cpa-cyclo[D-Cys-Tyr-D-Cit-Lys-Thr-Cys]-D-Tyr-NH$_2$<br>Purity (%) (HPLC): 98.5<br>MS (ESI) [M + H]$^+_{calc}$: 1115.4<br>MS (ESI) [M + H]$^+_{obs}$: 1115.7 | Example 1 or Example 2 |

TABLE 5-continued
Cyclic 8-mer Compounds and Characterization Data
| Compound No. | SEQ ID NO. | Structure | Methods |
|---|---|---|---|
| 2 | 2 | 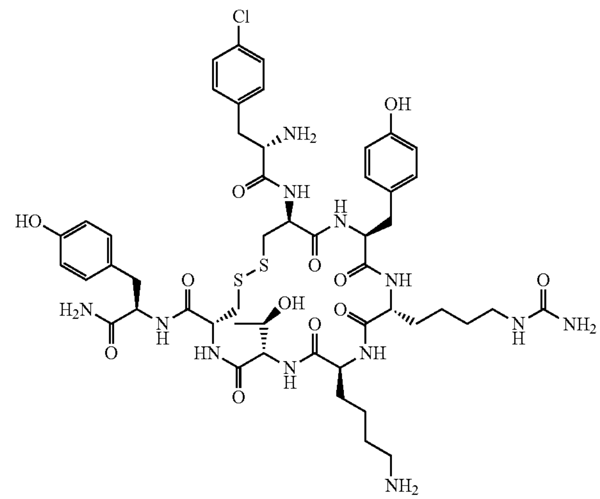 | Example 1 |
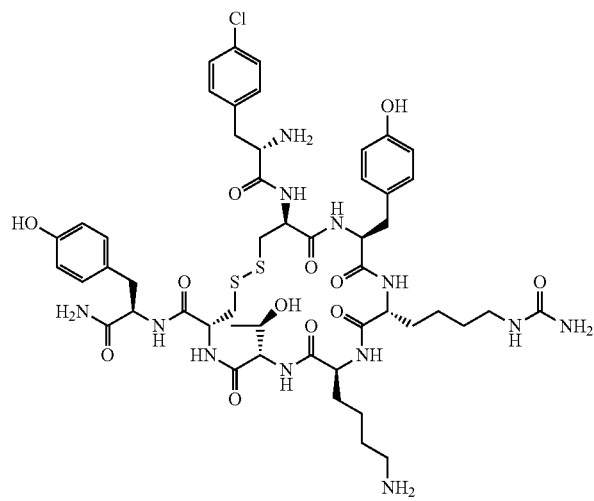
H-Cpa-cyclo[D-Cys-Tyr-D-HoCit-Lys-Thr-Cys]-D-Tyr-NH$_2$
Purity (%) (HPLC): 98.2
MS (ESI) [M + H]$^+$$_{calc}$: 1129.4
MS (ESI) [M + H]$^+$$_{obs}$: 1129.0
| 3 | 3 | | Example 1 |
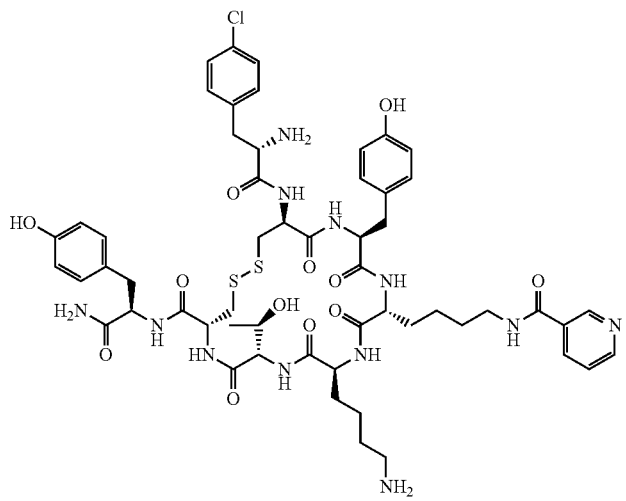
H-Cpa-cyclo[D-Cys-Tyr-D-Lys(N$^\varepsilon$-nicotinoyl)-Lys-Thr-Cys]-D-tyr-NH$_2$
Purity (%) (HPLC): 97.6
MS (ESI) [M + H]$^+$$_{calc}$: 1191.4
MS (ESI) [M + H]$^+$$_{obs}$: 1192.2

TABLE 5-continued

Cyclic 8-mer Compounds and Characterization Data

| Compound No. | SEQ ID NO. | Structure | Methods |
|---|---|---|---|
| 4 | 4 | H-Cpa-cyclo[D-Cys-Tyr-D-Phe(4-carbamoyl)-Lys-Thr-Cys]-D-Tyr-NH$_2$<br><br>Purity (%) (HPLC): 95.5<br>MS (ESI) [M + H]$^+_{calc}$: 1148.4<br>MS (ESI) [M + H]$^+_{obs}$: 1148.8 | Example 1 or Example 2 |
| 5 | 5 | H-Cpa-cyclo[D-Cys-Tyr-D-Phe(4-aminomethyl)-Lys-Thr-Cys]-D-Tyr-NH$_2$<br><br>Purity (%) (HPLC): 98.5<br>MS (ESI) [M + H]$^+_{calc}$: 1134.4<br>MS (ESI) [M + H]$^+_{obs}$: 1135.2 | Example 1 |

TABLE 5-continued
Cyclic 8-mer Compounds and Characterization Data
| Compound No. | SEQ ID NO. | Structure | Methods |
|---|---|---|---|
| 6 | 6 | 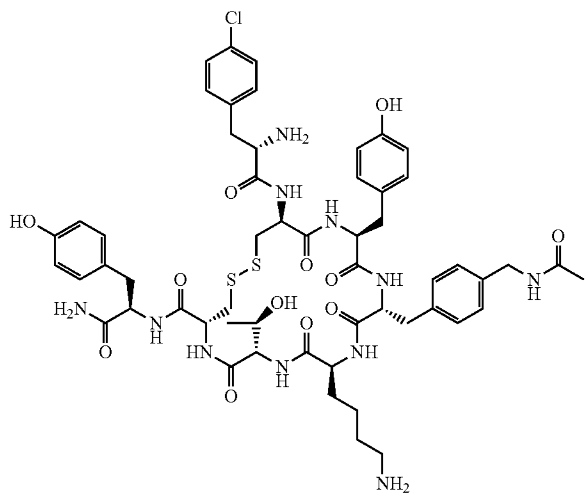 | Example 1 |
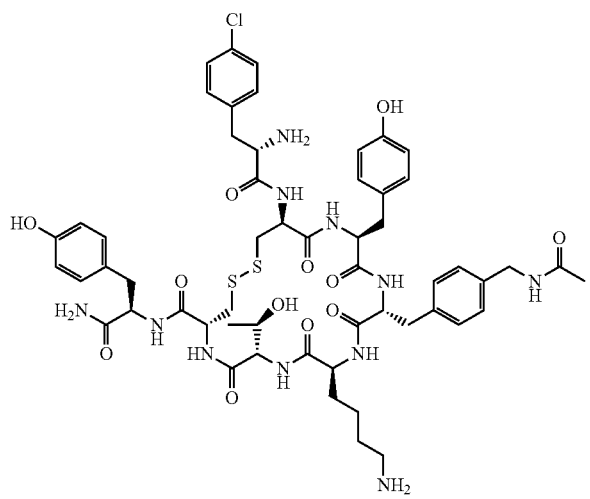
H-Cpa-cyclo[D-Cys-Tyr-D-Phe(4-acetamidomethyl)-
Lys-Thr-cys]-D-Tyr-NH$_2$
Purity (%) (HPLC): 98.6
MS (ESI) [M + H]$^+$$_{calc}$: 1176.4
MS (ESI) [M + H]$^+$$_{obs}$: 1177.3
| 7 | 7 | | Example 1 |
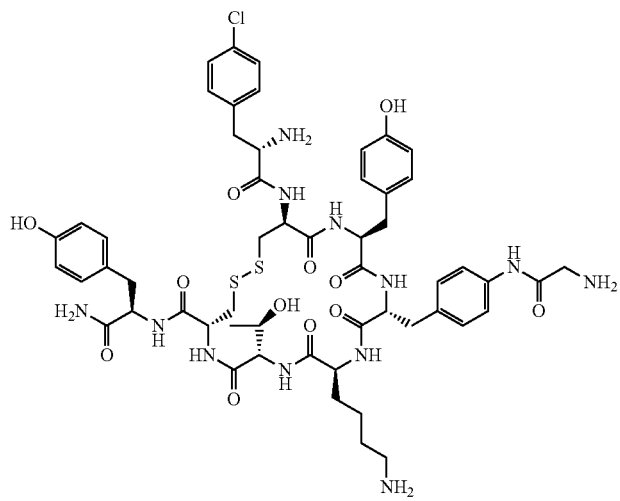
H-Cpa-cyclo[D-Cys-Tyr-D-Aph(Gly)-Lys-Thr-Cys]-D-Tyr-NH$_2$
Purity (%) (HPLC): 97.1
MS (ESI) [M + H]$^+$$_{calc}$: 1177.4
MS (ESI) [M + H]$^+$$_{obs}$: 1177.8

TABLE 5-continued
Cyclic 8-mer Compounds and Characterization Data
| Compound No. | SEQ ID NO. | Structure | Methods |
|---|---|---|---|
| 8 | 8 | 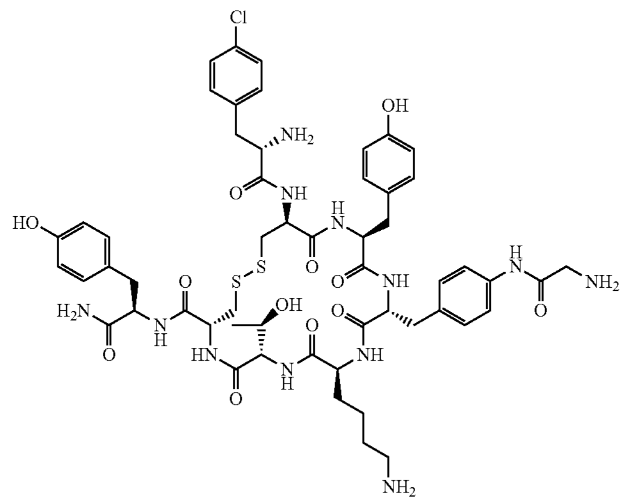 | Example 1 |
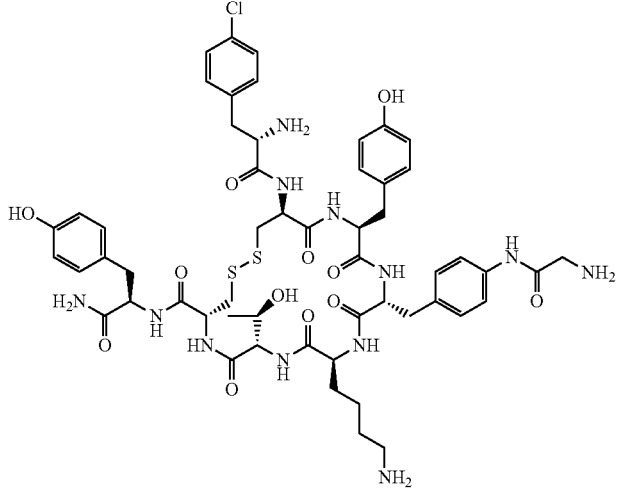
H-Cpa-cyclo[D-Cys-Tyr-D-Aph(Gly)-Lys-Thr-Cys]-D-Tyr-NH$_2$
Purity (%) (HPLC): 97.1
MS (ESI) [M + H]$^+_{calc}$: 1177.4
MS (ESI) [M + H]$^+_{obs}$: 1177.8
| | | | |
|---|---|---|---|
| 9 | 9 | | Example 1 |
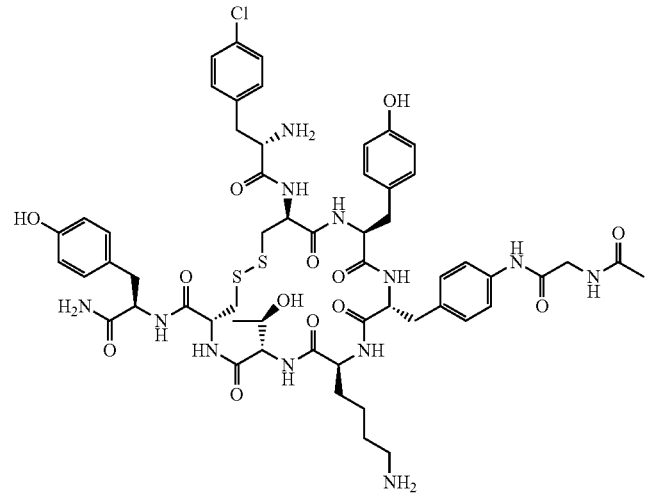
H-Cpa-cyclo[D-Cys-Tyr-D-4-(Gly-Ac)Aph-Lys-Thr-Cys]-D-Tyr-NH$_2$
Purity (%) (HPLC): 97.0
MS (ESI) [M + H]$^+_{calc}$: 1219.4
MS (ESI) [M + H]$^+_{obs}$: 1220.3

TABLE 5-continued
Cyclic 8-mer Compounds and Characterization Data
| Compound No. | SEQ ID NO. | Structure | Methods |
|---|---|---|---|
| 10 | 10 | 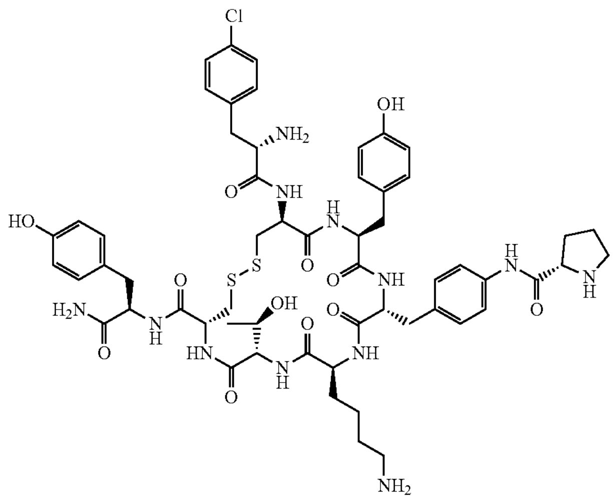 | Example 1 |
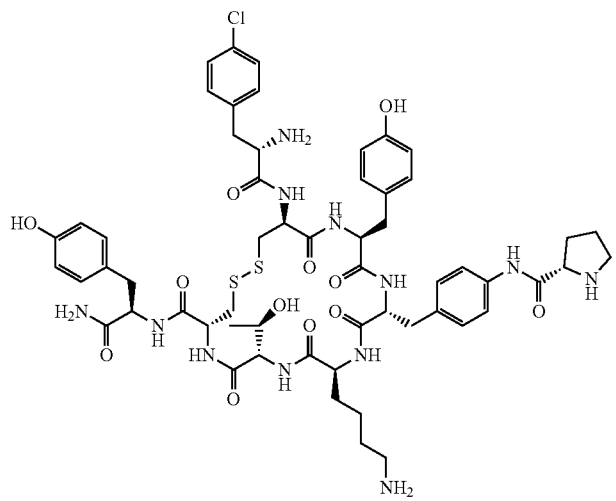
H-Cpa-cyclo[D-Cys-Tyr-D-Aph(Pro)-Lys-Thr-Cys]-D-Tyr-NH$_2$
Purity (%) (HPLC): 98.4
MS (ESI) $[M + H]^+_{calc}$: 1217.5
MS (ESI) $[M + H]^+_{obs}$: 1217.9
| 11 | 11 | | Example 1 |
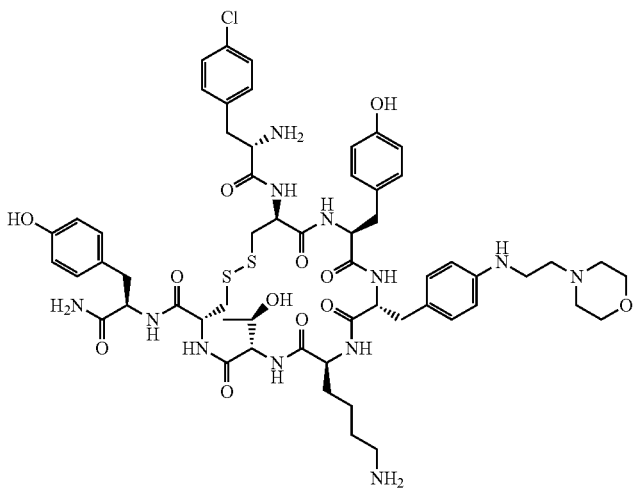
H-Cpa-cyclo[D-Cys-Tyr-D-Aph(2-(4-morpholinyl)ethyl)-Lys-Thr-Cys]-D-Tyr-NH$_2$
Purity (%) (HPLC): 97.2
MS (ESI) $[M + H]^+_{calc}$: 1233.5
MS (ESI) $[M + H]^+_{obs}$: 1233.8

TABLE 5-continued
Cyclic 8-mer Compounds and Characterization Data
| Compound No. | SEQ ID NO. | Structure | Methods |
|---|---|---|---|
| 12 | 12 | 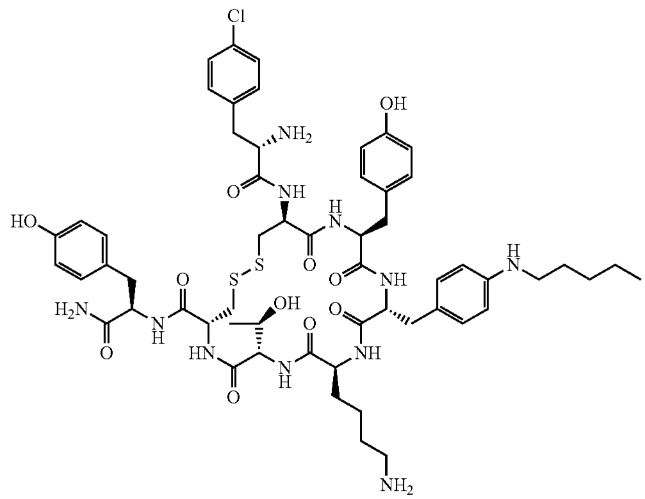 | Example 1 |
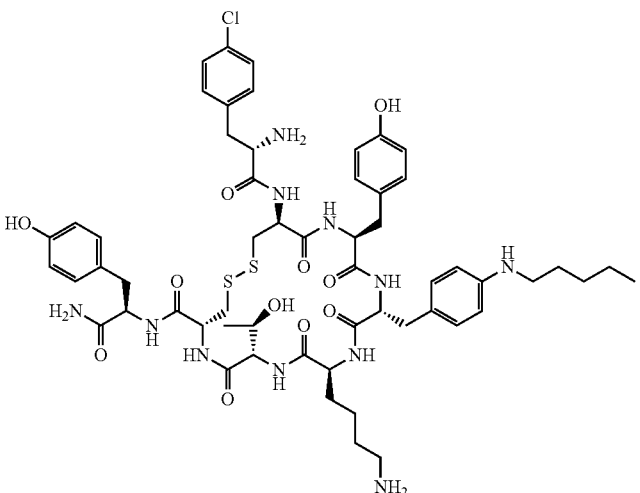
H-Cpa-cyclo[D-Cys-Tyr-D-Phe(4-n-pentylamino)-Lys-Thr-Cys]-D-Tyr-NH$_2$
Purity (%) (HPLC): 95.1
MS (ESI) [M + H]$^+$$_{calc}$: 1190.5
MS (ESI) [M + H]$^+$$_{obs}$: 1191.1
| 13 | 13 | | Example 1 |
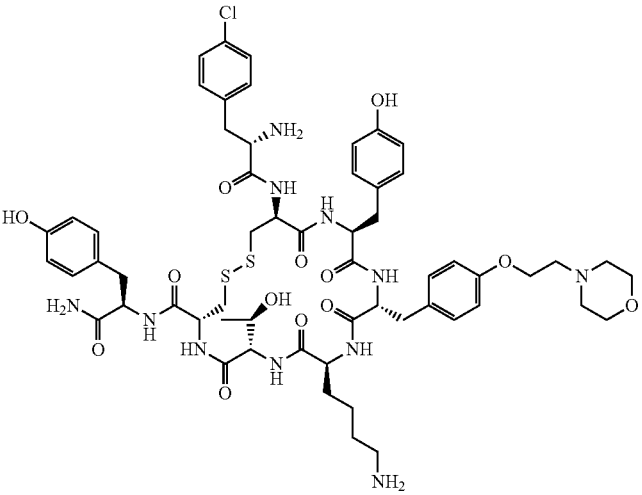
H-Cpa-cyclo[D-Cys-Tyr-D-Tyr(2-(4-morpholinyl)ethyl)-Lys-Thr-Cys]-D-Tyr-NH$_2$
Purity (%) (HPLC): 97.3
MS (ESI) [M + H]$^+$$_{calc}$: 1234.5
MS (ESI) [M + H]$^+$$_{obs}$: 1235.1

TABLE 5-continued
Cyclic 8-mer Compounds and Characterization Data
| Compound No. | SEQ ID NO. | Structure | Methods |
|---|---|---|---|
| 14 | 14 | 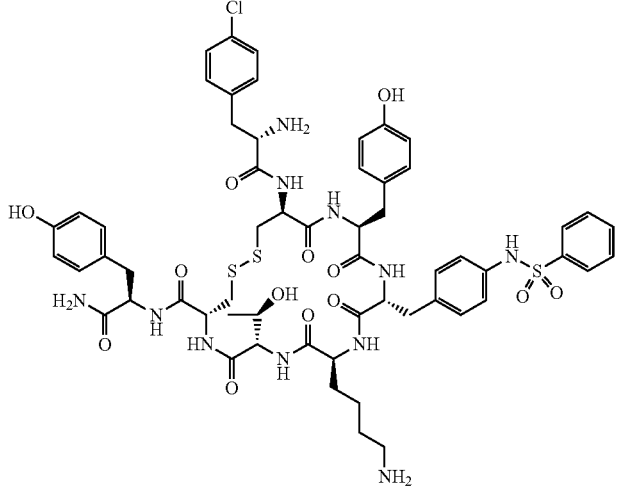  H-Cpa-cyclo[D-Cys-Tyr-D-Aph(benzenesulfonyl)-Lys-Thr-Cys]-D-Tyr-NH$_2$  Purity (%) (HPLC): 97.7  MS (ESI) [M + H]$^+_{calc}$: 1260.4  MS (ESI) [M + H]$^+_{obs}$: 1261.6 | Example 1 |
| 15 | 15 | 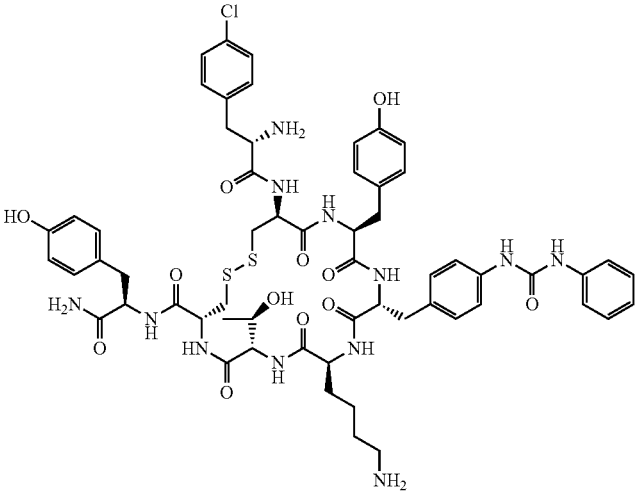  H-Cpa-cyclo[D-Cys-Tyr-D-Phe(4-phenylureido)-Lys-Thr-Cys]-D-Tyr-NH$_2$  Purity (%) (HPLC): 97.0  MS (ESI) [M + H]$^+_{calc}$: 1239.4  MS (ESI) [M + H]$^+_{obs}$: 1239.7 | Example 1 or Example 2 |

TABLE 5-continued
Cyclic 8-mer Compounds and Characterization Data
| Compound No. | SEQ ID NO. | Structure | Methods |
|---|---|---|---|
| 16 | 16 | 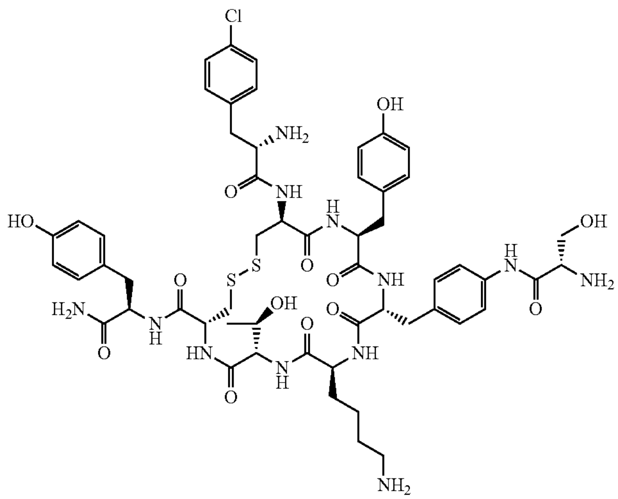 | Example 1 |
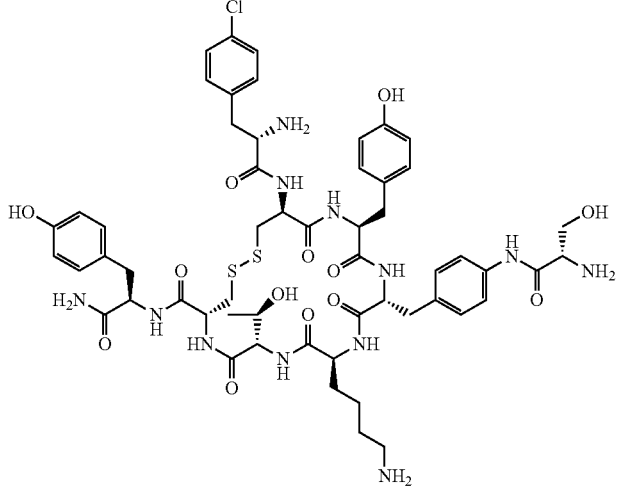
H-Cpa-cyclo[D-Cys-Tyr-D-Aph(Ser)-Lys-Thr-Cys]-D-Tyr-NH$_2$
Purity (%) (HPLC): 95.2
MS (ESI) [M + H]$^+_{calc}$: 1207.4
MS (ESI) [M + H]$^+_{obs}$: 1208.6
| 17 | 17 | | Example 1 |
H-Cpa-cyclo[D-Cys-Tyr-D-Aph(Lys)-Lys-Thr-Cys]-D-Tyr-NH$_2$
Purity (%) (HPLC): 97.0
MS (ESI) [M + H]$^+_{calc}$: 1248.5
MS (ESI) [M + H]$^+_{obs}$: 1249.6

TABLE 5-continued
Cyclic 8-mer Compounds and Characterization Data
| Compound No. | SEQ ID NO. | Structure | Methods |
|---|---|---|---|
| 18 | 18 | 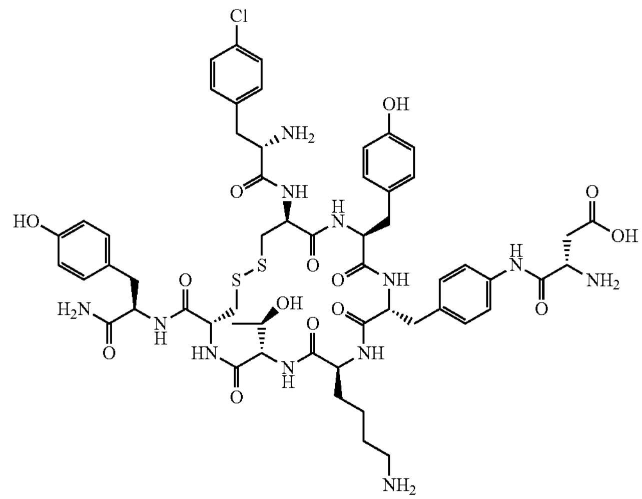 | Example 1 |
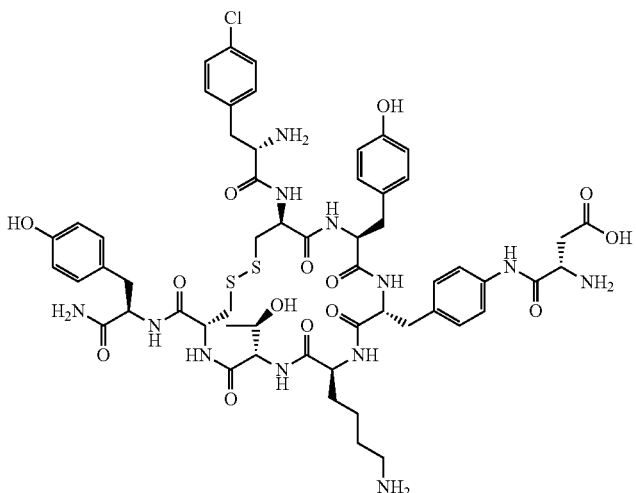
H-Cpa-cyclo[D-Cys-Tyr-D-Aph(Asp)-Lys-Thr-Cys]-D-Tyr-NH$_2$
Purity (%) (HPLC): 96.6
MS (ESI) [M + H]$^+_{calc}$: 1235.4
MS (ESI) [M + H]$^+_{obs}$: 1235.8
| 19 | 19 | | Example 1 |
H-Cpa-cyclo[D-Cys-Tyr-D-Aph(Asn)-Lys-Thr-Cys]-D-Tyr-NH$_2$
Purity (%) (HPLC): 95.8
MS (ESI) [M + H]$^+_{calc}$: 1234.5
MS (ESI) [M + H]$^+_{obs}$: 1234.0

TABLE 5-continued
Cyclic 8-mer Compounds and Characterization Data
| Compound No. | SEQ ID NO. | Structure | Methods |
|---|---|---|---|
| 20 | 20 | 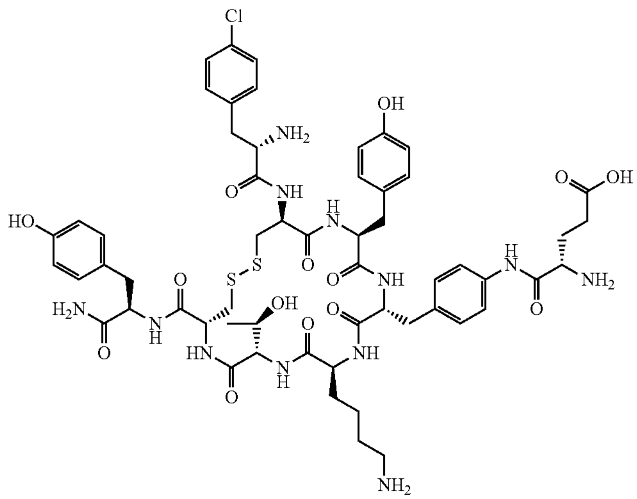 | Example 1 |
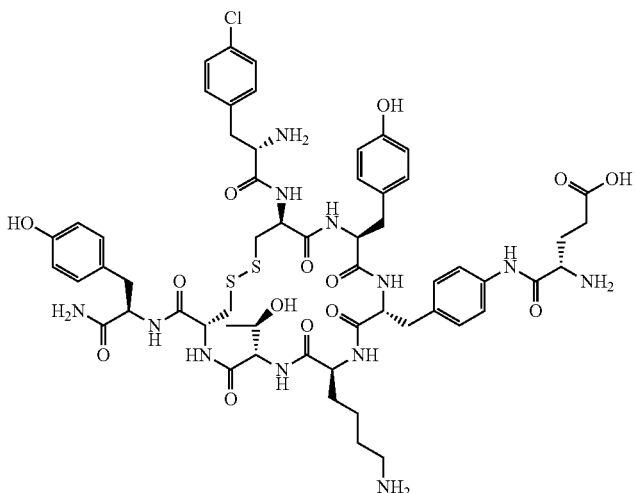
H-Cpa-cyclo[D-Cys-Tyr-D-Aph(Glu)-Lys-Thr-Cys]-D-Tyr-NH$_2$
Purity (%) (HPLC): 96.0
MS (ESI) [M + H]$^+_{calc}$: 1249.5
MS (ESI) [M + H]$^+_{obs}$: 1249.0
| | | | |
|---|---|---|---|
| 21 | 21 | | Example 1 |
H-Cpa-cyclo[D-Cys-Tyr-D-Aph(Gln)-Lys-Thr-Cys]-D-Tyr-NH$_2$
Purity (%) (HPLC): 95.2
MS (ESI) [M + H]$^+_{calc}$: 1248.5
MS (ESI) [M + H]$^+_{obs}$: 1249.2

TABLE 5-continued
Cyclic 8-mer Compounds and Characterization Data
| Compound No. | SEQ ID NO. | Structure | Methods |
|---|---|---|---|
| 22 | 22 | 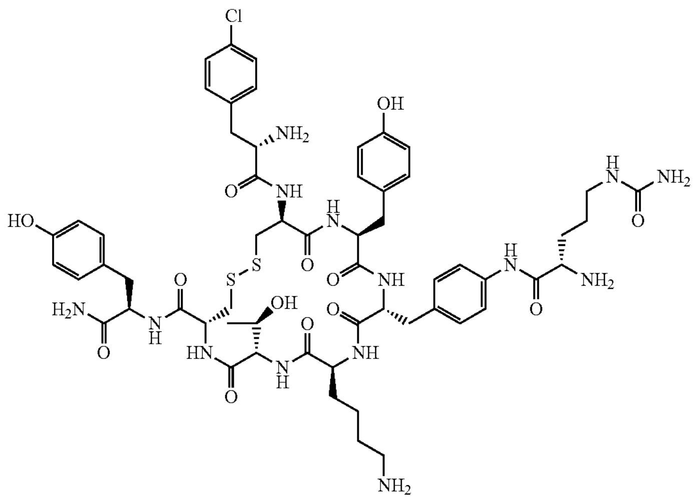 | Example 1 |
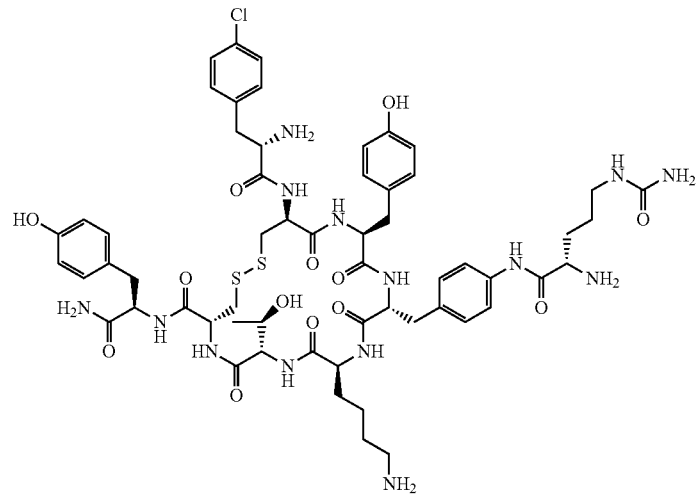
H-Cpa-cyclo[D-Cys-Tyr-D-Aph(Cit)-Lys-Thr-Cys]-D-Tyr-NH$_2$
Purity (%) (HPLC): 95.0
MS (ESI) [M + H]$^+_{calc}$: 1277.5
MS (ESI) [M + H]$^+_{obs}$: 1277.6
| | | | |
|---|---|---|---|
| 23 | 23 | | Example 1 |
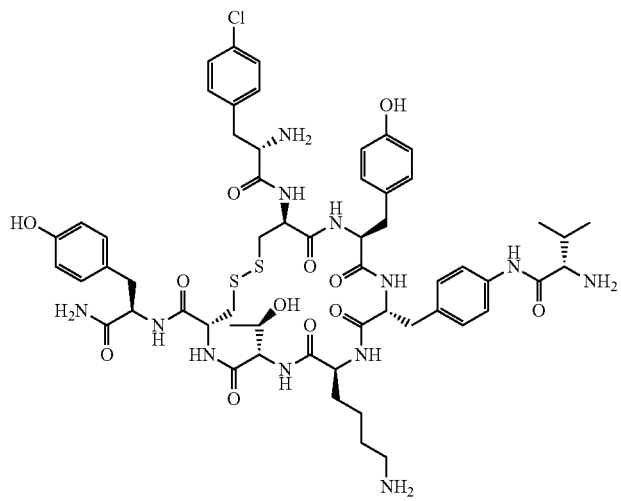
H-Cpa-cyclo[D-Cys-Tyr-D-Aph(Val)-Lys-Thr-Cys]-D-Tyr-NH$_2$
Purity (%) (HPLC): 96.9
MS (ESI) [M + H]$^+_{calc}$: 1219.5
MS (ESI) [M + H]$^+_{obs}$: 1220.6

TABLE 5-continued

Cyclic 8-mer Compounds and Characterization Data

| Compound No. | SEQ ID NO. | Structure | Methods |
|---|---|---|---|
| 24 | 24 | 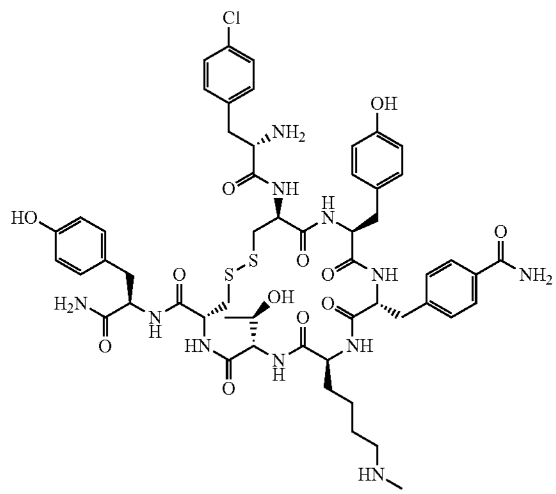 | Example 1 or Example 2 |

H-Cpa-cyclo[D-Cys-Tyr-D-Phe(4-carbamoyl)-
Lys(N$^\varepsilon$-Me)-Thr-Cys]-D-Tyr-NH$_2$ Purity (%) (HPLC): 97.5
MS (ESI) [M + H]+calc: 1162.4
MS (ESI) [M + H]+obs: 1162.8

| 25 | 25 | | Example 2 |

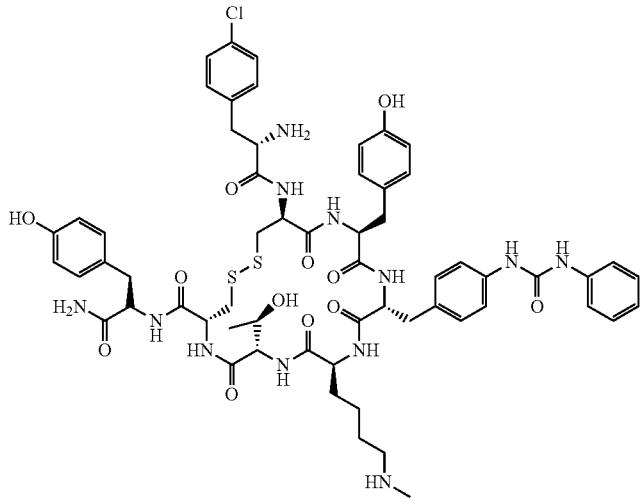

H-Cpa-cyclo[D-Cys-Tyr-D-Phe(4-phenylureido)-Lys(N$^\varepsilon$-Me)Thr-Cys]-D-Tyr-NH$_2$ Purity (%) (HPLC): 96.1
MS (ESI) [M + H]$^+$calc: 1253.5
MS (ESI) [M + H]$^+$obs: 1253.8

TABLE 5-continued

Cyclic 8-mer Compounds and Characterization Data

| Compound No. | SEQ ID NO. | Structure | Methods |
|---|---|---|---|
| 26 | 26 | 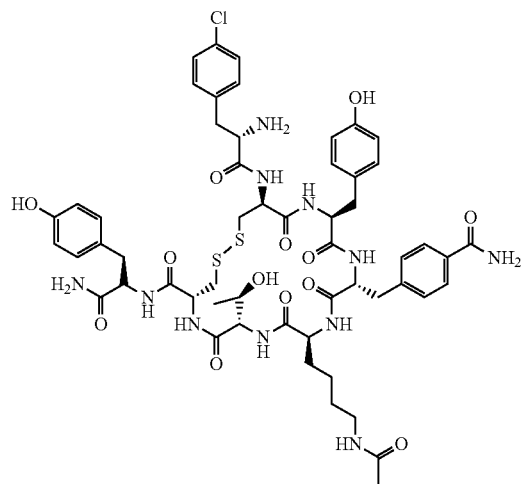<br>H-Cpa-cyclo[D-Cys-Tyr-D-Phe(4-carbamoyl)-Lys(N$^\varepsilon$-Ac)-Thr-Cys]-D-Tyr-NH$_2$<br><br>Purity (%) (HPLC): 100<br>MS (ESI) [M + H]$^+$calc: 1190.4<br>MS (ESI) [M + H]$^+$obs: 1190.7 | Example 2 |
| 27 | 27 | 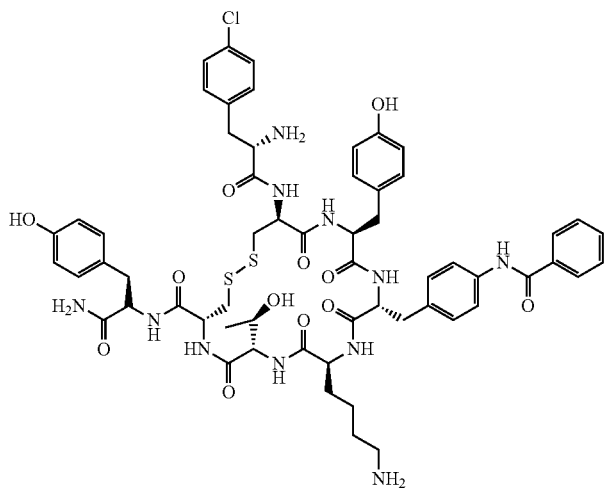<br>H-Cpa-cyclo[D-Cys-Tyr-D-Phe(4-(4-benzamidophenyl)-Lys-Thr-Cys]-D-Tyr-NH$_2$<br><br>Purity (%) (HPLC): 97.6<br>MS (ESI) [M + H]$^+$calc: 1224.4<br>MS (ESI) [M + H]$^+$obs: 1224.7 | Example 2 |

TABLE 5-continued

Cyclic 8-mer Compounds and Characterization Data

| Compound No. | SEQ ID NO. | Structure | Methods |
|---|---|---|---|
| 28 | 28 | 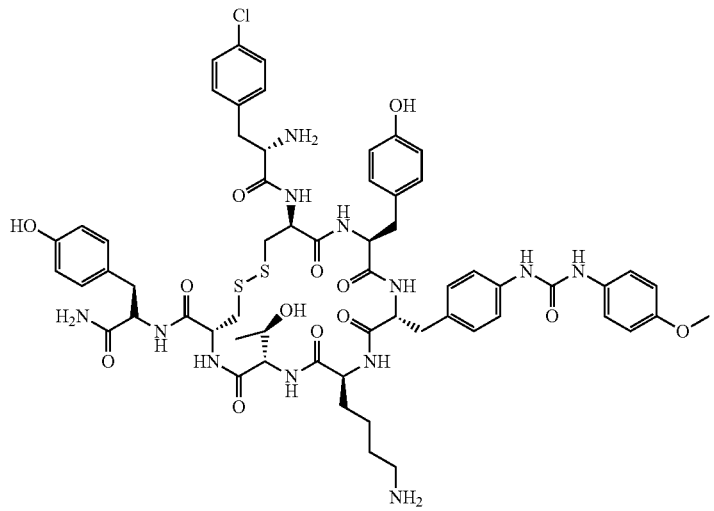<br>H-Cpa-cyclo[D-Cys-Tyr-D-Phe(4-(4-methoxyphenyl)ureido)-Lys-Thr-Cys]-D-Tyr-NH$_2$<br><br>Purity (%) (HPLC): 97.1<br>MS (ESI) [M + H]$^+_{calc}$: 1269.5<br>MS (ESI) [M + H]$^+_{obs}$: 1269.8 | Example 2 |
| 29 | 29 | 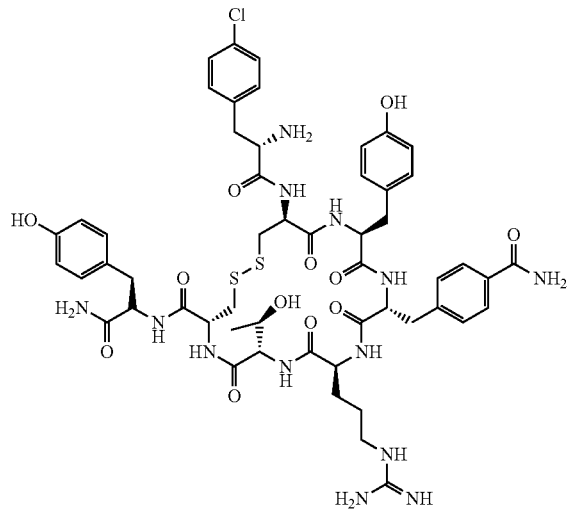<br>H-Cpa-cyclo[D-Cys-Tyr-D-Phe(4-carbamoyl)-Arg-Thr-Cys]-D-Tyr-NH$_2$<br><br>Purity (%) (HPLC): 99.1<br>MS (ESI) [M + H]$^+_{calc}$: 1176.4<br>MS (ESI) [M + H]$^+_{obs}$: 1176.7 | Example 2 |

TABLE 5-continued

Cyclic 8-mer Compounds and Characterization Data

| Compound No. | SEQ ID NO. | Structure | Methods |
|---|---|---|---|
| 30 | 30 | 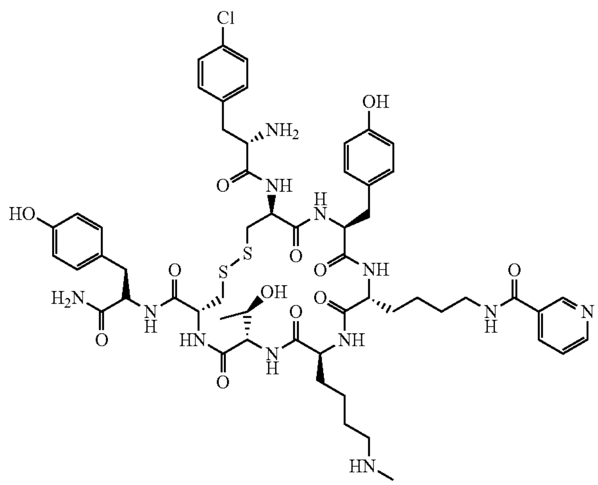 | Example 2 |
| 31 | 31 | 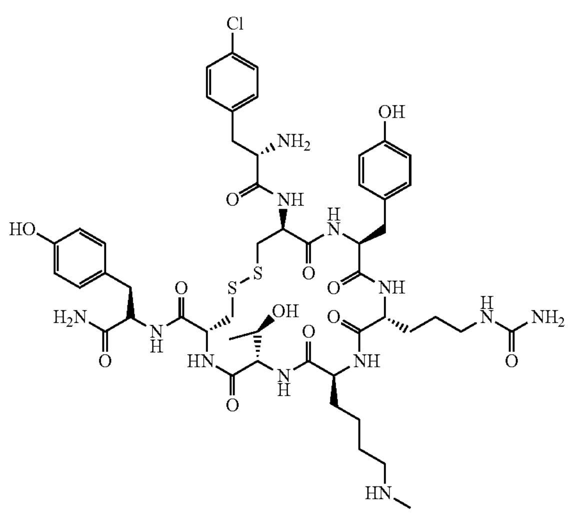 | Example 2 |

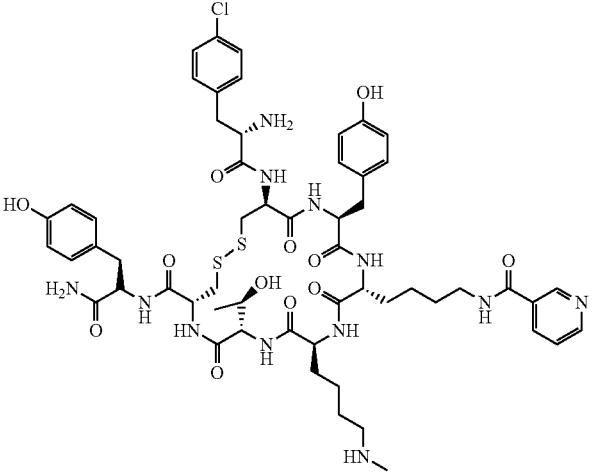

H-Cpa-cyclo[D-Cys-Tyr-D-Lys($N^\varepsilon$-nicotinoyl)-Lys($N^\varepsilon$-Me)-Thr-Cys]-D-Tyr-$NH_2$ Purity (%) (HPLC): 97.2
MS (ESI) $[M + H]^+_{calc}$: 1205.5
MS (ESI) $[M + H]^+_{obs}$: 1205.8

H-Cpa-cyclo[D-Cys-Tyr-D-Cit-Lys($N^\varepsilon$-Me)-Thr-Cys]-D-Tyr-$NH_2$

Purity (%) (HPLC): 98.3
MS (ESI) $[M + H]^+_{calc}$: 1129.4
MS (ESI) $[M + H]^+_{obs}$: 1129.7

TABLE 5-continued
Cyclic 8-mer Compounds and Characterization Data
| Compound No. | SEQ ID NO. | Structure | Methods |
|---|---|---|---|
| 32 | 32 | 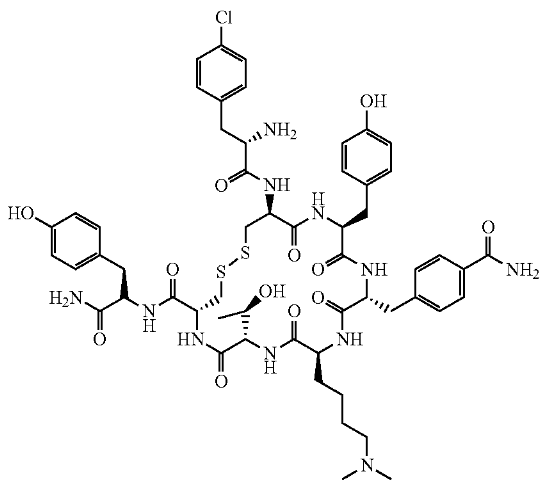 | Example 2 |
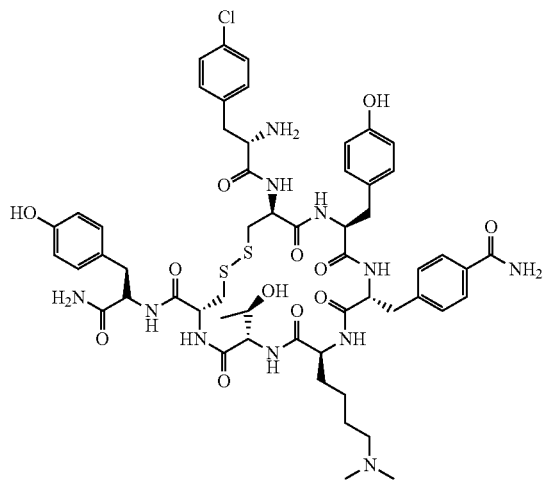
H-Cpa-cyclo[D-Cys-Tyr-D-Phe(4-carbamoyl)-
Lys($N^\varepsilon$-diMe)-Thr-Cys]-D-Tyr-NH$_2$
Purity (%) (HPLC): 97.6
MS (ESI) [M + H]$^+_{calc}$: 1176.4
MS (ESI) [M + H]$^+_{obs}$: 1176.9
| 33 | 33 | | Example 2 |
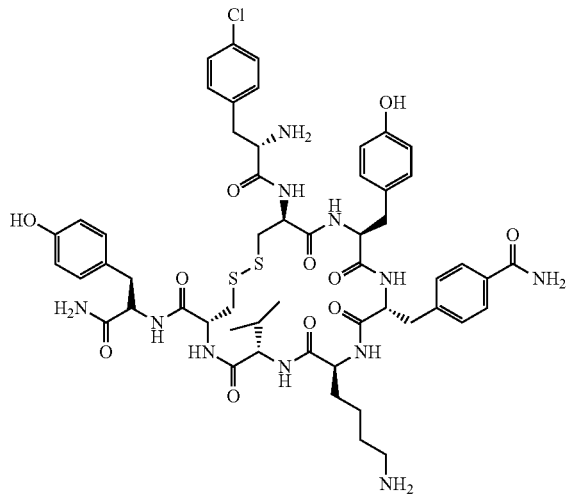
H-Cpa-cyclo[D-Cys-Tyr-D-Phe(4-carbamoyl)-Lys-Val-Cys]-D-Tyr-NH$_2$
Purity (%) (HPLC): 95.9
MS (ESI) [M + H]$^+_{calc}$: 1146.4
MS (ESI) [M + H]$^+_{obs}$: 1146.9

TABLE 5-continued
Cyclic 8-mer Compounds and Characterization Data
| Compound No. | SEQ ID NO. | Structure | Methods |
|---|---|---|---|
| 34 | 34 | 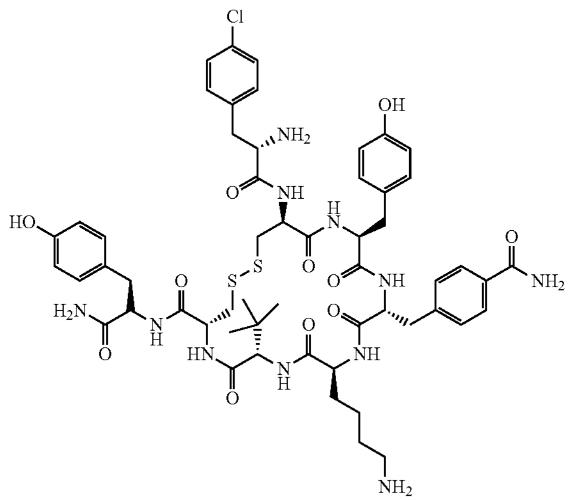 | Example 2 |
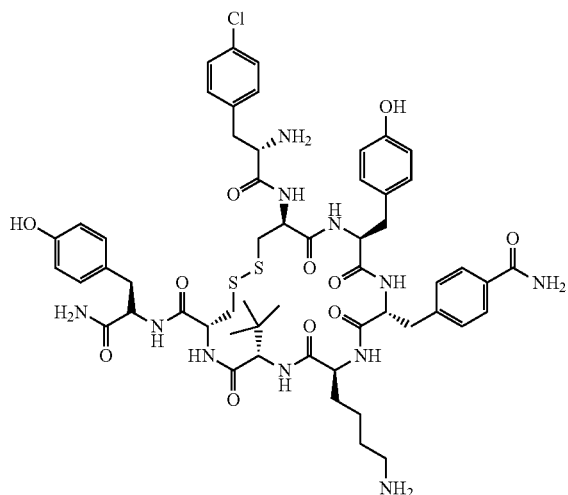
H-Cpa-cyclo[D-Cys-Tyr-D-Phe(4-carbamoyl)-Lys-Tle-Cys]-D-Tyr-NH$_2$
Purity (%) (HPLC): 97.1
MS (ESI) [M + H]$^+_{calc}$: 1160.4
MS (ESI) [M + H]$^+_{obs}$: 1160.9
| 35 | 35 | | Example 2 |
H-Cpa-cyclo[D-Cys-Phe-D-Phe(4-carbamoyl)-Lys-Thr-Cys]-D-Tyr-NH$_2$
Purity (%) (HPLC): 96.7
MS (ESI) [M + H]$^+_{calc}$: 1132.4
MS (ESI) [M + H]$^+_{obs}$: 1132.9

TABLE 5-continued
Cyclic 8-mer Compounds and Characterization Data
| Compound No. | SEQ ID NO. | Structure | Methods |
|---|---|---|---|
| 36 | 36 | 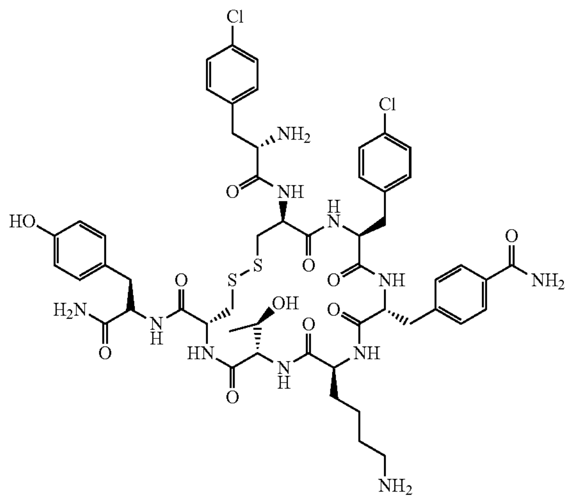 | Example 2 |
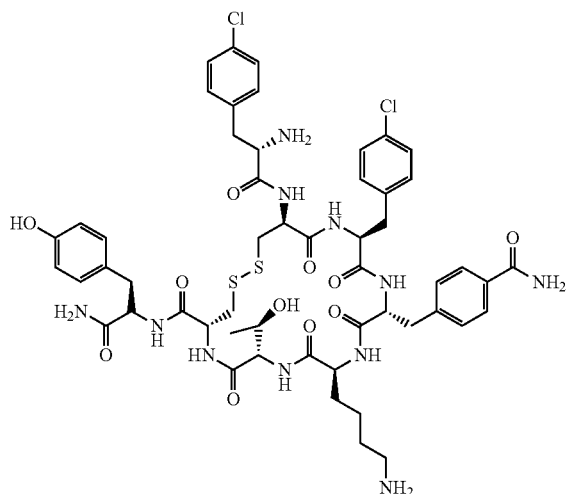
H-Cpa-cyclo[D-Cys-Cpa-D-Phe(4-carbamoyl)-Lys-Thr-Cys]-D-Tyr-NH$_2$
Purity (%) (HPLC): 98.7
MS (ESI) [M + H]$^+_{calc}$: 1166.4
MS (ESI) [M + H]$^+_{obs}$: 1166.8
| 37 | 37 | | Example 2 |
H-Cpa-cyclo[D-Cys-Tyr-D-Phe(4-carbamoyl)-Lys-Ser-Cys]-D-Tyr-NH$_2$
Purity (%) (HPLC): 99.2
MS (ESI) [M + H]$^+_{calc}$: 1134.4
MS (ESI) [M + H]$^+_{obs}$: 1134.8

TABLE 5-continued

Cyclic 8-mer Compounds and Characterization Data

| Compound No. | SEQ ID NO. | Structure | Methods |
|---|---|---|---|
| 38 | 38 | 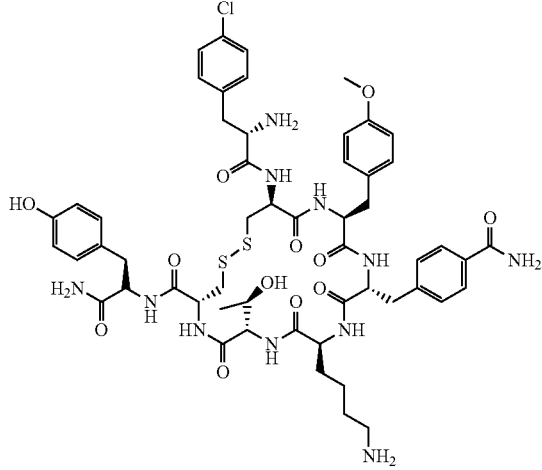<br>H-Cpa-cyclo[D-Cys-Tyr(Me)-D-Phe(4-carbamoyl)-Lys-Thr-Cys]D-Tyr-NH$_2$<br><br>Purity (%) (HPLC): 97.6<br>MS (ESI) [M + H]$^+_{calc}$: 1162.4<br>MS (ESI) [M + H]$^+_{obs}$: 1162.8 | Example 2 |
| 39 | 39 | 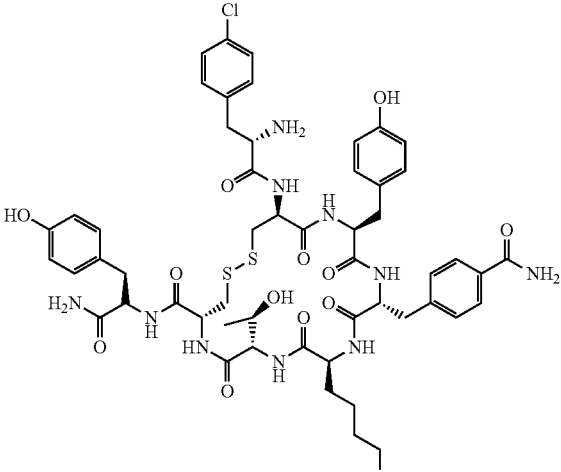<br>H-Cpa-cyclo[D-Cys-Tyr-D-Phe(4-carbamoyl)-Lys-Thr-Cys]-D-Tyr-NH$_2$<br><br>Purity (%) (HPLC): 96.7<br>MS (ESI) [M + H]$^+_{calc}$: 1148.4<br>MS (ESI) [M + H]$^+_{obs}$: 1148.8 | Example 2 |

TABLE 5-continued
Cyclic 8-mer Compounds and Characterization Data
| Compound No. | SEQ ID NO. | Structure | Methods |
|---|---|---|---|
| 40 | 40 | 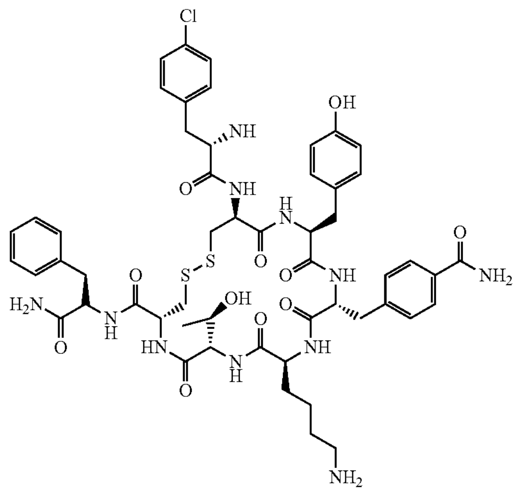 | Example 2 |
| 41 | 41 | 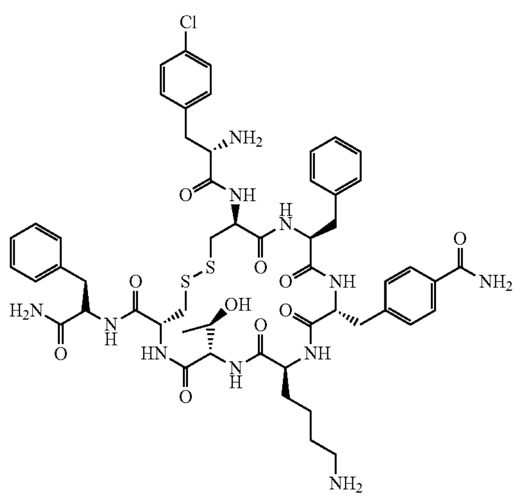 | Example 2 |
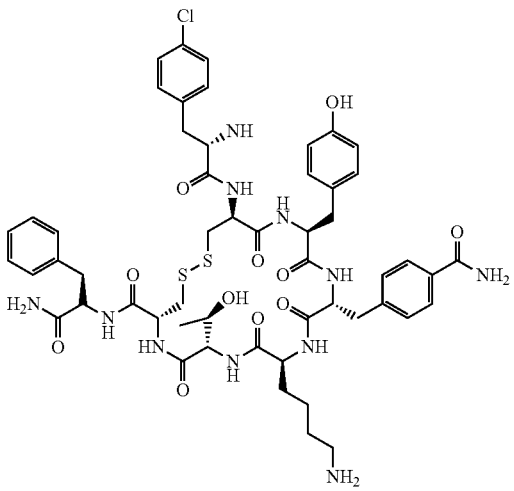
H-Cpa-cyclo[D-Cys-Tyr-D-Phe(4-carbamoyl)-
Lys-Thr-Cys]-D-Phe-NH$_2$
Purity (%) (HPLC): 96.5
MS (ESI) [M + H]$^+_{calc}$: 1132.4
MS (ESI) [M + H]$^+_{obs}$: 1132.8
H-Cpa-cyclo[D-Cys-Phe-D-Phe(4-carbamoyl)-
Lys-Thr-Cys]-D-Phe-NH$_2$
Purity (%) (HPLC): 97.9
MS (ESI) [M + H]$^+_{calc}$: 1116.4
MS (ESI) [M + H]$^+_{obs}$: 1116.8

TABLE 5-continued

Cyclic 8-mer Compounds and Characterization Data

| Compound No. | SEQ ID NO. | Structure | Methods |
|---|---|---|---|
| 42 | 42 | 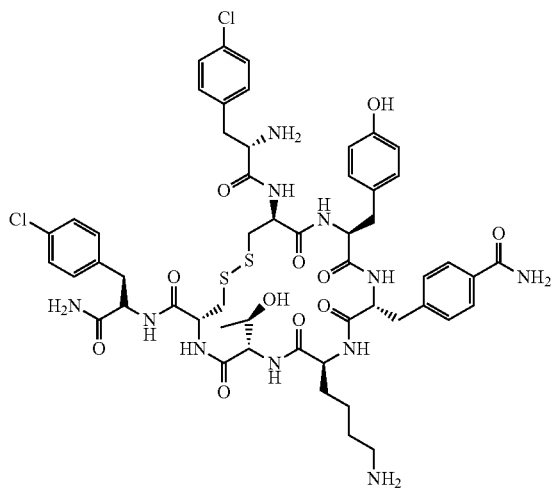  H-Cpa-cyclo[D-Cys-Tyr-D-Phe(4-carbamoyl)-Lys-Thr-Cys]-D-Cpa-NH$_2$<br><br>Purity (%) (HPLC): 92.8<br>MS (ESI) [M + H]$^+_{calc}$: 1166.4<br>MS (ESI) [M + H]$^+_{obs}$: 1166.7 | Example 2 |
| 43 | 43 | 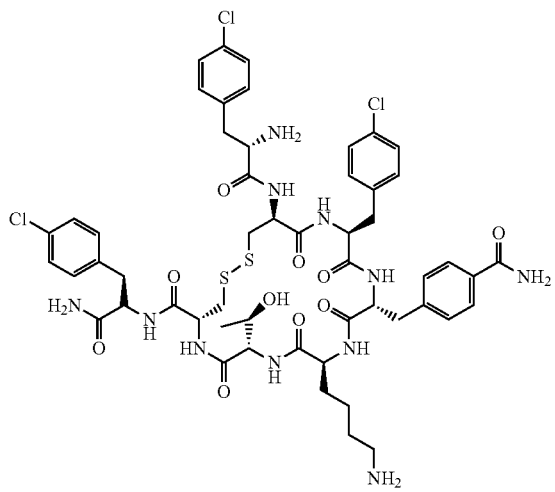  H-Cpa-cyclo[D-Cys-Cpa-D-Phe(4-carbamoyl)-Lys-Thr-Cys]-D-Cpa-NH$_2$<br><br>Purity (%) (HPLC): 97.5<br>MS (ESI) [M + H]$^+_{calc}$: 1184.3<br>MS (ESI) [M + H]$^+_{obs}$: 1184.7 | Example 2 |

TABLE 5-continued

Cyclic 8-mer Compounds and Characterization Data

| Compound No. | SEQ ID NO. | Structure | Methods |
|---|---|---|---|
| 44 | 44 | 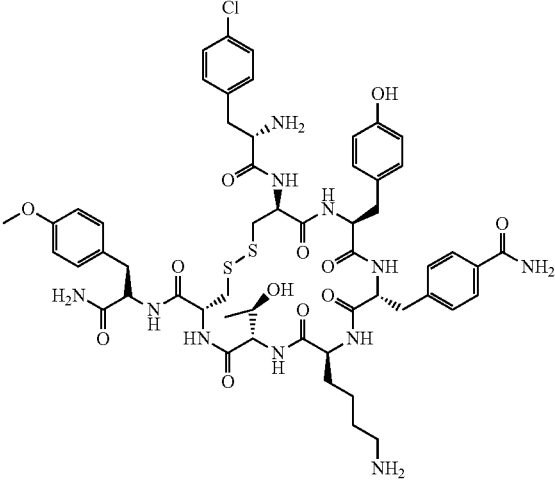 H-Cpa-cyclo[D-Cys-Tyr-D-Phe(4-carbamoyl)-Lys-Thr-Cys]-D-Tyr(Me)-NH$_2$<br>Purity (%) (HPLC): 96.7<br>MS (ESI) [M + H]$^+_{calc}$: 1162.4<br>MS (ESI) [M + H]$^+_{obs}$: 1162.8 | Example 2 |
| 45 | 45 | 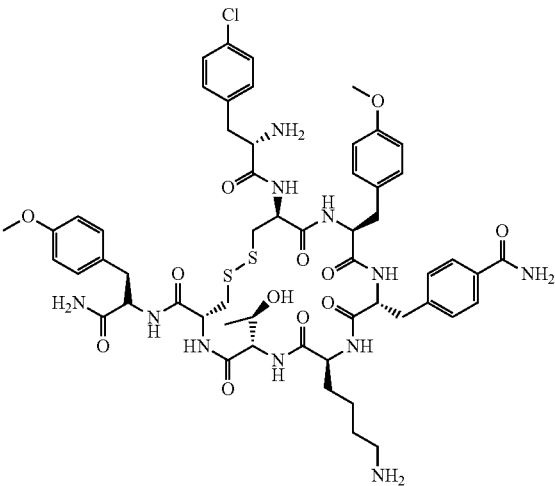 H-Cpa-cyclo[D-Cys-Tyr(Me)-D-Phe(4-carbamoyl)-Lys-Thr-Cys]-D-Tyr(Me)-NH$_2$<br>Purity (%) (HPLC): 95.3<br>MS (ESI) [M + H]$^+_{calc}$: 1176.4<br>MS (ESI) [M + H]$^+_{obs}$: 1176.8 | Example 2 |

TABLE 5-continued

Cyclic 8-mer Compounds and Characterization Data

| Compound No. | SEQ ID NO. | Structure | Methods |
|---|---|---|---|
| 46 | 46 | 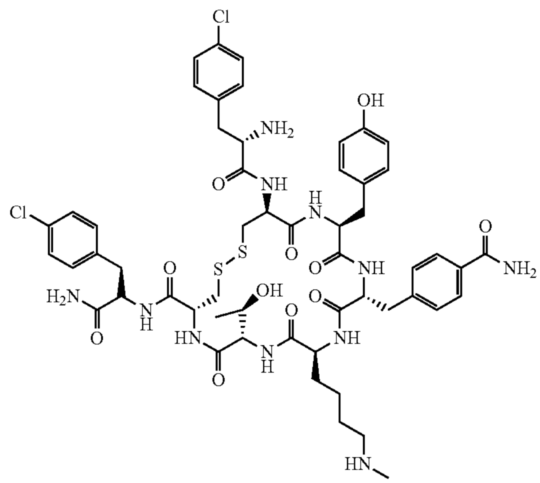 | Example 2 |

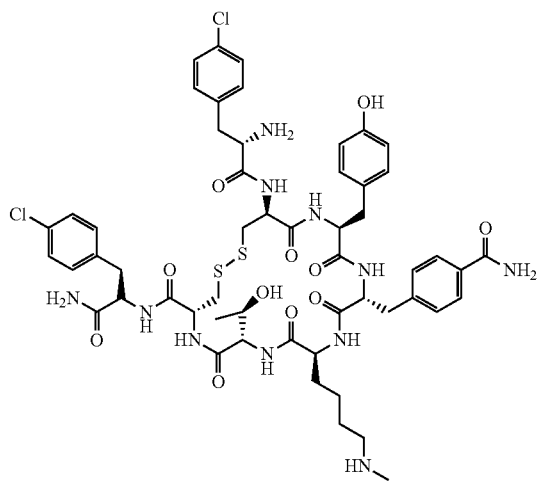

H-Cpa-cyclo[D-Cys-Tyr-D-Phe(4-carbamoyl)-Lys($N^\varepsilon$-Me)-Thr-Cys]-D-Cpa-$NH_2$ Purity (%) (HPLC): 98.4
MS (ESI) $[M + H]^+_{calc}$: 1180.4
MS (ESI) $[M + H]^+_{obs}$: 1180.6

| | | | |
|---|---|---|---|
| 47 | 47 | | Example 2 |

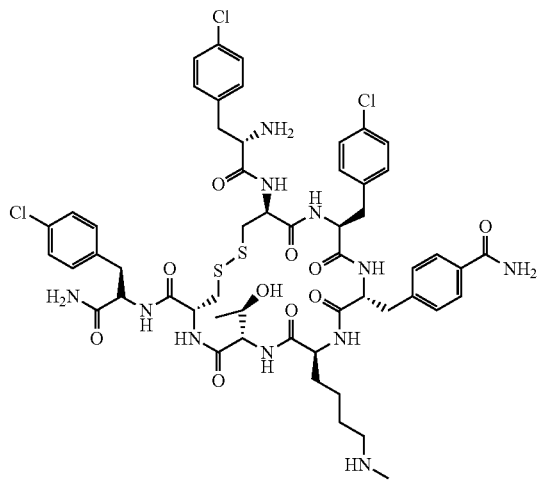

H-Cpa-cyclo[D-Cys-Cpa-D-Phe(4-carbamoyl)-Lys($N^\varepsilon$-Me)-Thr-Cys]-D-Cpa-$NH_2$ Purity (%) (HPLC): 100
MS (ESI) $[M + H]^+_{calc}$: 1198.4
MS (ESI) $[M + H]^+_{obs}$: 1198.6

TABLE 5-continued

Cyclic 8-mer Compounds and Characterization Data

| Compound No. | SEQ ID NO. | Structure | Methods |
|---|---|---|---|
| 48 | 48 | 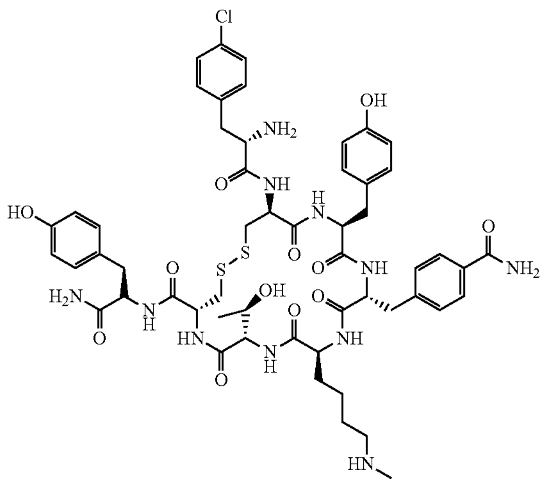 | Example 2 |

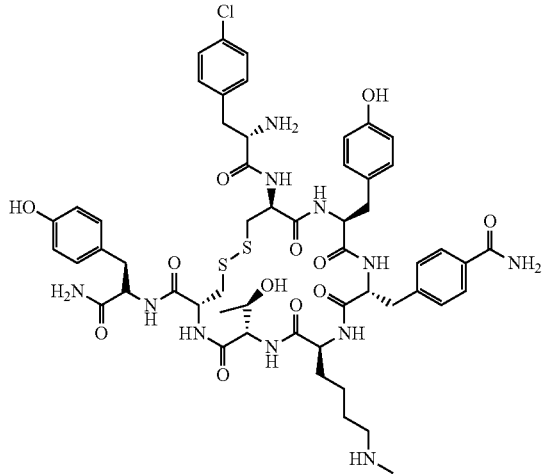

H-Cpa-cyclo[D-Cys-Cpa-D-Phe(4-carbamoyl)-Lys($N^\varepsilon$-Me)-Thr-Cys]-D-Tyr-$NH_2$ Purity (%) (HPLC): 92.0
MS (ESI) [M + H]$^+_{calc}$: 1180.4
MS (ESI) [M + H]$^+_{obs}$: 1180.6

| 49 | 49 | | Example 2 and General Method C |

H-β-Ala-Cpa-cyclo[D-Cys-Tyr-D-Phe(4-carbamoyl)-Lys($N^\varepsilon$-Me)-Thr-Cys]-D-Tyr-$NH_2$ Purity (%) (HPLC): 97.4
MS (ESI) [M + H]$^+_{calc}$: 1233.5
MS (ESI) [M + H]$^+_{obs}$: 1233.6

TABLE 5-continued

Cyclic 8-mer Compounds and Characterization Data

| Compound No. | SEQ ID NO. | Structure | Methods |
|---|---|---|---|
| 50 | 50 | 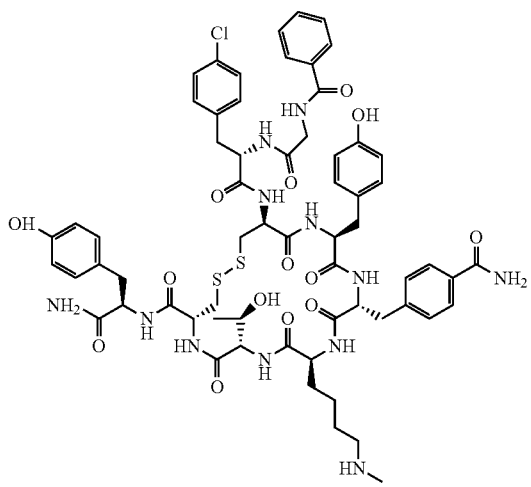
Ph(CO)NHCH$_2$(CO)-Cpa-cyclo[D-Cys-Tyr-D-Phe(4-carbamoyl)-Lys(N$^\varepsilon$-Me)-Thr-Cys]-D-Tyr-NH$_2$ Purity (%) (HPLC): >99.9
MS (ESI) [M + H]$^+$$_{calc}$: 1323.5
MS (ESI) [M + H]$^+$$_{obs}$: 1323.6 | Example 2 and General Method C |
| 51 | 51 | 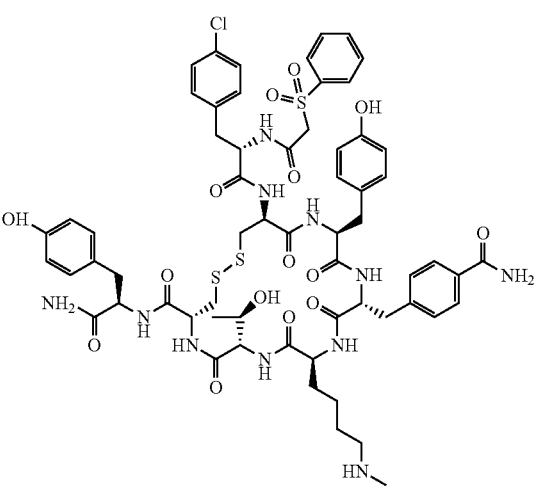
PhSO$_2$CH$_2$(CO)-Cpa-cyclo[D-Cys-Tyr-D-Phe(4-carbamoyl)-Lys(N$^\varepsilon$-Me)-Thr-Cys]-D-Tyr-NH$_2$ Purity (%) (HPLC): 95.8
MS (ESI) [M + H]$^+$$_{calc}$: 1344.4
MS (ESI) [M + H]$^+$$_{obs}$: 1344.5 | Example 2 and General Method C |

TABLE 5-continued

Cyclic 8-mer Compounds and Characterization Data

| Compound No. | SEQ ID NO. | Structure | Methods |
|---|---|---|---|
| 52 | 52 | t-BuCH$_2$(CO)-Cpa-cyclo[D-Cys-Tyr-D-Phe(4-carbamoyl)-Lys(N$^e$-Me)-Thr-Cys]D-Tyr-NH$_2$<br><br>Purity (%) (HPLC): 96.0<br>MS (ESI) [M + H]$^+$$_{calc}$: 1260.5<br>MS (ESI) [M + H]$^+$$_{obs}$: 1260.6 | Example 2 and General Method C |
| 53 | 53 | 2-Pyridyl(CO)-Cpa-cyclo[D-Cys-Tyr-D-Phe(4-carbamoyl)-Lys(N$^e$-Me)-Thr-Cys]-D-Tyr-NH$_2$<br><br>Purity (%) (HPLC): 98.5<br>MS (ESI) [M + H]$^+$$_{calc}$: 1267.4<br>MS (ESI) [M + H]$^+$$_{obs}$: 1267.6 | Example 2 and General Method C |

TABLE 5-continued

Cyclic 8-mer Compounds and Characterization Data

| Compound No. | SEQ ID NO. | Structure | Methods |
|---|---|---|---|
| 54 | 54 | 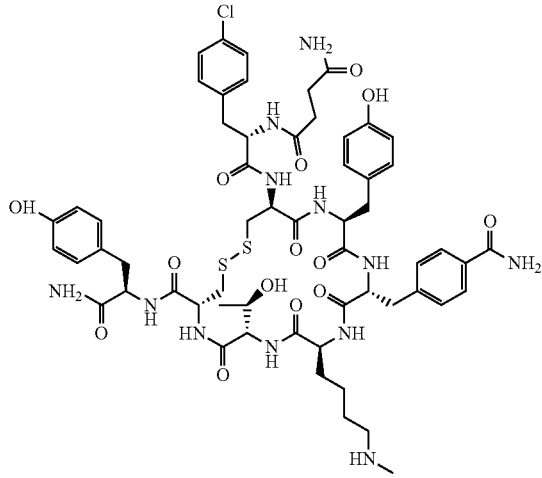  H$_2$N(CO)(CH$_2$)$_2$(CO)-Cpa-cyclo[D-Cys-Tyr-D-Phe(4-carbamoyl)-Lys(N$^\varepsilon$-Me)-Thr-Cys]-D-Tyr-NH$_2$<br><br>Purity (%) (HPLC): 91.0<br>MS (ESI) [M + H]$^+_{calc}$: 1261.5<br>MS (ESI) [M + H]$^+_{obs}$: 1261.6 | Example 2 and General Method C |
| 55 | 55 | 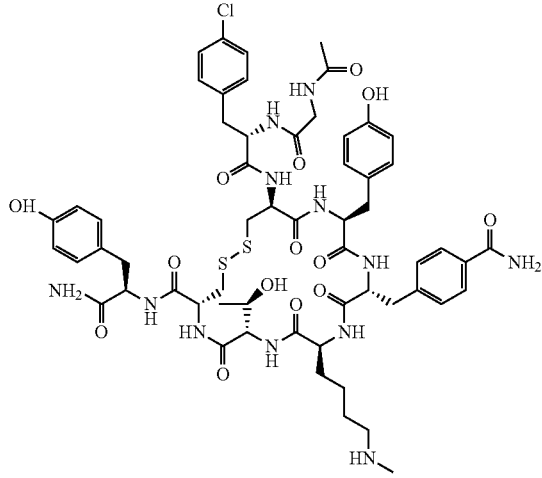  Ac-Gly-Cpa-cyclo[D-Cys-Tyr-D-Phe(4-carbamoyl)-Lys(N$^\varepsilon$-Me)-Thr-Cys]-D-Tyr-NH$_2$<br><br>Purity (%) (HPLC): 94.0<br>MS (ESI) [M + H]$^+_{calc}$: 1261.5<br>MS (ESI) [M + H]$^+_{obs}$: 1261.6 | Example 2 and General Method C |

TABLE 5-continued

Cyclic 8-mer Compounds and Characterization Data

| Compound No. | SEQ ID NO. | Structure | Methods |
|---|---|---|---|
| 56 | 56 | 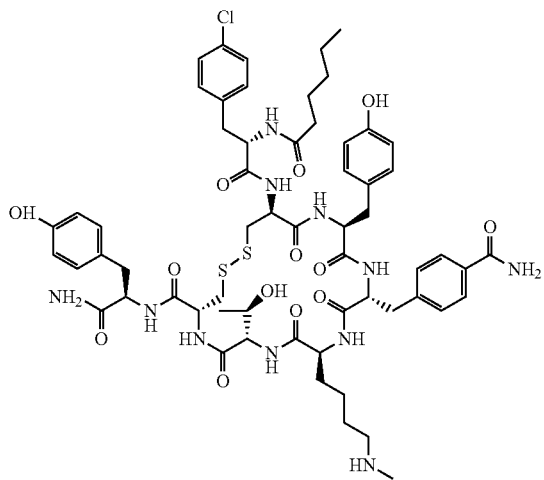CH$_3$(CH$_2$)$_4$(CO)-Cpa-cyclo[D-Cys-Tyr-D-Phe(4-carbamoyl)-Lys(N$^\varepsilon$-Me)-Thr-Cys]-D-Tyr-NH$_2$<br>Purity (%) (HPLC): 89.0<br>MS (ESI) [M + H]$^+$$_{calc}$: 1260.5<br>MS (ESI) [M + H]$^+$$_{obs}$: 1260.6 | Example 2 and General Method C |
| 57 | 57 | 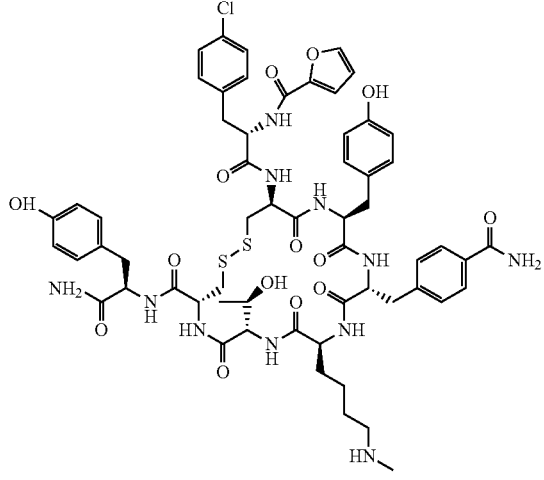(Furan-2-carboxy)-Cpa-cyclo[D-Cys-Tyr-D-Phe(4-carbamoyl-Lys(N$^\varepsilon$-Me)-Thr-Cys]-D-Tyr-NH$_2$<br>Purity (%) (HPLC): 99.0<br>MS (ESI) [M + H]$^+$$_{calc}$: 1256.4<br>MS (ESI) [M + H]$^+$$_{obs}$: 1256.6 | Example 2 and General Method C |

TABLE 5-continued

Cyclic 8-mer Compounds and Characterization Data

| Compound No. | SEQ ID NO. | Structure | Methods |
|---|---|---|---|
| 58 | 58 | CH$_3$O$_2$C(CH$_2$)$_2$(CO)-Cpa-cyclo[D-Cys-Tyr-D-Phe(4-carbamoyl)-Lys(N$^e$-Me)-Thr-Cys]-D-Tyr-NH$_2$<br><br>Purity (%) (HPLC): 93.0<br>MS (ESI) [M + H]$^+$$_{calc}$: 1276.5<br>MS (ESI) [M + H]$^+$$_{obs}$: 1276.5 | Example 2 and General Method C |
| 59 | 59 | H-Cpa-cyclo[D-Cys-Tyr-D-Phe(4-CN)-Lys-Thr-Cys]-D-Tyr-NH$_2$<br><br>Purity (%) (HPLC): 99.0<br>MS (ESI) [M + H]$^+$$_{calc}$: 1130.4<br>MS (ESI) [M + H]$^+$$_{obs}$: 1130.6 | Example 2 |

TABLE 5-continued
Cyclic 8-mer Compounds and Characterization Data
| Compound No. | SEQ ID NO. | Structure | Methods |
|---|---|---|---|
| 60 | 60 | 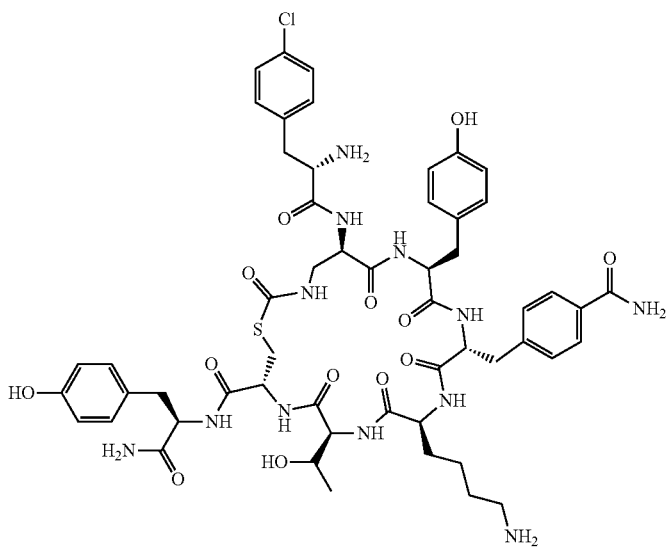<br>Purity (%) (HPLC): 98.0 (2:1 dr)<br>MS (ESI) [M + H]$^+_{calc}$: 1159.4<br>MS (ESI) [M + H]$^+_{obs}$: 1159.6 | Example 2 and General Method D |
| 61 | 61 | 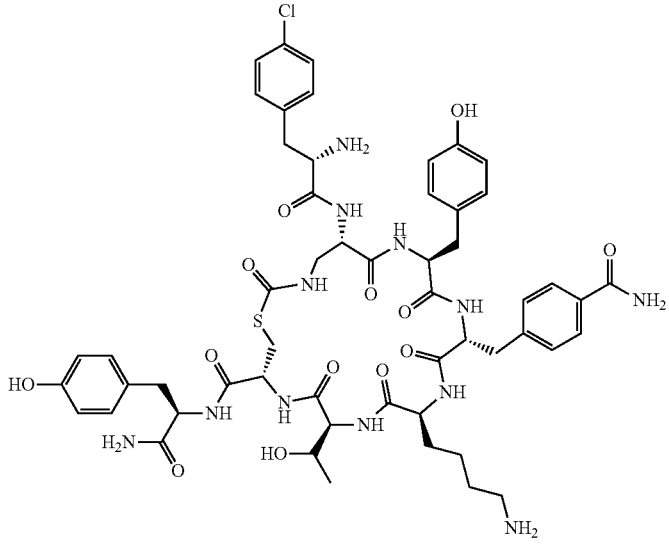<br>Purity (%) (HPLC): 97.6<br>MS (ESI) [M + H]$^+_{calc}$: 1159.4<br>MS (ESI) [M + H]$^+_{obs}$: 1159.7 | Example 2 and General Method D |

TABLE 5-continued
Cyclic 8-mer Compounds and Characterization Data
| Compound No. | SEQ ID NO. | Structure | Methods |
|---|---|---|---|
| 62 | 62 | 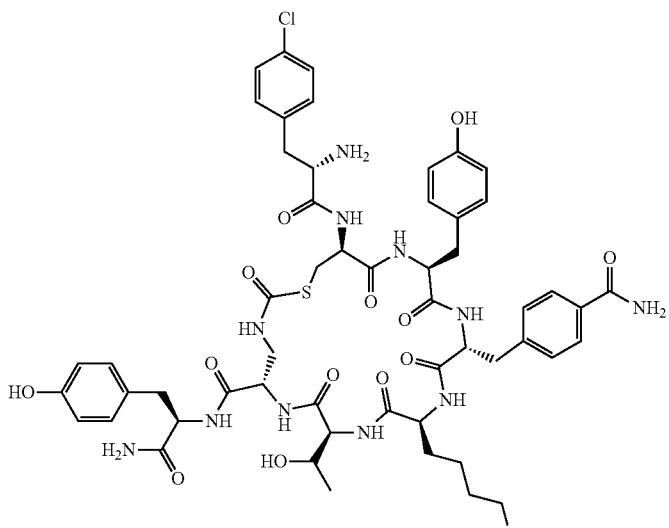  Purity (%) (HPLC): 96.2  MS (ESI) [M + H]$^+_{calc}$: 1159.4  MS (ESI) [M + H]$^+_{obs}$: 1159.6 | Example 2 and General Method D |
| 63 | 63 | 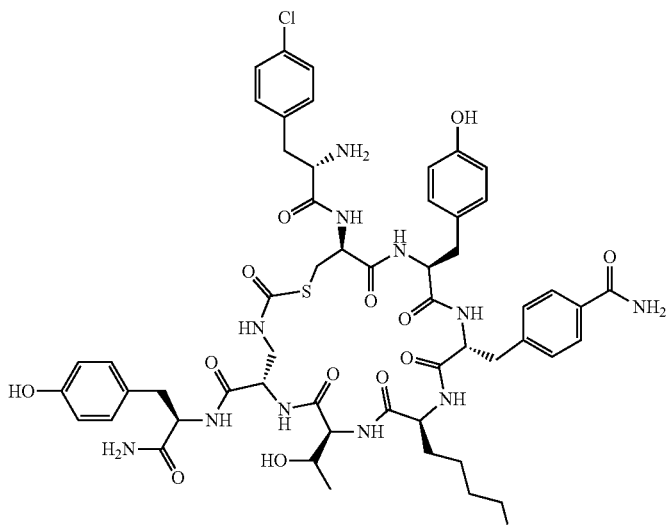  Purity (%) (HPLC): 97.7  MS (ESI) [M + H]$^+_{calc}$: 1173.5  MS (ESI) [M + H]$^+_{obs}$: 1173.6 | Example 2 and General Method D. |

TABLE 5-continued
Cyclic 8-mer Compounds and Characterization Data
| Compound No. | SEQ ID NO. | Structure | Methods |
|---|---|---|---|
| 64 | 64 | 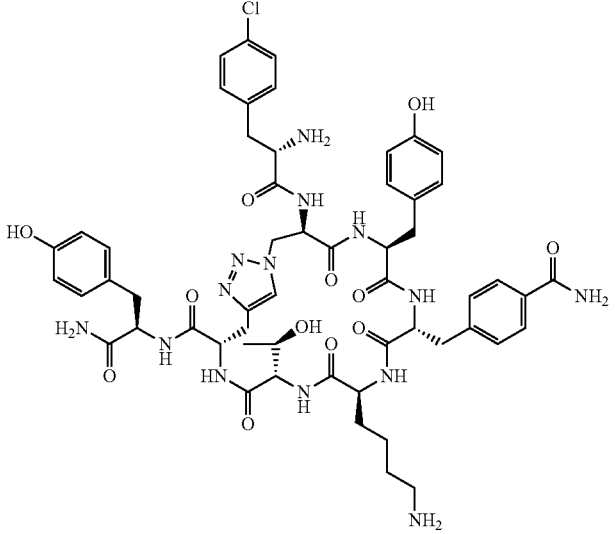<br>Purity (%) (HPLC): 94.0<br>MS (ESI) [M + H]$^+_{calc}$: 1151.5<br>MS (ESI) [M + H]$^+_{obs}$: 1151.9 | Example 2 and General Method E |
| 65 | 65 | 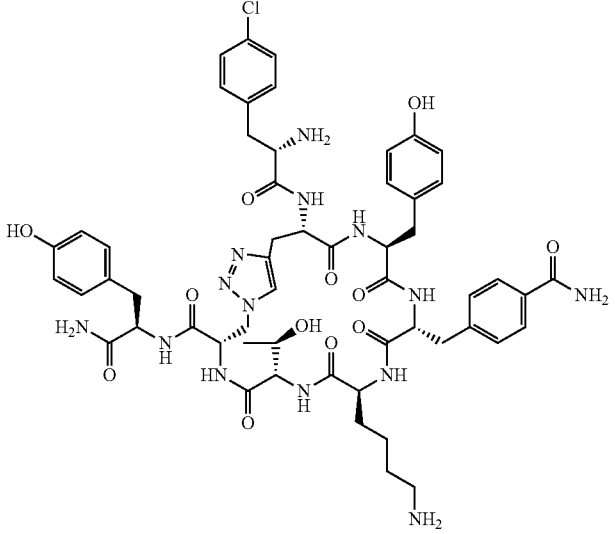<br>Purity (%) (HPLC): 98.0<br>MS (ESI) [M + H]$^+_{calc}$: 1151.5<br>MS (ESI) [M + H]$^+_{obs}$: 1151.9 | Example 2 and General Method E |

TABLE 5-continued
Cyclic 8-mer Compounds and Characterization Data
| Compound No. | SEQ ID NO. | Structure | Methods |
|---|---|---|---|
| 66 | 66 | 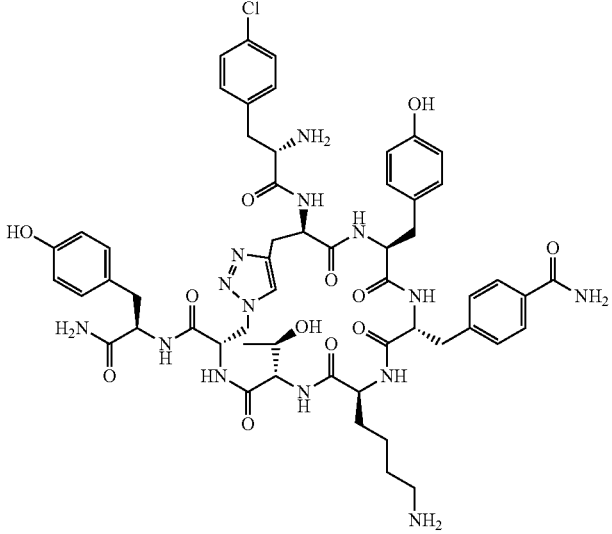  Purity (%) (HPLC): 100.0  MS (ESI) [M + H]$^+_{calc}$: 1151.5  MS (ESI) [M + H]$^+_{obs}$: 1151.9 | Example 2 and General Method E |
| 67 | 67 | 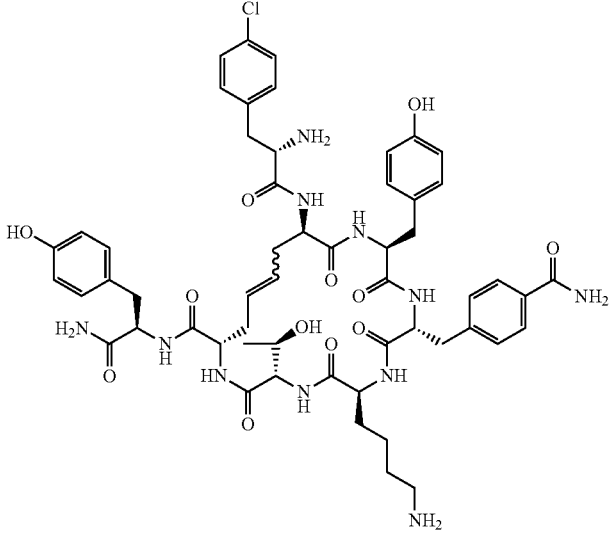  Purity (%) (HPLC): 99.0  MS (ESI) [M + H]$^+_{calc}$: 1110.5  MS (ESI) [M + H]$^+_{obs}$: 1111.0 | Example 2 and General Method F |

TABLE 5-continued
Cyclic 8-mer Compounds and Characterization Data
| Compound No. | SEQ ID NO. | Structure | Methods |
|---|---|---|---|
| 68 | 68 | 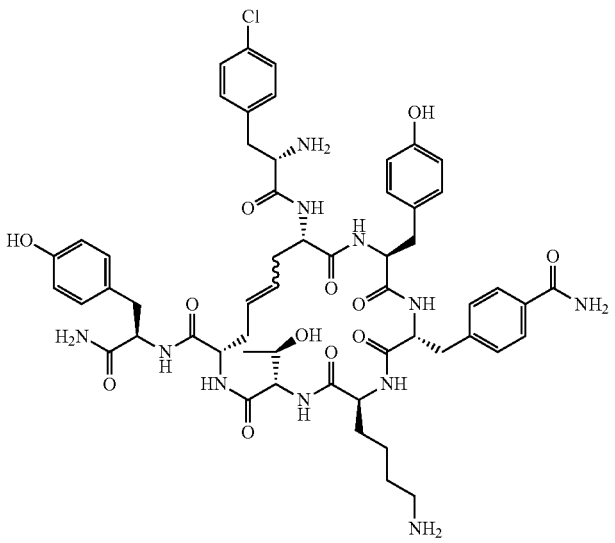<br>Purity (%) (HPLC): 96.0<br>MS (ESI) [M + H]$^+_{calc}$: 1110.5<br>MS (ESI) [M + H]$^+_{obs}$: 1110.8 | Example 2 and General Method F |
| 69 | 69 | 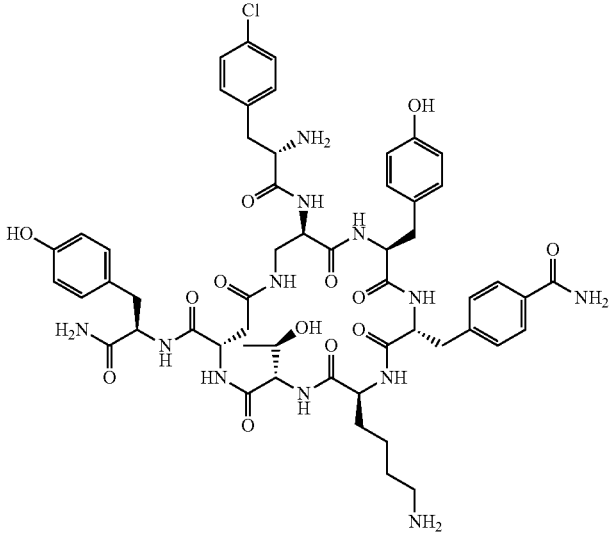<br>Purity (%) (HPLC): 93.0<br>MS (ESI) [M + H]$^+_{calc}$: 1127.5<br>MS (ESI) [M + H]$^+_{obs}$: 1127.7 | Example 2 and General Method G |

TABLE 5-continued
Cyclic 8-mer Compounds and Characterization Data
| Compound No. | SEQ ID NO. | Structure | Methods |
|---|---|---|---|
| 70 | 70 | 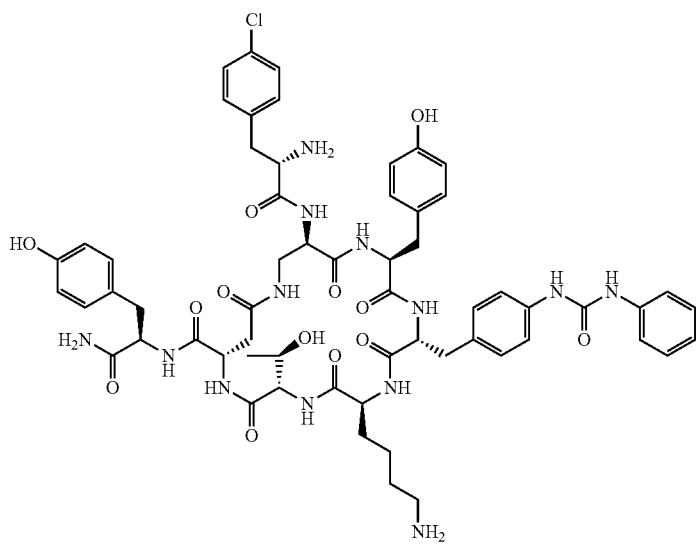 Purity (%) (HPLC): 97.0<br>MS (ESI) [M + H]$^+_{calc}$: 1218.5<br>MS (ESI) [M + H]$^+_{obs}$: 1218.7 | Example 2 and General Method G |
| 71 | 71 | 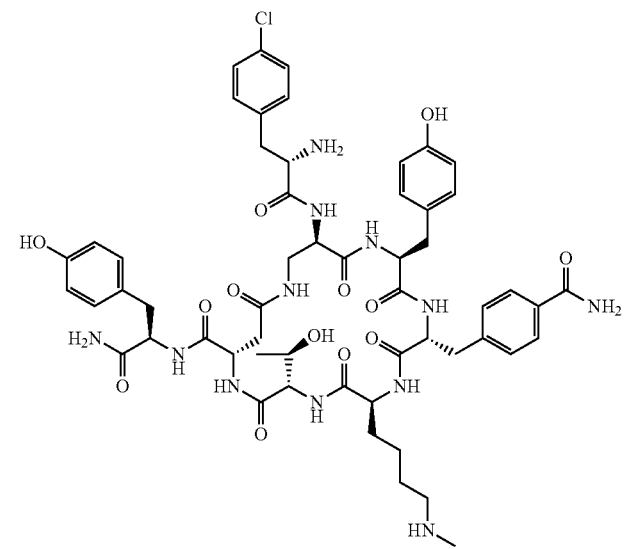 Purity (%) (HPLC): 97.0<br>MS (ESI) [M + H]$^+_{calc}$: 1141.5<br>MS (ESI) [M + H]$^+_{obs}$: 1141.7 | Example 2 and General Method G |

TABLE 5-continued

Cyclic 8-mer Compounds and Characterization Data

| Compound No. | SEQ ID NO. | Structure | Methods |
|---|---|---|---|
| 72 | 72 | H-Cpa-cyclo[D-Cys-Tyr-D-Phe(4-carbamoyl)-(N$^\alpha$-Me)Lys-Thr-Cys]-D-Tyr-NH$_2$<br><br>Purity (%) (HPLC): 93.4<br>MS (ESI) [M + H]$^+$$_{calc}$: 1162.4<br>MS (ESI) [M + H]$^+$$_{obs}$: 1161.9 | Example 2 and General Method I |
| 73 | 73 | H-Cpa-cyclo[D-Cys-Tyr-D-Phe(4-carbamoyl)-Lys-(N-Me)Thr-Cys]-D-Tyr-NH$_2$<br><br>Purity (%) (HPLC): 68.0/32.0 (mixture of 2 diastereomers)<br>MS (ESI) [M + H]$^+$$_{calc}$: 1162.4<br>MS (ESI) [M + H]$^+$$_{obs}$: 1162.6 | Example 2 and General Method I |

TABLE 5-continued

Cyclic 8-mer Compounds and Characterization Data

| Compound No. | SEQ ID NO. | Structure | Methods |
|---|---|---|---|
| 74 | 74 | 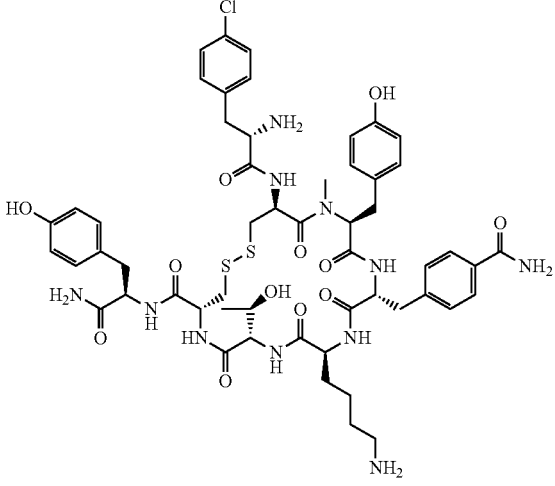<br>H-Cpa-cyclo[D-Cys-(N-Me)Tyr-D-Phe(4-carbamoyl)-Lys-Thr-Cys]-D-Tyr-NH$_2$<br><br>Purity (%) (HPLC): 91.0<br>MS (ESI) [M + H]$^+$$_{calc}$: 1162.4<br>MS (ESI) [M + H]$^+$$_{obs}$: 1162.5 | Example 2 and General Method I |
| 75 | 75 | 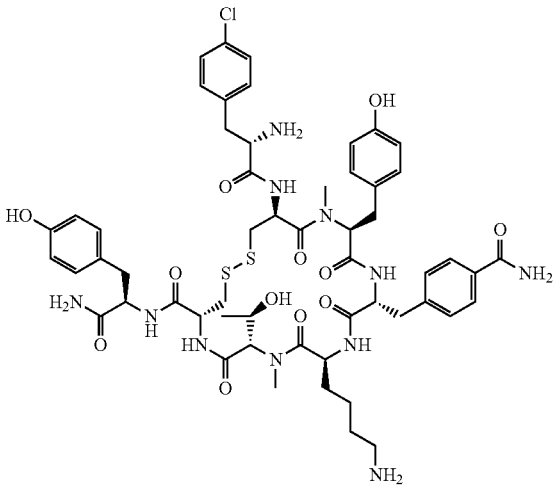<br>H-Cpa-cyclo[D-Cys-(N-Me)Tyr-D-Phe(4-carbamoyl)-Lys-(N-Me)Thr-Cys]-D-Tyr-NH$_2$<br><br>Purity (%) (HPLC): 73.3<br>MS (ESI) [M + H]$^+$$_{calc}$: 1176.4<br>MS (ESI) [M + H]$^+$$_{obs}$: 1176.7 | Example 2 and General Method I |

TABLE 5-continued

Cyclic 8-mer Compounds and Characterization Data

| Compound No. | SEQ ID NO. | Structure | Methods |
|---|---|---|---|
| 76 | 76 | 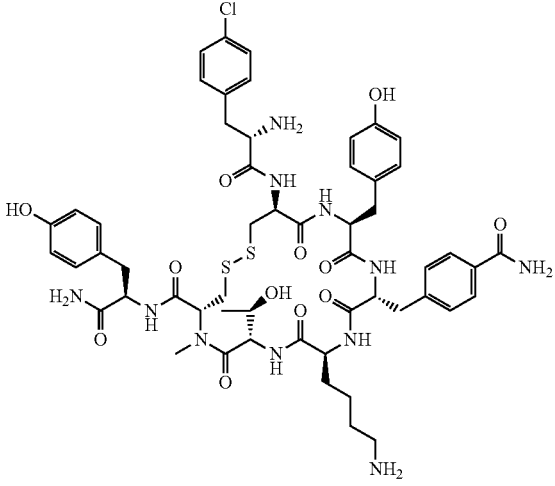  H-Cpa-cyclo[D-Cys-Tyr-D-Phe(4-carbamoyl)-Lys-Thr-(N-Me)Cys]-D-Tyr-NH$_2$<br><br>Purity (%) (HPLC): 95.0<br>MS (ESI) [M + H]$^+_{calc}$: 1162.4<br>MS (ESI) [M + H]$^+_{obs}$: 1162.6 | Example 2 and General Method I |
| 77 | 77 | 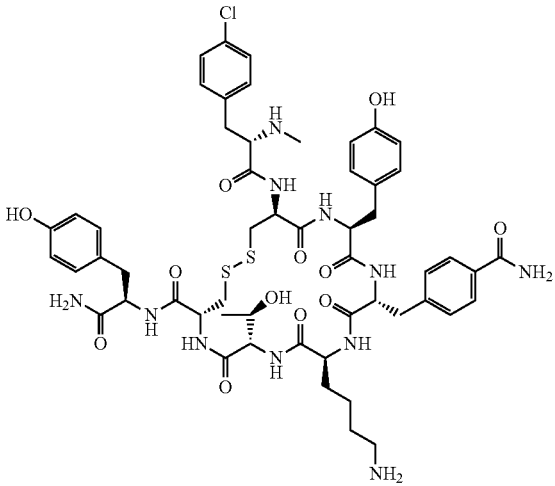  H-(N-Me)Cpa-cyclo[D-Cys-Tyr-D-Phe(4-carbamoyl)-Lys-Thr-Cys]-D-Tyr-NH$_2$<br><br>Purity (%) (HPLC): 96.0<br>MS (ESI) [M + H]$^+_{calc}$: 1162.4<br>MS (ESI) [M + H]$^+_{obs}$: 1162.6 | Example 2 and General Method I |

TABLE 5-continued

Cyclic 8-mer Compounds and Characterization Data

| Compound No. | SEQ ID NO. | Structure | Methods |
|---|---|---|---|
| 78 | 78 | 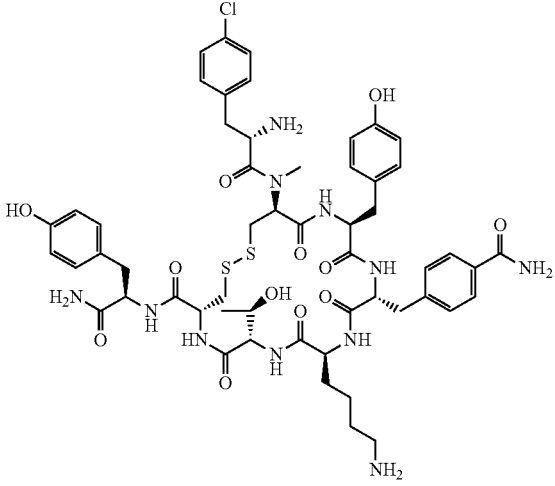<br>H-Cpa-cyclo[D-(N-Me)Cys-Tyr-D-Phe(4-carbamoyl)-Lys-Thr-Cys]-D-Tyr-NH$_2$<br><br>Purity (%) (HPLC): 97.3<br>MS (ESI) [M + H]$^+_{calc}$: 1162.4<br>MS (ESI) [M + H]$^+_{obs}$: 1162.6 | Example 2 and General Method I |
| 79 | 79 | 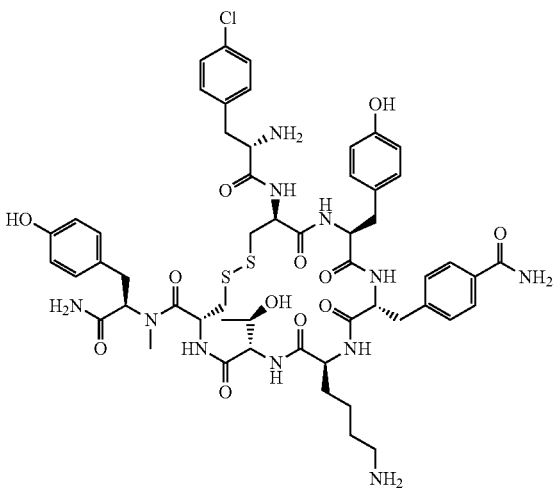<br>H-Cpa-cyclo[D-Cys-Tyr-D-Phe(4-carbamoyl)-Lys-Thr-Cys]-D-(N-Me)Tyr-NH$_2$<br><br>Purity (%) (HPLC): 97.0<br>MS (ESI) [M + H]$^+_{calc}$: 1162.4<br>MS (ESI) [M + H]$^+_{obs}$: 1162.6 | Example 2 and General Method I |

TABLE 5-continued

Cyclic 8-mer Compounds and Characterization Data

| Compound No. | SEQ ID NO. | Structure | Methods |
|---|---|---|---|
| 80 | 80 | 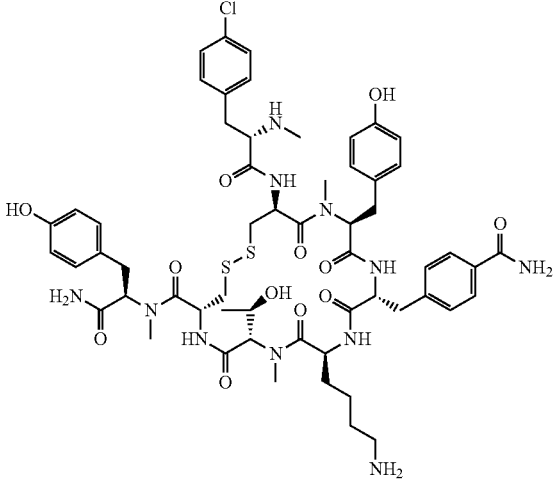 H-(N-Me)Cpa-cyclo[D-Cys-(N-Me)Tyr-D-Phe(4-carbamoyl)-Lys-(N-Me)Tyr-Cys]-D-(N-Me)Tyr-NH$_2$<br><br>Purity (%) (HPLC): 93.9<br>MS (ESI) [M + H]$^+_{calc}$: 1204.5<br>MS (ESI) [M + H]$^+_{obs}$: 1204.7 | Example 2 and General Method I |
| 81 | 81 | 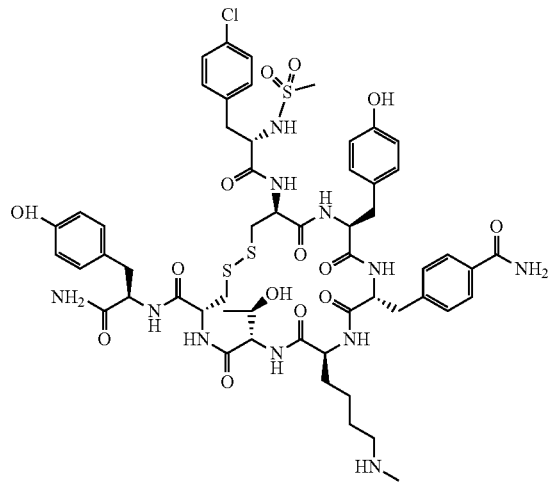 CH$_3$SO$_2$-Cpa-cyclo[D-Cys-Tyr-D-Phe(4-carbamoyl)-Lys(N$^\varepsilon$-Me)-Thr-Cys]-D-Tyr-NH$_2$<br><br>Purity (%) (HPLC): 97.8<br>MS (ESI) [M + H]$^+_{calc}$: 1240.4<br>MS (ESI) [M + H]$^+_{obs}$: 1240.5 | Example 2 and General Method J |

TABLE 5-continued

Cyclic 8-mer Compounds and Characterization Data

| Compound No. | SEQ ID NO. | Structure | Methods |
|---|---|---|---|
| 82 | 82 | 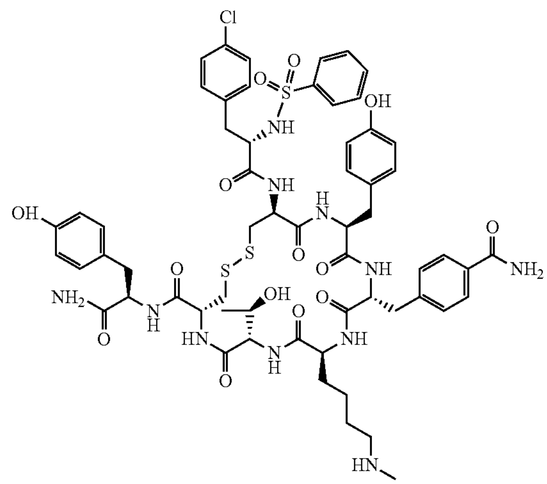 | Example 2 and General Method J |

PhSO$_2$-Cpa-cyclo[D-Cys-Tyr-D-Phe(4-carbamoyl)-Lys(N$^\varepsilon$-Me)-Thr-Cys]-D-Tyr-NH$_2$ Purity (%) (HPLC): 91.7
MS (ESI) [M + H]$^+_{calc}$: 1302.4
MS (ESI) [M + H]$^+_{obs}$: 1302.6

Antagonist Activity in Somatostatin Receptors (SSTRs)

The PathHunter® β-Arrestin assay monitors the activation of a GPCR in a homogenous, non-imaging assay format using a technology developed by DiscoveRx called Enzyme Fragment Complementation (EFC) with β-galactosidase (β-Gal) as the functional reporter. The enzyme is split into two inactive complementary portions (EA for Enzyme Acceptor and PK for ProLink) expressed as fusion proteins in the cell. EA is fused to β-Arrestin and PK is fused to the GPCR of interest. When the GPCR is activated and β-Arrestin is recruited to the receptor, ED and EA complementation occurs, restoring β-Gal activity which is measured using chemiluminescent PathHunter® Detection Reagents. For antagonist determination, cells were pre-incubated with the compounds followed by agonist challenge at the EC80 concentration. Data was normalized to the maximal and minimal response observed in the presence of EC80 ligand and vehicle. Compound activity was analyzed using CBIS data analysis suite ChemInnovation, Calif.). Percentage inhibition was calculated using the following formula: % Inhibition=100%×(1−(mean signal of test sample-mean signal of vehicle control)/(mean signal of EC80 control-mean signal of vehicle control)). Percentage inhibition was calculated at 10 concentrations in steps on a Log 3 scale ranging from 1μ down to 5e-5 μM. The results were plotted for IC50 calculation. IC50 values for compounds 1 to 80 are provided in Table 6. The results show that compounds 1-80 exhibited antagonistic activity with respect to somatostatin type 2 (SSTR2) receptors. In addition, compounds demonstrated good specificity to SSTR2 versus other SSTR subtypes.

TABLE 6

IC$_{50}$ Data for Cyclic 8-mer Compounds

| Compound | IC$_{50}$ SSTR1 (uM) | IC$_{50}$ SSTR2 (uM) | IC$_{50}$ SSTR3 (uM) | IC$_{50}$ SSTR4 (uM) | IC$_{50}$ SSTR5 (uM) |
|---|---|---|---|---|---|
| 1 | >1 | 0.034 | >1 | >1 | >1 |
| 2 |  | 0.181 | >1 |  |  |
| 3 |  | 0.251 | >1 |  |  |
| 4 | >1 | 0.017 | >1 | >1 | >1 |
| 5 |  | 0.213 | >1 |  |  |
| 6 |  | 0.166 | >1 |  |  |
| 7 | >1 | 0.031 | >1 | >1 | >1 |
| 8 |  | 0.084 | >1 |  |  |
| 9 |  | 0.104 | >1 |  |  |
| 10 |  | >1 | >1 |  |  |
| 11 |  | 0.243 | >1 |  |  |
| 12 | >1 | 0.017 | >1 | >1 | >1 |
| 13 |  | 0.334 | >1 |  |  |
| 14 | >1 | 0.021 | >1 | >1 | >1 |
| 15 | >1 | 0.001 | >1 | >1 | >1 |
| 16 |  | 0.234 | >1 |  |  |
| 17 |  | >1 | >1 |  |  |
| 18 |  | >1 | >1 |  |  |
| 19 |  | >1 | >1 |  |  |
| 20 |  | 0.924 | >1 |  |  |
| 21 |  | >1 | >1 |  |  |
| 22 |  | 0.417 | >1 |  |  |
| 23 |  | 0.458 | >1 |  |  |

TABLE 6-continued

IC$_{50}$ Data for Cyclic 8-mer Compounds

| Compound | IC$_{50}$ SSTR1 (uM) | IC$_{50}$ SSTR2 (uM) | IC$_{50}$ SSTR3 (uM) | IC$_{50}$ SSTR4 (uM) | IC$_{50}$ SSTR5 (uM) |
|---|---|---|---|---|---|
| 24 | >1 | 0.00096 | >1 | >1 | >1 |
| 25 |  | 0.00232 |  |  |  |
| 26 |  | >1 |  |  |  |
| 27 |  | 0.0347 |  |  |  |
| 28 |  | 0.104 |  |  |  |
| 29 |  | 0.398 |  |  |  |
| 30 |  | 0.177 |  |  |  |
| 31 |  | 0.0704 |  |  |  |
| 32 |  | 0.00246 |  |  |  |
| 33 |  | 0.0560 |  |  |  |
| 34 |  | 0.0434 |  |  |  |
| 35 |  | 0.0359 |  |  |  |
| 36 |  | 0.0287 |  |  |  |
| 37 |  | 0.0106 |  |  |  |
| 38 |  | 0.0244 |  |  |  |
| 39 |  | >1 |  |  |  |
| 40 |  | 0.0162 |  |  |  |
| 41 |  | 0.0244 |  |  |  |
| 42 |  | 0.00984 |  |  |  |
| 43 |  | 0.0256 |  |  |  |
| 44 |  | 0.0107 |  |  |  |
| 45 |  | 0.0146 |  |  |  |
| 46 |  | 0.000398 |  |  |  |
| 47 |  | 0.00151 |  |  |  |
| 48 |  | 0.00131 |  |  |  |
| 49 |  | 0.00286 |  |  |  |
| 50 |  | 0.00111 |  |  |  |
| 51 |  | 0.00145 |  |  |  |
| 52 |  | 0.00173 |  |  |  |
| 53 |  | 0.00428 |  |  |  |
| 54 |  | 0.00233 |  |  |  |
| 55 |  | 0.00335 |  |  |  |
| 56 |  | 0.00160 |  |  |  |
| 57 |  | 0.00365 |  |  |  |
| 58 |  | 0.00236 |  |  |  |
| 59 |  | 0.0391 |  |  |  |
| 60 |  | >1 |  |  |  |
| 61 |  | >1 |  |  |  |
| 62 |  | >1 |  |  |  |
| 63 |  | >1 |  |  |  |
| 64 |  | >1 |  |  |  |
| 65 |  | 0.688 |  |  |  |
| 66 |  | >1 |  |  |  |
| 67 |  | >1 |  |  |  |
| 68 |  | >1 |  |  |  |
| 69 |  | >1 |  |  |  |
| 70 |  | >1 |  |  |  |
| 71 |  | 0.0133 |  |  |  |
| 72 |  | 0.00577 |  |  |  |
| 73 |  | 0.547 |  |  |  |
| 74 |  | 0.159 |  |  |  |
| 75 |  | >1 |  |  |  |
| 76 |  | 0.400 |  |  |  |
| 77 |  | 0.00225 |  |  |  |
| 78 |  | 0.00679 |  |  |  |
| 79 |  | 0.0287 |  |  |  |
| 80 |  | >1 |  |  |  |

Hypoglycemic Challenges in Streptozotocin (STZ) Diabetic Rats

Methodologies

All animal experiments were approved by York University Animal Care Committee and conducted in accordance with the Canadian Council for Animal Care guidelines.

Male Sprague Dawley rats (initial weight 150-175 g) were purchased from Charles River Laboratories (Montreal, QC, Canada). Rats were housed in the York University Vivarium in a 12-hour light dark cycle. All animals were fed a standard rodent chow diet (14% fat, 54% carbohydrates, 32% fat & 3.0 calories/g of food) and water ad libitum. After a minimum of one week of acclimation, all animals received an intraperitoneal injection of streptozotocin (STZ) (Sigma) at a dose of 65 mg/kg body weight. After STZ injection, animals were provided with sugar water (5% solution) overnight. Any animals whose blood glucose was not greater than 10 mM within 2 days of STZ injection received a second injection.

One week after induction of diabetes, insulin treatment was initiated to maintain blood glucose values within a reasonable glucose controlled range in the fasted state (8-20 mM). Insulin pellets (LinChin, Toronto, ON, Canada) were implanted subcutaneously in any rat with blood glucose over 20 mM. Briefly, animals were anesthetized via inhaled isoflurane and pellets were implanted subcutaneously within the scapular region. One week later animals underwent their first hypoglycemic challenge (Hypoglycemic Challenge #1), followed by a second hypoglycemic challenge (Hypoglycemic Challenge #2) the following week (see below). Throughout the study, daily animals checks were conducted to assess body weight, blood glucose as well as food/calorie consumption. A schematic of the study design is shown in FIG. 1.

Hypoglycemic Challenges

Figure 2:
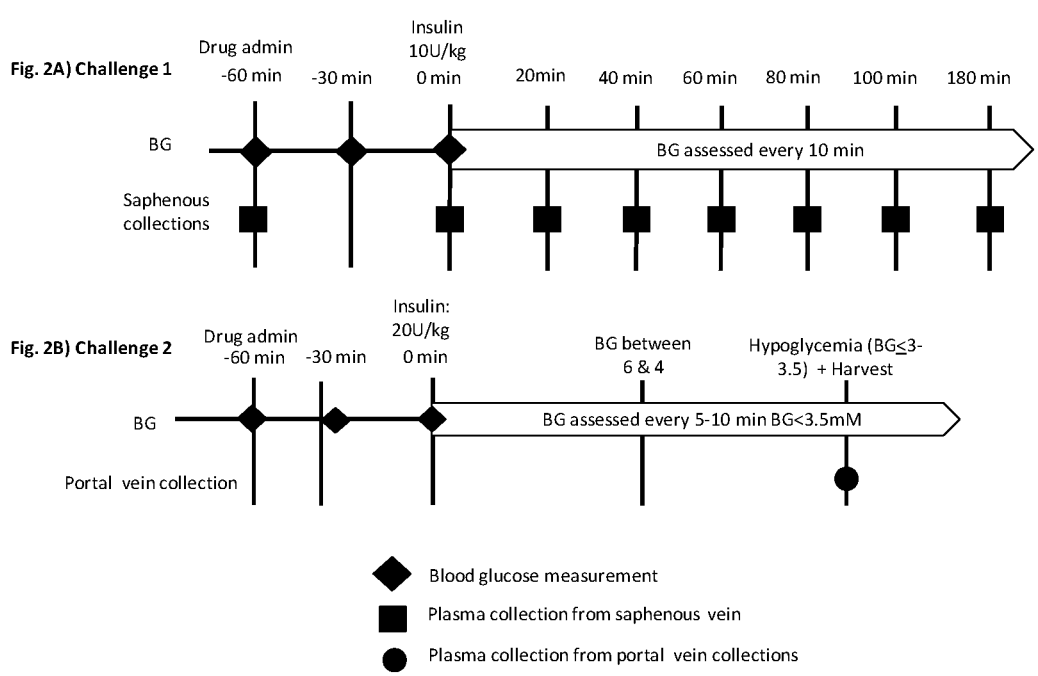
FIGS. 2A and 2B show a detailed procedure for the hypoglycemic challenges (FIG. 2A-Hypoglycemia Challenge #1.

Animals were divided into groups and received Compound 4, or Compound 24 or a corresponding dose of vehicle. Compounds were given 1 hour prior to commencement of the hypoglycemic challenge. On the morning of the hypoglycemic challenge, food was removed from the cage and a plasma sample was collected as baseline (prior to compound/vehicle administration), one-hour post drug/vehicle administration and at set points throughout the challenges. A schematic of the hypoglycemic challenges is shown in FIGS. 2A and 2B.

For Hypoglycemic Challenge #1, hypoglycemia was induced via subcutaneous administration of a bolus of insulin (10 U Novo Rapid insulin/kg body weight). Blood glucose was assessed every 10 minutes via saphenous vein puncture. Additionally, plasma was collected from the saphenous vein every 20 minutes, until 100-minutes post insulin administration. An additional plasma sample was collected 4-hours post drug administration (3 hours post insulin bolus) for mass spectrometry analysis of the compounds in plasma. If blood glucose went below 1.0 mM or animal showed signs of distress (weakness, convolutions, seizures etc.) the challenge was stopped and the animal was provided with food or an oral gavage of Dextrose. Further details of the experimental time course for the first challenge are shown in FIG. 2A.

One week after the first hypoglycemia challenge, a second similar hypoglycemic challenge (Hypoglycemia Challenge #2) was conducted; however this time a higher dose of insulin was given to insure that severe hypoglycemia developed (20 U Novo Rapid/kg body weight). Blood glucose was monitored, every 5-10 min, via saphenous vein puncture. When blood glucose reached 3.5 mM, the animal was anesthetized (via inhaled isoflurane) and a saphenous vein and portal vein plasma sample were collected. Subsequently, the animal pancreas and liver were excised and the animal was terminated via exsanguination. Tissue was flash frozen in liquid nitrogen and maintained at −80° C. Further details of the experimental time course for Hypoglycemia Challenge #2 are shown in FIG. 2B.

Results

Hypoglycemic Challenge #1

Figure 3:
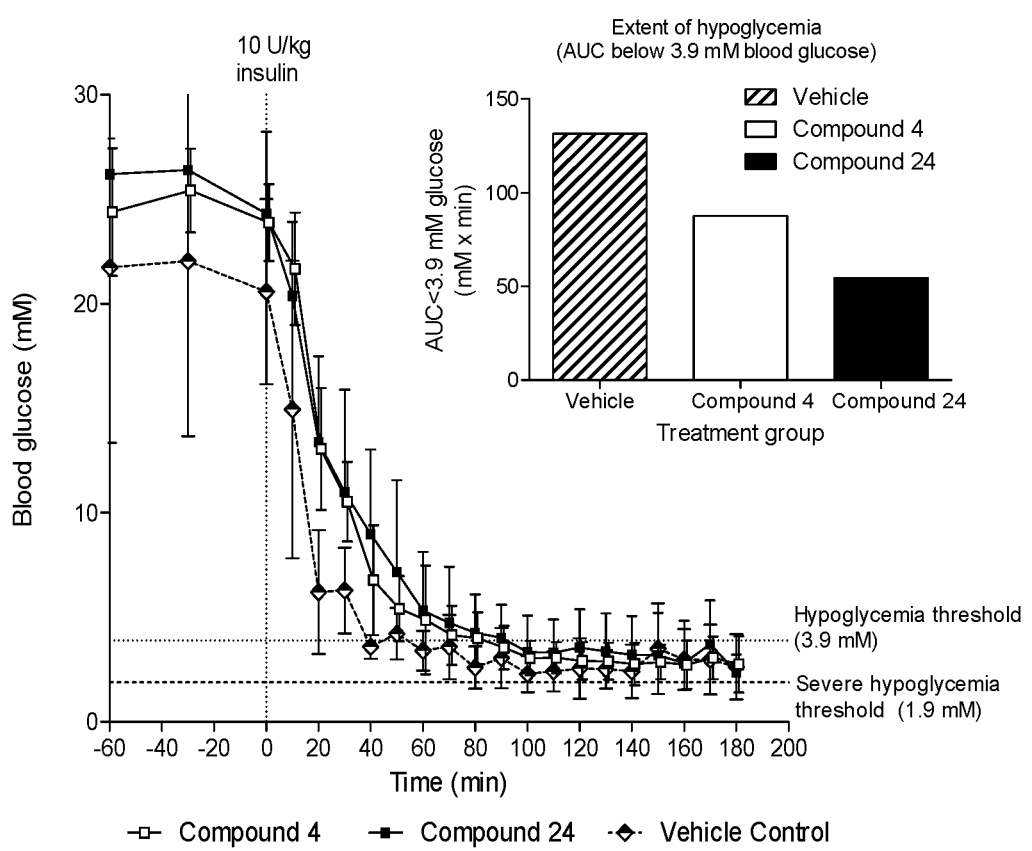
FIG. 3 is a graph showing blood glucose (BG) values measured over time in STZ diabetic Sprague Dawley rats treated with either vehicle control, Compound 4, or Compound 24 in Hypoglycemic Challenge #1. The inset graph provides measures of the extent of hypoglycemia of the animals from the BG vs time curves as represented by the area under the curve (AUC) for the blood glucose values over time.

FIG. 3 shows blood glucose (BG) values measured over time in STZ diabetic Sprague Dawley rats treated at t=−60 min with either vehicle control, Compound 4, or Compound 24, then treated with insulin 10 U/kg at t=0 min. The time course demonstrates that the diabetic rats experience a BG drop in response to insulin therapy, which can result in hypoglycemia (defined as a BG threshold of 3.9 mM or below). 2-Way ANOVA analysis demonstrates that Compound 24 has significantly higher BG values in the first 40 minutes after insulin therapy, compared with the Vehicle Control group, while the Compound 4 group had higher values in the first 20 minutes. From the BG vs time curves, the extent of hypoglycemia is represented by the area under the curve (AUC) for the blood glucose values over time. The AUC is calculated as the area below the 3.9 mM threshold value (inset graph). The AUC value was highest for the vehicle control group (132 mM×min), and lowest for the group treated with Compound 24 (55 mM×min). The graph represents the average±standard deviation values of BG. Sample sizes were N=9 for Compound 4 and Compound 24 treatment groups, and N=6 for the Vehicle Control group.

Time to Onset of Hypoglycemia in Hypoglycemia Challenge #1

Figure 4:
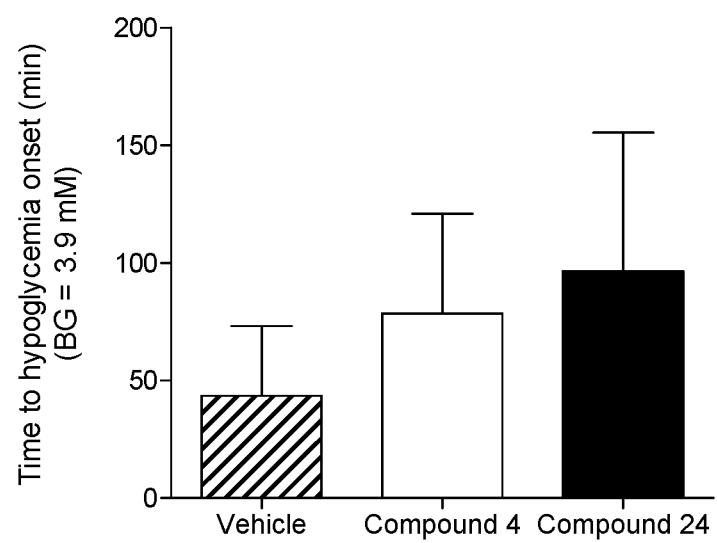
FIG. 4 is a graph showing the time to onset of hypoglycemia of the STZ diabetic Sprague Dawley rats treated with either vehicle control, Compound 4, or Compound 24 in Hypoglycemia Challenge #1.

FIG. 4 shows the time to onset of hypoglycemia which was determined by interpolating the data from FIG. 3 to determine the time at which each subject's BG first reached 3.9 mM. Rats in Vehicle Control group experienced onset of hypoglycemia on average 43 minutes after receiving a 10 U/kg insulin dose, whereas rats treated with Compound 24 experienced a delay in hypoglycemia onset, at an average 97 minutes after insulin administration. The results show that treatment can delay the onset of insulin induced hypoglycemia. This graph presents the average±standard deviation values of time to hypoglycemia onset. Sample sizes were N=9 for Compound 4 and Compound 24 treatment groups, and N=6 for the Vehicle Control group.

Proportion of Rats in Hypoglycemia as a Function of Time

Figure 5:
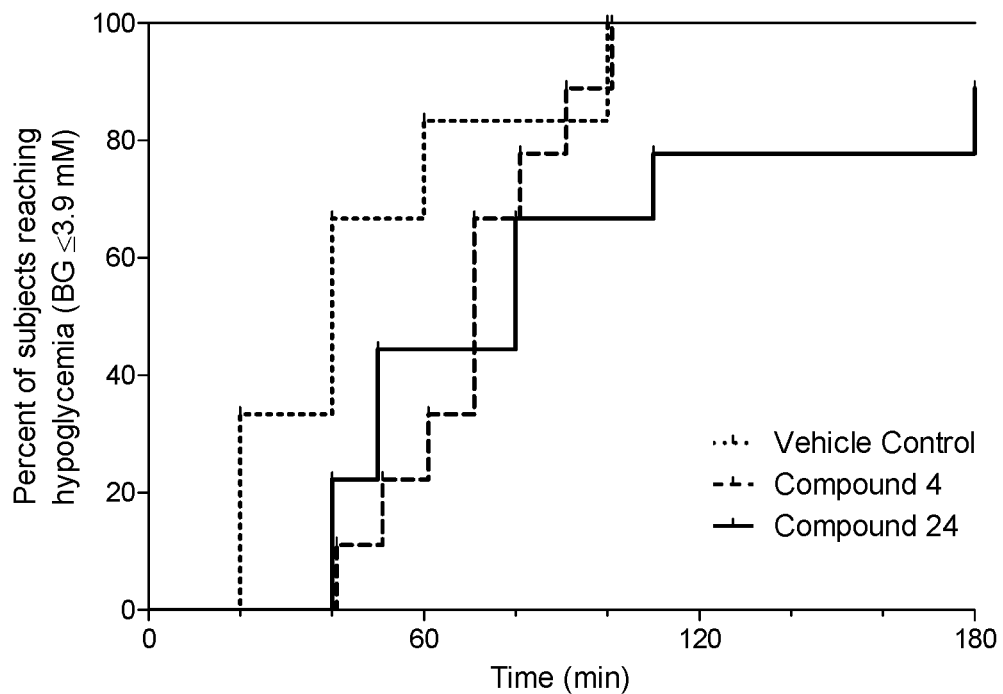
FIG. 5 is a graph showing the data from FIG. 3, presented as a survival curve, indicating the proportion of rats from each group that were in hypoglycemia (defined as the BG threshold of 3.9 mM) as a function of time.

FIG. 5 shows the data from FIG. 3, presented as a survival curve, indicating the proportion of rats from each group that were in hypoglycemia (defined as the BG threshold of 3.9 mM) at any given time. The graph illustrates that rats from the Vehicle Control group were the first to become hypoglycemic (2 of 6 rats became hypoglycemic 20 minutes after receiving insulin), and that 100% of the group reached hypoglycemia by 100 minutes after receiving insulin. In contrast, for rats treated with Compound 24, 2 of 9 rats first became hypoglycemia at 40 minutes. In the Compound 24 treated group, 1 rat never became hypoglycemic. The results show that treatment can delay or reduce the frequency of hypoglycemia.

Proportion of Rats in Severe Hypoglycemia as a Function of Time

Figure 6:
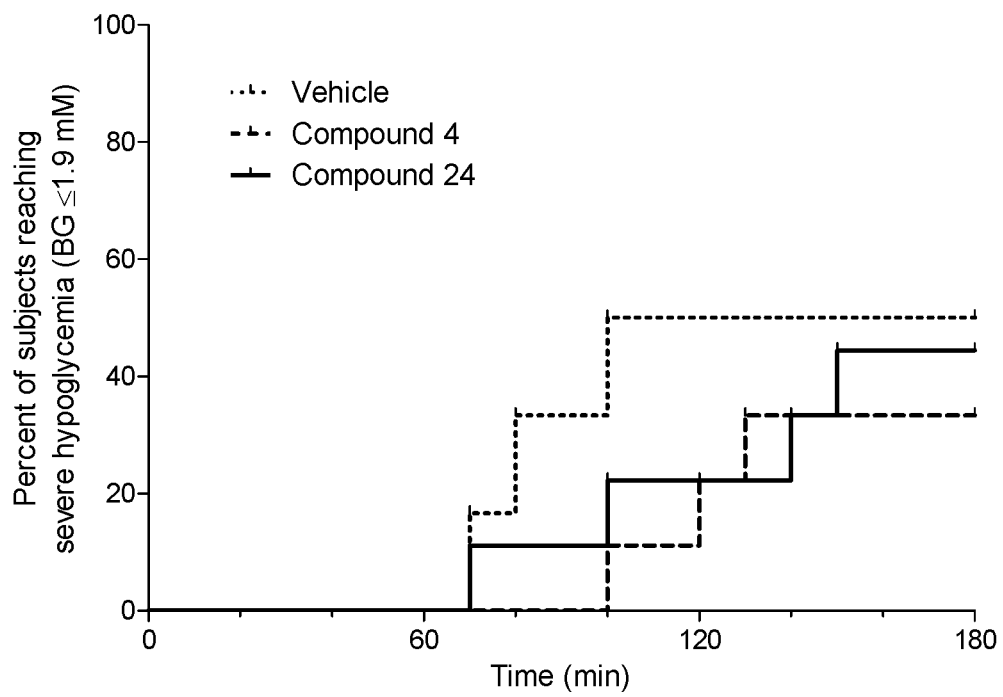
FIG. 6 is a graph showing the data from FIG. 3, presented as a survival curve, indicating the proportion of rats from each group that were in severe hypoglycemia (defined as the BG threshold of 1.9 mM) as a function of time.

FIG. 6 shows the data from FIG. 3, presented as a survival curve, indicating the proportion of rats from each group that were in severe hypoglycemia (defined as the BG threshold of 1.9 mM) at any given time. The graph illustrates that of rats from the Vehicle Control group, 50% experienced severe hypoglycemia within 100 minutes after receiving insulin. In contrast, for rats treated with Compound 24, the rate of onset and incidence of severe hypoglycemia was lower (44% after 150 minutes). For Compound 4, the rate was 33% after 130 minutes. The results show that treatment can delay or reduce the frequency of severe hypoglycemia.

Glucagon Responses to Hypoglycemia in Hypoglycemia Challenge #1

Figure 7A:
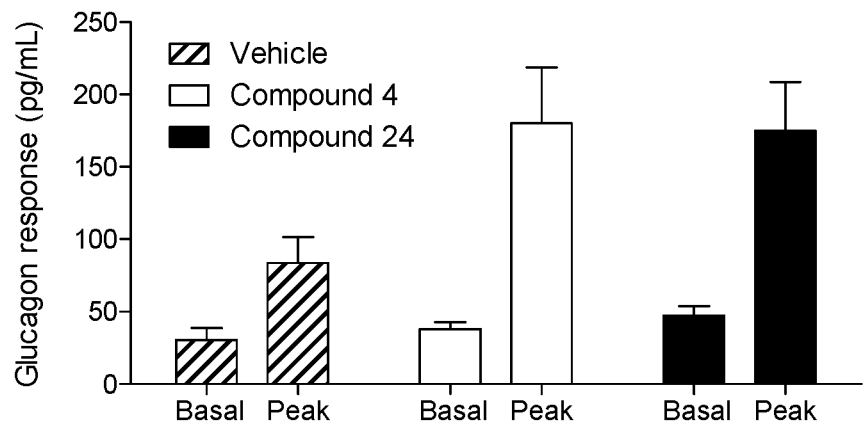
FIGS. 7A and 7B are graphs showing the response of glucagon to hypoglycemia in STZ diabetic Sprague Dawley rats treated with either vehicle control, Compound 4, or Compound 24 in Hypoglycemia Challenge #1.
Figure 7B:
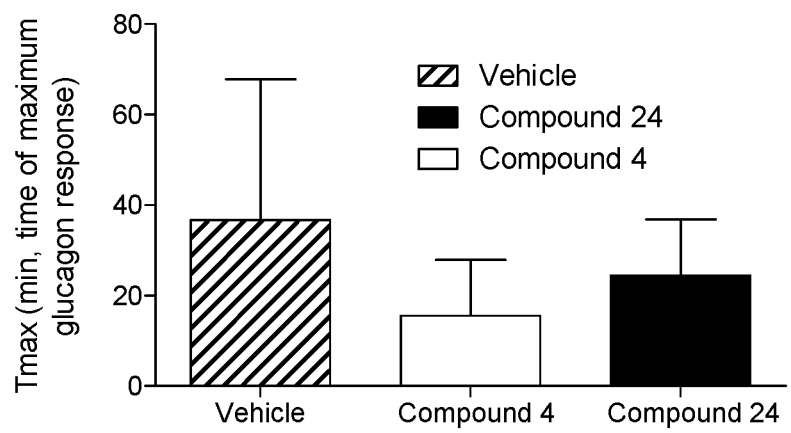

FIGS. 7A and 7B show the response of glucagon to hypoglycemia in Hypoglycemia Challenge #1. Glucagon values were collected in parallel with BG sampling (BG results shown in FIG. 3 to FIG. 6). From glucagon measures in saphenous blood samples collected at basal condition (t=−60 min), and from 0 to 100 minutes after insulin dosing, the basal and peak values measured over this time course is shown in FIG. 7A, with Tmax values describing the average time of peak response in each group shown in FIG. 7B. Peak glucagon values were 83, 180 and 175 pg/mL in the Vehicle Control, Compound 4 and Compound 24 treatment groups, respectively. The difference in peak values for treatment groups compared to Vehicle Control was significant (Bonferroni post-hoc test, 2-Way ANOVA). Average Tmax values were in the range of 15-36 minutes after insulin dosing for all groups. The results indicate that treatment resulted in a stronger glucagon secretory response to hypoglycemia in diabetic rats, compared to the vehicle control group. Graphs present average±standard deviation values. Sample sizes were N=9 for Compound 4 and Compound 24 treatment groups, and N=6 for the Vehicle Control group.

Hypoglycemic Challenge #2

Portal Blood Glucagon Concentration at Hypoglycemia During Hypoglycemia Challenge #2

Figure 8:
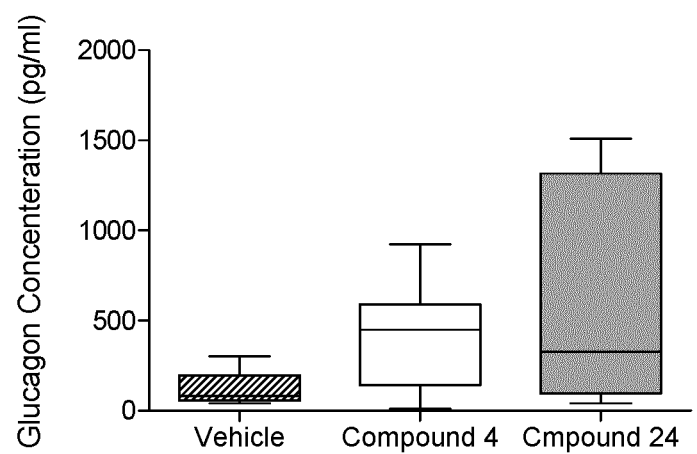
FIG. 8 is a graph showing portal blood glucagon concentrations at hypoglycemia in STZ diabetic Sprague Dawley rats treated with either vehicle control, Compound 4, or Compound 24 during Hypoglycemia Challenge #2.

FIG. 8 shows the portal glucagon concentrations at hypoglycemia during Hypoglycemia Challenge #2. One week after receiving a first insulin challenge to induce hypoglycemia (FIGS. 3-7), rats received a 20 U/kg insulin challenge to induce hypoglycemia. Once hypoglycemia was achieved (target BG 2.5 mM), the glucagon concentration in the subjects' portal blood was determined. The average concentration in the rats treated with Vehicle Control was 117 pg/mL. In contrast, the average values in the groups treated with Compound 4 or Compound 24 were 462 and 801 pg/mL, respectively, indicating that treatment promoted glucagon secretion from the pancreas of diabetic rats in hypoglycemia. In the Vehicle Control group, one sample was excluded from analysis due to contamination (N=5) while the treatment groups included N=9 subjects each. The Box plot shows the median, interquartile range and Whiskers indicate the minimum and maximum values for each group.

INFORMAL SEQUENCE TABLE WITH FREE TEXT
SEQ ID NO: 1
H-Cpa-cyclo[DCys-Tyr-DCit-Lys-Thr-Cys]-DTyr-NH$_2$
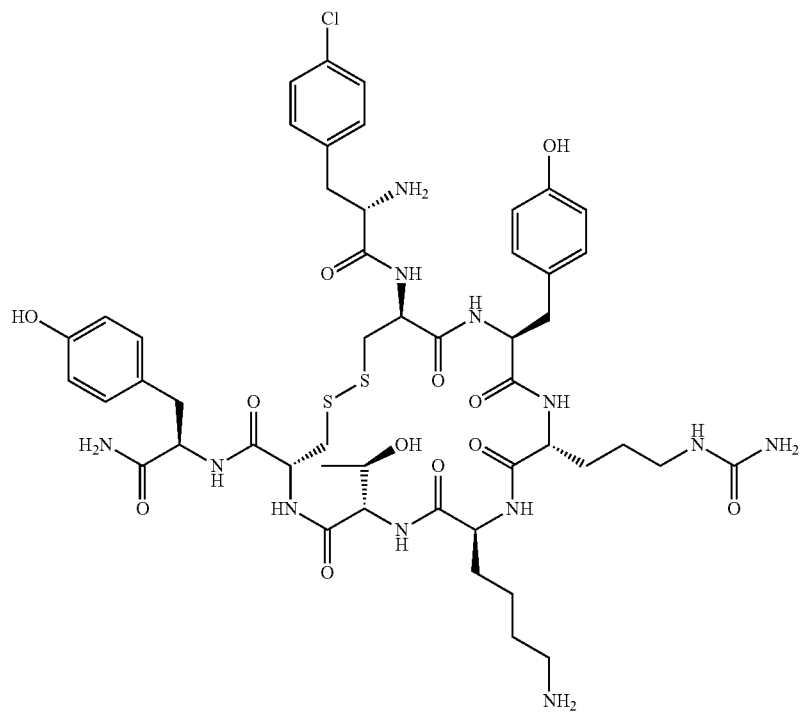 [SMILES: C[C@@H](O)[C@@H]1NC(=O)[C@H](CCCCN)NC(=O)[C@@H](CCCNC(N)=O)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 2
H-Cpa-cyclo[DCys-Tyr-DHoCit-Lys-Thr-Cys]-DTyr-NH$_2$
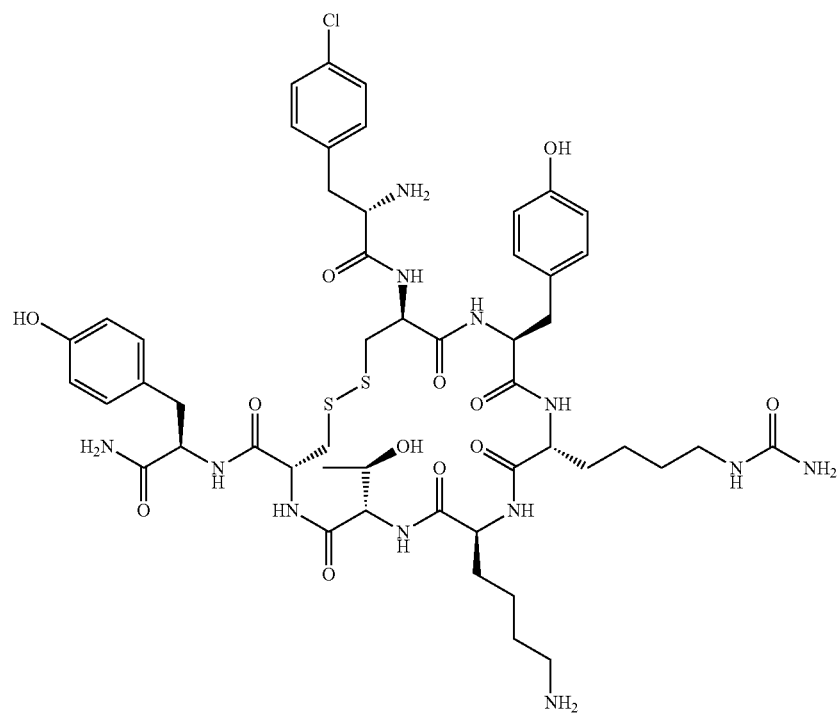 [SMILES: C[C@@H](O)[C@@H]1NC(=O)[C@H](CCCCN)NC(=O)[C@@H](CCCCNC(N)=O)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

-continued
INFORMAL SEQUENCE TABLE WITH FREE TEXT
SEQ ID NO: 3    H-Cpa-cyclo[DCys-Tyr-D-(N$^\varepsilon$-nicotinoyl)Lys-Lys-Thr-Cys]-DTyr-NH$_2$
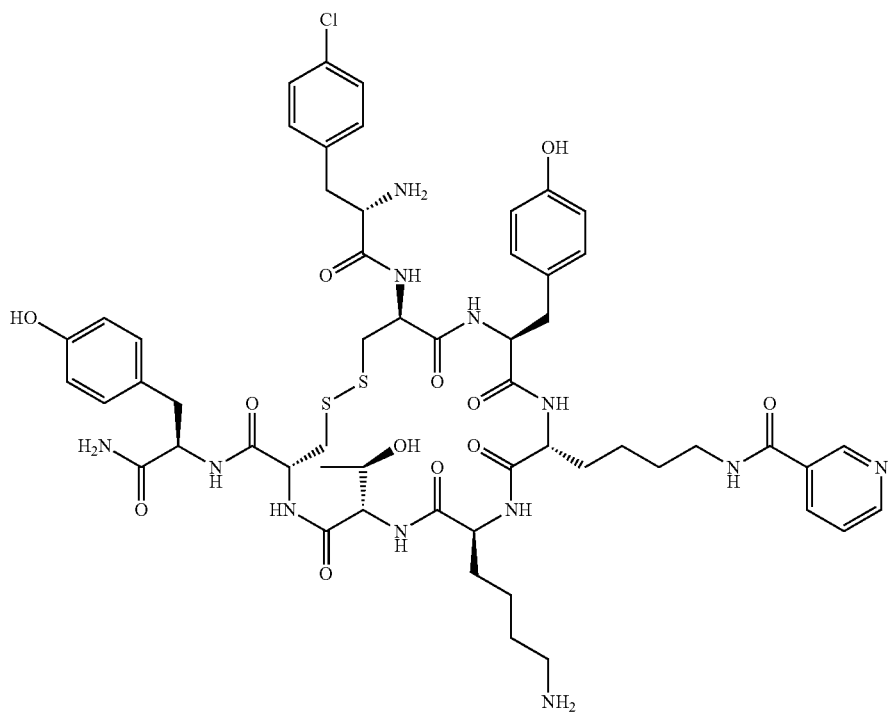 [SMILES: C[C@@H](O)[C@@H]1NC(=O)[C@H](CCCCN)NC(=O)[C@@H](CCCCNC(=O)c2cccnc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 4    H-Cpa-cyclo[DCys-Tyr-D-(4-carbamoyl)Phe-Lys-Thr-Cys]-DTyr-NH$_2$
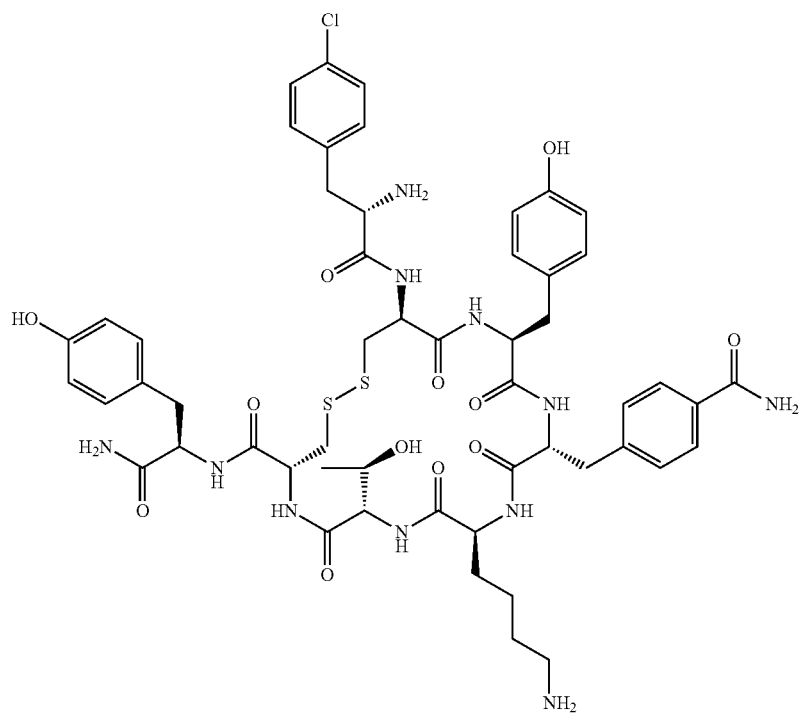 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

| INFORMAL SEQUENCE TABLE WITH FREE TEXT | | |
|---|---|---|
| SEQ ID NO: 5 | 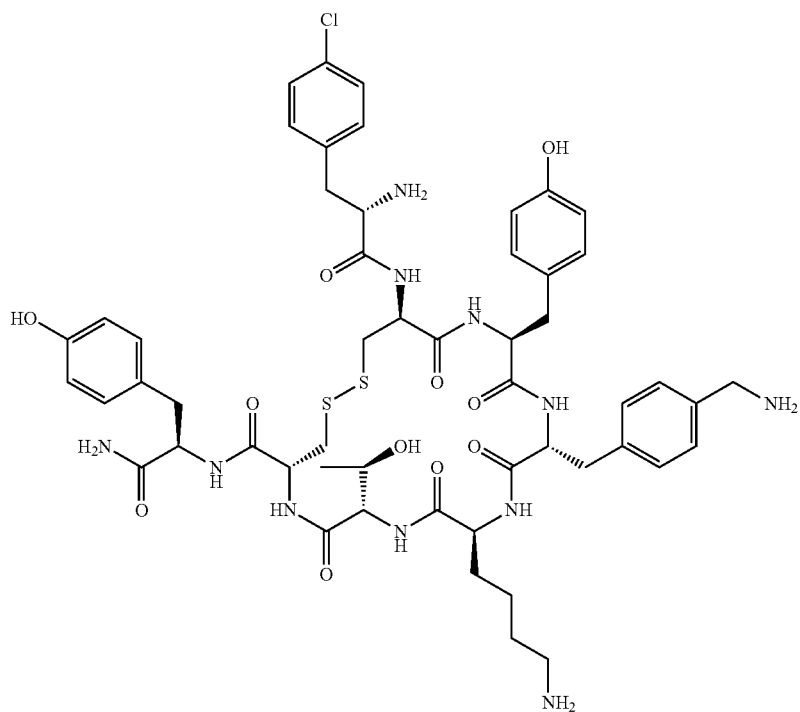 [SMILES: C[C@@H](O)[C@@H]1NC(=O)[C@H](CCCCN)NC(=O)[C@@H](Cc2ccc(CN)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O] | H-Cpa-cyclo[DCys-Tyr-D-(4-aminomethyl)Phe-Lys-Thr-Cys]-DTyr-NH$_2$ |
| SEQ ID NO: 6 | 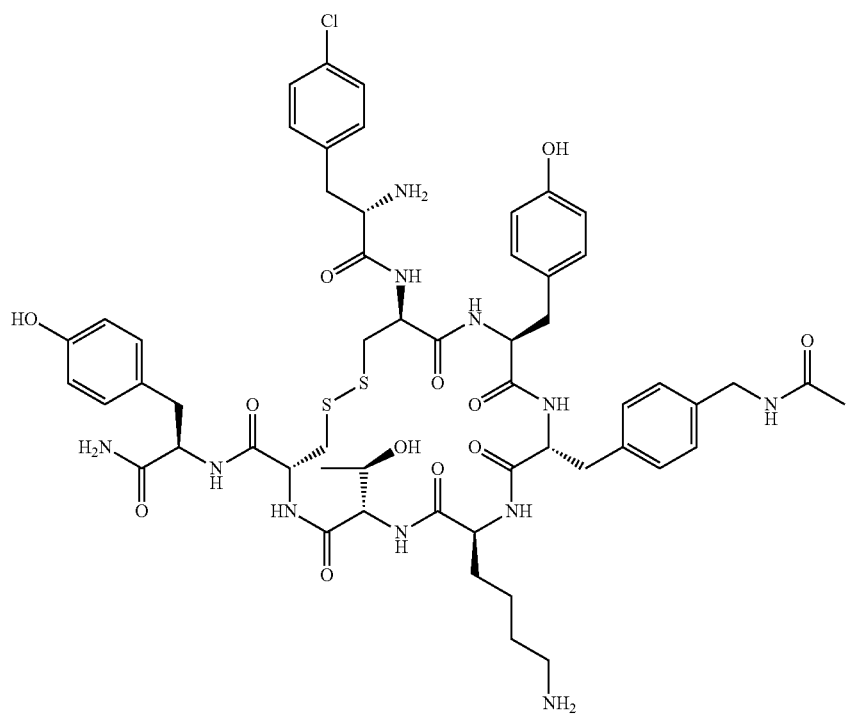 [SMILES: CC(=O)NCc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1] | H-Cpa-cyclo[DCys-Tyr-D-(4-acetamidomethyl)Phe-Lys-Thr-Cys]-DTyr-NH$_2$ |

INFORMAL SEQUENCE TABLE WITH FREE TEXT
SEQ ID NO: 7
H-Cpa-cyclo[DCys-Tyr-D-(4-ureido-methyl)Phe-Lys-Thr-Cys]-DTyr-NH2
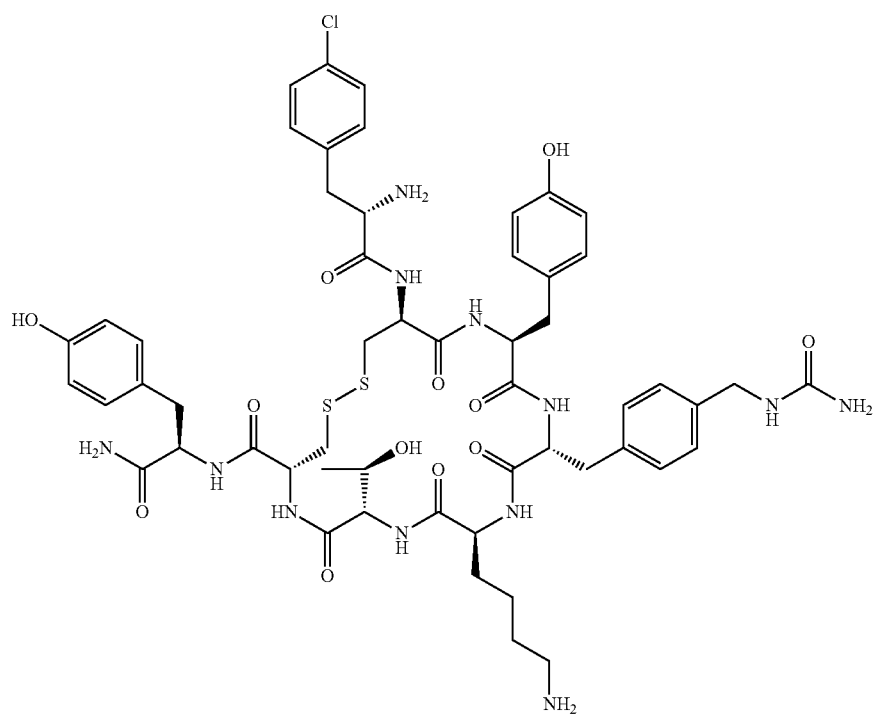 [SMILES: C[C@@H](O)[C@@H]1NC(=O)[C@H](CCCCN)NC(=O)[C@@H](Cc2ccc(CNC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 8
H-Cpa-cyclo[DCys-Tyr-D-4-(Gly)Aph-Lys-Thr-Cys]-DTyr-NH2
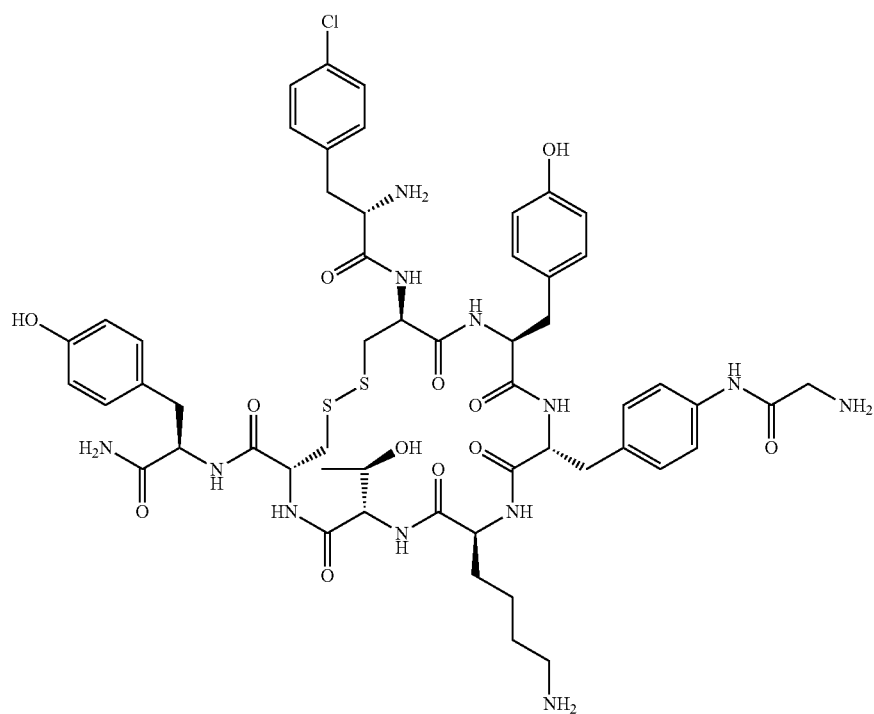 [SMILES: C[C@@H](O)[C@@H]1NC(=O)[C@H](CCCCN)NC(=O)[C@@H](Cc2ccc(NC(=O)CN)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

| INFORMAL SEQUENCE TABLE WITH FREE TEXT | |
|---|---|
| SEQ ID NO: 9 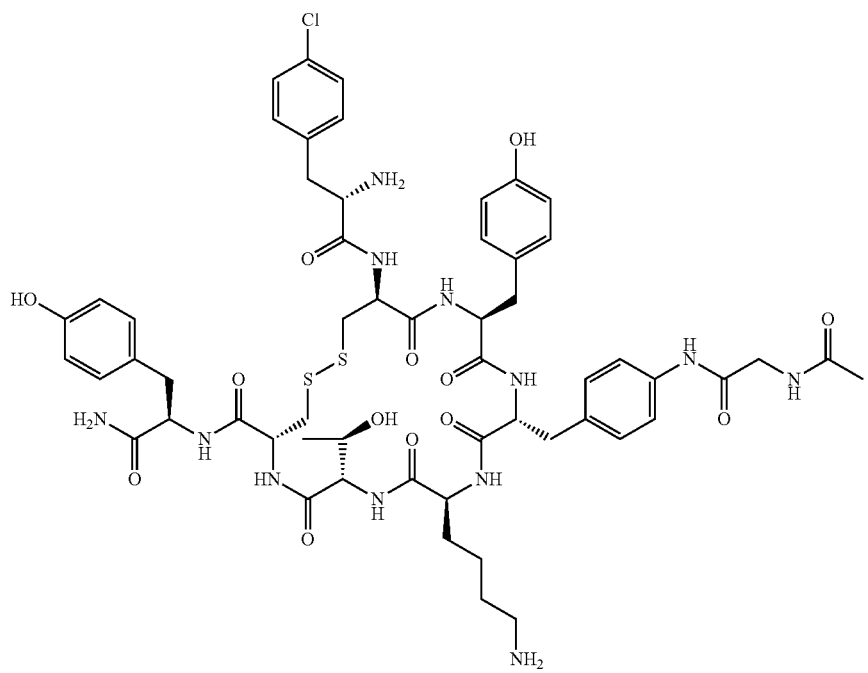 [SMILES: CC(=O)NCC(=O)Nc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1] | H-Cpa-cyclo[DCys-Tyr-D-4-(Gly-Ac)Aph-Lys-Thr-Cys]-DTyr-NH₂ |
| SEQ ID NO: 10 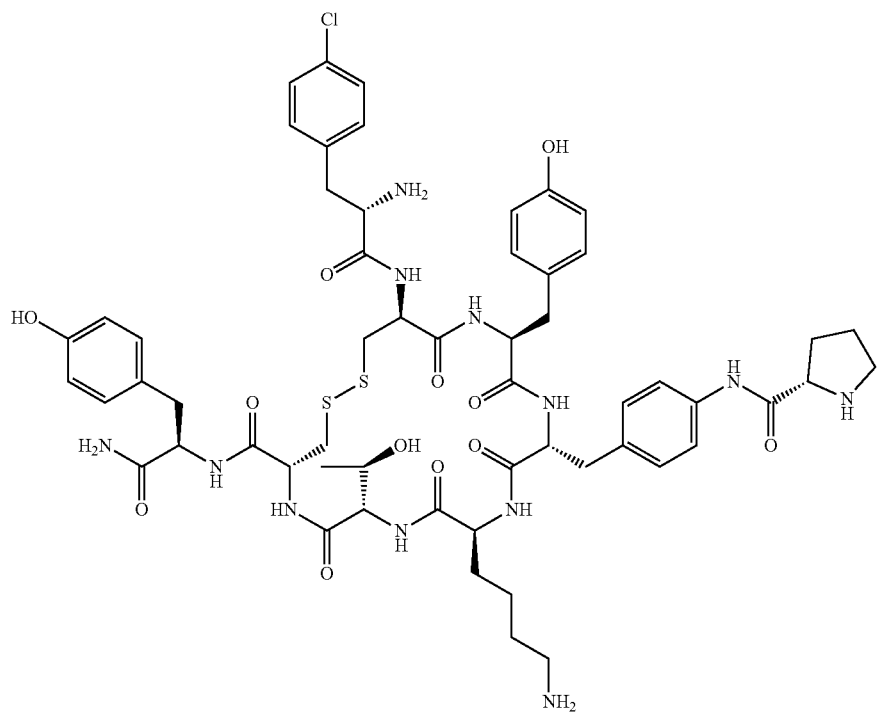 [SMILES: C[C@@H](O)[C@@H]1NC(=O)[C@H](CCCCN)NC(=O)[C@@H](Cc2ccc(NC(=O)[C@@H]3CCCN3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O] | H-Cpa-cyclo[DCys-Tyr-D-4-(Pro)Aph-Lys-Thr-Cys]-DTyr-NH₂ |

INFORMAL SEQUENCE TABLE WITH FREE TEXT
SEQ ID NO: 11
H-Cpa-cyclo[DCys-Tyr-D-4-(2-(4-morpholinyl)ethyl)Aph-Lys-Thr-Cys]-DTyr-NH$_2$
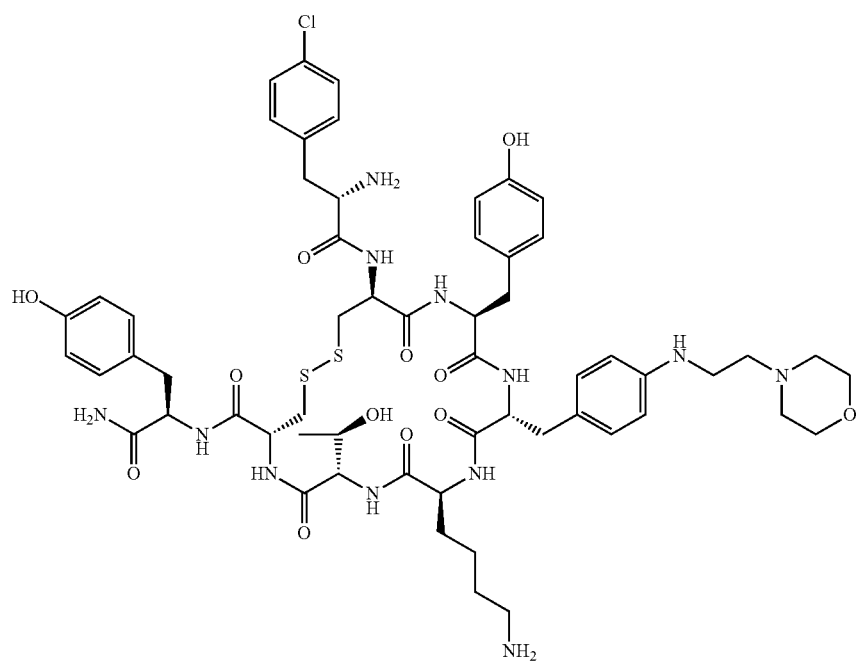 [SMILES: C[C@@H](O)[C@@H]1NC(=O)[C@H](CCCCN)NC(=O)[C@@H](Cc2ccc(NCCN3CCOCC3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 12
H-Cpa-cyclo[DCys-Tyr-D-4-(n-pentylamino)Phe-Lys-Thr-Cys]-DTyr-NH$_2$
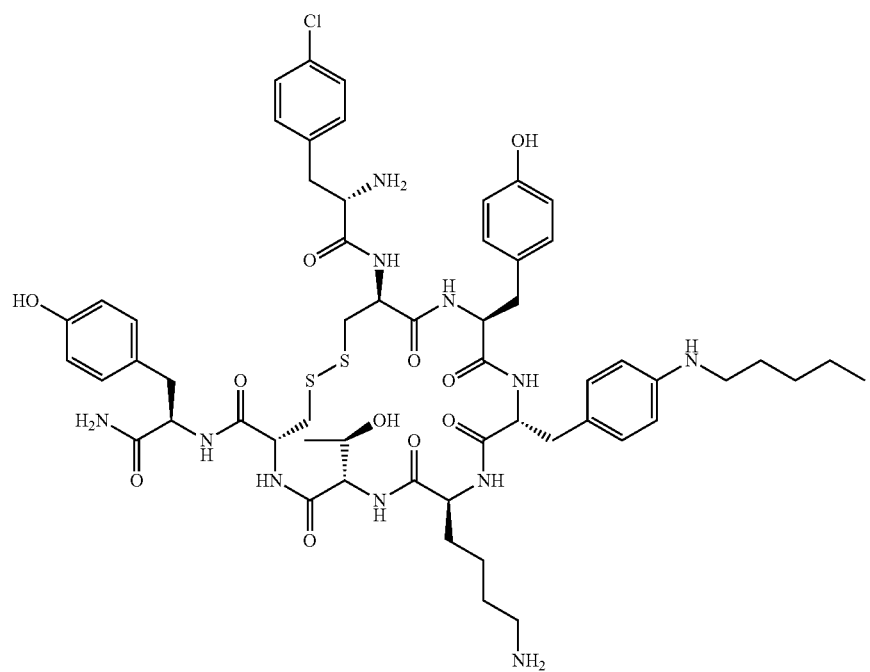 [SMILES: CCCCCNc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]

-continued
INFORMAL SEQUENCE TABLE WITH FREE TEXT
SEQ ID NO: 13
H-Cpa-cyclo[DCys-Tyr-D-(2-(4-morpholinyl)ethyl)Tyr-Lys-Thr-Cys]-DTyr-NH₂
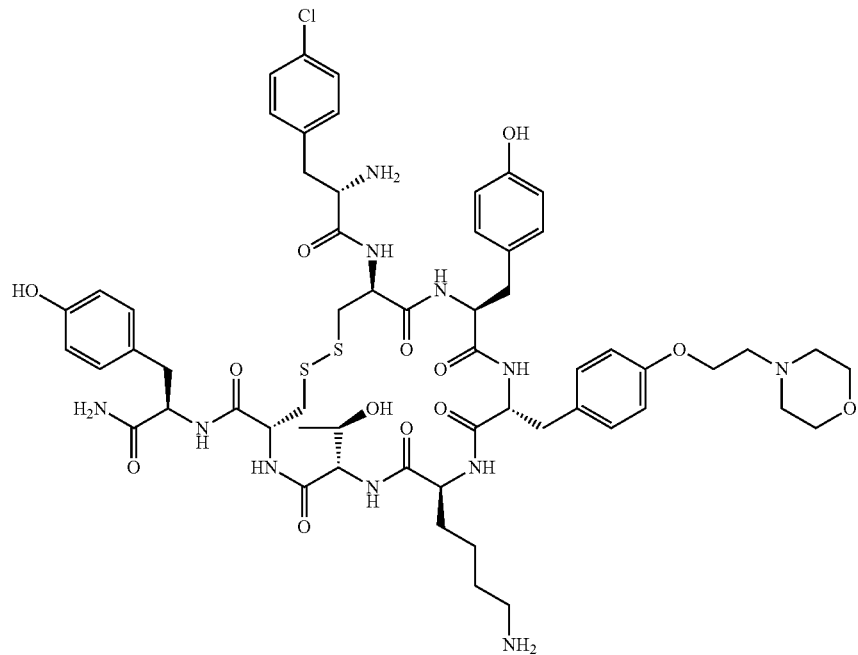 [SMILES: C[C@@H](O)[C@@H]1NC(=O)[C@H](CCCCN)NC(=O)[C@@H](Cc2ccc(OCCN3CCOCC3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 14
H-Cpa-cyclo[DCys-Tyr-D-4-(benzenesulfonyl)Aph-Lys-Thr-Cys]-DTyr-NH₂
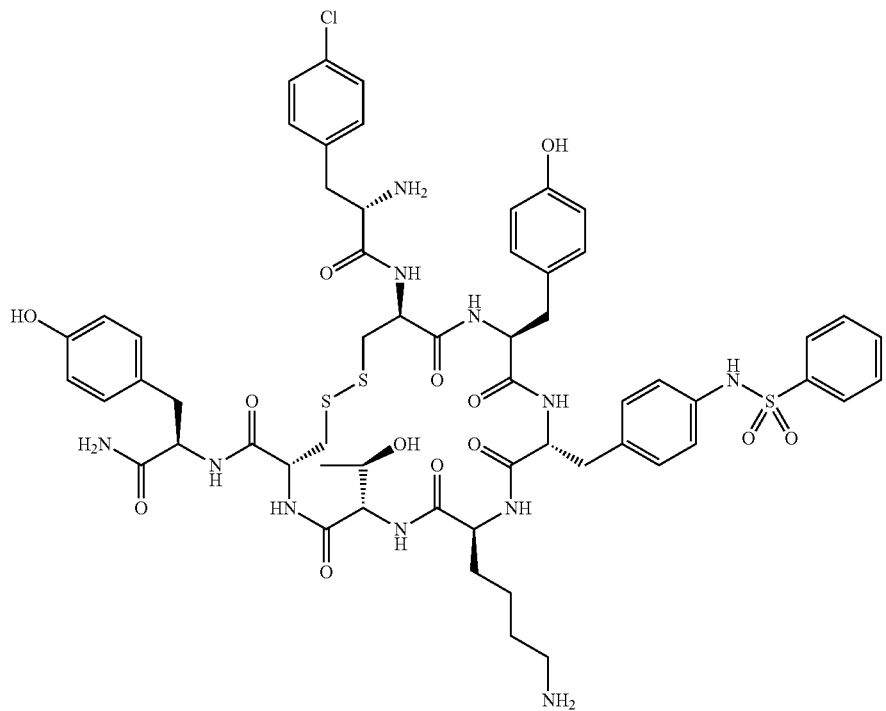 [SMILES: C[C@@H](O)[C@@H]1NC(=O)[C@H](CCCCN)NC(=O)[C@@H](Cc2ccc(NS(=O)(=O)c3ccccc3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

-continued
INFORMAL SEQUENCE TABLE WITH FREE TEXT
| SEQ ID NO: 15 | H-Cpa-cyclo[DCys-Tyr-D-4-(phenylureido)Phe-Lys-Thr-Cys]-DTyr-NH₂ |
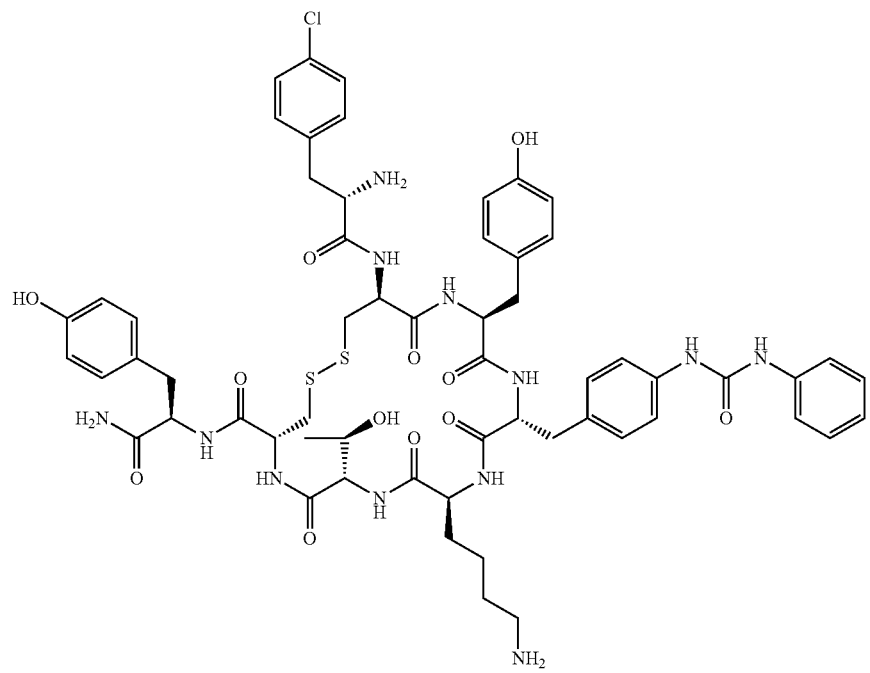 [SMILES: C[C@@H](O)[C@@H]1NC(=O)[C@H](CCCCN)NC(=O)[C@@H](Cc2ccc(NC(=O)Nc3ccccc3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
| SEQ ID NO: 16 | H-Cpa-cyclo[DCys-Tyr-D-4-(Ser)Aph-Lys-Thr-Cys]-DTyr-NH₂ |
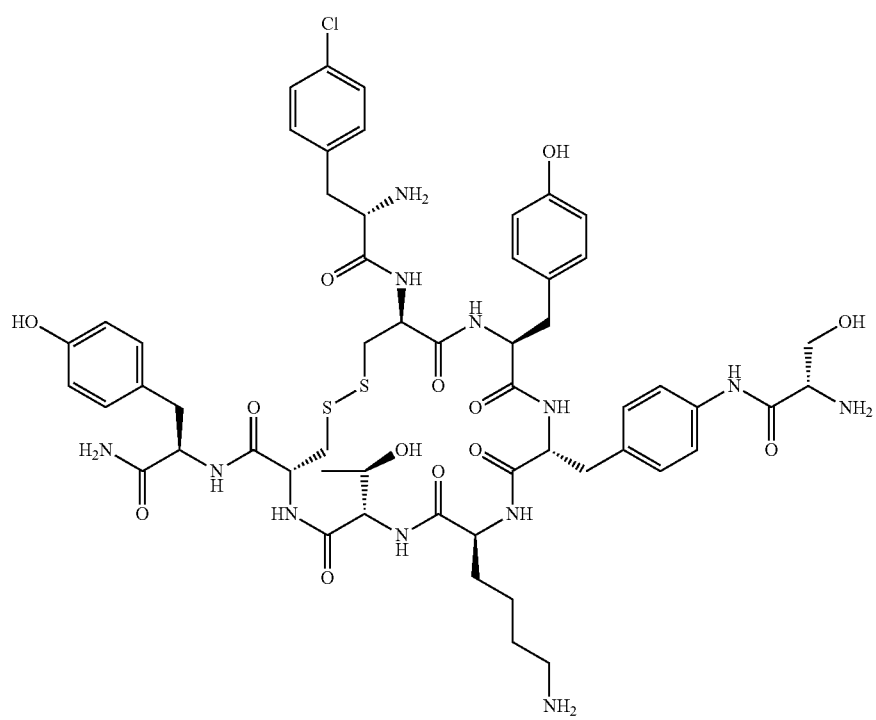 [SMILES: C[C@@H](O)[C@@H]1NC(=O)[C@H](CCCCN)NC(=O)[C@@H](Cc2ccc(NC(=O)[C@@H](N)CO)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

-continued
INFORMAL SEQUENCE TABLE WITH FREE TEXT
SEQ ID NO: 17
H-Cpa-cyclo[DCys-Tyr-D-4-(Lys)Aph-Lys-Thr-Cys]-DTyr-NH$_2$
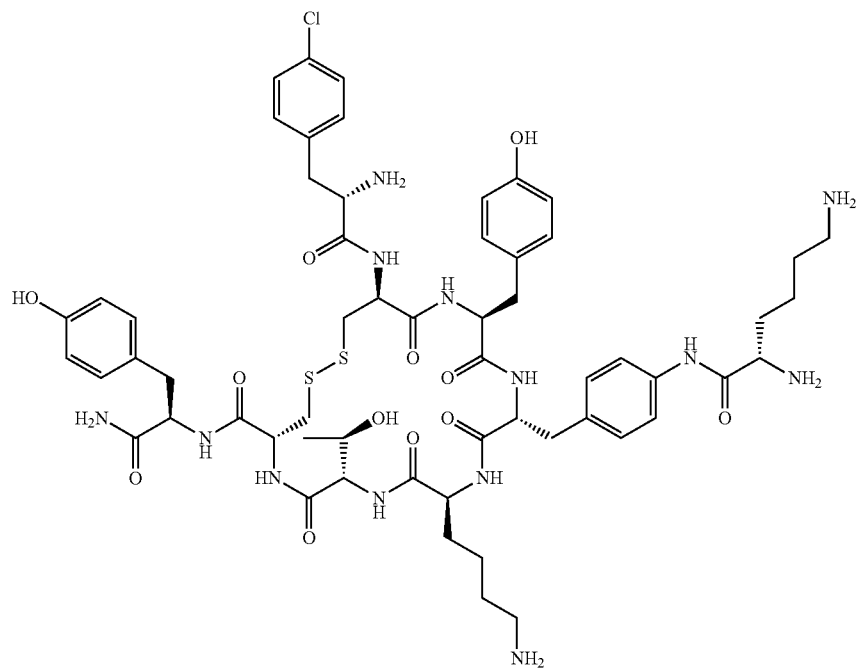 [SMILES: C[C@@H](O)[C@@H]1NC(=O)[C@H](CCCCN)NC(=O)[C@@H](Cc2ccc(NC(=O)[C@@H](N)CCCCN)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 18
H-Cpa-cyclo[DCys-Tyr-D-4-(Asp)Aph-Lys-Thr-Cys]-DTyr-NH$_2$
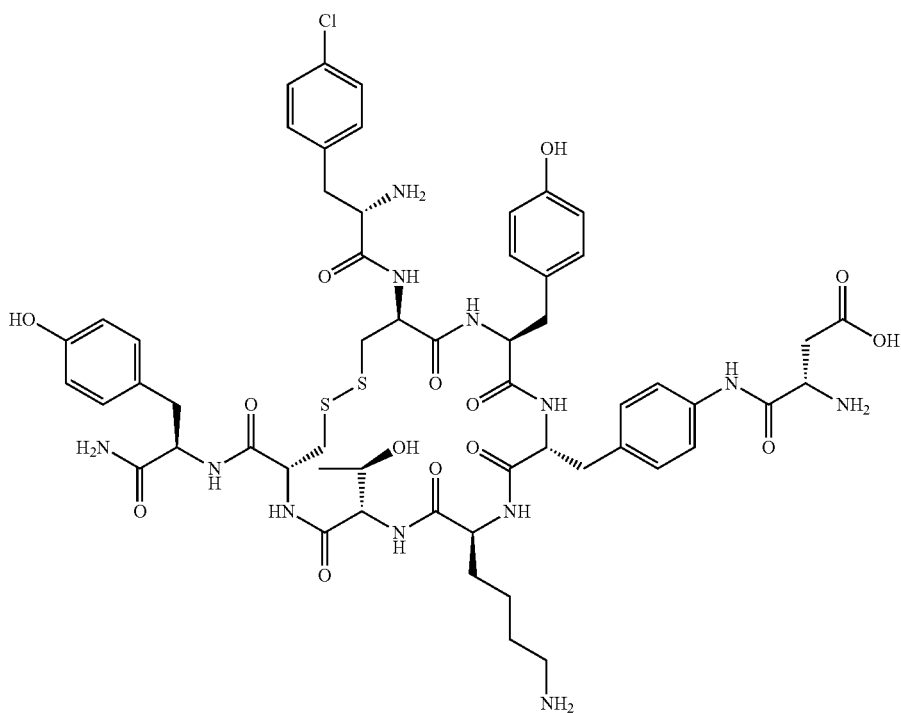 [SMILES: C[C@@H](O)[C@@H]1NC(=O)[C@H](CCCCN)NC(=O)[C@@H](Cc2ccc(NC(=O)[C@@H](N)CC(=O)O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

INFORMAL SEQUENCE TABLE WITH FREE TEXT
SEQ ID NO: 19
H-Cpa-cyclo[DCys-Tyr-D-4-(Asn)Aph-Lys-Thr-Cys]-DTyr-NH₂
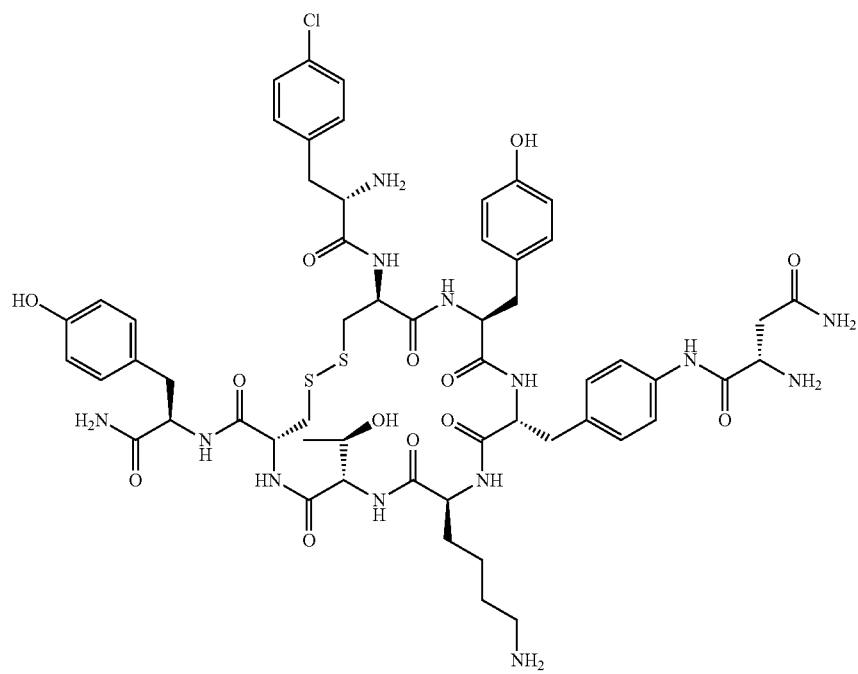 [SMILES: C[C@@H](O)[C@@H]1NC(=O)[C@H](CCCCN)NC(=O)[C@@H](Cc2ccc(NC(=O)[C@@H](N)CC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 20
H-Cpa-cyclo[DCys-Tyr-D-4-(Glu)Aph-Lys-Thr-Cys]-DTyr-NH₂
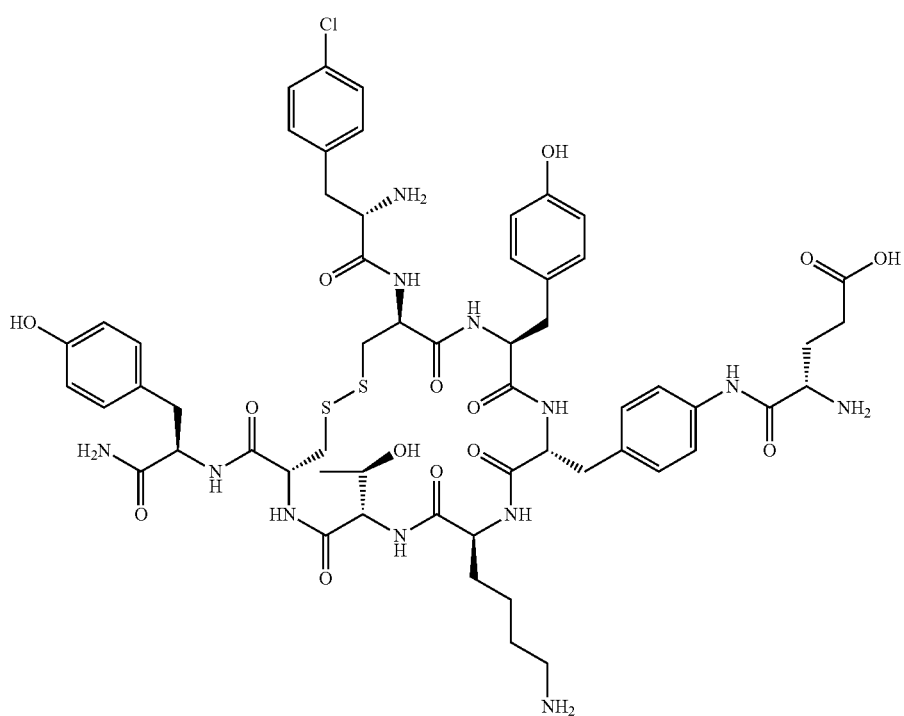 [SMILES: C[C@@H](O)[C@@H]1NC(=O)[C@H](CCCCN)NC(=O)[C@@H](Cc2ccc(NC(=O)[C@@H](N)CCC(=O)O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

INFORMAL SEQUENCE TABLE WITH FREE TEXT
SEQ ID NO: 21
H-Cpa-cyclo[DCys-Tyr-D-4-(Gln)Aph-Lys-Thr-Cys]-DTyr-NH$_2$
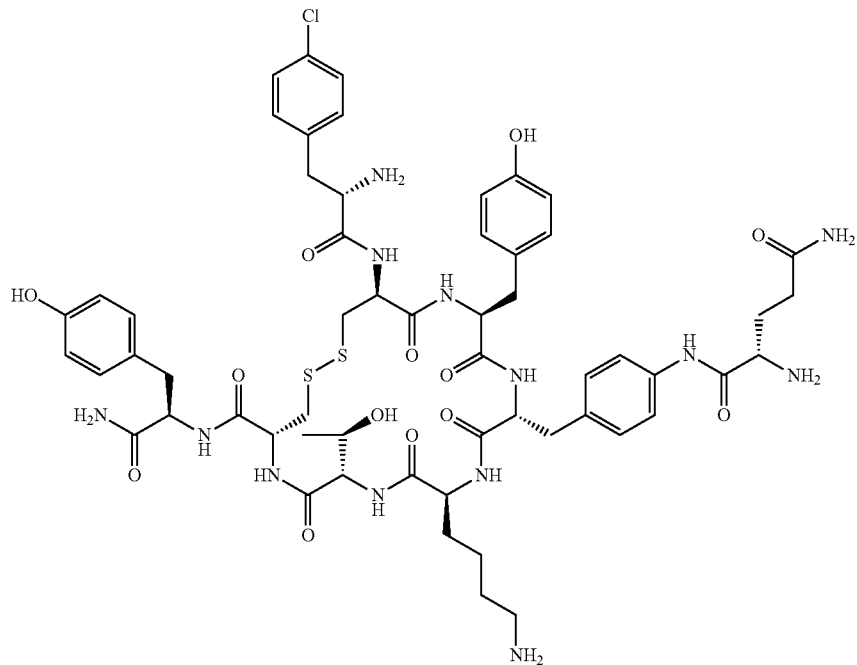 [SMILES: C[C@@H](O)[C@@H]1NC(=O)[C@H](CCCCN)NC(=O)[C@@H](Cc2ccc(NC(=O)[C@@H](N)CCC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 22
H-Cpa-cyclo[DCys-Tyr-D-4-(Cit)Aph-Lys-Thr-Cys]-DTyr-NH$_2$
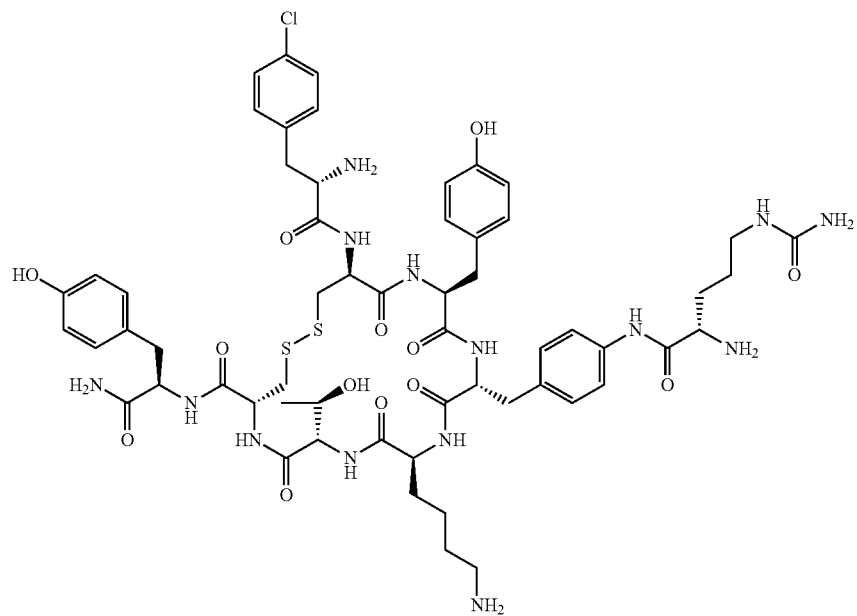 [SMILES: C[C@@H](O)[C@@H]1NC(=O)[C@H](CCCCN)NC(=O)[C@@H](Cc2ccc(NC(=O)[C@@H](N)CCCNC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]

| SEQ ID NO: 23 | H-Cpa-cyclo[DCys-Tyr-D-4-(Val)Aph-Lys-Thr-Cys]-DTyr-NH₂ |
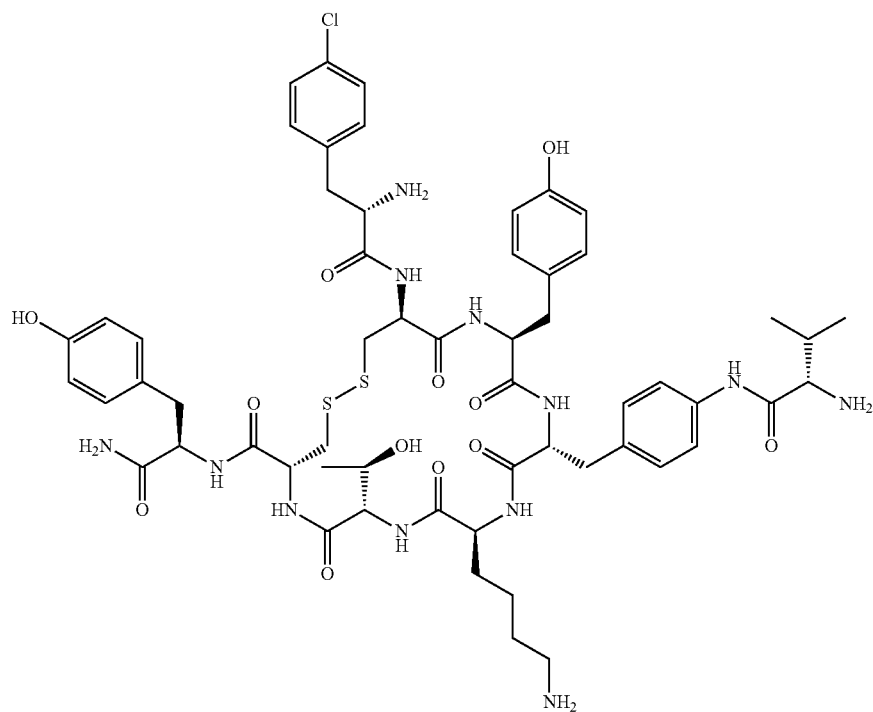 [SMILES: CC(C)[C@H](N)C(=O)Nc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]
| SEQ ID NO: 24 | H-Cpa-cyclo[DCys-Tyr-D-(4-carbamoyl)Phe-(Nᵉ-Me)Lys-Thr-Cys]-DTyr-NH₂ |
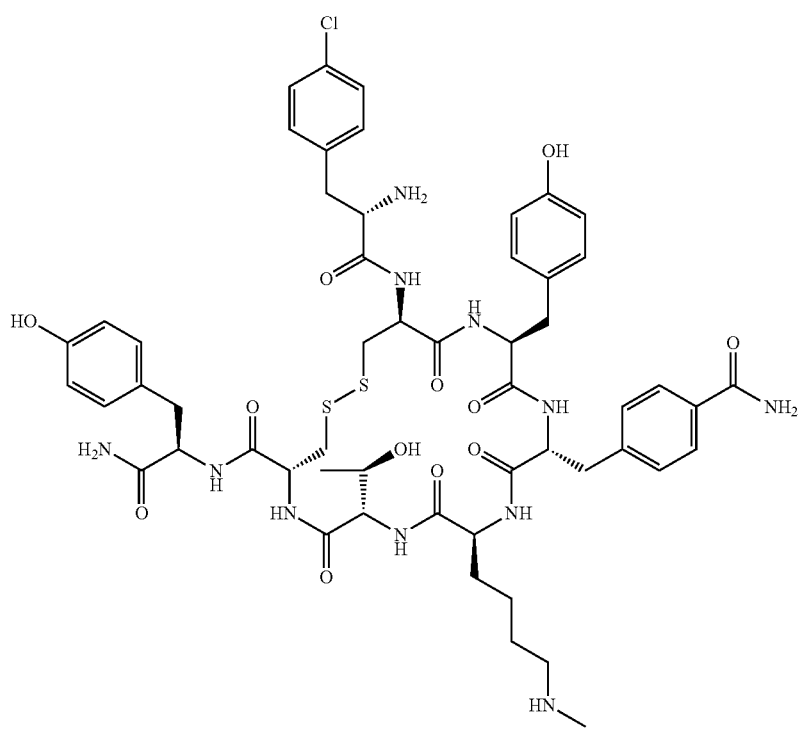 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC(=O)[C@H]([C@@H](C)O)NC1=O]

INFORMAL SEQUENCE TABLE WITH FREE TEXT
SEQ ID NO: 25 — H-Cpa-cyclo[DCys-Tyr-D-4-(phenylureido)Phe-(N-Me)Lys-Thr-Cys]-DTyr-NH$_2$
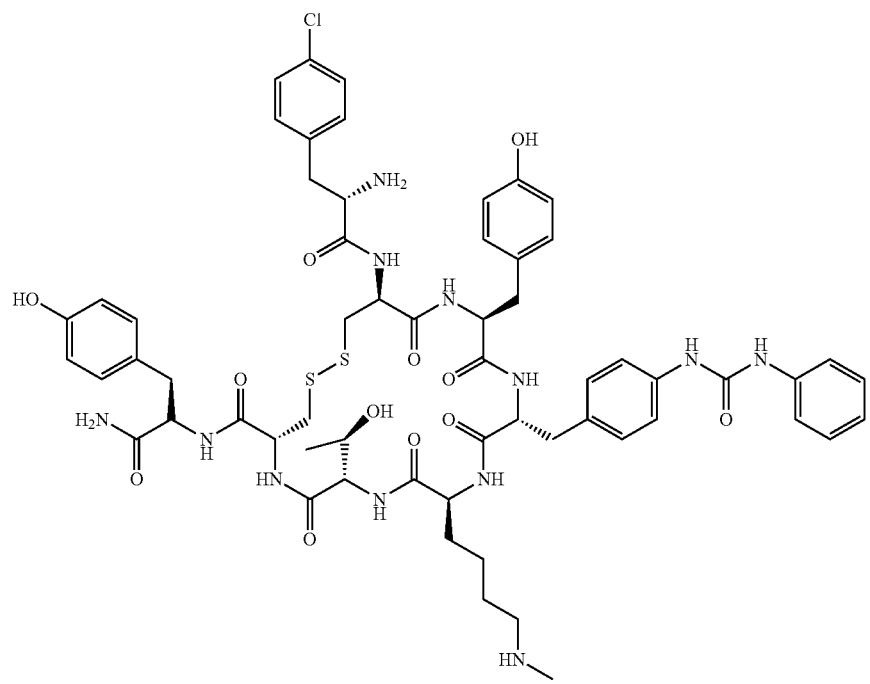
SEQ ID NO: 26 — H-Cpa-cyclo[DCys-Tyr-D-(4-carbamoyl)Phe-(N-Acetyl)Lys-Thr-Cys]-DTyr-NH$_2$
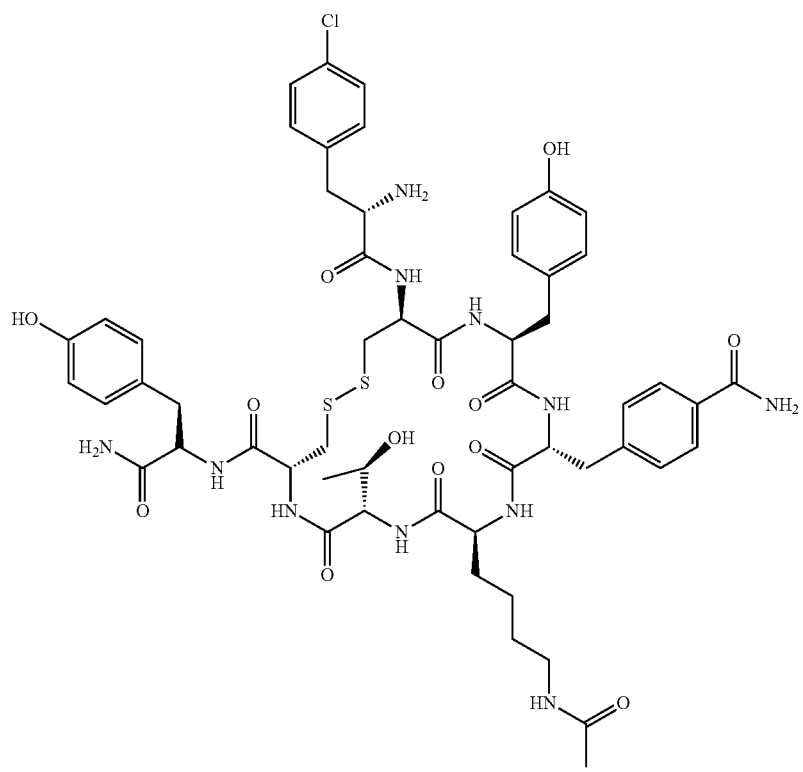

INFORMAL SEQUENCE TABLE WITH FREE TEXT
SEQ ID NO: 27
H-Cpa-cyclo[DCys-Tyr-D-(4-Benzamidophenyl)Phe-Lys-Thr-Cys]-DTyr-NH$_2$
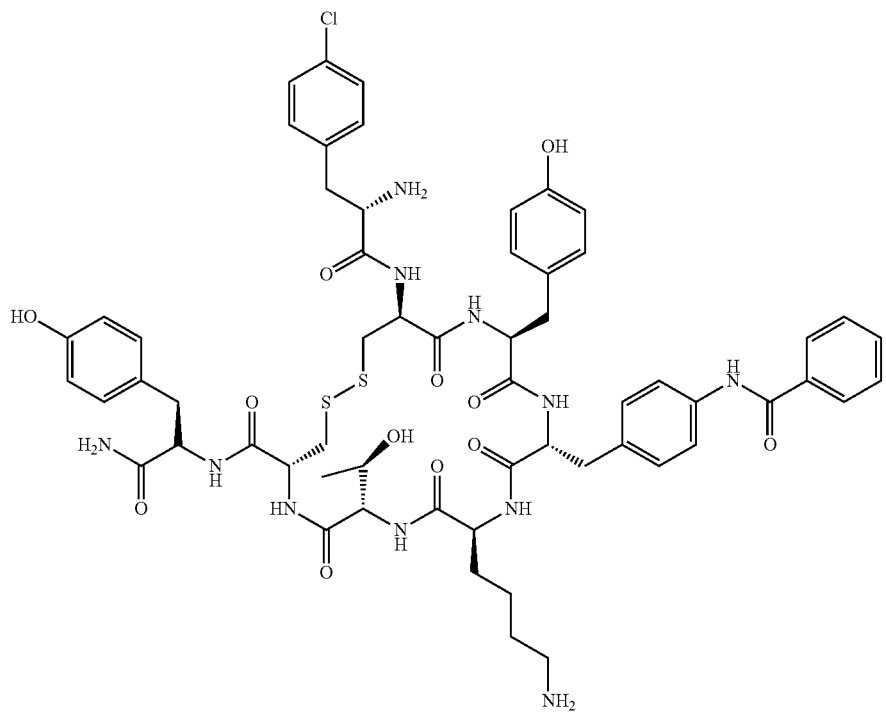
SEQ ID NO: 28
H-Cpa-cyclo[DCys-Tyr-D-(4-(4-methoxyphenyl)ureido)Phe-Lys-Thr-Cys]-DTyr-NH$_2$
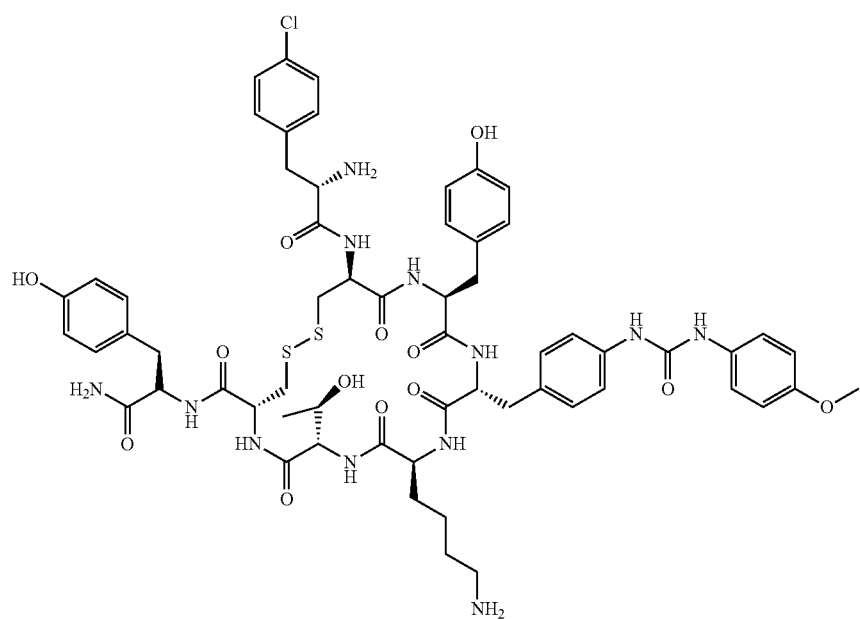

-continued
INFORMAL SEQUENCE TABLE WITH FREE TEXT
SEQ ID NO: 29
H-Cpa-cyclo[DCys-Tyr-D-(4-carbamoyl)Phe-Arg-Thr-Cys]-DTyr-NH₂
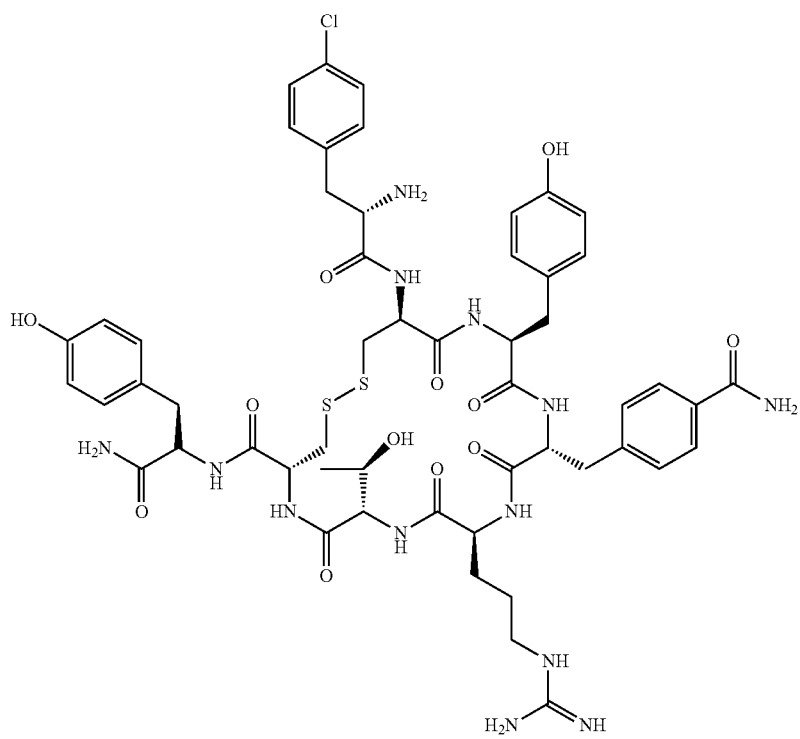
SEQ ID NO: 30
H-Cpa-cyclo[DCys-Tyr-D-(N-nicotinoyl)Lys-(N-Me)Lys-Thr-Cys]-DTyr-NH₂
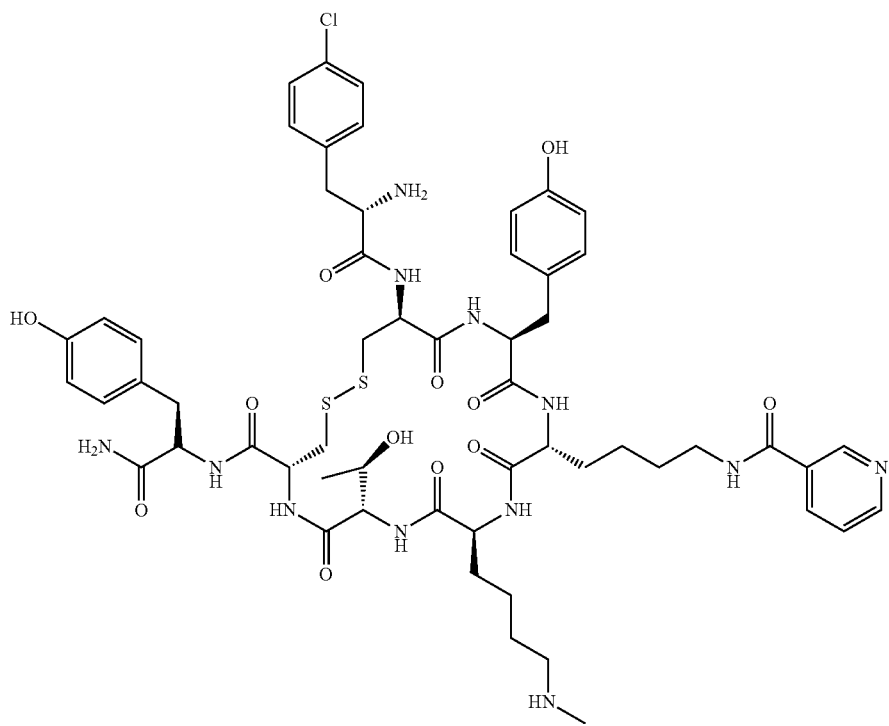

INFORMAL SEQUENCE TABLE WITH FREE TEXT
SEQ ID NO: 31
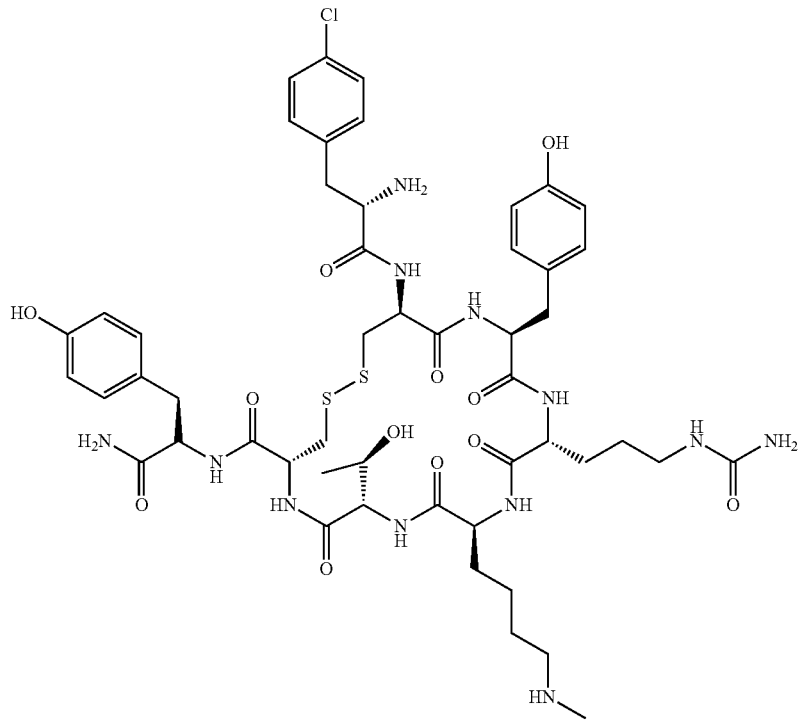
H-Cpa-cyclo[DCys-Tyr-D-Cit-(N-Me)Lys-Thr-Cys]-DTyr-NH$_2$
SEQ ID NO: 32
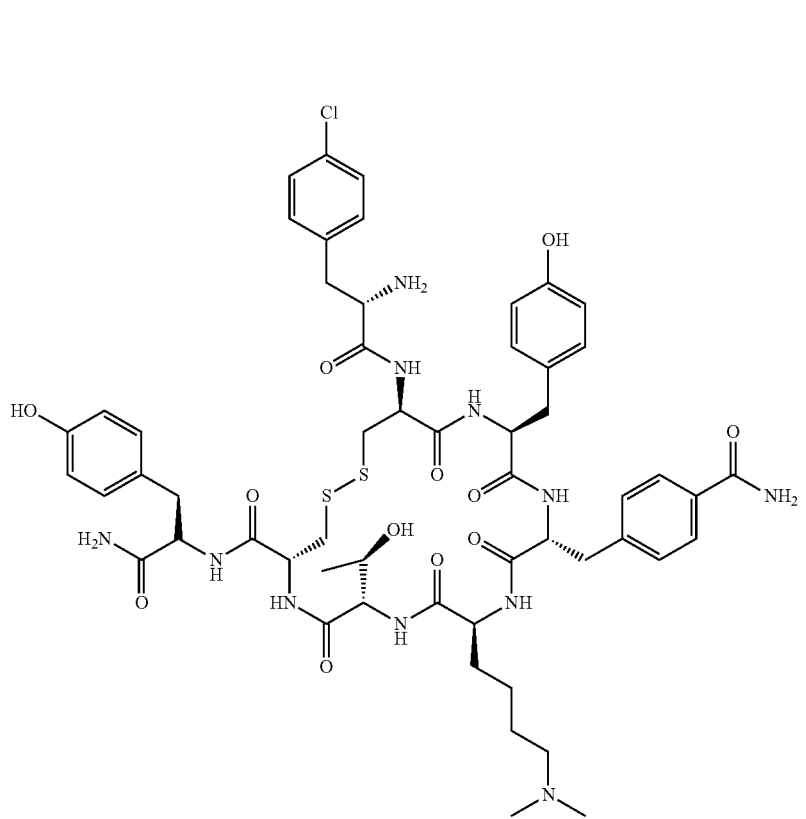
H-Cpa-cyclo[DCys-Tyr-D-(4-carbamoyl)Phe-(N-diMe)Lys-Thr-Cys]-DTyr-NH$_2$

INFORMAL SEQUENCE TABLE WITH FREE TEXT
SEQ ID NO: 33
H-Cpa-cyclo[DCys-Tyr-D-4-(carbamoyl)Phe-Lys-Val-Cys]-DTyr-NH₂
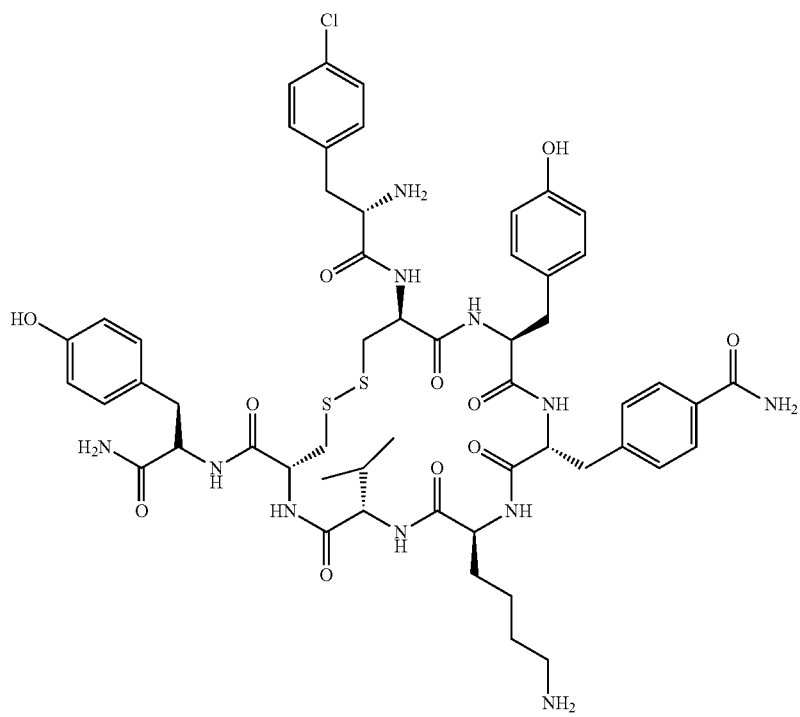
SEQ ID NO: 34
H-Cpa-cyclo[DCys-Tyr-D-4-(carbamoyl)Phe-Lys-tBu-Gly-Cys]-DTyr-NH₂
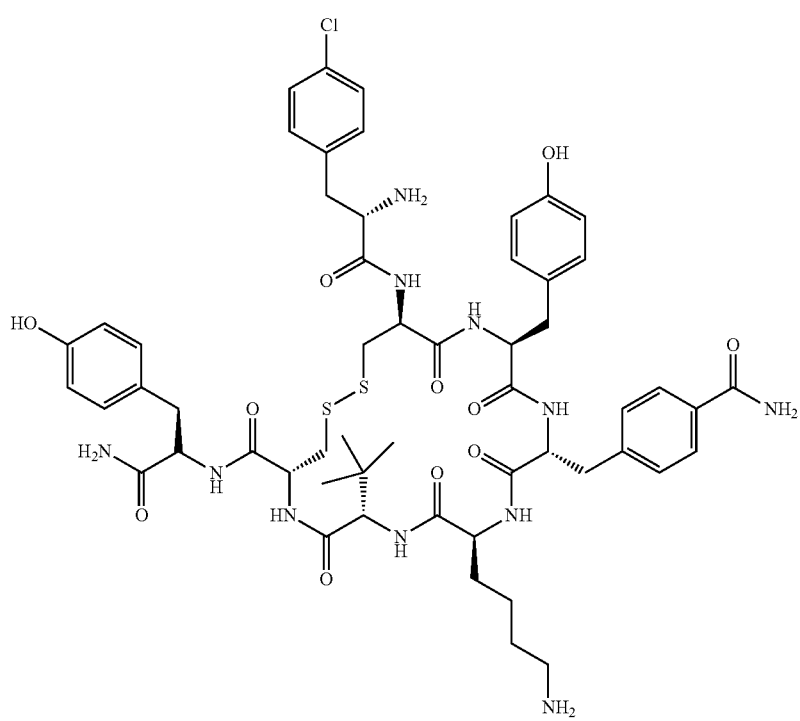

INFORMAL SEQUENCE TABLE WITH FREE TEXT
SEQ ID NO: 35
H-Cpa-cyclo[DCys-Phe-D-(4-carbamoyl)Phe-Lys-Thr-Cys]-DTyr-NH$_2$
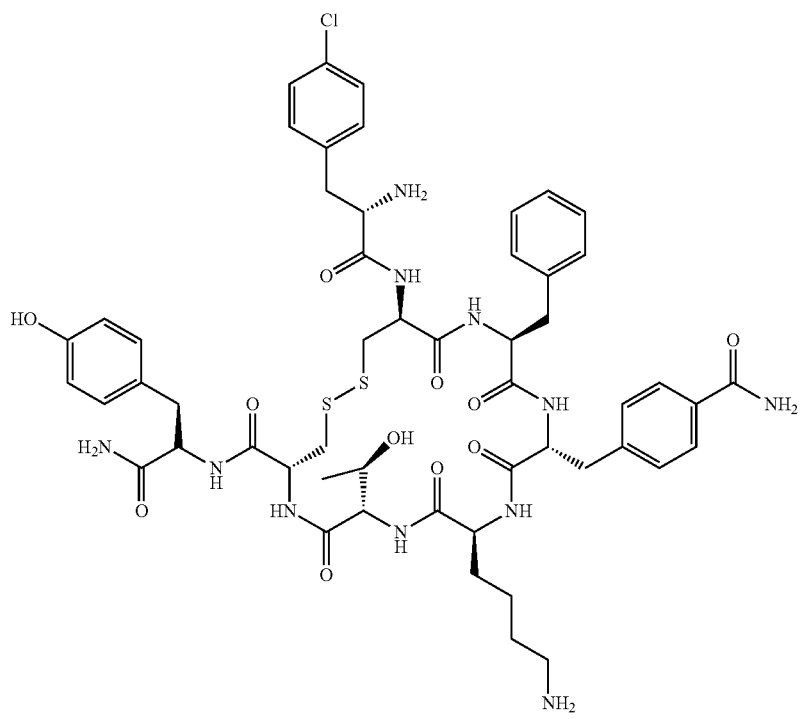
SEQ ID NO: 36
H-Cpa-cyclo[DCys-Cpa-D-(4-carbamoyl)Phe-Lys-Thr-Cys]-DTyr-NH$_2$
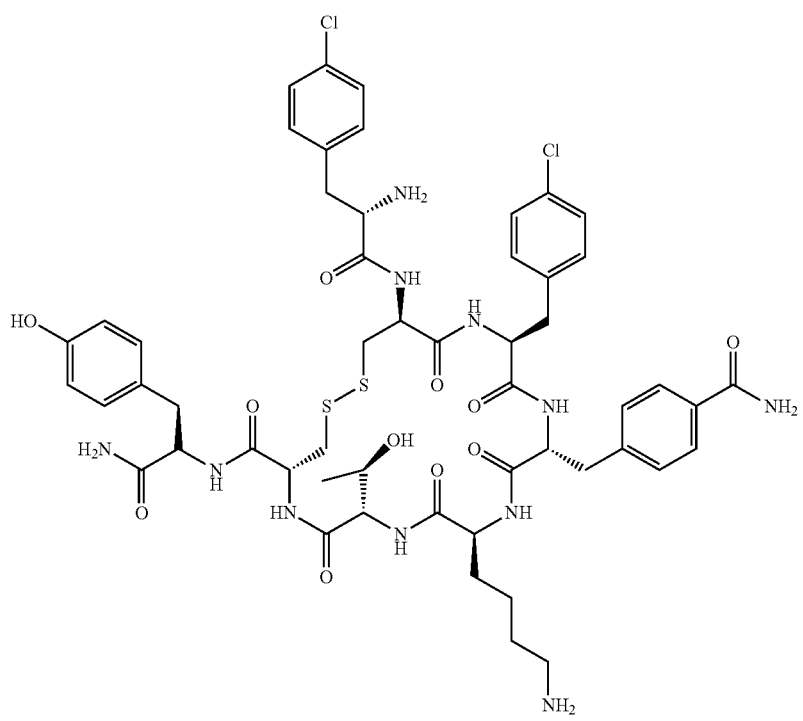

INFORMAL SEQUENCE TABLE WITH FREE TEXT
SEQ ID NO: 37
H-Cpa-cyclo[DCys-Tyr-D-(4-carbamoyl)Phe-Lys-Ser-Cys]-DTyr-NH₂
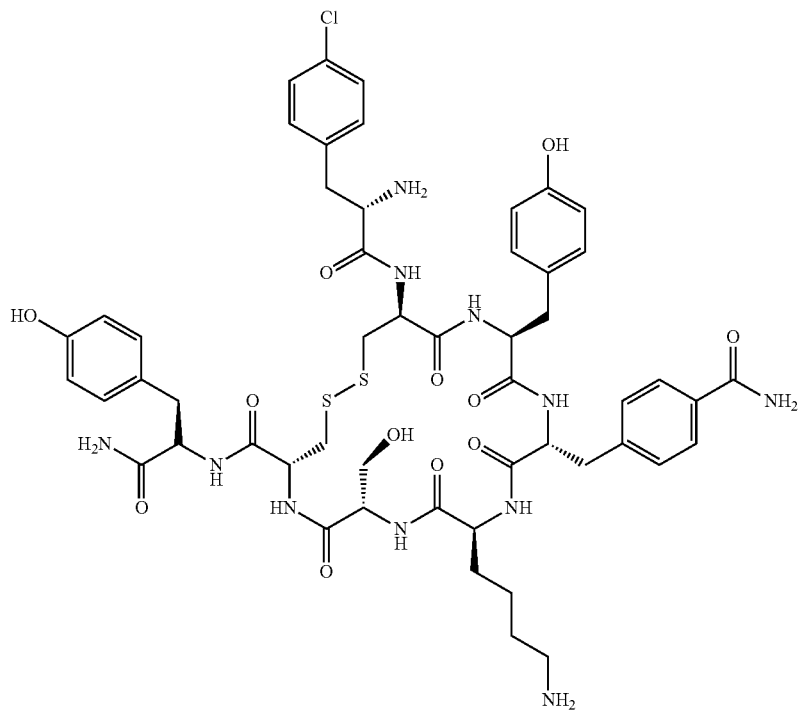
SEQ ID NO: 38
H-Cpa-cyclo[DCys-4-OMe-Phe-D-(4-carbamoyl)Phe-Lys-Thr-Cys]-DTyr-NH₂
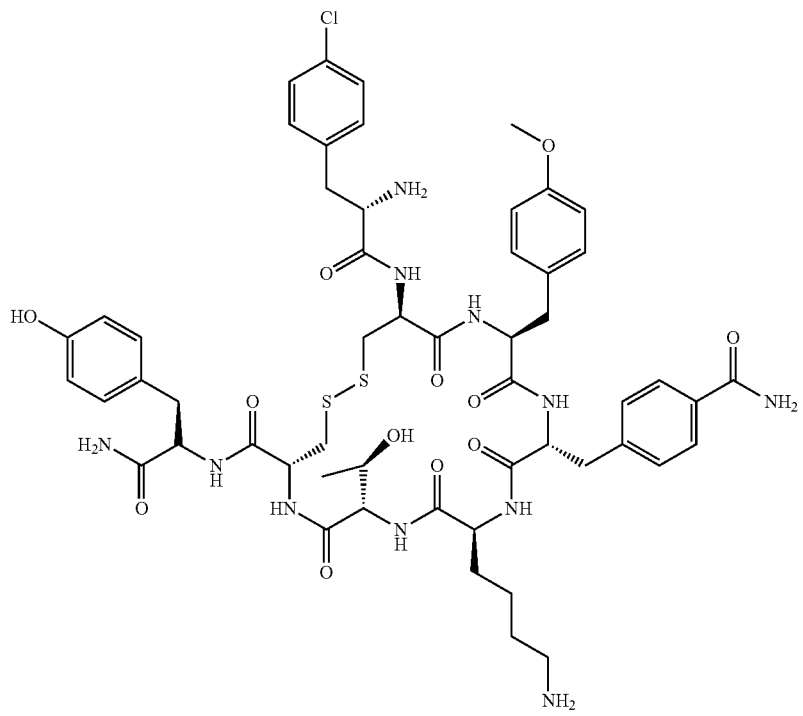

INFORMAL SEQUENCE TABLE WITH FREE TEXT
SEQ ID NO: 39
H-Cpa-cyclo[Cys-Tyr-D-(4-carbamoyl)Phe-Lys-Thr-Cys]-DTyr-NH₂
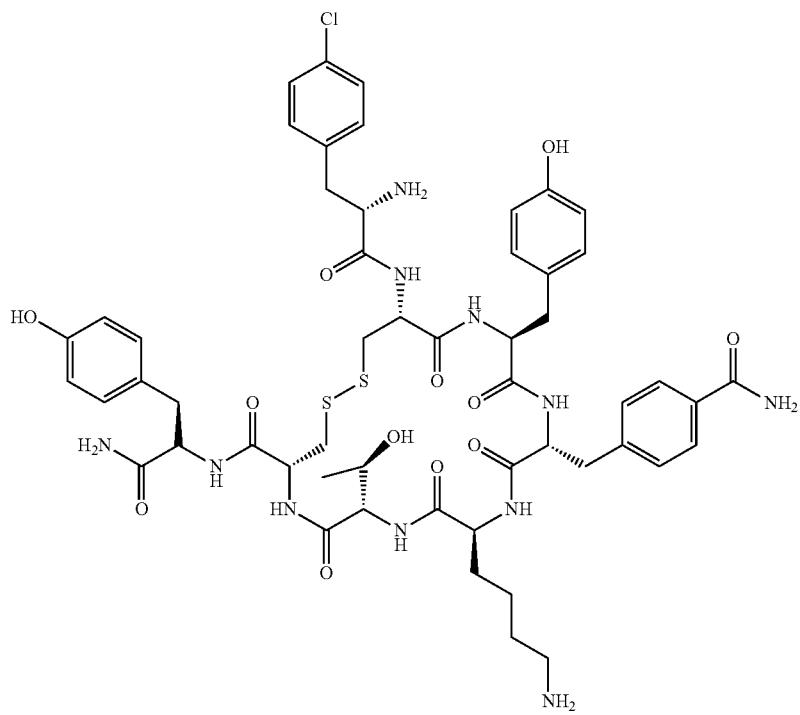
SEQ ID NO: 40
H-Cpa-cyclo[DCys-Tyr-D-(4-carbamoyl)Phe-Lys-Thr-Cys]-DPhe-NH₂
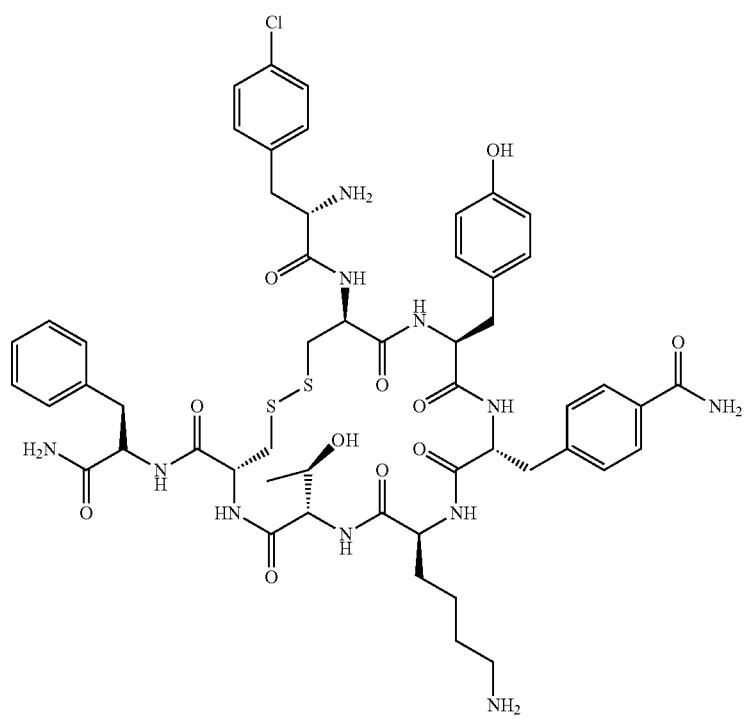

INFORMAL SEQUENCE TABLE WITH FREE TEXT
SEQ ID NO: 41
H-Cpa-cyclo[DCys-Phe-D-(4-carbamoyl)Phe-Lys-Thr-Cys]-DPhe-NH$_2$
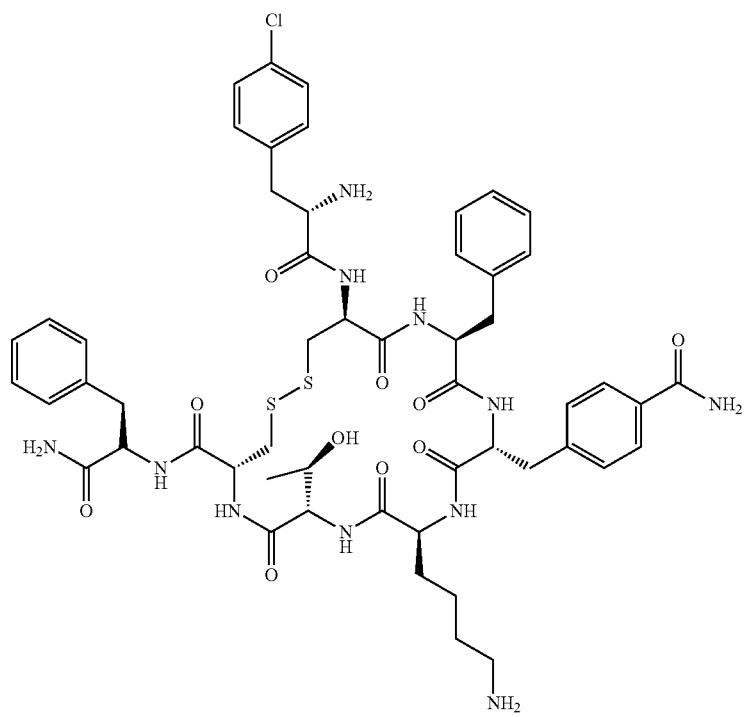
SEQ ID NO: 42
H-Cpa-cyclo[DCys-Tyr-D-(4-carbamoyl)Phe-Lys-Thr-Cys]-4-Cl-D-Phe-NH$_2$
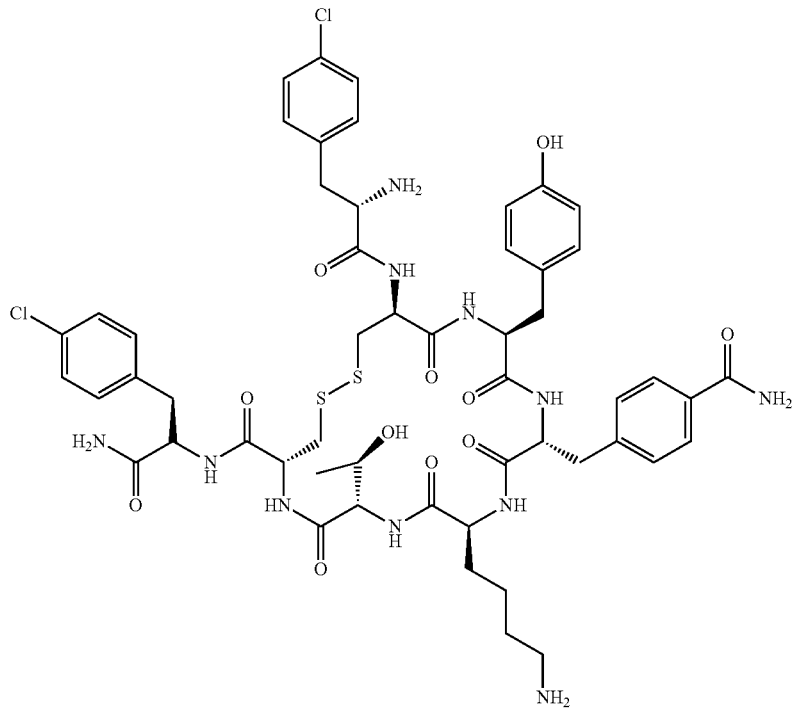

| INFORMAL SEQUENCE TABLE WITH FREE TEXT | |
|---|---|
| SEQ ID NO: 43 | H-Cpa-cyclo[DCys-4-Cl-Phe-D-(4-carbamoyl)Phe-Lys-Thr-Cys]-4-Cl-D-Phe-NH$_2$ |
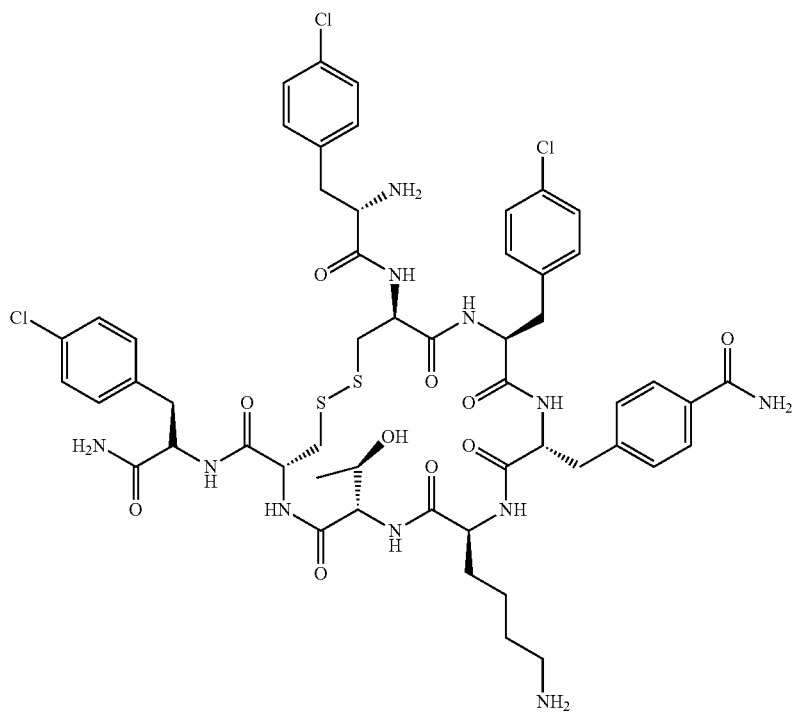
| | |
|---|---|
| SEQ ID NO: 44 | H-Cpa-cyclo[DCys-Tyr-D-(4-carbamoyl)Phe-Lys-Thr-Cys]-4-OMe-D-Phe-NH$_2$ |
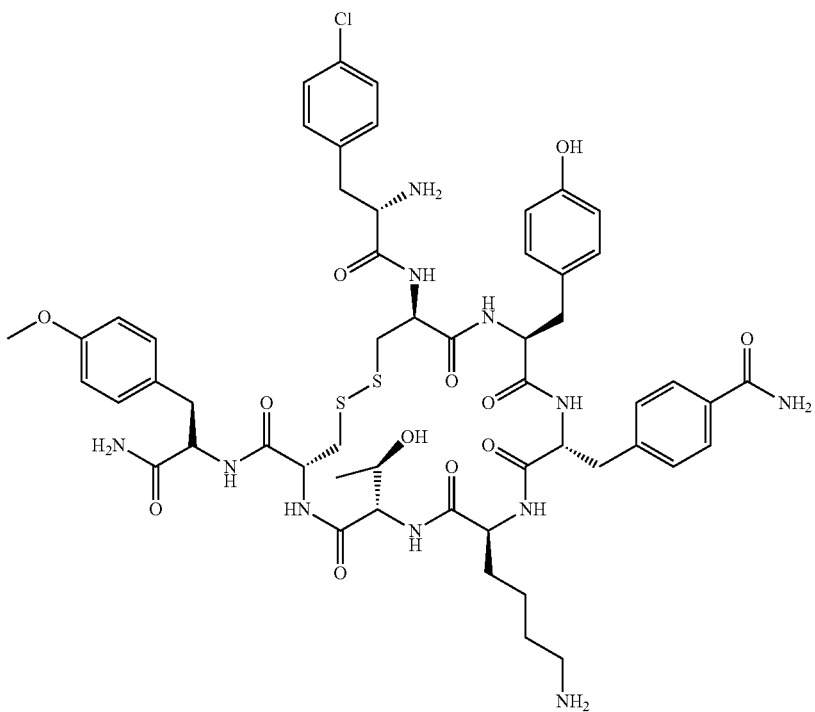

INFORMAL SEQUENCE TABLE WITH FREE TEXT
SEQ ID NO: 45
H-Cpa-cyclo[DCys-4-OMe-Phe-D-(4-carbamoyl)Phe-Lys-Thr-Cys]-4-OMe-D-Phe-NH$_2$
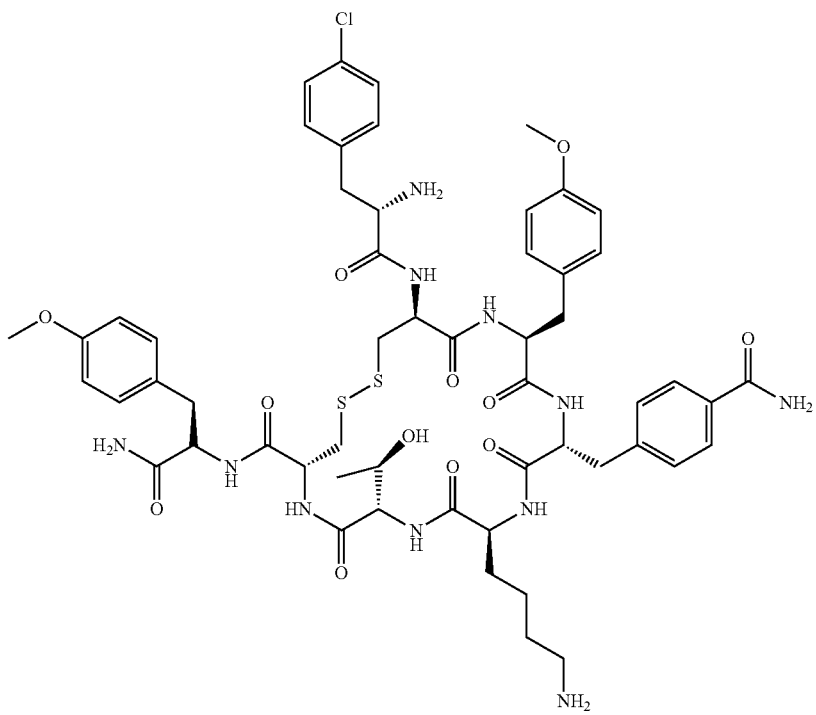
SEQ ID NO: 72
H-Cpa-cyclo[DCys-Tyr-D-(4-carbamoyl)Phe-(N-alpha-Me)Lys-Thr-Cys]-DTyr-NH$_2$
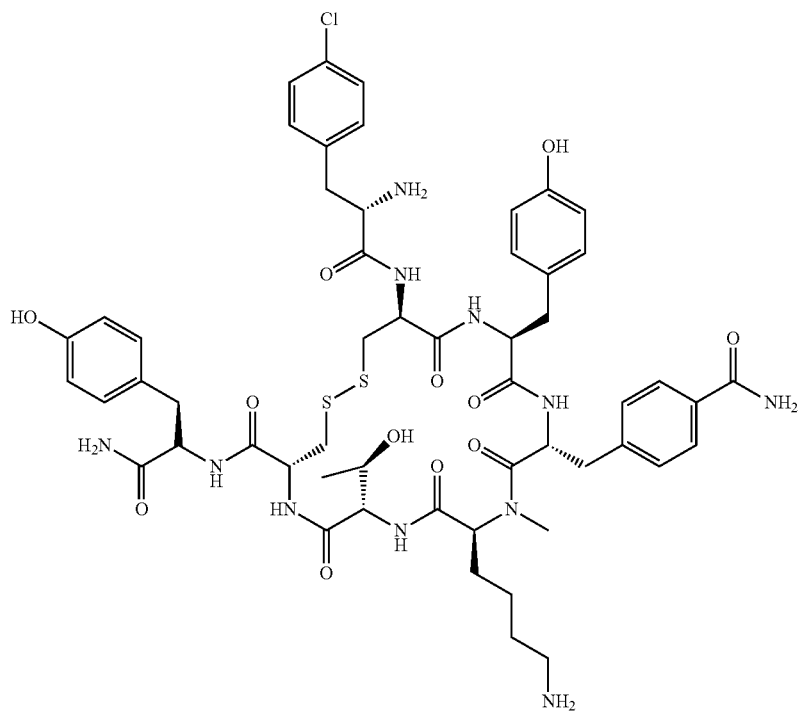

INFORMAL SEQUENCE TABLE WITH FREE TEXT
SEQ ID NO: 66
H-Cpa-cyclo[DXaa2-Tyr-Xaa4-Lys-Thr-Xaa7]-DTyr-NH$_2$
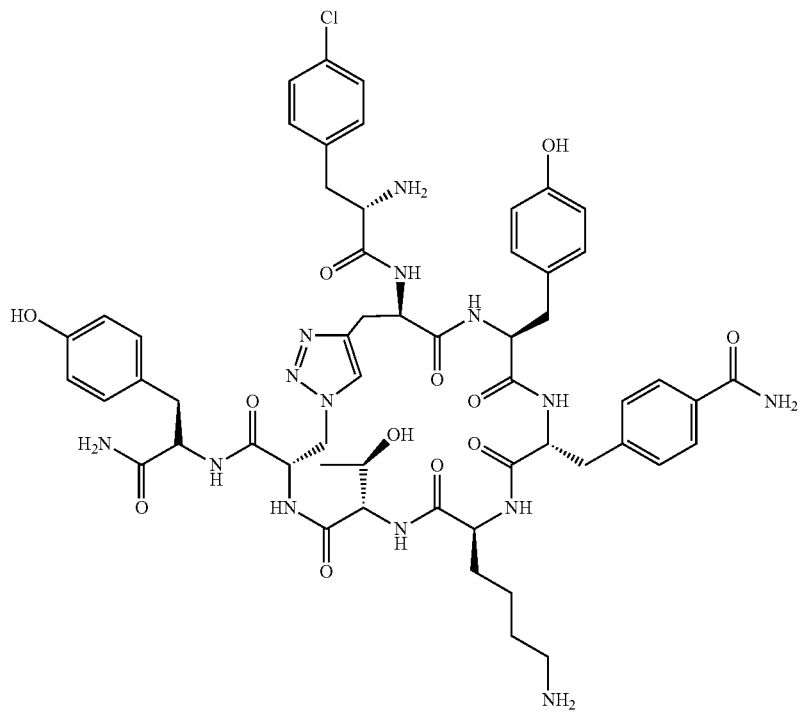
SEQ ID NO: 65
H-Cpa-cyclo[LXaa2-Tyr-Xaa4-Lys-Thr-Xaa7]-DTyr-NH$_2$
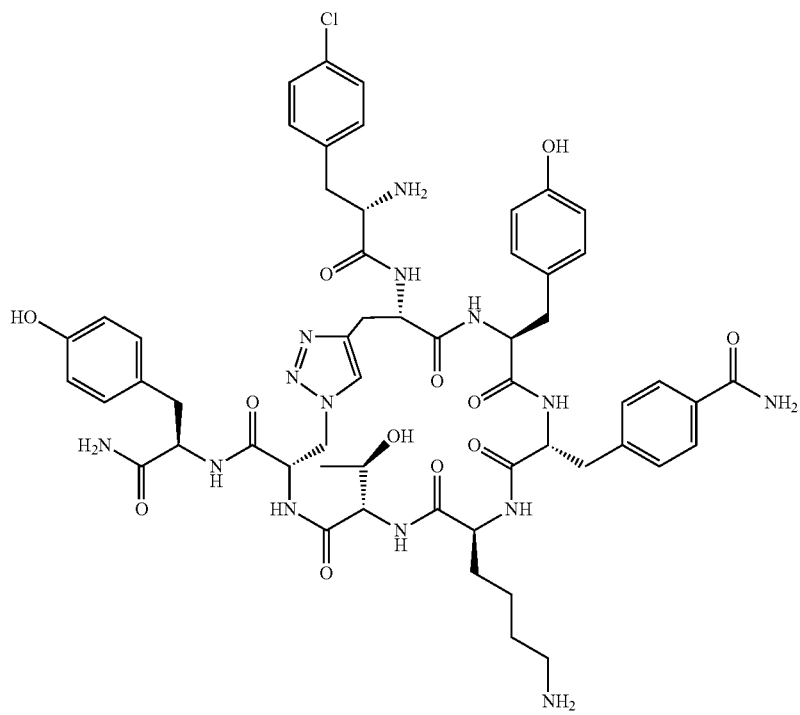 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)Cc2cn(nn2)C[C@@H](C(=O)N[C@H](Cc2ccc(O)cc2)C(N)=O)NC1=O]

INFORMAL SEQUENCE TABLE WITH FREE TEXT
SEQ ID NO: 64
H-Cpa-cyclo[DXaa2-Tyr-Xaa4-Lys-Thr-Xaa7]-DTyr-NH$_2$
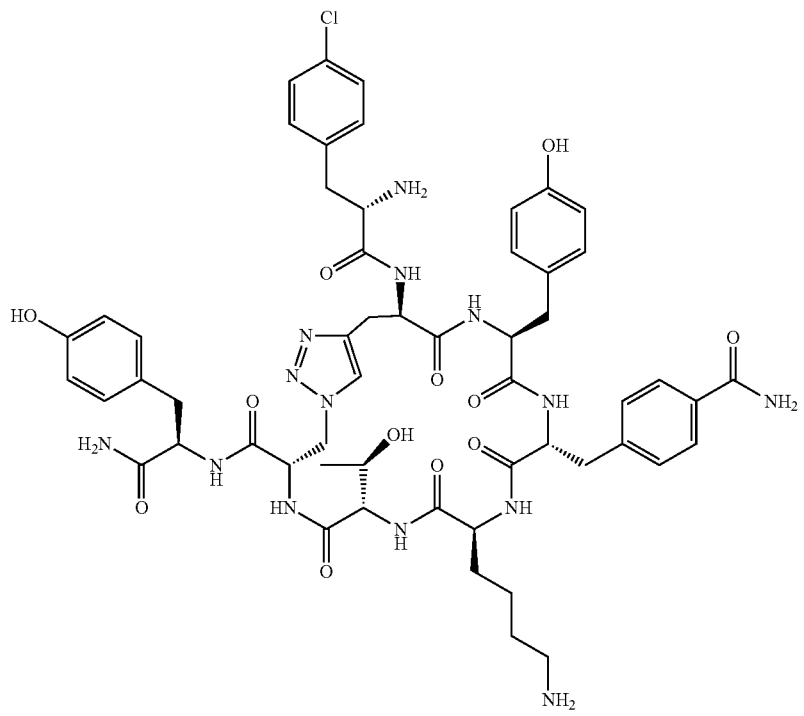 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)Cc2cn(nn2)C[C@@H](C(=O)N[C@H](Cc2ccc(O)cc2)C(N)=O)NC1=O]
SEQ ID NO: 67
H-Cpa-cyclo[DXaa2-Tyr-Xaa4-Lys-Thr-Xaa7]-DTyr-NH$_2$
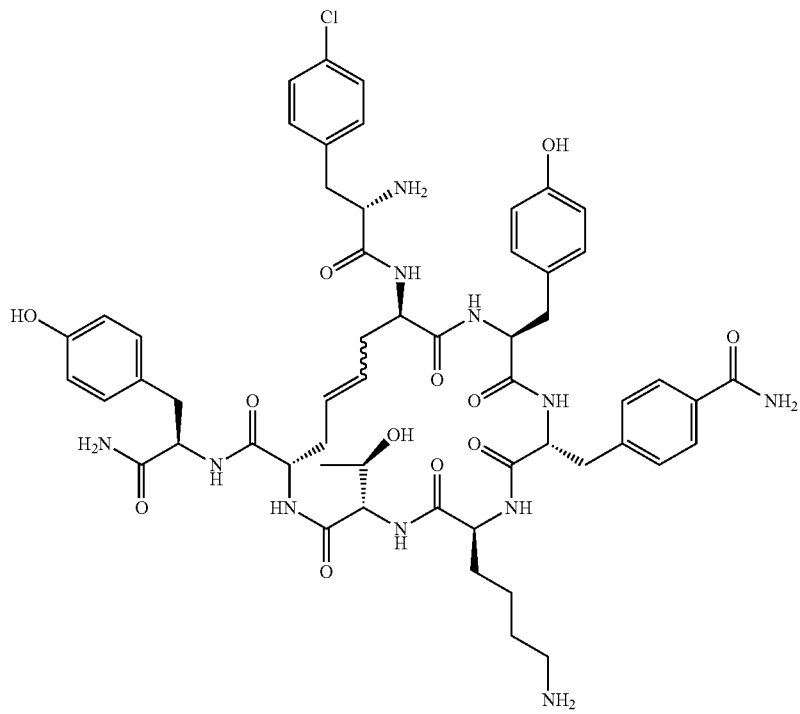 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CC=CC[C@@H](C(=O)N[C@H](Cc2ccc(O)cc2)C(N)=O)NC1=O]

INFORMAL SEQUENCE TABLE WITH FREE TEXT
SEQ ID NO: 68
H-Cpa-cyclo[Xaa2-Tyr-Xaa4-Lys-Thr-Xaa7]-DTyr-NH$_2$
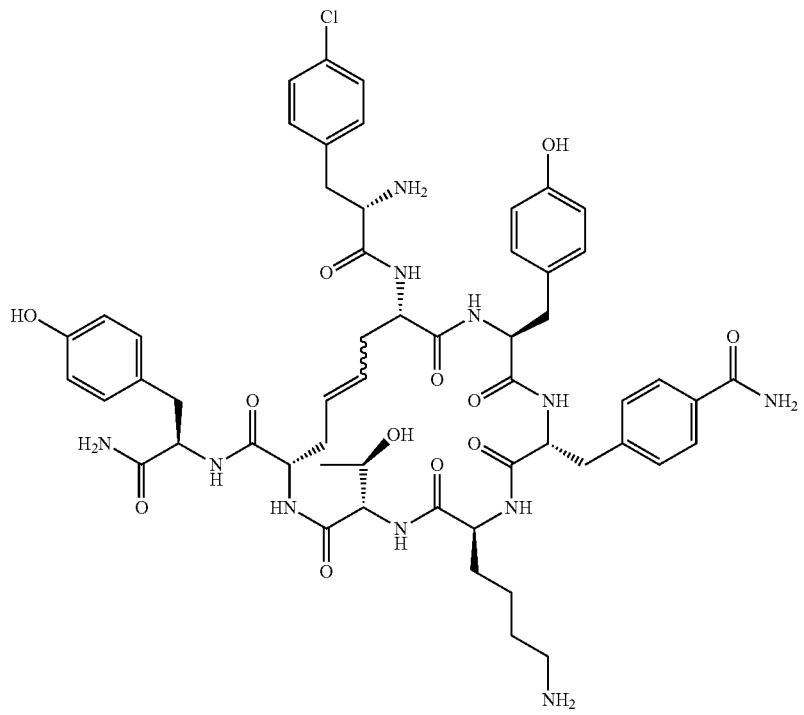 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)CC=CC[C@@H](C(=O)N[C@H](Cc2ccc(O)cc2)C(N)=O)NC1=O]
SEQ ID NO: 69
H-Cpa-cyclo[DDap-Tyr-DPhe(4-CONH$_2$)-Lys-Thr-Asp]-DTyr-NH$_2$
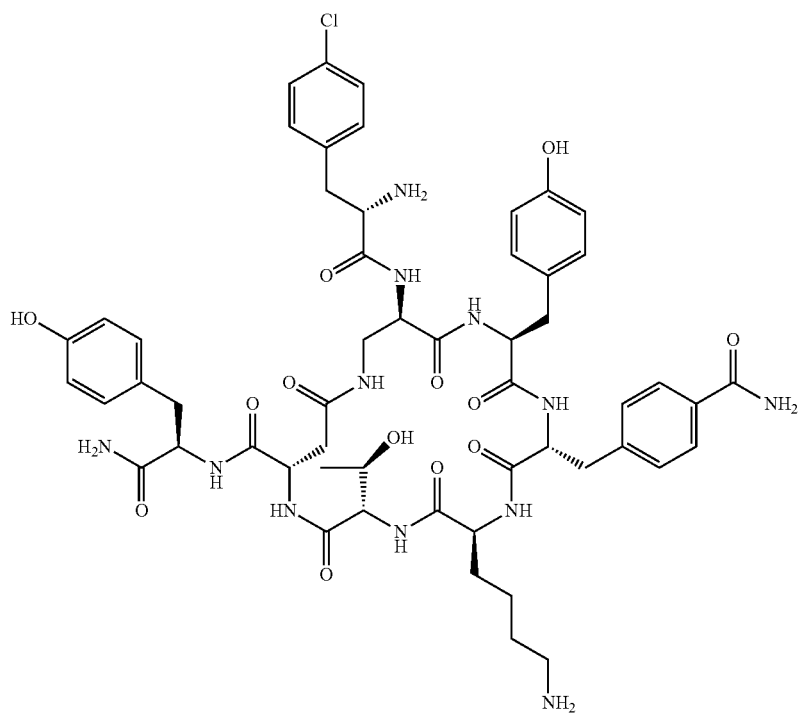 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)C[C@@H](C(=O)N[C@H](Cc2ccc(O)cc2)C(N)=O)NC1=O]

-continued
INFORMAL SEQUENCE TABLE WITH FREE TEXT
SEQ ID NO: 60                                    H-Cpa-cyclo[DDap-Tyr-DPhe(4-CONH$_2$)-Lys-Thr-Cys]-DTyr-NH$_2$
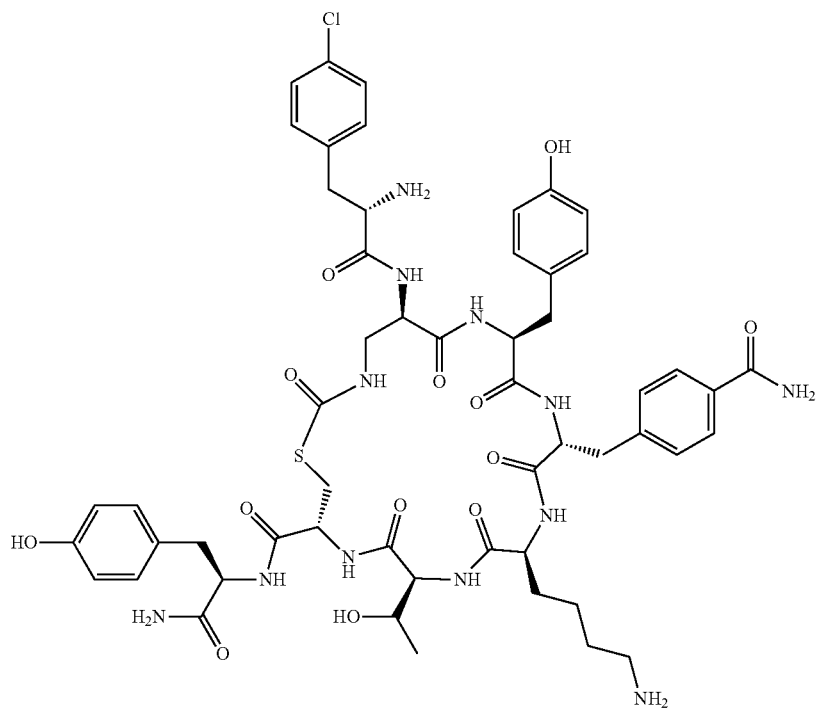 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)SC[C@@H](C(=O)N[C@H](Cc2ccc(O)cc2)C(N)=O)NC1=O]
SEQ ID NO: 70                                    H-Cpa-cyclo[DDap-Tyr-Xaa4-Lys-Thr-Asp]-DTyr-NH$_2$
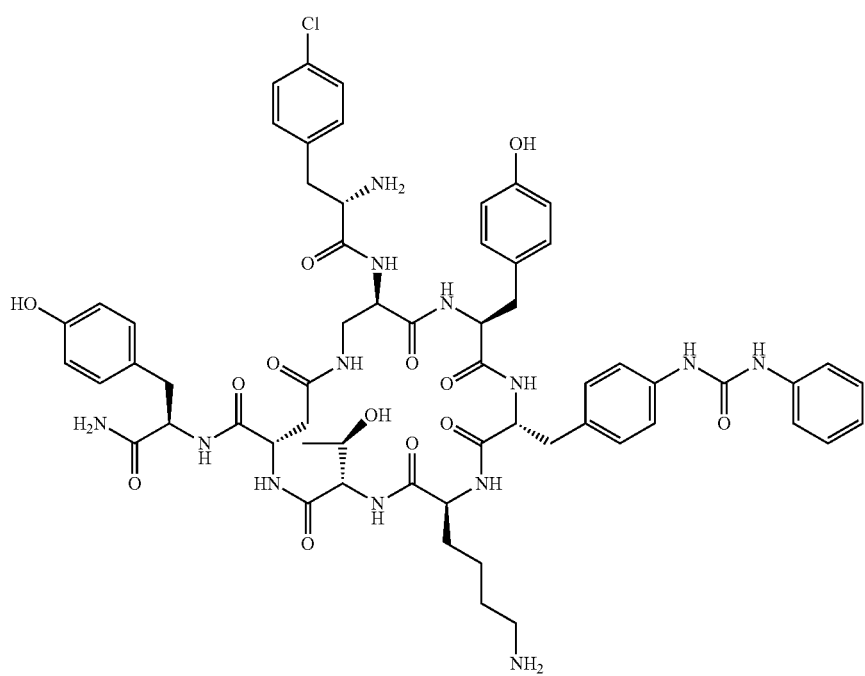 [SMILES: C[C@@H](O)[C@@H]1NC(=O)[C@H](CCCCN)NC(=O)[C@@H](Cc2ccc(NC(=O)Nc3ccccc3)cc2)NC(=O)[C@H](Cc2ccc(O)cc2)NC(=O)[C@H](NC(=O)[C@@H](N)Cc2ccc(Cl)cc2)CNC(=O)C[C@@H](C(=O)N[C@H](Cc2ccc(O)cc2)C(N)=O)NC1=O]

| INFORMAL SEQUENCE TABLE WITH FREE TEXT | |
|---|---|
| SEQ ID NO: 71 | H-Cpa-cyclo[DDap-Tyr-DPhe(4-CONH$_2$)-Lys(Me)-Thr-Asp]-DTyr-NH$_2$ |
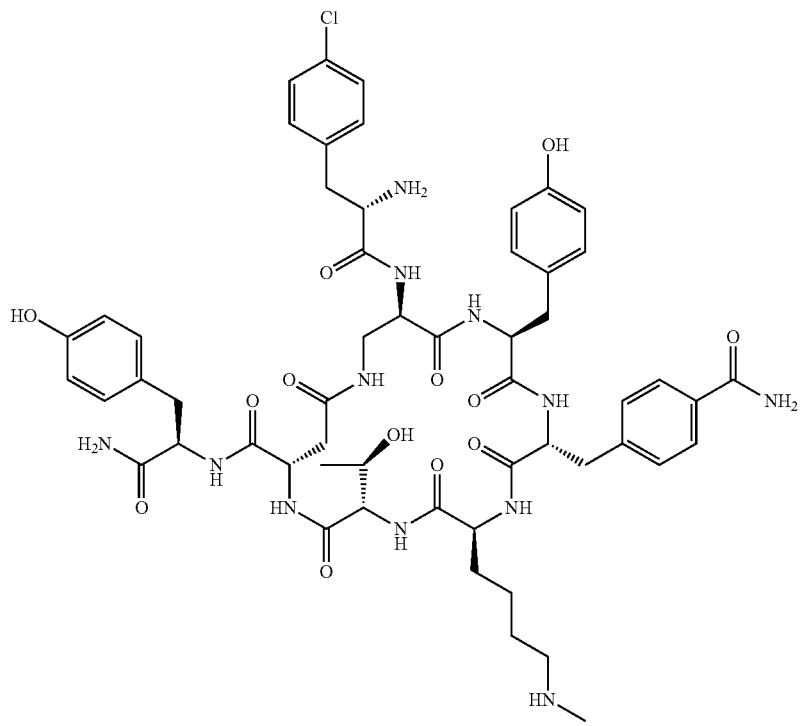 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)C[C@@H](C(=O)N[C@H](Cc2ccc(O)cc2)C(N)=O)NC(=O)[C@H]([C@@H](C)O)NC1=O]
| | |
|---|---|
| SEQ ID NO: 54 | Xaa0-Cpa-cyclo[Xaa2-Tyr-DPhe(4-CONH$_2$)-Lys(Me)-Thr-Xaa7]-DTyr-NH$_2$ |
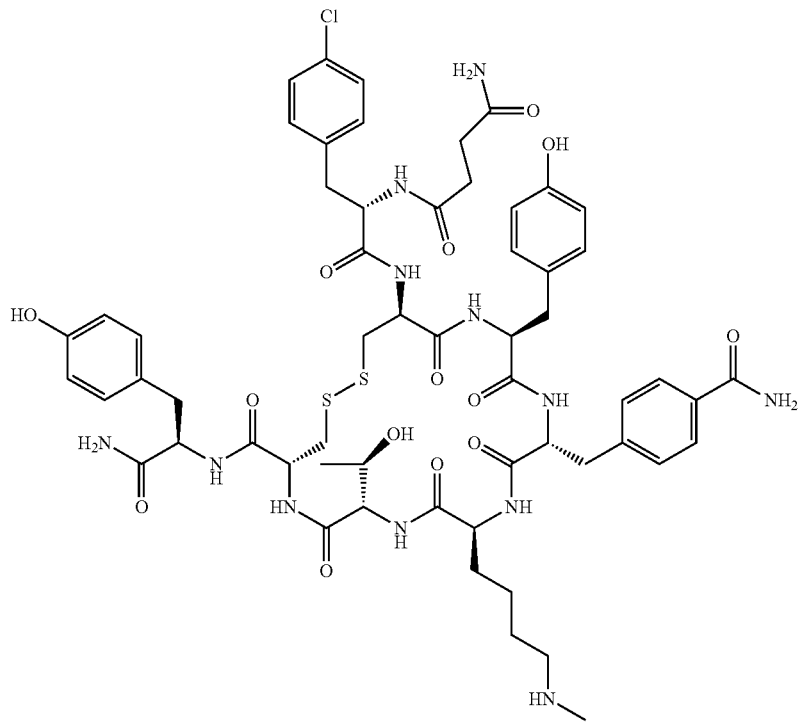 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCC(N)=O)CSSC[C@@H](C(=O)N[C@H](Cc2ccc(O)cc2)C(N)=O)NC(=O)[C@H]([C@@H](C)O)NC1=O]

INFORMAL SEQUENCE TABLE WITH FREE TEXT
SEQ ID NO: 55
Ac-Gly-Cpa-cyclo[Xaa2-Tyr-DPhe(4-CONH$_2$)-Lys(Me)-Thr-Xaa7]-DTyr-NH$_2$
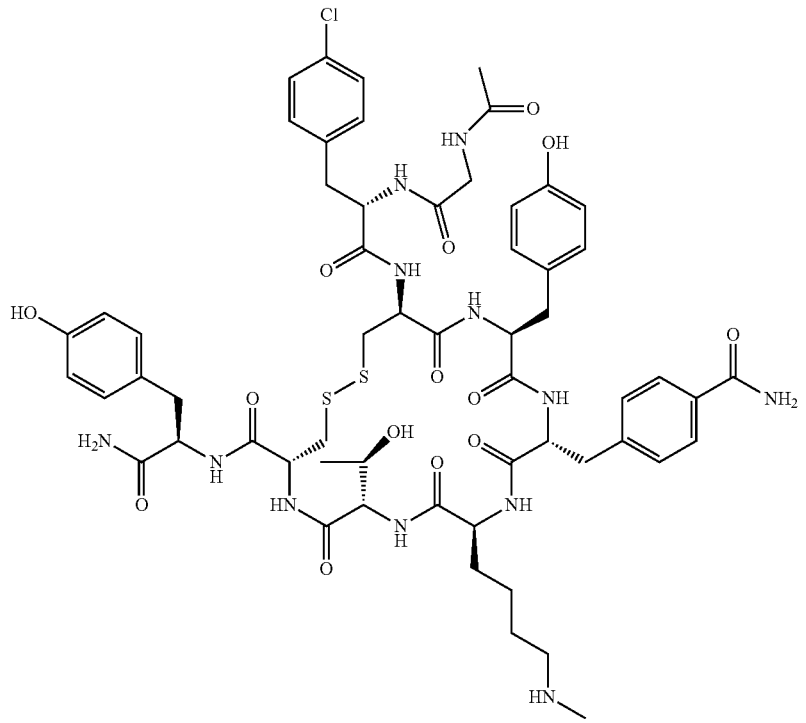 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CNC(C)=O)CSSC[C@@H](C(=O)N[C@H](Cc2ccc(O)cc2)C(N)=O)NC(=O)[C@H]([C@@H](C)O)NC1=O]
SEQ ID NO: 61
H-Cpa-cyclo[Dap-Tyr-DPhe(4-CONH$_2$)-Lys-Thr-Cys]-DTyr-NH$_2$
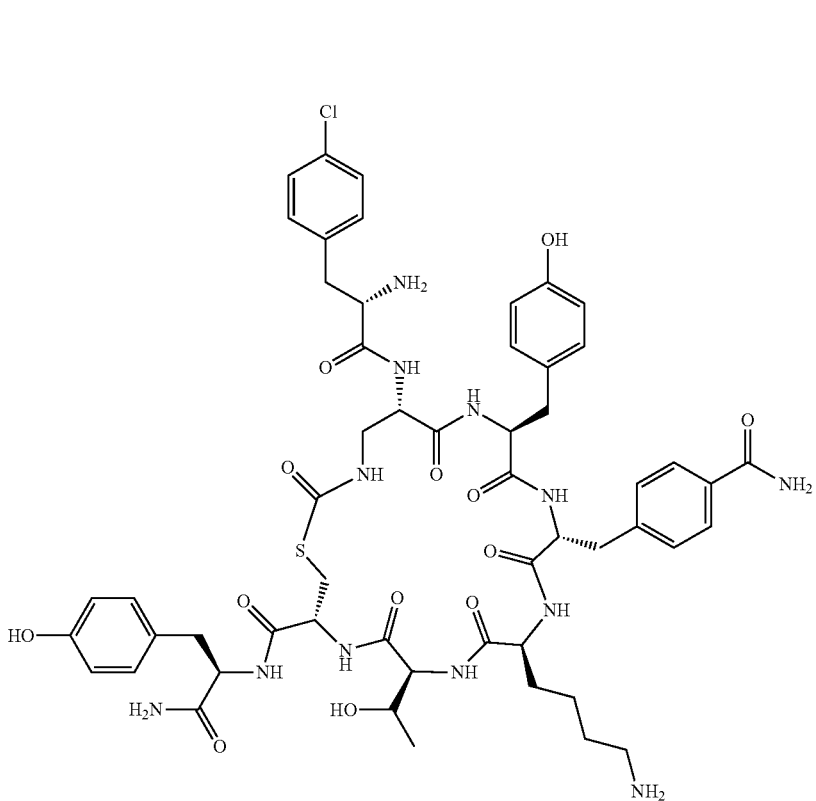 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)CNC(=O)SC[C@@H](C(=O)N[C@H](Cc2ccc(O)cc2)C(N)=O)NC1=O]

INFORMAL SEQUENCE TABLE WITH FREE TEXT
SEQ ID NO: 49
H-βAla-Cpa-cyclo[DCys-Tyr-DPhe(4-CONH$_2$)-Lys(Me)-Thr-Cys]-DTyr-NH$_2$
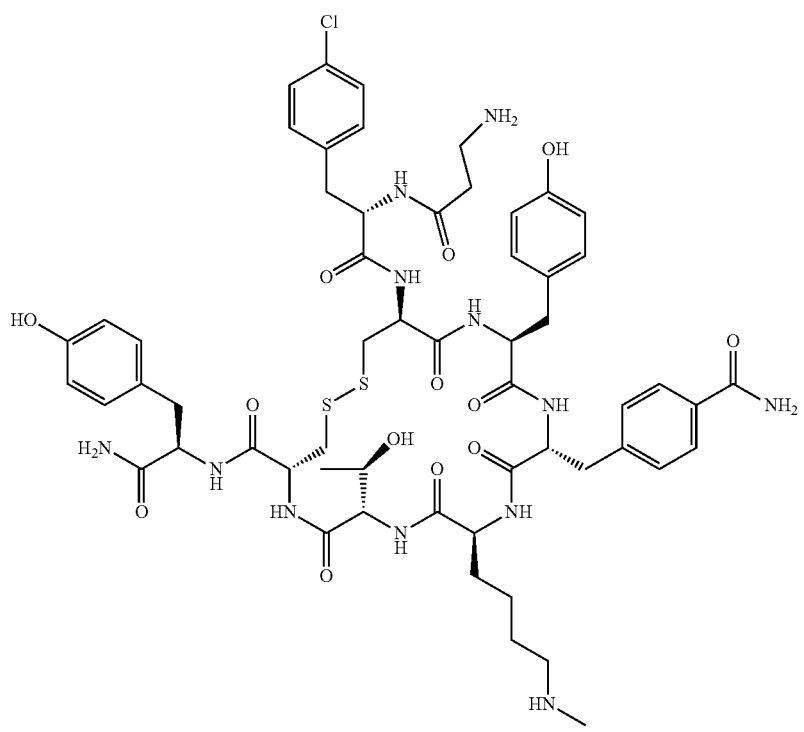 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCN)CSSC[C@@H](C(=O)N[C@H](Cc2ccc(O)cc2)C(N)=O)NC(=O)[C@H]([C@@H](C)O)NC1=O]
SEQ ID NO: 51
Xaa0-Cpa-cyclo[DCys-Tyr-DPhe(4-CONH$_2$)-Lys(Me)-Thr-Cys]-DTyr-NH$_2$
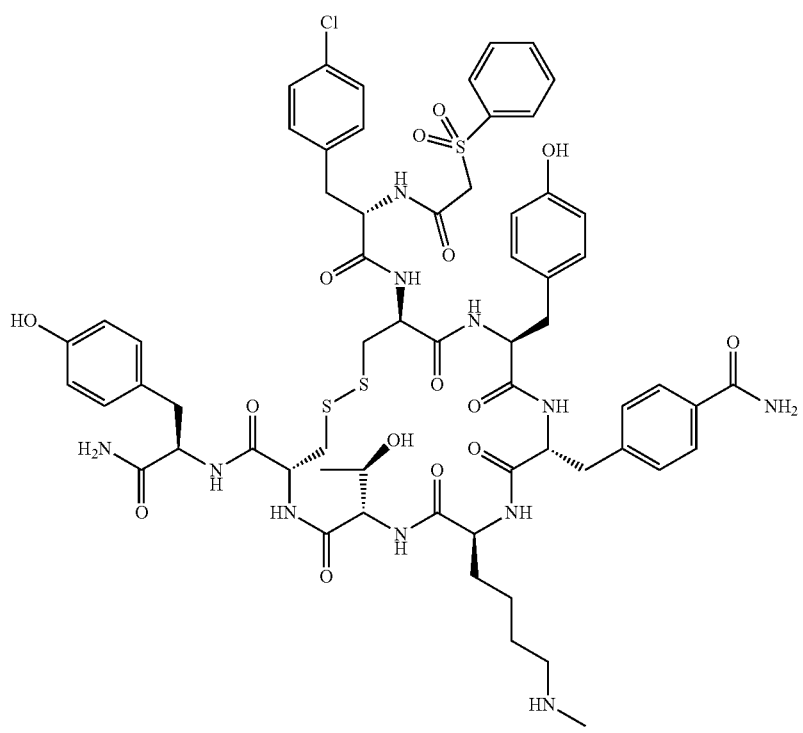 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CS(=O)(=O)c2ccccc2)CSSC[C@@H](C(=O)N[C@H](Cc2ccc(O)cc2)C(N)=O)NC(=O)[C@H]([C@@H](C)O)NC1=O]

INFORMAL SEQUENCE TABLE WITH FREE TEXT
SEQ ID NO: 50
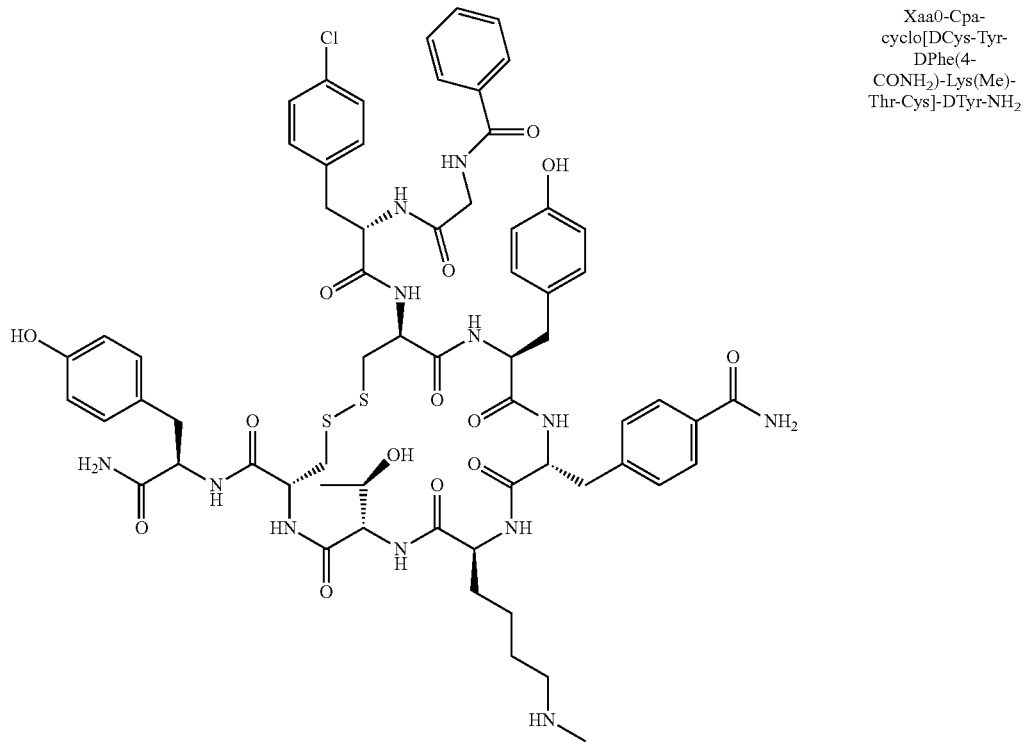
Xaa0-Cpa-cyclo[DCys-Tyr-DPhe(4-CONH$_2$)-Lys(Me)-Thr-Cys]-DTyr-NH$_2$
SEQ ID NO: 52
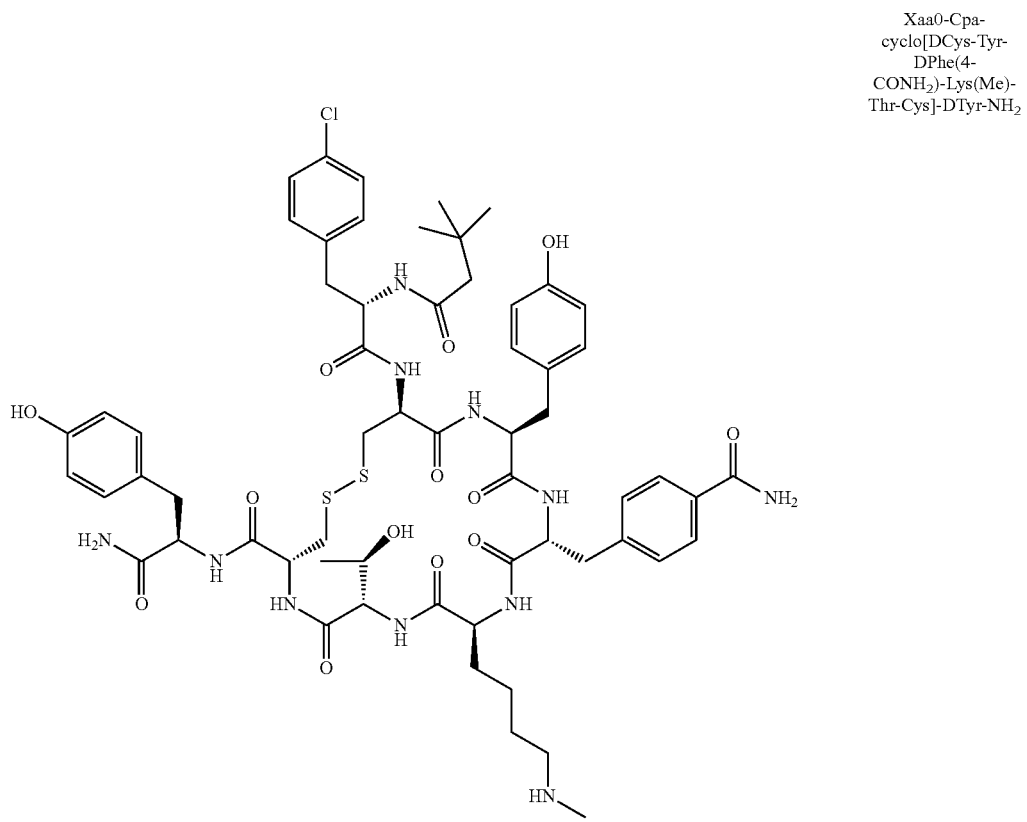
Xaa0-Cpa-cyclo[DCys-Tyr-DPhe(4-CONH$_2$)-Lys(Me)-Thr-Cys]-DTyr-NH$_2$ -continued
INFORMAL SEQUENCE TABLE WITH FREE TEXT
| SEQ ID NO: 53 | | Xaa0-Cpa-cyclo[DCys-Tyr-DPhe(4-CONH$_2$)-Lys(Me)-Thr-Cys]-DTyr-NH$_2$ |
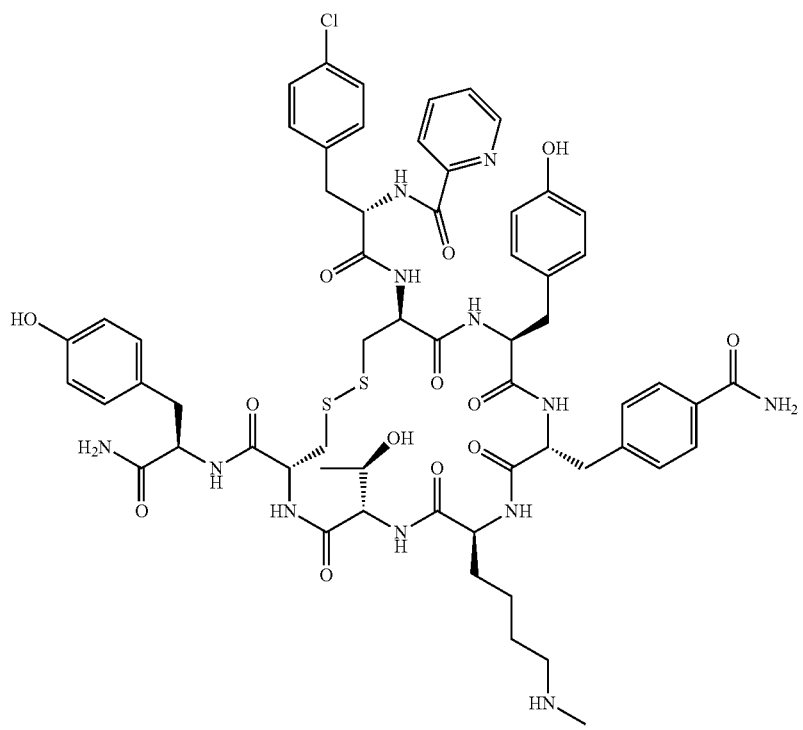 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)c2ccccn2)CSSC[C@@H](C(=O)N[C@H](Cc2ccc(O)cc2)C(N)=O)NC(=O)[C@H]([C@@H](C)O)NC1=O]
| SEQ ID NO: 46 | | H-Cpa-cyclo[DCys-Tyr-D-(4-carbamoyl)Phe-(N-Me)Lys-Thr-Cys]-DCpa-NH$_2$ |
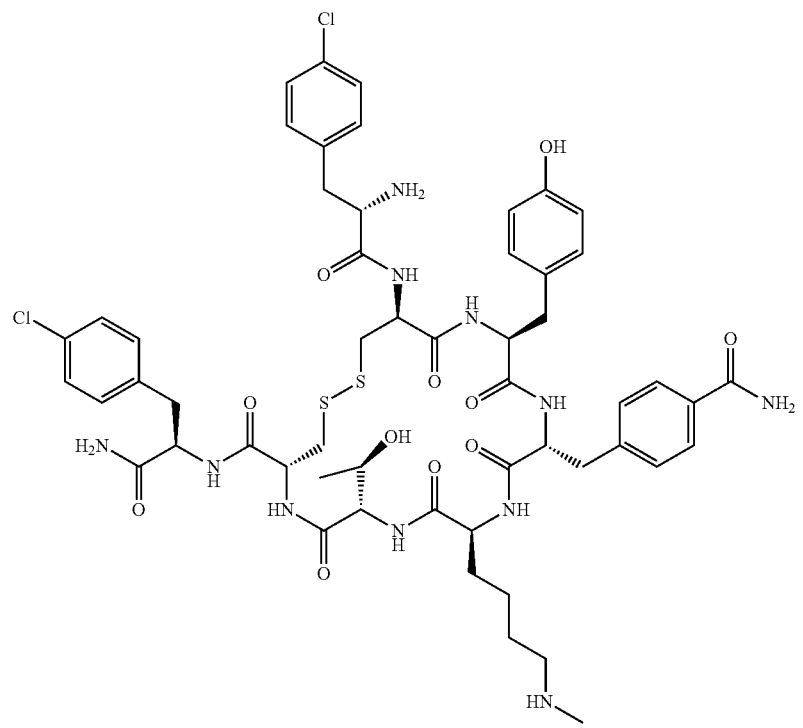 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(Cl)cc2)C(N)=O)NC(=O)[C@H]([C@@H](C)O)NC1=O]

| | |
|---|---|
| SEQ ID NO: 47 | H-Cpa-cyclo[DCys-Cpa-D-(4-carbamoyl)Phe-(N-Me)Lys-Thr-Cys]-DCpa-NH₂ |
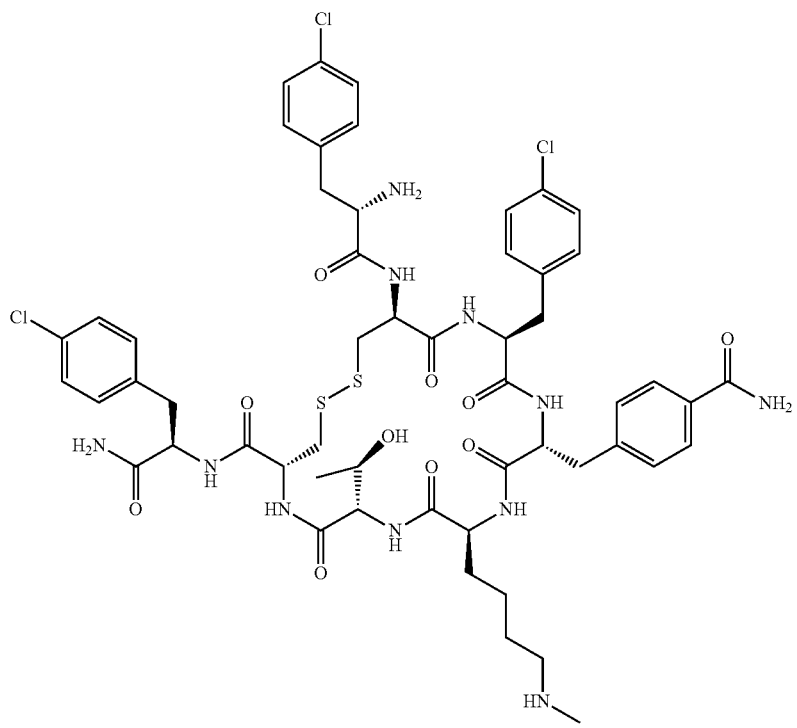 [SMILES: CNCCCC[C@@H]1NC(=O)[C@@H](Cc2ccc(C(N)=O)cc2)NC(=O)[C@H](Cc2ccc(Cl)cc2)NC(=O)[C@H](NC(=O)[C@@H](N)Cc2ccc(Cl)cc2)CSSC[C@@H](C(=O)N[C@H](Cc2ccc(Cl)cc2)C(N)=O)NC(=O)[C@H]([C@@H](C)O)NC1=O]
| | |
|---|---|
| SEQ ID NO: 48 | H-Cpa-cyclo[DCys-Cpa-D-(4-carbamoyl)Phe-(N-Me)Lys-Thr-Cys]-DTyr-NH₂ |
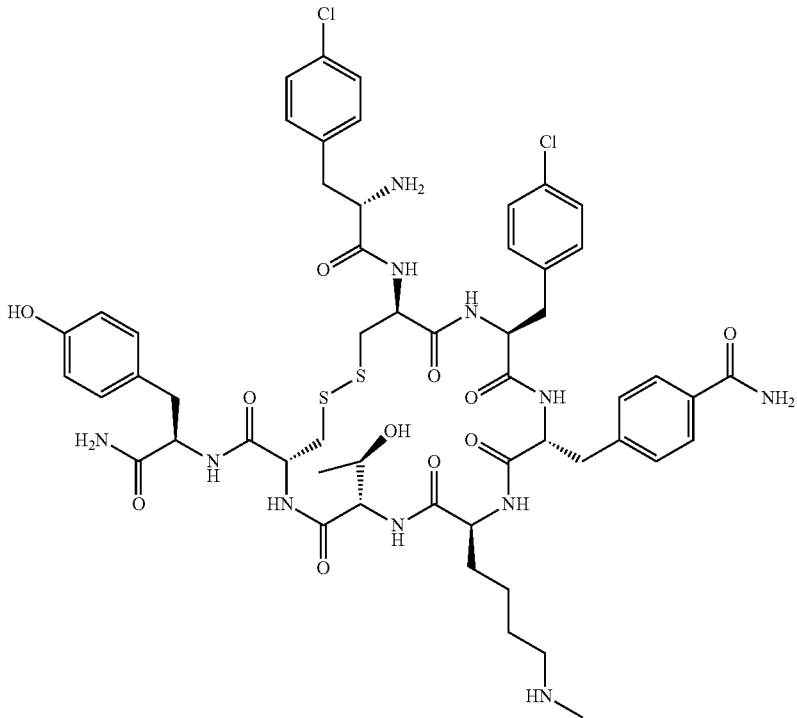 [SMILES: CNCCCC[C@@H]1NC(=O)[C@@H](Cc2ccc(C(N)=O)cc2)NC(=O)[C@H](Cc2ccc(Cl)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC(=O)[C@H]([C@@H](C)O)NC1=O]

| INFORMAL SEQUENCE TABLE WITH FREE TEXT |
SEQ ID NO: 58
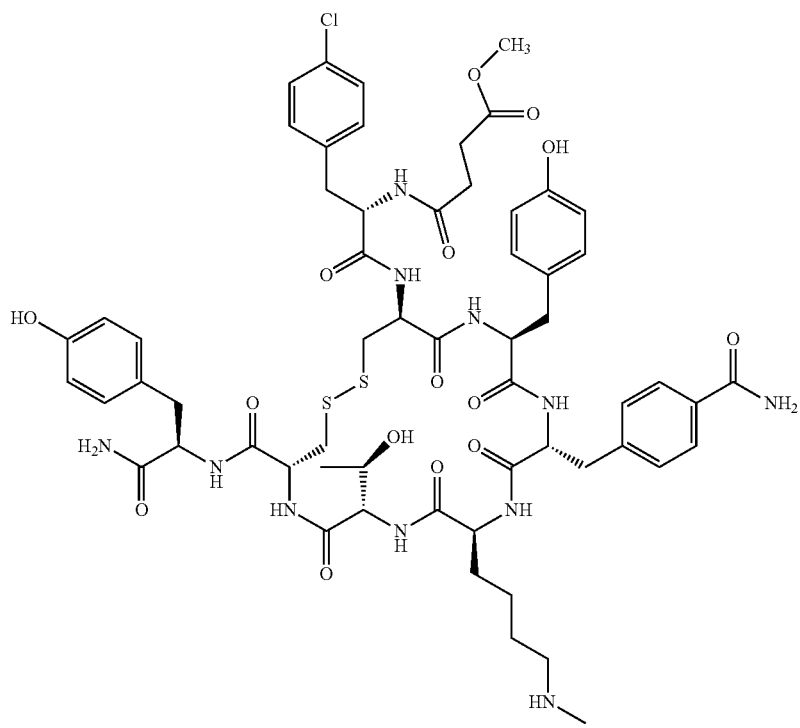 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCC(=O)OC)CSSC[C@@H](C(=O)N[C@H](Cc2ccc(O)cc2)C(N)=O)NC(=O)[C@H]([C@@H](C)O)NC1=O]
Xaa0-Cpa-cyclo[DCys-Tyr-DPhe(4-CONH$_2$)-Lys(Me)-Thr-Cys]-DTyr-NH$_2$
SEQ ID NO: 56
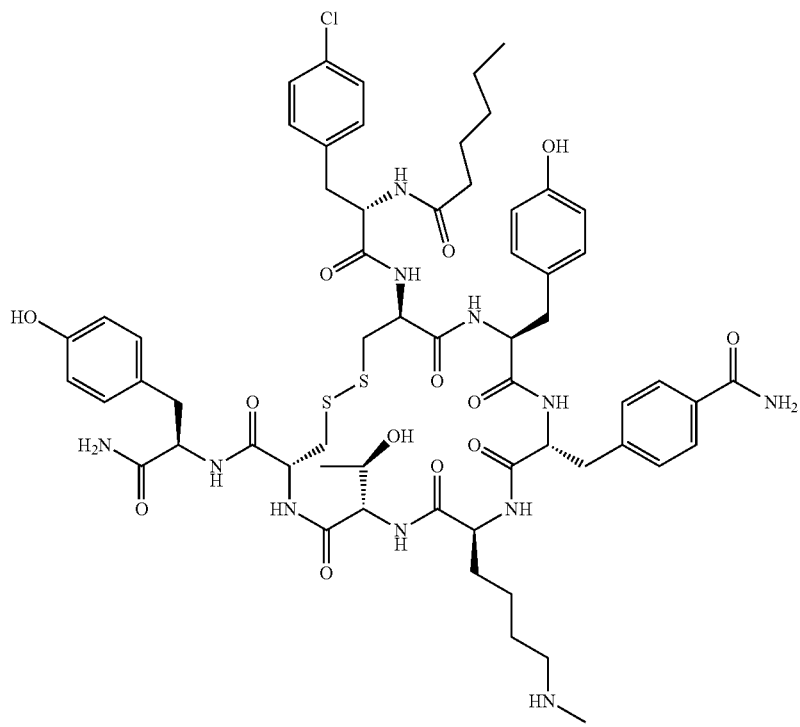 [SMILES: CCCCCC(=O)N[C@@H](Cc1ccc(Cl)cc1)C(=O)N[C@@H]1CSSC[C@@H](C(=O)N[C@H](Cc2ccc(O)cc2)C(N)=O)NC(=O)[C@H]([C@@H](C)O)NC(=O)[C@H](CCCCNC)NC(=O)[C@@H](Cc2ccc(C(N)=O)cc2)NC(=O)[C@H](Cc2ccc(O)cc2)NC1=O]
Xaa0-Cpa-cyclo[DCys-Tyr-DPhe(4-CONH$_2$)-Lys(Me)-Thr-Cys]-DTyr-NH$_2$ -continued
INFORMAL SEQUENCE TABLE WITH FREE TEXT
SEQ ID NO: 57
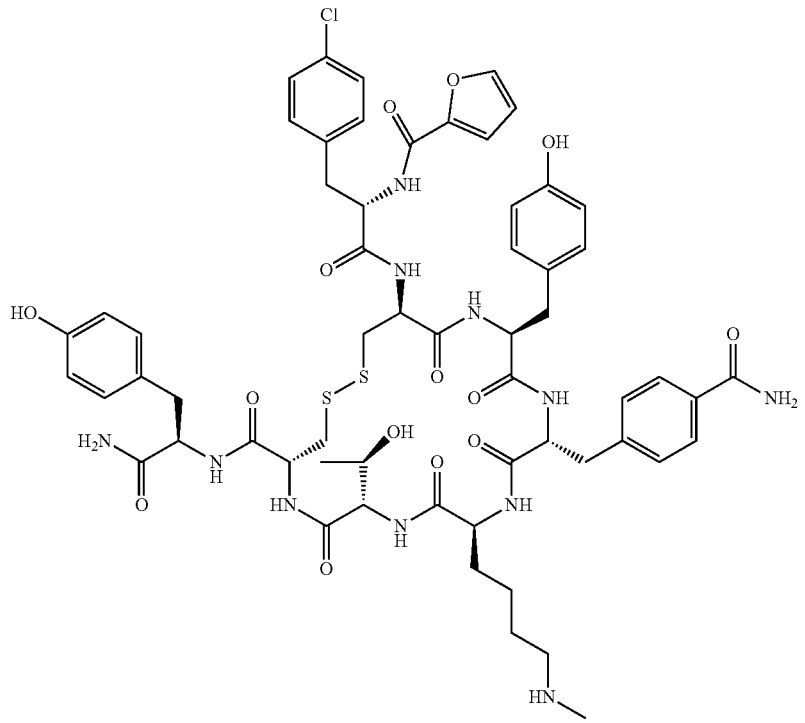 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)c2ccco2)CSSC[C@@H](C(=O)N[C@H](Cc2ccc(O)cc2)C(N)=O)NC(=O)[C@H]([C@@H](C)O)NC1=O]
Xaa0-Cpa-cyclo[DCys-Tyr-DPhe(4-CONH$_2$)-Lys(Me)-Thr-Cys]-DTyr-NH$_2$
SEQ ID NO: 62
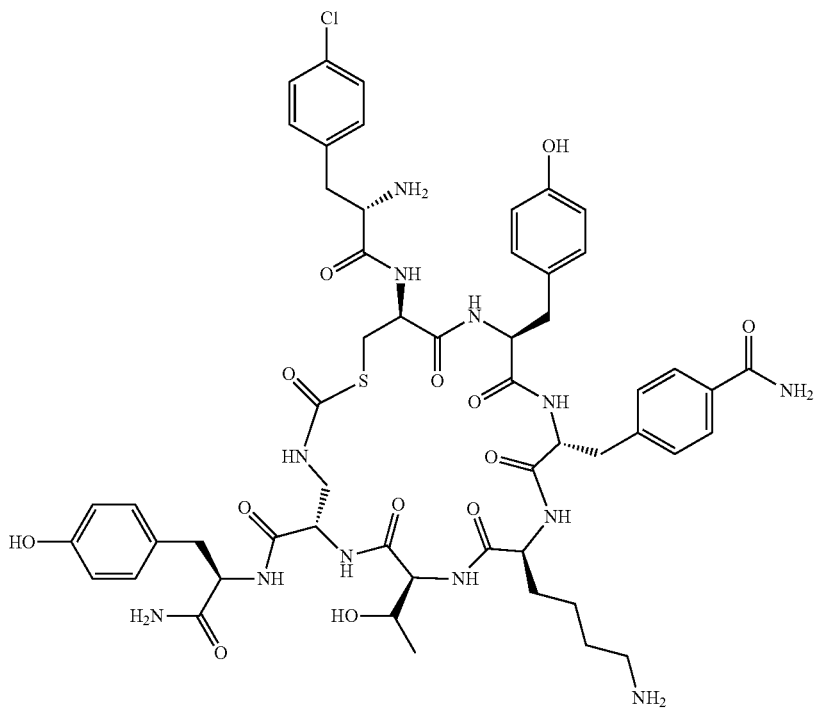 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSC(=O)NC[C@@H](C(=O)N[C@H](Cc2ccc(O)cc2)C(N)=O)NC1=O]
H-Cpa-cyclo[DCys-Tyr-DPhe(4-CONH$_2$)-Lys-Thr-Dap]-DTyr-NH$_2$

| INFORMAL SEQUENCE TABLE WITH FREE TEXT | |
|---|---|
| SEQ ID NO: 63 | H-Cpa-cyclo[DCys-Tyr-DPhe(4-CONH$_2$)-Lys(Me)-Thr-Dap]-DTyr-NH$_2$ |
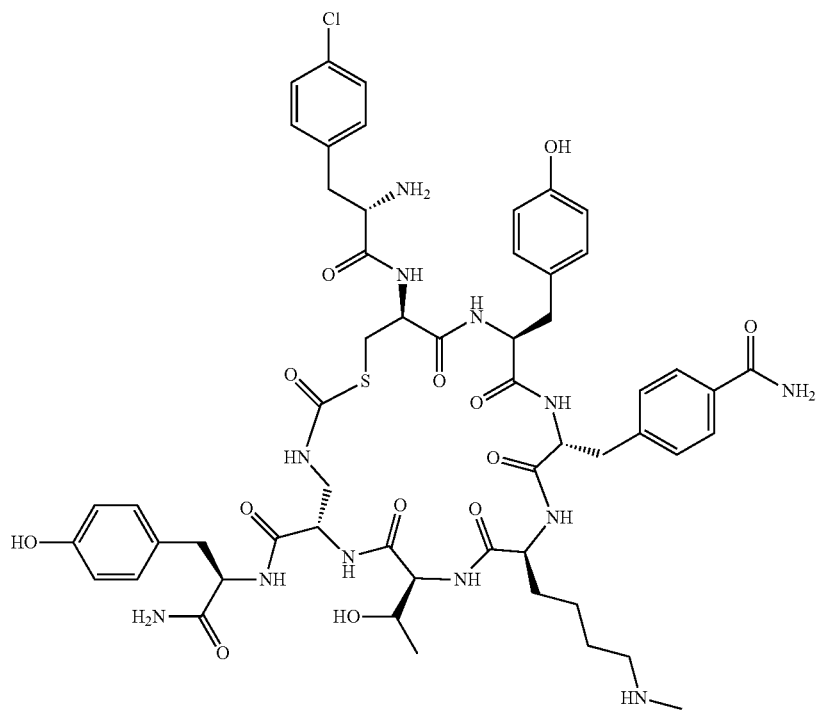 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSC(=O)NC[C@@H](C(=O)N[C@H](Cc2ccc(O)cc2)C(N)=O)NC(=O)[C@H](C(C)O)NC1=O]
| | |
|---|---|
| SEQ ID NO: 73 | H-Cpa-[DCys-Tyr-DPhe(4-carbamoyl)-Lys-NMeThr-Cys]-DTyr-NH$_2$ |
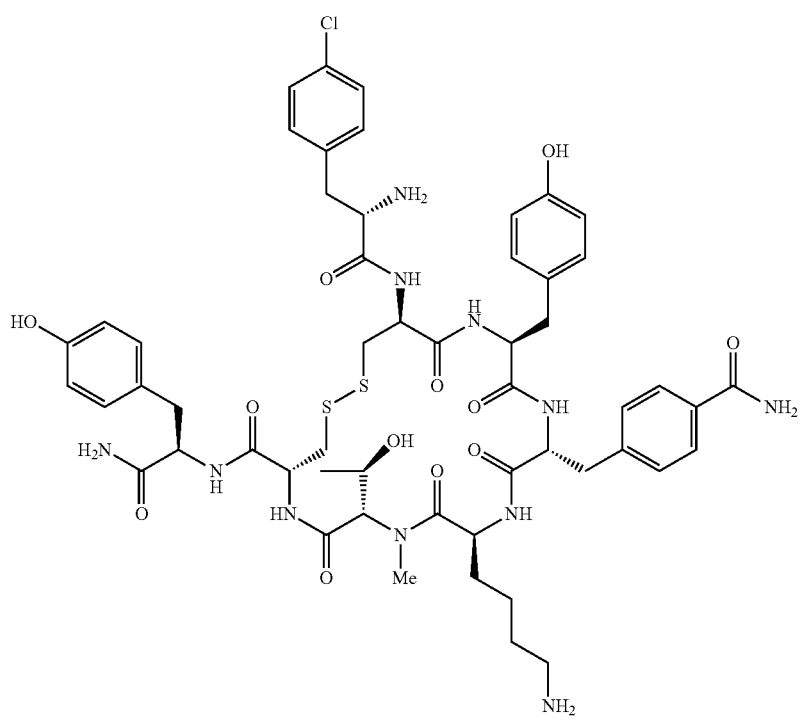 [SMILES: C[C@@H](O)[C@H]1C(=O)N[C@H](C(=O)N[C@H](Cc2ccc(O)cc2)C(N)=O)CSSC[C@@H](NC(=O)[C@@H](N)Cc2ccc(Cl)cc2)C(=O)N[C@@H](Cc2ccc(O)cc2)C(=O)N[C@H](Cc2ccc(C(N)=O)cc2)C(=O)N[C@@H](CCCCN)C(=O)N1C]

INFORMAL SEQUENCE TABLE WITH FREE TEXT
SEQ ID NO: 74
H-Cpa-[DCys-NMeTyr-DPhe(4-carbamoyl)-Lys-Thr-Cys]-DTyr-NH$_2$
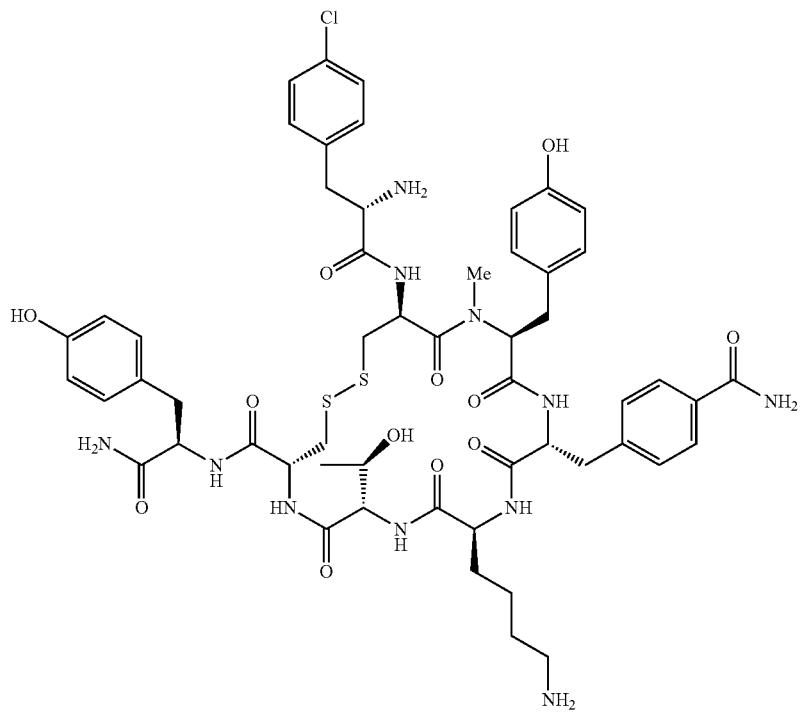 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)N(C)C(=O)[C@H](NC(=O)[C@@H](N)Cc2ccc(Cl)cc2)CSSC[C@@H](C(=O)N[C@H](Cc2ccc(O)cc2)C(N)=O)NC1=O]
SEQ ID NO: 75
H-Cpa-[DCys-NMeTyr-DPhe(4-carbamoyl)-Lys-NMeThr-Cys]-DTyr-NH$_2$
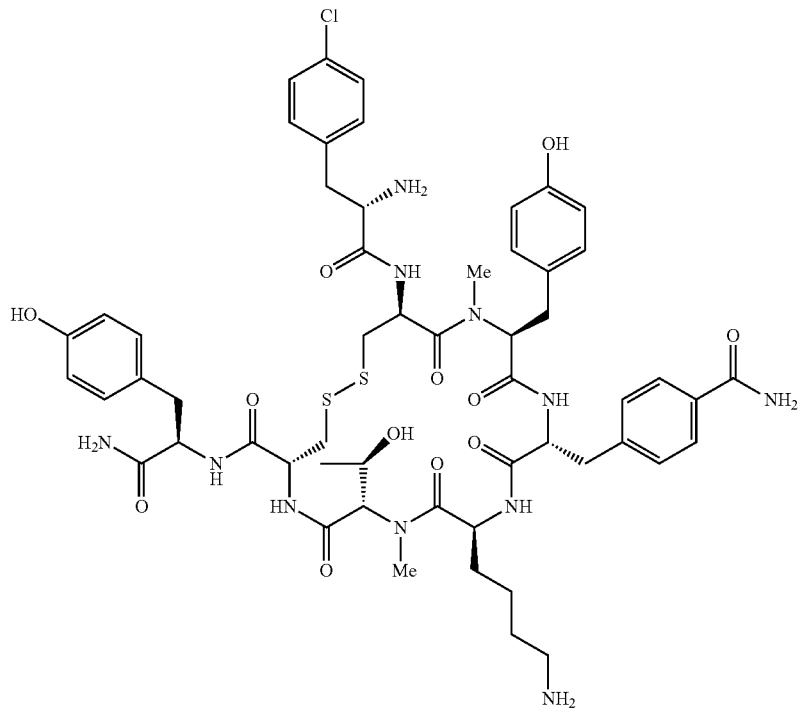 [SMILES: C[C@@H](O)[C@H]1C(=O)N[C@H](C(=O)N[C@H](Cc2ccc(O)cc2)C(N)=O)CSSC[C@@H](NC(=O)[C@@H](N)Cc2ccc(Cl)cc2)C(=O)N(C)[C@@H](Cc2ccc(O)cc2)C(=O)N[C@H](Cc2ccc(C(N)=O)cc2)C(=O)N[C@@H](CCCCN)C(=O)N1C]

INFORMAL SEQUENCE TABLE WITH FREE TEXT
SEQ ID NO: 76
H-Cpa-[DCys-Tyr-DPhe(4-carbamoyl)-Lys-Thr-NMeCys]-DTyr-NH$_2$
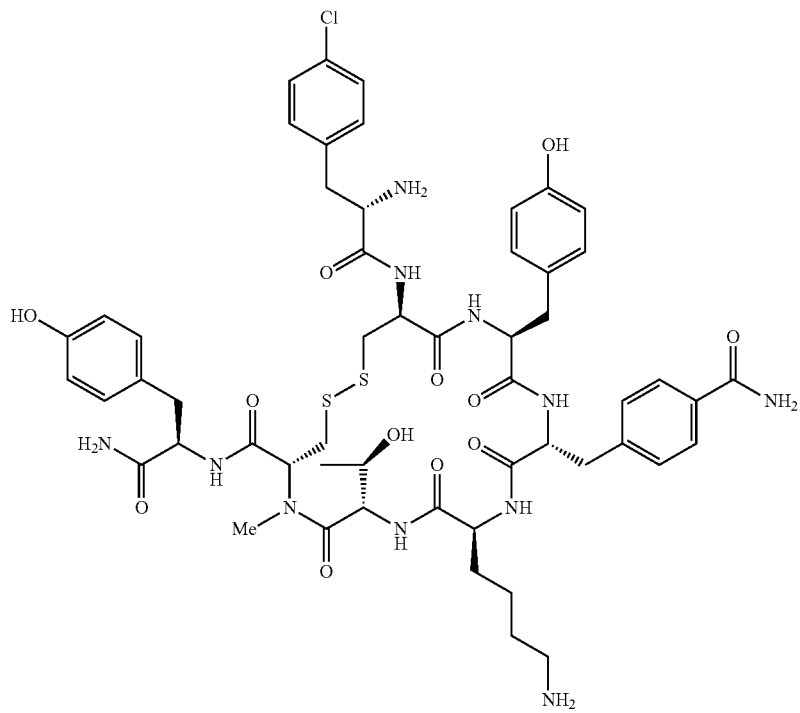 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)N(C)C1=O]
SEQ ID NO: 77
H-NMeCpa-[DCys-Tyr-DPhe(4-carbamoyl)-Lys-Thr-Cys]-DTyr-NH$_2$
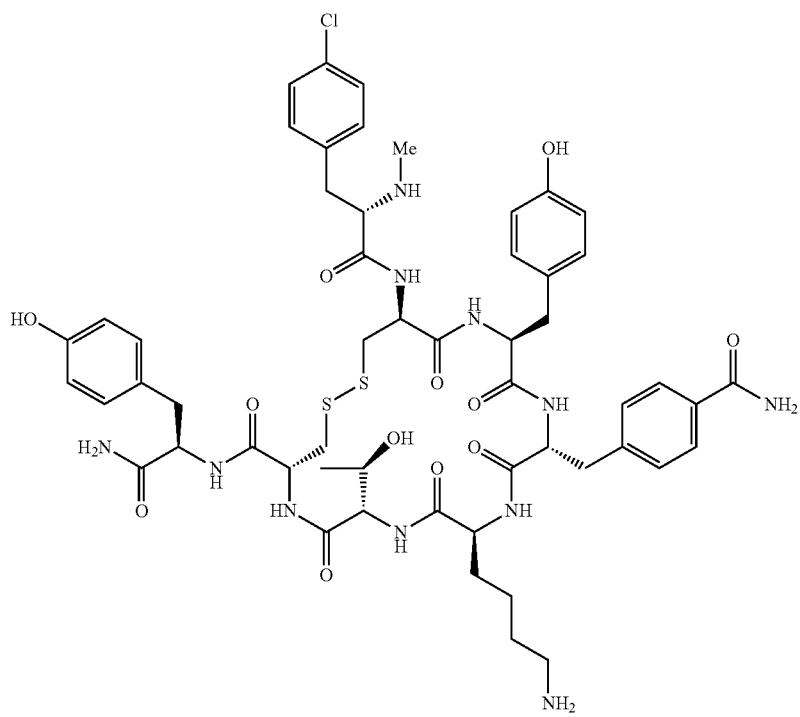 [SMILES: CN[C@@H](Cc1ccc(Cl)cc1)C(=O)N[C@@H]1CSSC[C@@H](C(=O)N[C@H](Cc2ccc(O)cc2)C(N)=O)NC(=O)[C@H]([C@@H](C)O)NC(=O)[C@H](CCCCN)NC(=O)[C@@H](Cc2ccc(C(N)=O)cc2)NC(=O)[C@H](Cc2ccc(O)cc2)NC1=O]

| | |
|---|---|
| SEQ ID NO: 59 | H-Cpa-[DCys-Tyr-DPhe(4-CN)-Lys-Thr-Cys]-DTyr-NH$_2$ |
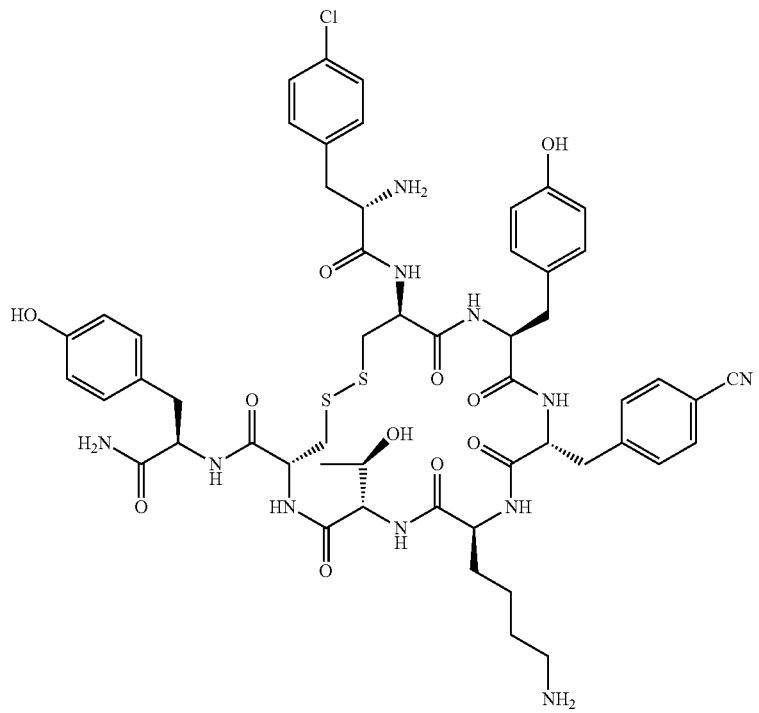 [SMILES: C[C@@H](O)[C@@H]1NC(=O)[C@H](CCCCN)NC(=O)[C@@H](Cc2ccc(C#N)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
| | |
|---|---|
| SEQ ID NO: 78 | H-Cpa-[NMeDCys-Tyr-DPhe(4-carbamoyl)-Lys-Thr-Cys]-DTyr-NH$_2$ |
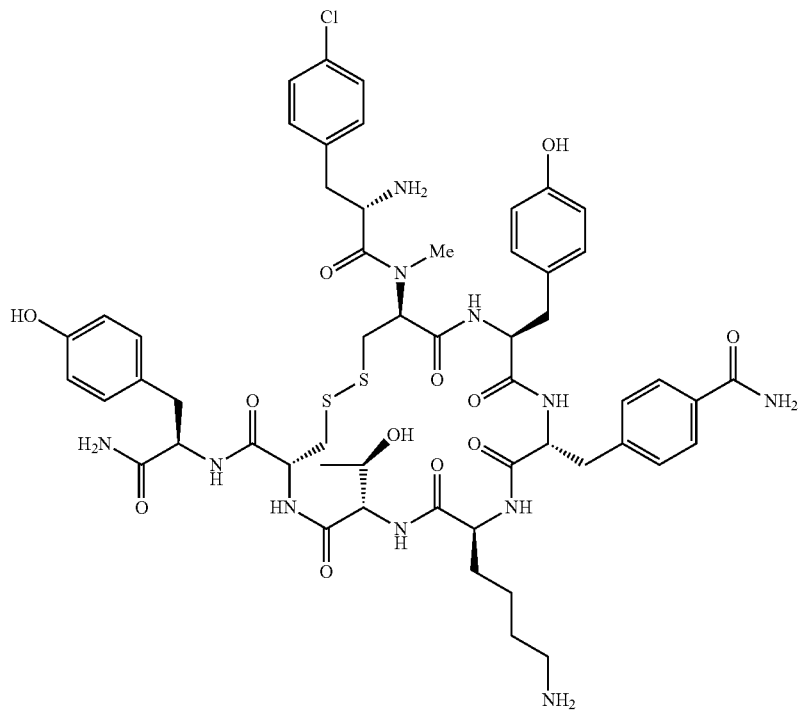 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](N(C)C(=O)[C@@H](N)Cc2ccc(Cl)cc2)CSSC[C@@H](C(=O)N[C@H](Cc2ccc(O)cc2)C(N)=O)NC1=O]

| SEQ ID NO: 79 | H-Cpa-[DCys-Tyr-DPhe(4-carbamoyl)-Lys-Thr-Cys]-NMeDTyr-NH$_2$ |
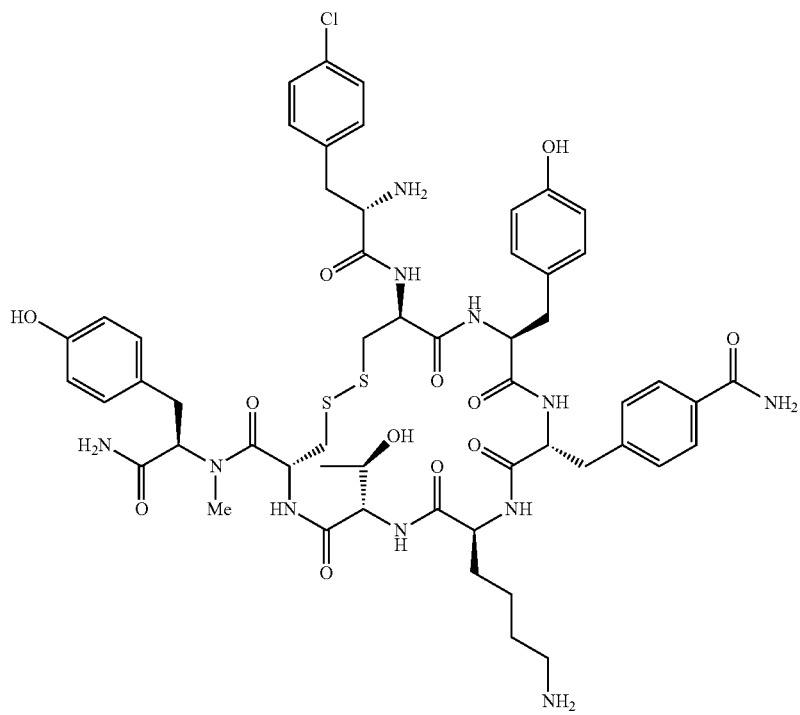 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N(C)[C@H](Cc2ccc(O)cc2)C(N)=O)NC1=O]
| SEQ ID NO: 80 | H-NMeCpa-[DCys-NMeTyr-DPhe(4-carbamoyl)-Lys-NMeThr-Cys]-NMeDTyr-NH$_2$ |
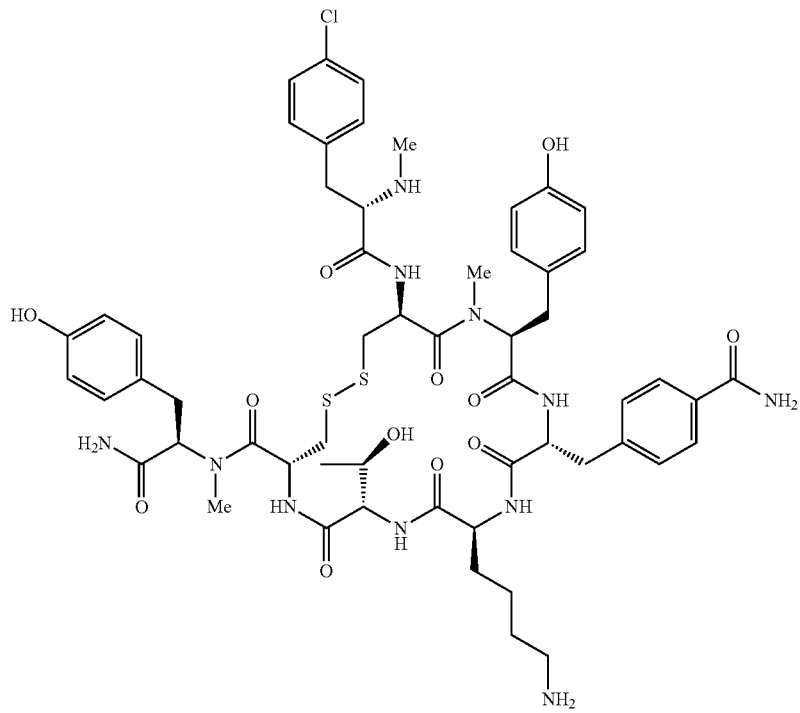 [SMILES: CN[C@@H](Cc1ccc(Cl)cc1)C(=O)N[C@@H]1CSSC[C@@H](C(=O)N(C)[C@H](Cc2ccc(O)cc2)C(N)=O)NC(=O)[C@H]([C@@H](C)O)NC(=O)[C@H](CCCCN)NC(=O)[C@@H](Cc2ccc(C(N)=O)cc2)NC(=O)[C@H](Cc2ccc(O)cc2)N(C)C1=O]

INFORMAL SEQUENCE TABLE WITH FREE TEXT
SEQ ID NO: 81
H-N-methyl-sulfonylCpa-DCys-Tyr-DPhe4-carbamoyl-LysMe-Thr-Cys-DTyr-NH₂
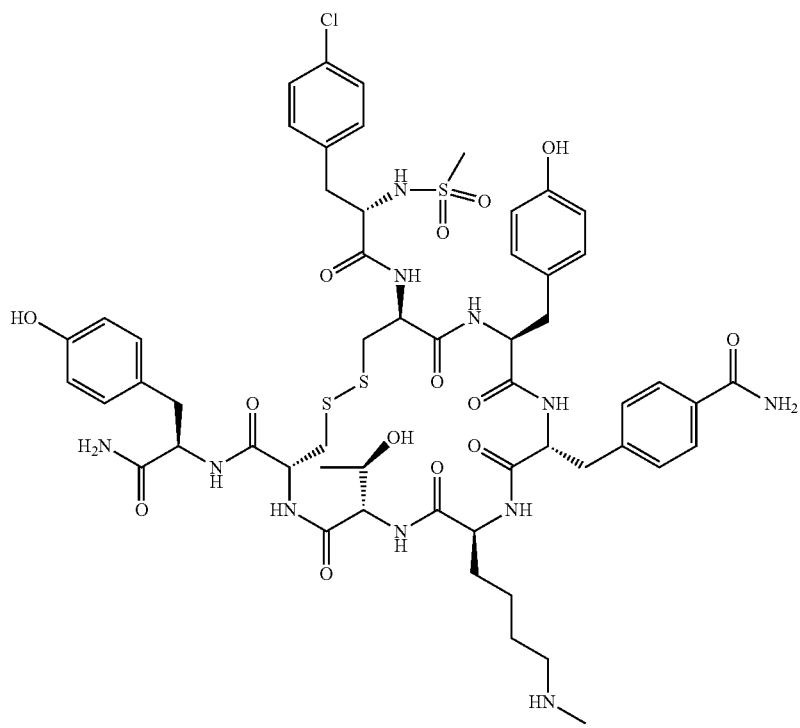 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NS(C)(=O)=O)CSSC[C@@H](C(=O)N[C@H](Cc2ccc(O)cc2)C(N)=O)NC(=O)[C@H]([C@@H](C)O)NC1=O]
SEQ ID NO: 82
H-N-phenyl-sulfonylCpa-Dcys-Tyr-DPhe4-carbamoyl-LysMe-Thr-Cys-DTyr-NH2
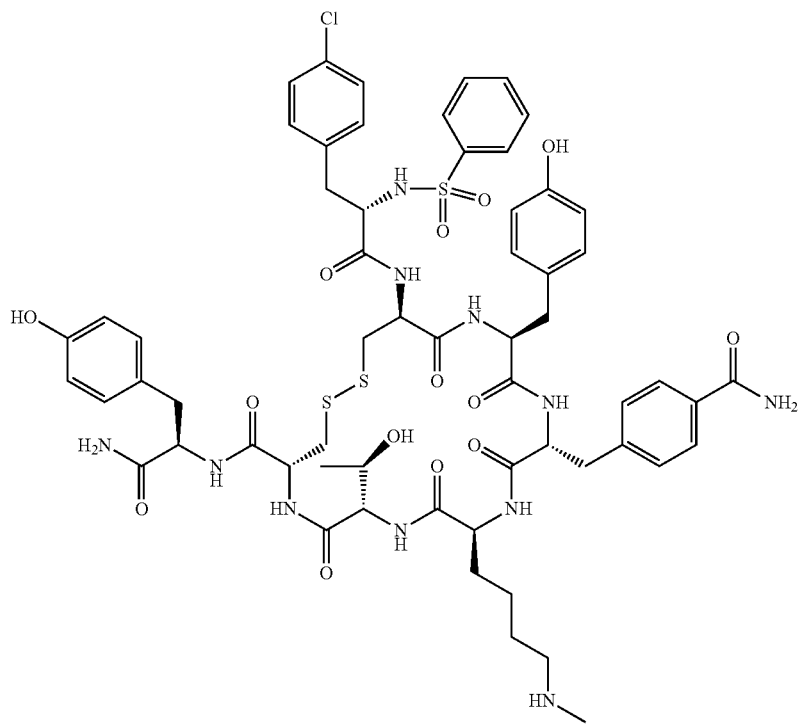 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NS(=O)(=O)c2ccccc2)CSSC[C@@H](C(=O)N[C@H](Cc2ccc(O)cc2)C(N)=O)NC(=O)[C@H]([C@@H](C)O)NC1=O]

INFORMAL SEQUENCE TABLE WITH FREE TEXT

SEQ ID NO: 83

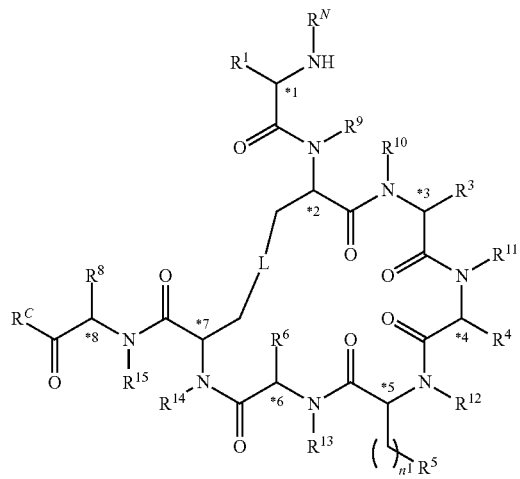

*AA1*-cylco[*AA2*-*AA3*-*AA4*-*AA5*-*AA6*-*AA7*]-*AA8*-

SEQ ID NO: 84

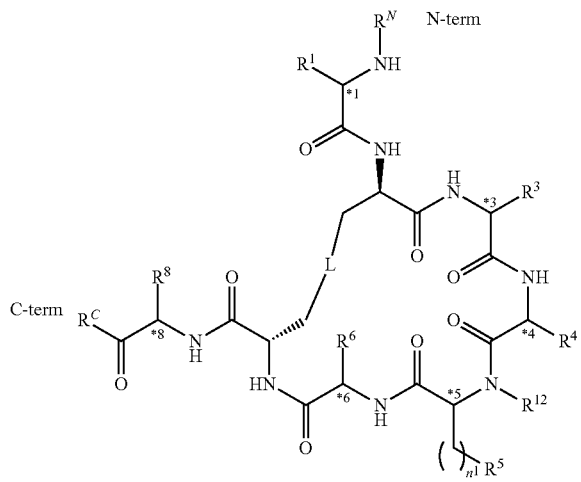

*AA9*-cyclo[*AA10*-*AA11*-*AA12*-*AA13*-*AA14*-*AA15*]-*AA16*-

*AA1*

$R^N$ is selected from the group consisting of: (i) H; (ii) $C_{1-6}$ alkyl; (iii) —C(O)$R^{17}$, wherein $R^{17}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (iv) —C(O)$C_{1-6}$ alkylene-C(O)O$R^{18}$, wherein $R^{18}$ is H or $C_{1-6}$ alkyl optionally substituted with one or more substituents; (v) —C(O)$C_{1-6}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{20}$ is H or $C_{1-6}$ alkyl; (vi) —C(O)$C_{1-6}$ alkylene-N$R^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (vii) —C(O) $C_{1-6}$ alkylene-C(O)N$R^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (viii) —C(O)$C_{1-6}$ alkylene-S(O)$_2R^{25}$, wherein $R^{25}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (ix) —S(O)$_2R^{26}$, wherein $R^{26}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; $R^1$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene (5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene ($C_{6-10}$ aryl) and —$C_{1-6}$ alkylene(5- to 10-membered heteroaryl) is optionally substituted with one or more substituents; chiral centre *1 is in the S configuration or the R configuration;

*AA2*

$R^9$ is H or $C_{1-6}$ alkyl; chiral centre *2 is in the S configuration or the R configuration;

*AA3*

$R^3$ is selected from the group consisting of: (i) $C_{6-10}$ aryl which is optionally substituted with one or more substituents; (ii) 5- to 10-membered heteroaryl which is optionally substituted with one or more substituents; (iii) —$C_{1-6}$ alkylene($C_{6-10}$ aryl), wherein the $C_{6-10}$ aryl is optionally substituted with one or more substituents, and wherein the $C_{1-6}$ alkylene is optionally substituted with one or more substituents; (iv) —$C_{1-6}$ alkylene(5- to 10-membered heteroaryl), wherein the 5- to 10-membered heteroaryl is optionally substituted with one or more substituents, and wherein the $C_{1-6}$ alkylene is optionally substituted with one or more substituents; (v) —$C_{1-6}$ alkylene-$NR^{27}C(O)R^{28}$, wherein: $R^{27}$ is H or $C_{1-6}$ alkyl; $R^{28}$ is selected from the group consisting of $C_{1-6}$ alkyl, $C_{6-10}$ aryl, 5- to 10-membered heteroaryl, and —$NR^{29}R^{30}$, wherein the $C_{1-6}$ alkyl is optionally substituted with one or more substituents, and wherein the $C_{6-10}$ aryl and 5- to 10-membered heteroaryl are optionally substituted with one or more substituents; and wherein each of $R^{29}$ and $R^{30}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (vi) —($C_{6-10}$ arylene)-$C(O)NR^{31}R^{32}$ or —$C_{1-6}$ alkylene-($C_{6-10}$ arylene)-$C(O)NR^{31}R^{32}$, wherein each of $R^{31}$ and $R^{32}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (vii) —($C_{6-10}$ arylene)-$NR^{33}R^{34}$ or —$C_{1-6}$ alkylene-($C_{6-10}$ arylene)-$NR^{33}R^{34}$, wherein: each of $R^{33}$ and $R^{34}$ is independently selected from the group consisting of H, $C_{1-6}$ alkyl, $C_{6-10}$ aryl, 5- to 10-membered heteroaryl, —$C(O)R^{35}$, —$C(O)NR^{36}R^{37}$, and —$SO_2R^{38}$, wherein the $C_{1-6}$ alkyl is optionally substituted with one or more substituents, and wherein the $C_{6-10}$ aryl and 5- to 10-membered heteroaryl are optionally substituted with one or more substituents; $R^{35}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents; each of $R^{36}$ and $R^{37}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and $R^{38}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (viii) —($C_{6-10}$ arylene)-$SO_2NR^{39}R^{40}$ or —$C_1$ alkylene-($C_{6-10}$ arylene)-$SO_2NR^{39}R^{40}$, wherein each of $R^{39}$ and $R^{40}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (ix) —($C_{6-10}$ arylene)-($C_{1-6}$ alkylene)-$NR^{41}R^{42}$ or —$C_{1-6}$ alkylene-($C_{6-10}$ arylene)-($C_{1-6}$ alkylene)-$NR^{41}R^{42}$, wherein: each of $R^{41}$ and $R^{42}$ is independently selected from the group consisting of H, $C_{1-6}$ alkyl, $C_{6-10}$ aryl, 5- to 10-membered heteroaryl, —$C(O)R^{43}$, and —$C(O)NR^{44}R^{45}$, wherein the $C_{1-6}$ alkyl is optionally substituted with one or more substituents, and wherein the $C_{6-10}$ aryl and 5- to 10-membered heteroaryl are optionally substituted with one or more substituents; $R^{43}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-$N(R^{47})$—C(O)—$CHR^{48}$—$NR^{49}R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —$C(O)NH_2$, and —N(H)C(O)$NH_2$, and each of $R^{49}$ and $R^{50}$ is independently H, $CH_3$ or acetyl; $R^{10}$ is H or $C_{1-6}$ alkyl; chiral centre *3 is in the S configuration or the R configuration;

*AA4*

$R^4$ is selected from the group consisting of: (i) —$C_{1-6}$ alkylene-$N(R^{53})C(O)NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl; (ii) —$C_{1-6}$ alkylene-$N(R^{55})C(O)R^{54}$, wherein $R^{54}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl; (iii) —($C_{6-10}$ arylene)-$C(O)NR^{56}R^{57}$ or —$C_{1-6}$ alkylene-($C_{6-10}$ arylene)-$C(O)NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (iv) —($C_{6-10}$ arylene)-$N(R^{59})C(O)R^{58}$ or —$C_{1-6}$ alkylene-($C_{6-10}$ arylene)-$N(R^{59})C(O)R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl; (v) —($C_{6-10}$ arylene)-N($R^{62}$)C(O)NR$^{60}$R$^{61}$ or —$C_{1-6}$ alkylene-($C_{6-10}$ arylene)-N($R^{62}$)C(O)NR$^{60}$R$^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl; (vi) —($C_{6-10}$ arylene)-N($R^{64}$)SO$_2$R$^{3}$ or —$C_{1-6}$ alkylene-($C_{6-10}$ arylene)-N($R^{64}$)SO$_2$R$^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl; (vii) —($C_{6-10}$ arylene)-SO$_2$NR$^{65}$R$^{66}$ or —$C_{1-6}$ alkylene-($C_{6-10}$ arylene)-SO$_2$NR$^{65}$R$^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (viii) —($C_{6-10}$ arylene)-($C_{1-6}$ alkylene)-NR$^{67}$R$^{68}$ or —$C_{1-6}$ alkylene-($C_{6-10}$ arylene)-($C_{1-6}$ alkylene)-NR$^{67}$R$^{68}$, wherein: each of $R^{67}$ and $R^{68}$ is independently selected from the group consisting of H, $C_{1-6}$ alkyl, $C_{6-10}$ aryl, 5- to 10-membered heteroaryl, —C(O)R$^{69}$, and —C(O)NR$^{70}$R$^{71}$, wherein the $C_{1-6}$ alkyl is optionally substituted with one or more substituents, and wherein the $C_{6-10}$ aryl and 5- to 10-membered heteroaryl are optionally substituted with one or more substituents; $R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (ix) —($C_{6-10}$ arylene)-NR$^{72}$R$^{73}$ or —$C_{1-6}$ alkylene-($C_{6-10}$ arylene)-NR$^{72}$R$^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (x) —($C_{6-10}$ arylene)-OR$^{74}$ or —$C_{1-6}$ alkylene-($C_{6-10}$ arylene)-OR$^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (xi) —$C_{1-6}$ alkylene-($C_{6-10}$ arylene)-N($R^{75}$)—C(O)—CHR$^{76}$—NR$^{77}$R$^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{77}$ and $R^{78}$ is independently H, CH$_3$ or acetyl; and (xii) —$C_{1-6}$ alkylene-($C_{6-10}$ arylene)-CN; $R^{11}$ is H or $C_{1-6}$ alkyl; chiral centre *4 is in the S configuration or the R configuration;

\*AA5\*

$R^5$ is selected from the group consisting of: (i) —NR$^{79}$R$^{80}$, wherein each of $R^{79}$ and $R^{80}$ is independently selected from the group consisting of H, $C_{1-6}$ alkyl, —C(O)R$^{81}$, and —C(=NR$^{82}$)NR$^{83}$R$^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, $R^{81}$ is selected from the group consisting of H, —NH$_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl; and (ii) —N$^+$R$^{85}$R$^{86}$R$^{87}$, wherein each of $R^{85}$, $R^{86}$, and $R^{87}$ is independently $C_{1-6}$ alkyl; $n^1$ is 1, 2, 3, 4, 5, or 6; $R^{12}$ is H or $C_{1-6}$ alkyl; chiral centre *5 is in the S configuration or the R configuration;

\*AA6\*

$R^6$ is $C_{1-6}$ alkyl optionally substituted with one or more substituents; $R^8$ is selected from the group consisting of $C_{1-6}$ alkyl, $C_{6-10}$ aryl, 5- to 10-membered heteroaryl, —$C_{1-6}$ alkylene($C_{6-10}$ aryl) and —$C_{1-6}$ alkylene(5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_6$ alkylene($C_{6-10}$ aryl) and —$C_{1-6}$ alkylene(5- to 10-membered heteroaryl) is optionally substituted with one or more substituents; $R^{13}$ is H or $C_{1-6}$ alkyl; chiral centre *6 is in the S configuration or the R configuration;

\*AA7\*

$R^{14}$ is H or $C_{1-6}$ alkyl; chiral centre *7 is in the S configuration or the R configuration;

\*AA8\*

$R^C$ is OH or NHR$^{16}$, wherein $R^{16}$ is H or $C_{1-6}$ alkyl optionally substituted with one or more substituents; $R^{15}$ is H or $C_{1-6}$ alkyl; chiral centre *8 is in the S configuration or the R configuration,

\*L1\*

L is selected from the group consisting of:

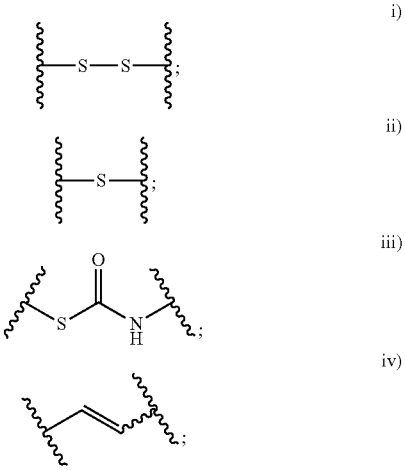

-continued

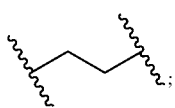;

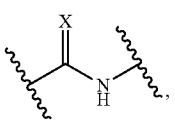, wherein X is S or O; and

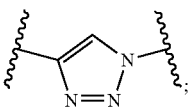 [SMILES: *c1cn(*)nn1];

provided that:
i) when $R^C$ is $NH_2$, $R^N$ is H or —C(O)CH$_2$N$_3$, $R^1$ is

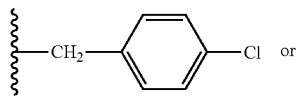 or

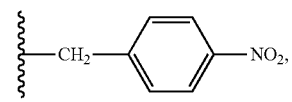, $R^3$ is

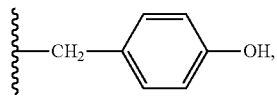,

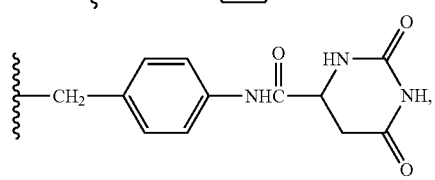,

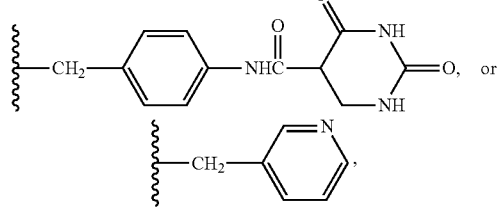, or

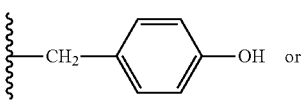, $R^5$ is $NH_2$, $n^1$ is 4, $R^6$ is —CH(OH)(CH$_3$), $R^8$ is

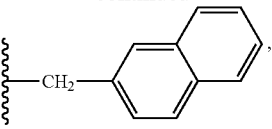 or

-continued v) 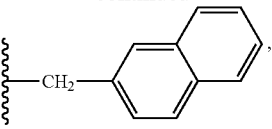, vi) each of $R^9$, $R^{10}$, $R^{11}$, $R^{12}$, $R^{13}$, $R^{14}$ and $R^{15}$ is H, and L is

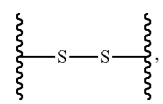, then $R^4$ is not

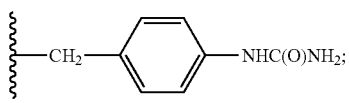;

and ii) when $R^C$ is $NH_2$, $R^N$ is H, $R^1$ is

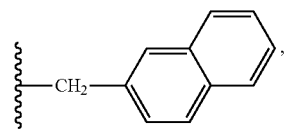, $R^3$ is

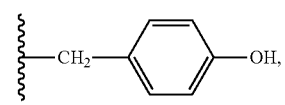, $R^5$ is $NH_2$, $n^1$ is 4, $R^6$ is —CH(CH$_3$)$_2$, $R^8$ is —CH(OH)(CH$_3$), each of $R^9$, $R^{10}$, $R^{11}$, $R^{12}$, $R^{13}$, $R^{14}$ and $R^{15}$ is H, and L is

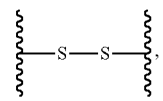, then $R^4$ is not

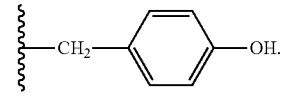.

*AA9*

$R^N$ is H, CH$_3$ or acetyl; $R^1$ is selected from the group consisting of C$_{6-10}$ aryl, 5- to 10-membered heteroaryl, —C$_{1-6}$ alkylene(C$_{6-10}$ aryl) and —C$_{1-6}$ alkylene(5- to 10-membered heteroaryl), wherein the C$_{6-10}$ aryl and the C$_{6-10}$ aryl of —C$_{1-6}$ alkylene(C$_{6-10}$ aryl) and the 5- to 10-membered heteroaryl and the 5- to 10-membered heteroaryl of —C$_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents; chiral centre *1 is in the S configuration or the R configuration;

*AA10*

Is Ala and is joined to *AA15* via *L2* wherein *L2* attaches to the methyl side chain;

*AA11*

$R^3$ is selected from the group consisting of: (i) $C_{6-10}$ aryl which is optionally substituted with one or more substituents; (ii) 5- to 10-membered heteroaryl which is optionally substituted with one or more substituents; (iii) —$C_{1-6}$ alkylene($C_{6-10}$ aryl), wherein the $C_{6-10}$ aryl is optionally substituted with one or more substituents, and wherein the $C_{1-6}$ alkylene is optionally substituted with one or more substituents; (iv) —$C_{1-6}$ alkylene(5- to 10-membered heteroaryl), wherein the 5- to 10-membered heteroaryl is optionally substituted with one or more substituents, and wherein the $C_{1-6}$ alkylene is optionally substituted with one or more substituents; (v) —$NR^{27}C(O)R^{28}$ or —$C_{1-6}$ alkylene-$NR^{27}C(O)R^{28}$, wherein: $R^{27}$ is H or $C_{1-6}$ alkyl; $R^{28}$ is selected from the group consisting of $C_{1-6}$ alkyl, $C_{6-10}$ aryl, 5- to 10-membered heteroaryl, and —$NR^{29}R^{30}$, wherein the $C_{1-6}$ alkyl is optionally substituted with one or more substituents, and wherein the $C_{6-10}$ aryl and 5- to 10-membered heteroaryl are optionally substituted with one or more substituents; and wherein each of $R^{29}$ and $R^{30}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (vi) —($C_{6-10}$ arylene)-$C(O)NR^{31}R^{32}$ or —$C_{1-6}$ alkylene-($C_{6-10}$ arylene)-$C(O)NR^{31}R^{32}$, wherein each of $R^{31}$ and $R^{32}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (vii) —($C_{6-10}$ arylene)-$NR^{33}R^{34}$ or —$C_{1-6}$ alkylene-($C_{6-10}$ arylene)-$NR^{33}R^{34}$, wherein: each of $R^{33}$ and $R^{34}$ is independently selected from the group consisting of H, $C_{1-6}$ alkyl, $C_{6-10}$ aryl, 5- to 10-membered heteroaryl, —$C(O)R^{35}$, —$C(O)NR^{36}R^{37}$, and —$SO_2R^{38}$, wherein the $C_{1-6}$ alkyl is optionally substituted with one or more substituents, and wherein the $C_{6-10}$ aryl and 5- to 10-membered heteroaryl are optionally substituted with one or more substituents; $R^{35}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents; each of $R^{36}$ and $R^{37}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and $R^{38}$ is selected from the group consisting of $C_{1-6}$ alkyl, $C_{6-10}$ aryl, and 5- to 10-membered heteroaryl, wherein the $C_{1-6}$alkyl is optionally substituted with one or more substituents, and wherein the $C_{6-10}$ aryl and 5- to 10-membered heteroaryl are optionally substituted with one or more substituents; (viii) —($C_{6-10}$ arylene)-$SO_2NR^{39}R^{40}$ or —$C_{1-6}$ alkylene-($C_{6-10}$ arylene)-$SO_2NR^{39}R^{40}$, wherein each of $R^{39}$ and $R^{40}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (ix) —($C_{6-10}$ arylene)-($C_{1-6}$ alkylene)-$NR^{41}R^{42}$ or —$C_{1-6}$ alkylene-($C_{6-10}$ arylene)-($C_{1-6}$ alkylene)-$NR^{41}R^{42}$, wherein: each of $R^{41}$ and $R^{42}$ is independently selected from the group consisting of H, $C_{1-6}$ alkyl, $C_{6-10}$ aryl, 5- to 10-membered heteroaryl, —$C(O)R^{43}$, and —$C(O)NR^{44}R^{45}$, wherein the $C_{1-6}$alkyl is optionally substituted with one or more substituents, and wherein the $C_{6-10}$ aryl and 5- to 10-membered heteroaryl are optionally substituted with one or more substituents; $R^{43}$ is selected from the group consisting of $C_{1-6}$ alkyl, $C_{6-10}$ aryl, and 5- to 10-membered heteroaryl, wherein the $C_{1-6}$alkyl is optionally substituted with one or more substituents, and wherein the $C_{6-10}$ aryl and 5- to 10-membered heteroaryl are optionally substituted with one or more substituents; and each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-$N(R^{47})$—$C(O)$—$CHR^{48}$—$NR^{49}R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —$C(O)NH_2$, and —$N(H)C(O)NH_2$, and each of $R^{49}$ and $R^{50}$ is independently H, $CH_3$ or acetyl; chiral centre *3 is in the S configuration or the R configuration;

*AA12*

$R^4$ is selected from the group consisting of: (i) —$N(R^{53})C(O)NR^{51}R^{52}$ or —$C_{1-6}$ alkylene-$N(R^{53})C(O)NR^{51}R^{52}$, wherein each of $R^{51}$ and $R^{52}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{53}$ is H or $C_{1-6}$ alkyl; (ii) —$N(R^{55})C(O)R^{54}$ or —$C_{1-6}$ alkylene-$N(R^{55})C(O)R^{54}$, wherein $R^{54}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{55}$ is H or $C_{1-6}$ alkyl; (iii) —($C_{6-10}$ arylene)-$C(O)NR^{56}R^{57}$ or —$C_{1-6}$ alkylene-($C_{6-10}$ arylene)-$C(O)NR^{56}R^{57}$, wherein each of $R^{56}$ and $R^{57}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (iv) —($C_{6-10}$ arylene)-$N(R^{59})C(O)R^{58}$ or —$C_{1-6}$ alkylene-($C_{6-10}$ arylene)-$N(R^{59})C(O)R^{58}$, wherein $R^{58}$ is selected from the group consisting of $C_{1-6}$ alkyl, $C_{6-10}$ aryl, 5- to 10-membered heteroaryl, and 5- to 10-membered heterocycloalkyl, wherein the $C_{1-6}$ alkyl is optionally substituted with one or more substituents, and wherein the $C_{6-10}$ aryl, 5- to 10-membered heteroaryl, and 5- to 10-membered heterocycloalkyl are optionally substituted with one or more substituents, and wherein $R^{59}$ is H or $C_{1-6}$ alkyl; (v) —($C_{6-10}$ arylene)-N($R^{62}$)C(O)N$R^{60}R^{61}$ or —$C_{1-6}$ alkylene-($C_{6-10}$ arylene)-N($R^{62}$)C(O)N$R^{60}R^{61}$, wherein each of $R^{60}$ and $R^{61}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{62}$ is H or $C_{1-6}$ alkyl; (vi) —($C_{6-10}$ arylene)-N($R^{64}$)SO$_2R^{63}$ or —$C_{1-6}$ alkylene-($C_{6-10}$ arylene)-N($R^{64}$)SO$_2R^{63}$, wherein $R^{63}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{64}$ is H or $C_{1-6}$ alkyl; (vii) —($C_{6-10}$ arylene)-SO$_2$N$R^{65}R^{66}$ or —$C_{1-6}$ alkylene-($C_{6-10}$ arylene)-SO$_2$N$R^{65}R^{66}$, wherein each of $R^{65}$ and $R^{66}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (viii) —($C_{6-10}$ arylene)-($C_{1-6}$ alkylene)-N$R^{67}R^{68}$ or —$C_{1-6}$ alkylene-($C_{6-10}$ arylene)-($C_{1-6}$ alkylene)-N$R^{67}R^{68}$, wherein: each of $R^{67}$ and $R^{68}$ is independently selected from the group consisting of H, $C_{1-6}$ alkyl, $C_{6-10}$ aryl, 5- to 10-membered heteroaryl, —C(O)$R^{69}$, and —C(O)N$R^{70}R^{71}$, wherein the $C_{1-6}$ alkyl is optionally substituted with one or more substituents, and wherein the $C_{6-10}$ aryl and 5- to 10-membered heteroaryl are optionally substituted with one or more substituents; $R^{69}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{70}$ and $R^{71}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (ix) —($C_{6-10}$ arylene)-N$R^{72}R^{73}$ or —$C_{1-6}$ alkylene-($C_{6-10}$ arylene)-N$R^{72}R^{73}$, wherein each of $R^{72}$ and $R^{73}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; (x) —($C_{6-10}$ arylene)-O$R^{74}$ or —$C_{1-6}$ alkylene-($C_{6-10}$ arylene)-O$R^{74}$, wherein $R^{74}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-N($R^{75}$)—C(O)—CH$R^{76}$—N$R^{77}R^{78}$, wherein $R^{75}$ is H or CH$_3$, $R^{76}$ is H or $C_{1-6}$ alkyl optionally substituted with one or more substituents each independently selected from the group consisting of hydroxyl, —COOH, —NH$_2$, —C(O)NH$_2$, and —N(H)C(O)NH$_2$, and each of $R^{77}$ and $R^{78}$ is independently H, CH$_3$ or acetyl; chiral centre *4 is in the S configuration or the R configuration;

*AA13*

$R^5$ is selected from the group consisting of: (i) —N$R^{79}R^{80}$, wherein each of $R^{79}$ and $R^{80}$ is independently selected from the group consisting of H, $C_{1-6}$ alkyl, —C(O)$R^{81}$, and —C(=N$R^{82}$)N$R^{83}R^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, $R^{81}$ is selected from the group consisting of H, —NH$_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl; and (ii) —N$^+R^{85}R^{86}R^{87}$, wherein each of $R^{85}$, $R^{86}$, and $R^{87}$ is independently $C_{1-6}$ alkyl; $n^1$ is 1, 2, 3, 4, 5, or 6; $R^{12}$ is H or CH$_3$; chiral centre *5 is in the S configuration;

*AA14*

$R^6$ is $C_{106}$ alkyl optionally substituted with one or more substituents; chiral centre *6 is in the S configuration or the R configuration;

*AA15*

Is Ala and is joined to *AA9* via *L2* wherein *L2* attaches to the methyl side chain;

*AA16*

$R^C$ is OH or NH$_2$; $R^8$ is selected from the group consisting of $C_{6-10}$ aryl, 5- to 10-membered heteroaryl, —$C_{1-6}$ alkylene ($C_{6-10}$ aryl) and —$C_{1-6}$ alkylene(5- to 10-membered heteroaryl), wherein the $C_{6-10}$ aryl and the $C_{6-10}$ aryl of —$C_{1-6}$ alkylene($C_{6-10}$ aryl) and the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents; chiral centre *8 is in the S configuration or the R configuration,

*L2*

L is selected from the group consisting of:

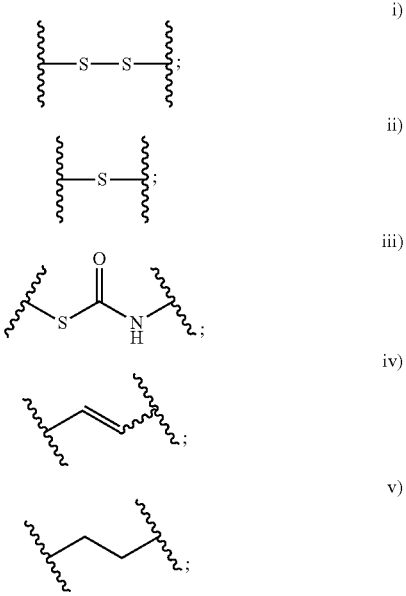

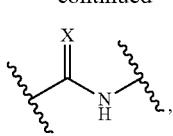

wherein X is S or O; and

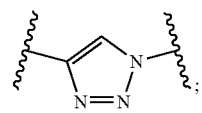

provided that:
when L is

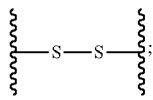 [SMILES: *SS*]

$R^4$ is —$CH_2$-(phenylene)-N(H)C(O)$NH_2$; $R^3$ is —$CH_2$-(phenyl) or —$CH_2$-(phenylene)-N(H)C(O)$R^{35}$, wherein the phenyl of —$CH_2$-(phenyl) is substituted with hydroxy and wherein $R^{35}$ is 2,6-dioxohexahydropyrimidine; $R^5$ is $NH_2$; $n^1$ is 4; $R^{12}$ is H; $R^6$ is —CH(OH)($CH_3$); and $R^8$ is —$CH_2$-(phenyl) or —$CH_2$-(napthyl), wherein the phenyl is substituted with hydroxy, then $R^1$ is not —$CH_2$-(phenyl), wherein the phenyl is substituted with —Cl or —$NO_2$.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) and all publications, including but not limited to patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

---

SEQUENCE LISTING

```
<160> NUMBER OF SEQ ID NOS: 85

<210> SEQ ID NO 1
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DCit
<220> FEATURE:
<221> NAME/KEY: misc_feature
<222> LOCATION: (8)..(8)
<223> OTHER INFORMATION: Xaa is DTyr-NH2

<400> SEQUENCE: 1

Xaa Xaa Tyr Xaa Lys Thr Cys Xaa
1               5

<210> SEQ ID NO 2
<211> LENGTH: 8
<212> TYPE: PRT
<213> ORGANISM: Artificial Sequence
```

```
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DHoCit
<220> FEATURE:
<221> NAME/KEY: misc_feature
<222> LOCATION: (8)..(8)
<223> OTHER INFORMATION: Xaa is DTyr-NH2

<400> SEQUENCE: 2

Xaa Xaa Tyr Xaa Lys Thr Cys Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D_(Nepsilon-nicotinoyl)Lys
<220> FEATURE:
<221> NAME/KEY: misc_feature
<222> LOCATION: (8)..(8)
<223> OTHER INFORMATION: Xaa is DTyr-NH2

<400> SEQUENCE: 3

Xaa Xaa Tyr Xaa Lys Thr Cys Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
```

```
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 4

Xaa Xaa Tyr Xaa Lys Thr Cys Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-aminomethyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 5

Xaa Xaa Tyr Xaa Lys Thr Cys Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-acetamidomethyl)Phe
<220> FEATURE:
<221> NAME/KEY: misc_feature
<222> LOCATION: (8)..(8)
```

<223> OTHER INFORMATION: Xaa is Lys-Thr-Cys]-DTyr-NH2

<400> SEQUENCE: 6

Xaa Xaa Tyr Xaa Lys Thr Cys Xaa
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-ureidomethyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 7

Xaa Xaa Tyr Xaa Lys Thr Cys Xaa
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Gly)Aph
<220> FEATURE:
<221> NAME/KEY: misc_feature
<222> LOCATION: (8)..(8)
<223> OTHER INFORMATION: Xaa is DTyr-NH2

<400> SEQUENCE: 8

Xaa Xaa Tyr Xaa Lys Thr Cys Xaa
1               5

<210> SEQ ID NO 9
<211> LENGTH: 8
<212> TYPE: PRT

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Gly-Ac)Aph
<220> FEATURE:
<221> NAME/KEY: misc_feature
<222> LOCATION: (8)..(8)
<223> OTHER INFORMATION: Xaa is DTyr-NH2

<400> SEQUENCE: 9

Xaa Xaa Tyr Xaa Lys Thr Cys Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Pro)Aph
<220> FEATURE:
<221> NAME/KEY: misc_feature
<222> LOCATION: (8)..(8)
<223> OTHER INFORMATION: Xaa is DTyr-NH2

<400> SEQUENCE: 10

Xaa Xaa Tyr Xaa Lys Thr Cys Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
```

-continued

```
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(2-(4-morpholinyl)ethyl)Aph
<220> FEATURE:
<221> NAME/KEY: misc_feature
<222> LOCATION: (8)..(8)
<223> OTHER INFORMATION: Xaa is DTyr-NH2

<400> SEQUENCE: 11

Xaa Xaa Tyr Xaa Lys Thr Cys Xaa
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(n-pentylamino)Phe
<220> FEATURE:
<221> NAME/KEY: misc_feature
<222> LOCATION: (8)..(8)
<223> OTHER INFORMATION: Xaa is DTyr-NH2

<400> SEQUENCE: 12

Xaa Xaa Tyr Xaa Lys Thr Cys Xaa
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(2-(4-morpholinyl)ethyl)Tyr
<220> FEATURE:
<221> NAME/KEY: misc_feature
```

```
<222> LOCATION: (8)..(8)
<223> OTHER INFORMATION: Xaa is DTyr-NH2

<400> SEQUENCE: 13

Xaa Xaa Tyr Xaa Lys Thr Cys Xaa
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(benzenesulfonyl)Aph
<220> FEATURE:
<221> NAME/KEY: misc_feature
<222> LOCATION: (8)..(8)
<223> OTHER INFORMATION: DTyr-NH2

<400> SEQUENCE: 14

Xaa Xaa Tyr Xaa Lys Thr Cys Xaa
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(phenylureido)Phe
<220> FEATURE:
<221> NAME/KEY: misc_feature
<222> LOCATION: (8)..(8)
<223> OTHER INFORMATION: Xaa is DTyr-NH2

<400> SEQUENCE: 15

Xaa Xaa Tyr Xaa Lys Thr Cys Xaa
1               5

<210> SEQ ID NO 16
<211> LENGTH: 8
```

```
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Ser)Aph
<220> FEATURE:
<221> NAME/KEY: misc_feature
<222> LOCATION: (8)..(8)
<223> OTHER INFORMATION: Xaa is DTyr-NH2

<400> SEQUENCE: 16

Xaa Xaa Tyr Xaa Lys Thr Cys Xaa
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Lys)Aph
<220> FEATURE:
<221> NAME/KEY: misc_feature
<222> LOCATION: (8)..(8)
<223> OTHER INFORMATION: Xaa is DTyr-NH2

<400> SEQUENCE: 17

Xaa Xaa Tyr Xaa Lys Thr Cys Xaa
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
```

```
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Asp)Aph
<220> FEATURE:
<221> NAME/KEY: misc_feature
<222> LOCATION: (8)..(8)
<223> OTHER INFORMATION: Xaa is DTyr-NH2

<400> SEQUENCE: 18

Xaa Xaa Tyr Xaa Lys Thr Cys Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Asn)Aph
<220> FEATURE:
<221> NAME/KEY: misc_feature
<222> LOCATION: (8)..(8)
<223> OTHER INFORMATION: Xaa is DTyr-NH2

<400> SEQUENCE: 19

Xaa Xaa Tyr Xaa Lys Thr Cys Xaa
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Glu)Aph
<220> FEATURE:
```

<221> NAME/KEY: misc_feature
<222> LOCATION: (8)..(8)
<223> OTHER INFORMATION: Xaa is DTyr-NH2

<400> SEQUENCE: 20

Xaa Xaa Tyr Xaa Lys Thr Cys Xaa
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
    position 7 are joined by a disulfide linker
<220> FEATURE:
<221> NAME/KEY: misc_feature
<222> LOCATION: (4)..(4)
<223> OTHER INFORMATION: Xaa is D-4-(Gln)Aph
<220> FEATURE:
<221> NAME/KEY: misc_feature
<222> LOCATION: (8)..(8)
<223> OTHER INFORMATION: Xaa is DTyr-NH2

<400> SEQUENCE: 21

Xaa Xaa Tyr Xaa Lys Thr Cys Xaa
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
    position 7 are joined by a disulfide linker
<220> FEATURE:
<221> NAME/KEY: misc_feature
<222> LOCATION: (4)..(4)
<223> OTHER INFORMATION: Xaa is D-4-(Cit)Aph
<220> FEATURE:
<221> NAME/KEY: misc_feature
<222> LOCATION: (8)..(8)
<223> OTHER INFORMATION: Xaa is DTyr-NH2

<400> SEQUENCE: 22

Xaa Xaa Tyr Xaa Lys Thr Cys Xaa
1               5

<210> SEQ ID NO 23

```
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(Val)Aph
<220> FEATURE:
<221> NAME/KEY: misc_feature
<222> LOCATION: (8)..(8)
<223> OTHER INFORMATION: Xaa is DTyr-NH2

<400> SEQUENCE: 23

Xaa Xaa Tyr Xaa Lys Thr Cys Xaa
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-Epsilon-Me)Lys
<220> FEATURE:
<221> NAME/KEY: misc_feature
<222> LOCATION: (8)..(8)
<223> OTHER INFORMATION: Xaa is DTyr-NH2

<400> SEQUENCE: 24

Xaa Xaa Tyr Xaa Xaa Thr Cys Xaa
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
```

```
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(phenylureido)Phe
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
<222> LOCATION: (8)..(8)
<223> OTHER INFORMATION: Xaa is DTyr-NH2

<400> SEQUENCE: 25

Xaa Xaa Tyr Xaa Xaa Thr Cys Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-Acetyl)Lys
<220> FEATURE:
<221> NAME/KEY: misc_feature
<222> LOCATION: (8)..(8)
<223> OTHER INFORMATION: Xaa is DTyr-NH2

<400> SEQUENCE: 26

Xaa Xaa Tyr Xaa Xaa Thr Cys Xaa
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
```

```
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-Benzamidophenyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 27

Xaa Xaa Tyr Xaa Lys Thr Cys Xaa
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-(4-methoxyphenyl)ureido)Phe
<220> FEATURE:
<221> NAME/KEY: misc_feature
<222> LOCATION: (8)..(8)
<223> OTHER INFORMATION: Xaa is DTyr-NH2

<400> SEQUENCE: 28

Xaa Xaa Tyr Xaa Lys Thr Cys Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
```

```
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 29

Xaa Xaa Tyr Xaa Arg Thr Cys Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(N-nicotinoyl)Lys
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
<222> LOCATION: (8)..(8)
<223> OTHER INFORMATION: Xaa is DTyr-NH2

<400> SEQUENCE: 30

Xaa Xaa Tyr Xaa Xaa Thr Cys Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-Cit
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
```

```
<222> LOCATION: (8)..(8)
<223> OTHER INFORMATION: Xaa is DTyr-NH2

<400> SEQUENCE: 31

Xaa Xaa Tyr Xaa Xaa Thr Cys Xaa
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-diMe)Lys
<220> FEATURE:
<221> NAME/KEY: misc_feature
<222> LOCATION: (8)..(8)
<223> OTHER INFORMATION: Xaa is DTyr-NH2

<400> SEQUENCE: 32

Xaa Xaa Tyr Xaa Xaa Thr Cys Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 33

Xaa Xaa Tyr Xaa Lys Val Cys Xaa
1               5
```

```
<210> SEQ ID NO 34
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-4-(carbamoyl)Phe
<220> FEATURE:
<221> NAME/KEY: misc_feature
<222> LOCATION: (6)..(6)
<223> OTHER INFORMATION: Xaa is tBu-Gly
<220> FEATURE:
<221> NAME/KEY: misc_feature
<222> LOCATION: (8)..(8)
<223> OTHER INFORMATION: Xaa is DTyr-NH2

<400> SEQUENCE: 34

Xaa Xaa Tyr Xaa Lys Xaa Cys Xaa
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 35

Xaa Xaa Phe Xaa Lys Thr Cys Xaa
1               5

<210> SEQ ID NO 36
<211> LENGTH: 8
<212> TYPE: PRT
<213> ORGANISM: Artificial Sequence
<220> FEATURE:
```

-continued

```
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is Cpa
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 36

Xaa Xaa Xaa Xaa Lys Thr Cys Xaa
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa isD-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 37

Xaa Xaa Tyr Xaa Lys Ser Cys Xaa
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
```

```
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is 4-OMe-Phe
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 38

Xaa Xaa Xaa Xaa Lys Thr Cys Xaa
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DTyr-NH2

<400> SEQUENCE: 39

Xaa Cys Tyr Xaa Lys Thr Cys Xaa
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
```

```
<220> FEATURE:
<221> NAME/KEY: misc_feature
<222> LOCATION: (8)..(8)
<223> OTHER INFORMATION: Xaa is DPhe-NH2

<400> SEQUENCE: 40

Xaa Xaa Tyr Xaa Lys Thr Cys Xaa
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is DPhe-NH2

<400> SEQUENCE: 41

Xaa Xaa Phe Xaa Lys Thr Cys Xaa
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is 4-Cl-D-Phe-NH2

<400> SEQUENCE: 42

Xaa Xaa Tyr Xaa Lys Thr Cys Xaa
1               5
```

```
<210> SEQ ID NO 43
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is 4-Cl-Phe
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is 4-Cl-D-Phe-NH2

<400> SEQUENCE: 43

Xaa Xaa Xaa Xaa Lys Thr Cys Xaa
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is 4-OMe-D-Phe-NH2

<400> SEQUENCE: 44

Xaa Xaa Tyr Xaa Lys Thr Cys Xaa
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is 4-OMe-Phe
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (8)..(8)
<223> OTHER INFORMATION: Xaa is 4-OMe-D-Phe-NH2

<400> SEQUENCE: 45

Xaa Xaa Xaa Xaa Lys Thr Cys Xaa
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
<222> LOCATION: (8)..(8)
<223> OTHER INFORMATION: Xaa is DCpa-NH2

<400> SEQUENCE: 46

Xaa Xaa Tyr Xaa Xaa Thr Cys Xaa
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
```

```
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is Cpa
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
<222> LOCATION: (8)..(8)
<223> OTHER INFORMATION: Xaa is DCpa-NH2

<400> SEQUENCE: 47

Xaa Xaa Xaa Xaa Xaa Thr Cys Xaa
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is Cpa
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-Me)Lys
<220> FEATURE:
<221> NAME/KEY: misc_feature
<222> LOCATION: (8)..(8)
<223> OTHER INFORMATION: Xaa is DTyr-NH2

<400> SEQUENCE: 48

Xaa Xaa Xaa Xaa Xaa Thr Cys Xaa
1               5

<210> SEQ ID NO 49
<211> LENGTH: 9
<212> TYPE: PRT
<213> ORGANISM: Artificial Sequence
<220> FEATURE:
```

```
<223> OTHER INFORMATION: Synthetic Sequence
<220> FEATURE:
<221> NAME/KEY: misc_feature
<222> LOCATION: (1)..(1)
<223> OTHER INFORMATION: X

```
<210> SEQ ID NO 51
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is (Phenylsulfonyl)acetic acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 51

Xaa Xaa Xaa Tyr Xaa Xaa Thr Cys Xaa
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is t-Butylacetic Acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 52
```

```
Xaa Xaa Xaa Tyr Xaa Xaa Thr Cys Xaa
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is Picolinic Acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 53

Xaa Xaa Xaa Tyr Xaa Xaa Thr Cys Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is 4-amino-4-oxobutanoic acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
```

```
<221> NAME/KEY: misc_feature
<222> LOCATION: (9)..(9)
<223> OTHER INFORMATION: Xaa is DTyr-NH2

<400> SEQUENCE: 54

Xaa Xaa Xaa Tyr Xaa Xaa Thr Cys Xaa
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is Ac-Gly
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 55

Xaa Xaa Xaa Tyr Xaa Xaa Thr Cys Xaa
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is Hexanoic Acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
```

<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 56

Xaa Xaa Xaa Tyr Xaa Xaa Thr Cys Xaa
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is 2-Furoic Acid
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 57

Xaa Xaa Xaa Tyr Xaa Xaa Thr Cys Xaa
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is monomethyl succinate
<220> FEATURE:
<221> NAME/KEY: misc_feature
<222> LOCATION: (2)..(2)
<223> OTHER INFORMATION: Xaa is Cpa
<220> FEATURE:
<221> NAME/KEY: misc_feature
<222> LOCATION: (3)..(3)
<223> OTHER INFORMATION: Xaa is DCys
<220> FEATURE:
<221> NAME/KEY: misc_feature
<222> LOCATION: (3)..(8)
<223> OTHER INFORMATION: Cyclic Peptide: AA at position 3 and AA at

```
      position 8 are joined by a disulfide linker
<220> FEATURE:
<221> NAME/KEY: misc_feature
<222> LOCATION: (5)..(5)
<223> OTHER INFORMATION: Xaa is DPhe(4-CONH2)
<220> FEATURE:
<221> NAME/KEY: misc_feature
<222> LOCATION: (6)..(6)
<223> OTHER INFORMATION: Xaa is Lys(Me)
<220> FEATURE:
<221> NAME/KEY: misc_feature
<222> LOCATION: (9)..(9)
<223> OTHER INFORMATION: Xaa is DTyr-NH2

<400> SEQUENCE: 58

Xaa Xaa Xaa Tyr Xaa Xaa Thr Cys Xaa
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe(4-CN)
<220> FEATURE:
<221> NAME/KEY: misc_feature
<222> LOCATION: (8)..(8)
<223> OTHER INFORMATION: Xaa is DTyr-NH2

<400> SEQUENCE: 59

Xaa Xaa Tyr Xaa Lys Thr Cys Xaa
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DDap
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a thiocarbamate linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
```

```
<222> LOCATION: (8)..(8)
<223> OTHER INFORMATION: Xaa is DTyr-NH2

<400> SEQUENCE: 60

Xaa Xaa Tyr Xaa Lys Thr Cys Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is Dap
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a thiocarbamate linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
<222> LOCATION: (8)..(8)
<223> OTHER INFORMATION: Xaa is DTyr-NH2

<400> SEQUENCE: 61

Xaa Xaa Tyr Xaa Lys Thr Cys Xaa
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a thiocarbamate linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
<222> LOCATION: (7)..(7)
<223> OTHER INFORMATION: Xaa is Dap
<220> FEATURE:
<221> NAME/KEY: misc_feature
<222> LOCATION: (8)..(8)
<223> OTHER INFORMATION: Xaa is DTyr-NH2

<400> SEQUENCE: 62

Xaa Xaa Tyr Xaa Lys Thr Xaa Xaa
1               5
```

```
<210> SEQ ID NO 63
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a thiocarbamate linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
<222> LOCATION: (5)..(5)
<223> OTHER INFORMATION: Xaa is Lys(Me)
<220> FEATURE:
<221> NAME/KEY: misc_feature
<222> LOCATION: (7)..(7)
<223> OTHER INFORMATION: Xaa is Dap
<220> FEATURE:
<221> NAME/KEY: misc_feature
<222> LOCATION: (8)..(8)
<223> OTHER INFORMATION: Xaa is DTyr-NH2

<400> SEQUENCE: 63

Xaa Xaa Tyr Xaa Xaa Thr Xaa Xaa
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DAla joined to a 1,2,3-triazole-1,4-diyl
      linker via the side chain
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a 1,2,3-triazole-1,4-diyl linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (7)..(7)
<223> OTHER INFORMATION: Xaa is Ala joined to a 1,2,3-triazole-1,4-diyl
      linker via the side chain
<220> FEATURE:
<221> NAME/KEY: misc_feature
<222> LOCATION: (8)..(8)
<223> OTHER INFORMATION: Xaa is DTyr-NH2

<400> SEQUENCE: 64
```

```
Xaa Xaa Tyr Xaa Lys Thr Xaa Xaa
1               5
```

<210> SEQ ID NO 65
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is LAla joined to a 1,2,3-triazole-1,4-diyl
      linker via the side chain
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a 1,2,3-triazole-1,4-diyl linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (7)..(7)
<223> OTHER INFORMATION: Xaa is Ala joined to a 1,2,3-triazole-1,4-diyl
      linker via the side chain
<220> FEATURE:
<221> NAME/KEY: misc_feature
<222> LOCATION: (8)..(8)
<223> OTHER INFORMATION: Xaa is DTyr-NH2

<400> SEQUENCE: 65

```
Xaa Xaa Tyr Xaa Lys Thr Xaa Xaa
1               5
```

<210> SEQ ID NO 66
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DAla joined to a 1,2,3-triazole-1,4-diyl
      linker via the side chain
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a 1,2,3-triazole-1,4-diyl linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (7)..(7)
<223> OTHER INFORMATION: Xaa is Ala joined to a 1,2,3-triazole-1,4-diyl
      linker via the side chain
<220> FEATURE:
<221> NAME/KEY: misc_feature
<222> LOCATION: (8)..(8)
<223> OTHER INFORMATION: Xaa is DTyr-NH2

```
<400> SEQUENCE: 66

Xaa Xaa Tyr Xaa Lys Thr Xaa Xaa
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DAla joined to a ethen-1,2-diyl linker
      via the side chain
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a ethen-1,2-diyl linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (7)..(7)
<223> OTHER INFORMATION: Xaa is Ala joined to a ethen-1,2-diyl linker
      via the side chain
<220> FEATURE:
<221> NAME/KEY: misc_feature
<222> LOCATION: (8)..(8)
<223> OTHER INFORMATION: Xaa is DTyr-NH2

<400> SEQUENCE: 67

Xaa Xaa Tyr Xaa Lys Thr Xaa Xaa
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is LAla joined to a ethen-1,2-diyl linker
      via the side chain
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a ethen-1,2-diyl linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (7)..(7)
<223> OTHER INFORMATION: Xaa is Ala joined to a ethen-1,2-diyl linker
      via the side chain
<220> FEATURE:
<221> NAME/KEY: misc_feature
<222> LOCATION: (8)..(8)
<223> OTHER INFORMATION: Xaa is DTyr-NH2
```

<400> SEQUENCE: 68

Xaa Xaa Tyr Xaa Lys Thr Xaa Xaa
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DDap
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a amide linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
<222> LOCATION: (8)..(8)
<223> OTHER INFORMATION: Xaa is DTyr-NH2

<400> SEQUENCE: 69

Xaa Xaa Tyr Xaa Lys Thr Asp Xaa
1               5

<210> SEQ ID NO 70
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DDap
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a amide linker
<220> FEATURE:
<221> NAME/KEY: misc_feature
<222> LOCATION: (4)..(4)
<223> OTHER INFORMATION: Xaa is D-4-(phenylureido)Phe
<220> FEATURE:
<221> NAME/KEY: misc_feature
<222> LOCATION: (8)..(8)
<223> OTHER INFORMATION: Xaa is DTyr-NH2

<400> SEQUENCE: 70

Xaa Xaa Tyr Xaa Lys Thr Asp Xaa
1               5

<210> SEQ ID NO 71
<211> LENGTH: 8
<212> TYPE: PRT
<213> ORGANISM: Artificial Sequence -continued

```
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DDap
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a amide linker
<220> FEATURE:
<221> NAME/KEY: misc_feature
<222> LOCATION: (4)..(4)
<223> OTHER INFORMATION: Xaa is DPhe(4-CONH2)
<220> FEATURE:
<221> NAME/KEY: misc_feature
<222> LOCATION: (5)..(5)
<223> OTHER INFORMATION: Xaa is Lys(Me)
<220> FEATURE:
<221> NAME/KEY: misc_feature
<222> LOCATION: (8)..(8)
<223> OTHER INFORMATION: Xaa is DTyr-NH2

<400> SEQUENCE: 71

Xaa Xaa Tyr Xaa Xaa Thr Asp Xaa
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is D-(4-carbamoyl)Phe
<220> FEATURE:
<221> NAME/KEY: misc_feature
<222> LOCATION: (5)..(5)
<223> OTHER INFORMATION: Xaa is (N-alpha-Me)Lys
<220> FEATURE:
<221> NAME/KEY: misc_feature
<222> LOCATION: (8)..(8)
<223> OTHER INFORMATION: Xaa is DTyr-NH2

<400> SEQUENCE: 72

Xaa Xaa Tyr Xaa Xaa Thr Cys Xaa
1               5

<210> SEQ ID NO 73
<211> LENGTH: 8
<212> TYPE: PRT
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (6)..(6)
<223> OTHER INFORMATION: Xaa is NMeThr
<220> FEATURE:
<221> NAME/KEY: misc_feature
<222> LOCATION: (8)..(8)
<223> OTHER INFORMATION: Xaa is DTyr-NH2

<400> SEQUENCE: 73

Xaa Xaa Tyr Xaa Lys Xaa Cys Xaa
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is NMeTyr
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (8)..(8)
<223> OTHER INFORMATION: Xaa is DTyr-NH2

<400> SEQUENCE: 74

Xaa Xaa Xaa Xaa Lys Thr Cys Xaa
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
```

```
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is NMeTyr
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (6)..(6)
<223> OTHER INFORMATION: Xaa is NMeThr
<220> FEATURE:
<221> NAME/KEY: misc_feature
<222> LOCATION: (8)..(8)
<223> OTHER INFORMATION: Xaa is DTyr-NH2

<400> SEQUENCE: 75

Xaa Xaa Xaa Xaa Lys Xaa Cys Xaa
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (7)..(7)
<223> OTHER INFORMATION: Xaa is NMeCys
<220> FEATURE:
<221> NAME/KEY: misc_feature
<222> LOCATION: (8)..(8)
<223> OTHER INFORMATION: Xaa is DTyr-NH2

<400> SEQUENCE: 76

Xaa Xaa Tyr Xaa Lys Thr Xaa Xaa
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
```

```
<223> OTHER INFORMATION: Xaa is H-NMeCpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (8)..(8)
<223> OTHER INFORMATION: Xaa is DTyr-NH2

<400> SEQUENCE: 77

Xaa Xaa Tyr Xaa Lys Thr Cys Xaa
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is NMeDCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (8)..(8)
<223> OTHER INFORMATION: Xaa is DTyr-NH2

<400> SEQUENCE: 78

Xaa Xaa Tyr Xaa Lys Thr Cys Xaa
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-Cpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
```

```
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (8)..(8)
<223> OTHER INFORMATION: Xaa is NMeDTyr-NH2

<400> SEQUENCE: 79

Xaa Xaa Tyr Xaa Lys Thr Cys Xaa
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-NMeCpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (3)..(3)
<223> OTHER INFORMATION: Xaa is NMeTyr
<220> FEATURE:
<221> NAME/KEY: misc_feature
<222> LOCATION: (4)..(4)
<223> OTHER INFORMATION: Xaa is DPhe(4-carbamoyl)
<220> FEATURE:
<221> NAME/KEY: misc_feature
<222> LOCATION: (6)..(6)
<223> OTHER INFORMATION: Xaa is NMeThr
<220> FEATURE:
<221> NAME/KEY: misc_feature
<222> LOCATION: (8)..(8)
<223> OTHER INFORMATION: Xaa is NMeDTyr-NH2

<400> SEQUENCE: 80

Xaa Xaa Xaa Xaa Lys Xaa Cys Xaa
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-N-methylsulfonylCpa
<220> FEATURE:
<221> NAME/KEY: misc_feature
<222> LOCATION: (2)..(2)
<223> OTHER INFORMATION: Xaa is DCys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe4-carbamoyl
```

```
<220> FEATURE:
<221> NAME/KEY: misc_feature
<222> LOCATION: (5)..(5)
<223> OTHER INFORMATION: Xaa is LysMe
<220> FEATURE:
<221> NAME/KEY: misc_feature
<222> LOCATION: (8)..(8)
<223> OTHER INFORMATION: Xaa is DTyr-NH2

<400> SEQUENCE: 81

Xaa Xaa Tyr Xaa Xaa Thr Cys Xaa
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Xaa is H-N-phenylsulfonylCpa
<220> FEATURE:
<221> NAME/KEY: misc_feature
<222> LOCATION: (2)..(2)
<223> OTHER INFORMATION: Xaa is Dcys
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a disulfide linker
<220> FEATURE:
<221> NAME/KEY: misc_feature
<222> LOCATION: (4)..(4)
<223> OTHER INFORMATION: Xaa is DPhe4-carbamoyl
<220> FEATURE:
<221> NAME/KEY: misc_feature
<222> LOCATION: (5)..(5)
<223> OTHER INFORMATION: Xaa is LysMe
<220> FEATURE:
<221> NAME/KEY: misc_feature
<222> LOCATION: (8)..(8)
<223> OTHER INFORMATION: Xaa is DTyr-NH2

<400> SEQUENCE: 82

Xaa Xaa Tyr Xaa Xaa Thr Cys Xaa
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(8)
<223> OTHER INFORMATION: Each AA may independently be in the R or S
      configuration
<220> FEATURE:
<221> NAME/KEY: misc_feature
<222> LOCATION: (1)..(1)
<223> OTHER INFORMATION: Xaa is as set out in *AA1*
<220> FEATURE:
<221> NAME/KEY: misc_feature
<222> LOCATION: (2)..(2)
<223> OTHER INFORMATION: Xaa is as set out in *AA2*
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a linker as set out in *L1*
<220> FEATURE:
<221> NAME/KEY: misc_feature
```

```
<222> LOCATION: (3)..(3)
<223> OTHER INFORMATION: Xaa is as set out in *AA3*
<220> FEATURE:
<221> NAME/KEY: misc_feature
<222> LOCATION: (4)..(4)
<223> OTHER INFORMATION: Xaa is as set out in *AA4*
<220> FEATURE:
<221> NAME/KEY: misc_feature
<222> LOCATION: (5)..(5)
<223> OTHER INFORMATION: Xaa is as set out in *AA5*
<220> FEATURE:
<221> NAME/KEY: misc_feature
<222> LOCATION: (6)..(6)
<223> OTHER INFORMATION: Xaa is as set out in *AA6*
<220> FEATURE:
<221> NAME/KEY: misc_feature
<222> LOCATION: (7)..(7)
<223> OTHER INFORMATION: Xaa is as set out in *AA7*
<220> FEATURE:
<221> NAME/KEY: misc_feature
<222> LOCATION: (8)..(8)
<223> OTHER INFORMATION: Xaa is as set out in *AA8*

<400> SEQUENCE: 83

Xaa Xaa Xaa Xaa Xaa Xaa Xaa Xaa
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: Amino acid may be in the R or S configuration
<220> FEATURE:
<221> NAME/KEY: misc_feature
<222> LOCATION: (1)..(1)
<223> OTHER INFORMATION: Xaa is as set out in *AA9*
<220> FEATURE:
<221> NAME/KEY: misc_feature
<222> LOCATION: (2)..(2)
<223> OTHER INFORMATION: Amino acid is in the S configuration when the
      side chain is bonded to an S atom or N atom of Linker *L2* and is
      in the R configurationwhen the side chain is boded to a C atom of
      Linker *L2*
<220> FEATURE:
<221> NAME/KEY: misc_feature
<222> LOCATION: (2)..(2)
<223> OTHER INFORMATION: Xaa is as set out in *AA10*
<220> FEATURE:
<221> NAME/KEY: misc_feature
<222> LOCATION: (2)..(7)
<223> OTHER INFORMATION: Cyclic Peptide: AA at position 2 and AA at
      position 7 are joined by a linker as set out in *L2*
<220> FEATURE:
<221> NAME/KEY: misc_feature
<222> LOCATION: (3)..(3)
<223> OTHER INFORMATION: Amino acid may be in the R or S configuration
<220> FEATURE:
<221> NAME/KEY: misc_feature
<222> LOCATION: (3)..(3)
<223> OTHER INFORMATION: Xaa is as set out in *AA11*
<220> FEATURE:
<221> NAME/KEY: misc_feature
<222> LOCATION: (4)..(4)
<223> OTHER INFORMATION: Amino acid may be in the R or S configuration
<220> FEATURE:
<221> NAME/KEY: misc_feature
<222> LOCATION: (4)..(4)
<223> OTHER INFORMATION: Xaa is as set out in *AA12*
<220> FEATURE:
<221> NAME/KEY: misc_feature
<222> LOCATION: (5)..(5)
<223> OTHER INFORMATION: Amino acid is in the S configuration
```

```
<220> FEATURE:
<221> NAME/KEY: misc_feature
<222> LOCATION: (5)..(5)
<223> OTHER INFORMATION: Xaa is as set out in *AA13*
<220> FEATURE:
<221> NAME/KEY: misc_feature
<222> LOCATION: (6)..(6)
<223> OTHER INFORMATION: Amino acid may be in the R or S configuration
<220> FEATURE:
<221> NAME/KEY: misc_feature
<222> LOCATION: (6)..(6)
<223> OTHER INFORMATION: Xaa is as set out in *AA14*
<220> FEATURE:
<221> NAME/KEY: misc_feature
<222> LOCATION: (7)..(7)
<223> OTHER INFORMATION: Amino acid is in the S configuration when the
      side chain is bonded to an S atom or N atom of Linker *L2* and is
      in the R configuration when the side chain is boded to a C atom of
      Linker *L2*
<220> FEATURE:
<221> NAME/KEY: misc_feature
<222> LOCATION: (7)..(7)
<223> OTHER INFORMATION: Xaa is as set out in *AA15*
<220> FEATURE:
<221> NAME/KEY: misc_feature
<222> LOCATION: (8)..(8)
<223> OTHER INFORMATION: Amino acid may be in the R or S configuration
<220> FEATURE:
<221> NAME/KEY: misc_feature
<222> LOCATION: (8)..(8)
<223> OTHER INFORMATION: Xaa is as set out in *AA16*

<400> SEQUENCE: 84

Xaa Xaa Xaa Xaa Xaa Xaa Xaa Xaa
1               5

<210> SEQ ID NO 85
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 85

Phe Trp Lys Thr
1
```

What is claimed is:

1. A compound having the structure of Formula I:

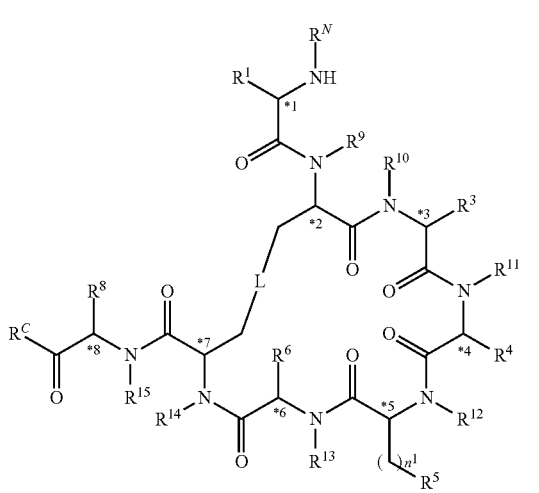

Formula I or a salt thereof, wherein:

$R^C$ is OH or $NHR^{16}$, wherein $R^{16}$ is H or $C_{1-6}$ alkyl optionally substituted with one or more substituents;

$R^N$ is selected from the group consisting of:

(i) H;

(ii) $C_{1-6}$ alkyl;

(iii) —$C(O)R^{17}$, wherein $R^{17}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(iv) —$C(O)C_{1-6}$ alkylene-$C(O)OR^{18}$, wherein $R^{18}$ is H or $C_{1-6}$ alkyl optionally substituted with one or more substituents;

(v) —$C(O)C_{1-6}$ alkylene-$N(R^{20})C(O)R^{19}$, wherein $R^{19}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents, and wherein $R^{20}$ is H or $C_{1-6}$ alkyl;

(vi) —C(O)C$_{1-6}$ alkylene-NR$^{21}$R$^{22}$, wherein each of R$^{21}$ and R$^{22}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(vii) —C(O)C$_{1-6}$ alkylene-C(O)NR$^{23}$R$^{24}$, wherein each of R$^{23}$ and R$^{24}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(viii) —C(O)C$_{1-6}$ alkylene-S(O)$_2$R$^{25}$, wherein R$^{25}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and (ix) —S(O)$_2$R$^{26}$, wherein R$^{26}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

R$^1$ is selected from the group consisting of C$_{1-6}$ alkyl, C$_{6-10}$ aryl, 5- to 10-membered heteroaryl, —C$_{1-6}$ alkylene(C$_{6-10}$ aryl) and —C$_{1-6}$ alkylene(5- to 10-membered heteroaryl), wherein the C$_{1-6}$ alkyl, the C$_{6-10}$ aryl, the C$_{6-10}$ aryl of —C$_{1-6}$ alkylene(C$_{6-10}$ aryl), the 5- to 10-membered heteroaryl and the 5- to 10-membered heteroaryl of —C$_{1-6}$ alkylene(5- to 10-membered heteroaryl) are optionally substituted with one or more substituents, and wherein the C$_{1-6}$ alkylene of —C$_{1-6}$ alkylene(C$_{6-10}$ aryl) and —C$_{1-6}$ alkylene(5- to 10-membered heteroaryl) is optionally substituted with one or more substituents;

R$^3$ is selected from the group consisting of:
(i) C$_{6-10}$ aryl which is optionally substituted with one or more substituents;
(ii) 5- to 10-membered heteroaryl which is optionally substituted with one or more substituents;
(iii) —C$_{1-6}$ alkylene(C$_{6-10}$ aryl), wherein the C$_{6-10}$ aryl is optionally substituted with one or more substituents, and wherein the C$_{1-6}$ alkylene is optionally substituted with one or more substituents;
(iv) —C$_{1-6}$ alkylene(5- to 10-membered heteroaryl), wherein the 5- to 10-membered heteroaryl is optionally substituted with one or more substituents, and wherein the C$_{1-6}$ alkylene is optionally substituted with one or more substituents;
(v) —C$_{1-6}$ alkylene-NR$^{27}$C(O)R$^{28}$, wherein:
R$^{27}$ is H or C$_{1-6}$ alkyl;
R$^{28}$ is selected from the group consisting of C$_{1-6}$ alkyl, C$_{6-10}$ aryl, 5- to 10-membered heteroaryl, and —NR$^{29}$R$^{30}$, wherein the C$_{1-6}$ alkyl is optionally substituted with one or more substituents, and wherein the C$_{6-10}$ aryl and 5- to 10-membered heteroaryl are optionally substituted with one or more substituents; and
wherein each of R$^{29}$ and R$^{30}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(vi) —(C$_{6-10}$ arylene)-C(O)NR$^{31}$R$^{32}$ or —C$_{1-6}$ alkylene-(C$_{6-10}$ arylene)-C(O)NR$^{31}$R$^{32}$, wherein each of R$^{31}$ and R$^{32}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(vii) —(C$_{6-10}$ arylene)-NR$^{33}$R$^{34}$ or —C$_{1-6}$ alkylene-(C$_{6-10}$ arylene)-NR$^{33}$R$^{34}$, wherein:
each of R$^{33}$ and R$^{34}$ is independently selected from the group consisting of H, C$_{1-6}$ alkyl, C$_{6-10}$ aryl, 5- to 10-membered heteroaryl, —C(O)R$^{35}$, —C(O)NR$^{36}$R$^{37}$, and —SO$_2$R$^{38}$, wherein the C$_{1-6}$ alkyl is optionally substituted with one or more substituents, and wherein the C$_{6-10}$ aryl and 5- to 10-membered heteroaryl are optionally substituted with one or more substituents;
R$^{35}$ is selected from the group consisting of C$_{1-6}$ alkyl, C$_{6-10}$ aryl, 5- to 10-membered heteroaryl, and 5- to 10-membered heterocycloalkyl, wherein the C$_{1-6}$ alkyl is optionally substituted with one or more substituents, and wherein the C$_{6-10}$ aryl, 5- to 10-membered heteroaryl, and 5- to 10-membered heterocycloalkyl are optionally substituted with one or more substituents;
each of R$^{36}$ and R$^{37}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents; and
R$^{38}$ is selected from the group consisting of C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(viii) —(C$_{6-10}$ arylene)-SO$_2$NR$^{39}$R$^{40}$ or —C$_{1-6}$ alkylene-(C$_{6-10}$ arylene)-SO$_2$NR$^{39}$R$^{40}$, wherein each of R$^{39}$ and R$^{40}$ is independently selected from the group consisting of H, C$_{1-6}$ alkyl, C$_{6-10}$ aryl, and 5- to 10-membered heteroaryl, wherein the C$_{1-6}$ alkyl is optionally substituted with one or more substituents, and wherein the C$_{6-10}$ aryl and 5- to 10-membered heteroaryl are optionally substituted with one or more substituents;

(ix) —(C$_{6-10}$ arylene)-(C$_{1-6}$ alkylene)-NR$^{41}$R$^{42}$ or —C$_{1-6}$ alkylene-(C$_{6-10}$ arylene)-(C$_{1-6}$ alkylene)-NR$^{41}$R$^{42}$, wherein:
each of R$^{41}$ and R$^{42}$ is independently selected from the group consisting of H, C$_{1-6}$ alkyl, C$_{6-10}$ aryl, 5- to 10-membered heteroaryl, —C(O)R$^{43}$, and —C(O)NR$^{44}$R$^{45}$, wherein the C$_{1-6}$ alkyl is optionally substituted with one or more substituents, and wherein the C$_{6-10}$ aryl and 5- to 10-membered heteroaryl are optionally substituted with one or more substituents;

$R^{43}$ is selected from the group consisting of $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and each of $R^{44}$ and $R^{45}$ is independently selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents;

(x) —($C_{6-10}$ arylene)-$OR^{46}$ or —$C_{1-6}$ alkylene-($C_{6-10}$ arylene)-$OR^{46}$, wherein $R^{46}$ is selected from the group consisting of H, $C_{1-6}$ alkyl, $C_{6-10}$ aryl, and 5- to 10-membered heteroaryl, wherein the $C_{1-6}$ alkyl is optionally substituted with one or more substituents, and wherein the $C_{6-10}$ aryl and 5- to 10-membered heteroaryl are optionally substituted with one or more substituents; and (xi) —$C_{1-6}$ alkylene-($C_{6-10}$ arylene)-$N(R^{47})$—C(O)—$CHR^{48}$—$NR^{49}R^{50}$, wherein $R^{47}$ is H or $CH_3$, $R^{48}$ is H or $C_{1-6}$ alkyl optionally substituted with one or more substituents each independently selected from the group consisting of hydroxyl, —COOH, —$NH_2$, —C(O)$NH_2$, and —N(H)C(O)$NH_2$, and each of $R^{49}$ and $R^{50}$ is independently H, $CH_3$ or acetyl;

$R^4$ is

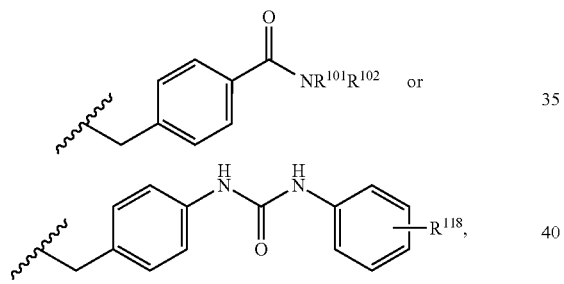

wherein each of $R^{101}$ and $R^{102}$ is independently selected from the group consisting of H, $C_{1-6}$ alkyl, $C_{6-10}$ aryl, and 5- to 10-membered heteroaryl and $R^{118}$ is selected from the group consisting of H, halogen, hydroxy, —$NO_2$, and $C_{1-6}$ alkoxy;

$R^5$ is selected from the group consisting of:
(i) —$NR^{79}R^{80}$, wherein each of $R^{79}$ and $R^{80}$ is independently selected from the group consisting of H, $C_{1-6}$ alkyl, —C(O)$R^{81}$, and —C(=$NR^{82}$)$NR^{83}R^{84}$, or $R^{79}$ and $R^{80}$, together with the N atom to which they are attached, form 5- to 10-membered heteroaryl or 5- to 10-membered heterocycloalkyl, wherein the $C_{1-6}$ alkyl is optionally substituted with one or more substituents, and wherein the 5- to 10-membered heteroaryl and 5- to 10-membered heterocycloalkyl are optionally substituted with one or more substituents, $R^{81}$ is selected from the group consisting of H, —$NH_2$, $C_{1-16}$ alkyl, $C_{1-6}$ haloalkyl, $C_{6-10}$ aryl, and 5- to 10-membered heteroaryl; and each of $R^{82}$, $R^{83}$, and $R^{84}$ is independently selected from the group consisting of H, $C_{1-16}$ alkyl, $C_{1-6}$ haloalkyl, $C_{6-10}$ aryl, and 5- to 10-membered heteroaryl; and (ii) —$N^+R^{85}R^{86}R^{87}$, wherein each of $R^{85}$, $R^{86}$, and $R^{87}$ is independently $C_{1-6}$ alkyl;

$n^1$ is 1, 2, 3, 4, 5, or 6;

$R^6$ is $C_{1-6}$ alkyl optionally substituted with one or more substituents;

$R^8$ is selected from the group consisting of $C_{1-6}$ alkyl, $C_{6-10}$ aryl, 5- to 10-membered heteroaryl, —$C_{1-6}$ alkylene($C_{6-11}$) aryl) and —$C_{1-6}$ alkylene(5- to 10-membered heteroaryl), wherein the $C_{1-6}$ alkyl, the $C_{6-10}$ aryl, the $C_{6-10}$ aryl of —$C_{1-6}$ alkylene($C_{6-10}$ aryl), the 5- to 10-membered heteroaryl and the 5- to 10-membered heteroaryl of —$C_{1-6}$ alkylene(5- to 10-membered heteroaryl) are optionally substituted with one or more substituents, and wherein the $C_{1-6}$ alkylene of —$C_{1-6}$ alkylene($C_{6-10}$ aryl) and —$C_{1-6}$ alkylene(5- to 10-membered heteroaryl) is optionally substituted with one or more substituents;

$R^9$ is H or $C_{1-6}$ alkyl;
$R^{10}$ is H or $C_{1-6}$ alkyl;
$R^{11}$ is H or $C_{1-6}$ alkyl;
$R^{12}$ is H or $C_{1-6}$ alkyl;
$R^{13}$ is H or $C_{1-6}$ alkyl;
$R^{14}$ is H or $C_{1-6}$ alkyl;
$R^{15}$ is H or $C_{1-6}$ alkyl; and
L is selected from the group consisting of:

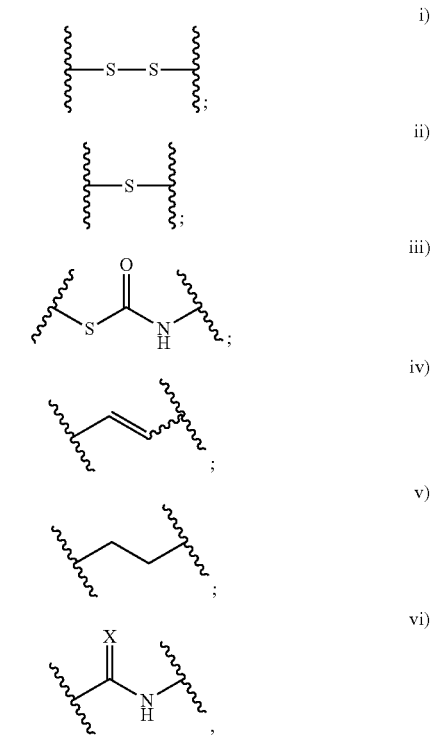

wherein X is S or O; and

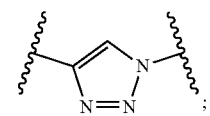

chiral centre *1 is in the S configuration or the R configuration;
chiral centre *2 is in the S configuration or the R configuration;
chiral centre *3 is in the S configuration or the R configuration;
chiral centre *4 is in the S configuration or the R configuration;
chiral centre *5 is in the S configuration or the R configuration;
chiral centre *6 is in the S configuration or the R configuration;
chiral centre *7 is in the S configuration or the R configuration; and
chiral centre *8 is in the S configuration or the R configuration, provided that:

i) when $R^C$ is $NH_2$, $R^N$ is H or —C(O)CH$_2$N$_3$, $R^1$ is

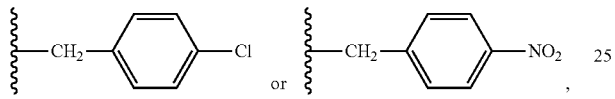

or $R^3$ is

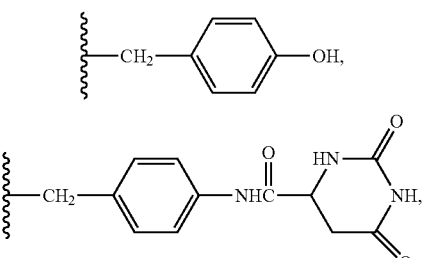

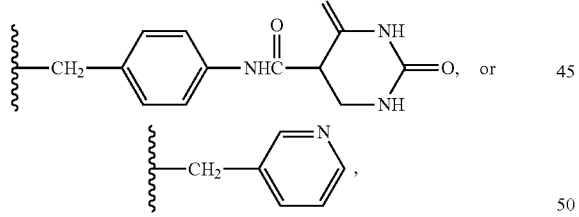

or

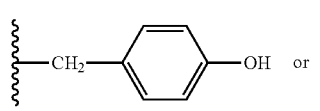

$R^5$ is $NH_2$, $n^1$ is 4, $R^6$ is —CH(OH)(CH$_3$), $R^8$ is

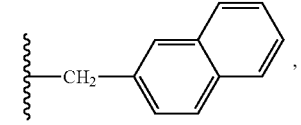

each of $R^9$, $R^{10}$, $R^{11}$, $R^{12}$, $R^{13}$, $R^{14}$ and $R^{15}$ is H, an L is

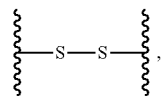 [SMILES: *SS*]

then $R^4$ is not

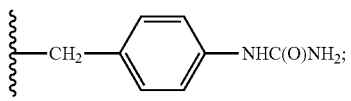

and ii) when $R^C$ is $NH_2$, $R^N$ is H, $R^1$ is

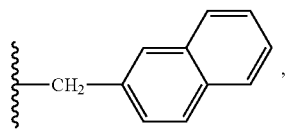 [SMILES: *Cc1ccc2ccccc2c1]

$R^3$ is

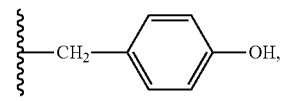

$R^5$ is $NH_2$, $n^1$ is 4, $R^6$ is —CH(CH$_3$)$_2$, $R^8$ is —CH(OH)(CH$_3$), each of $R^9$, $R^{10}$, $R^{11}$, $R^{12}$, $R^{13}$, $R^{14}$ and $R^{15}$ is H, and L is

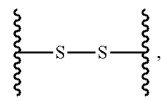

then $R^4$ is not

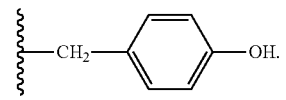

2. The compound or salt of claim 1, wherein $R^4$ is

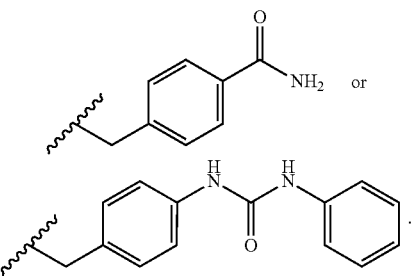

3. The compound or salt of claim 2, wherein $R^4$ is

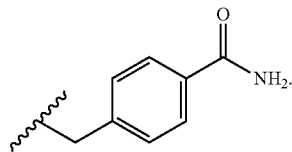

4. The compound or salt of claim 1, wherein $R^5$ is —$NR^{79}R^{80}$ and each of $R^{79}$ and $R^{80}$ is independently selected from the group consisting of H, $C_{1-6}$ alkyl, —C(O)$R^{81}$, and —C(=$NR^{82}$)$NR^{83}R^{84}$, wherein $R^{81}$ is $C_{1-6}$ alkyl and each of $R^{82}$, $R^{83}$, and $R^{84}$ is H.

5. The compound or salt of claim 4, wherein $R^5$ is —$NR^{79}R^{80}$ and each of $R^{79}$ and $R^{80}$ is independently selected from the group consisting of H and $C_{1-6}$ alkyl.

6. The compound or salt of claim 5, wherein $R^5$ is —$NH_2$, —$NHCH_3$ or —$N(CH_3)_2$.

7. The compound or salt of claim 6, wherein $R^5$ is —$NH_2$.

8. The compound or salt of claim 6, wherein $R^5$ is —$NHCH_3$.

9. The compound or salt of claim 6, wherein $R^5$ is —$N(CH_3)_2$.

10. The compound or salt of claim 1, wherein $n^1$ is 3 or 4.

11. The compound or salt of claim 10, wherein $n^1$ is 4.

12. The compound or salt of claim 1, wherein $R^C$ is OH or $NH_2$.

13. The compound or salt of claim 12, wherein $R^C$ is $NH_2$.

14. The compound or salt of claim 1, wherein $R^N$ is selected from the group consisting of:
(i) H;
(ii) $C_{1-6}$ alkyl;
(iii) —C(O)$R^{17}$, wherein $R^{17}$ is selected from the group consisting of $C_{1-6}$ alkyl, $C_{6-10}$ aryl, and 5- to 10-membered heteroaryl;
(iv) —C(O)$C_{1-6}$ alkylene-C(O)O$R^{18}$, wherein $R^{18}$ is H or $C_{1-6}$ alkyl;
(v) —C(O)$C_{1-6}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl;
(vi) —C(O)$C_{1-6}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl;
(vii) —C(O)$C_{1-6}$ alkylene-C(O)$NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl;
(viii) —C(O)$C_{1-6}$ alkylene-S(O)$_2R^{25}$, wherein $R^{25}$ is selected from the group consisting of $C_{1-6}$ alkyl, $C_{6-10}$ aryl, and 5- to 10-membered heteroaryl; and
(ix) —S(O)$_2R^{26}$, wherein $R^{26}$ is selected from the group consisting of $C_{1-6}$ alkyl, $C_{6-10}$ aryl, and 5- to 10-membered heteroaryl.

15. The compound or salt of claim 14, wherein $R^N$ is selected from the group consisting of:
(i) H;
(ii) $C_{1-6}$ alkyl;
(iii) —C(O)$R^{17}$, wherein $R^{17}$ is selected from the group consisting of $C_{1-6}$ alkyl, $C_{6-10}$ aryl, and 5- to 10-membered heteroaryl;
(iv) —C(O)$C_{1-3}$ alkylene-C(O)O$R^{18}$, wherein $R^{18}$ is H or $C_{1-6}$ alkyl;
(v) —C(O)$C_{1-3}$ alkylene-N($R^{20}$)C(O)$R^{19}$, wherein $R^{19}$ is selected from the group consisting of $C_{1-6}$ alkyl, $C_{6-10}$ aryl, and 5- to 10-membered heteroaryl, and wherein $R^{20}$ is H or $C_{1-6}$ alkyl;
(vi) —C(O)$C_{1-3}$ alkylene-$NR^{21}R^{22}$, wherein each of $R^{21}$ and $R^{22}$ is independently selected from the group consisting of H, $C_{1-6}$ alkyl, $C_{6-10}$ aryl, and 5- to 10-membered heteroaryl;
(vii) —C(O)$C_{1-3}$ alkylene-C(O)$NR^{23}R^{24}$, wherein each of $R^{23}$ and $R^{24}$ is independently selected from the group consisting of H, $C_{1-6}$ alkyl, $C_{6-10}$ aryl, and 5- to 10-membered heteroaryl; and
(viii) —C(O)$C_{1-3}$ alkylene-S(O)$_2R^{25}$, wherein $R^{25}$ is selected from the group consisting of $C_{1-6}$ alkyl, $C_{6-10}$ aryl, and 5- to 10-membered heteroaryl.

16. The compound or salt of claim 14, wherein $R^N$ is selected from the group consisting of H, $C_{1-6}$ alkyl, —C(O)$R^{17}$, —C(O)$C_{1-6}$ alkylene-C(O)O$R^{18}$, —C(O)$C_{1-6}$ alkylene-N($R^{20}$)C(O)$R^{19}$, C(O)$C_{1-6}$ alkylene-$NR^{21}R^{22}$, C(O)$C_{1-6}$ alkylene-C(O)$NR^{23}R^{24}$, and —C(O)$C_{1-6}$ alkylene-S(O)$_2R^{25}$, wherein $R^{17}$ is $C_{1-6}$ alkyl or 5- to 6-membered heteroaryl, $R^{18}$ is $C_{1-6}$ alkyl, $R^{19}$ is $C_{1-6}$ alkyl or $C_6$ aryl, each of $R^{20}$, $R^{21}$, $R^{22}$, $R^{23}$ and $R^{24}$ is H, and $R^{25}$ is $C_6$ aryl.

17. The compound or salt of claim 16, wherein $R^N$ is selected from the group consisting of H, $C_{1-3}$ alkyl, —C(O)$R^{17}$, —C(O)$C_{1-3}$ alkylene-C(O)O$R^{18}$, —C(O)$C_{1-3}$ alkylene-N($R^{20}$)C(O)$R^{19}$, —C(O)$C_{1-3}$ alkylene-$NR^{21}R^{22}$, —C(O)$C_{1-3}$ alkylene-C(O)$NR^{23}R^{24}$, and —C(O)$C_{1-3}$ alkylene-S(O)$_2R^{25}$, wherein $R^{17}$ is $C_{1-6}$ alkyl or 5- to 6-membered heteroaryl, $R^{18}$ is $C_{1-3}$ alkyl, $R^{19}$ is $C_{1-3}$ alkyl or $C_6$ aryl, each of $R^{20}$, $R^{21}$, $R^{22}$, $R^{23}$ and $R^{24}$ is H, and $R^{25}$ is $C_6$ aryl.

18. The compound or salt of claim 17, wherein $R^N$ is H.

19. The compound or salt of claim 1, wherein $R^1$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy.

20. The compound or salt of claim 19, wherein $R^1$ is —$C_{1-2}$ alkylene($C_6$ aryl), wherein the $C_6$ aryl is optionally substituted with one or more substituents each independently selected from the group consisting of halogen, hydroxyl, —$NO_2$, and $C_{1-6}$ alkoxy.

21. The compound or salt of claim 20, wherein $R^1$ is

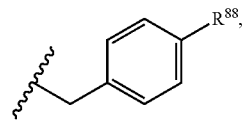

wherein $R^{88}$ is H, halogen, hydroxyl or $C_{1-3}$ alkoxy.

22. The compound or salt of claim 21, wherein $R^{88}$ is Cl.

23. The compound or salt of claim 1, wherein $R^3$ is —$C_{1-3}$ alkylene($C_{6-10}$ aryl), wherein the $C_{6-10}$ aryl is optionally substituted with one or more substituents each independently selected from the group consisting of halogen, hydroxy, —$NO_2$, and $C_{1-6}$ alkoxy.

24. The compound or salt of claim 23, wherein $R^3$ is —$C_{1-2}$ alkylene($C_6$ aryl), wherein the $C_6$ aryl is optionally substituted with one or more substituents each independently selected from the group consisting of halogen, hydroxyl, —$NO_2$, and $C_{1-6}$ alkoxy.

25. The compound or salt of claim 24, wherein $R^3$ is

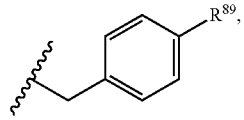

wherein $R^{89}$ is H, halogen, hydroxyl or $C_{1-3}$ alkoxy.

26. The compound or salt of claim 25, wherein $R^{89}$ is Cl or hydroxyl.

27. The compound or salt of claim 26, wherein $R^{89}$ is hydroxyl.

28. The compound or salt of claim 1, wherein $R^6$ is $C_{1-6}$ alkyl optionally substituted with hydroxyl.

29. The compound or salt of claim 28, wherein $R^6$ is selected from the group consisting of —CH(CH$_3$)OH, —CH(CH$_3$)$_2$, —C(CH$_3$)$_3$, —CH$_2$OH and —CH$_2$CH$_3$.

30. The compound or salt of claim 29, wherein $R^6$ is —CH(CH$_3$)OH.

31. The compound or salt of claim 1, wherein $R^8$ is —$C_{1-3}$ alkylene($C_{6-10}$ aryl), wherein the $C_{6-10}$ aryl is optionally substituted with one or more substituents each independently selected from the group consisting of halogen, hydroxy, —NO$_2$, and $C_{1-6}$ alkoxy.

32. The compound or salt of claim 31, wherein $R^8$ is —$C_{1-2}$ alkylene($C_6$ aryl), wherein the $C_6$ aryl is optionally substituted with one or more substituents each independently selected from the group consisting of halogen, hydroxyl, —NO$_2$, and $C_{1-6}$ alkoxy.

33. The compound or salt of claim 32, wherein $R^8$ is

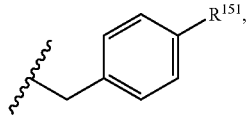

wherein $R^{151}$ is H, halogen, hydroxyl or $C_{1-3}$ alkoxy.

34. The compound or salt of claim 33, wherein $R^{151}$ is Cl or hydroxyl.

35. The compound or salt of claim 34, wherein $R^{151}$ is hydroxyl.

36. The compound or salt of claim 1, wherein each of $R^9$, $R^{10}$, $R^{11}$, $R^{12}$, $R^{13}$, $R^{14}$, and $R^{15}$ is independently H or $C_{1-3}$ alkyl.

37. The compound or salt of claim 36, wherein each of $R^9$, $R^{10}$, $R^{11}$, $R^{13}$, $R^{14}$, and $R^{15}$ is H.

38. The compound or salt of claim 36, wherein $R^{12}$ is H or CH$_3$.

39. The compound or salt of claim 38, wherein $R^{12}$ is H.

40. The compound or salt of claim 1, wherein L is

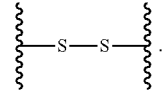 [SMILES: *SS*]

41. The compound or salt of claim 1, wherein chiral centre *1 is in the S configuration, chiral centre *2 is in the S configuration, chiral centre *3 is in the S configuration, chiral centre *4 is in the R configuration, chiral centre *5 is in the S configuration, chiral centre *6 is in the S configuration, chiral centre *7 is in the R configuration, and chiral centre *8 is in the R configuration.

42. A compound selected from:

| Compound No. | Structure |
|---|---|
| 1 | 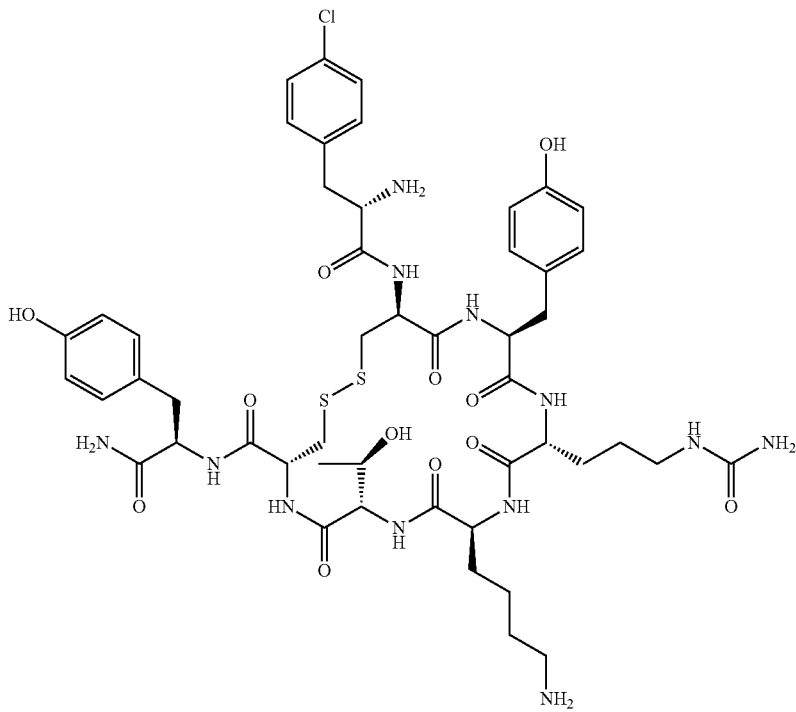 [SMILES: C[C@@H](O)[C@@H]1NC(=O)[C@H](CCCCN)NC(=O)[C@@H](CCCNC(N)=O)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]<br>H-Cpa-cyclo[D-Cys-Tyr-D-Cit-Lys-Thr-Cys]-D-Tyr-NH$_2$ |

-continued
| Compound No. | Structure |
|---|---|
| 2 | 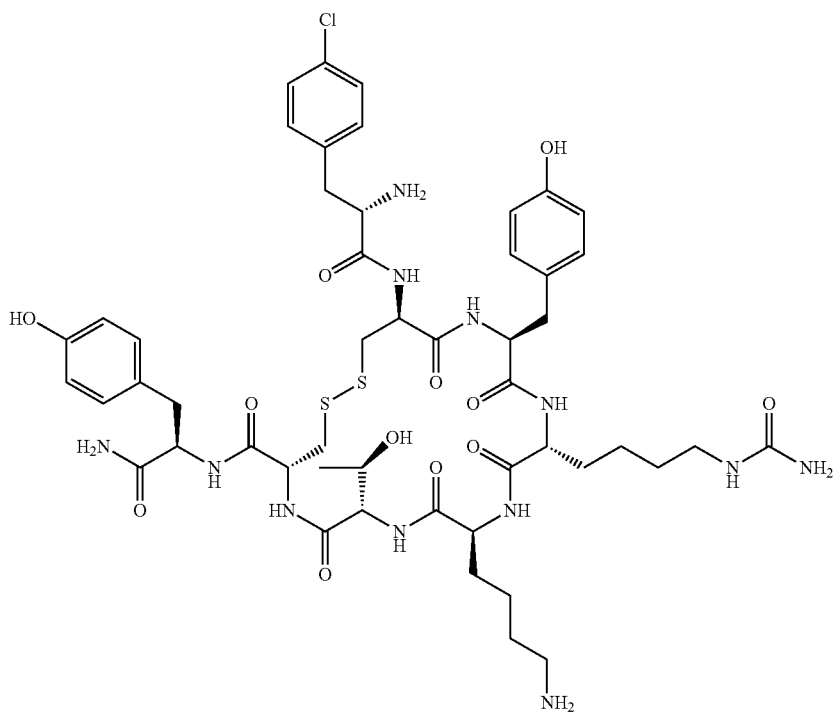 [SMILES: C[C@@H](O)[C@@H]1NC(=O)[C@H](CCCCN)NC(=O)[C@@H](CCCCNC(N)=O)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]   H-Cpa-cyclo[D-Cys-Tyr-D-HoCit-Lys-Thr-Cys]-D-Tyr-NH$_2$ |
| 3 | 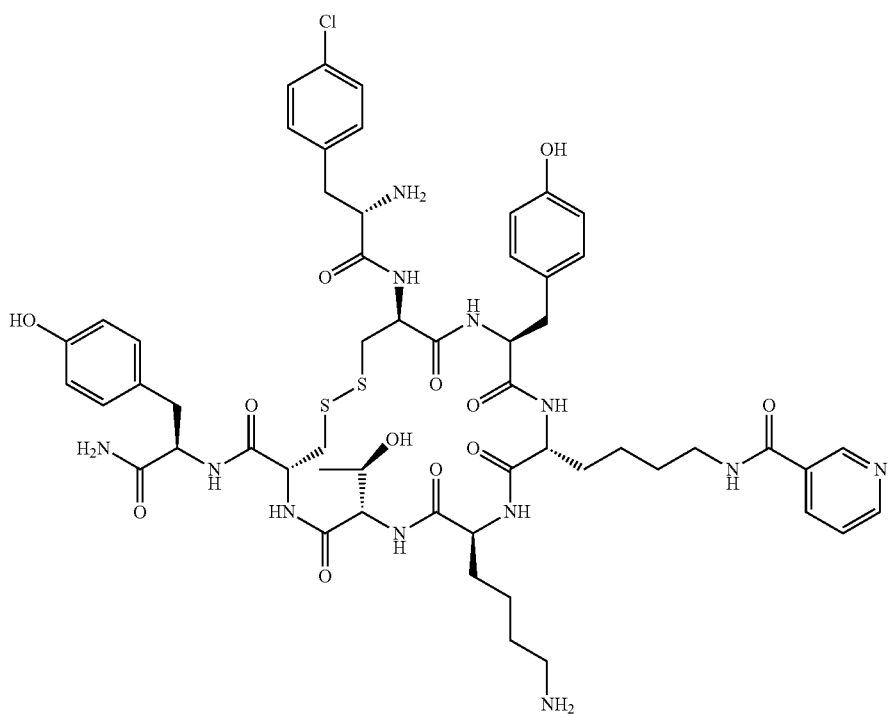 [SMILES: C[C@@H](O)[C@@H]1NC(=O)[C@H](CCCCN)NC(=O)[C@@H](CCCCNC(=O)c2cccnc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]   H-Cpa-cyclo[D-Cys-Tyr-D-Lys(N$^\varepsilon$-nicotinoyl)-Lys-Thr-Cys]-D-Tyr-NH$_2$ |

| Compound No. | Structure |
|---|---|
| 4 | 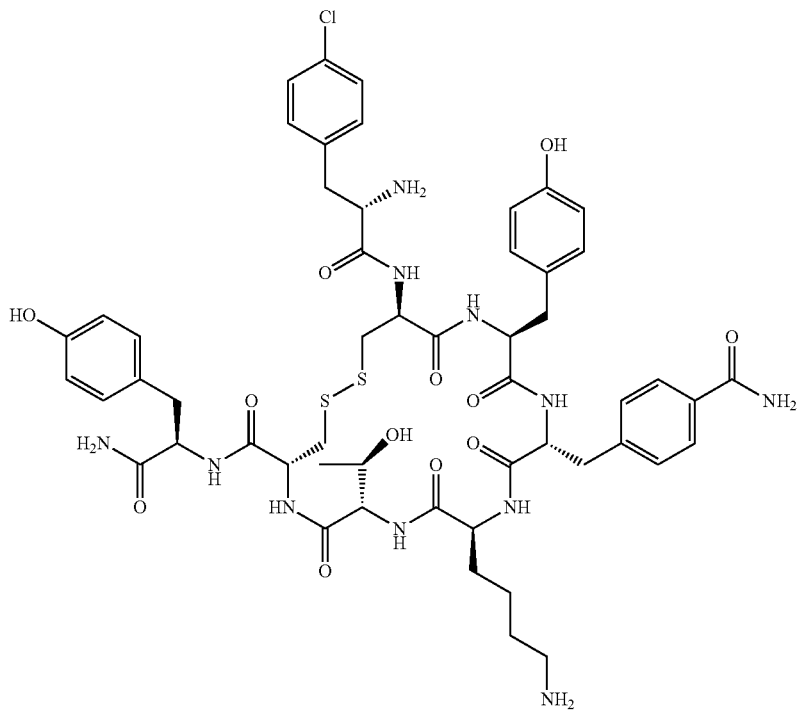 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O] H-Cpa-cyclo[D-Cys-Tyr-D-Phe(4-carbamoyl)-Lys-Thr-Cys]-D-Tyr-NH$_2$ |
| 5 | 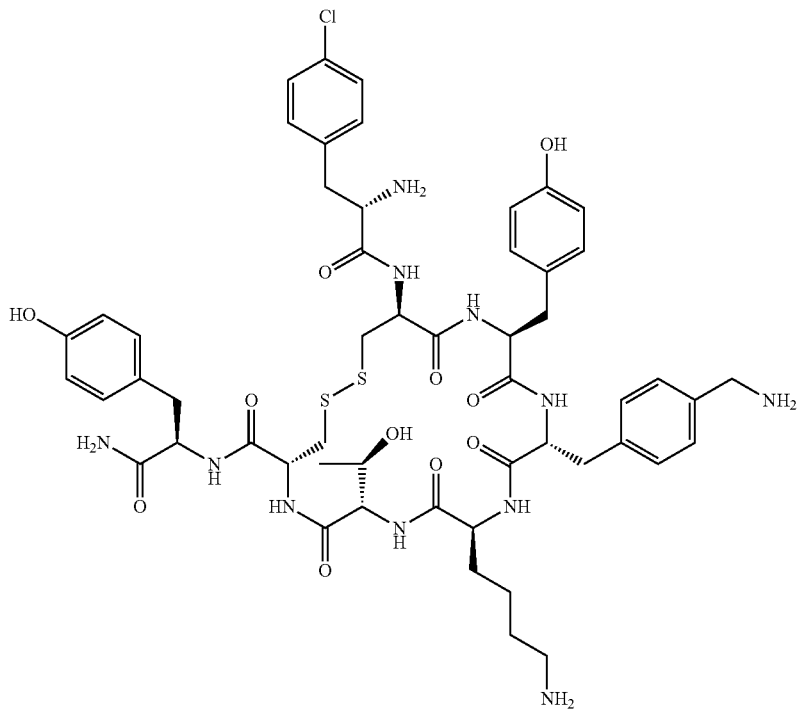 [SMILES: C[C@@H](O)[C@@H]1NC(=O)[C@H](CCCCN)NC(=O)[C@@H](Cc2ccc(CN)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O] H-Cpa-cyclo[D-Cys-Tyr-D-Phe(4-aminomethyl)-Lys-Thr-Cys]-D-Tyr-NH$_2$ |

| Compound No. | Structure |
|---|---|
| 6 | 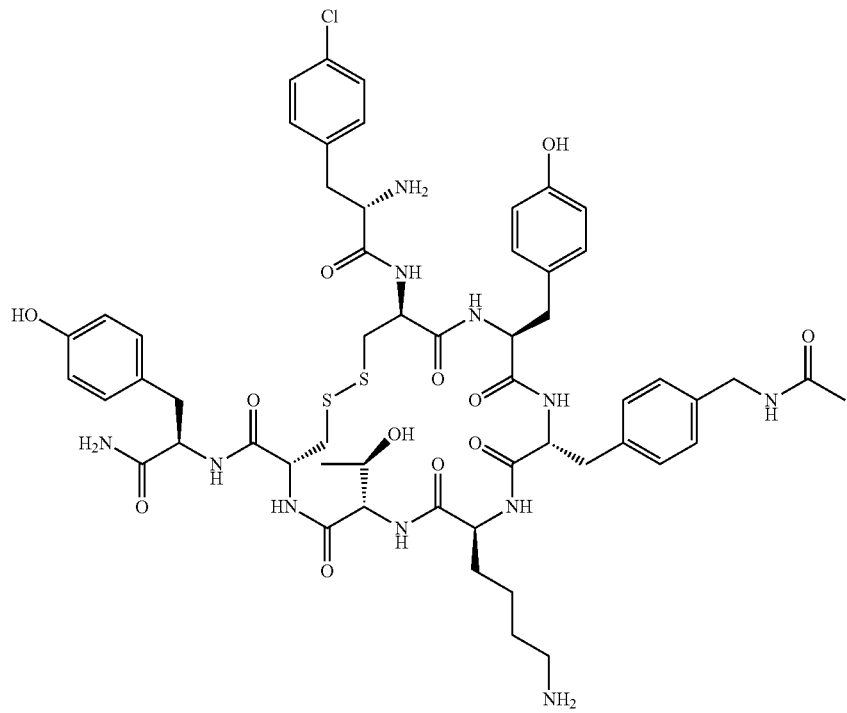 [SMILES: CC(=O)NCc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]
H-Cpa-cyclo[D-Cys-Tyr-D-Phe(4-ureidomethyl)-Lys-Thr-Cys]-D-Tyr-NH$_2$ |
| 7 | 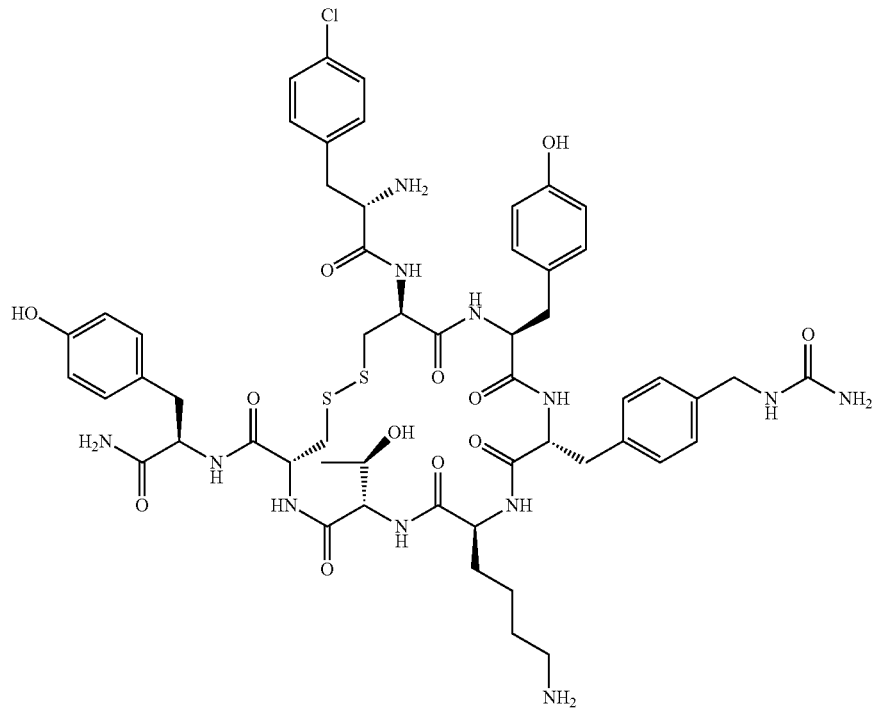 [SMILES: C[C@@H](O)[C@@H]1NC(=O)[C@H](CCCCN)NC(=O)[C@@H](Cc2ccc(CNC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Phe(4-acetamidomethyl)-Lys-Thr-Cys]-D-Tyr-NH$_2$ |

-continued
| Compound No. | Structure |
|---|---|
8
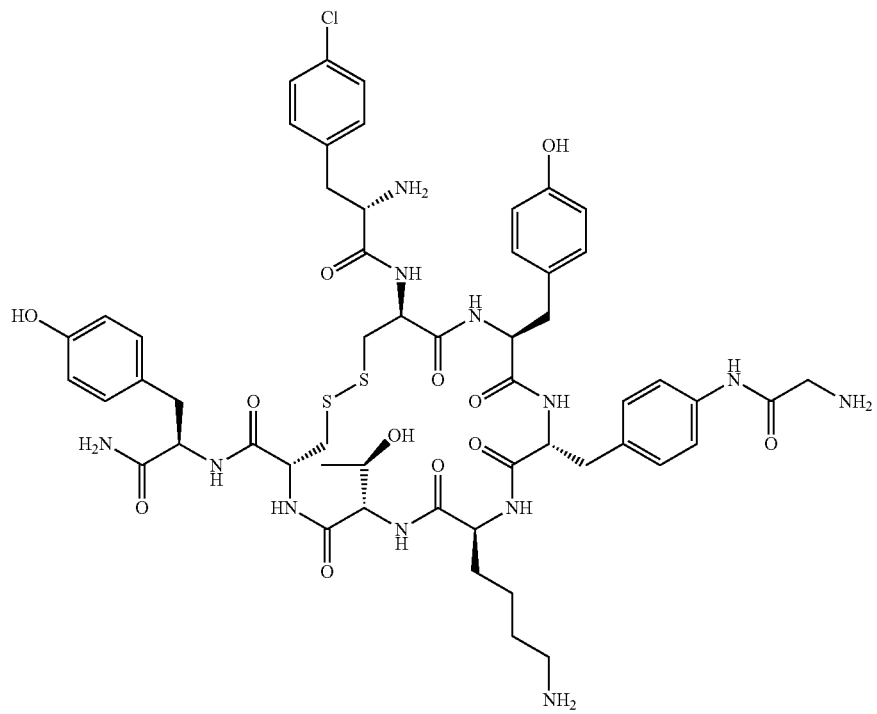 [SMILES: C[C@@H](O)[C@@H]1NC(=O)[C@H](CCCCN)NC(=O)[C@@H](Cc2ccc(NC(=O)CN)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Gly)-Lys-Thr-Cys]-D-Tyr-NH$_2$
9
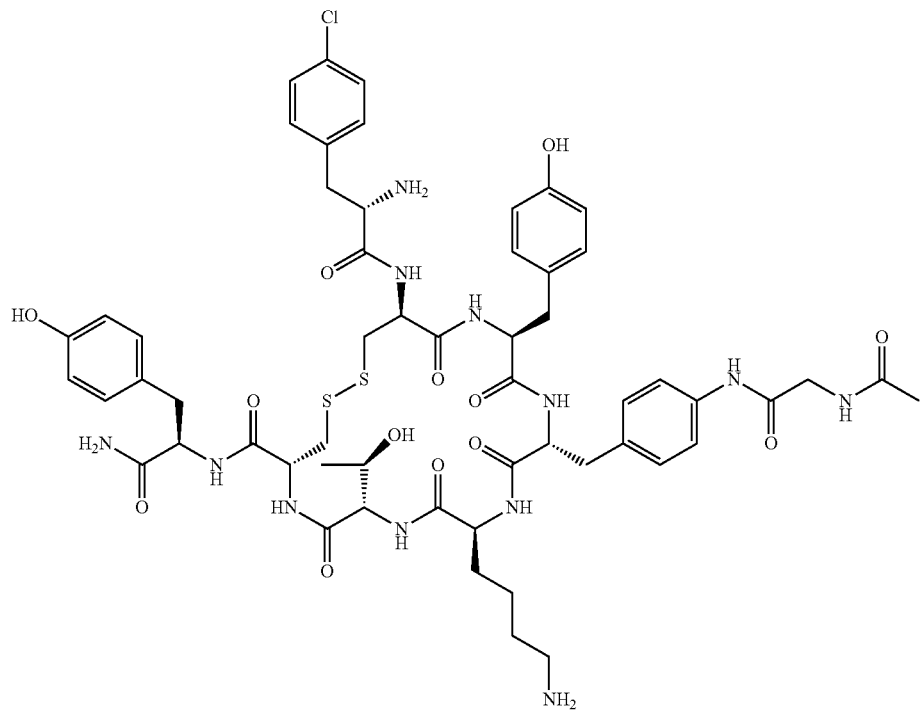 [SMILES: CC(=O)NCC(=O)Nc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]
H-Cpa-cyclo[D-Cys-Tyr-D-4-(Gly-Ac)Aph-Lys-Thr-Cys]-D-Tyr-NH$_2$

| Compound No. | Structure |
|---|---|
| 10 | 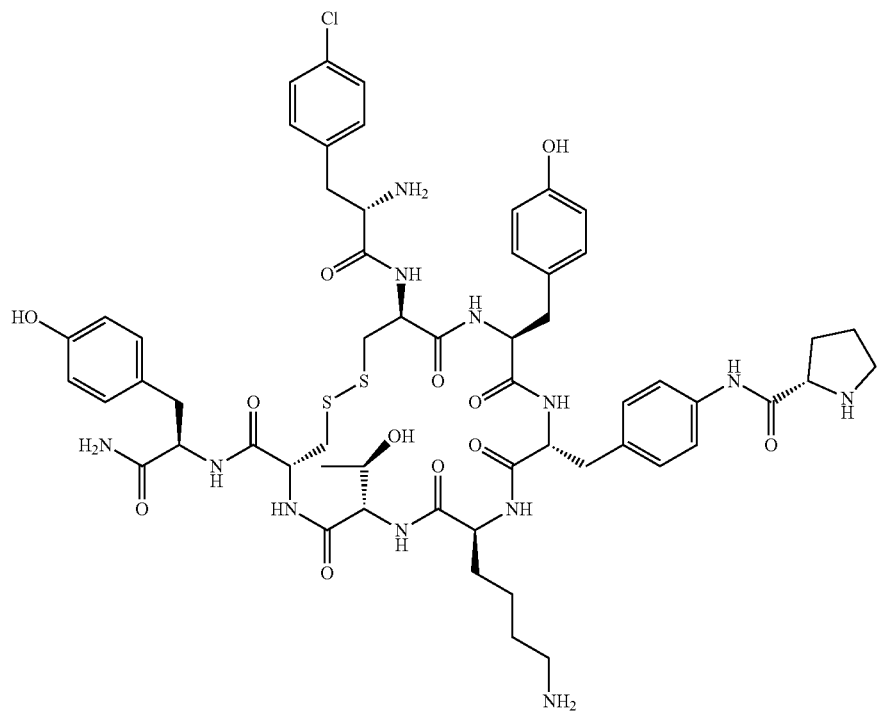 [SMILES: C[C@@H](O)[C@@H]1NC(=O)[C@H](CCCCN)NC(=O)[C@@H](Cc2ccc(NC(=O)[C@@H]3CCCN3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Pro)-Lys-Thr-Cys]-D-Tyr-NH₂ |
| 11 | 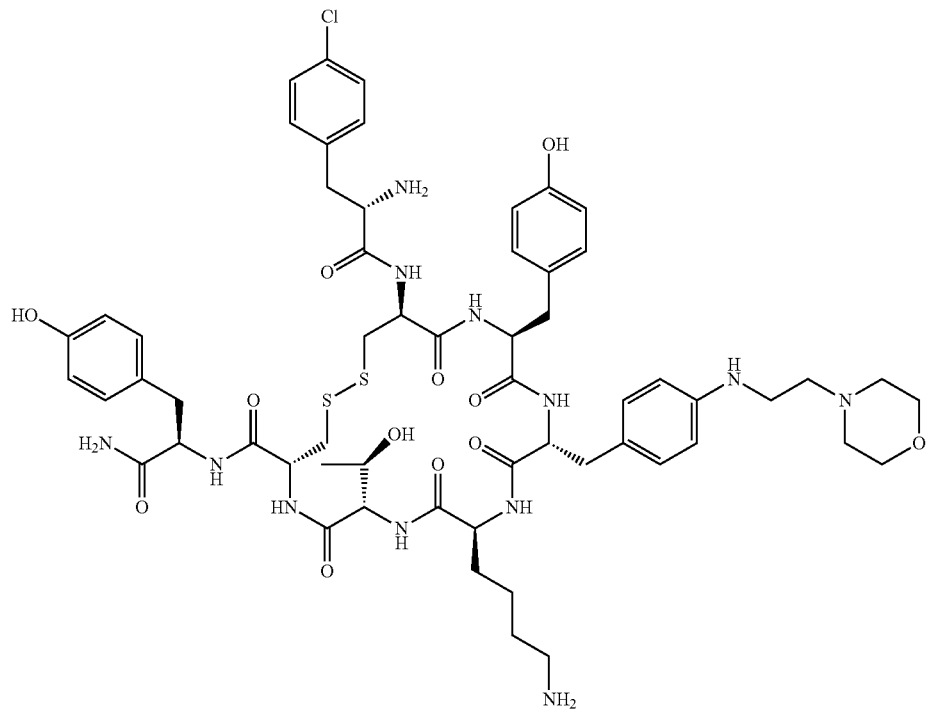 [SMILES: C[C@@H](O)[C@@H]1NC(=O)[C@H](CCCCN)NC(=O)[C@@H](Cc2ccc(NCCN3CCOCC3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(2-(4-morpholinyl)ethyl)-Lys-Thr-Cys]-D-Tyr-NH₂ |

| Compound No. | Structure |
|---|---|
| 12 | 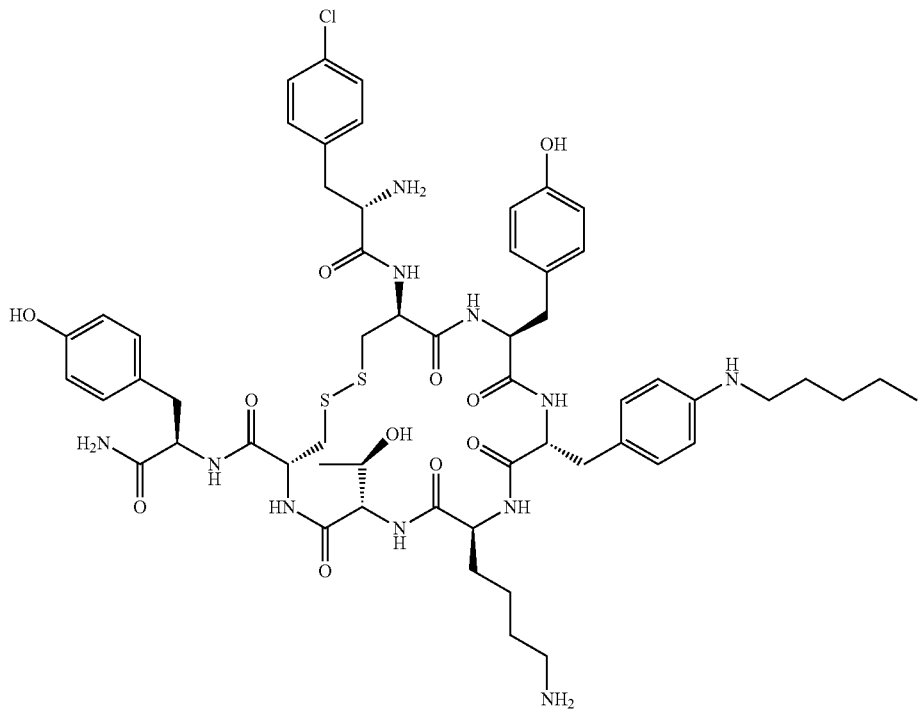 [SMILES: CCCCCNc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]<br>H-Cpa-cyclo[D-Cys-Tyr-D-Phe(4-n-pentylamino)-Lys-Thr-Cys]-D-Tyr-NH$_2$ |
| 13 | 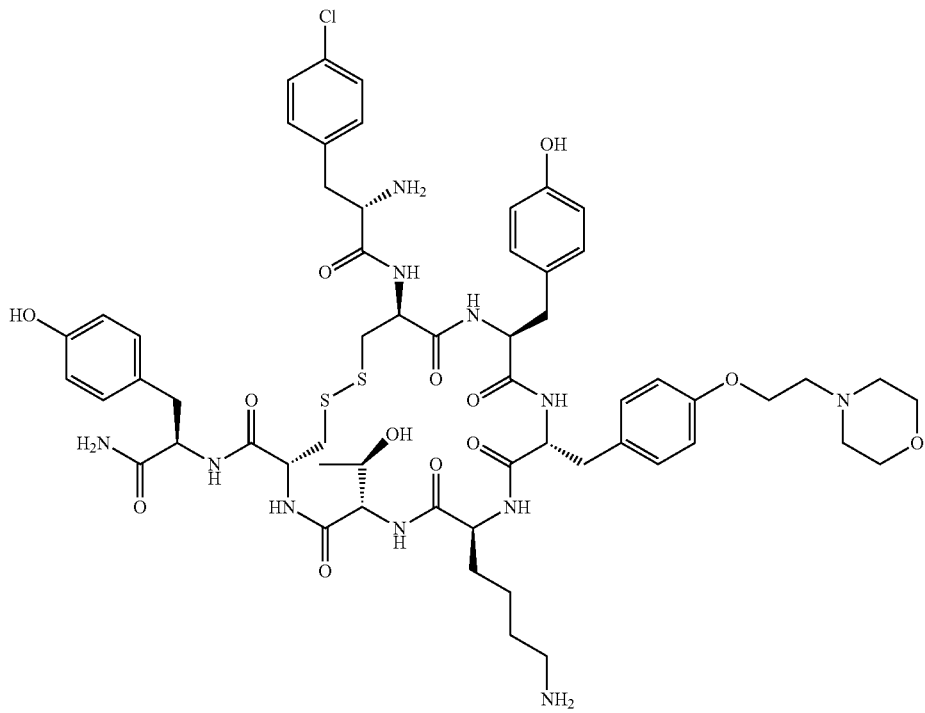 [SMILES: C[C@@H](O)[C@@H]1NC(=O)[C@H](CCCCN)NC(=O)[C@@H](Cc2ccc(OCCN3CCOCC3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]<br>H-Cpa-cyclo[D-Cys-Tyr-D-Tyr(2-(4-morpholinyl)ethyl)-Lys-Thr-Cys]-D-Tyr-NH$_2$ |

| Compound No. | Structure |
|---|---|
| 14 | 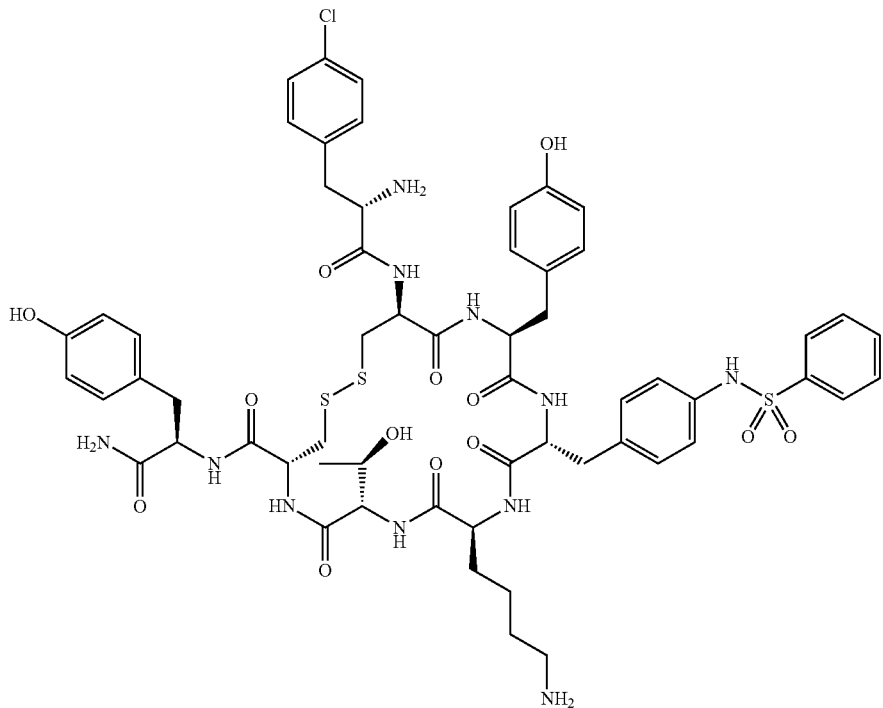 [SMILES: C[C@@H](O)[C@@H]1NC(=O)[C@H](CCCCN)NC(=O)[C@@H](Cc2ccc(NS(=O)(=O)c3ccccc3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(benzenesulfonyl)-Lys-Thr-Cys]-D-Tyr-NH$_2$ |
| 15 | 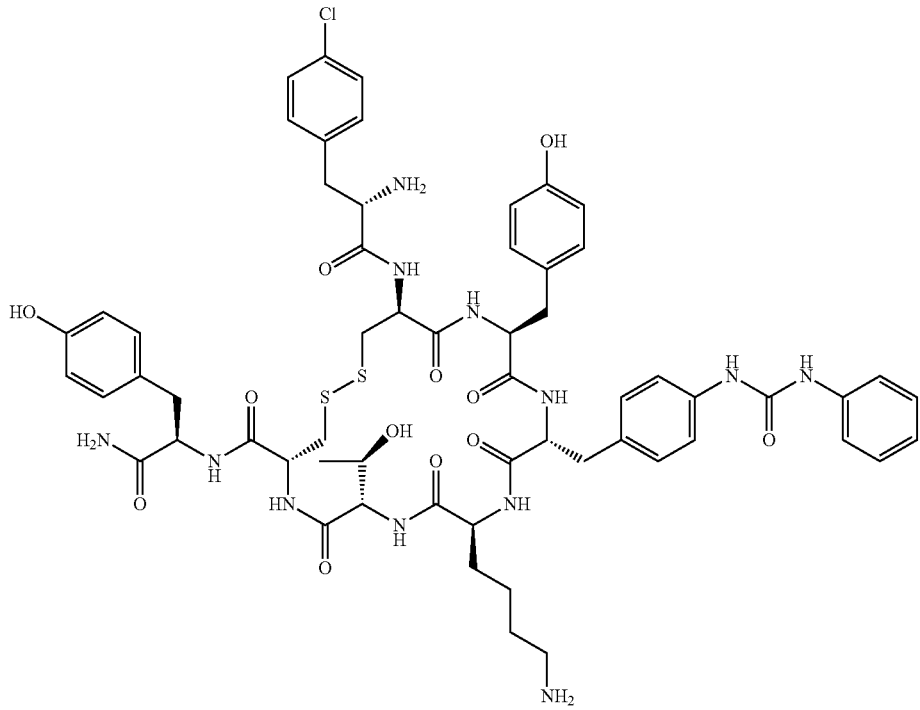 [SMILES: C[C@@H](O)[C@@H]1NC(=O)[C@H](CCCCN)NC(=O)[C@@H](Cc2ccc(NC(=O)Nc3ccccc3)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Phe(4-phenylureido)-Lys-Thr-Cys]-D-Tyr-NH$_2$ |

| Compound No. | Structure |
|---|---|
| 16 | 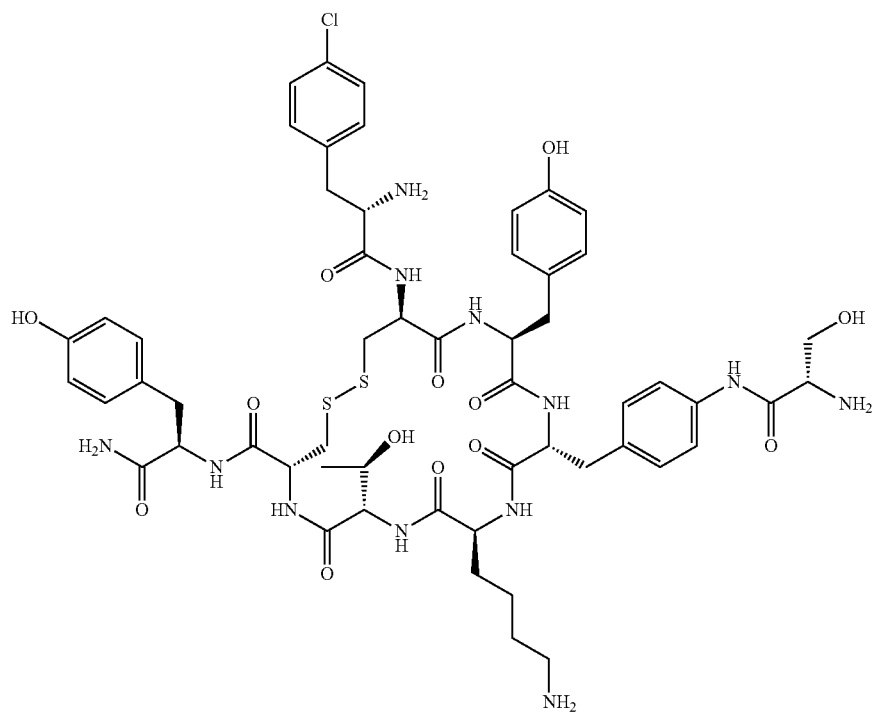 [SMILES: C[C@@H](O)[C@@H]1NC(=O)[C@H](CCCCN)NC(=O)[C@@H](Cc2ccc(NC(=O)[C@@H](N)CO)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Ser)-Lys-Thr-Cys]-D-Tyr-NH$_2$ |
| 17 | 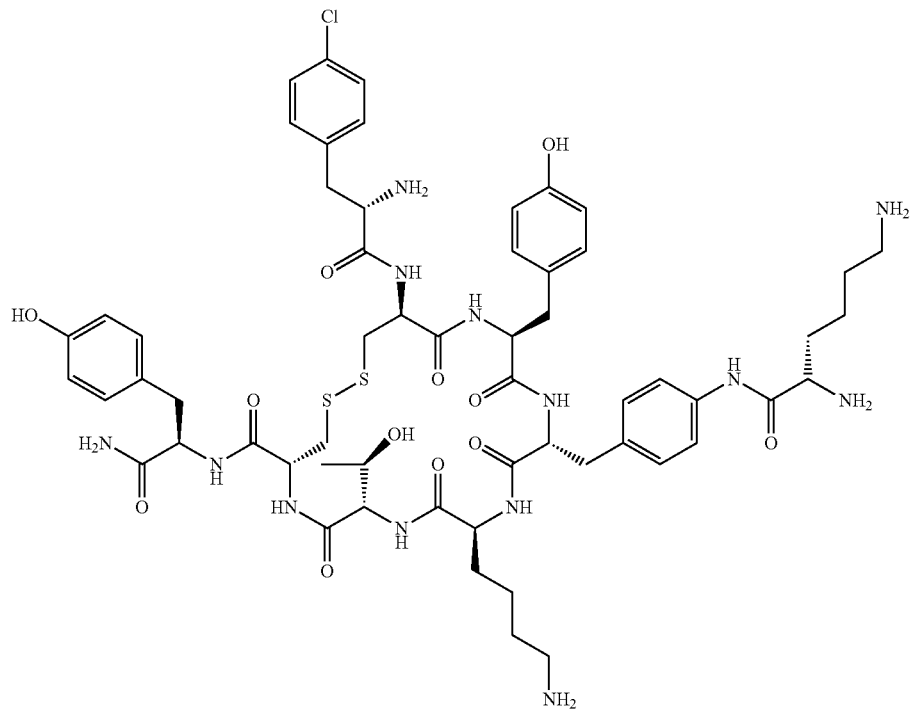
H-Cpa-cyclo[D-Cys-Tyr-D-Aph(Lys)-Lys-Thr-Cys]-D-Tyr-NH$_2$ |

| Compound No. | Structure |
|---|---|
| 18 | 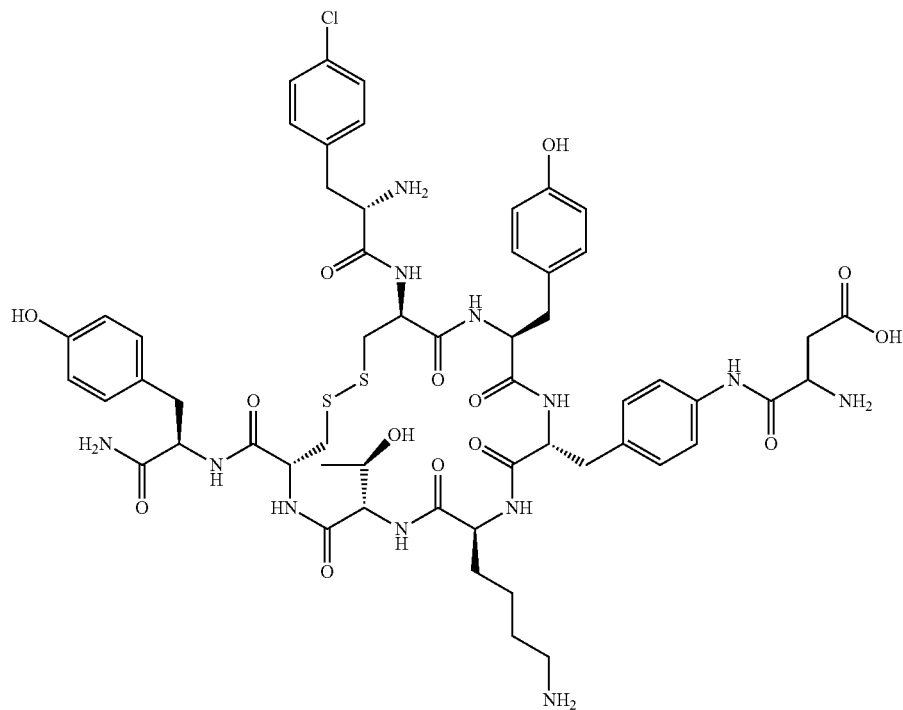 [SMILES: C[C@@H](O)[C@@H]1NC(=O)[C@H](CCCCN)NC(=O)[C@@H](Cc2ccc(NC(=O)C(N)CC(=O)O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Asp)-Lys-Thr-Cys]-D-Tyr-NH$_2$ |
| 19 | 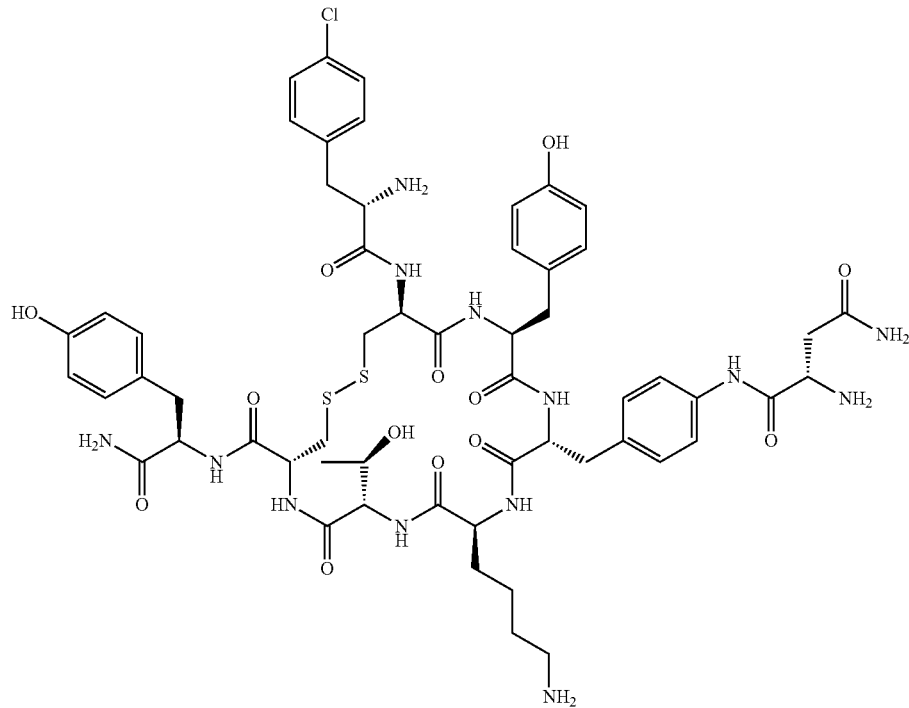 [SMILES: C[C@@H](O)[C@@H]1NC(=O)[C@H](CCCCN)NC(=O)[C@@H](Cc2ccc(NC(=O)[C@@H](N)CC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Asn)-Lys-Thr-Cys]-D-Tyr-NH$_2$ |

| Compound No. | Structure |
|---|---|
| 20 | 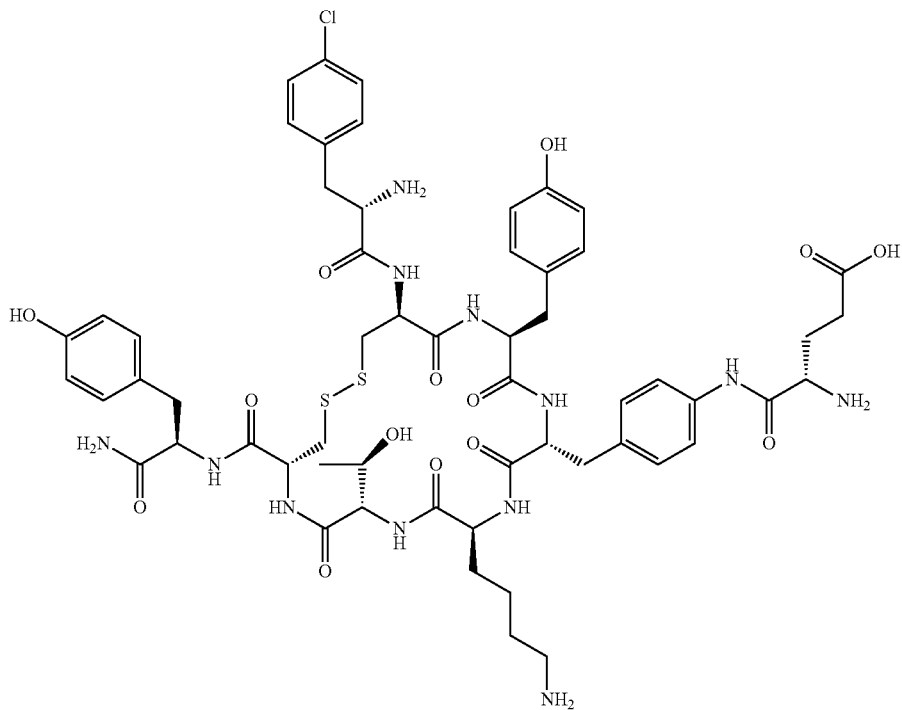 [SMILES: C[C@@H](O)[C@@H]1NC(=O)[C@H](CCCCN)NC(=O)[C@@H](Cc2ccc(NC(=O)[C@@H](N)CCC(=O)O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Glu)-Lys-Thr-Cys]-D-Tyr-NH$_2$ |
| 21 | 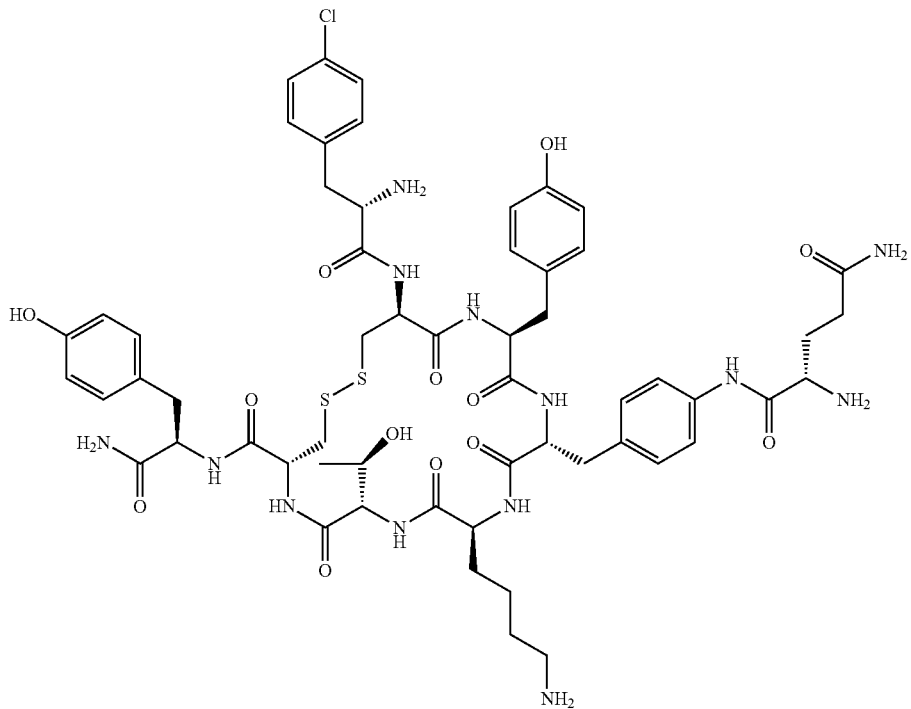 [SMILES: C[C@@H](O)[C@@H]1NC(=O)[C@H](CCCCN)NC(=O)[C@@H](Cc2ccc(NC(=O)[C@@H](N)CCC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Gln)-Lys-Thr-Cys]-D-Tyr-NH$_2$ |

| Compound No. | Structure |
|---|---|
| 22 | 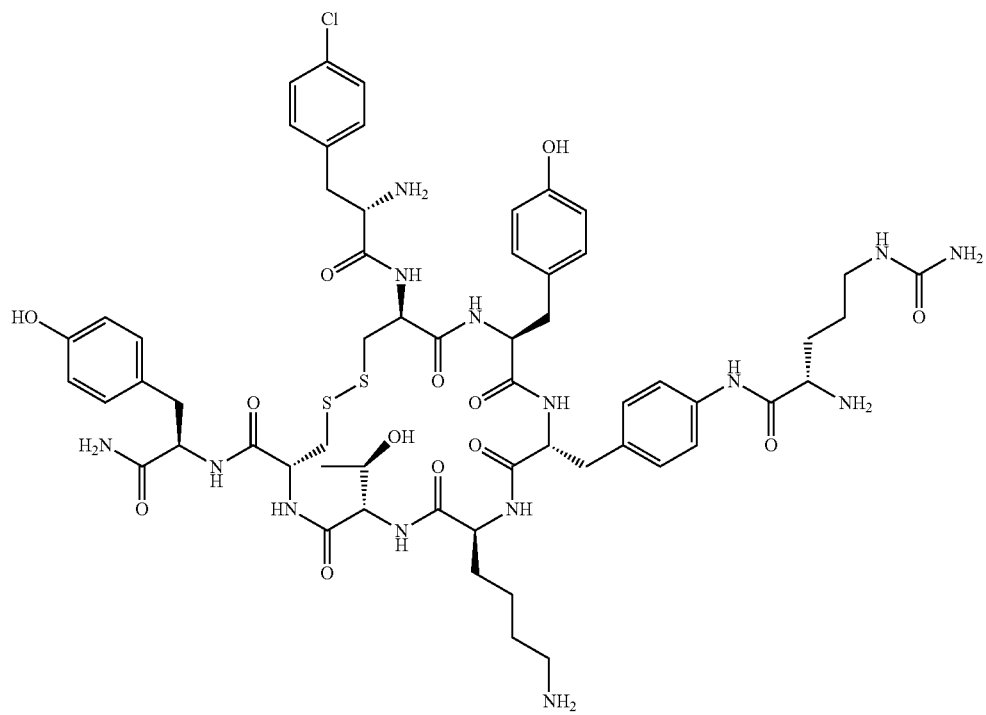 [SMILES: C[C@@H](O)[C@@H]1NC(=O)[C@H](CCCCN)NC(=O)[C@@H](Cc2ccc(NC(=O)[C@@H](N)CCCNC(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Aph(Cit-Lys-Thr-Cys]-D-Tyr-NH$_2$ |
| 23 | 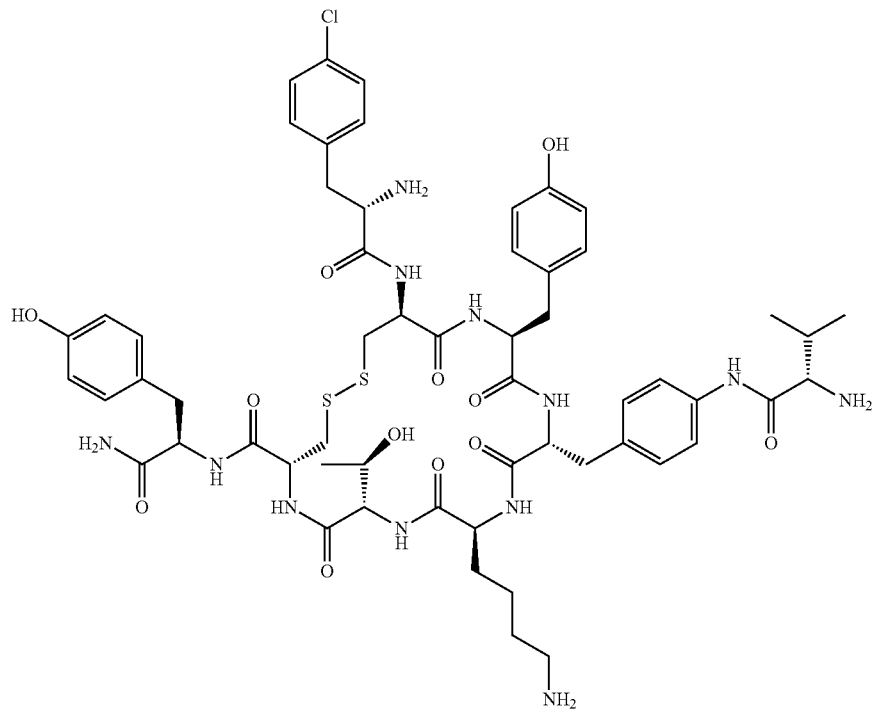 [SMILES: CC(C)[C@H](N)C(=O)Nc1ccc(C[C@H]2NC(=O)[C@H](Cc3ccc(O)cc3)NC(=O)[C@H](NC(=O)[C@@H](N)Cc3ccc(Cl)cc3)CSSC[C@@H](C(=O)N[C@H](Cc3ccc(O)cc3)C(N)=O)NC(=O)[C@H]([C@@H](C)O)NC(=O)[C@H](CCCCN)NC2=O)cc1]
H-Cpa-cyclo[D-Cys-Tyr-D-Aph(Val)-Lys-Thr-Cys]-D-Tyr-NH$_2$ |

| Compound No. | Structure |
|---|---|
| 24 | 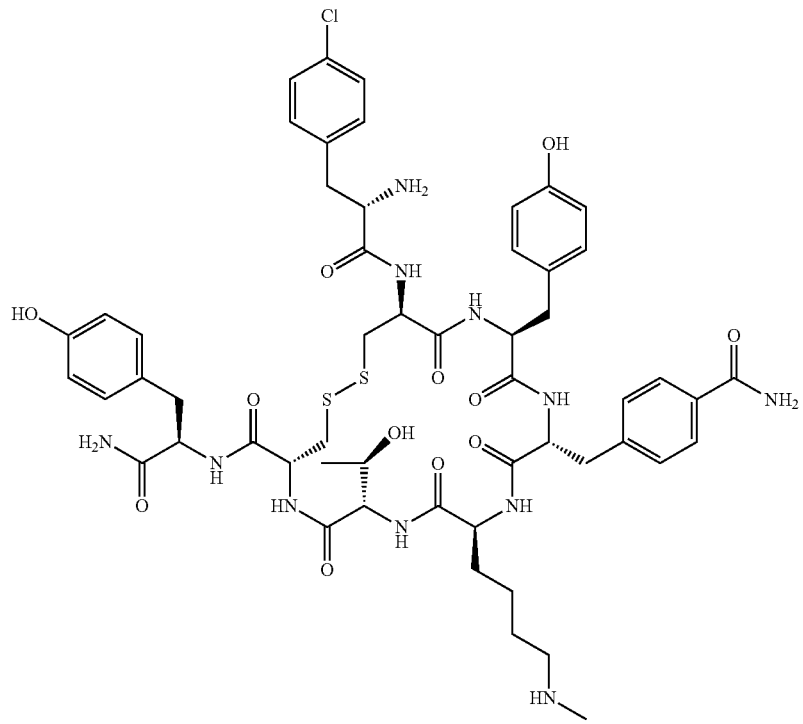 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC(=O)[C@H]([C@@H](C)O)NC1=O]
H-Cpa-cyclo[D-Cys-Tyr-D-Phe(4-carbamoyl)-Lys(N^ε-Me)-Thr-Cys]-D-Tyr-NH$_2$ |
| 25 | 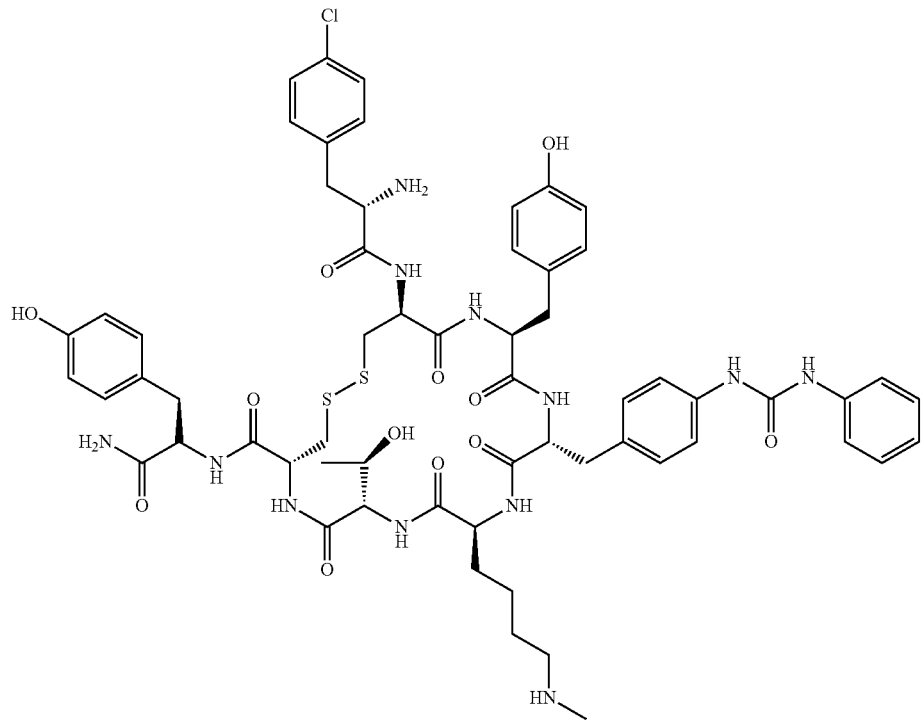
H-Cpa-cyclo[D-Cys-Tyr-D-Phe(4-phenylureido)-Lys(N^ε-Me)-Thr-Cys]-D-Tyr-NH$_2$ |

| Compound No. | Structure |
|---|---|
| 26 | 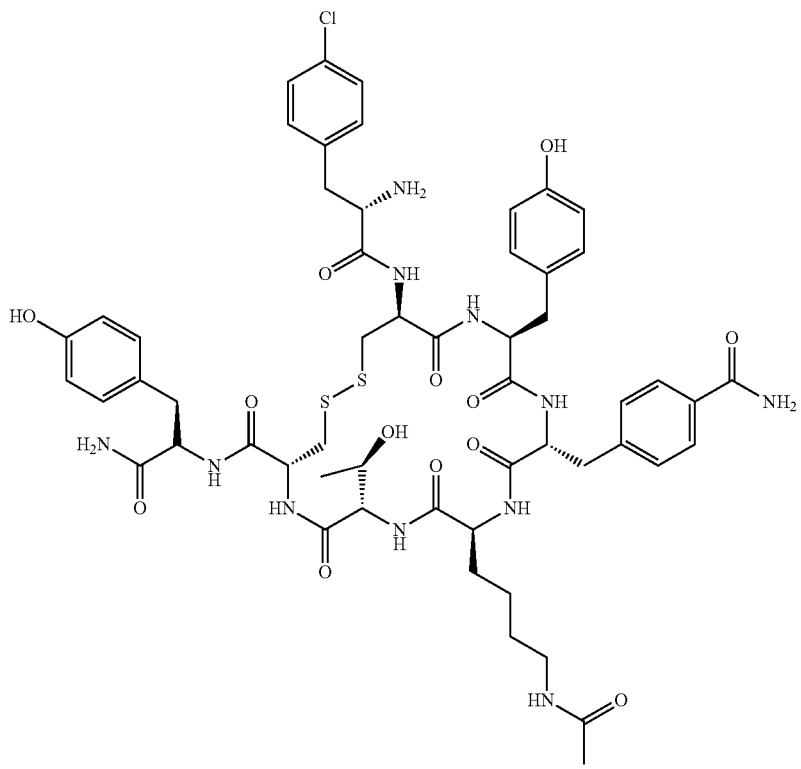<br>H-Cpa-cyclo[D-Cys-Tyr-D-Phe(4-carbamoyl)-Lys(N$^\varepsilon$-Ac)-Thr-Cys]-D-Tyr-NH$_2$ |
| 27 | 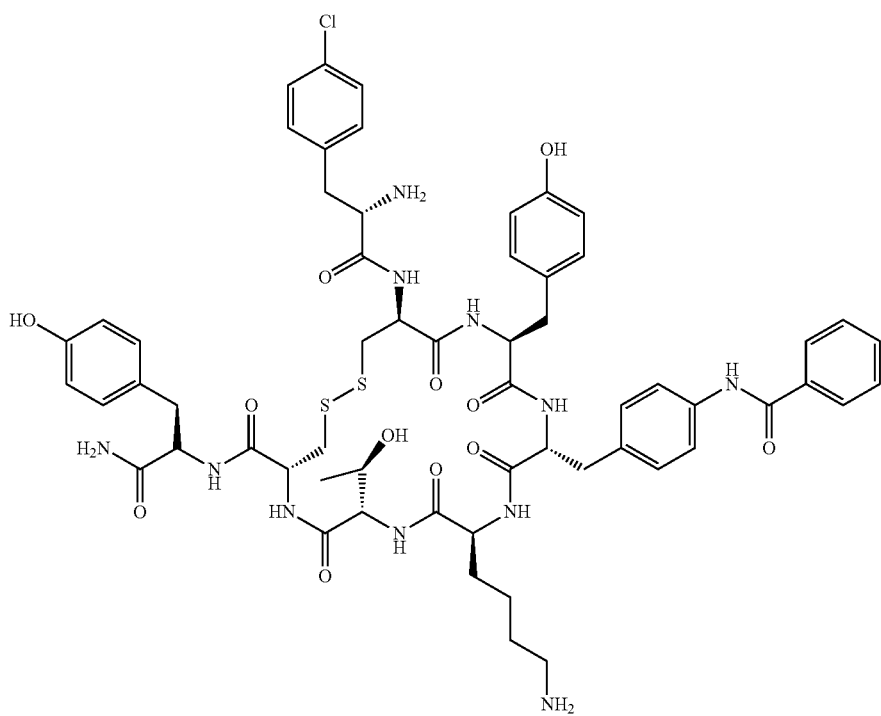<br>H-Cpa-cyclo[D-Cys-Tyr-D-Phe(4-benzamidophenyl)-Lys-Thr-Cys]-D-Tyr-NH$_2$ |

| Compound No. | Structure |
|---|---|
| 28 | 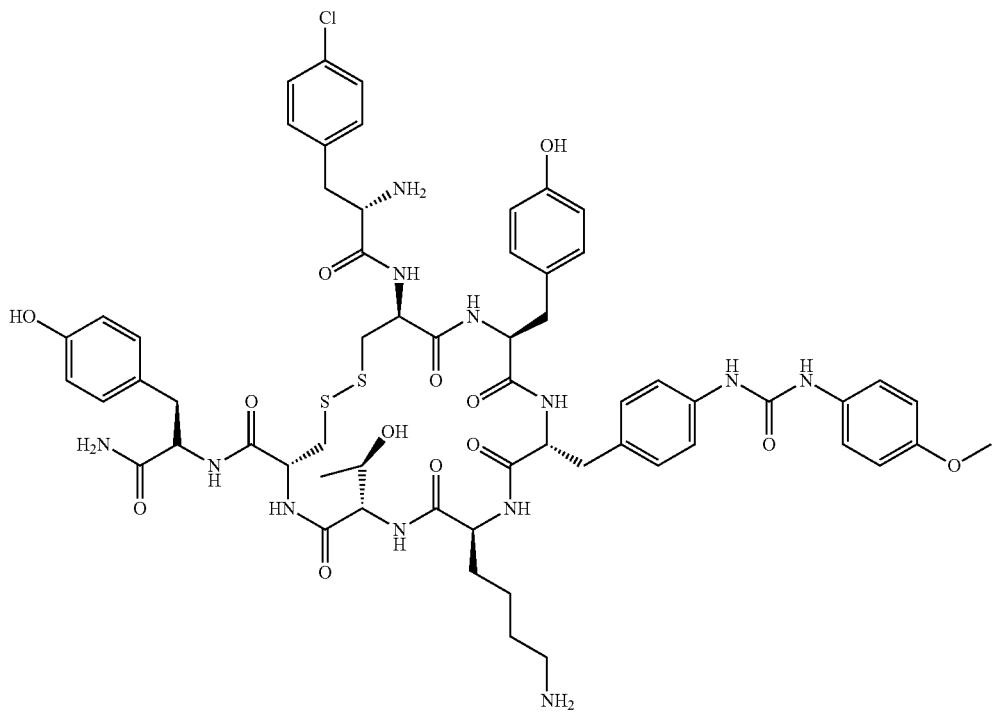<br>H-Cpa-cyclo[D-Cys-Tyr-D-Phe(4-(4-methoxyphenyl)ureido)-Lys-Thr-Cys]-D-Tyr-NH$_2$ |
| 29 | 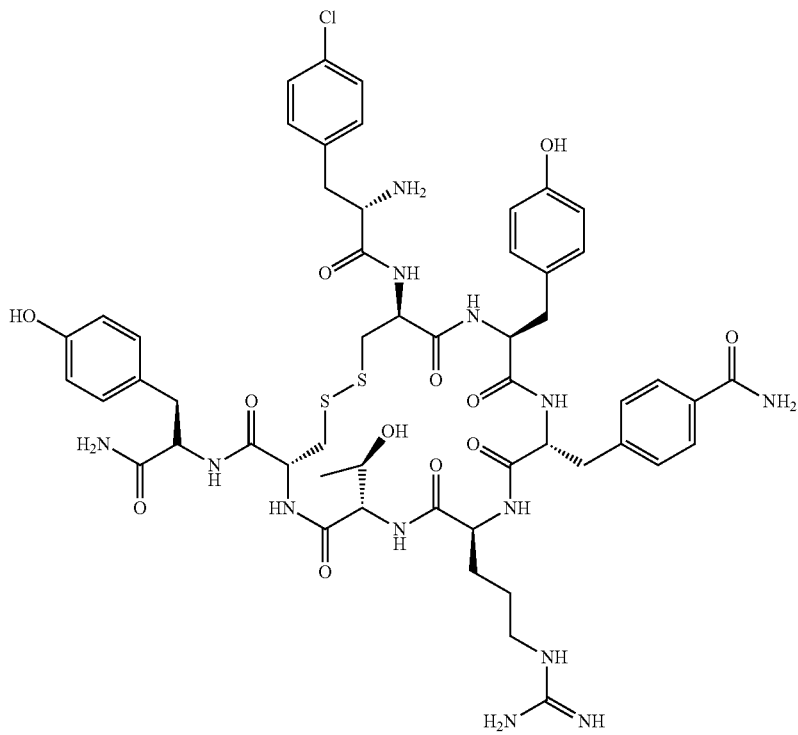<br>H-Cpa-cyclo[D-Cys-Tyr-D-Phe(4-carbamoyl)-Arg-Thr-Cys]-D-Tyr-NH$_2$ |

-continued
| Compound No. | Structure |
|---|---|
30
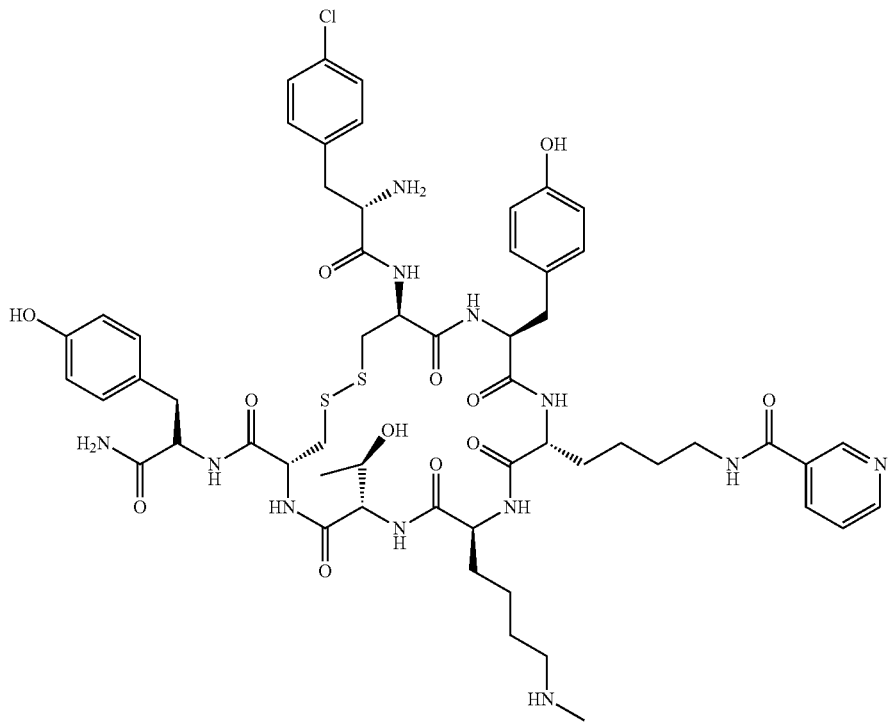
H-Cpa-cyclo[D-Cys-Tyr-D-Lys(N$^\varepsilon$-nicotinoyl)-Lys(N$^\varepsilon$-Me)-Thr-Cys]-D-Tyr-NH$_2$
31
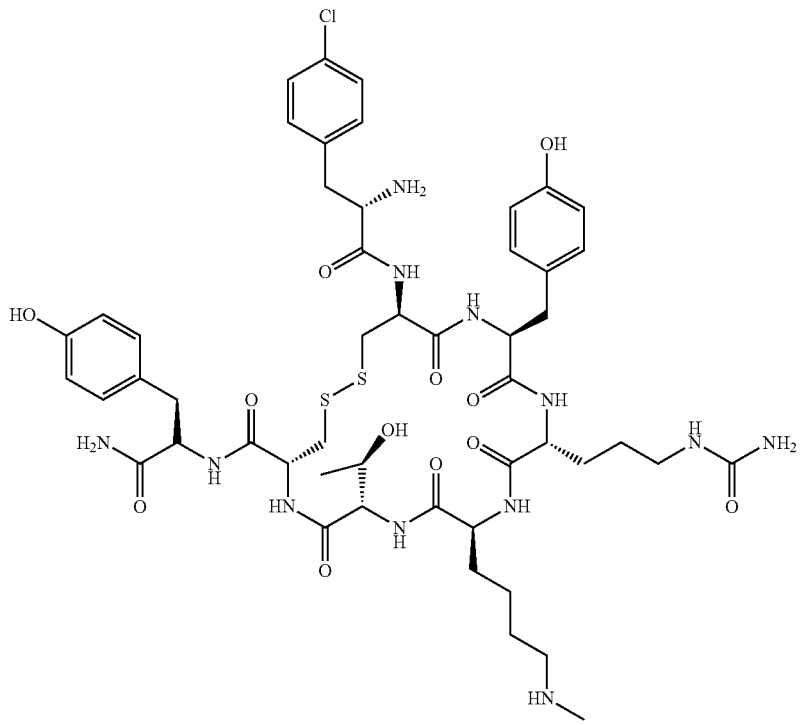
H-Cpa-cyclo[D-Cys-Tyr-D-Cit-Lys(N$^\varepsilon$-Me)-Thr-Cys]-D-Tyr-NH$_2$

| Compound No. | Structure |
|---|---|
| 32 | 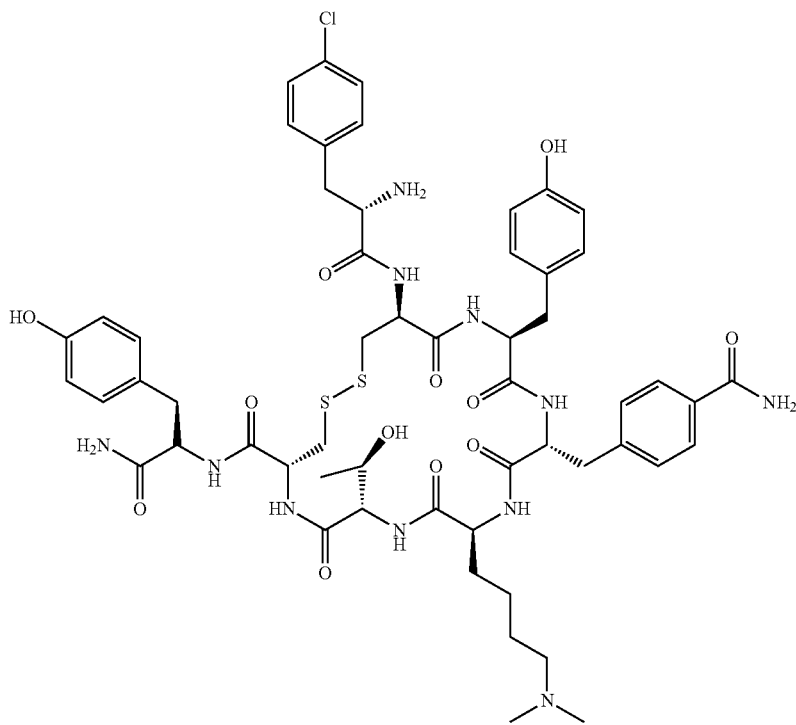<br>H-Cpa-cyclo[D-Cys-Tyr-D-Phe(4-carbamoyl)-Lys(N$^\varepsilon$-diMe)-Thr-Cys]-D-Tyr-NH$_2$ |
| 33 | 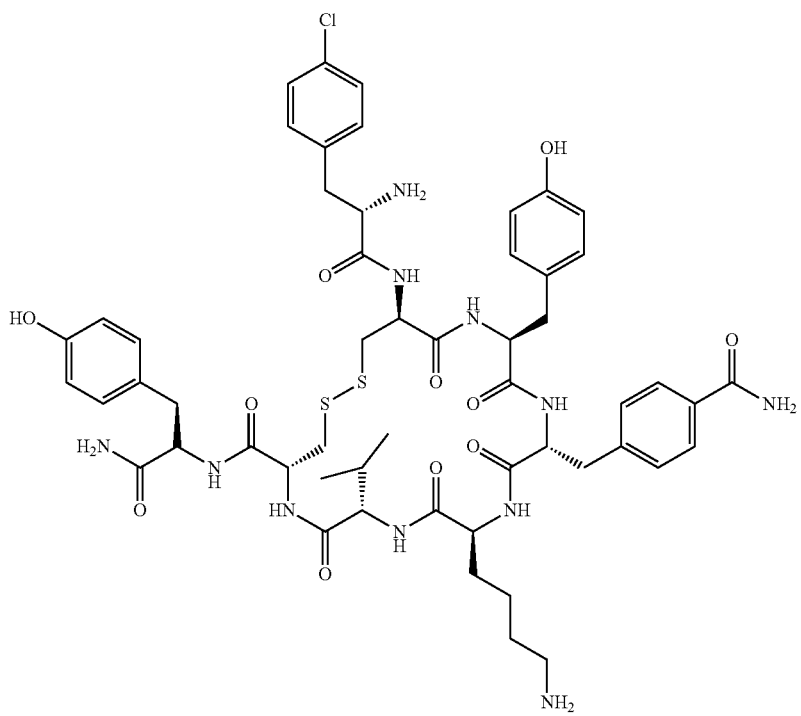<br>H-Cpa-cyclo[D-Cys-Tyr-D-Phe(4-carbamoyl)-Lys-Val-Cys]-P-Tyr-NH$_2$ |

| Compound No. | Structure |
|---|---|
| 34 | 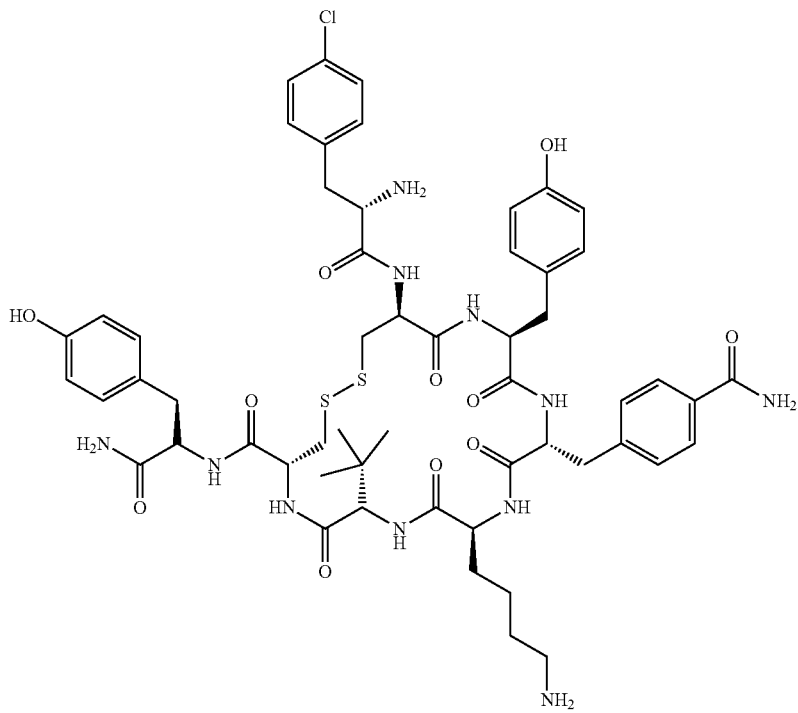<br>H-Cpa-cyclo[D-Cys-Tyr-D-Phe(4-carbamoyl)-Lys-Tle-Cys]-D-Tyr-NH$_2$ |
| 35 | 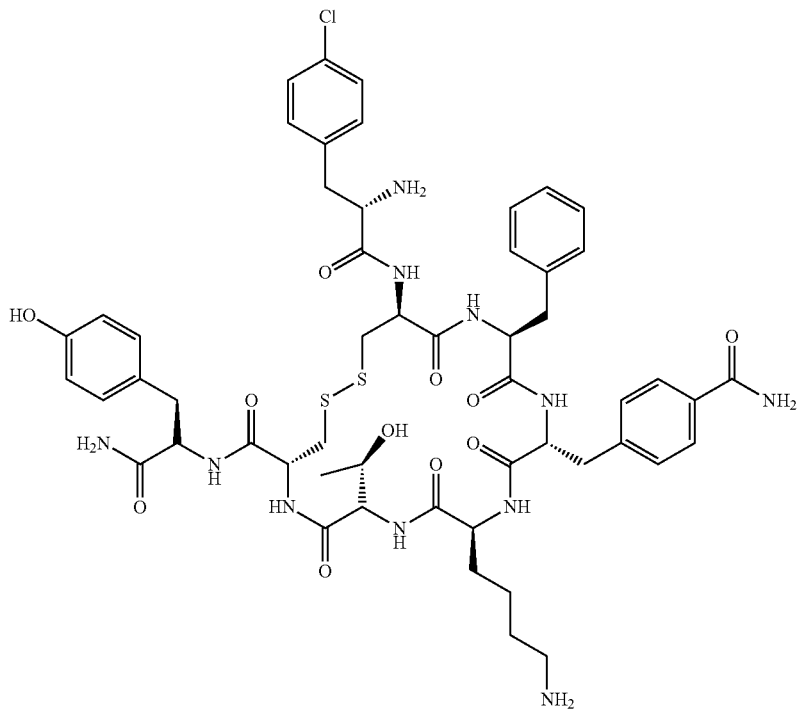<br>H-Cpa-cyclo[D-Cys-Phe-D-Phe(4-carbamoyl)-Lys-Thr-Cys]-D-Tyr-NH$_2$ |

| Compound No. | Structure |
|---|---|
| 36 | 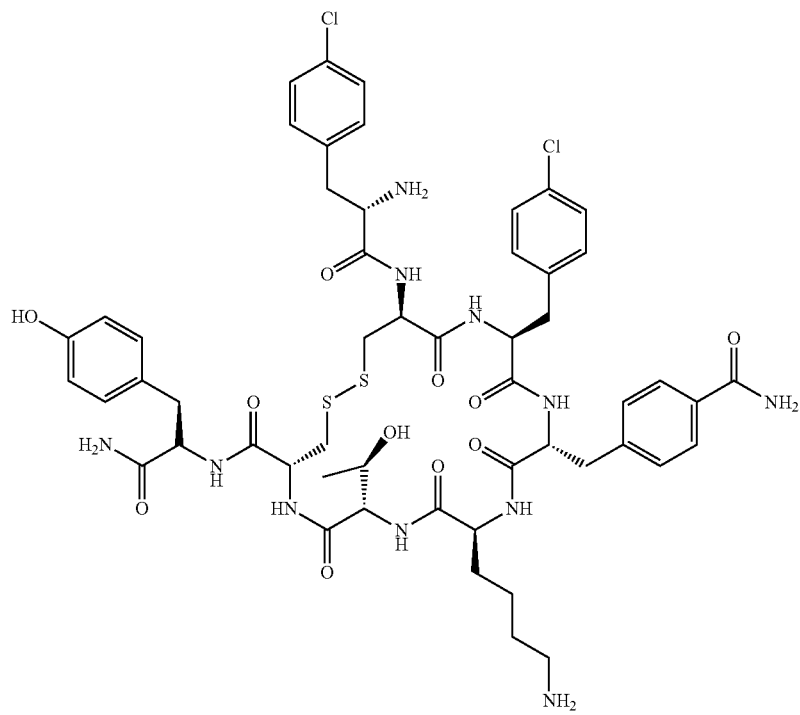<br>H-Cpa-cyclo[D-Cys-Cpa-D-Phe(4-carbamoyl)-Lys-Thr-Cys]-D-Tyr-NH₂ |
| 37 | 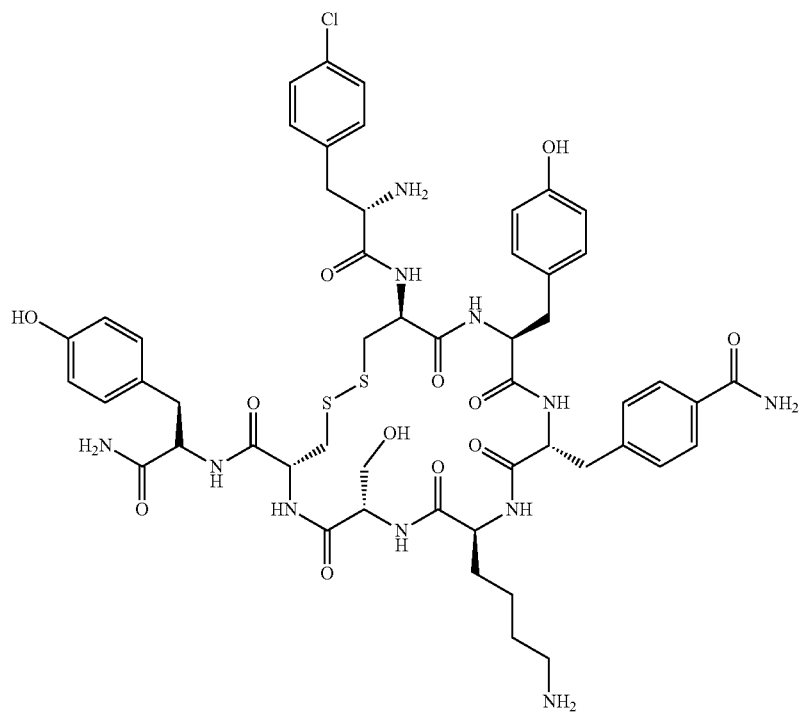<br>H-Cpa-cyclo[D-Cys-Tyr-D-Phe(4-carbamoyl)-Lys-Ser-Cys]-D-Tyr-NH₂ |

| Compound No. | Structure |
|---|---|
| 38 | 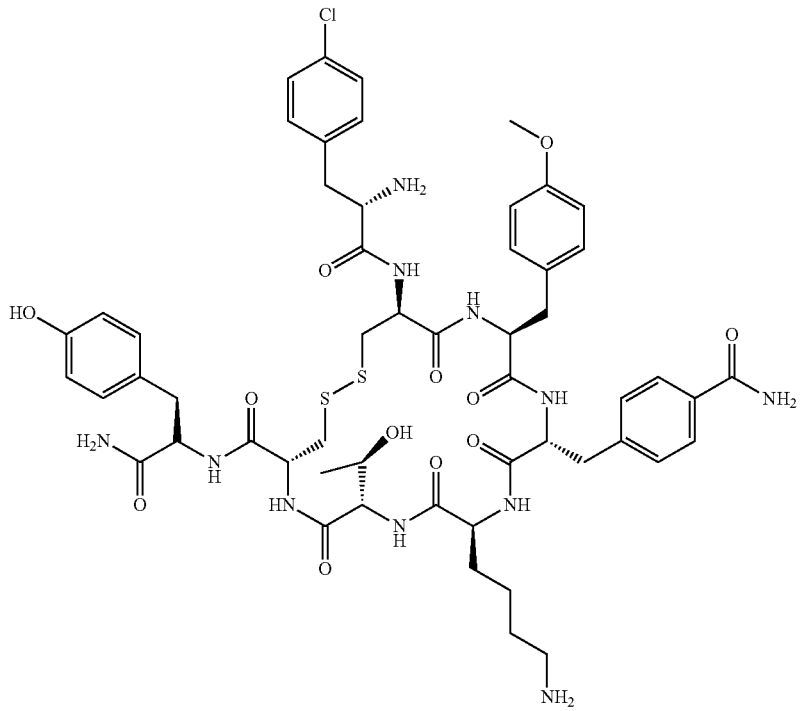
H-Cpa-cyclo[D-Cys-Tyr(Me)-D-Phe(4-carbamoyl)-Lys-Thr-Cys]-D-Tyr-NH₂ |
| 39 | 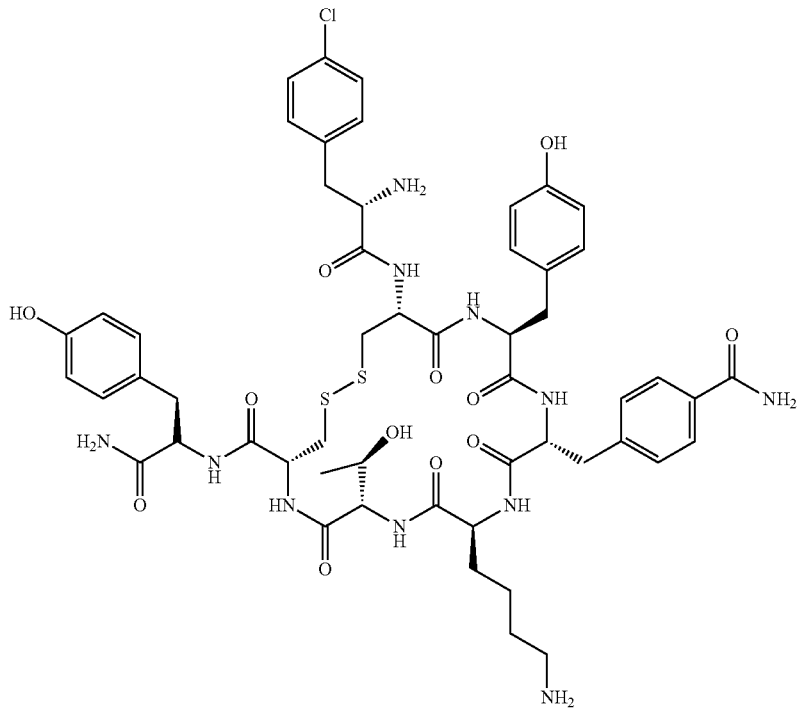
H-Cpa-cyclo[Cys-Tyr-D-Phe(4-carbamoyl)-Lys-Thr-Cys]-D-Tyr-NH₂ |

| Compound No. | Structure |
|---|---|
| 40 | 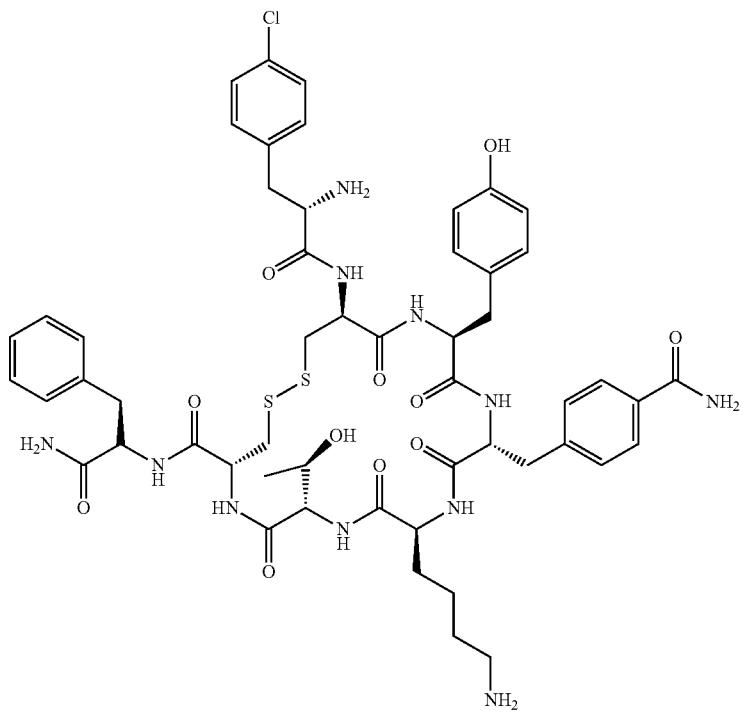
H-Cpa-cyclo[D-Cys-Tyr-D-Phe(4-carbamoyl)-Lys-Thr-Cys]-D-Phe-NH₂ |
| 41 | 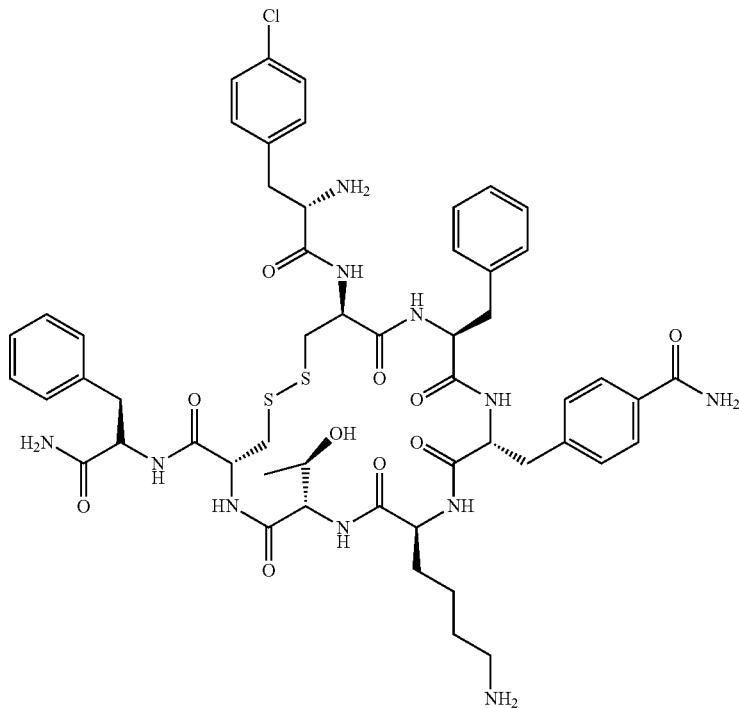
H-Cpa-cyclo[D-Cys-Phe-D-Phe(4-carbamoyl)-Lys-Thr-Cys]-D-Phe-NH₂ |

| Compound No. | Structure |
|---|---|
| 42 | 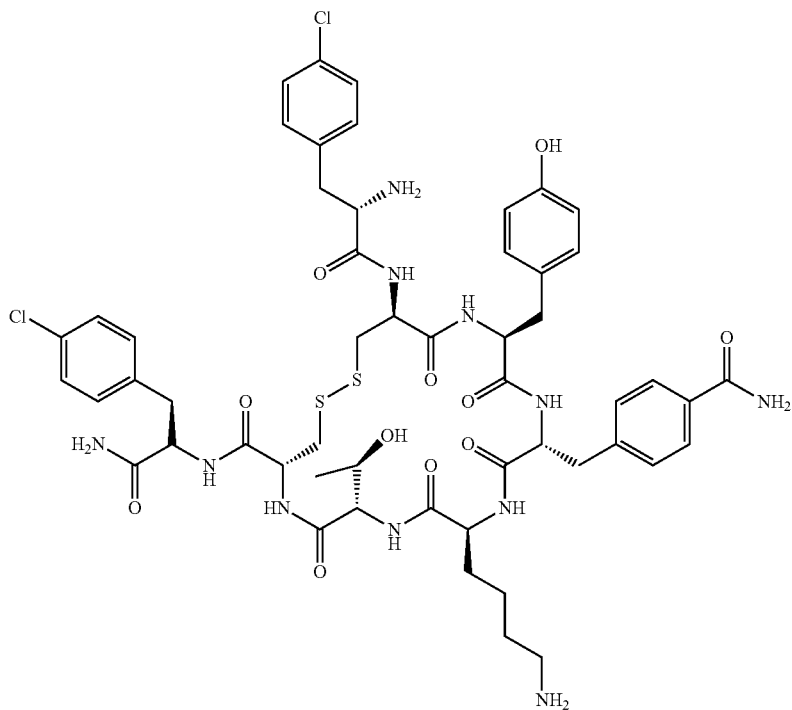<br>H-Cpa-cyclo[D-Cys-Tyr-D-Phe(4-carbamoyl)-Lys-Thr-Cys]-D-Cpa-NH$_2$ |
| 43 | 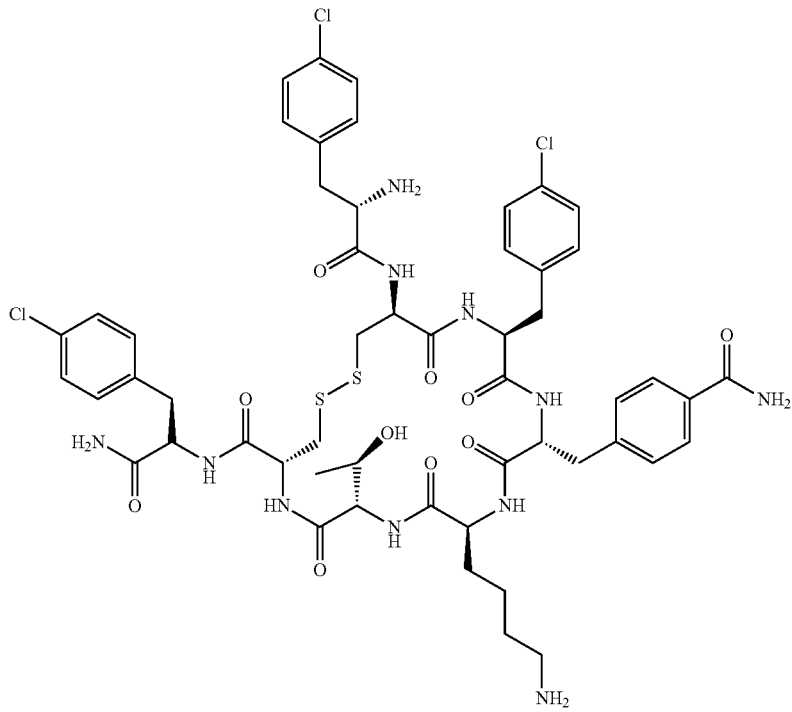<br>H-Cpa-cyclo[D-Cys-Cpa-D-Phe(4-carbamoyl)-Lys-Thr-Cys]-D-Cpa-NH$_2$ |

| Compound No. | Structure |
|---|---|
| 44 | 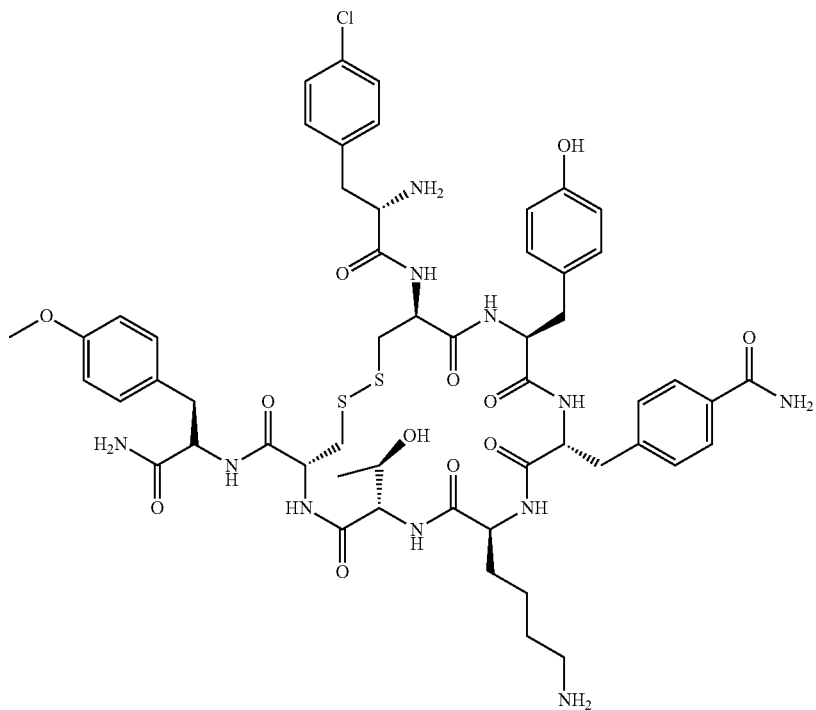 H-Cpa-cyclo[D-Cys-Tyr-D-Phe(4-carbamoyl)-Lys-Thr-Cys]-D-Tyr(Me)-NH$_2$ |
| 45 | 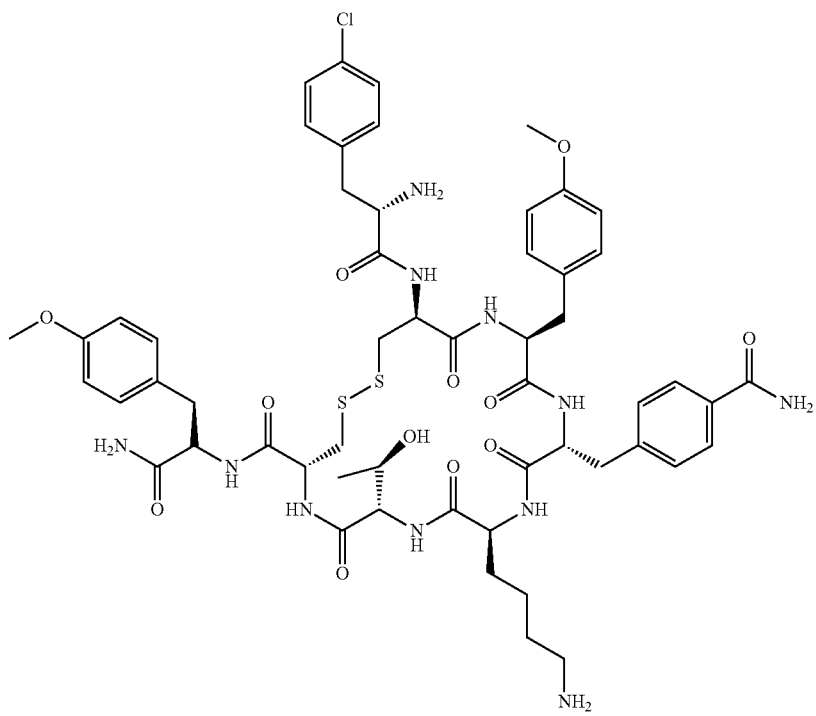 H-Cpa-cyclo[D-Cys-Tyr(Me)-D-Phe(4-carbamoyl)-Lys-Thr-Cys]-D-Tyr(Me)-NH$_2$ |

| Compound No. | Structure |
|---|---|
| 46 | 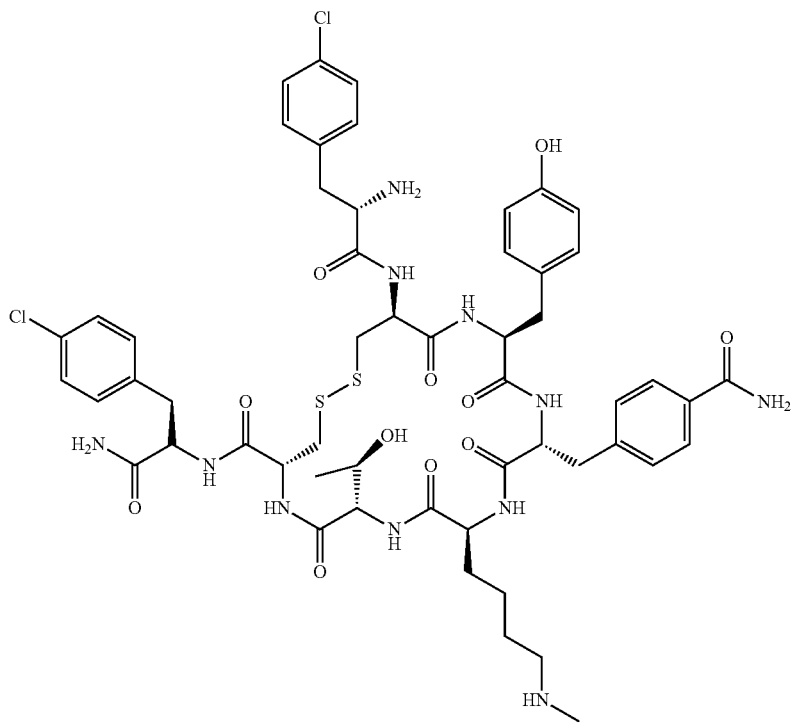<br>H-Cpa-cyclo[D-Cys-Tyr-D-Phe(4-carbamoyl)-Lys(N$^\varepsilon$-Me)-Thr-Cys]-D-Cpa-NH$_2$ |
| 47 | 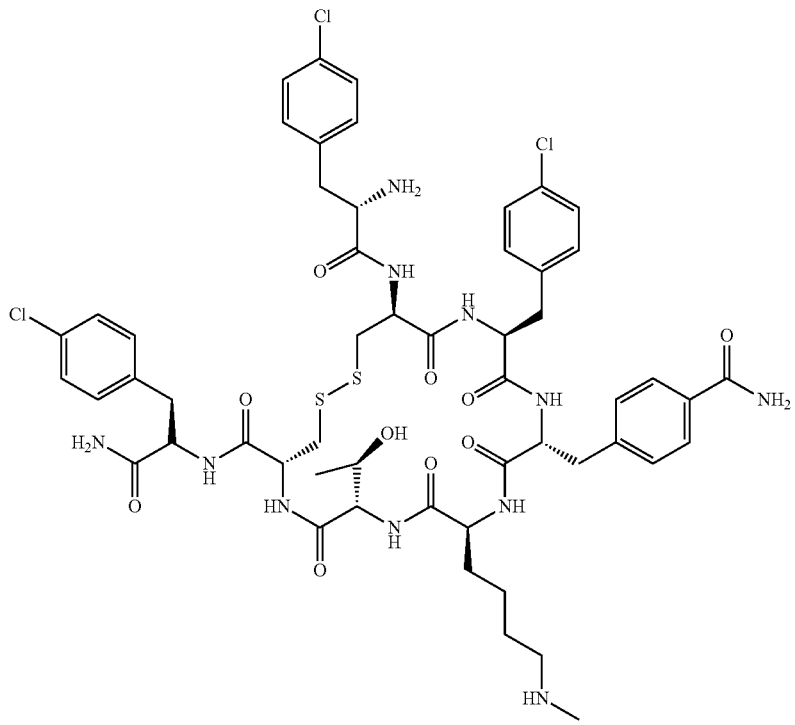<br>H-Cpa-cyclo[D-Cys-Cpa-D-Phe(4-carbamoyl)-Lys(N$^\varepsilon$-Me)-Thr-Cys]-D-Cpa-NH$_2$ |

| Compound No. | Structure |
|---|---|
| 48 | 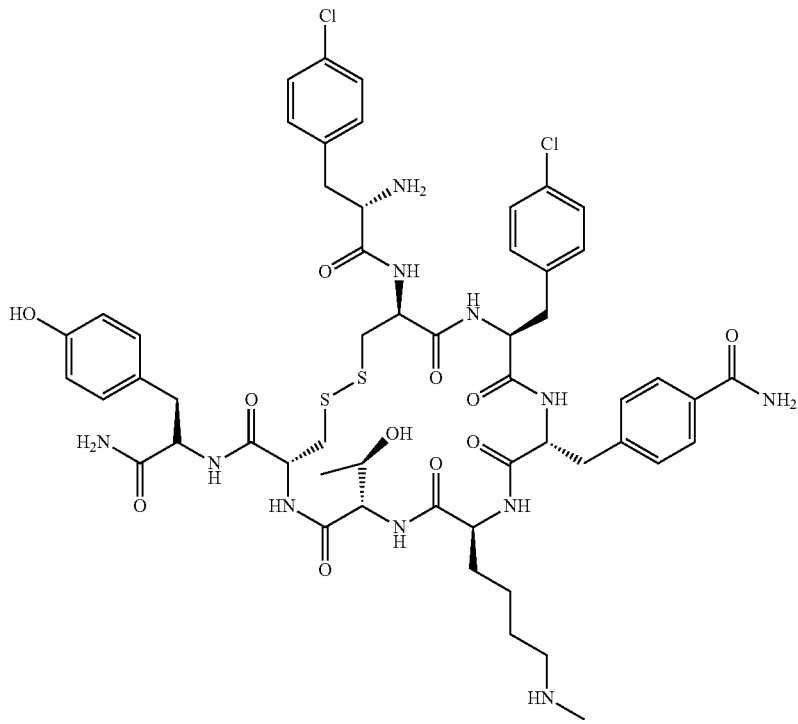
H-Cpa-cyclo[D-Cys-Cpa-D-Phe(4-carbamoyl)-Lys(N$^\varepsilon$-Me)-Thr-Cys]-D-Tyr-NH$_2$ |
| 49 | 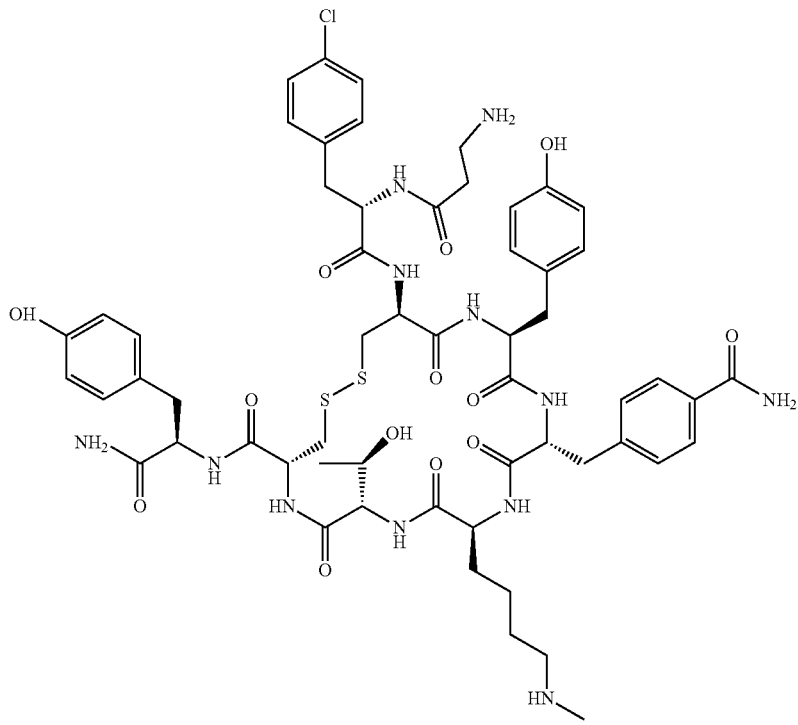 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCN)CSSC[C@@H](C(=O)N[C@H](Cc2ccc(O)cc2)C(N)=O)NC(=O)[C@H]([C@@H](C)O)NC1=O]
H-β-Ala-Cpa-cyclo[D-Cys-Tyr-D-Phe(4-carbamoyl)-Lys(N$^\varepsilon$-Me)-Thr-Cys]-D-Tyr-NH$_2$ |

| Compound No. | Structure |
|---|---|
| 50 | 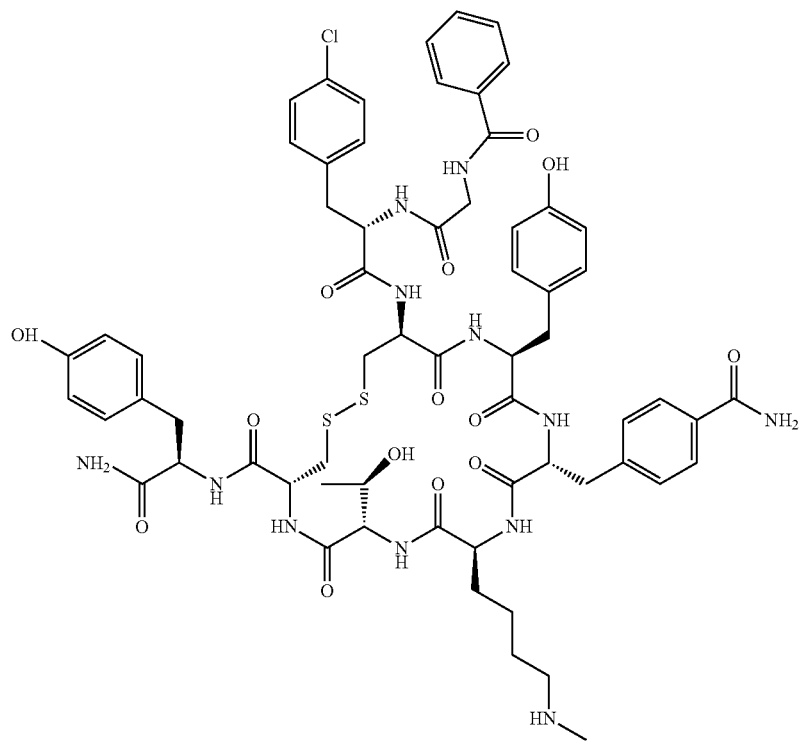 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CNC(=O)c2ccccc2)CSSC[C@@H](C(=O)N[C@H](Cc2ccc(O)cc2)C(N)=O)NC(=O)[C@H]([C@@H](C)O)NC1=O] Ph(CO)NHCH₂(CO)-Cpa-cyclo[D-Cys-Tyr-D-Phe(4-carbamoyl)-Lys(Nᵉ-Me)-Thr-Cys]-D-Tyr-NH₂ |
| 51 | 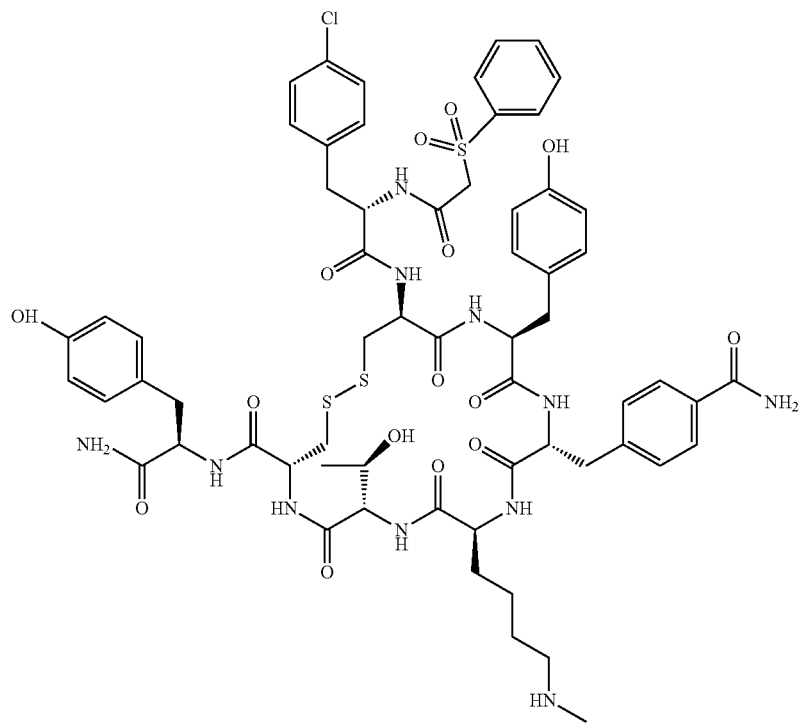 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CS(=O)(=O)c2ccccc2)CSSC[C@@H](C(=O)N[C@H](Cc2ccc(O)cc2)C(N)=O)NC(=O)[C@H]([C@@H](C)O)NC1=O] PhSO₂CH₂(CO)-Cpa-cyclo[D-Cys-Tyr-D-Phe(4-carbamoyl)-Lys(Nᵉ-Me)-Thr-Cys]-D-Tyr-NH₂ |

| Compound No. | Structure |
|---|---|
| 52 | 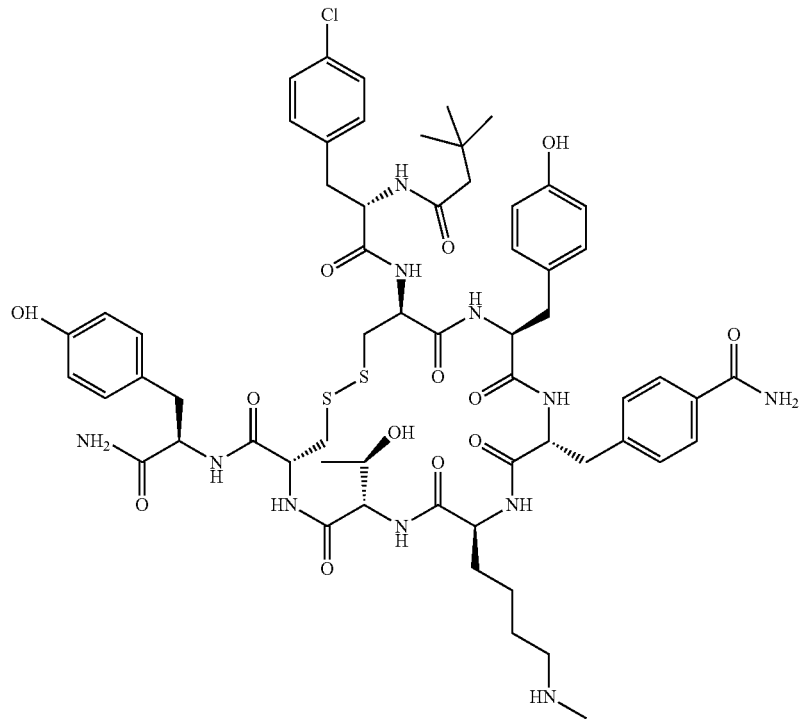 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CC(C)(C)C)CSSC[C@@H](C(=O)N[C@H](Cc2ccc(O)cc2)C(N)=O)NC(=O)[C@H]([C@@H](C)O)NC1=O]<br>t-BuCH₂(CO)-Cpa-cyclo[D-Cys-Tyr-D-Phe(4-carbamoyl)-Lys(Nᵉ-Me)-Thr-Cys]-D-Tyr-NH₂ |
| 53 | 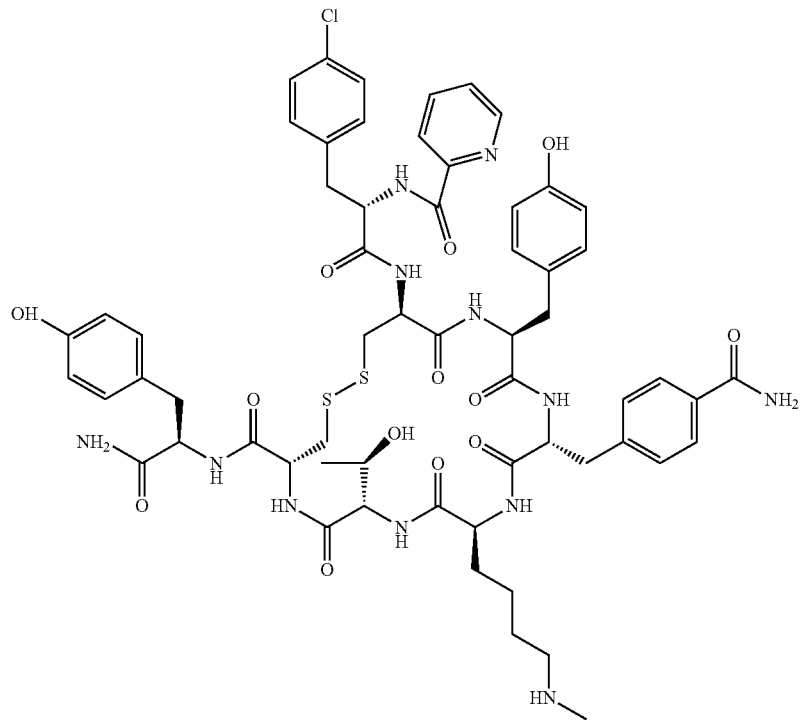 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)c2ccccn2)CSSC[C@@H](C(=O)N[C@H](Cc2ccc(O)cc2)C(N)=O)NC(=O)[C@H]([C@@H](C)O)NC1=O]<br>2-Pyridyl(CO)-Cpa-cyclo[D-Cys-Tyr-D-Phe(4-carbamoyl)-Lys(Nᵉ-Me)-Thr-Cys]-D-Tyr-NH₂ |

| Compound No. | Structure |
|---|---|
| 54 | 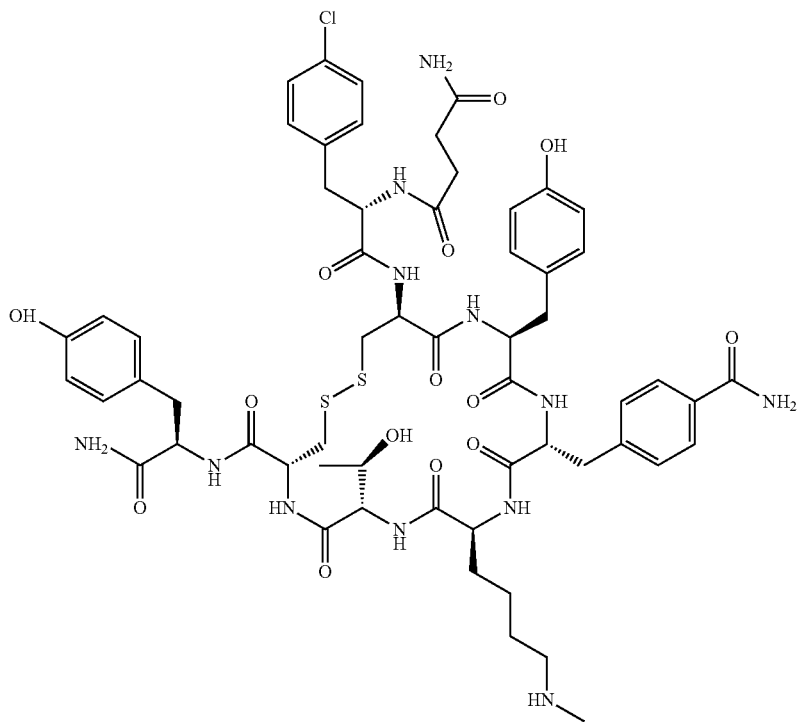 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCC(N)=O)CSSC[C@@H](C(=O)N[C@H](Cc2ccc(O)cc2)C(N)=O)NC(=O)[C@H]([C@@H](C)O)NC1=O] H₂N(CO)(CH₂)₂(CO)-Cpa-cyclo[D-Cys-Tyr-D-Phe(4-carbamoyl)-Lys(Nᵉ-Me)-Thr-Cys]-D-Tyr-NH₂ |
| 55 | 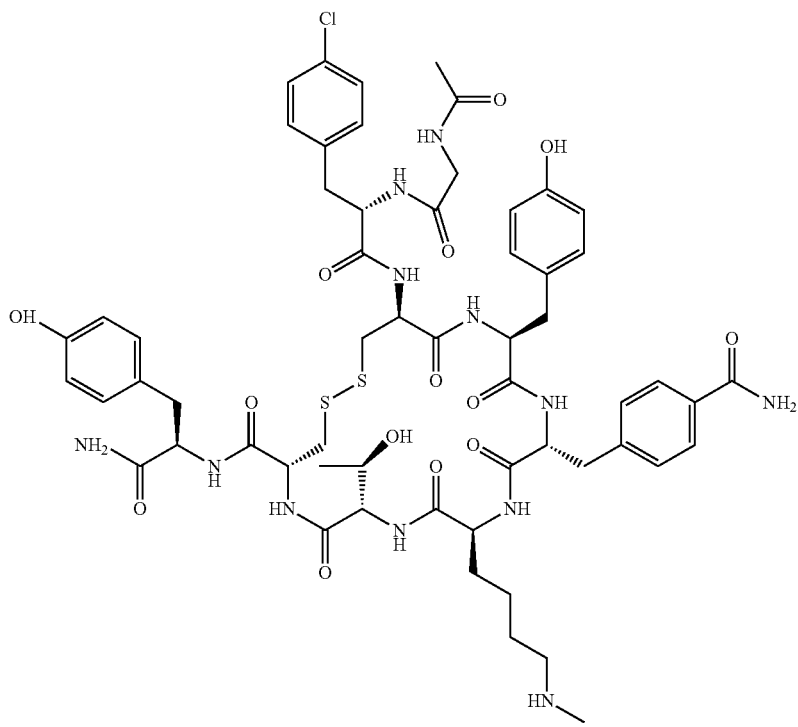 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CNC(C)=O)CSSC[C@@H](C(=O)N[C@H](Cc2ccc(O)cc2)C(N)=O)NC(=O)[C@H]([C@@H](C)O)NC1=O] Ac-Gly-Cpa-cyclo[D-Cys-Tyr-D-Phe(4-carbamoyl)-Lys(Nᵉ-Me)-Thr-Cys]D-Tyr-NH₂ |

| Compound No. | Structure |
|---|---|
| 56 | 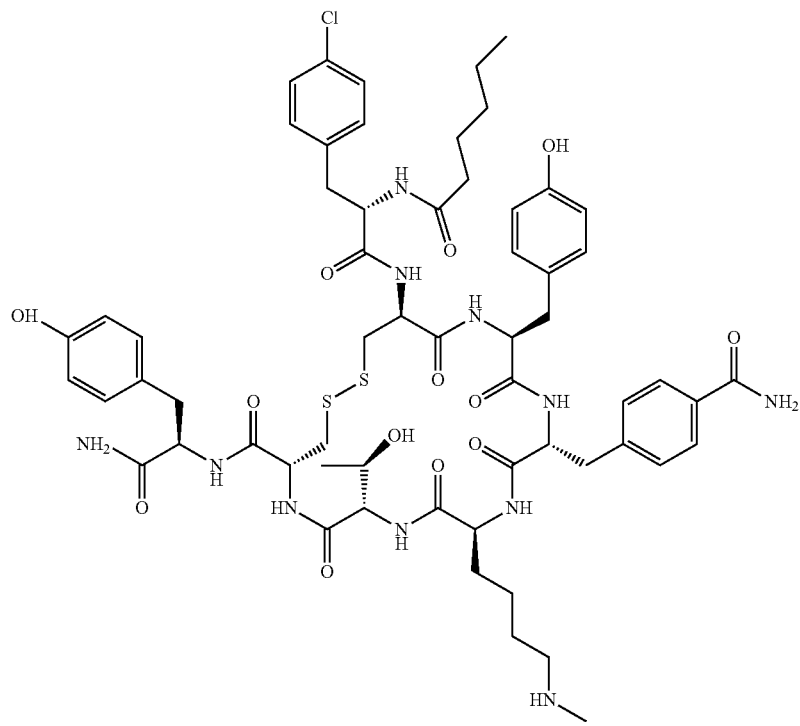 [SMILES: CCCCCC(=O)N[C@@H](Cc1ccc(Cl)cc1)C(=O)N[C@@H]1CSSC[C@@H](C(=O)N[C@H](Cc2ccc(O)cc2)C(N)=O)NC(=O)[C@H]([C@@H](C)O)NC(=O)[C@H](CCCCNC)NC(=O)[C@@H](Cc2ccc(C(N)=O)cc2)NC(=O)[C@H](Cc2ccc(O)cc2)NC1=O] CH₃(CH₂)₄(CO)-Cpa-cyclo[D-Cys-Tyr-D-Phe(4-carbamoyl)-Lys(N$^\varepsilon$-Me)-Thr-Cys]-D-Tyr-NH₂ |
| 57 | 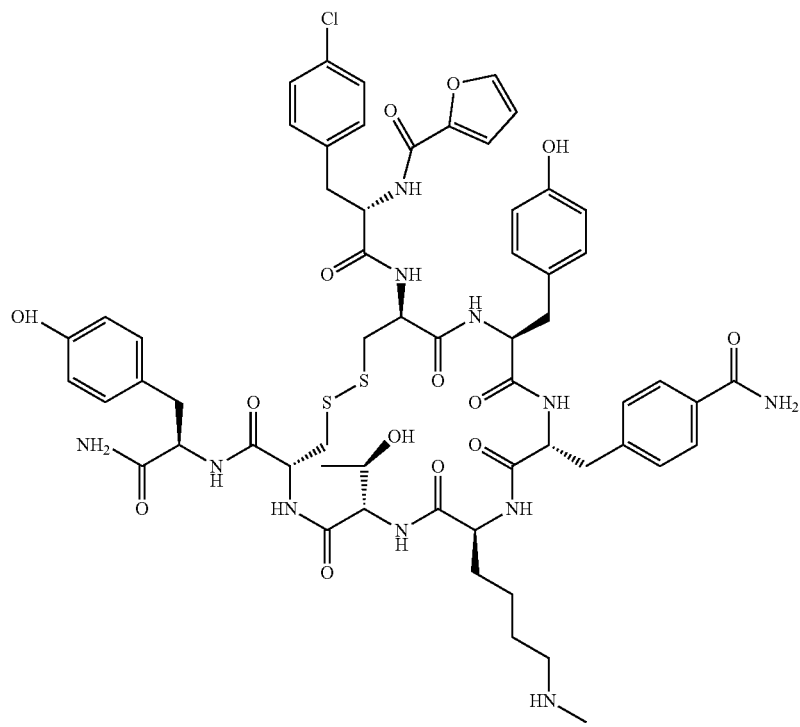 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)c2ccco2)CSSC[C@@H](C(=O)N[C@H](Cc2ccc(O)cc2)C(N)=O)NC(=O)[C@H]([C@@H](C)O)NC1=O] (Furan-2-carboxy)-Cpa-cyclo[D-Cys-Tyr-D-Phe(4-carbamoyl)-Lys(N$^\varepsilon$-Me)-Thr-Cys]-D-Tyr-NH₂ |

-continued
| Compound No. | Structure |
|---|---|
58
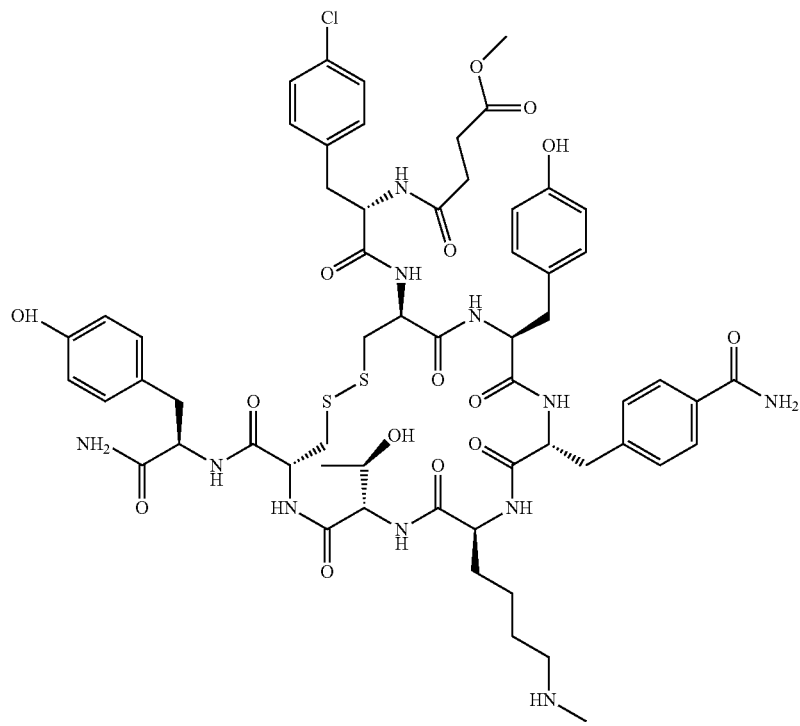 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NC(=O)CCC(=O)OC)CSSC[C@@H](C(=O)N[C@H](Cc2ccc(O)cc2)C(N)=O)NC(=O)[C@H]([C@@H](C)O)NC1=O]
CH₃O₂C(CH₂)₂(CO)-Cpa-cyclo[D-Cys-Tyr-D-Phe(4-carbamoyl)-Lys(N$^\epsilon$-Me)-Thr-Cys]-D-Tyr-NH₂
59
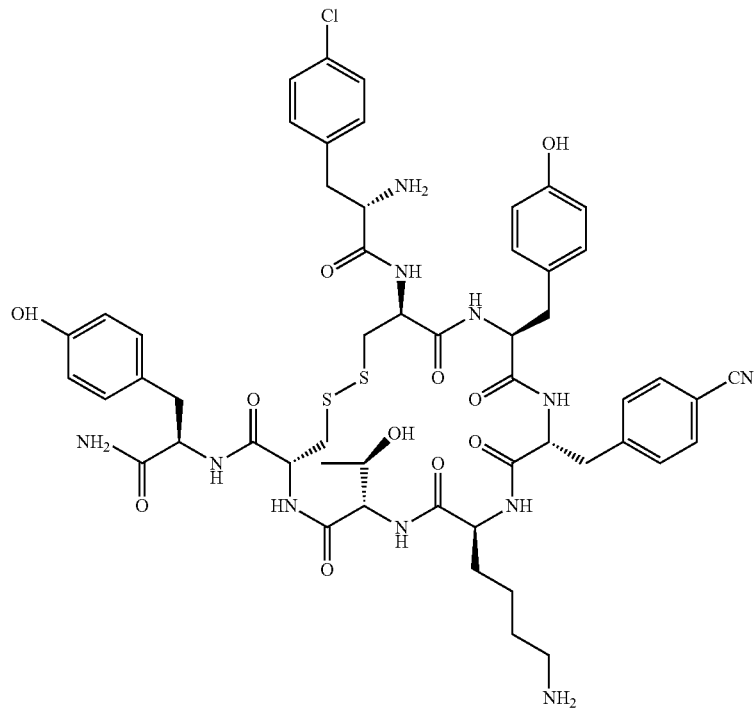 [SMILES: C[C@@H](O)[C@@H]1NC(=O)[C@H](CCCCN)NC(=O)[C@@H](Cc2ccc(C#N)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Phe(4-CN)-Lys-Thr-Cys]-D-Tyr-NH₂

| Compound No. | Structure |
|---|---|
| 60 | 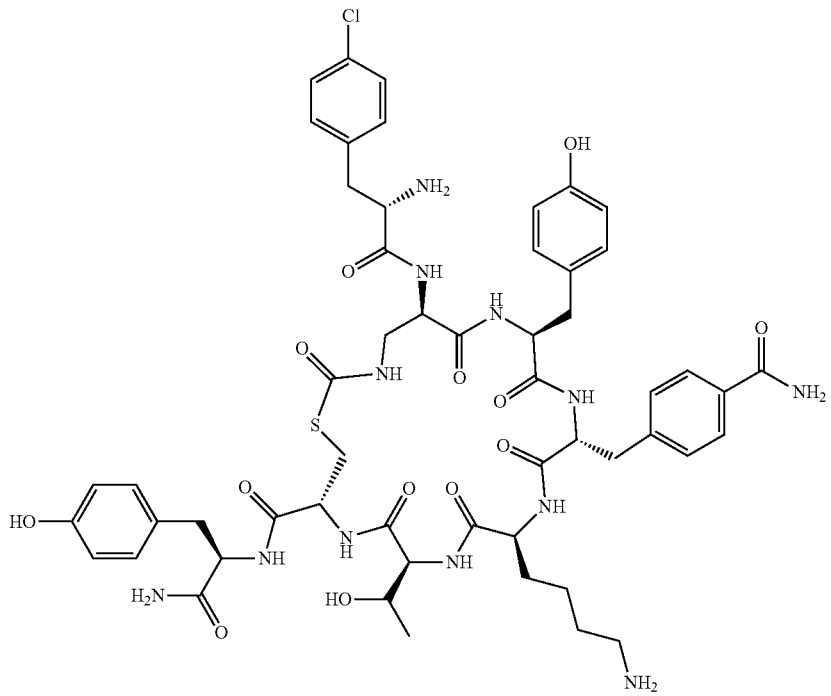 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)SC[C@@H](C(=O)N[C@H](Cc2ccc(O)cc2)C(N)=O)NC1=O] |
| 61 | 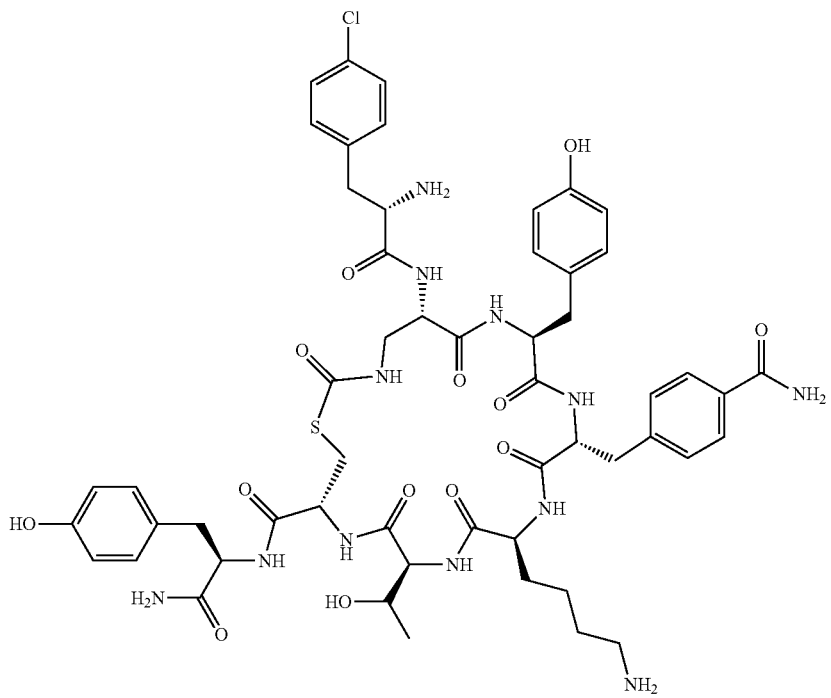 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)CNC(=O)SC[C@@H](C(=O)N[C@H](Cc2ccc(O)cc2)C(N)=O)NC1=O] |

-continued
| Compound No. | Structure |
|---|---|
| 62 | 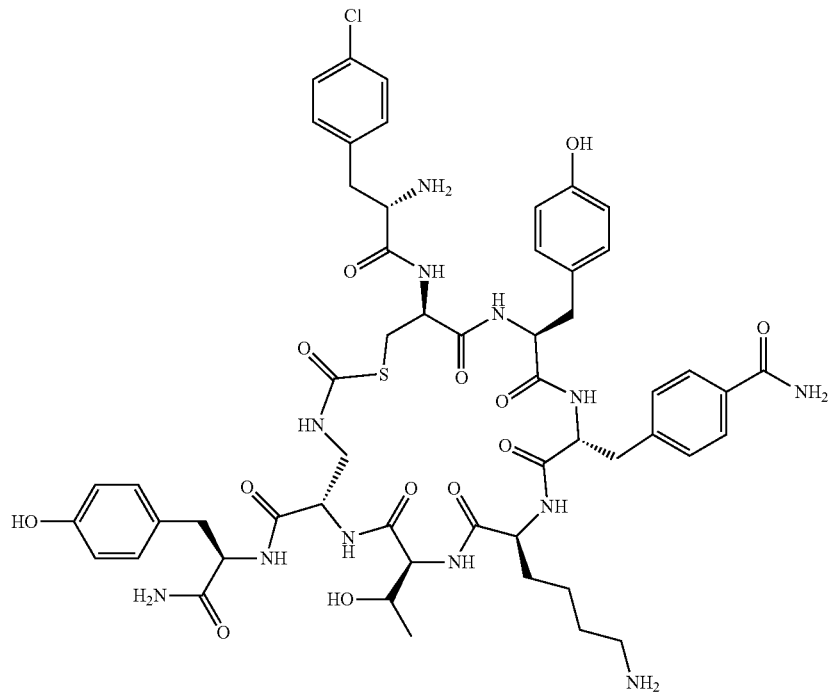 [SMILES: CC(O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSC(=O)NC[C@@H](C(=O)N[C@H](Cc2ccc(O)cc2)C(N)=O)NC1=O] |
| 63 | 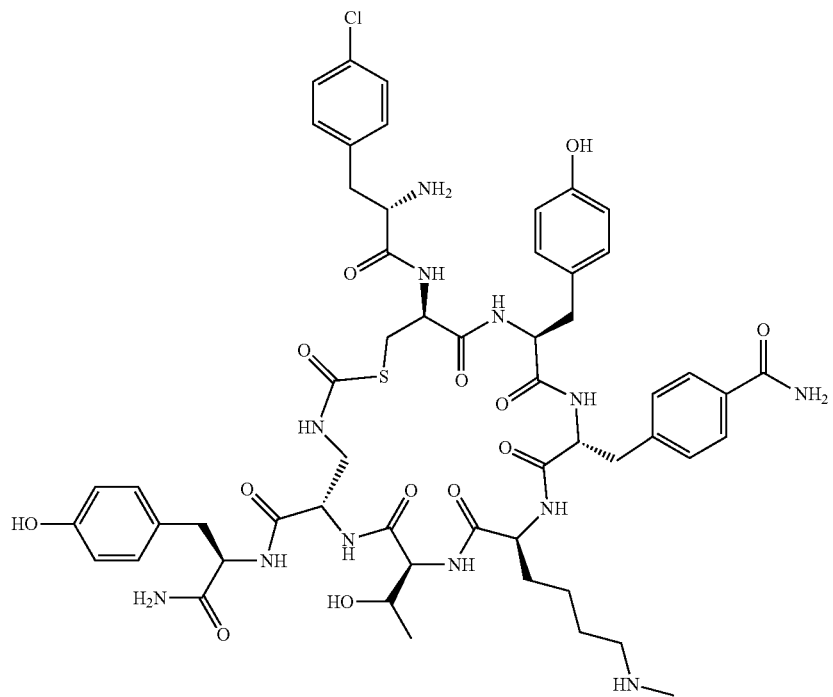 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSC(=O)NC[C@@H](C(=O)N[C@H](Cc2ccc(O)cc2)C(N)=O)NC(=O)[C@H](C(C)O)NC1=O] |

| Compound No. | Structure |
|---|---|
| 64 | 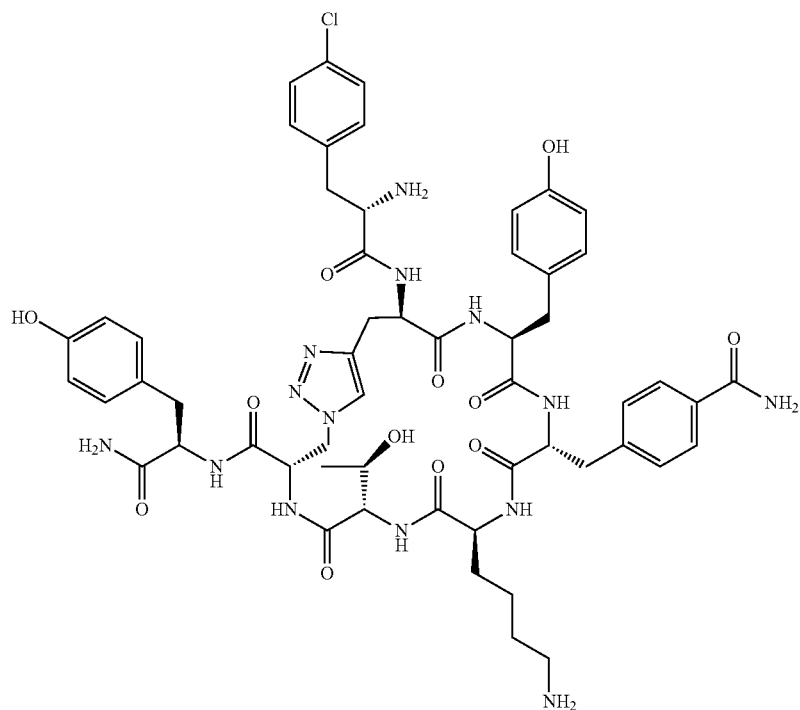 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)Cc2cn(nn2)C[C@@H](C(=O)N[C@H](Cc2ccc(O)cc2)C(N)=O)NC1=O] |
| 65 | 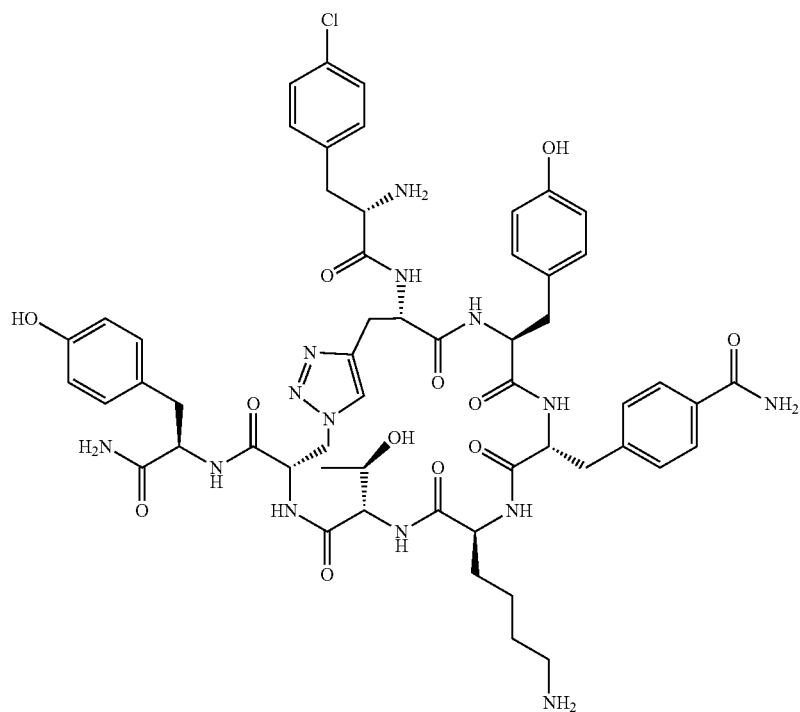 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)Cc2cn(nn2)C[C@@H](C(=O)N[C@H](Cc2ccc(O)cc2)C(N)=O)NC1=O] |

| Compound No. | Structure |
|---|---|
| 66 | 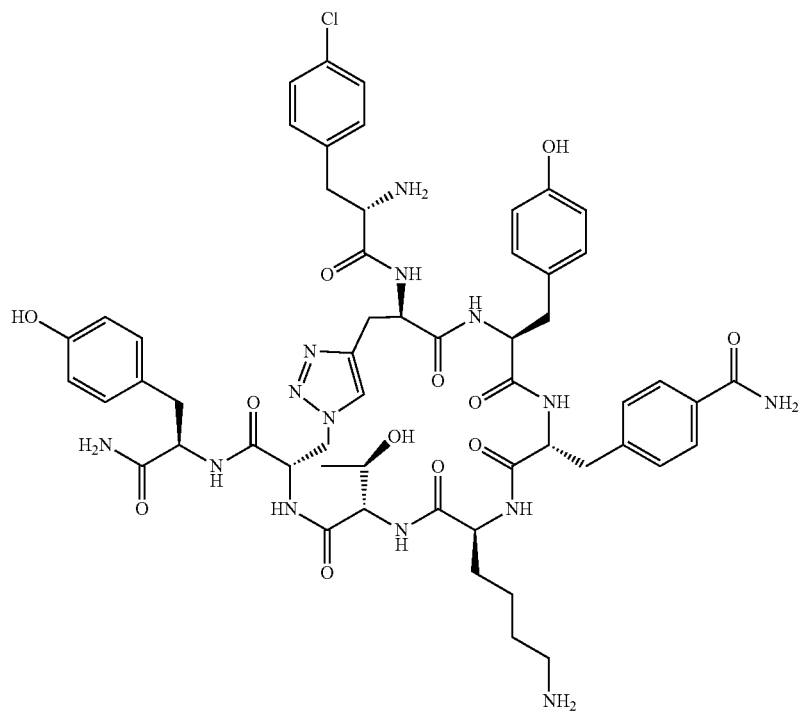 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)Cc2cn(nn2)C[C@@H](C(=O)N[C@H](Cc2ccc(O)cc2)C(N)=O)NC1=O] |
| 67 | 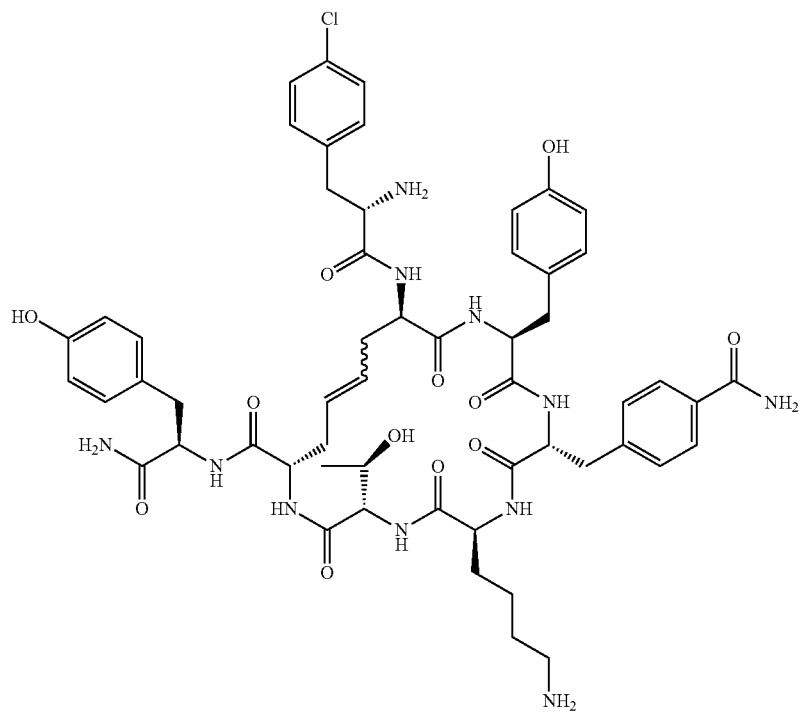 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CC=CC[C@@H](C(=O)N[C@H](Cc2ccc(O)cc2)C(N)=O)NC1=O] |

| Compound No. | Structure |
|---|---|
| 68 | 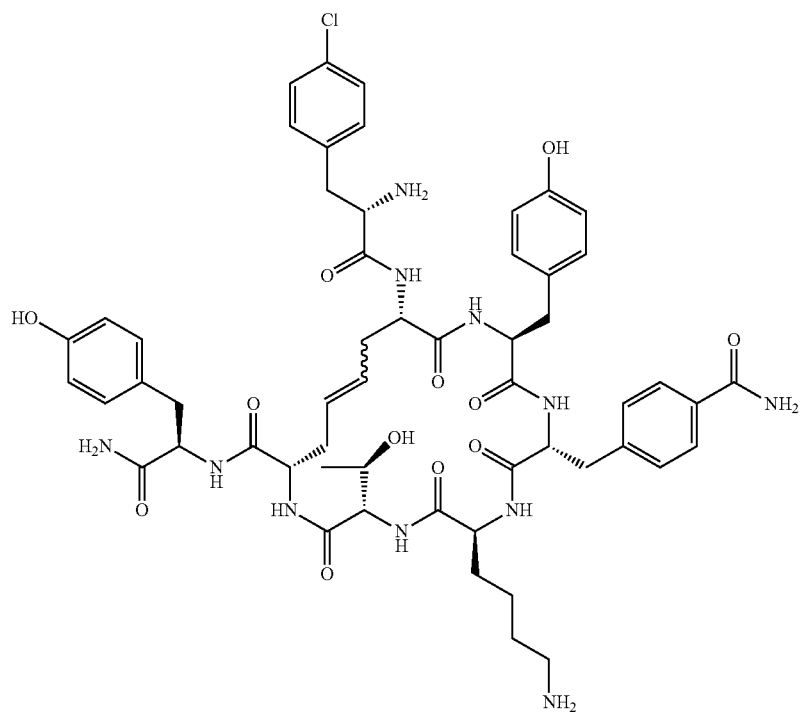 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@@H](NC(=O)[C@@H](N)Cc2ccc(Cl)cc2)CC=CC[C@@H](C(=O)N[C@H](Cc2ccc(O)cc2)C(N)=O)NC1=O] |
| 69 | 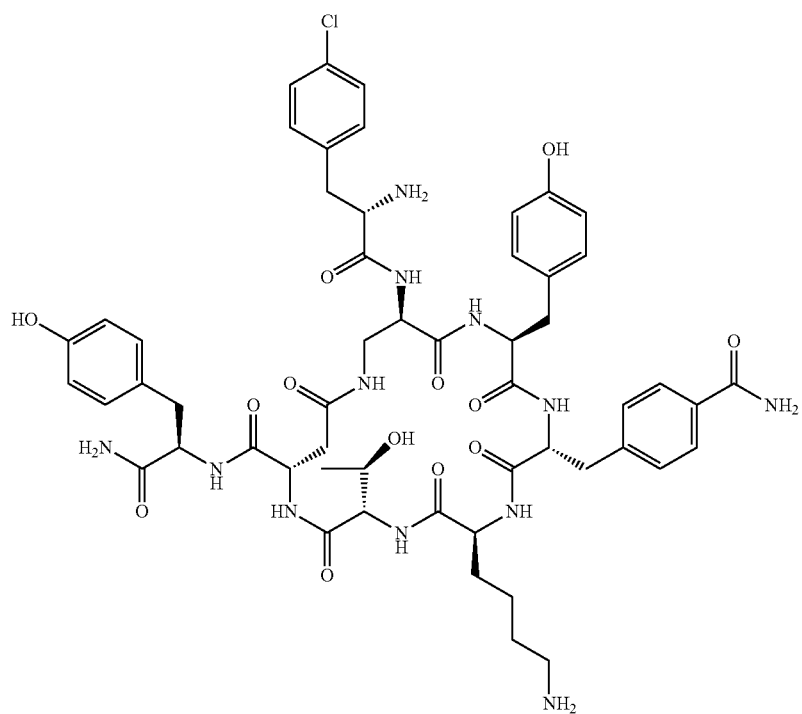 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)C[C@@H](C(=O)N[C@H](Cc2ccc(O)cc2)C(N)=O)NC1=O] |

| Compound No. | Structure |
|---|---|
| 70 | 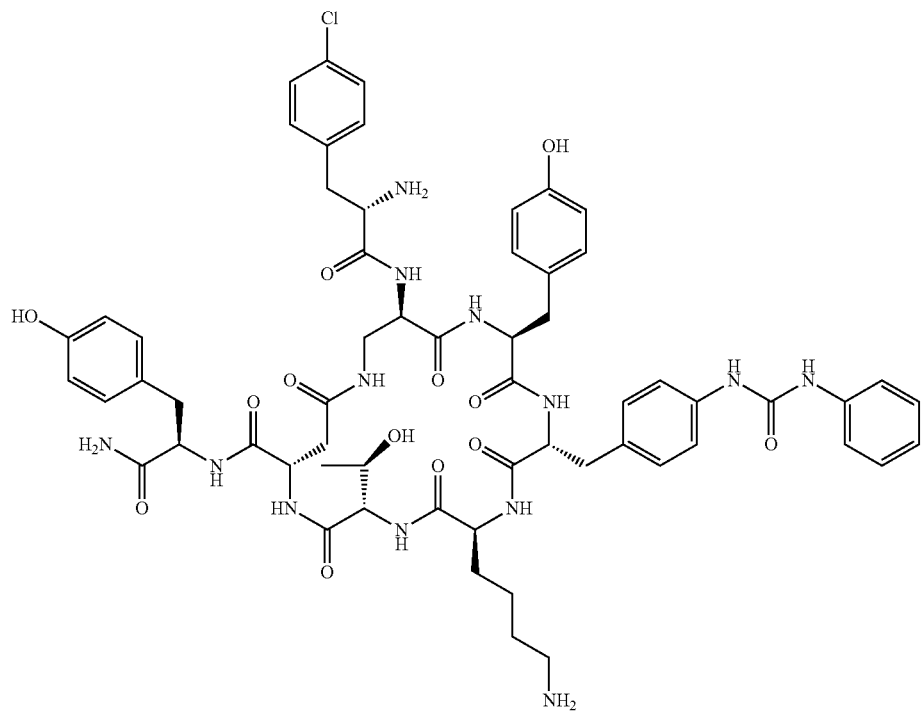 |
| 71 | 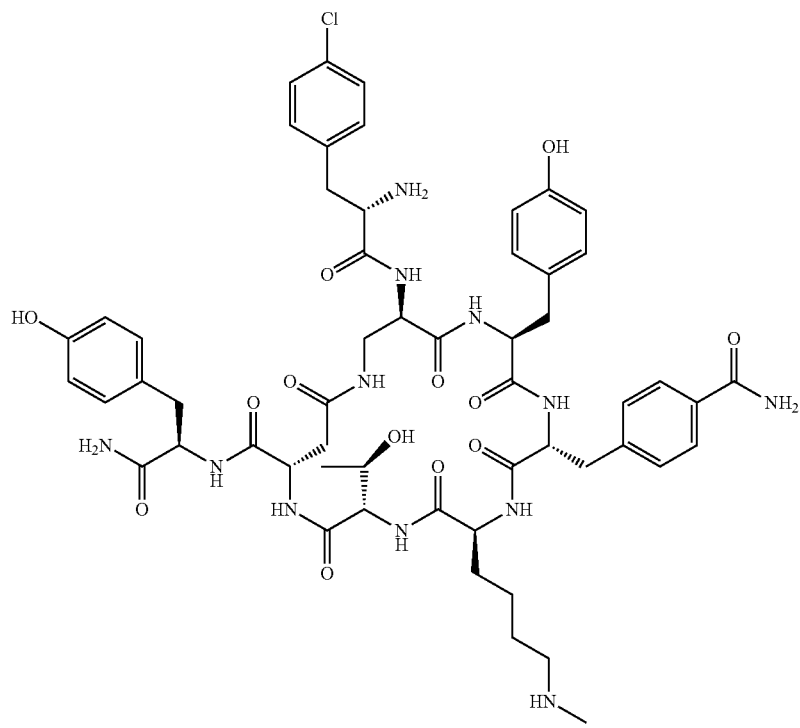 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CNC(=O)C[C@@H](C(=O)N[C@H](Cc2ccc(O)cc2)C(N)=O)NC(=O)[C@H]([C@@H](C)O)NC1=O] |

-continued
| Compound No. | Structure |
|---|---|
72
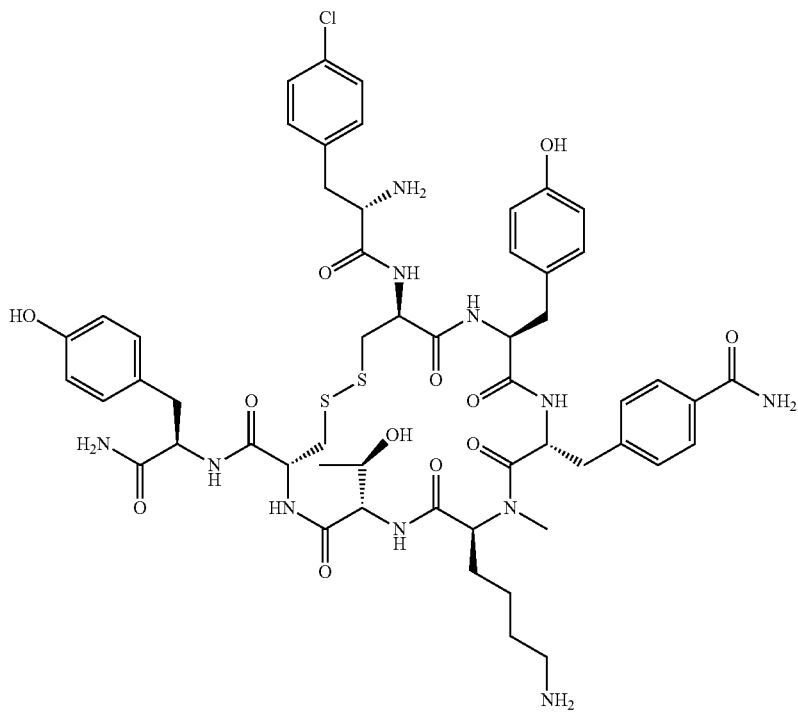 [SMILES: C[C@@H](O)[C@@H]1NC(=O)[C@H](CCCCN)N(C)C(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)NC1=O]
H-Cpa-cyclo[D-Cys-Tyr-D-Phe(4-carbamoyl)-(N$^\alpha$-Me)Lys-Thr-Cys]-D-Tyr-NH$_2$
73
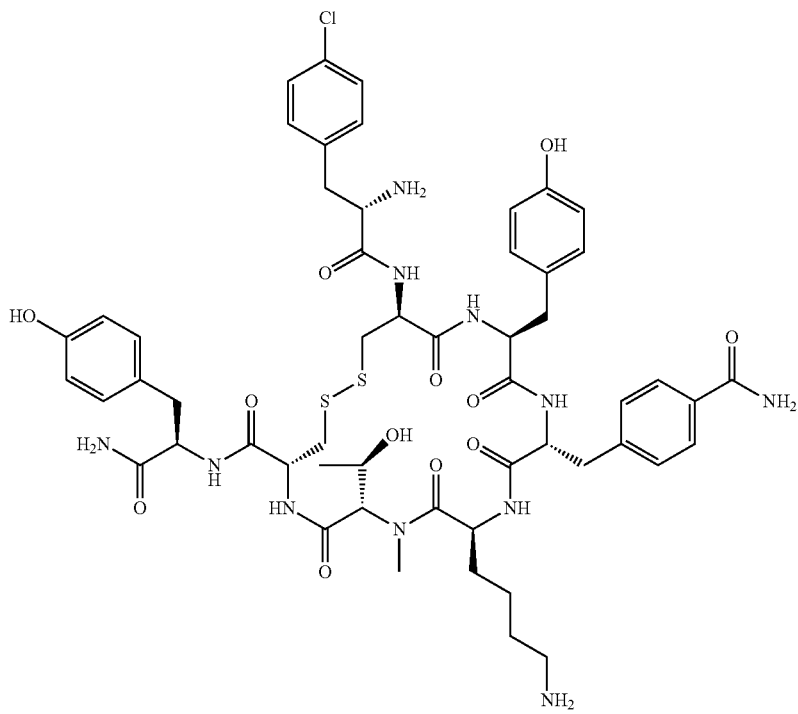 [SMILES: C[C@@H](O)[C@H]1C(=O)N[C@H](C(=O)N[C@H](Cc2ccc(O)cc2)C(N)=O)CSSC[C@@H](NC(=O)[C@@H](N)Cc2ccc(Cl)cc2)C(=O)N[C@@H](Cc2ccc(O)cc2)C(=O)N[C@H](Cc2ccc(C(N)=O)cc2)C(=O)N[C@@H](CCCCN)C(=O)N1C]
H-Cpa-cyclo[D-Cys-Tyr-D-Phe(4-carbamoyl)-Lys-(N-Me)Thr-Cys]-D-Tyr-NH$_2$

| Compound No. | Structure |
|---|---|
| 74 | 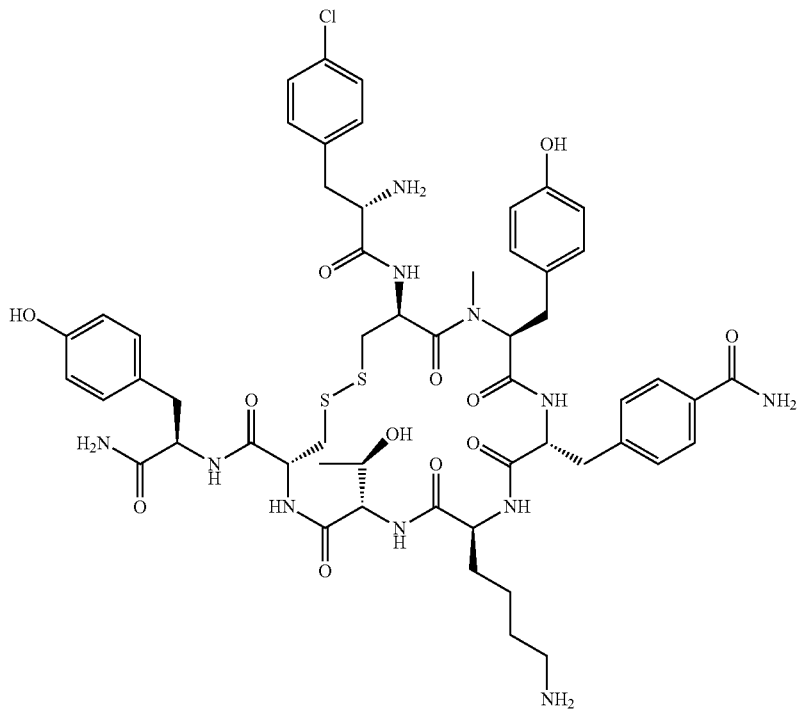 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)N(C)C(=O)[C@H](NC(=O)[C@@H](N)Cc2ccc(Cl)cc2)CSSC[C@@H](C(=O)N[C@H](Cc2ccc(O)cc2)C(N)=O)NC1=O]<br>H-Cpa-cyclo[D-Cys-(N-Me)Tyr-D-Phe(4-carbamoyl)-Lys-Thr-Cys]-D-Tyr-NH$_2$ |
| 75 | 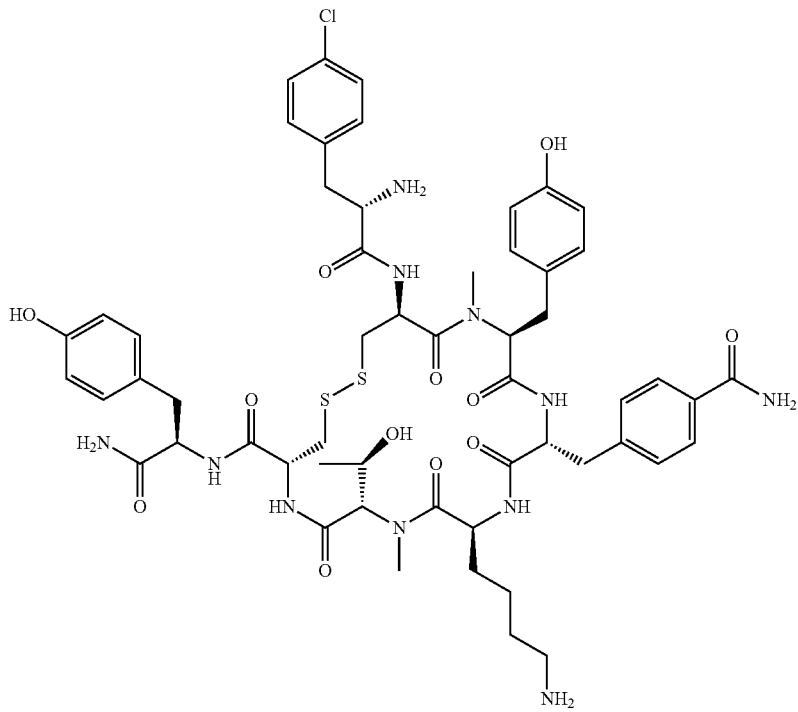 [SMILES: C[C@@H](O)[C@H]1C(=O)N[C@H](C(=O)N[C@H](Cc2ccc(O)cc2)C(N)=O)CSSC[C@@H](NC(=O)[C@@H](N)Cc2ccc(Cl)cc2)C(=O)N(C)[C@@H](Cc2ccc(O)cc2)C(=O)N[C@H](Cc2ccc(C(N)=O)cc2)C(=O)N[C@@H](CCCCN)C(=O)N1C]<br>H-Cpa-cyclo[D-Cys-(N-Me)Tyr-D-Phe(4-carbamoyl)-Lys-(N-Me)Thr-Cys]D-Tyr-NH$_2$ |

-continued
| Compound No. | Structure |
|---|---|
76
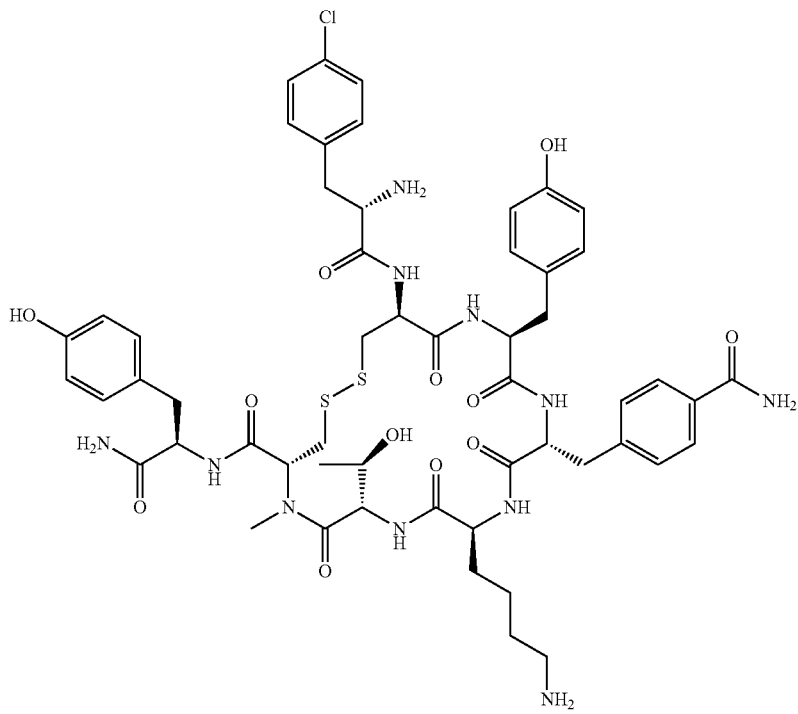 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N[C@H](Cc2ccc(O)cc2)C(N)=O)N(C)C1=O]
H-Cpa-cyclo[D-Cys-Tyr-D-Phe(4-carbamoyl)-Lys-Thr-(N-Me)Cys]-D-Tyr-NH₂
77
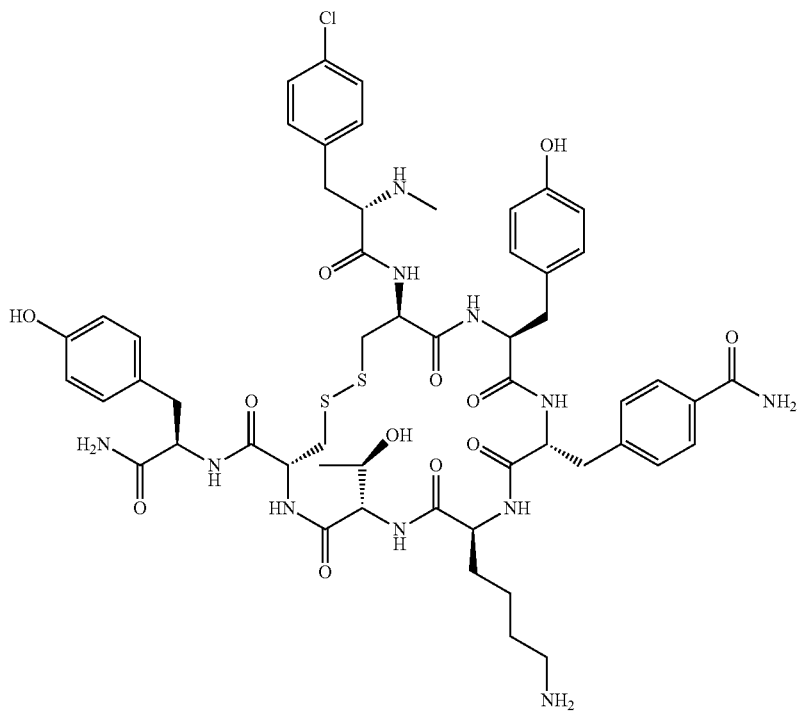 [SMILES: CN[C@@H](Cc1ccc(Cl)cc1)C(=O)N[C@@H]1CSSC[C@@H](C(=O)N[C@H](Cc2ccc(O)cc2)C(N)=O)NC(=O)[C@H]([C@@H](C)O)NC(=O)[C@H](CCCCN)NC(=O)[C@@H](Cc2ccc(C(N)=O)cc2)NC(=O)[C@H](Cc2ccc(O)cc2)NC1=O]
H-(N-Me)Cpa-cyclo[D-Cys-Tyr-D-Phe(4-carbamoyl)-Lys-Thr-Cys]-D-Tyr-NH₂

-continued
| Compound No. | Structure |
|---|---|
| 78 | 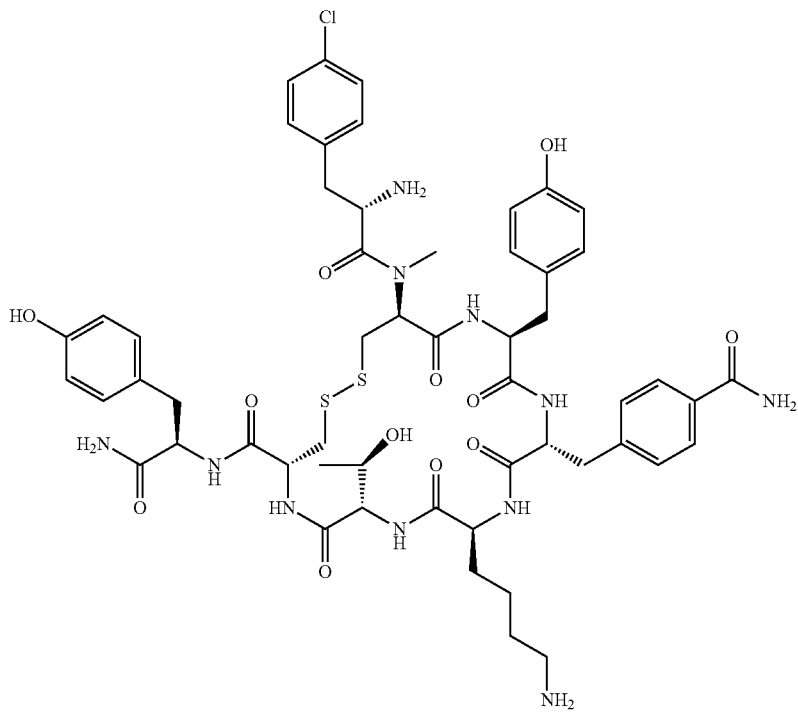 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](N(C)C(=O)[C@@H](N)Cc2ccc(Cl)cc2)CSSC[C@@H](C(=O)N[C@H](Cc2ccc(O)cc2)C(N)=O)NC1=O]<br>H-Cpa-cyclo[D-(N-Me)Cys-Tyr-D-Phe(4-carbamoyl)-Lys-Thr-Cys]-D-Tyr-NH$_2$ |
| 79 | 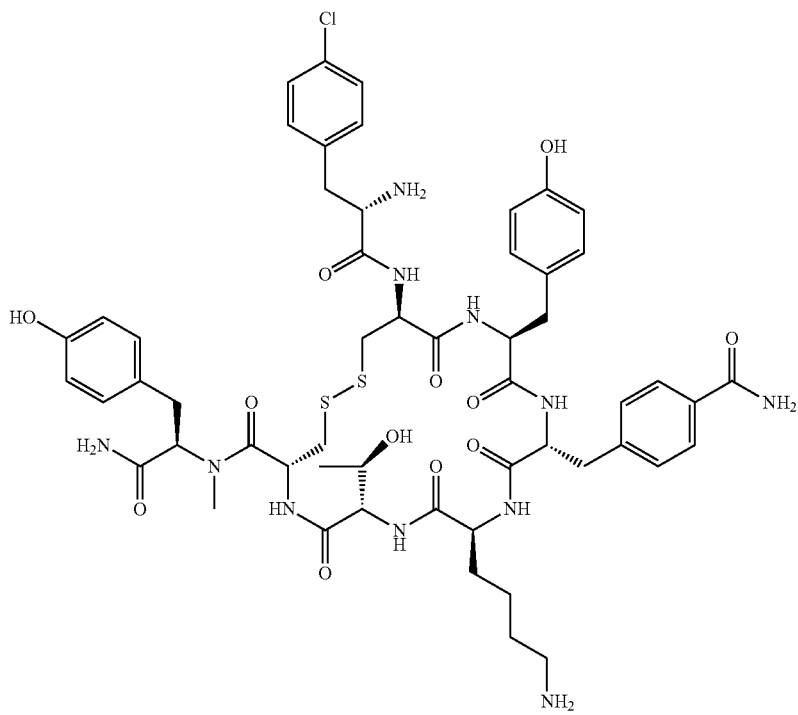 [SMILES: C[C@@H](O)[C@@H]1NC(=O)[C@H](CCCCN)NC(=O)[C@@H](Cc2ccc(C(N)=O)cc2)NC(=O)[C@H](Cc2ccc(O)cc2)NC(=O)[C@H](NC(=O)[C@@H](N)Cc2ccc(Cl)cc2)CSSC[C@@H](C(=O)N(C)[C@H](Cc2ccc(O)cc2)C(N)=O)NC1=O]<br>H-Cpa-cyclo[D-Cys-Tyr-D-Phe(4-carbamoyl)-Lys-Thr-Cys]-D-(N-Me)Tyr-NH$_2$ |

-continued
| Compound No. | Structure |
|---|---|
80
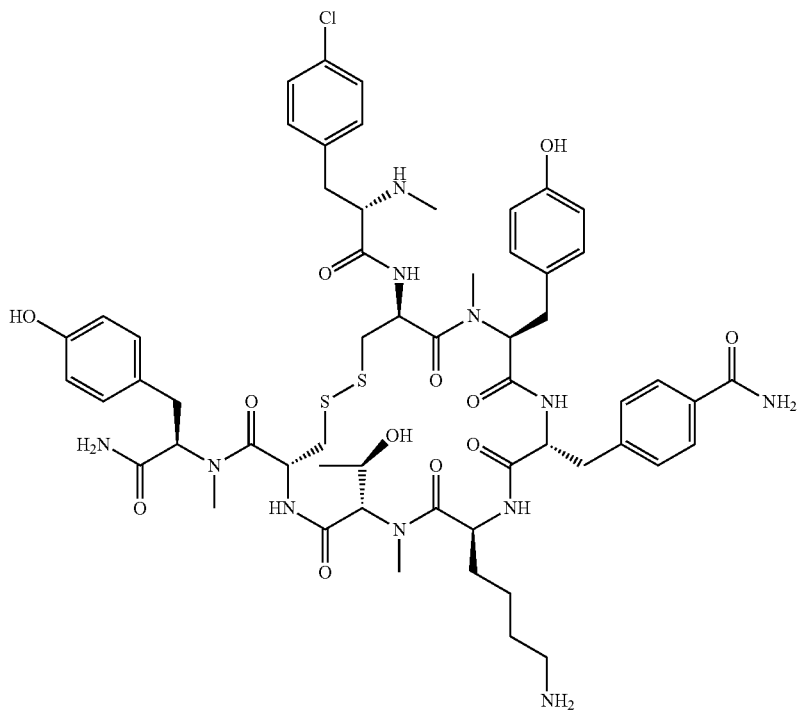 [SMILES: CN[C@@H](Cc1ccc(Cl)cc1)C(=O)N[C@@H]1CSSC[C@@H](C(=O)N(C)[C@H](Cc2ccc(O)cc2)C(N)=O)NC(=O)[C@H]([C@@H](C)O)N(C)C(=O)[C@H](CCCCN)NC(=O)[C@@H](Cc2ccc(C(N)=O)cc2)NC(=O)[C@H](Cc2ccc(O)cc2)N(C)C1=O]
H-(N-Me)Cpa-cyclo[D-Cys-(N-Me)Tyr-D-Phe(4-carbamoyl)-Lys-(N-Me)Thr-Cys]-D-(N-Me)Tyr-NH$_2$
81
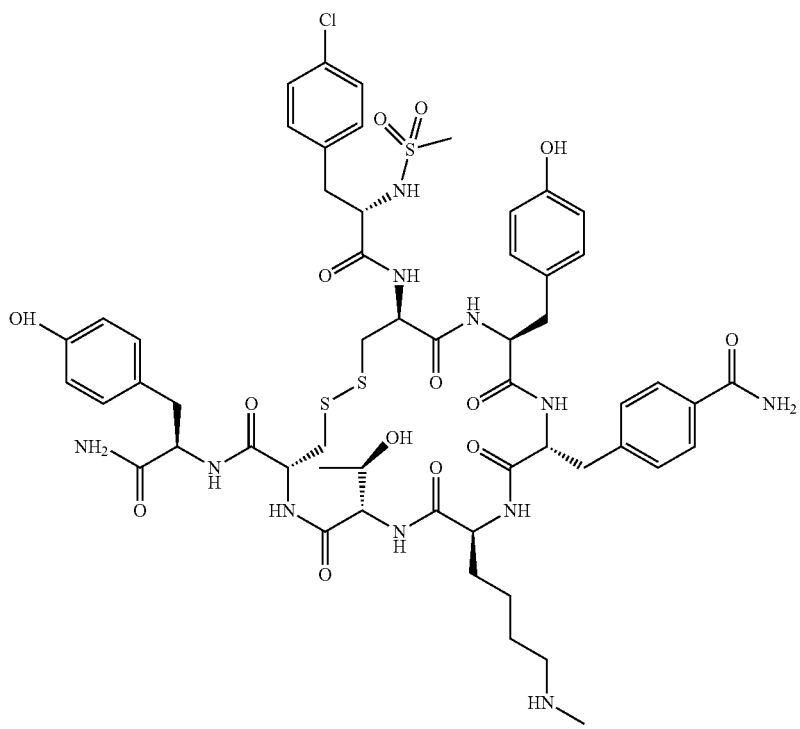 [SMILES: CNCCCC[C@@H]1NC(=O)[C@@H](Cc2ccc(C(N)=O)cc2)NC(=O)[C@H](Cc2ccc(O)cc2)NC(=O)[C@H](NC(=O)[C@H](Cc2ccc(Cl)cc2)NS(C)(=O)=O)CSSC[C@@H](C(=O)N[C@H](Cc2ccc(O)cc2)C(N)=O)NC(=O)[C@H]([C@@H](C)O)NC1=O]
CH$_3$SO$_2$-Cpa-cyclo[D-Cys-Tyr-D-Phe(4-carbamoyl)-Lys(N$^\varepsilon$-Me)-Thr-Cys]-D-Tyr-NH$_2$

| Compound No. | Structure |
|---|---|
| 82 | 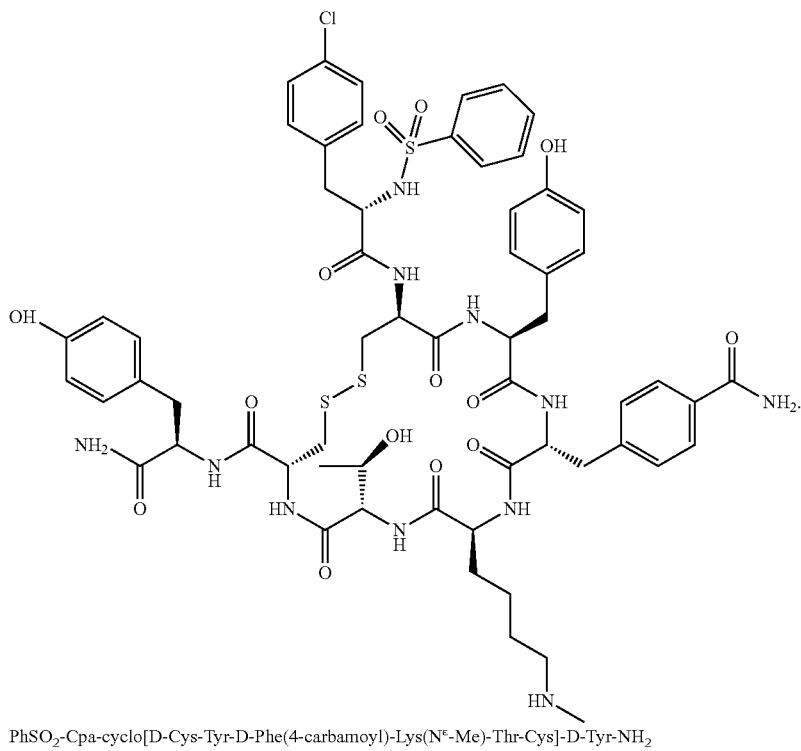<br>PhSO$_2$-Cpa-cyclo[D-Cys-Tyr-D-Phe(4-carbamoyl)-Lys(N$^\varepsilon$-Me)-Thr-Cys]-D-Tyr-NH$_2$ |

43. A pharmaceutical composition comprising a compound as defined in claim 1 or a pharmaceutically acceptable salt thereof and a pharmaceutically acceptable carrier.

44. A method of inhibiting an activity of an SSTR2 receptor in a subject, the method comprising administering a compound of claim 1 or a pharmaceutically acceptable salt thereof, to a subject in need thereof.

45. A method of preventing or treating hypoglycemia in a subject, the method comprising administering a compound of claim 1, or a pharmaceutically acceptable salt thereof, to a subject in need thereof.

46. The method of 45, wherein the hypoglycemia is insulin-induced hypoglycemia.

47. A method of treating diabetes in a subject, the method comprising administering a compound of claim 1, or a pharmaceutically acceptable salt thereof, to a subject in need thereof.

48. A compound having the structure:
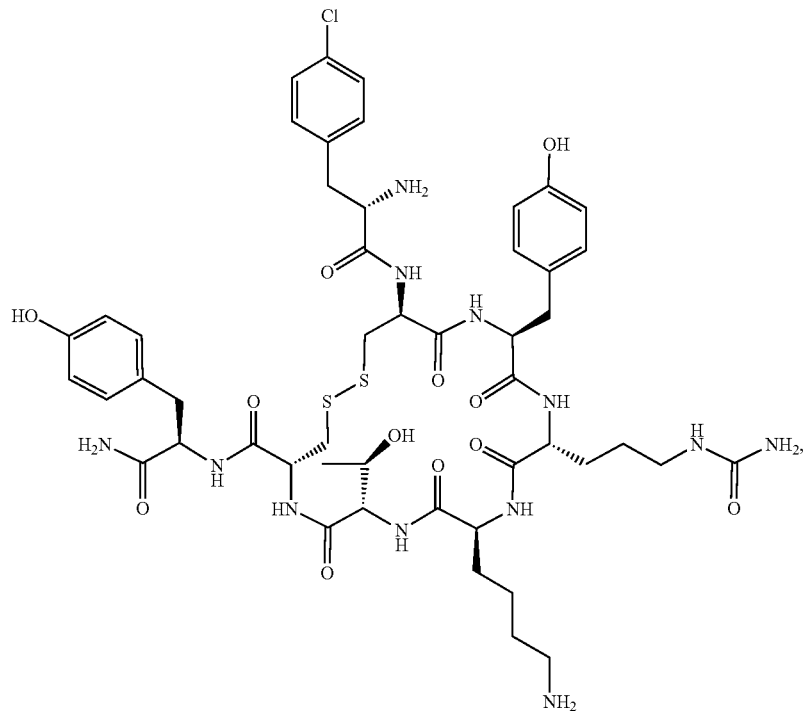
(Compound 1)
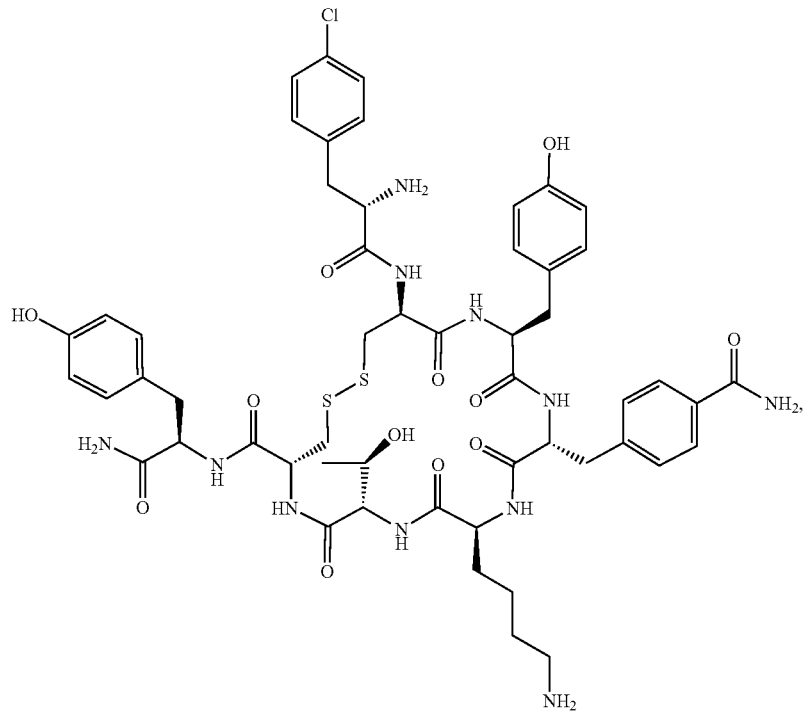
(Compound 4)

(Compound 7)
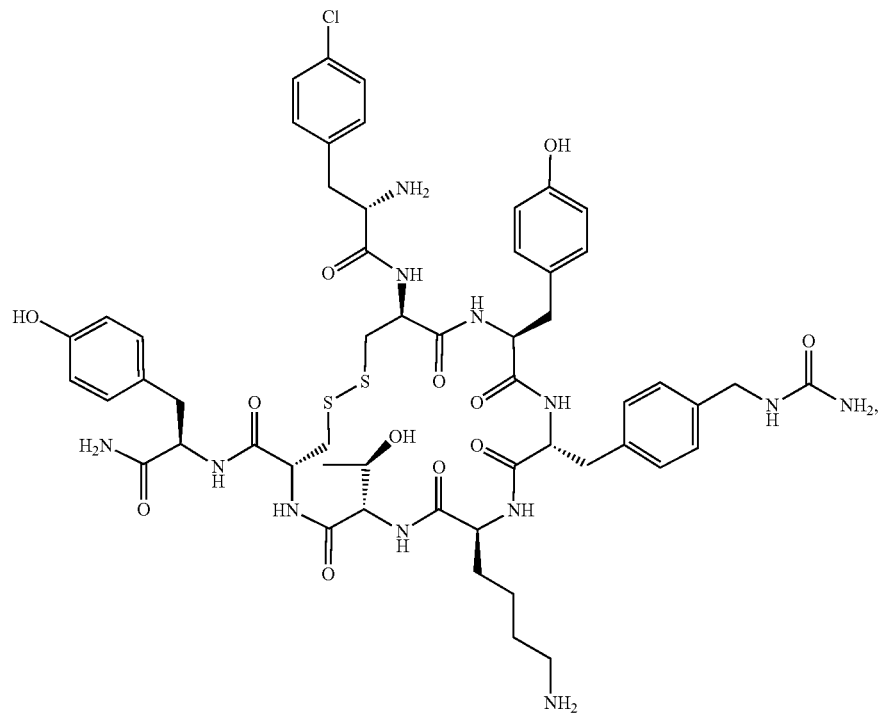
(Compound 15)
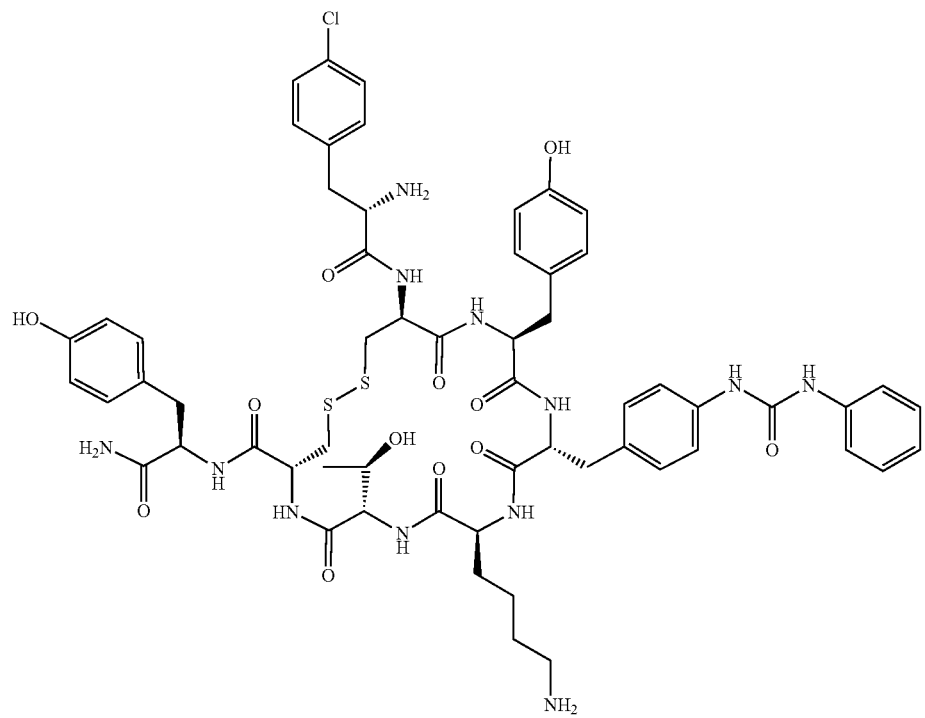

-continued
(Compound 24)
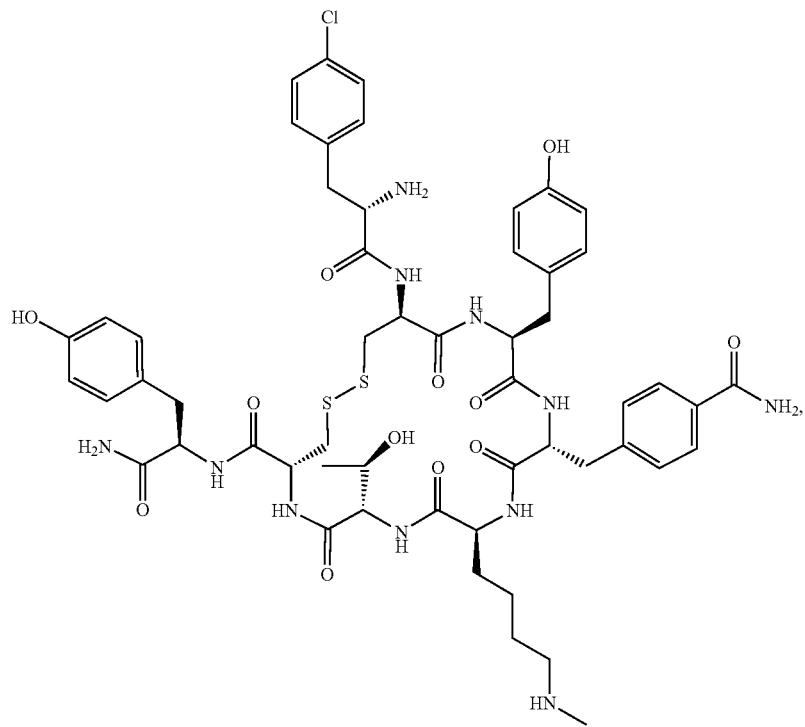
(Compound 32)
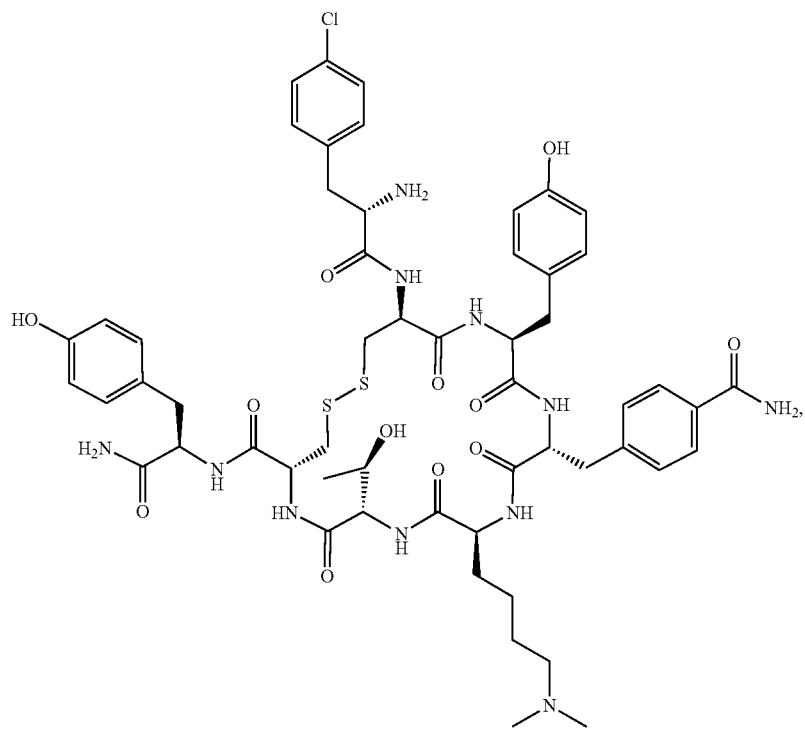

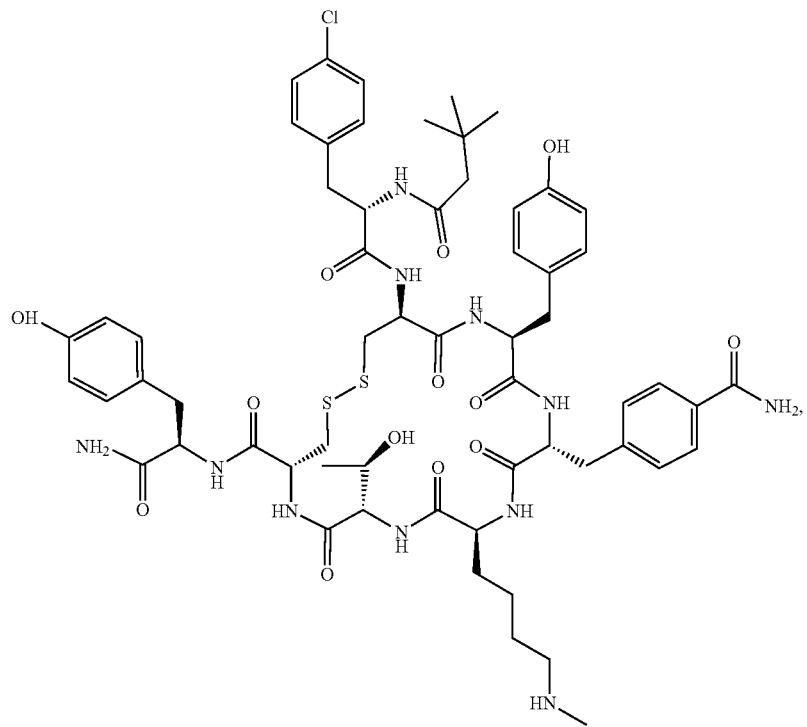
(Compound 52)
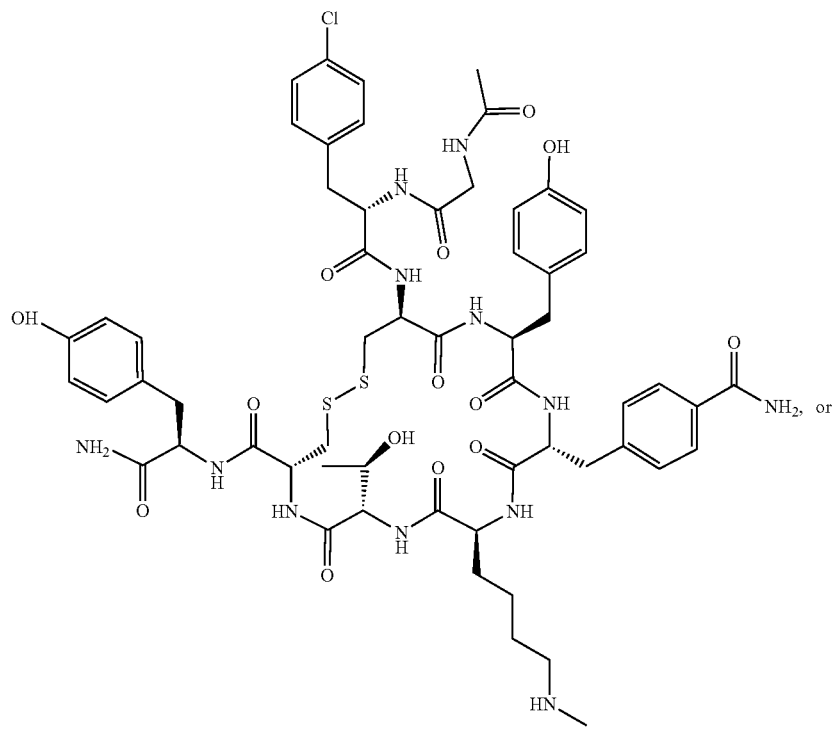
(Compound 55)

(Compound 72)
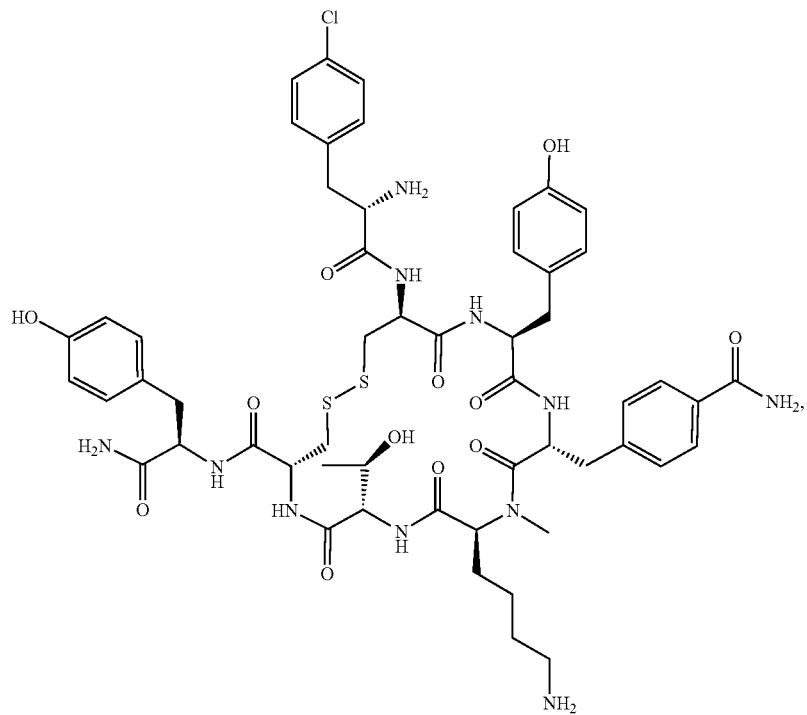
or a salt thereof.
* * * * *

UNITED STATES PATENT AND TRADEMARK OFFICE
CERTIFICATE OF CORRECTION

PATENT NO.        : 11,279,732 B2
APPLICATION NO.   : 16/076826
DATED             : March 22, 2022
INVENTOR(S)       : Arns et al.

It is certified that error appears in the above-identified patent and that said Letters Patent is hereby corrected as shown below:

In the Claims

In Claim 1, Column 530, Lines 7-8, delete "–$C_{1-6}$ alkylene($C_{6-11}$ aryl)" and insert -- –$C_{1-6}$ alkylene($C_{6-10}$ aryl)-- therefor.

In Claim 42, Column 541, in Compound 6, delete "H-Cpa-cyclo[D-Cys-Tyr-D-Phe(4-ureidomethyl)-Lys-Thr-Cys]-D-Tyr-$NH_2$" and insert --H-Cpa-cyclo[D-Cys-Tyr-D-Phe(4-acetamidomethyl)-Lys-Thr-Cys]-D-Tyr-$NH_2$-- therefor.

In Claim 42, Column 541, in Compound 7, delete "H-Cpa-cyclo[D-Cys-Tyr-D-Phe(4-acetamidomethyl)-Lys-Thr-Cys]-D-Tyr-$NH_2$" and insert --H-Cpa-cyclo[D-Cys-Tyr-D-Phe(4-ureidomethyl)-Lys-Thr-Cys]-D-Tyr-$NH_2$-- therefor.

In Claim 42, Column 557, in Compound 22, delete "H-Cpa-cyclo[D-Cys-Tyr-D-Aph(Cit-Lys-Thr-Cys]-D-Tyr-$NH_2$" and insert --H-Cpa-cyclo[D-Cys-Tyr-D-Aph(Cit)-Lys-Thr-Cys]-D-Tyr-$NH_2$-- therefor.

In Claim 42, Column 567, in Compound 33, delete "H-Cpa-cyclo[D-Cys-Tyr-D-Phe(4-carbamoyl)-Lys-Val-Cys]-P-Tyr-$NH_2$" and insert --H-Cpa-cyclo[D-Cys-Tyr-D-Phe(4-carbamoyl)-Lys-Val-Cys]-D-Tyr-$NH_2$-- therefor.

Signed and Sealed this
Tenth Day of May, 2022

Katherine Kelly Vidal
*Director of the United States Patent and Trademark Office*